United States Patent
Mazed

(10) Patent No.: US 10,529,003 B2
(45) Date of Patent: *Jan. 7, 2020

(54) OPTICAL BIOMODULE FOR DETECTION OF DISEASES AT AN EARLY ONSET

(71) Applicant: Mohammad A. Mazed, Yorba Linda, CA (US)

(72) Inventor: Mohammad A. Mazed, Chino Hills, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 15/731,577

(22) Filed: Jul. 3, 2017

(65) Prior Publication Data

US 2017/0316487 A1     Nov. 2, 2017

Related U.S. Application Data

(63) Continuation-in-part of application No. 14/120,835, filed on Jul. 1, 2014, now Pat. No. 9,823,737, which is a continuation of application No. 13/448,378, filed on Apr. 16, 2012, now Pat. No. 9,697,556, and a continuation of application No. 13/663,376, filed on Oct. 29, 2012, now Pat. No. 9,557,271, which is a continuation-in-part of application No. 13/135,832, filed on Jul. 15, 2011, now abandoned, which is a continuation-in-part of application No. 12/573,012, filed on Oct. 2, 2009, now Pat. No. 8,017,147, which is a continuation-in-part of application No. 12/390,302, filed on Feb. 20, 2009, now abandoned, which is a continuation-in-part of application No. 12/169,523, filed on Jul. 8, 2008, now abandoned, said application No. 14/120,835 is a continuation-in-part of application No. 12/238,286, filed on Sep. 25, 2008, now abandoned.

(60) Provisional application No. 62/497,979, filed on Dec. 12, 2016, provisional application No. 61/957,343, filed on Jul. 1, 2013, provisional application No. 61/517,204, filed on Apr. 15, 2011, provisional application No. 61/742,074, filed on Aug. 1, 2012,
(Continued)

(51) Int. Cl.
| | |
|---|---|
| G01N 33/551 | (2006.01) |
| G06Q 30/06 | (2012.01) |
| G06Q 30/02 | (2012.01) |
| H04W 4/029 | (2018.01) |
| G01N 33/543 | (2006.01) |
| G06Q 20/12 | (2012.01) |

(52) U.S. Cl.
CPC ... *G06Q 30/0631* (2013.01); *G01N 33/54373* (2013.01); *G01N 33/551* (2013.01); *G06Q 30/02* (2013.01); *G06Q 30/06* (2013.01); *G06Q 30/0639* (2013.01); *H04W 4/029* (2018.02); *G06Q 20/12* (2013.01)

(58) Field of Classification Search
None
See application file for complete search history.

(56) References Cited

U.S. PATENT DOCUMENTS

| | | | |
|---|---|---|---|
| 7,170,050 B2* | 1/2007 | Turner | G01N 21/00 250/251 |
| 7,476,503 B2* | 1/2009 | Turner | B01L 3/5085 435/6.11 |
| 2003/0174992 A1* | 9/2003 | Levene | B82Y 20/00 385/129 |

* cited by examiner

*Primary Examiner* — Christopher L Chin

(57) ABSTRACT

An optical biomodule for detecting a disease specific biomarker(s), utilizing enhanced fluorescence emission (due to integration of a three-dimensional (3-D) protruded structure (s)) in a fluidic container/zero-mode waveguide, upon chemical binding of a disease specific biomarker(s) with its corresponding disease specific biomarker binder(s) (e.g., an aptamer(s)) is disclosed.

25 Claims, 128 Drawing Sheets

Related U.S. Application Data provisional application No. 61/631,071, filed on Dec. 27, 2011, provisional application No. 61/274,306, filed on Aug. 14, 2009, provisional application No. 61/043,059, filed on Apr. 7, 2008.

INDIRECT INTERACTION
DIRECT INTERACTION

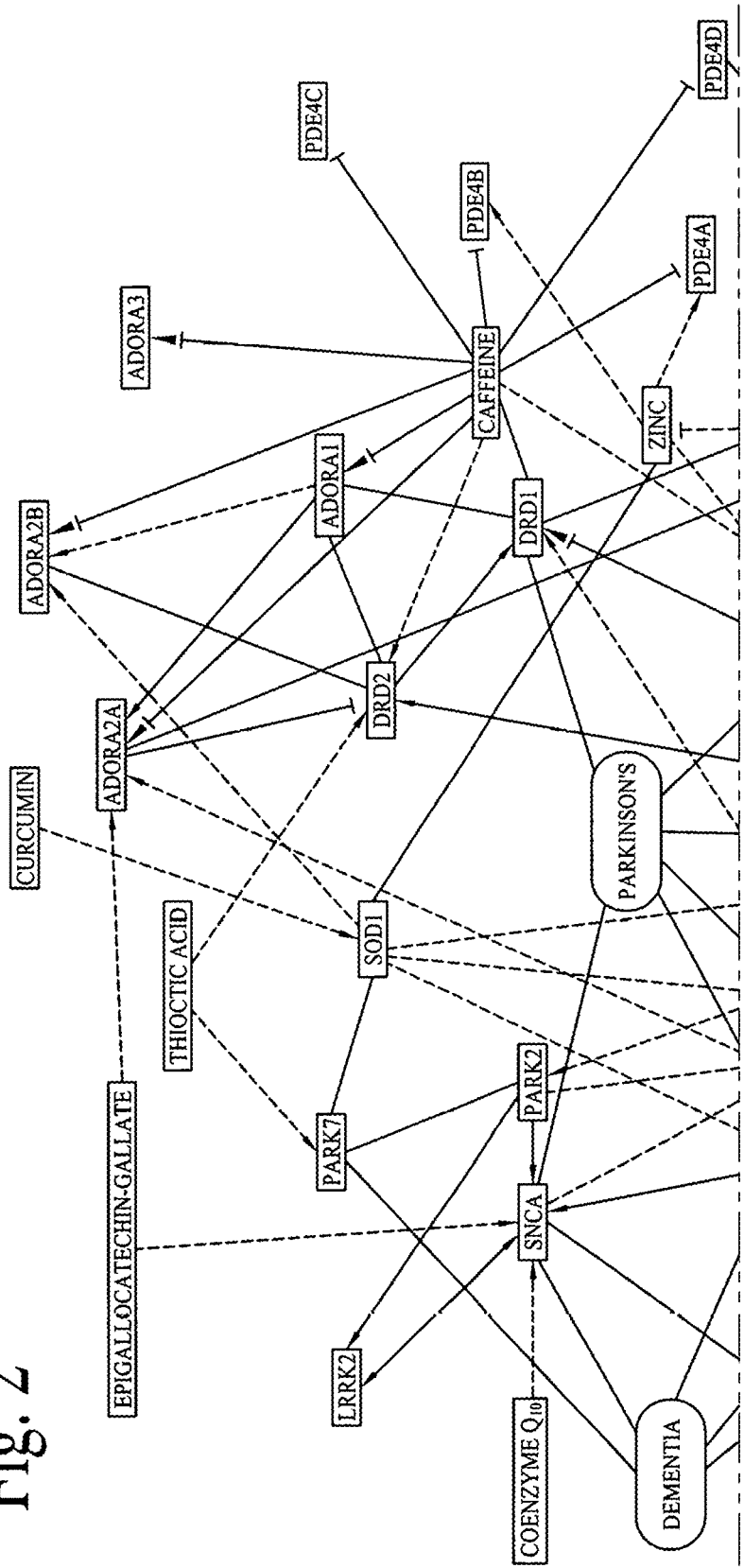

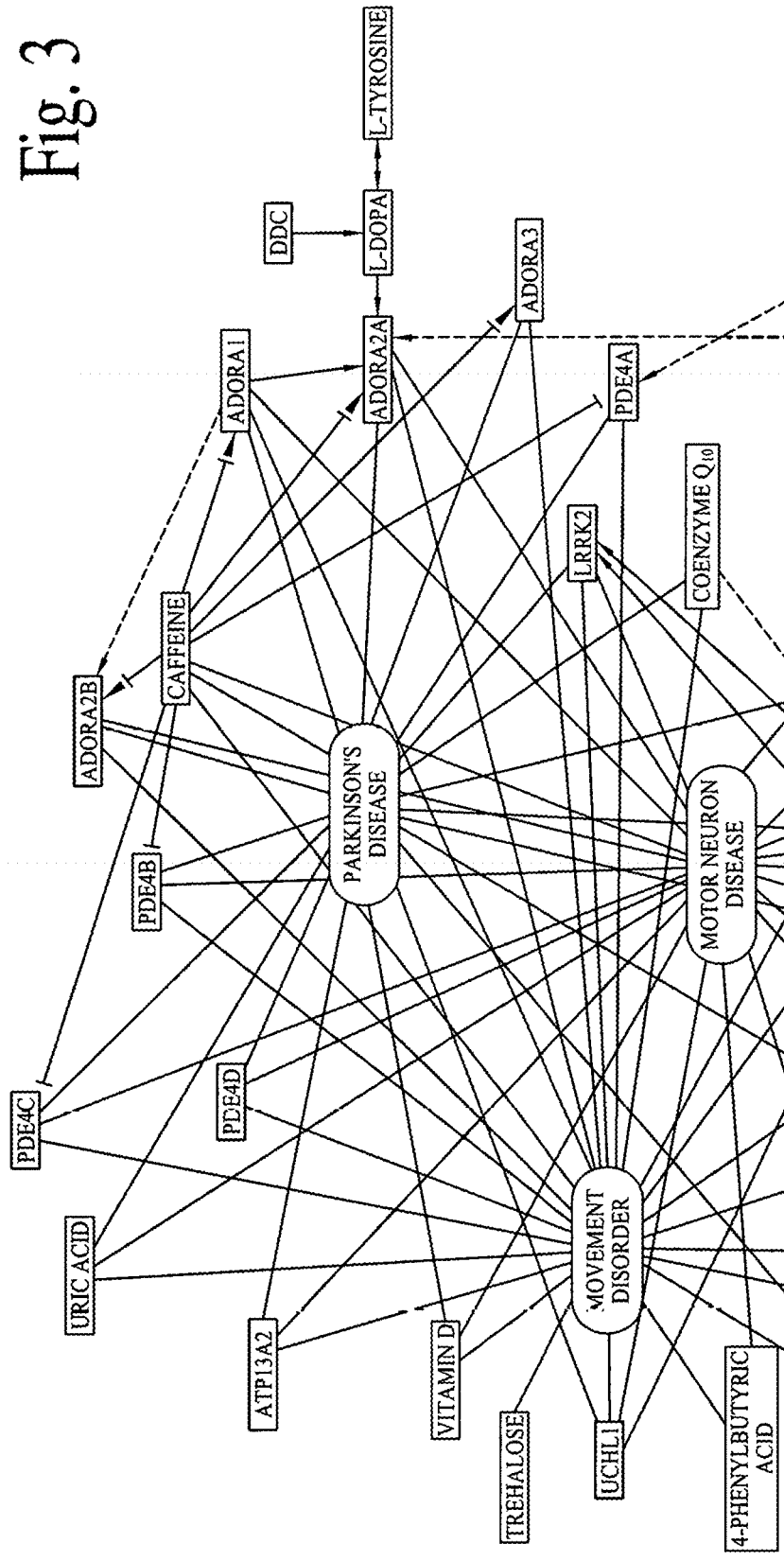

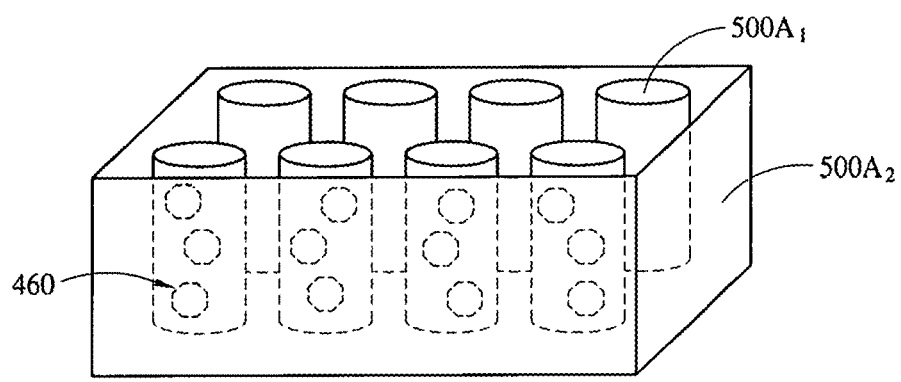
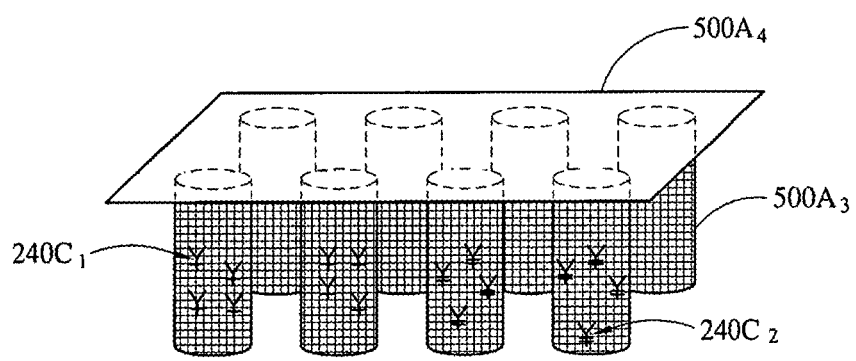
Fig. 12D

EXAMPLES OF THREE-DIMENSIONAL (3-D) PROTRUDED OPTICAL NANOANTENNA (ONA)
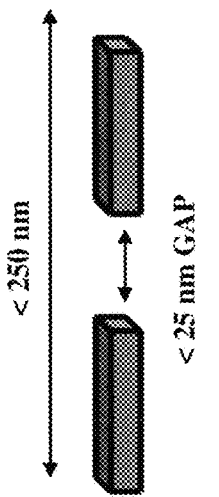
FIG. 12J
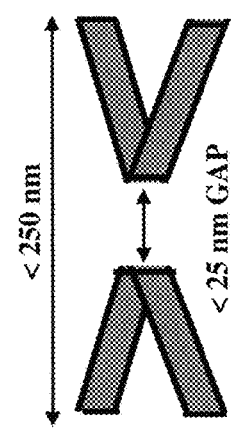
FIG. 12M
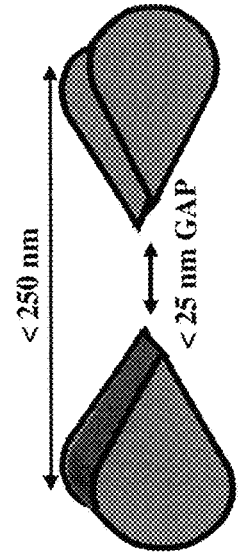
FIG. 12O
FIG. 12I
FIG. 12L
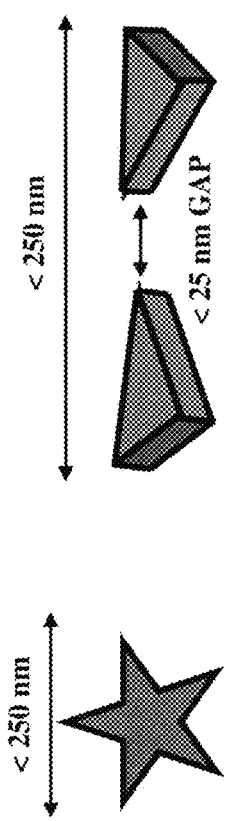
FIG. 12H
FIG. 12K
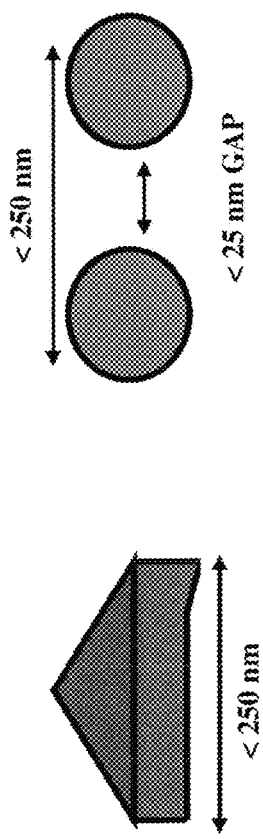
FIG. 12N

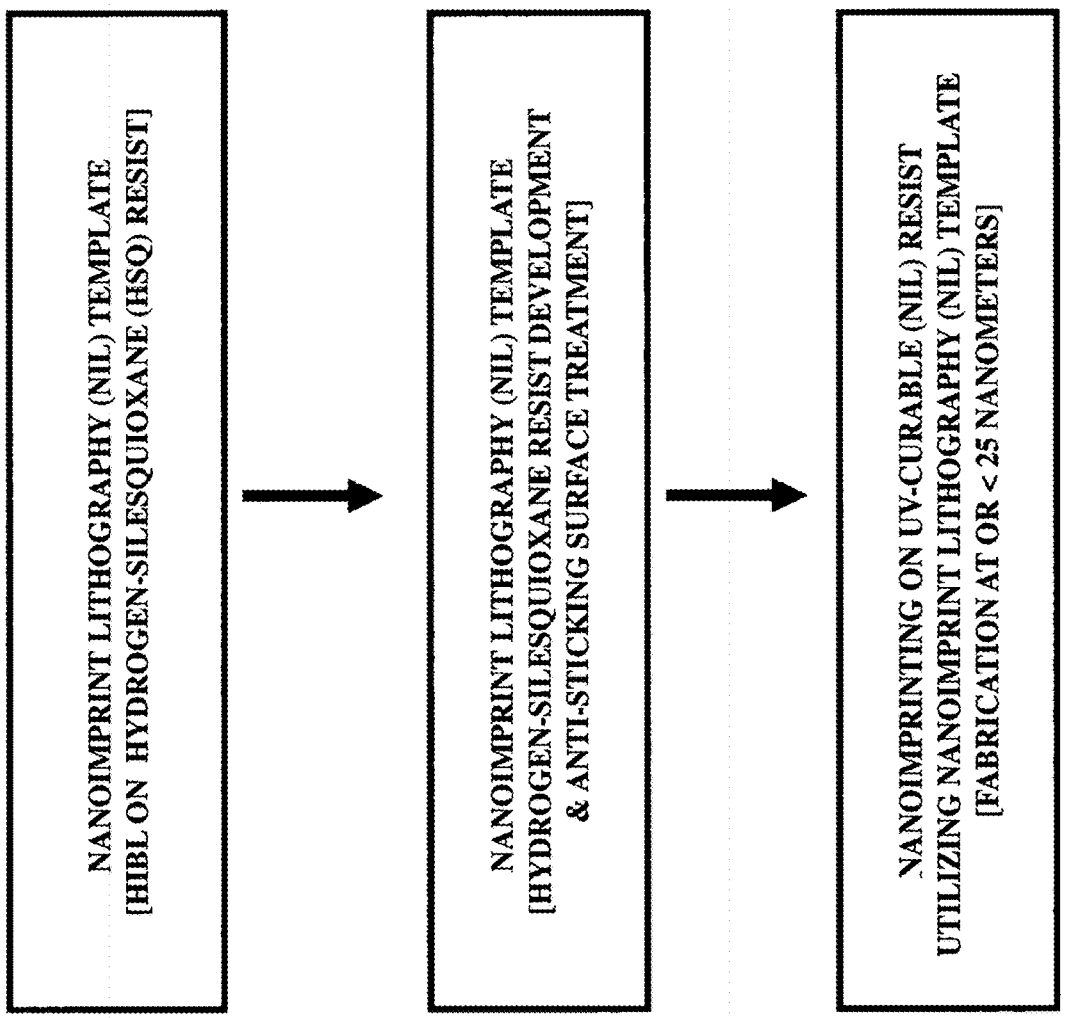
FIG. 12P1

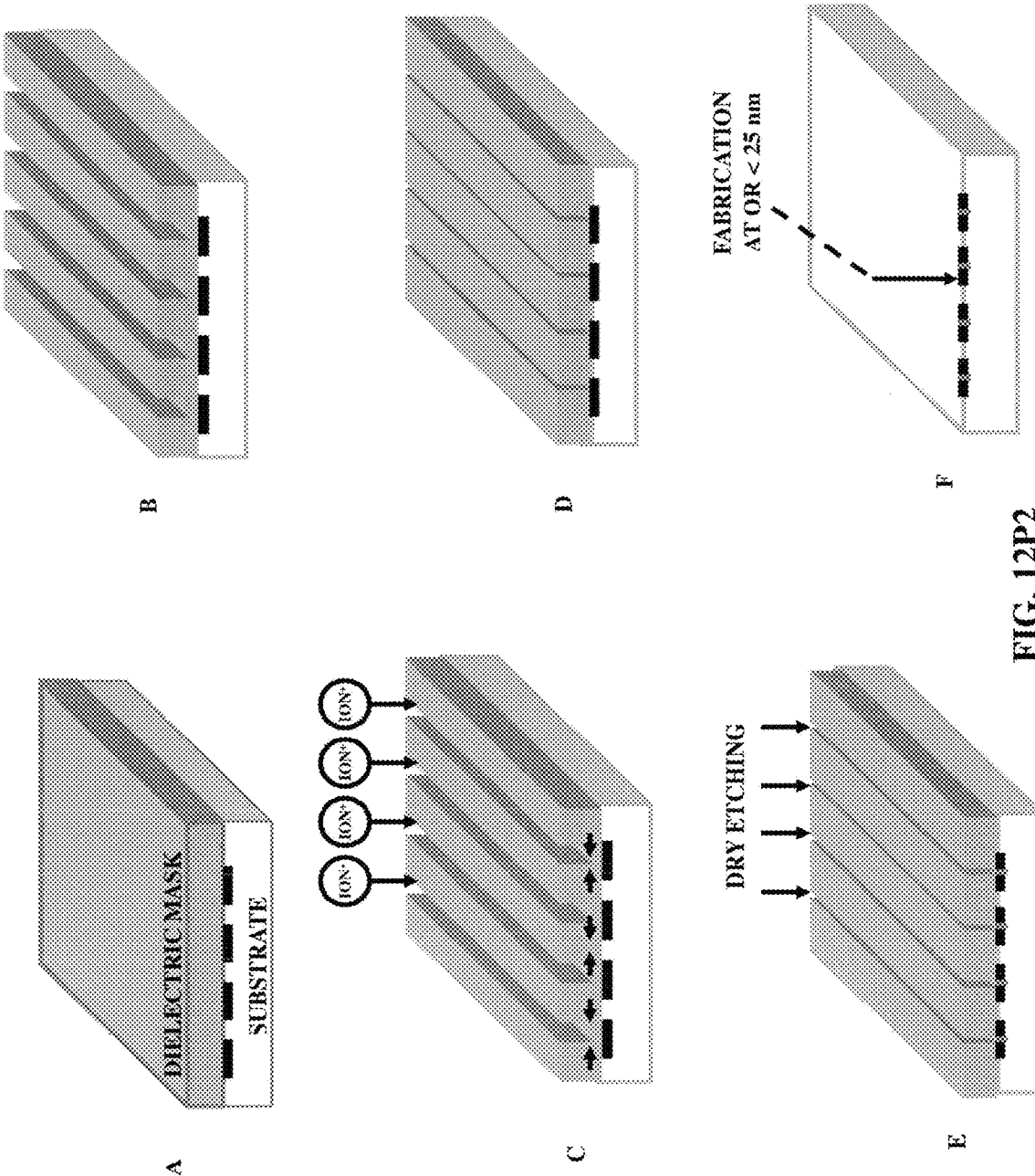
FIG. 12P2

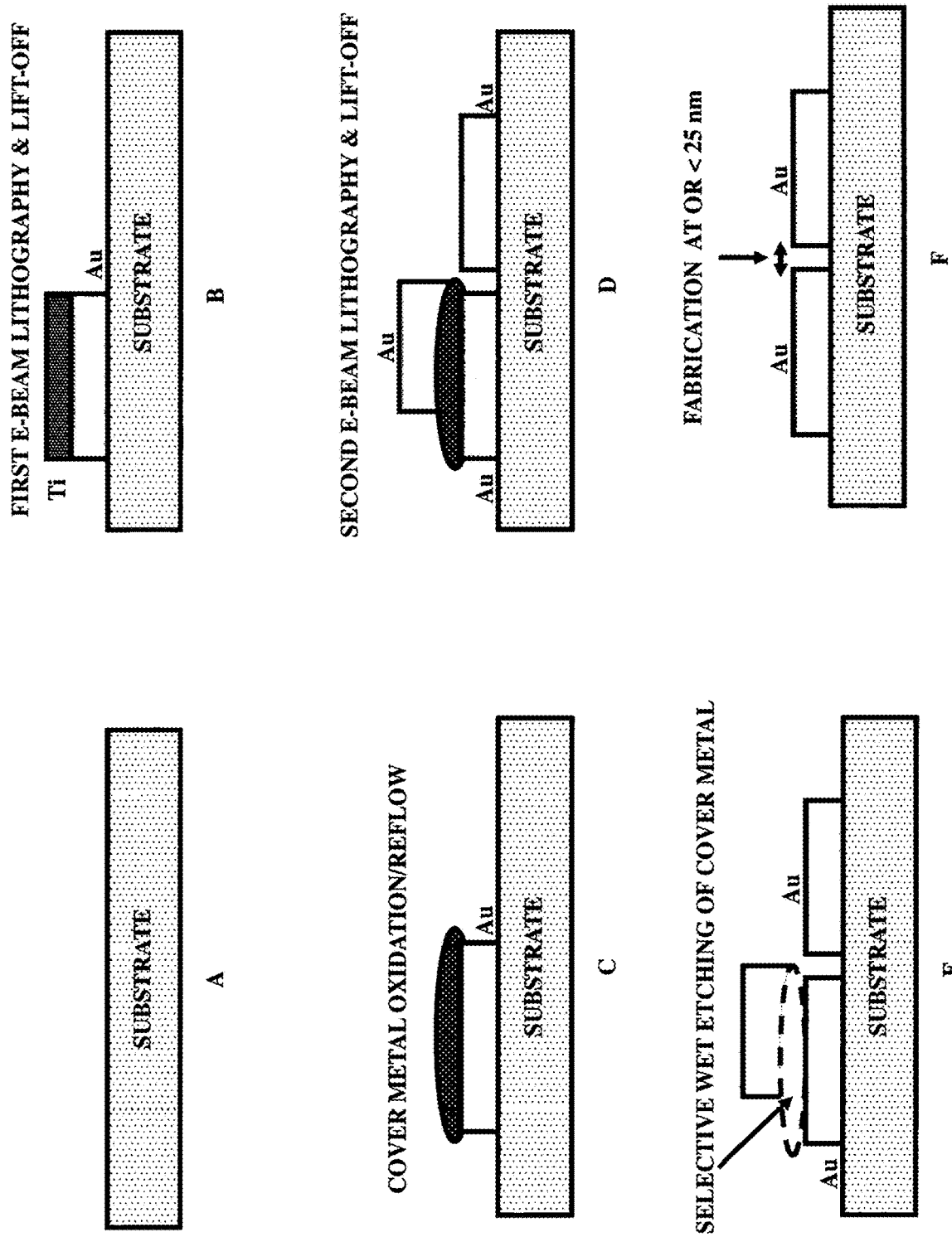
FIG. 12P3

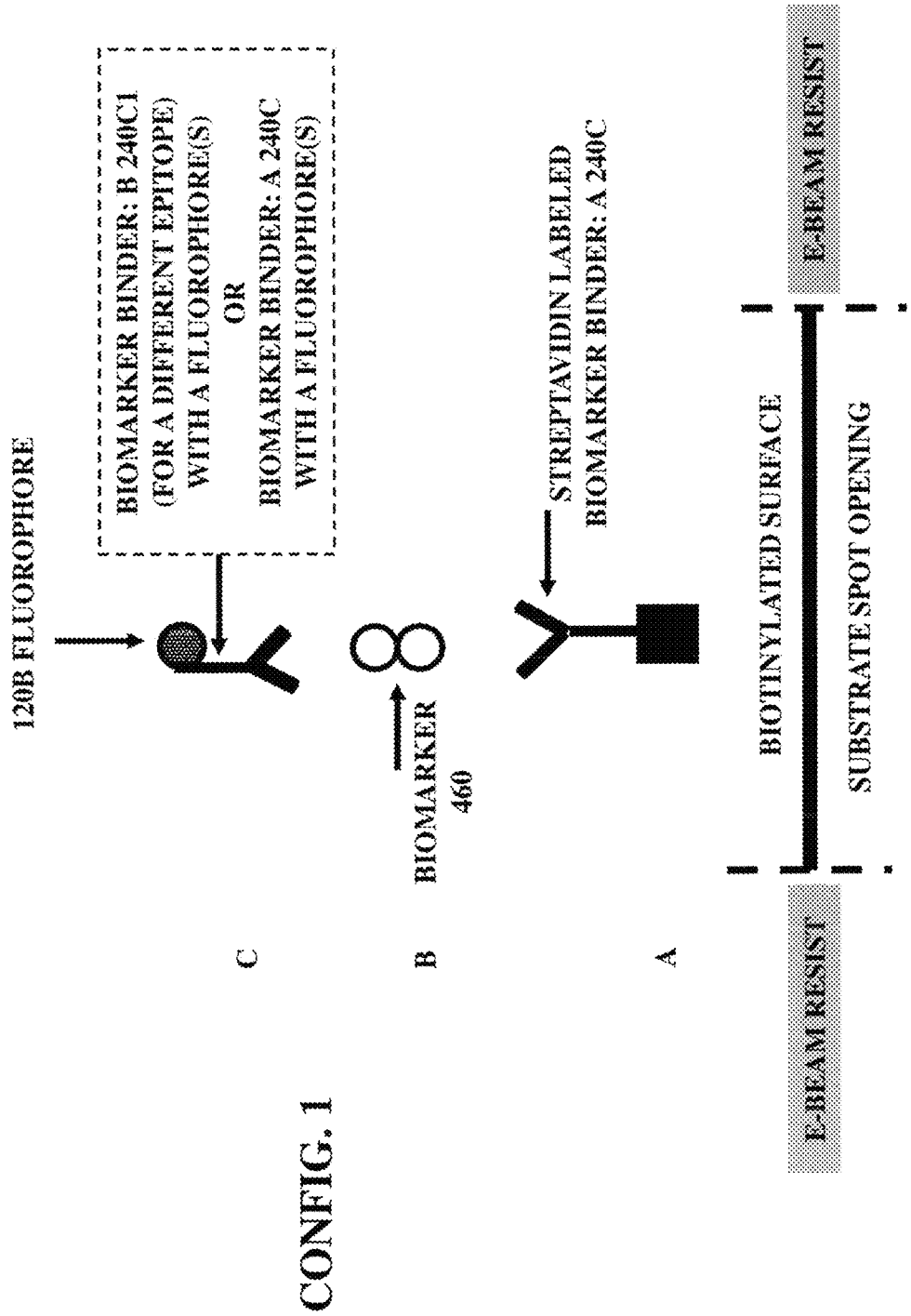

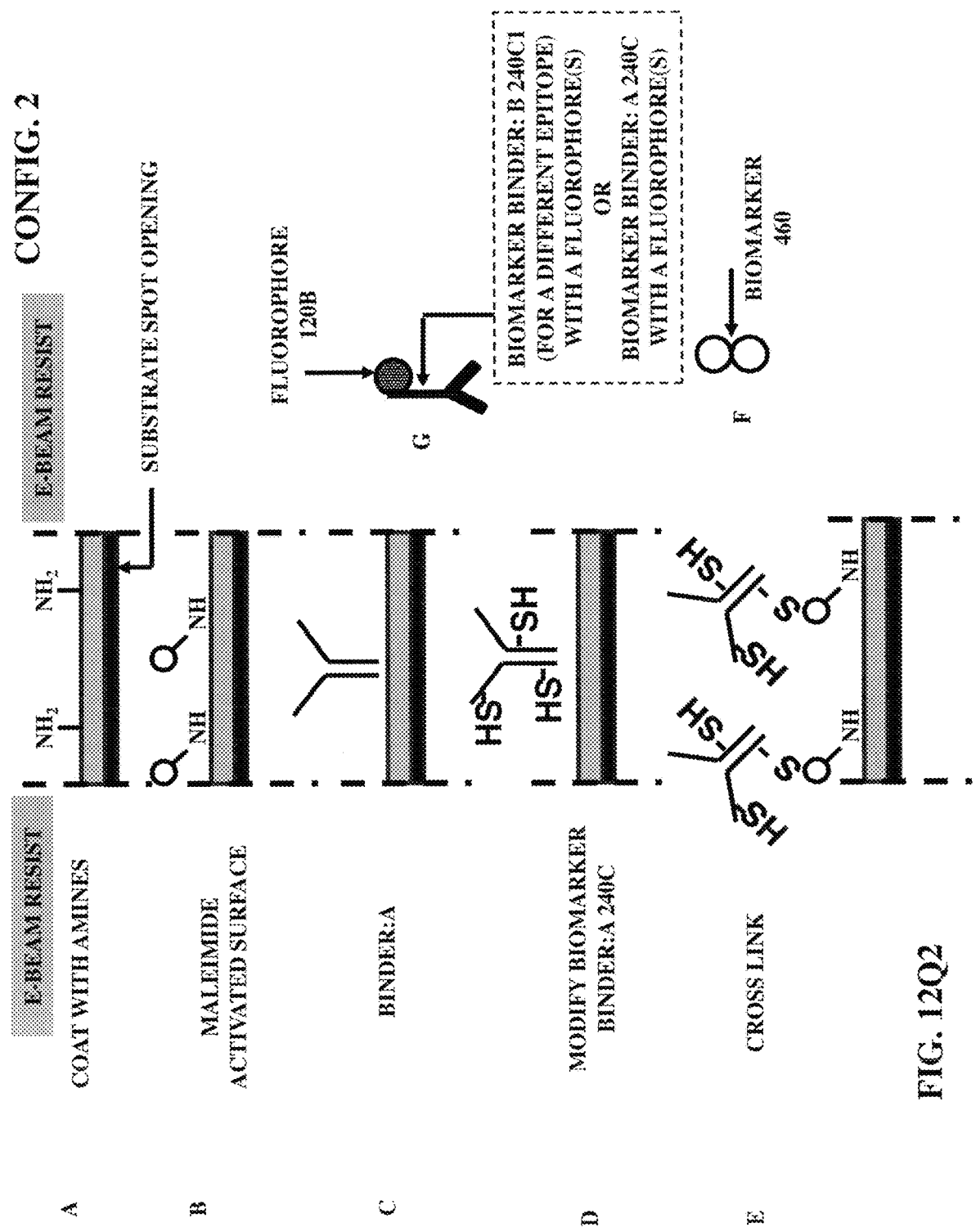

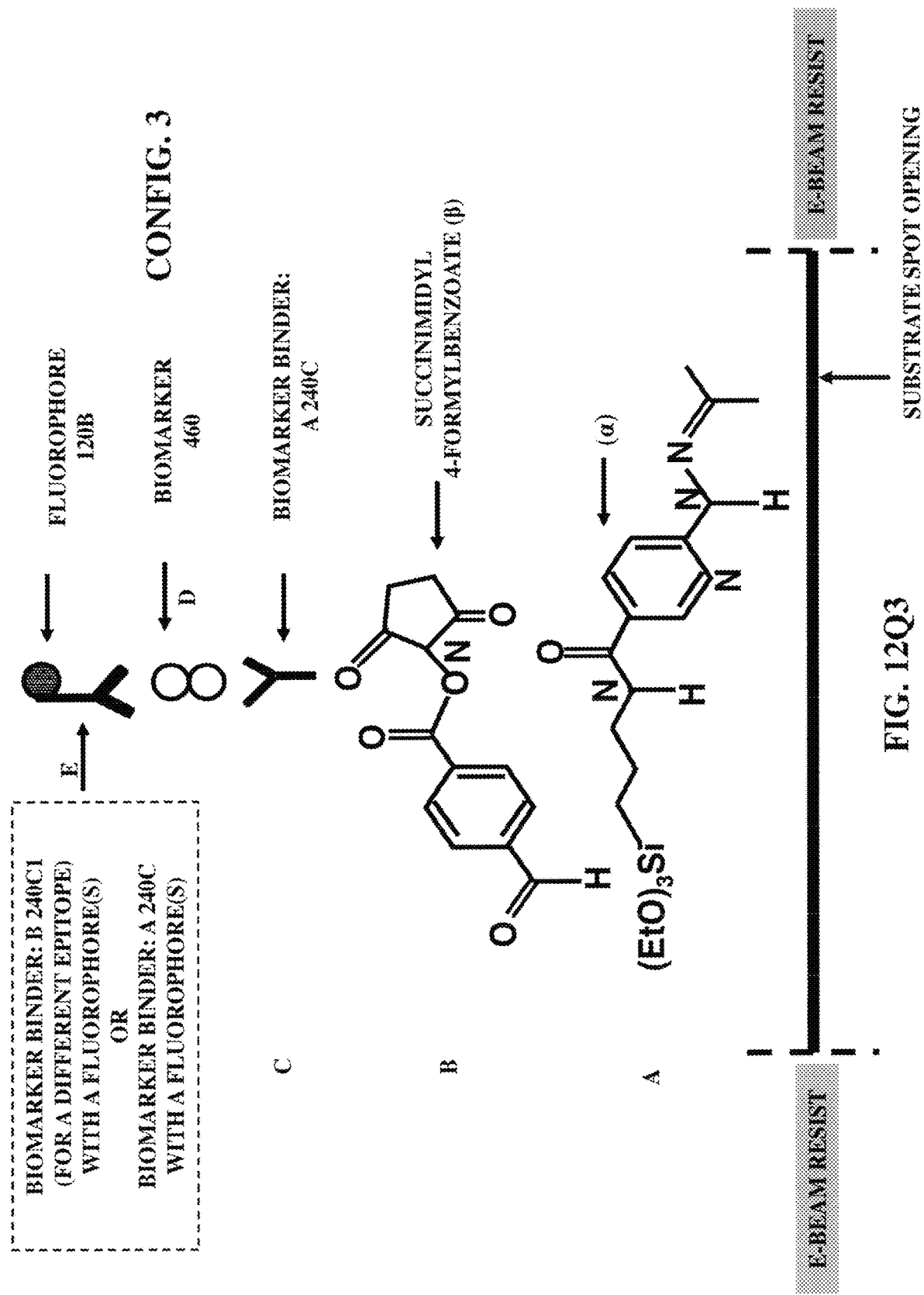
FIG. 12Q3

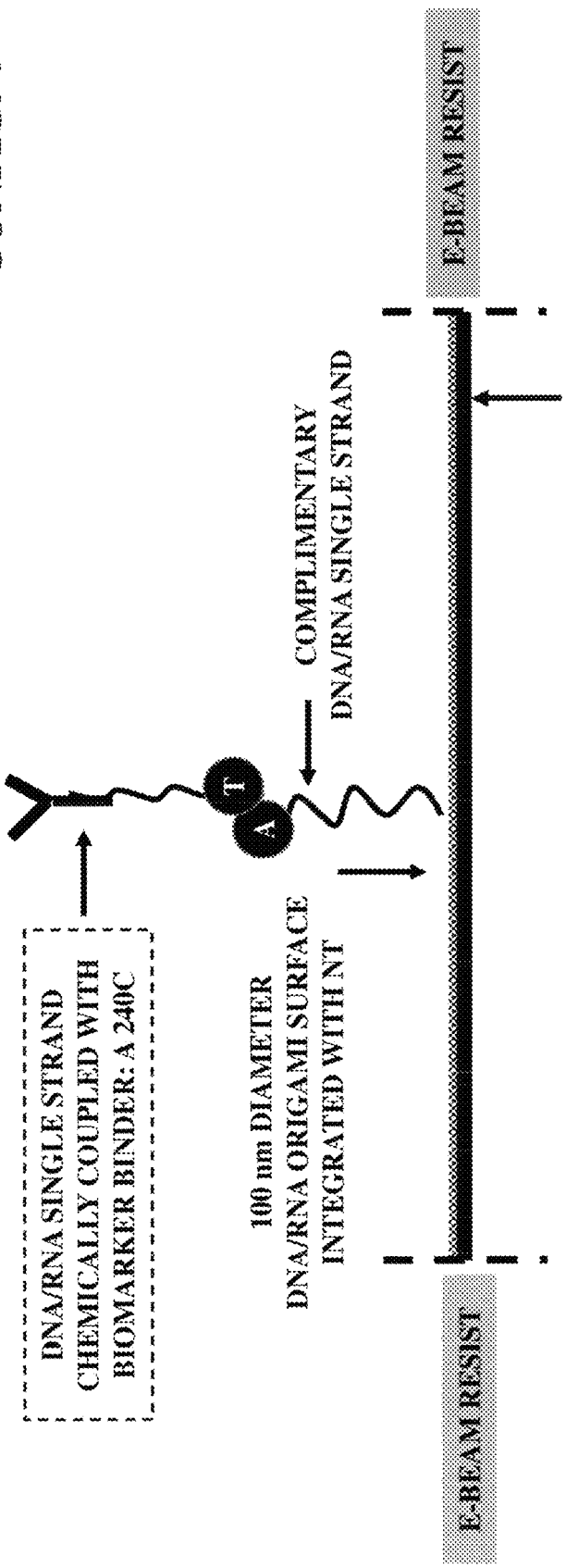
FIG. 12Q4

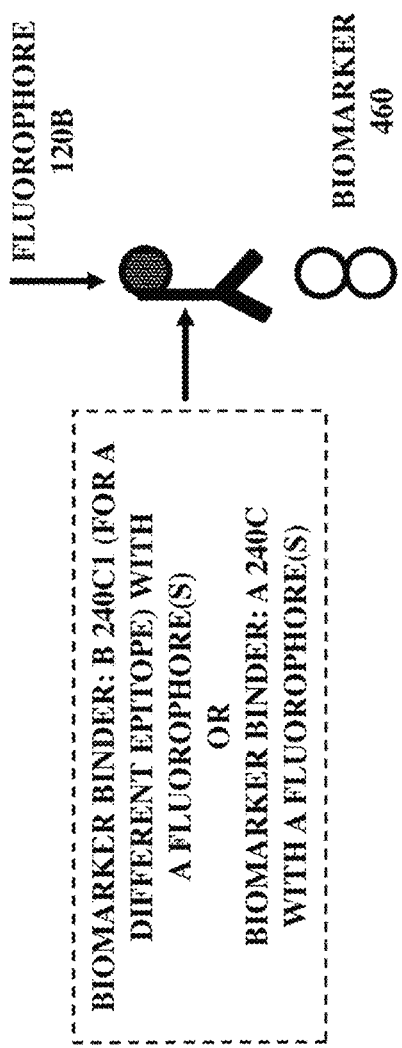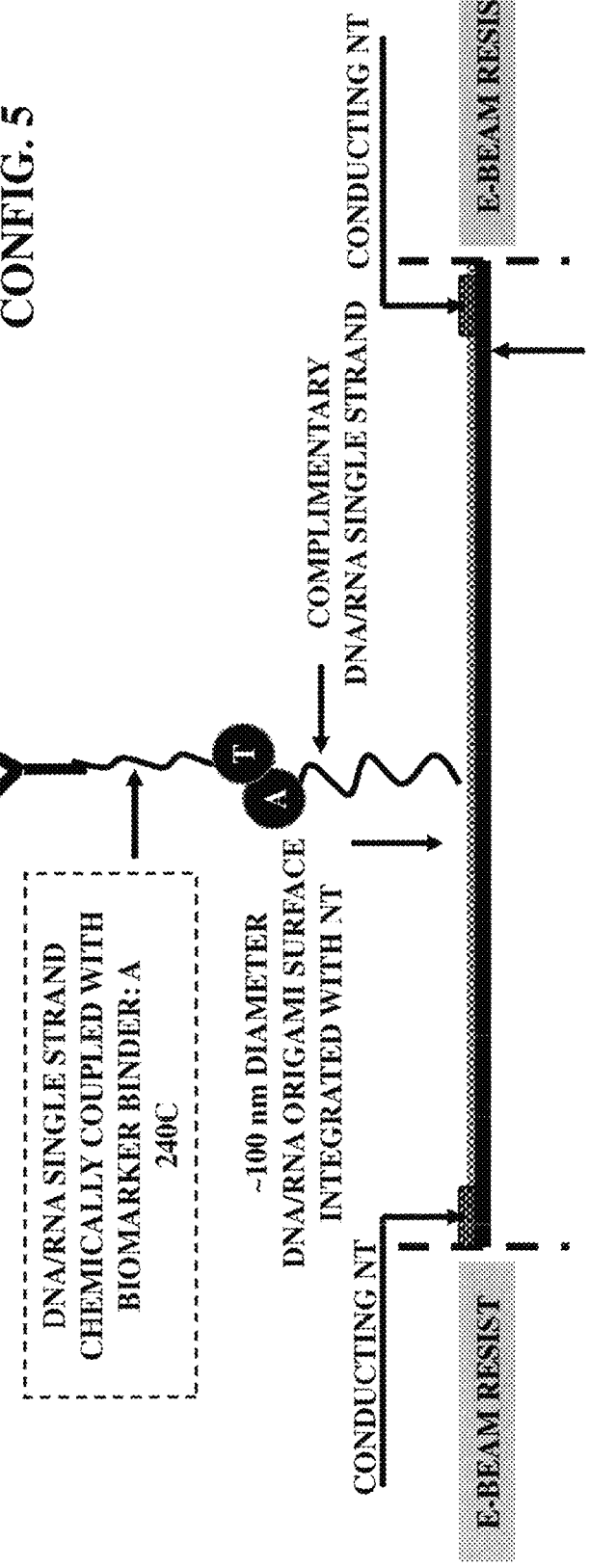
FIG. 12Q5

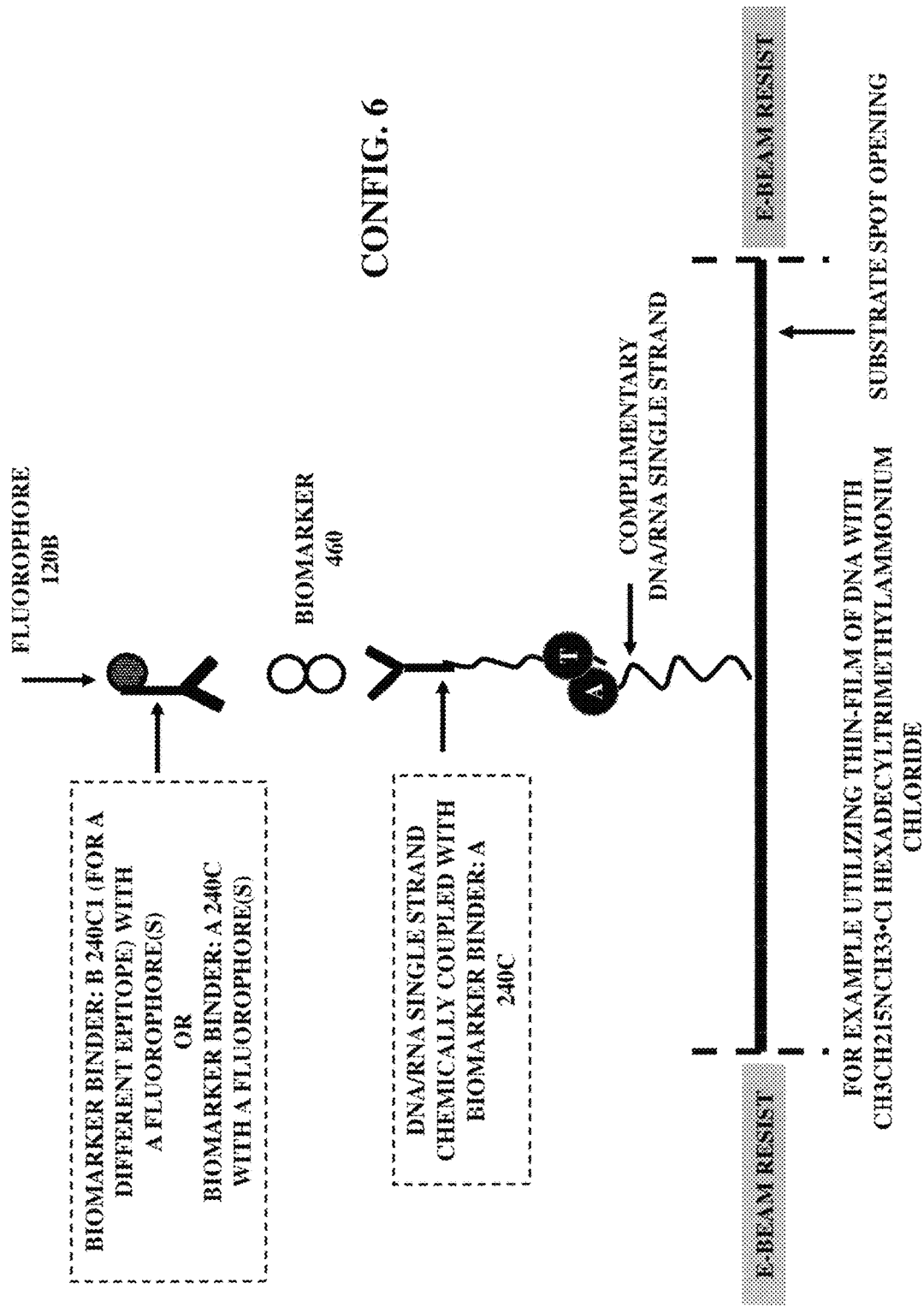

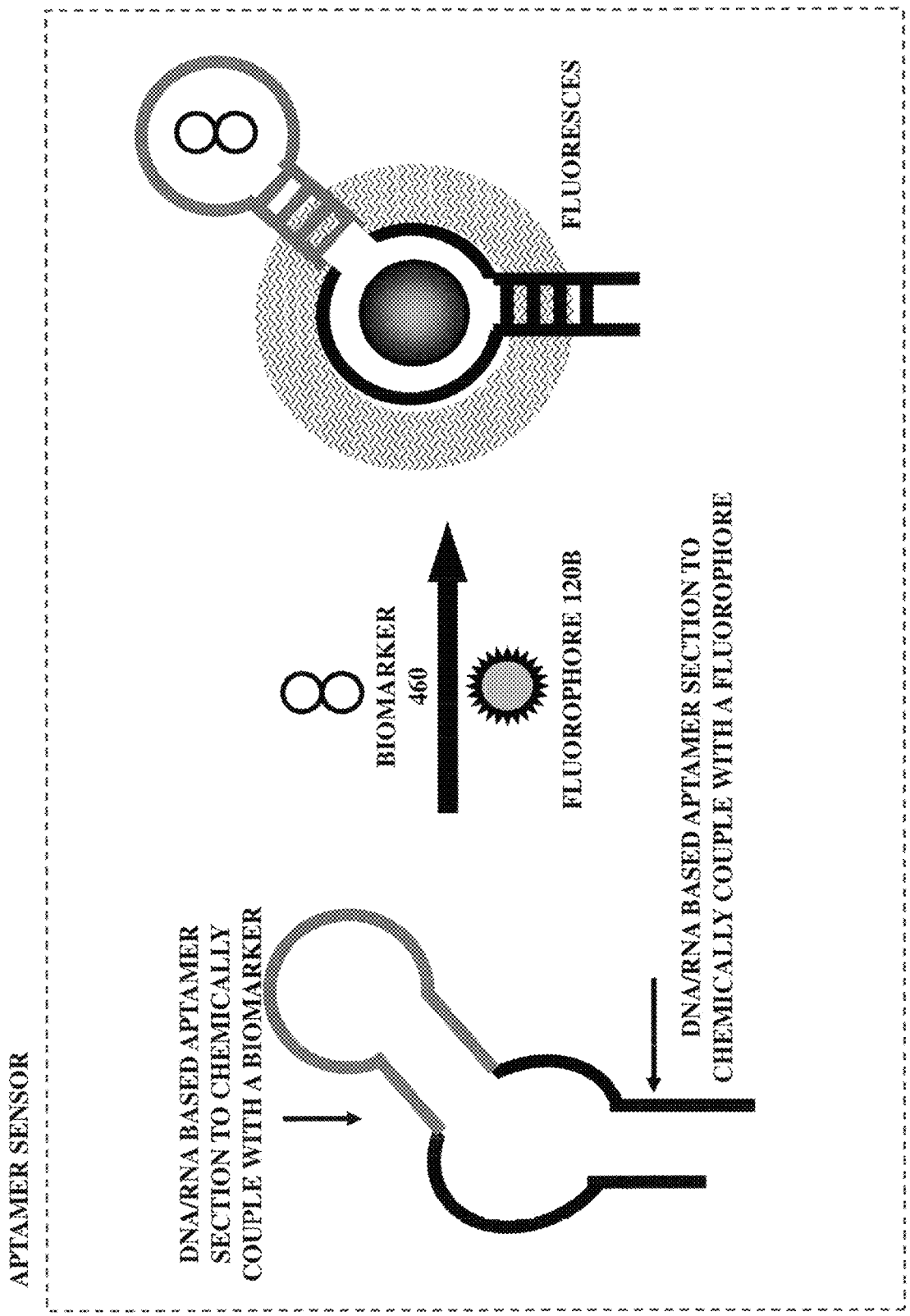
FIG. 12R1

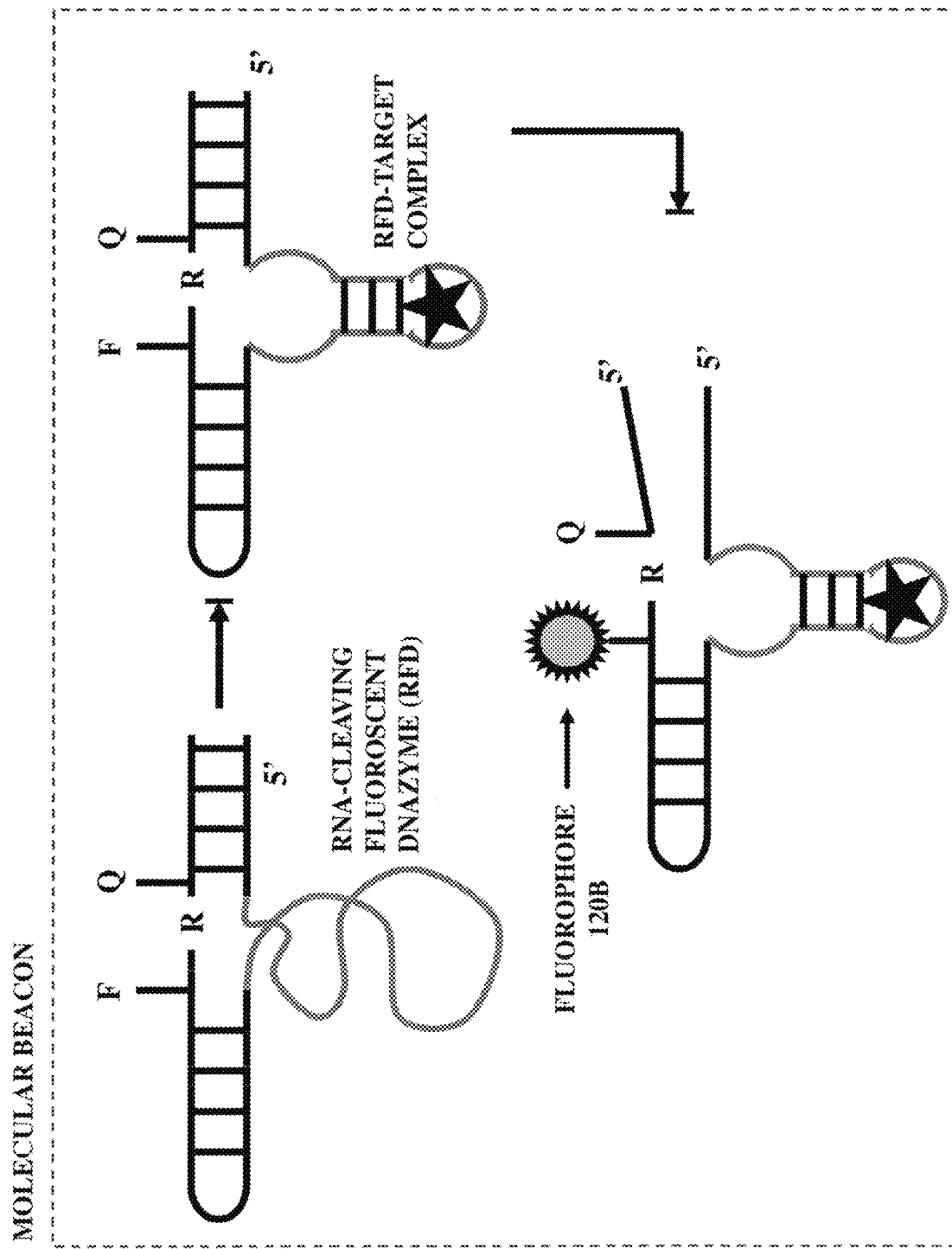
FIG. 12R2

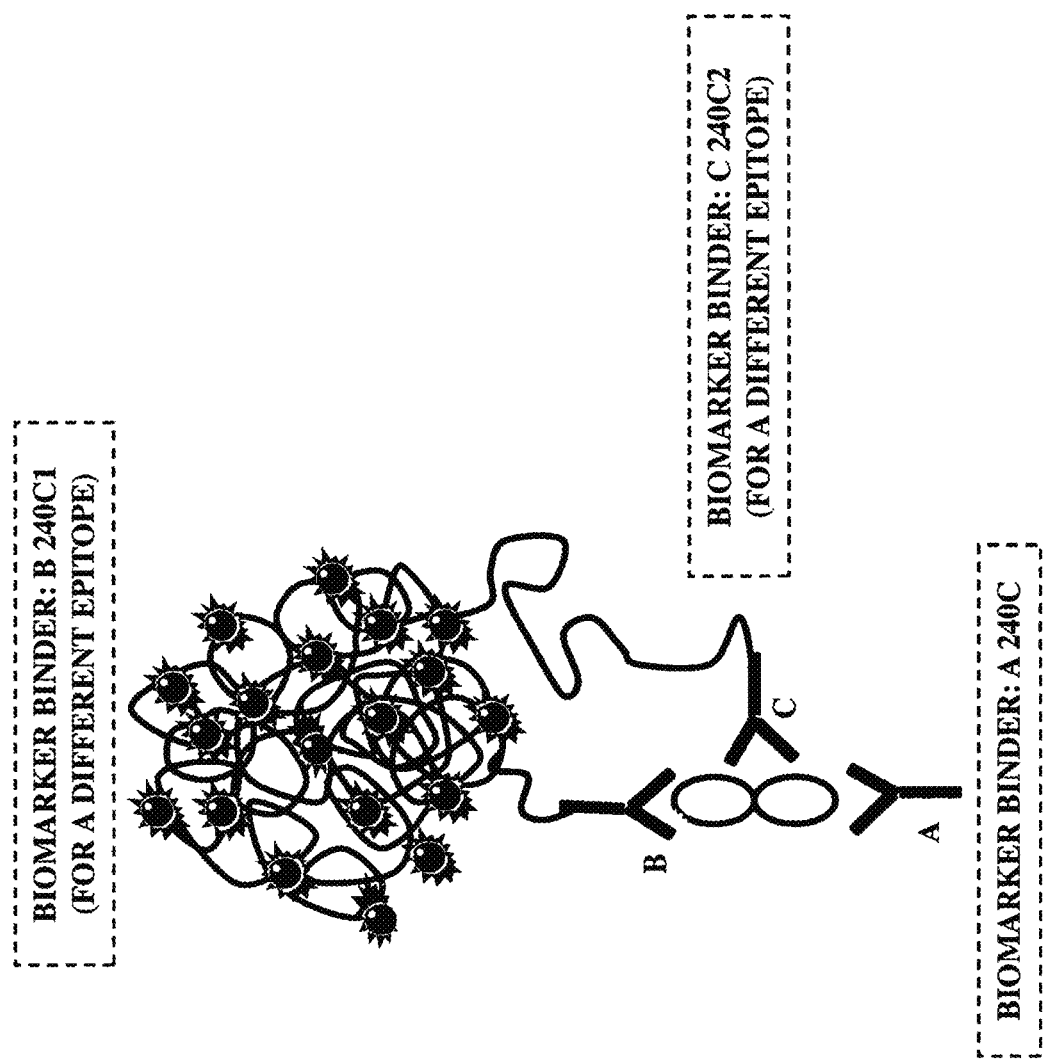
FIG. 12R3

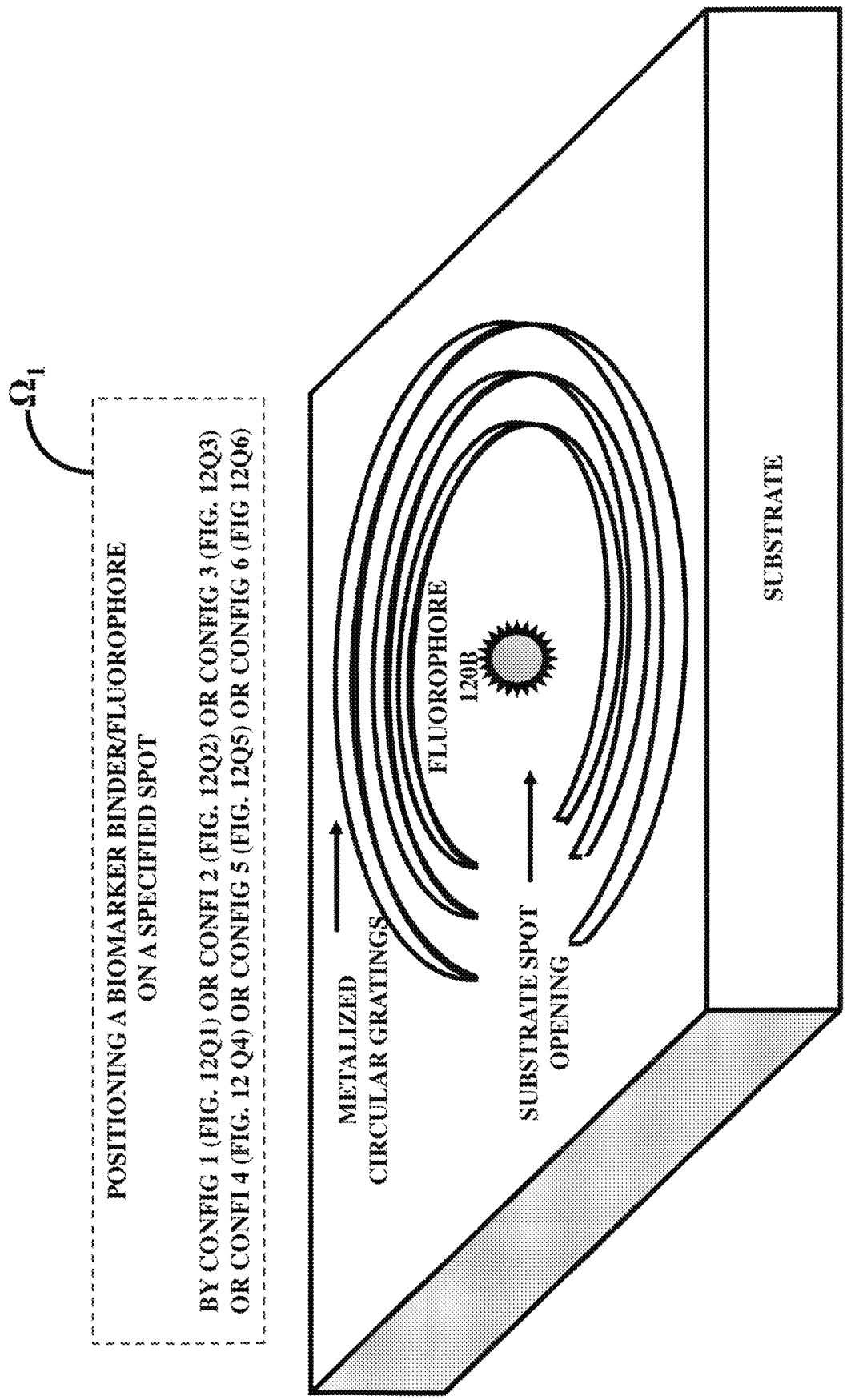
FIG. 12S1

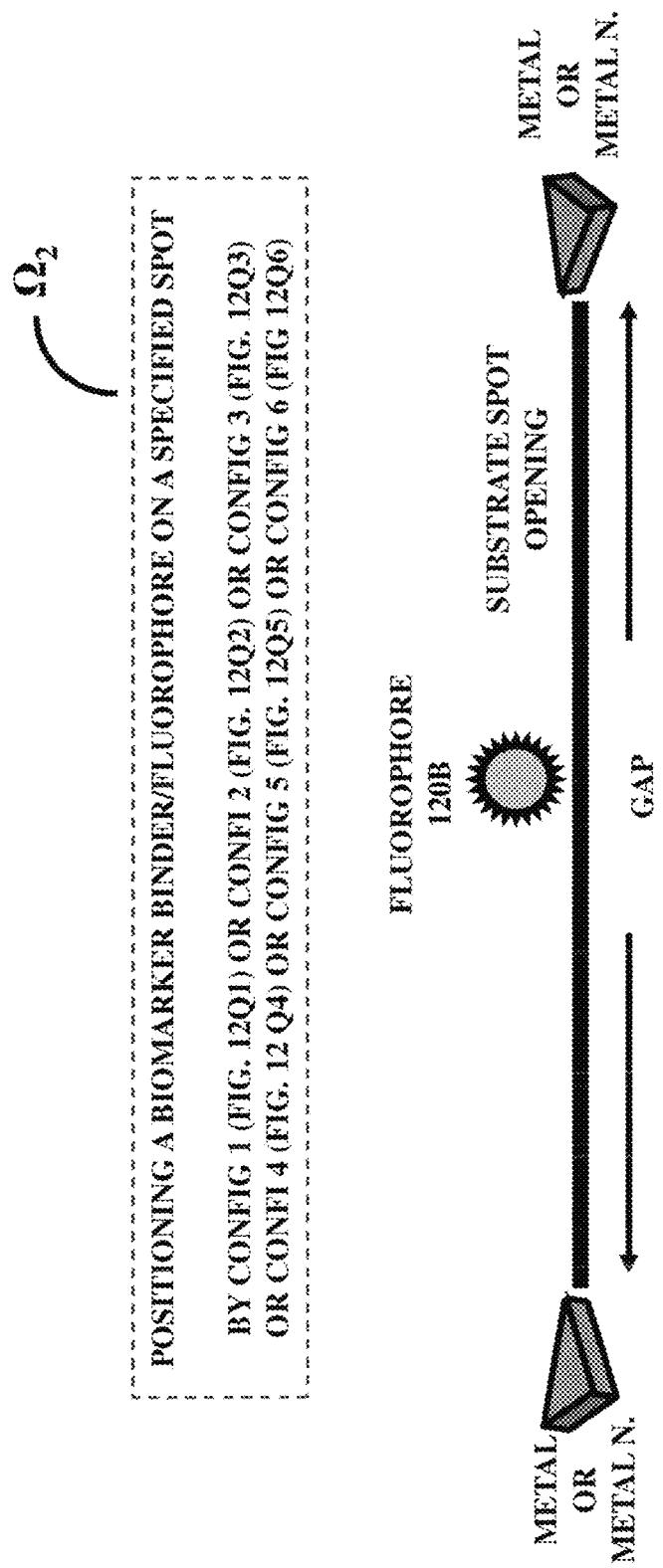
FIG. 12S2

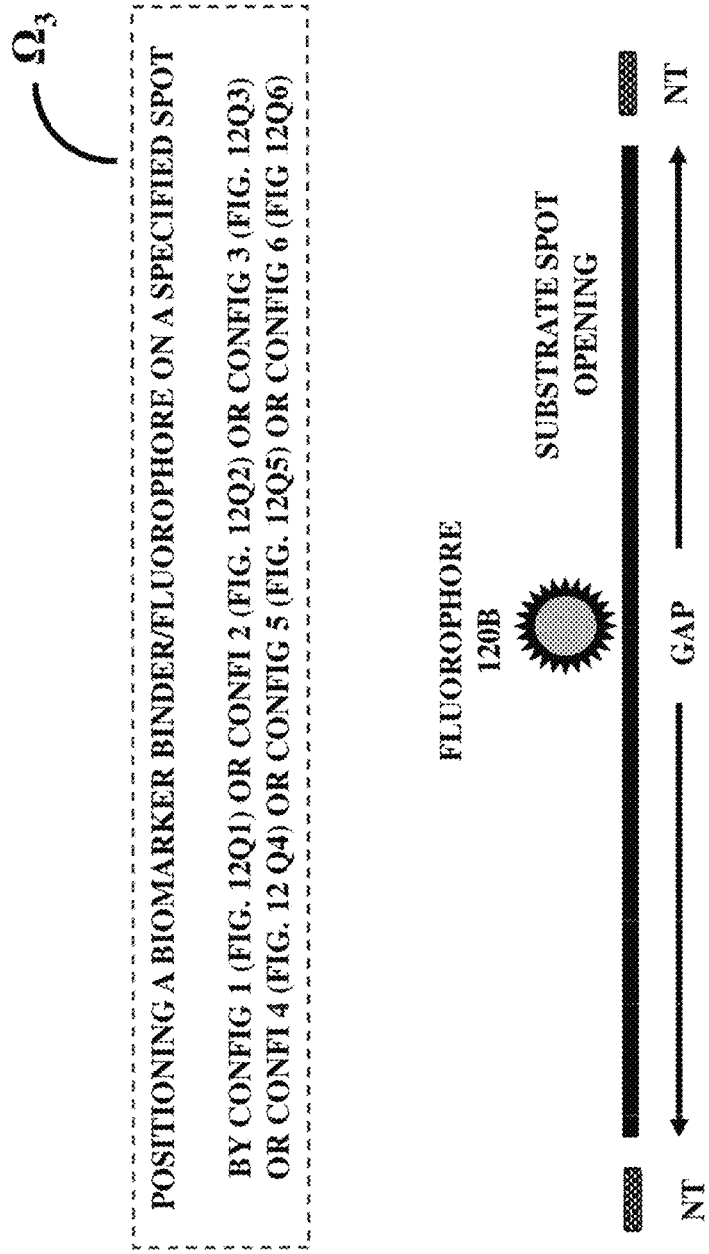

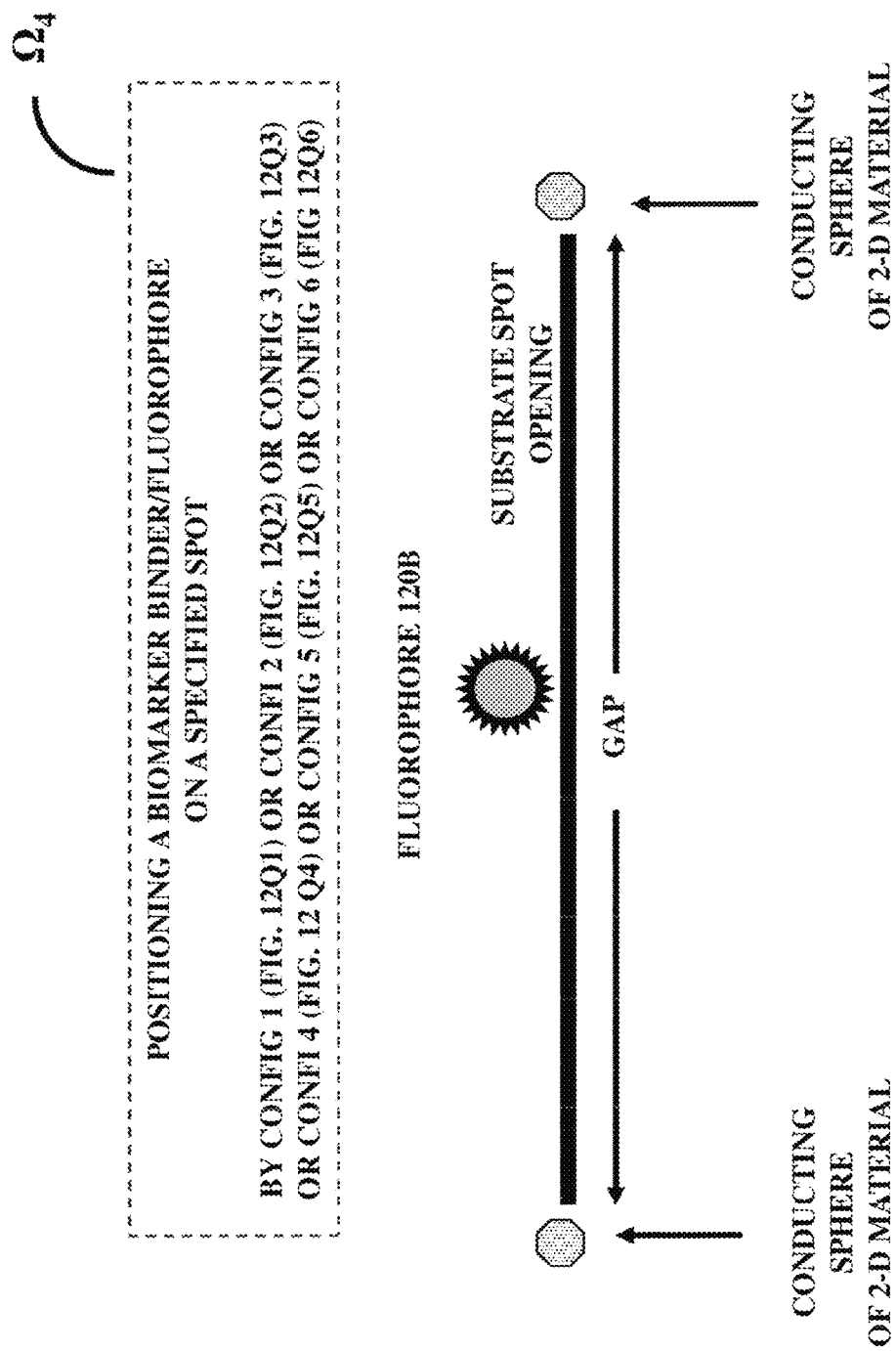
FIG. 12S4

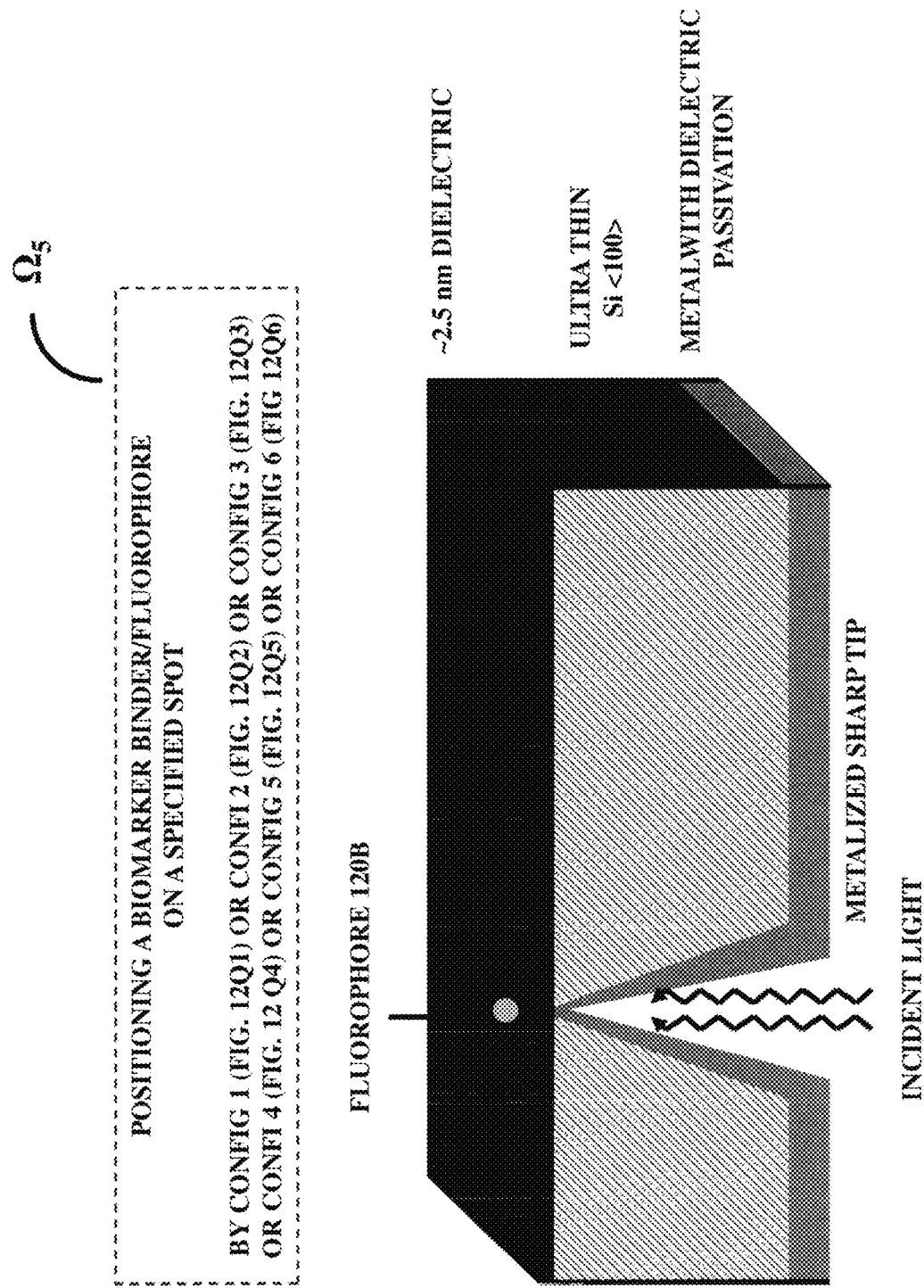
FIG. 12S5

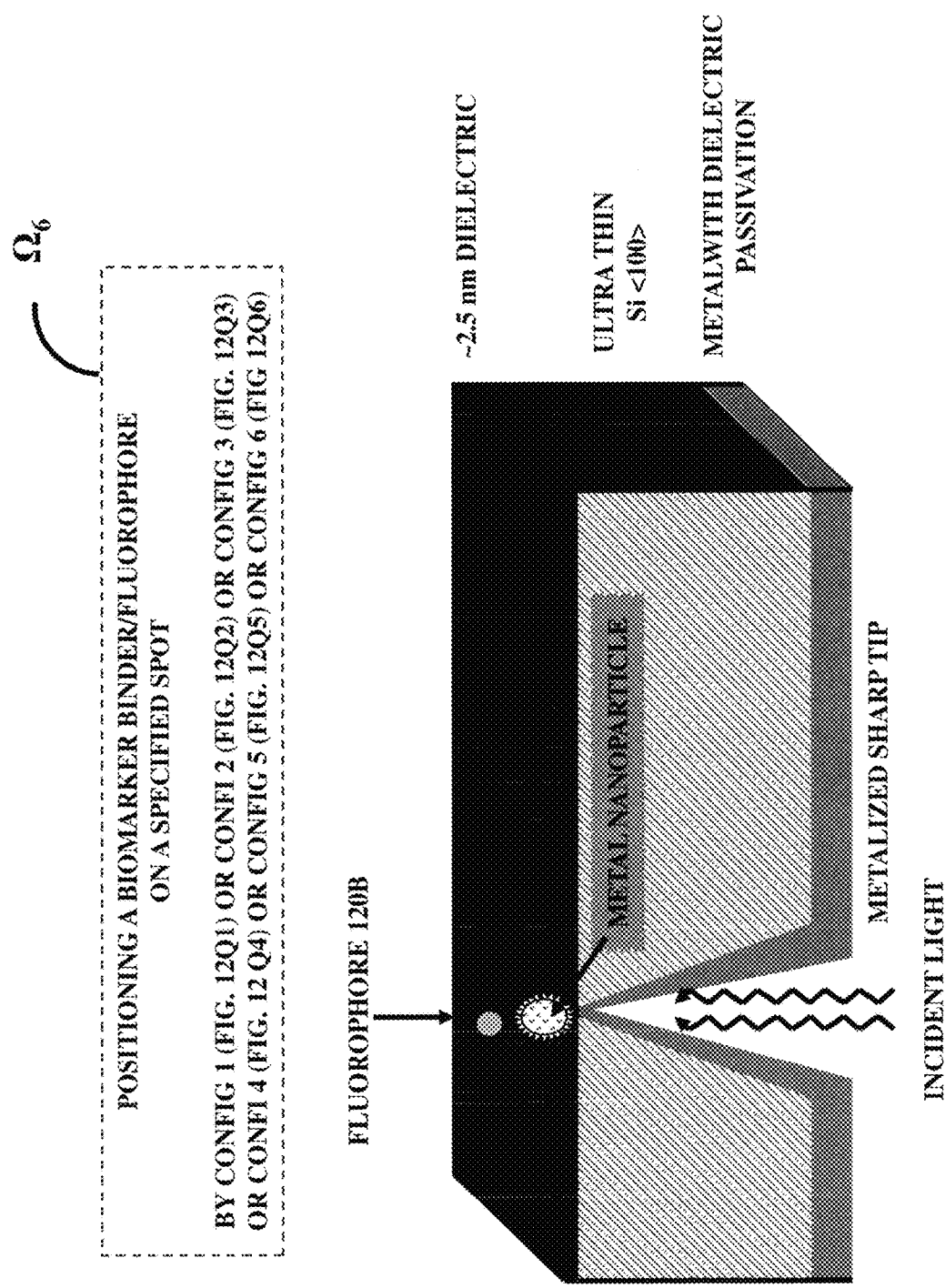
FIG. 12S6

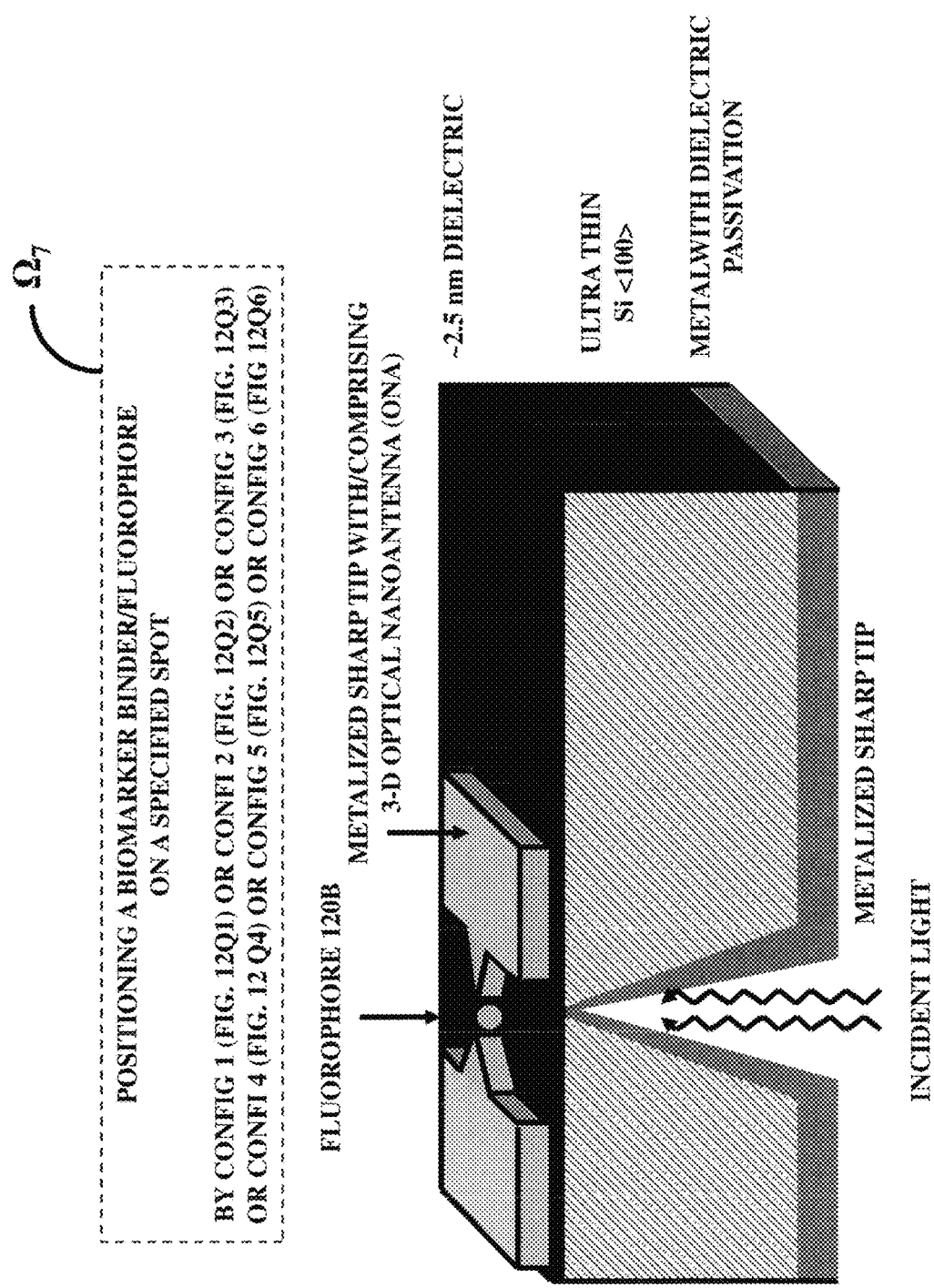
FIG. 12S7

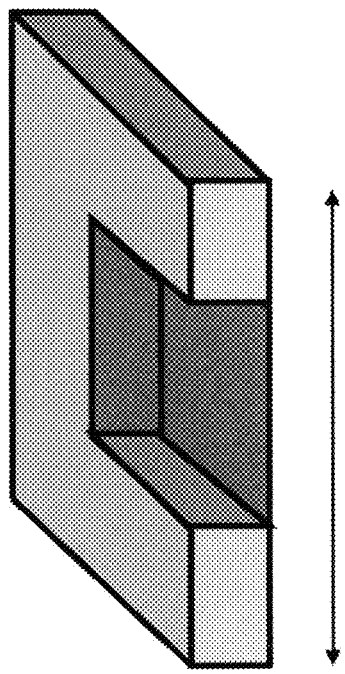
FIG. 12T1  <400 nm
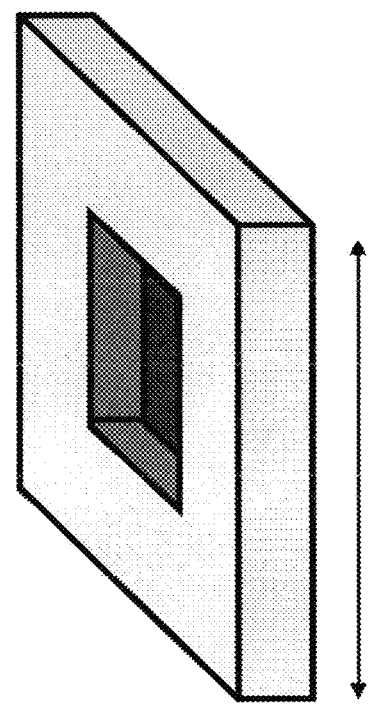
FIG. 12T2  <400 nm

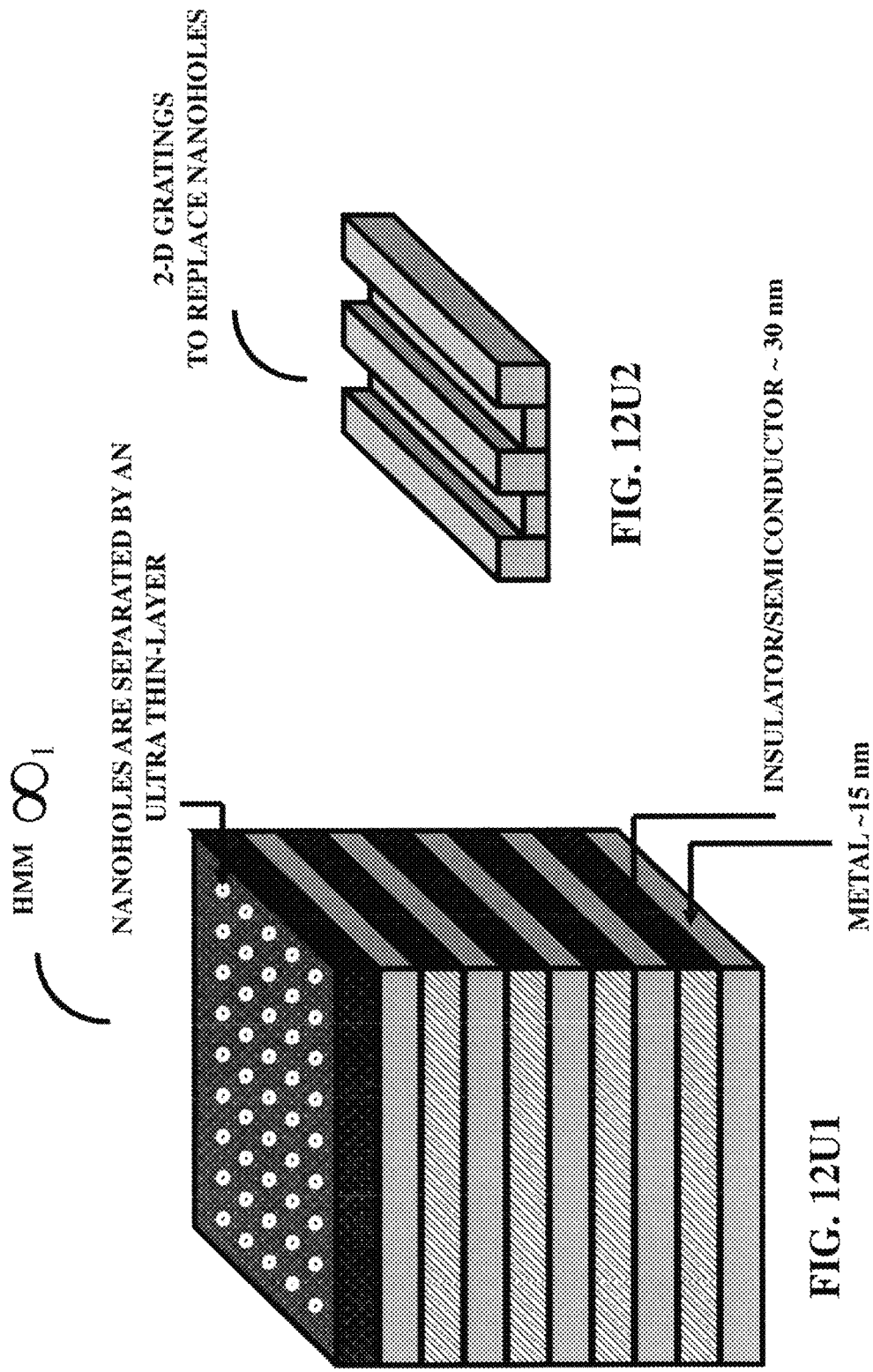

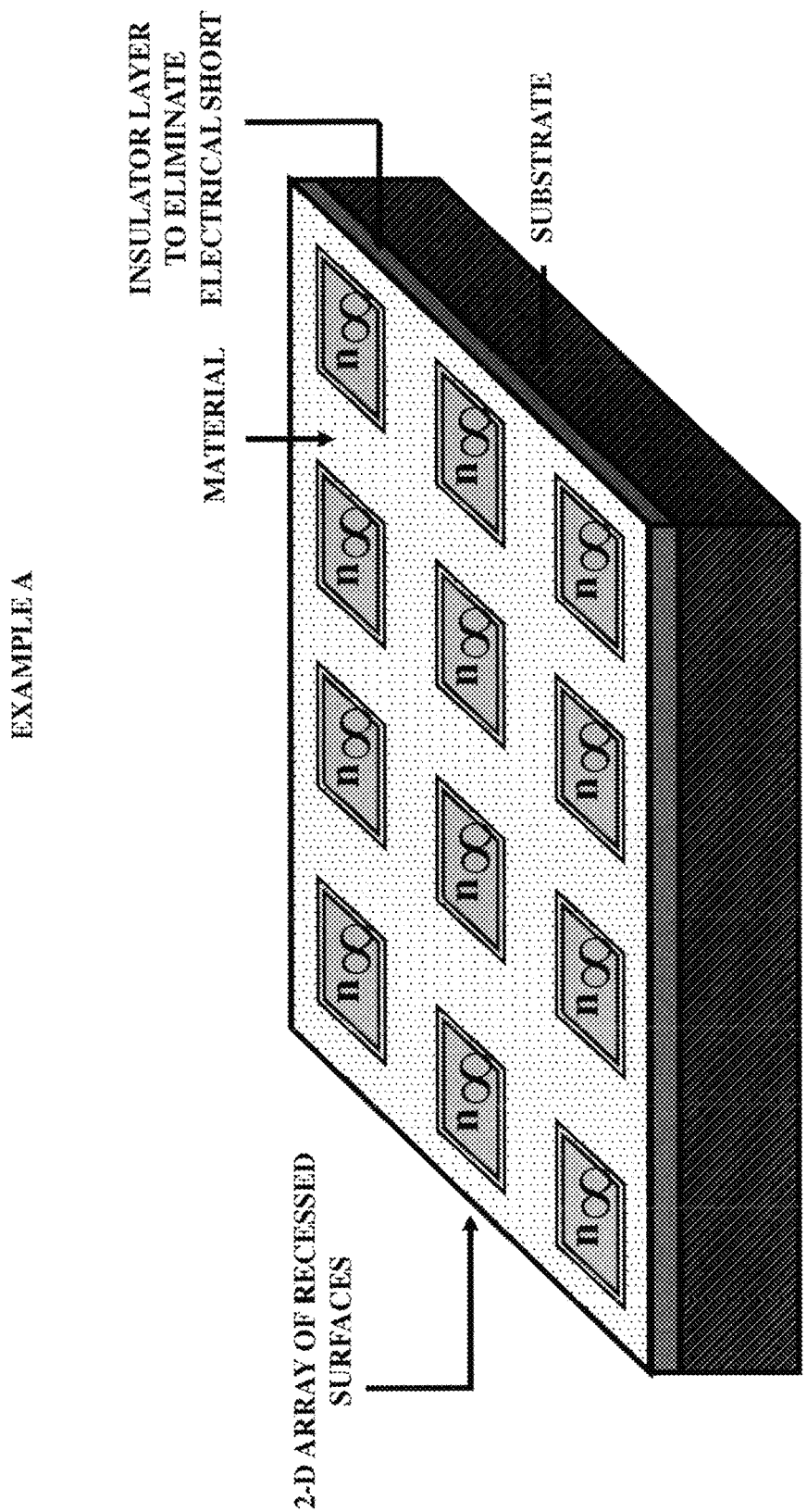
FIG. 12W1

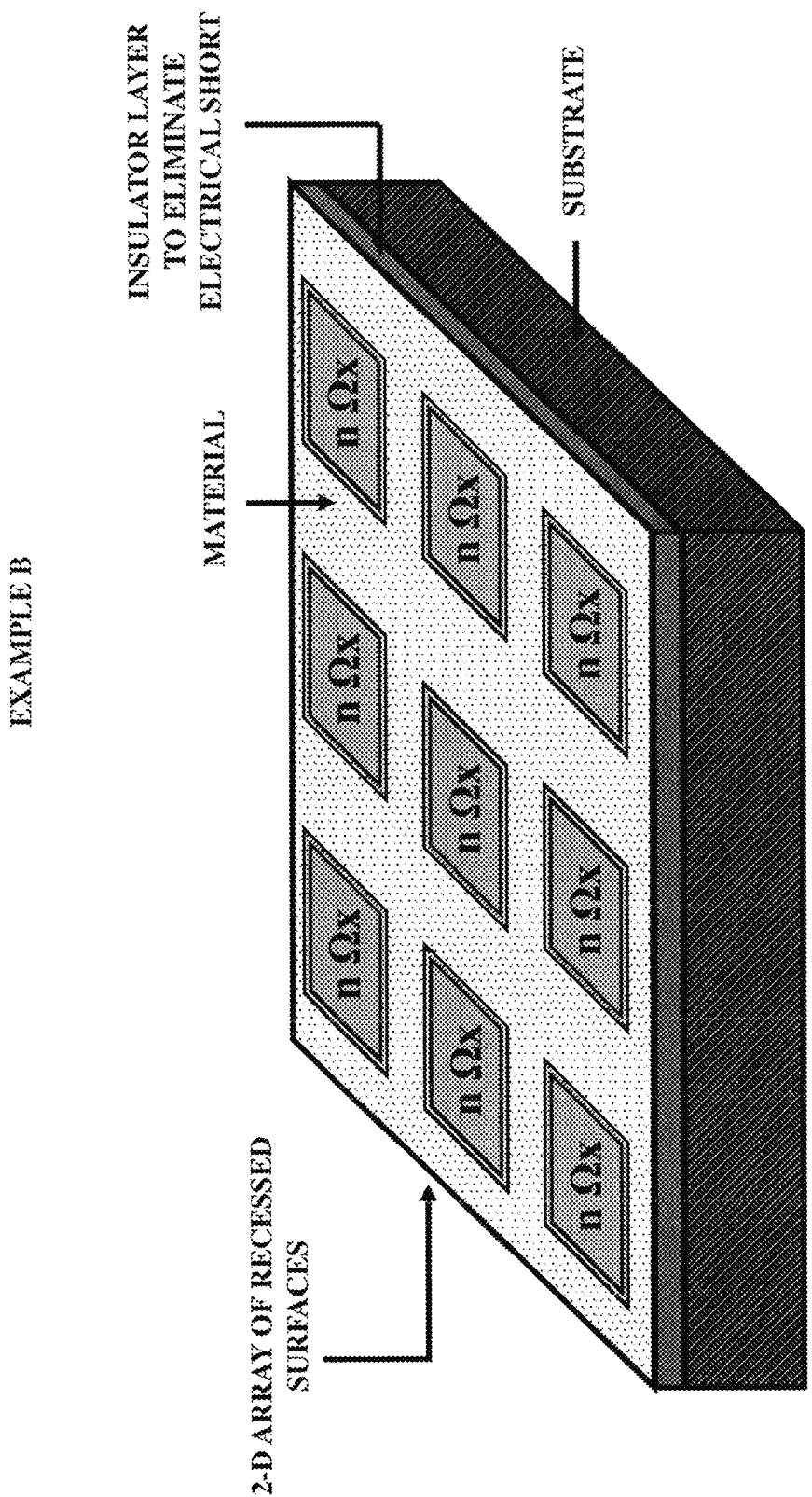
FIG. 12W2

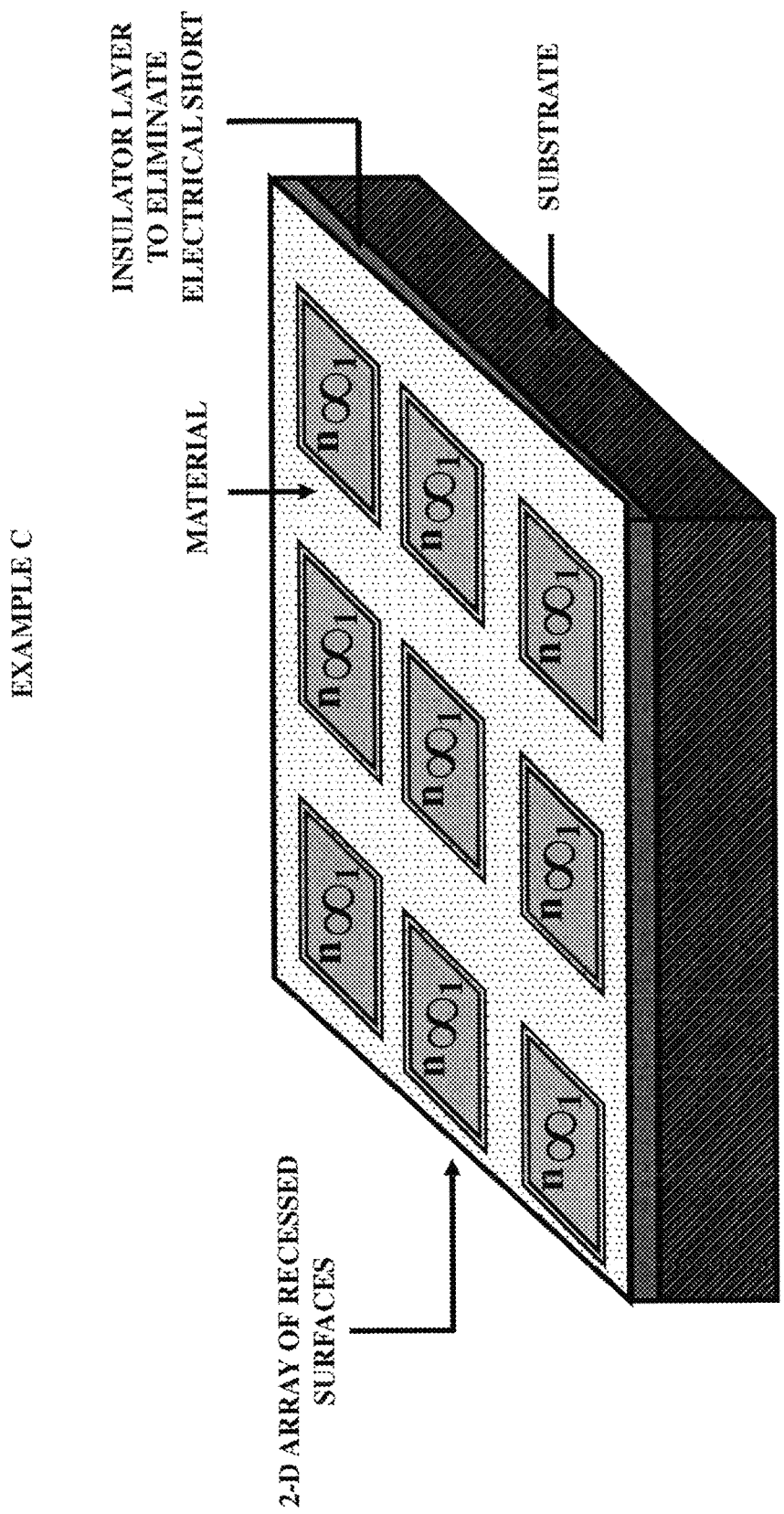
FIG. 12W3

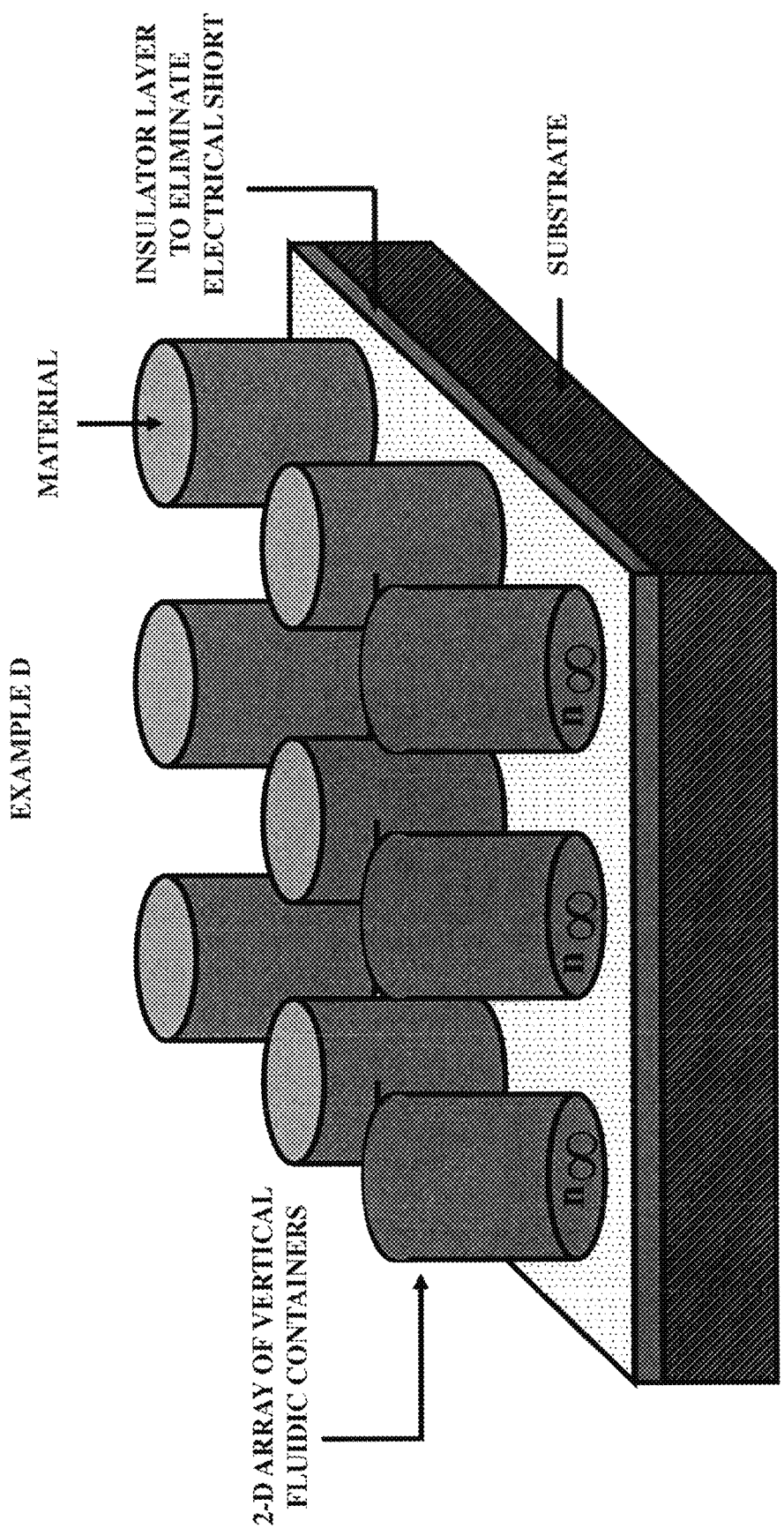
FIG. 12W4

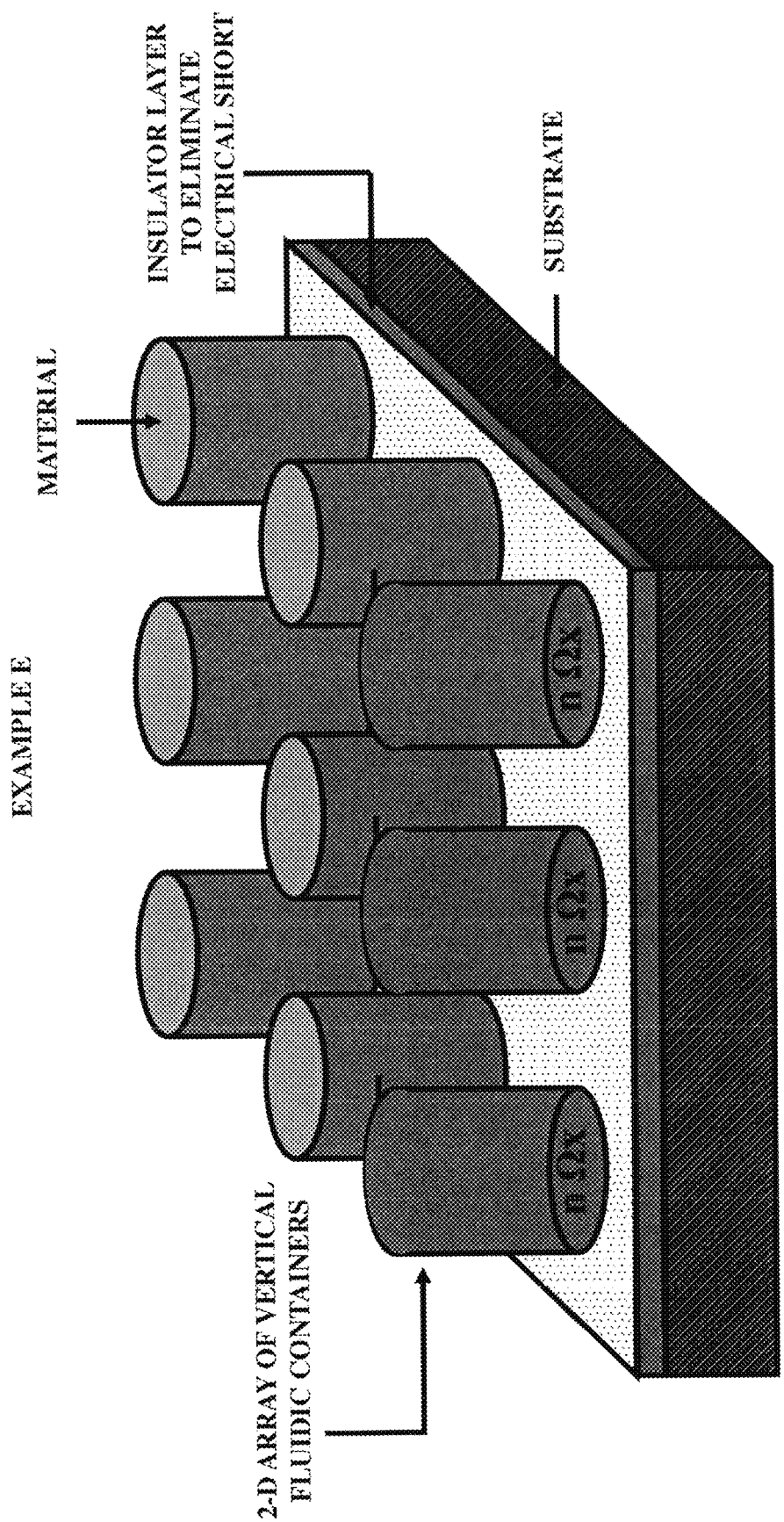
FIG. 12W5

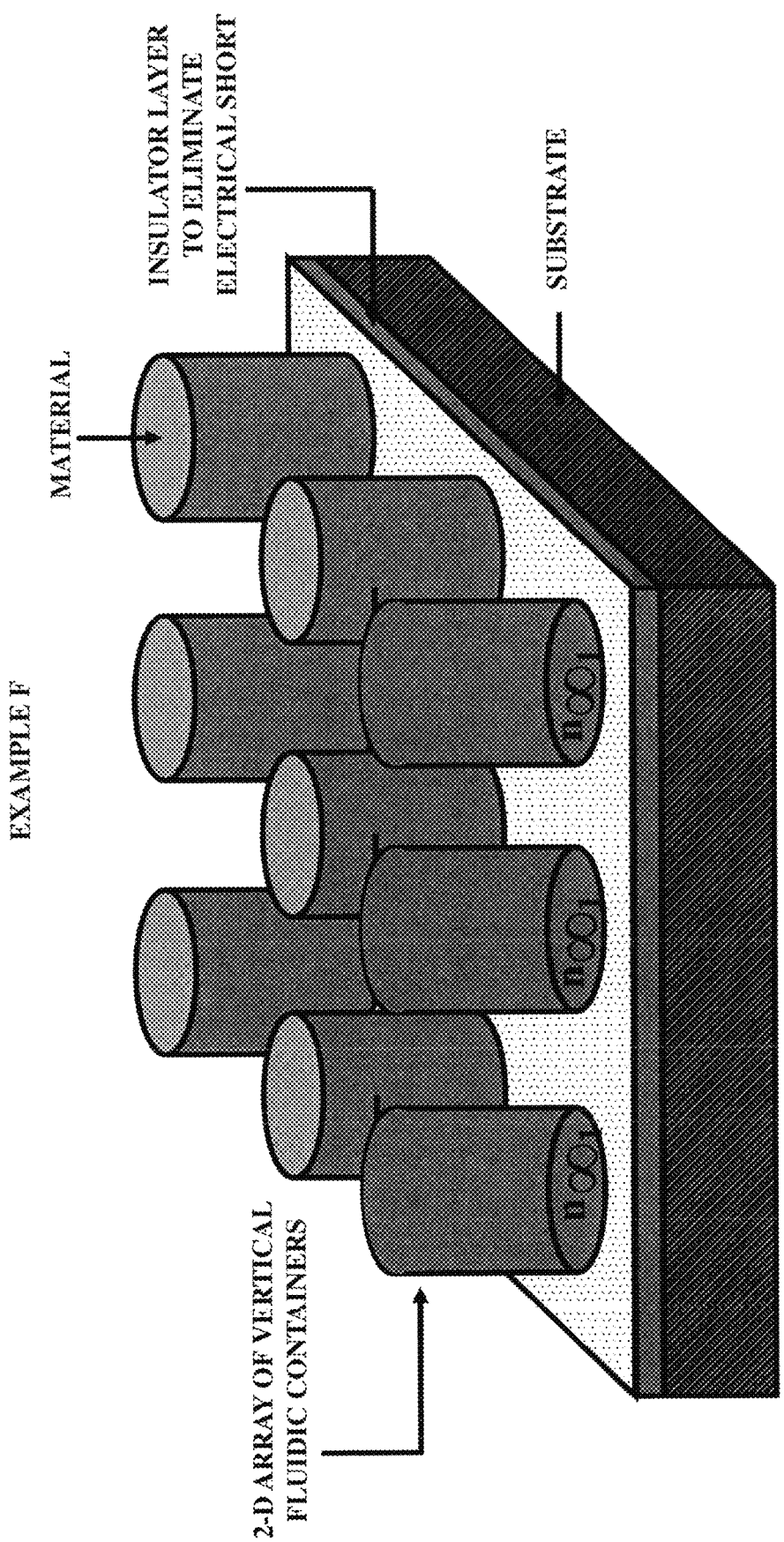
FIG. 12W6

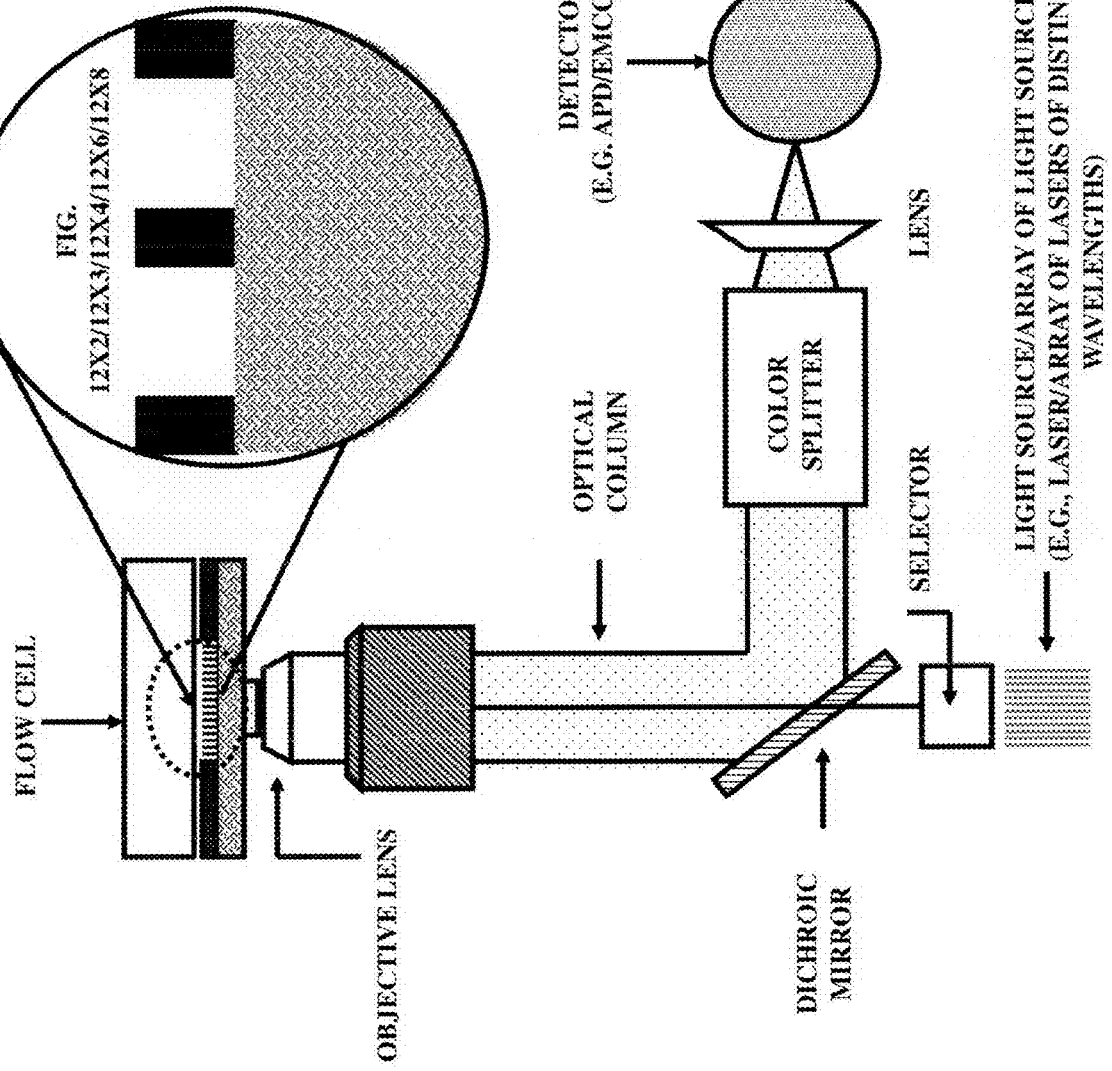
FIG. 12X1

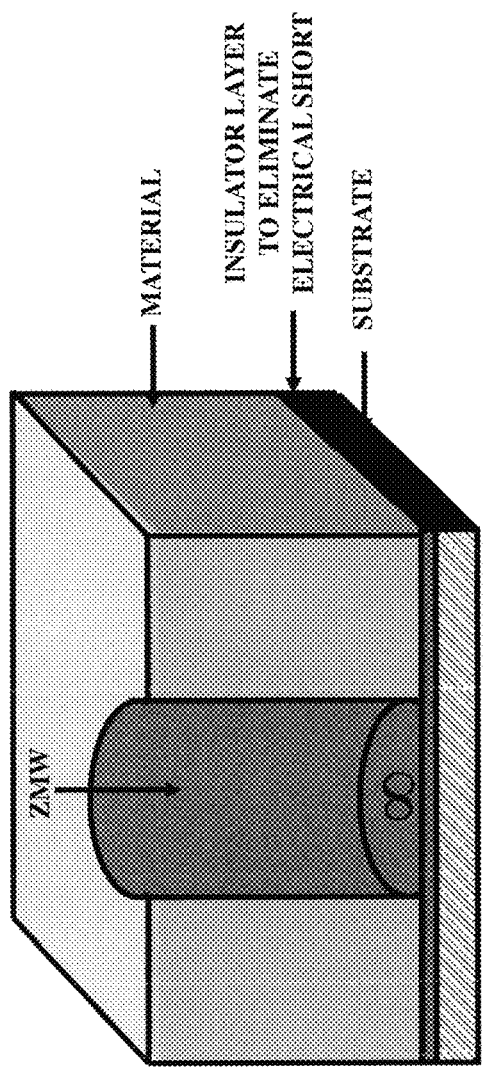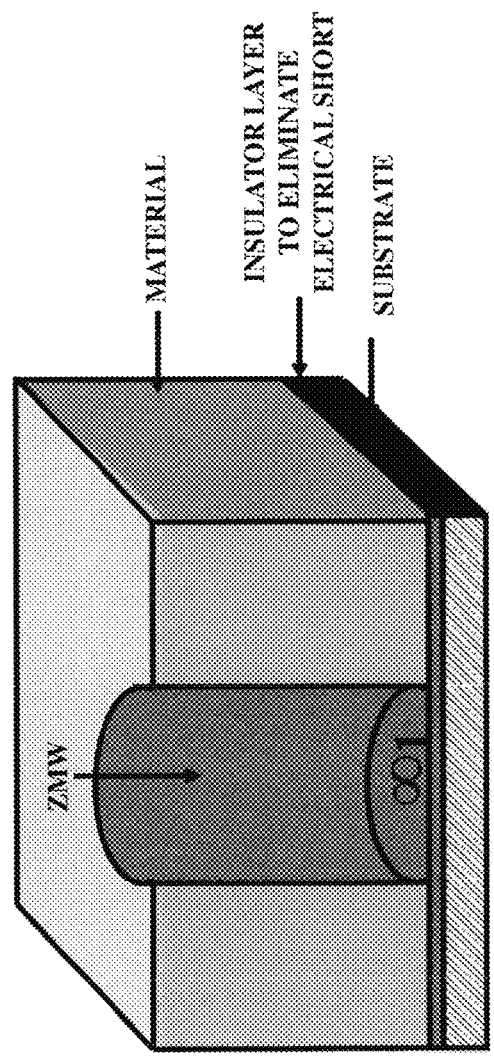
FIG. 12X2
FIG. 12X3

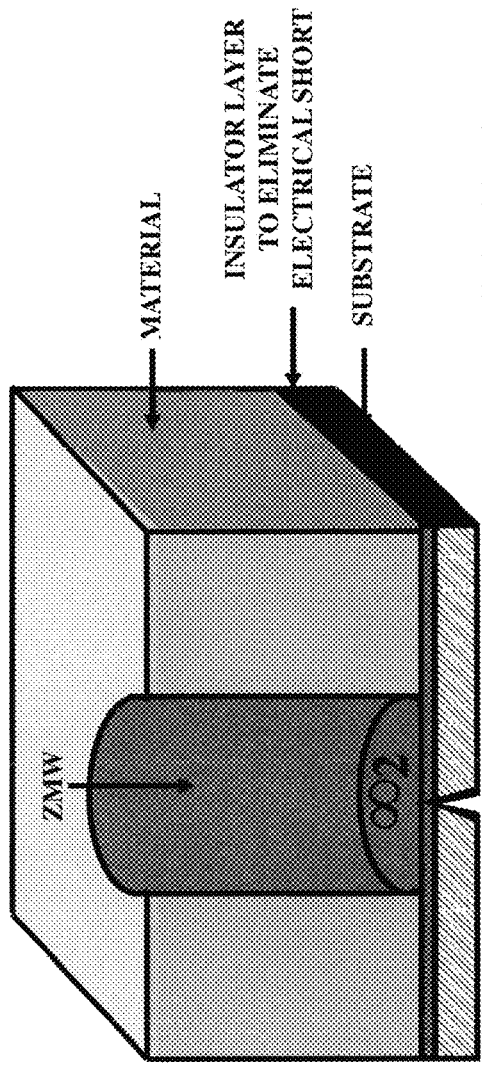
FIG. 12X4
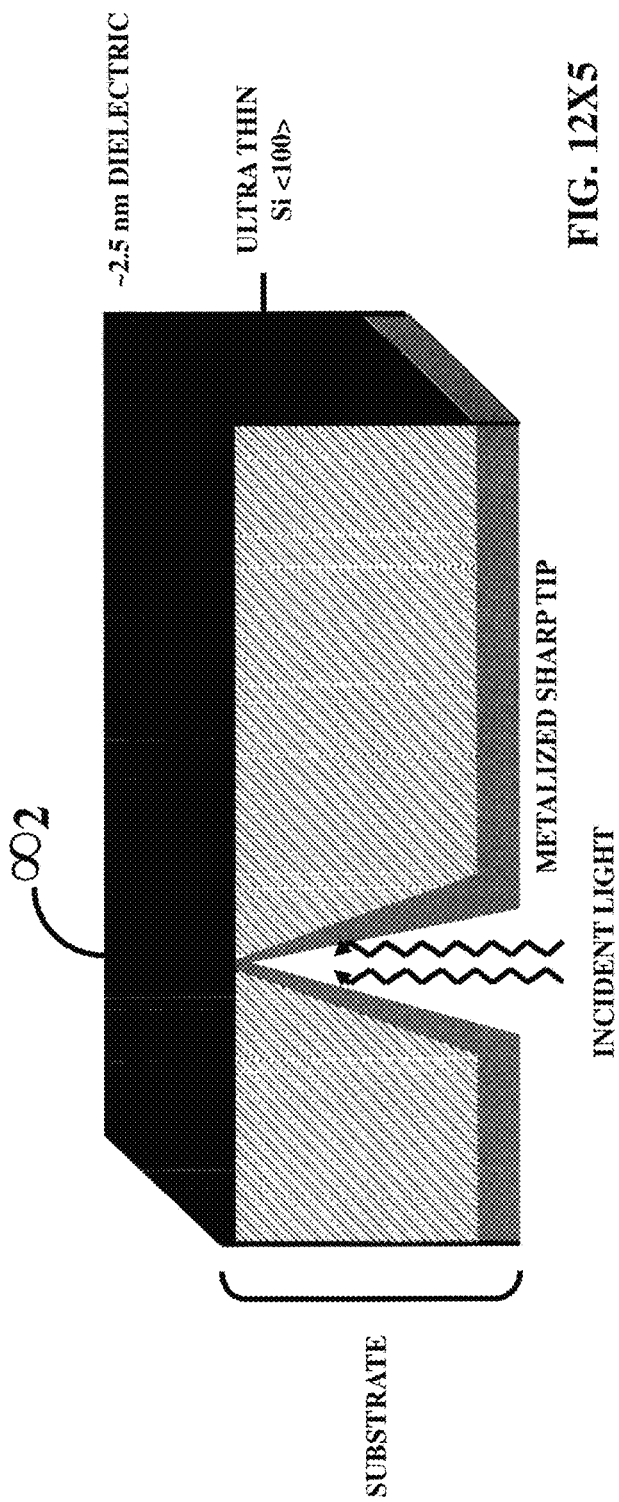
FIG. 12X5

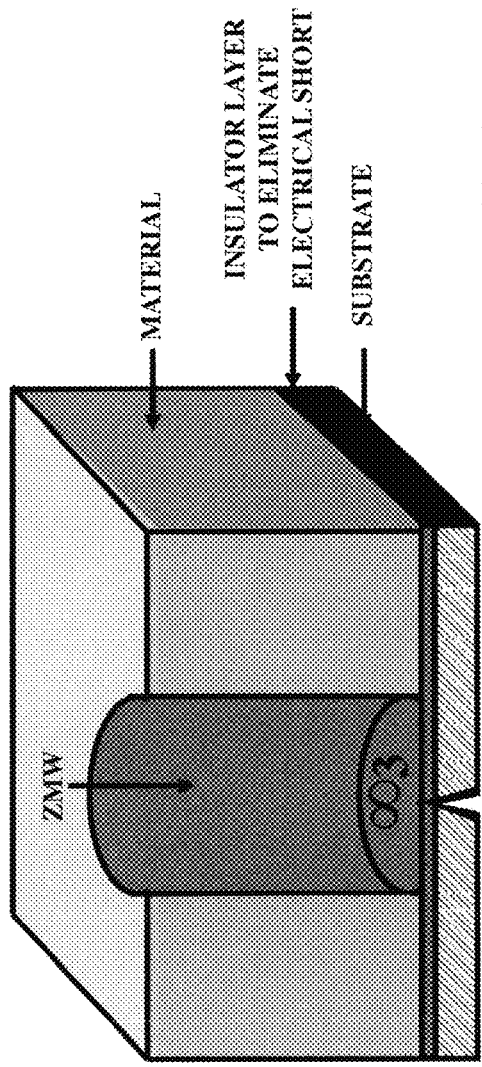
FIG. 12X6
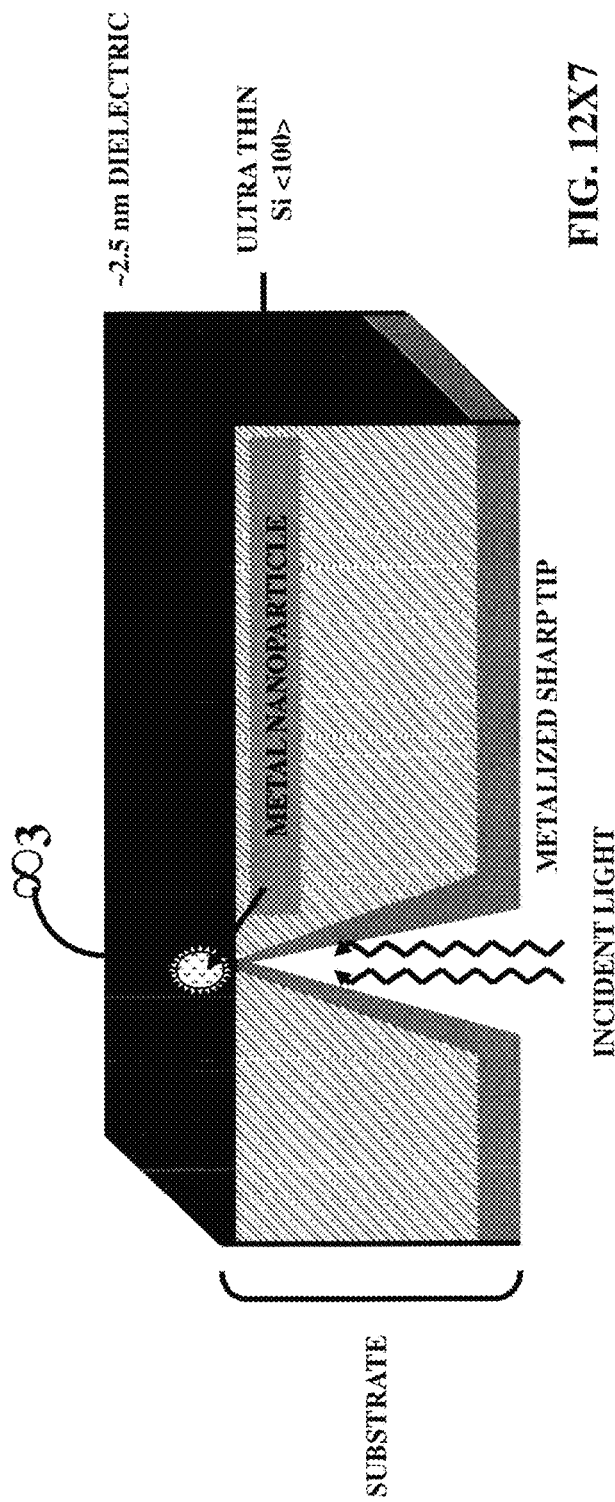
FIG. 12X7

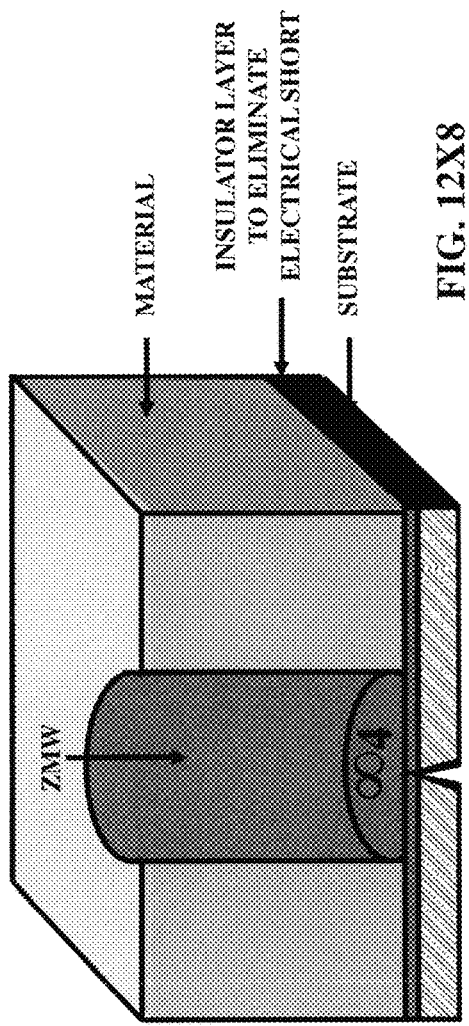
FIG. 12X8
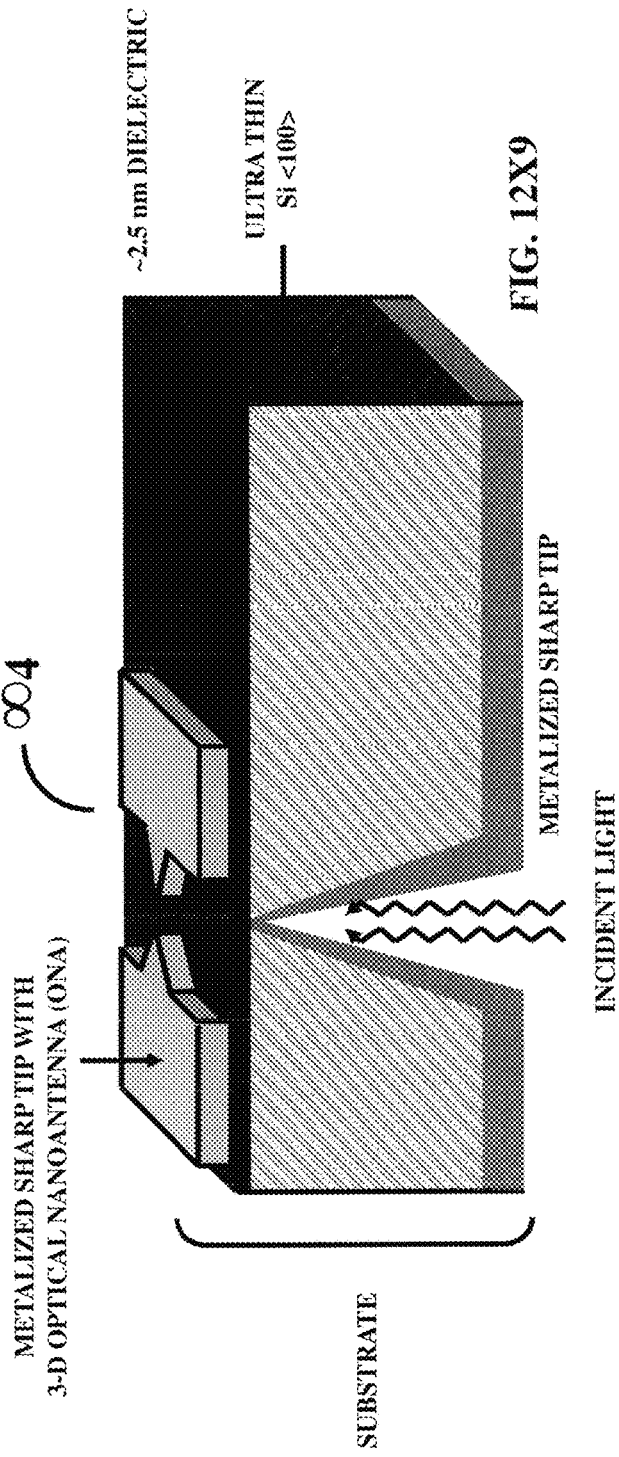
FIG. 12X9

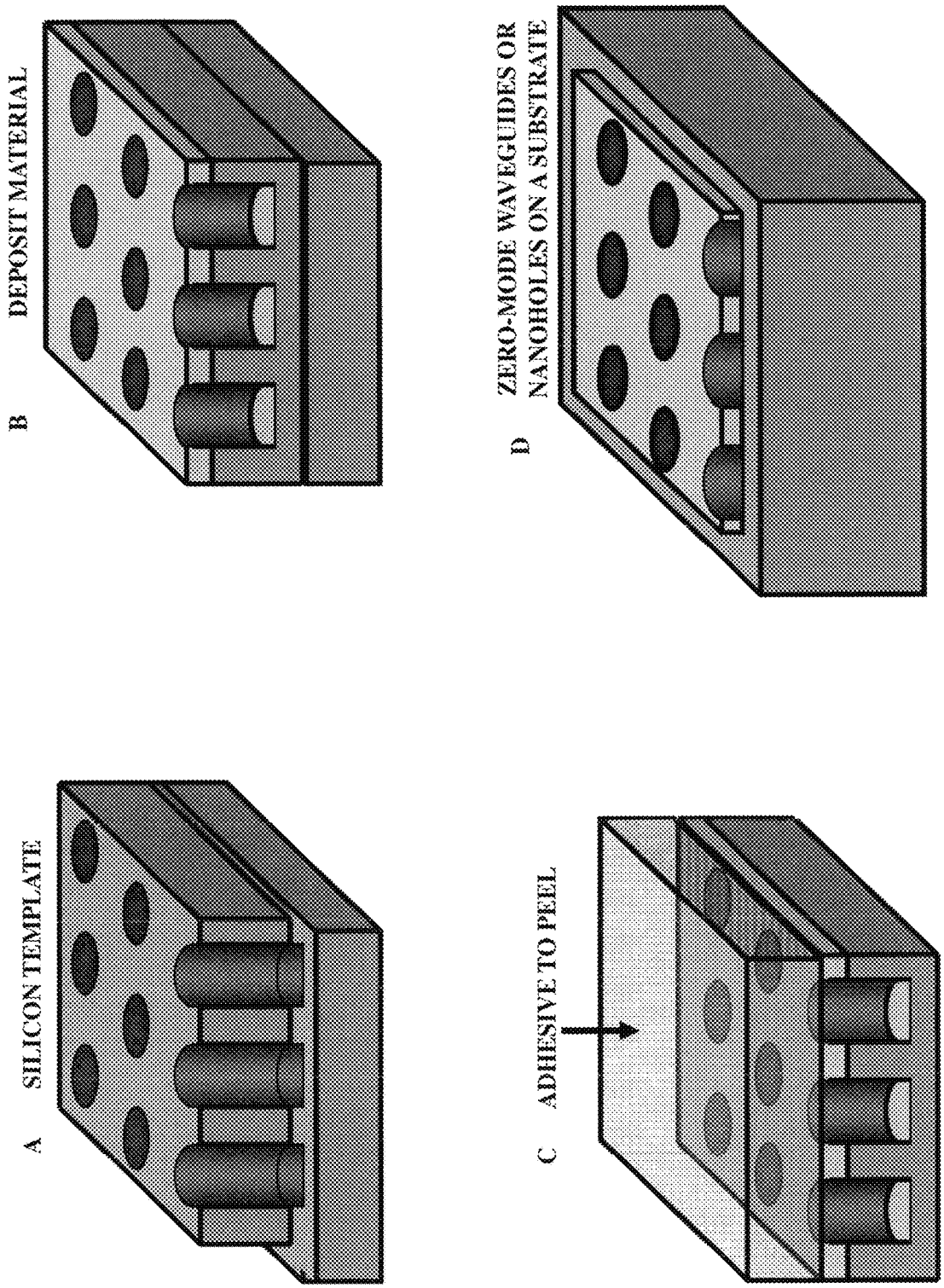
FIG. 12X10

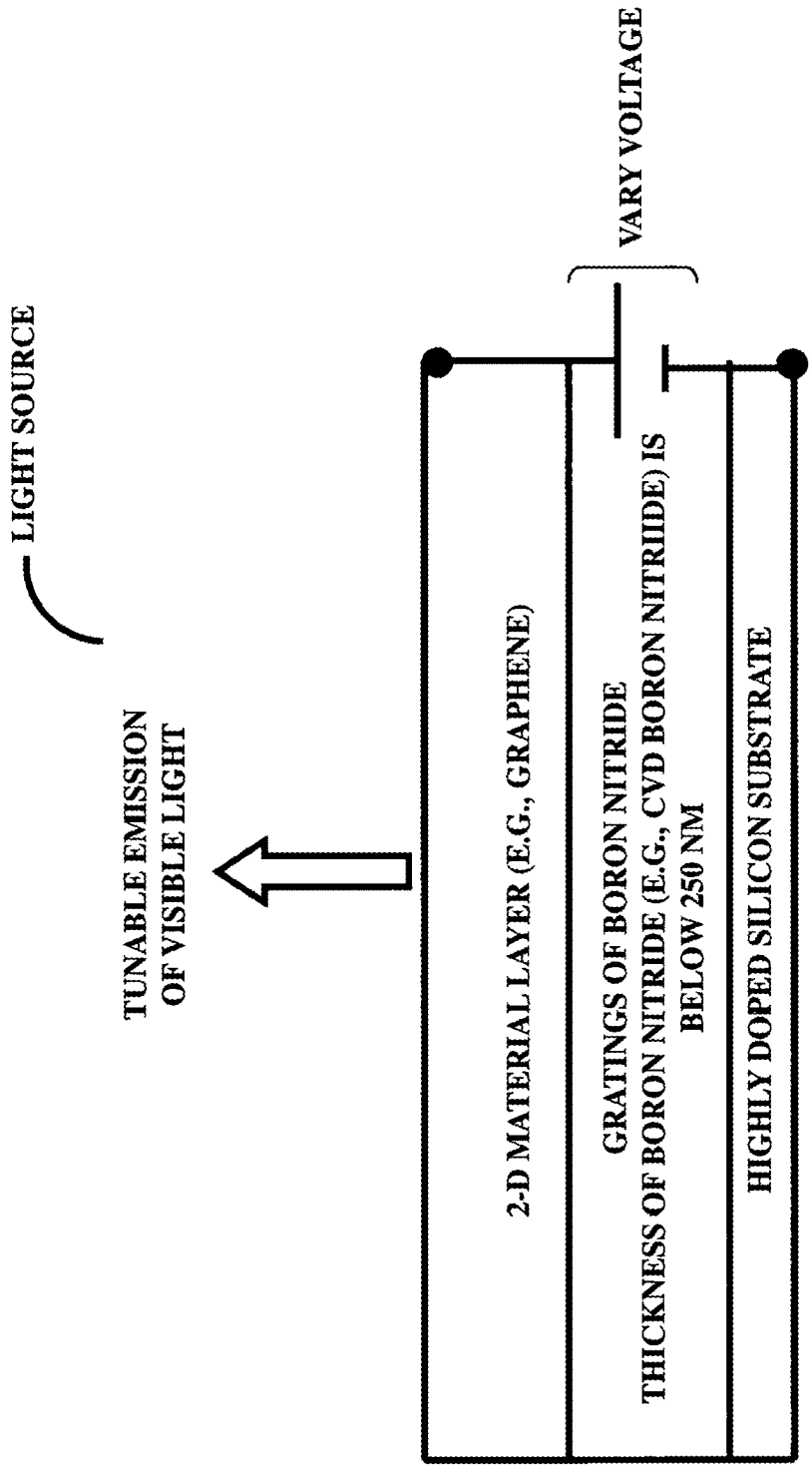
FIG. 12Z1

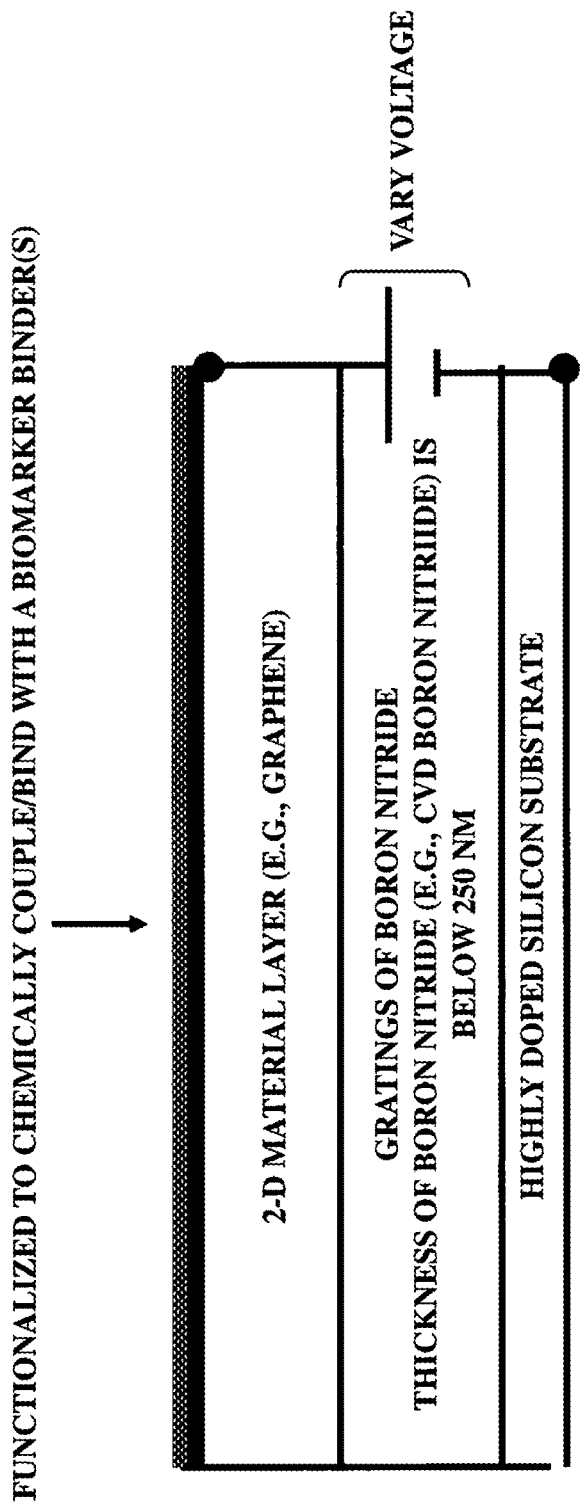
FIG. 12Z2

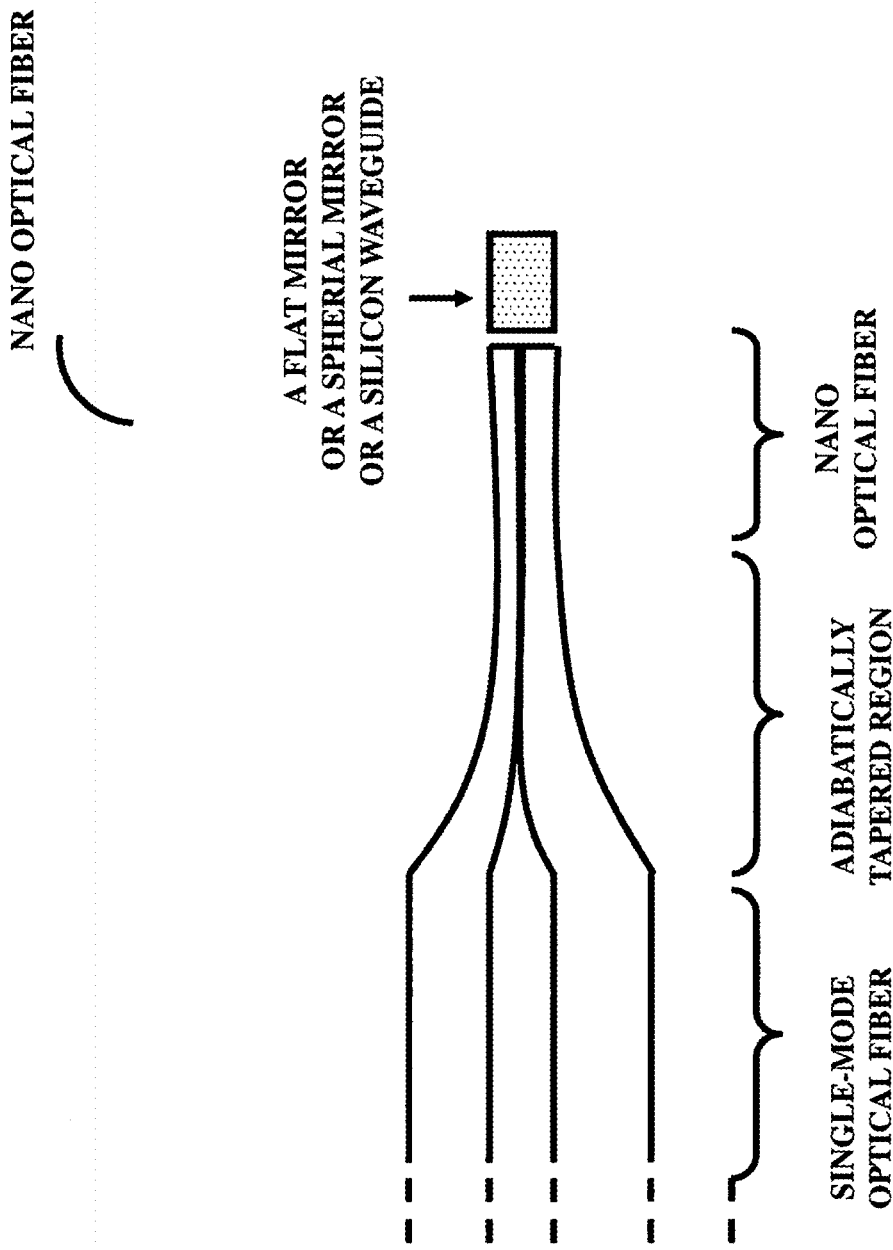
FIG. 12Z3

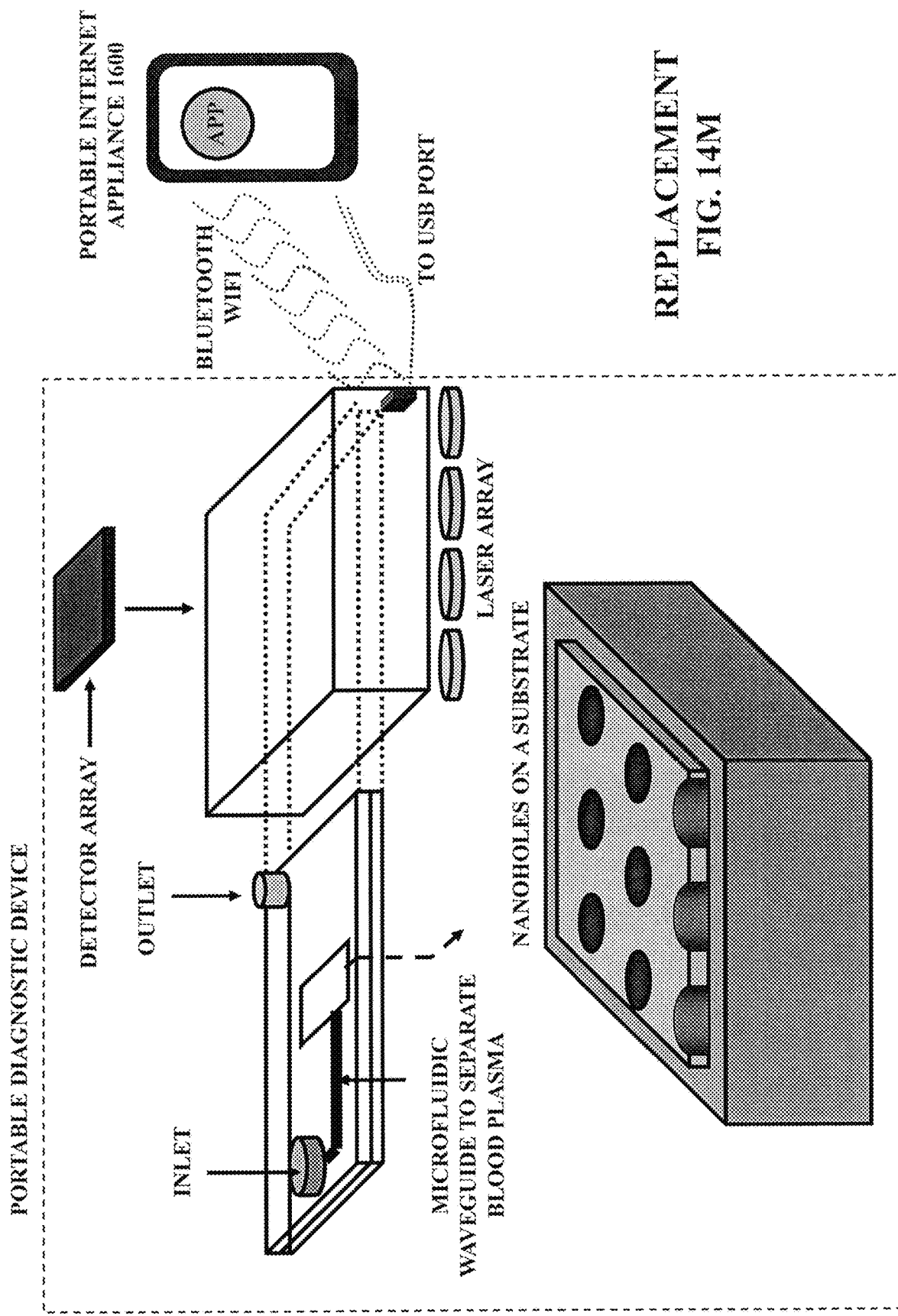

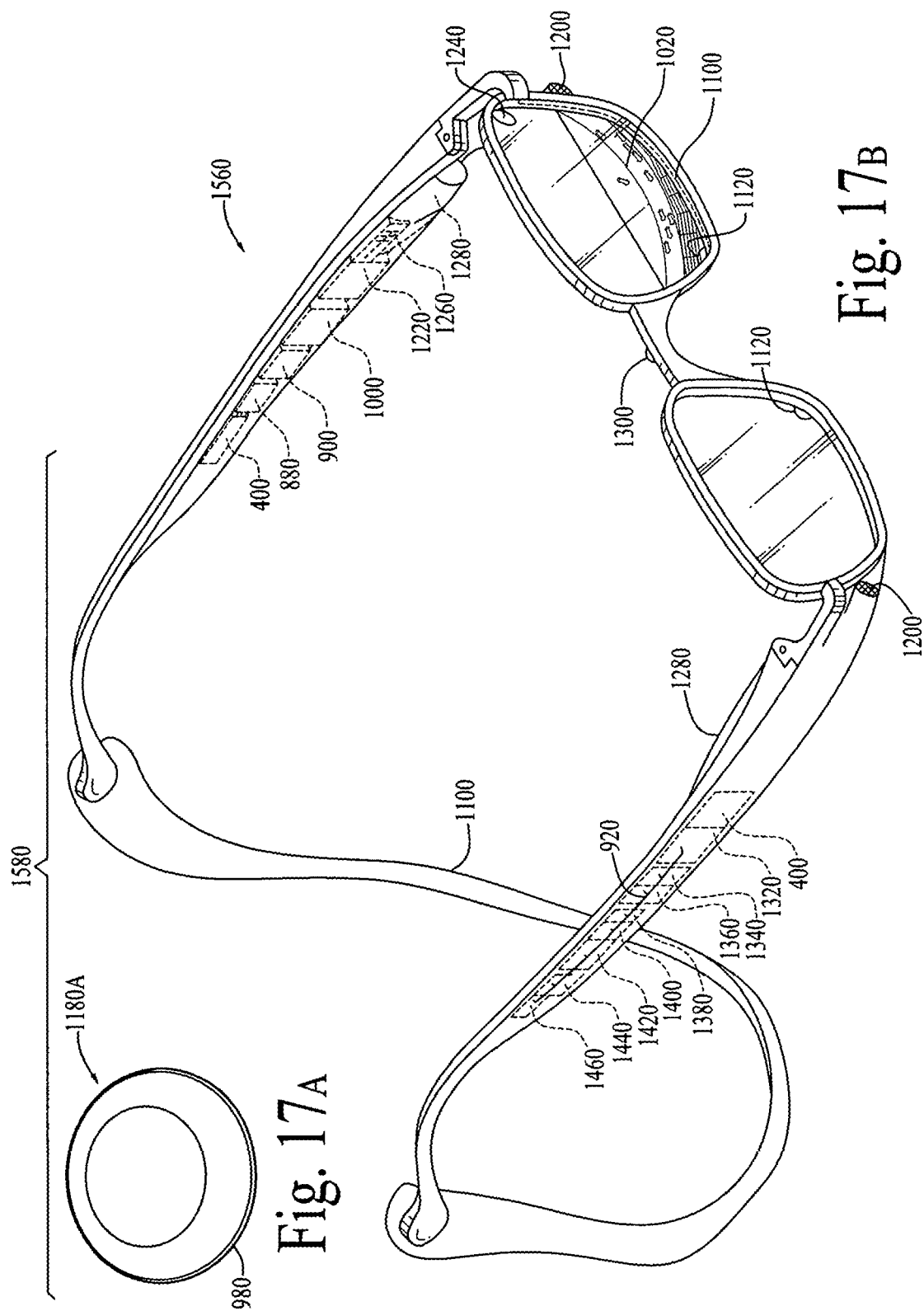

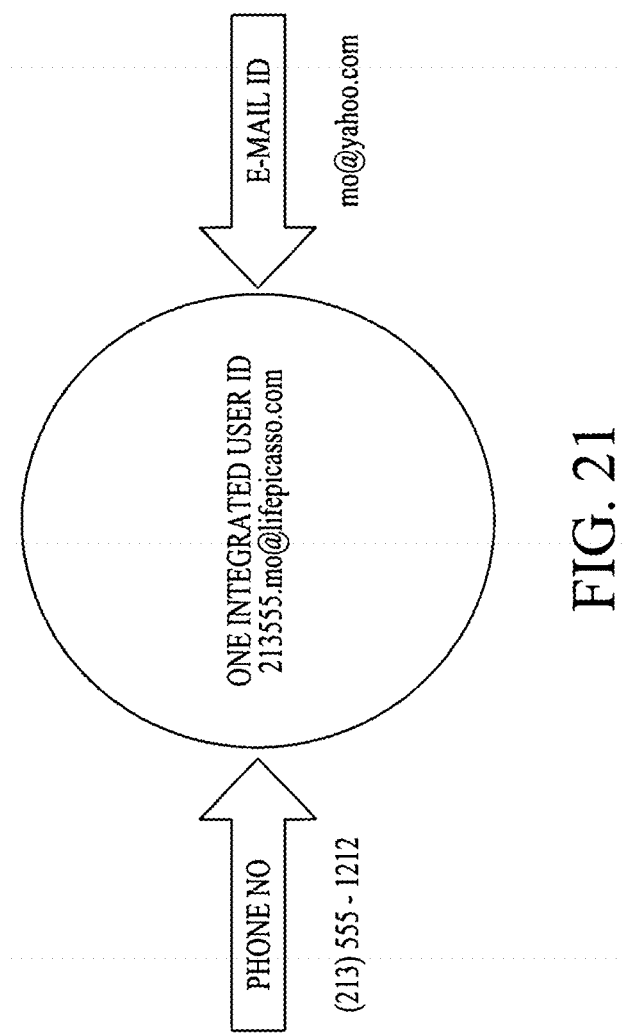

OPTICAL BIOMODULE FOR DETECTION OF DISEASES AT AN EARLY ONSET

CROSS REFERENCE OF RELATED APPLICATIONS

The present application claims priority to: U.S. Provisional Patent Application No. 62/497,979 entitled "BIOMODULE TO DETECT A DISEASE AT AN EARLY ONSET", filed on Dec. 12, 2016.

The present application is a continuation-in-part (CIP) of U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015).

The present application is a continuation-in-part (CIP) of U.S. Non-Provisional patent application Ser. No. 14/120,835 entitled "AUGMENTED REALITY PERSONAL ASSISTANT APPARATUS", filed on Jul. 1, 2014 (which claims priority to: U.S. Provisional Patent Application No. 61/957,343 entitled "AUGMENTED REALITY PERSONAL ASSISTANT", filed on Jul. 1, 2013).

The present application is a continuation-in-part (CIP) of U.S. Non-Provisional patent application Ser. No. 13/448,378 entitled "SYSTEM & METHOD FOR MACHINE LEARNING BASED USER APPLICATION", filed on Apr. 16, 2012, wherein U.S. Non-Provisional patent application Ser. No. 13/448,378 resulted in an issuance of U.S. Pat. No. 9,697,556 on Jul. 4, 2017 (which claims priority to: U.S. Provisional Patent Application No. 61/517,204 entitled "INTELLIGENT SOCIAL E-COMMERCE" filed on Apr. 15, 2011).

Furthermore, the present application is a continuation-in-part (CIP) of U.S. Non-Provisional patent application Ser. No. 13/663,376 entitled "OPTICAL BIOMODULE FOR DETECTION OF DISEASES", filed on Oct. 29, 2012, wherein U.S. Non-Provisional patent application Ser. No. 13/663,376 resulted in an issuance of U.S. Pat. No. 9,557,271 on Jan. 31, 2017 (which claims priority to: U.S. Provisional Patent Application No. 61/742,074 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Aug. 1, 2012; U.S. Provisional Patent Application No. 61/631,071 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Dec. 27, 2011; and U.S. Provisional Patent Application No. 61/628,060 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Oct. 24, 2011), which is a continuation-in-part (CIP) of U.S. Non-Provisional patent application Ser. No. 13/135,832 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Jul. 15, 2011.

which is a continuation-in-part (CIP) of U.S. Non-Provisional patent application Ser. No. 12/573,012 entitled, "NUTRITIONAL SUPPLEMENT FOR THE PREVENTION OF CARDIOVASCULAR DISEASE, ALZHEIMER'S DISEASE, DIABETES AND REGULATION AND REDUCTION OF BLOOD SUGAR AND INSULIN RESISTANCE", filed on Oct. 2, 2009, wherein U.S. Non-Provisional patent application Ser. No. 12/573,012 resulted in an issuance of U.S. Pat. No. 8,017,147 on Sep. 13, 2011.

The entire contents of all Non-Provisional Patent Applications, all Provisional Patent Applications as listed in the previous paragraph and/or Application Data Sheet (ADS) are hereby incorporated by reference.

FIELD OF THE INVENTION

The present invention generally relates to (a) chemical compositions for lowering the risks of Alzheimer's, Cardiovascular and Diabetes diseases, (b) delivery (nanodelivery and molecular coupling) of bioactive compounds and/or bioactive molecules and (c) disease diagnostics (molecular nanodiagnostics).

The present invention also relates to (d) a wearable augmented reality subsystem, (e) a wearable subsystem and (f) a portable internet appliance in healthcare; when connected with ambient/always on sensors.

BACKGROUND OF THE INVENTION

One of the most intriguing discoveries is that many risk factors for Cardiovascular, Type-1 Diabetes and Type-2 Diabetes diseases can be risk factors for Alzheimer's disease (also known as Type-3 Diabetes disease). High blood cholesterol levels are important risk factors for Alzheimer's disease. If blood flow is restricted because of plaque accumulation/buildup in a human brain, less oxygen gets to a human brain and fewer waste residues leave a human brain.

Type-1 Diabetes disease can be caused by autoimmune destruction of insulin-producing cells in the pancreas, resulting in high blood sugar. The drugs that block effector-memory T cells can delay and/or prevent Type-1 Diabetes disease.

Type-2 Diabetes disease can be linked to excessive iron, diseased pancreas and metabolic syndrome/obesity-hence macrophages in fat tissues. The macrophages in fat tissues produce cytokine molecules, which can cause inflammations in the pancreas. Such inflammations in the pancreas can increase the insulin (a hormone needed to convert carbohydrates, foods and glucose into energy needed for daily life) resistance and gradually the pancreas loses its ability to produce insulin. Type-2 Diabetes disease is marked by high levels of blood glucose resulting from defects in glucose production and/or glucose inaction and/or insulin production and/or insulin inaction. Type-2 Diabetes disease and obesity can be linked with cryptochrome, a protein. Cryptochrome can regulate/modulate/synchronize the biological clock and glucose level in a human body. An increased level of cryptochrome can suppress/inhibit the production of enzymes (in the liver) for glucose generation during fasting (gluconeogenesis). Bioactive compounds and/or bioactive molecules that enhance the activity of calcineurin/NFAT can be effective against Type-2 Diabetes disease, wherein the beta cells do not produce enough insulin. Type-2 Diabetes disease is caused by insufficient numbers of insulin-producing beta cells. But Type-2 Diabetes disease not only lacks insulin, but also produces too much glucagon. Normally, about 50% of the insulin produced by the pancreas is immediately destroyed by the liver; but there may be a mechanism to regulate how much insulin enters the bloodstream. Insulin degrading enzyme (IDE) is a protease, an enzyme that chops proteins or peptides into smaller pieces. If insulin degrading enzyme is inhibited, insulin can remain in the blood stream longer. Insulin is involved in a surprisingly wide range of important processes, including memory and cognition—thus insulin degrading enzyme inhibitors may have multiple therapeutic applications. Insulin degrading enzyme is a thiol-sensitive zinc-metallopeptidase.

Both Type-1 and Type-2 Diabetes diseases can lead to serious complications (e.g., high blood pressure, kidney disease and premature death). But people with Type-1 and Type-2 Diabetes diseases can control/manage the diseases to lower the risks of serious complications.

The risk of Alzheimer's disease can be linked with obesity and Type-2 Diabetes disease. SorCS1 transport protein can control how the insulin receptor moves around a cell/neuron. Deficiency in SorCS1 transport protein can increase the risk of developing Alzheimer's disease, because amyloid precursor protein (APP) spends too much time in the region of the neuron wherein amyloid precursor protein is broken down into amyloid beta (Aβ) protein. A human brain has a low antioxidant level and requires a large volume of blood pumped through it to function properly. The biochemical reaction of glucose (in blood) with proteins is known as glycation. Glycation can cause problems in a human brain. The glucose molecule can be split up/divided open by enzymes for energy consumption in a human brain and two (2) reactive aldehydes can crosslink with proteins in a human brain—thus leading to a decreased blood flow. Another possible link is leptin, a hormone. Leptin is released by fat cells in a human body and acts on the leptin receptors in a human brain to regulate hunger. There are a number of leptin receptors all over a human body including in the hypothalamus of a human brain. Higher levels of leptin can suppress appetite and enhance metabolism. Leptin also plays a key role in modulating insulin. But obesity can create leptin resistance—thus leptin is not transported efficiently in a human brain. Higher levels of leptin in a human brain may lower the risk of developing Alzheimer's disease. Leptin can also reduce the production of amyloid beta protein; wherein amyloid beta protein is involved in Alzheimer's disease. Although obesity is often associated with insulin resistance and Diabetes disease, this is not always the case. However, when T-bet protein is absent, the relationship between fat and insulin resistance can be altered. T-bet is a protein that regulates the differentiation and function of immune cells.

Clinical and epidemiological studies have found that Type-2 Diabetes disease and hyperinsulinaemia increased the risk of developing Alzheimer's disease. The link between hyperinsulinaemia and Alzheimer's disease may be insulin degrading enzyme. This enzyme degrades both insulin and amylin peptides related to the pathology of Type-2 Diabetes disease along with amyloid-beta peptide, a short peptide found in excess in the Alzheimer's brain.

SUMMARY OF THE INVENTION

Chemical Compositions

The present invention relates to chemical compositions (various embodiments) of bioactive compounds for lowering the risks of Alzheimer's, Cardiovascular and Diabetes diseases.

Furthermore, the present invention relates to a chemical composition of a sugar free sweetener for people with Type-2 Diabetes disease.

Furthermore, the present invention relates to various chemical compositions (various embodiments) of a sugar free super-sweetener for people with Type-2 Diabetes disease.

Passive Delivery

The present invention relates to passive delivery (various embodiments) of bioactive compounds and/or bioactive molecules.

Active Delivery

The present invention relates to active delivery (various embodiments) of bioactive compounds and/or bioactive molecules.

Nanodelivery/Molecular Coupling

The present invention relates to targeted nanodelivery and molecular coupling (various embodiments) of bioactive compounds and/or bioactive molecules.

Diagnostics

The present invention relates to a photonic crystal cavity based integrated optical diagnostic biomodule to detect a disease specific biomarker/an array of disease specific biomarkers.

Furthermore, the present invention relates to various fluid container based integrated optical diagnostic biomodule(s) to detect a disease specific biomarker/an array of disease specific biomarkers.

Furthermore, the present invention relates to various field effect transistor (FET) based integrated electrical diagnostic biomodule(s) to detect a disease specific biomarker/an array of disease specific biomarkers.

Furthermore, the present invention relates to a nanohole based single molecule DNA/RNA sequencing electrical diagnostic biomodule to detect a disease specific biomarker/an array of disease specific biomarkers.

Furthermore, the present invention relates to an x-ray fluorescence diagnostic biomodule for detection of a disease specific biomarker/an array of disease specific biomarkers.

Furthermore, the present invention relates to a retinal contact lens subsystem to detect a disease specific biomarker/an array of disease specific biomarkers.

Furthermore, the present invention relates to a plasmonic interferometer based integrated optical diagnostic biomodule to detect a disease specific biomarker/an array of disease specific biomarkers.

Integrated Diagnostics-Delivery System

The present invention relates to an integrated bioelectronics subsystem to detect a disease specific biomarker/an array of disease specific biomarkers and actively deliver bioactive compounds and/or bioactive molecules.

Furthermore, the present invention relates to a retinal contact lens subsystem to deliver bioactive compounds and/or bioactive molecules.

Lab-On-Chip (LOC) Diagnostics

The present invention relates to various Lab-on-Chip subsystems and their applications in personalized healthcare.

Wearable Augmented Reality Subsystem with Connected Ambient/Always on Sensors

The present invention relates to a wearable augmented reality subsystem with connected ambient/always on sensors and its applications in personalized healthcare.

Wearable Personal Assistant Subsystem with Connected Ambient/Always on Sensors

The present invention relates to a wearable subsystem with connected ambient/always on sensors and its applications in personalized healthcare.

Portable Internet Appliance with Connected Ambient/Always on Sensors

The present invention relates to a portable internet appliance with connected ambient/always on sensors and its applications in personalized healthcare.

BRIEF DESCRIPTION OF THE TABLES

The present invention is better understood upon consideration of the description in conjunction with the following Tables and Figures.

Table-1A and Table-1B, wherein each table illustrates a composition of a mixture of micronutrients. Table-1C illustrates a composition of a mixture of micronutrients for topical use. Table-1D, Table-1E, Table-1F, Table-1G, Table-1H, Table-1I, Table-1J and Table-1K, wherein each table illustrates a composition of a mixture of micronutrients.

Table-2A and Table-2B, wherein each table illustrates a composition of a mixture of antioxidants.

Table-3A illustrates a composition of a multi-serve antioxidant liquid. Table-3B and Table-3C, wherein each table illustrates a composition of a single-serve antioxidant liquid. Table-3D illustrates a composition of a mixture of botanicals. Table-3E illustrates a composition of a mixture of electrolytes and dextrose.

Table-4 illustrates a composition of a biodegradable plastic material.

Table-5 illustrates a composition of a mixture for expression of beneficial $NrF_2$ protein.

Table-6 illustrates molecular docking score with the mammalian Target of Rapamycin (mTOR), utilizing computational chemistry software.

Table-7A, Table-7B, Table-7C and Table-7D, wherein each table illustrates a composition of a mixture for suppressing/inhibiting the mammalian Target of Rapamycin.

Table-8A, Table-8B, Table-8C, Table-8D and Table-8E, wherein each table illustrates a composition of a mixture for lowering the risk of Alzheimer's disease.

Table-9 illustrates a composition of a mixture for lowering the risks of Cardiovascular disease.

Table-10A, Table-10B, Table-10C and Table-10D, wherein each table illustrates a composition of a mixture for lowering the risk of Type-2 Diabetes disease.

Table-11 illustrates a composition of a mixture of sugar-free sweetener for people with Type-2 Diabetes disease.

Table-12A, Table-12B, Table-12C, Table-12D, Table-12E, Table-12F, Table-12G, Table-12H, Table-12I, Table-12J, Table-12K, Table-12L and Table-12M, wherein each table illustrates a composition of a mixture of sugar-free super-sweetener for people with Type-2 Diabetes disease.

Table-13A, Table-13B, Table-13C, Table-13D, Table-13E, Table-13F, Table-13G, Table-13H, Table-13I, Table-13J, Table-13K, Table-13L, Table-13M, Table-13N, Table-13O, Table-13P, Table-13Q, Table-13R, Table-13S, Table-13T, Table-13U, Table-13V and Table-13W, wherein each table illustrates a composition of a mixture of chewable/soluble strip for health.

Table-13X illustrates a composition of probiotics. Table-13Y illustrates a composition of chemicals and minerals to protect against aging. Table-13Z1 illustrates another composition of chemicals and minerals to protect against aging. Table-13Z2 illustrates another composition of chemicals to protect against aging. Table-13Z3 illustrates another composition of chemicals to protect against aging. Table-13Z4 illustrates another composition of chemicals to protect against aging.

Table-14A illustrates various compositions of a biodegradable scaffold. Table-14B illustrates various compositions of a biodegradable scaffold, integrated with various nanowire field effect transistors.

Table-15 illustrates a composition of a biodegradable plastic material.

Table-16A illustrates various compositions for a nanostructured mesh. Table-16B illustrates various compositions for a nanostructured mesh, integrated with various nanowire field effect transistors.

BRIEF DESCRIPTION OF THE FIGURES

FIG. 2 illustrates graphical interactions of Alzheimer's, Dementia and Parkinson's disease related genes/proteins with a set of bioactive compounds and/or bioactive molecules, according to comprehensive biological pathway analysis software. FIG. 2A illustrates a section of FIG. 2

FIG. 3 illustrates graphical interactions of Alzheimer's, Dementia and Parkinson's disease related genes/proteins with a set of bioactive compounds and/or bioactive molecules, according to comprehensive biological pathway analysis software. FIG. 3A illustrates a section of FIG. 3

FIGS. 7A, 7B, 7C, 7D, 7E, 7F, 7G, 7H, 7I, 7J, 7K, 7L and 7M illustrate a passive (via a micropatch) delivery of bioactive compounds and/or bioactive molecules, utilizing thin-films, nanocrystals and microelectro-mechanical-system (MEMS) reservoirs.

FIGS. 12D, 12E, 12F and 12G illustrate (an array of microcapillaries based) integrated optical diagnostic biomodules (various other embodiments) to detect up to two (2) million or more disease specific biomarkers.

FIGS. 12H-12O illustrate eight embodiments of a three-dimensional (3-D) protruded optical nanoantenna.

FIGS. 12P1-12P3 illustrate three fabrication/construction methods for patterning dimension at or less than 25 nanometers.

FIGS. 12Q1-12Q6 illustrate six fabrication/construction methods for positioning a fluorophore (coupled with a biomarker binder) at a specified position on a substrate FIG. 12R1 illustrates an aptamer sensor.

FIG. 12R2 illustrates a molecular beacon.

FIG. 12R3 illustrates chemically coupled three distinct biomarker binder (e.g., an antibody/synthetically designed antibody/aptamer) A, B and C, wherein the distinct biomarker binder B and the distinct biomarker binder C are then chemically coupled with a plus ligation arm of short sequences of a biological material (e.g., oligonucleotides) and a minus ligation arm of short sequences of a biological material (e.g., oligonucleotides) respectively. Thus, generating a randomly coiled single stranded structure composed of hundreds of copies of a biological material, relying on proximity extension array (PEA) method and thus, subsequently leading to covalently hybridization of fluorescent or enzyme-labeled biological material.

FIGS. 12S1-12S7 illustrates seven examples of positioning a biomarker binder/fluorophore at a specified position with respect to a three-dimensional protruded structure.

FIG. 12T1 illustrates an open enclosure for a three-dimensional protruded optical nanoantenna.

FIG. 12T2 illustrates a closed enclosure for a three-dimensional protruded optical nanoantenna.

FIG. 12U1 illustrates a hyperbolic metamaterial surface.

FIG. 12U2 illustrates gratings for a hyperbolic metamaterial surface.

FIGS. 12W1-12W6 illustrate six (example) embodiments of the array of fluidic containers, incorporating various embodiments of three-dimensional protruded structures.

FIG. 12X1 illustrates an embodiment of an optical diagnostic biomodule, utilizing a one-dimensional/two-dimensional of zero-mode waveguides, incorporating various embodiments of three-dimensional protruded structures.

FIGS. 12X2-12X9 illustrate five embodiments of the zero-mode waveguides, incorporating various three-dimensional protruded structures.

FIG. 12X10 illustrates a fabrication/construction method for patterning an array of zero-mode waveguides/nanoholes

FIG. 12Z1 illustrates a light source/tunable light source in the visible spectrum, utilizing a two-dimensional (e.g., graphene) material.

FIG. 12Z2 illustrates a light source/tunable light source in the visible spectrum, utilizing a two-dimensional material, wherein a two-dimensional material is functionalized with a biomarker binder.

FIG. 12Z3 illustrates a nano optical fiber.

FIG. 14M illustrates a portable diagnostic device, which can be coupled with a portable internet appliance (e.g., an iPhone).

FIGS. 17A, 17B, 17C and 17D illustrate a near real-time/real-time wearable bioelectronics subsystem, as an augmented reality personal assistant to eavesdrop on a user's communication and anonymously recommend a solution to the user.

FIG. 19O illustrates a nanoscope for detecting various RNAs and proteins within exosomes from a human body's blood.

FIG. 20 also illustrates interactions with a hologram, utilizing the portable internet appliance.

FIG. 21 illustrates realization of one integrated user identification merging a cell phone number and e-mail identification.

DETAIL DESCRIPTION OF THE INVENTION

Bioactive Compounds &/or Bioactive Molecules Interactions with Genes/Proteins

Figures 1, 1A:
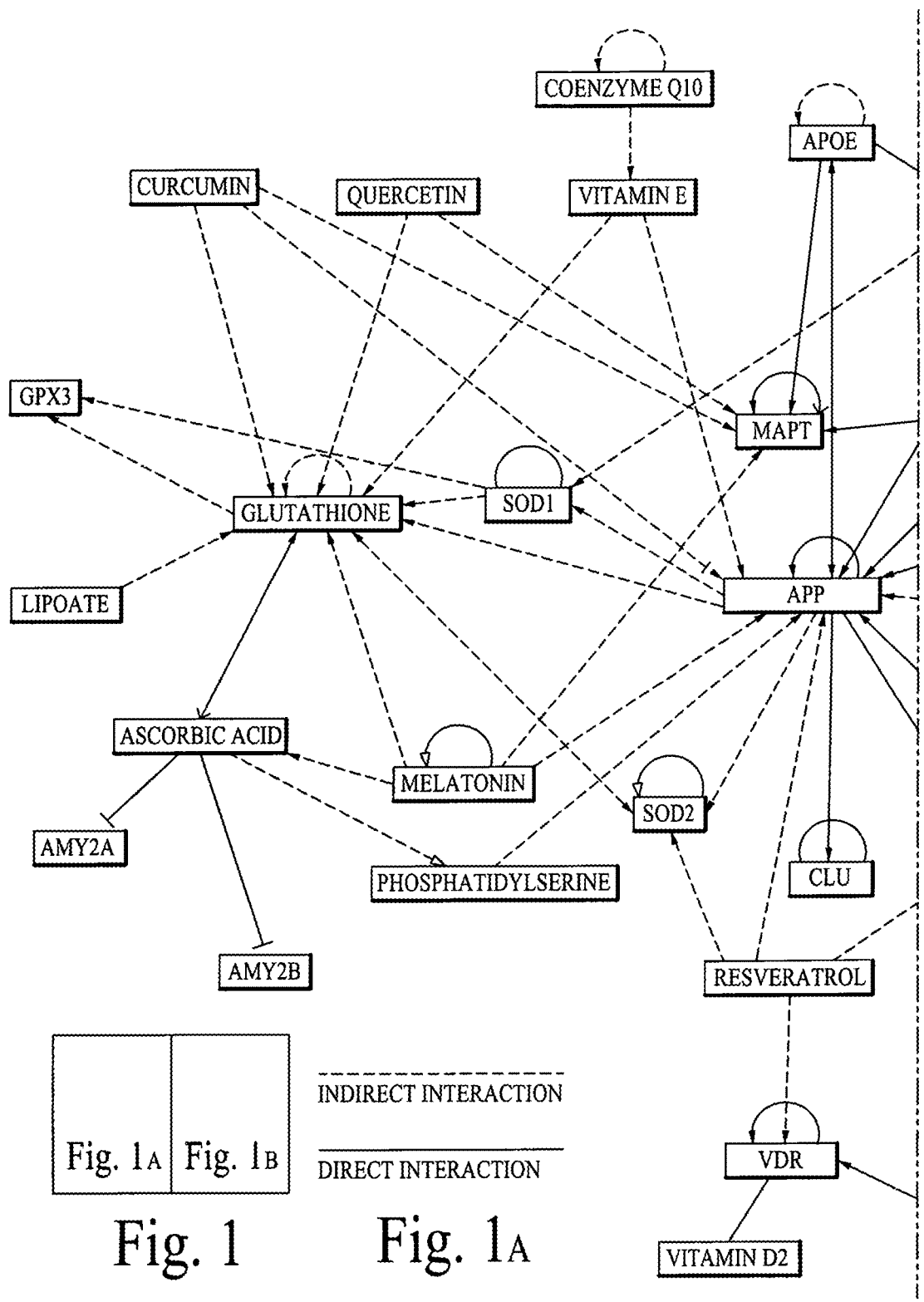
FIG. 1 illustrates graphical interactions of Alzheimer's disease related genes/proteins with a set of bioactive compounds (e.g., an antioxidant, enzymatic antioxidant, enzyme, micronutrient (mineral/vitamin) and drug) and/or bioactive molecules (e.g., enzyme molecule, protein molecule, small molecule, therapeutic molecule, DNA, gene, ribozyme, RNA, messenger RNA (mRNA), micro RNA (miRNA), Piwi-interacting RNA (piRNA) and small interfering RNA (siRNA)), according to comprehensive biological pathway analysis (BPA) software.
FIG. 1A illustrates a section of FIG. 1
Figure 1B:
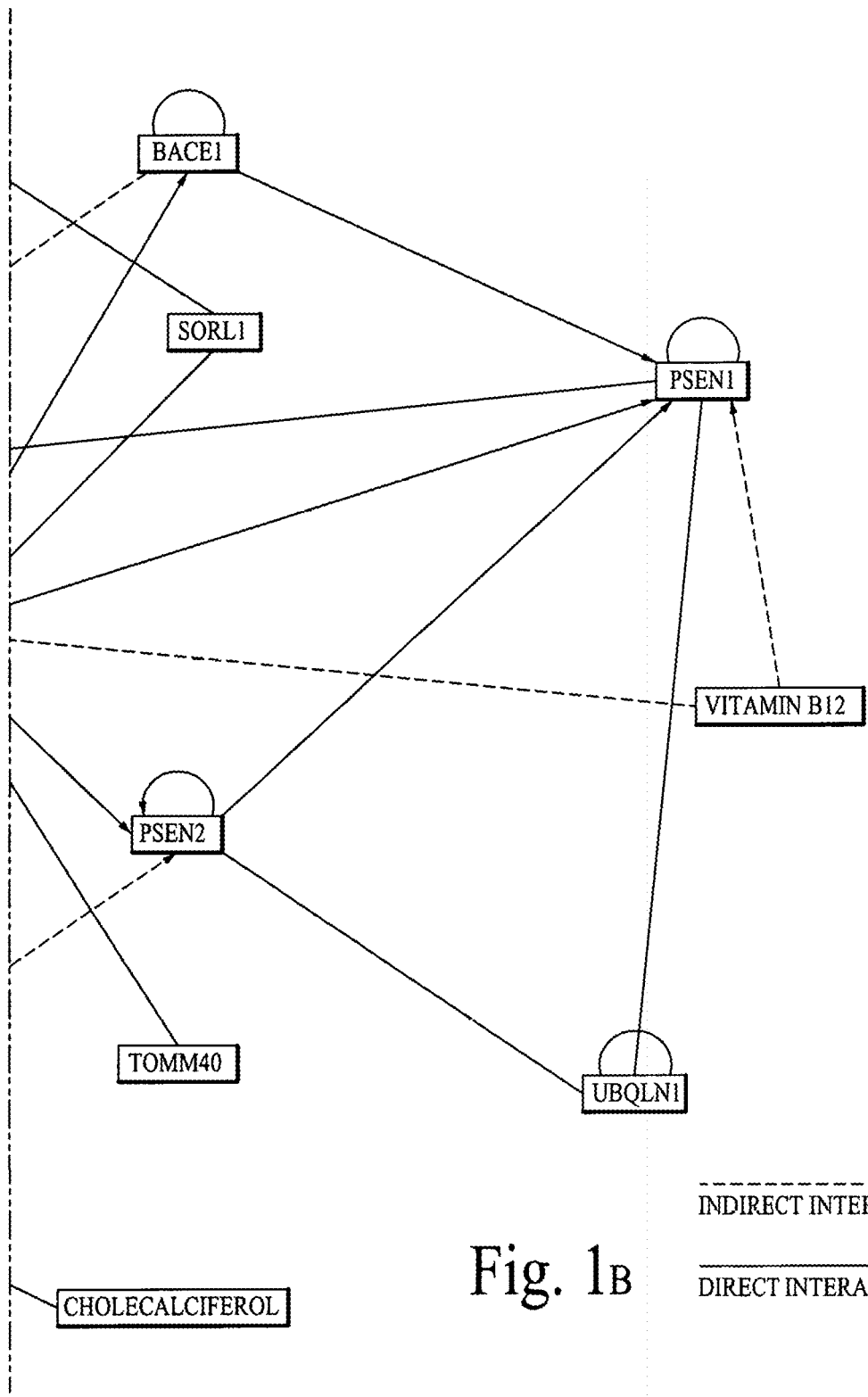
FIG. 1B illustrates a section of FIG. 1, wherein both sections are separated by a dotted line.

FIG. 1 illustrates direct and indirect graphical interactions of Alzheimer's disease related genes/proteins (e.g., APOE, APP, BACE1, CLU, MAPT/TAU, PSEN1, PSEN2, SORL1, TOMM40 and UBQLN1) with a set of bioactive compounds and/or bioactive molecules, utilizing comprehensive biological pathway analysis software. FIG. 1A illustrates a section of FIG. 1 and FIG. 1B illustrates a section of FIG. 1, wherein both sections are separated by a dotted line.

Figure 2B:
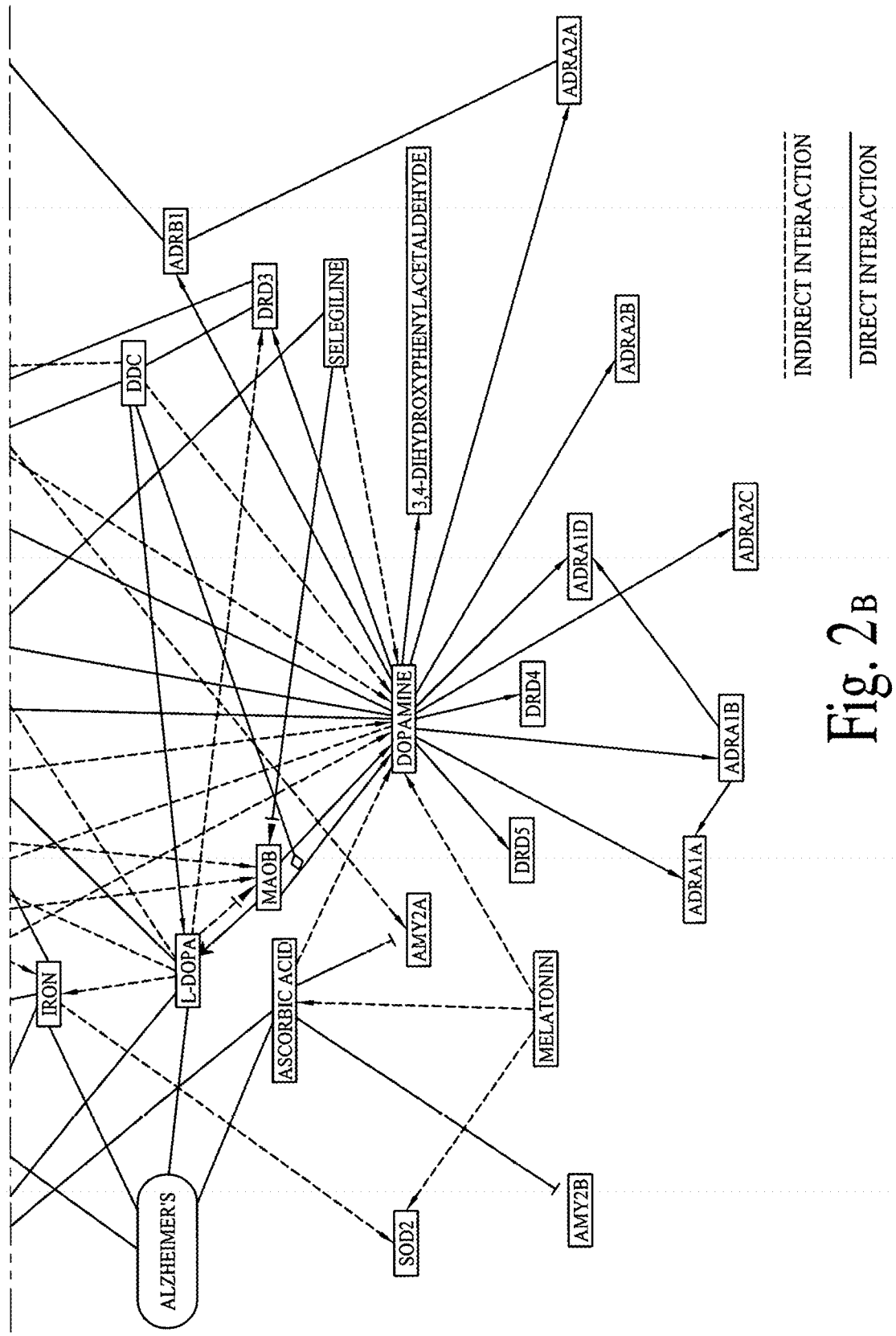
FIG. 2B illustrates a section of FIG. 2, wherein both sections are separated by a dotted line.
Figure 3B:
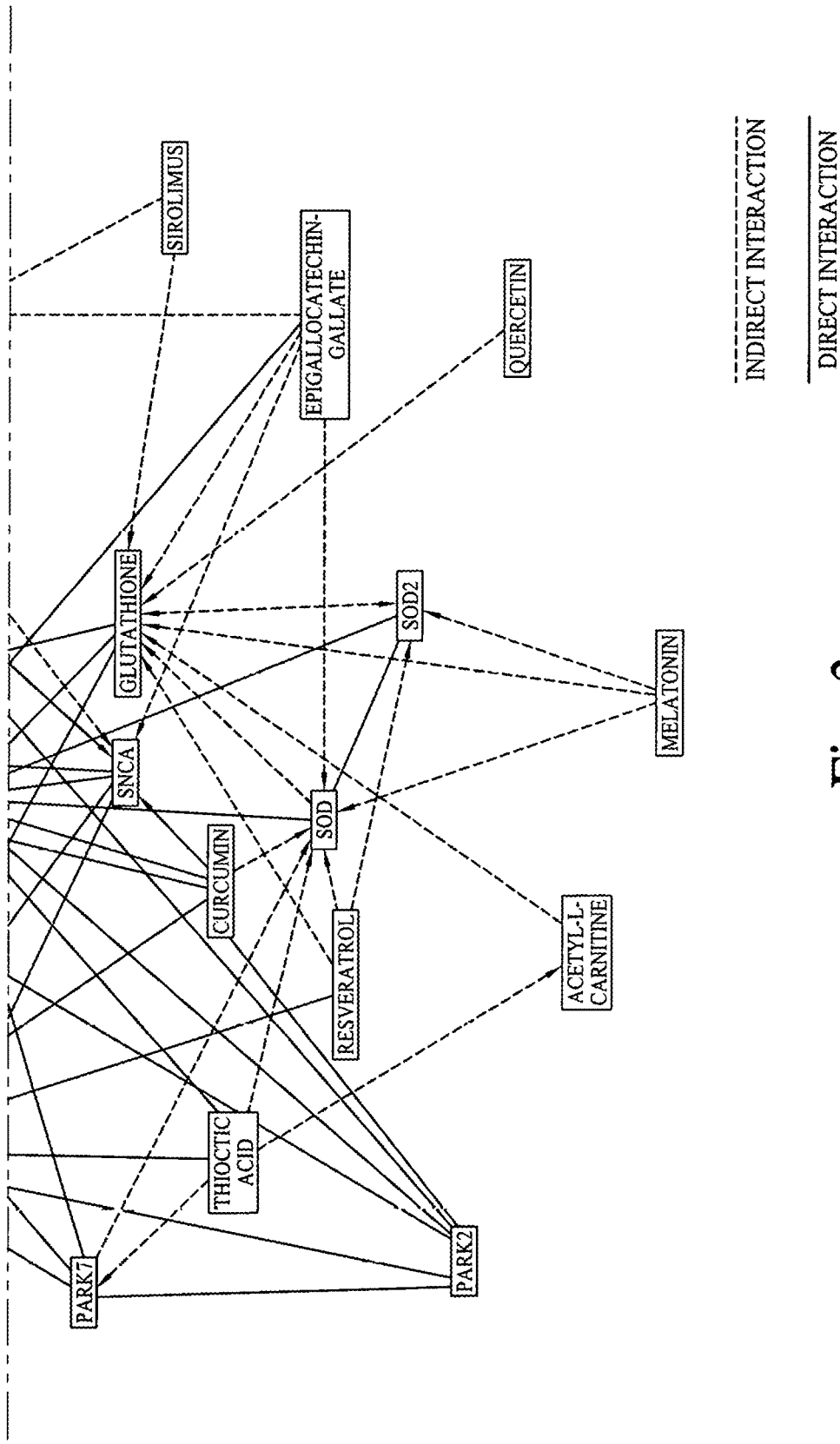
FIG. 3B illustrates a section of FIG. 3, wherein both sections are separated by a dotted line.

FIG. 2 illustrates direct and indirect graphical interactions of Alzheimer's, Dementia and Parkinson's disease related genes/proteins (e.g., DOPAMINE, LRRK2, MAOB, PARK2 and SNCA) with a set of bioactive compounds and/or bioactive molecules, utilizing comprehensive biological pathway analysis software. FIG. 2A illustrates a section of FIG. 2 and FIG. 2B illustrates a section of FIG. 2, wherein both sections are separated by a dotted line. FIG. 3 illustrates direct and indirect graphical interactions of Alzheimer's, Dementia and Parkinson's disease related genes/proteins (e.g., DOPAMINE, LRRK2, MAOB, PARK2 and SNCA) with a set of bioactive compounds and/or bioactive molecules, utilizing comprehensive biological pathway analysis software. FIG. 3A illustrates a section of FIG. 3 and FIG. 3B illustrates a section of FIG. 3, wherein both sections are separated by a dotted line.

Figures 4, 4A:
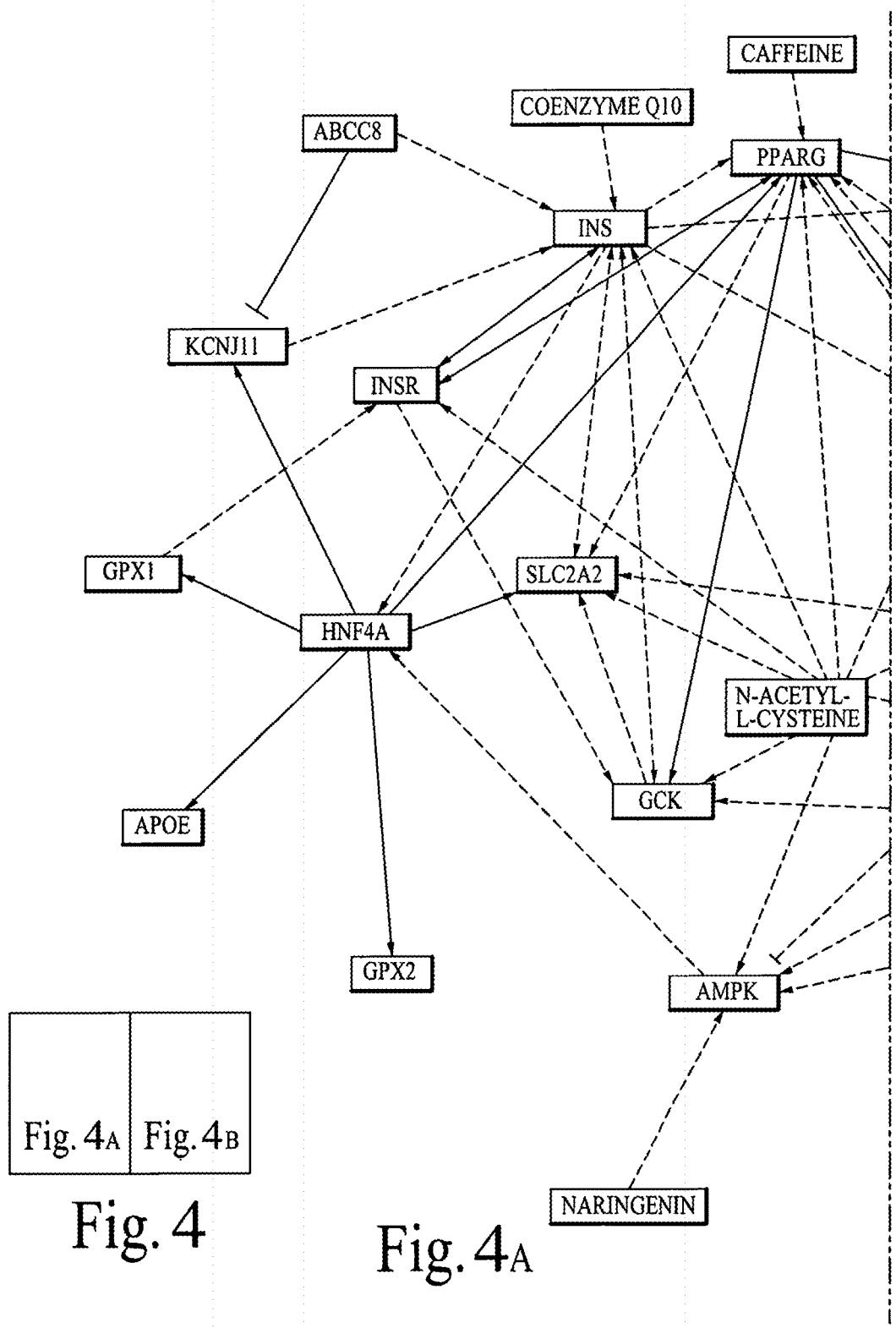
FIG. 4 illustrates graphical interactions of Type-2 Diabetes disease related genes/proteins with a set of bioactive compounds and/or bioactive molecules, according to comprehensive biological pathway analysis software.
FIG. 4A illustrates a section of FIG. 4

FIG. 4 illustrates direct and indirect graphical interactions of Type-2 Diabetes disease related genes/proteins (e.g., ABCC8, GCK, HNF4A, INS, INSR, KCNJ11, LPL, PPARG and SLC2A2) with a set of bioactive compounds and/or bioactive molecules, utilizing comprehensive biological pathway analysis software. FIG. 4A illustrates a section of FIG. 4 and FIG. 4B illustrates a section of FIG. 4, wherein both sections are separated by a dotted line.

Furthermore, Alzheimer's disease related gene/protein APOE is linked with Type-2 Diabetes disease related gene/protein HNF4A.

FIGS. 1A, 1B, 2A, 2B, 3A and 3B are critical to design compositions for lowering the risks of Alzheimer's disease.

Figure 4B:
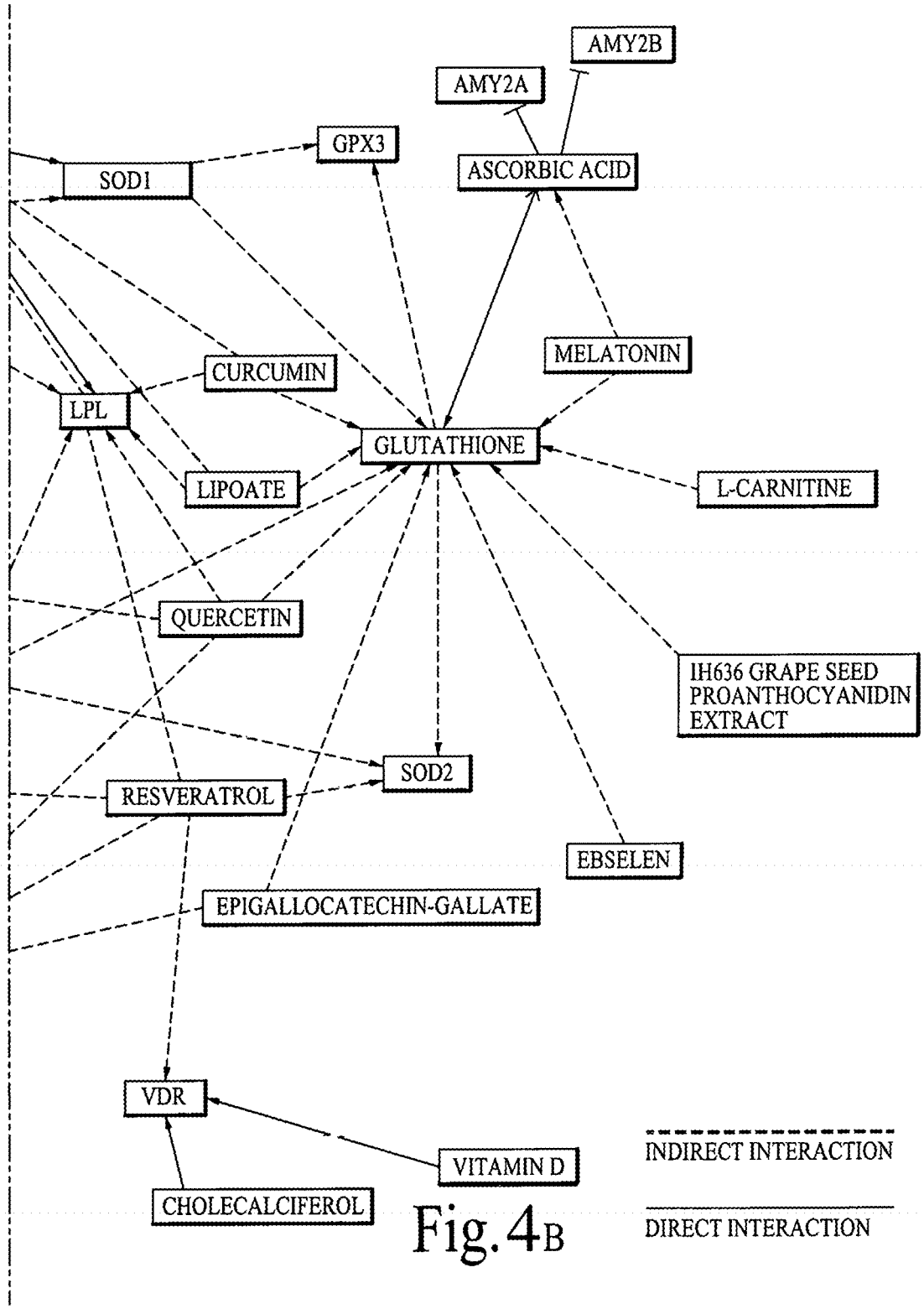
FIG. 4B illustrates a section of FIG. 4, wherein both sections are separated by a dotted line.

FIGS. 4A and 4B are critical to design compositions for lowering the risks of Diabetes disease.

Figure 5A:
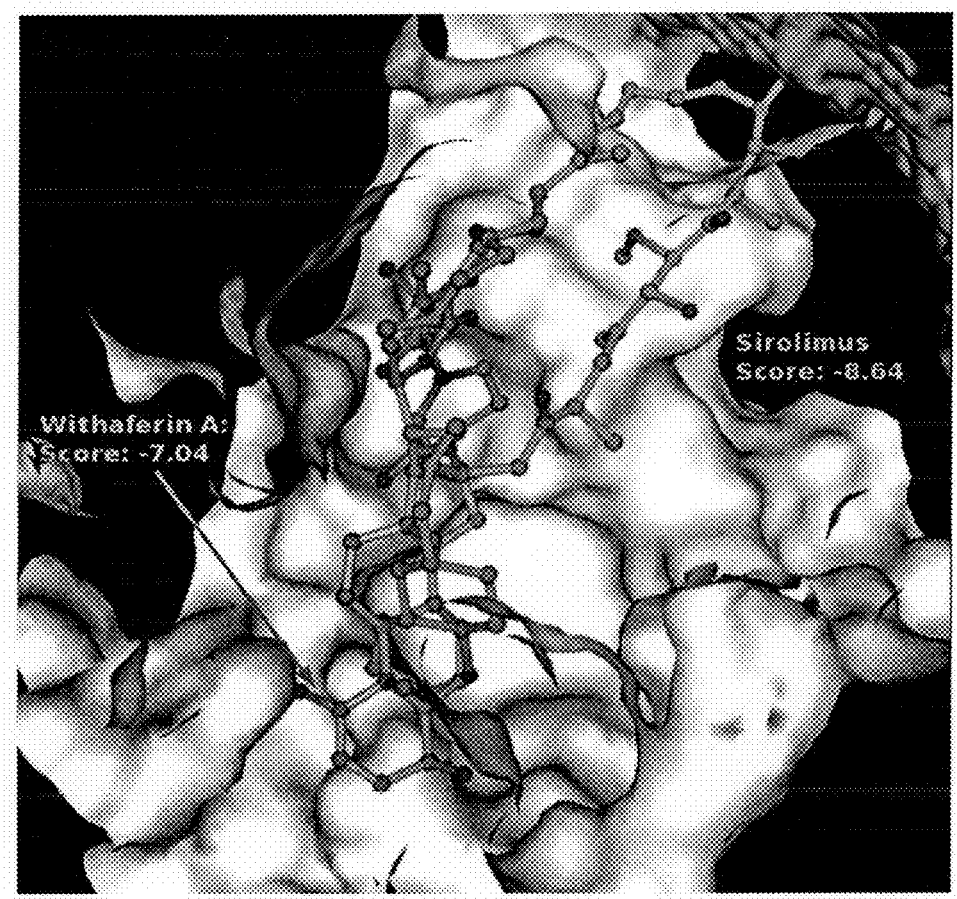
FIGS. 5A and 5B illustrate molecular docking score with the mammalian Target of Rapamycin, according to comprehensive molecular docking analysis software.
Figure 5B:
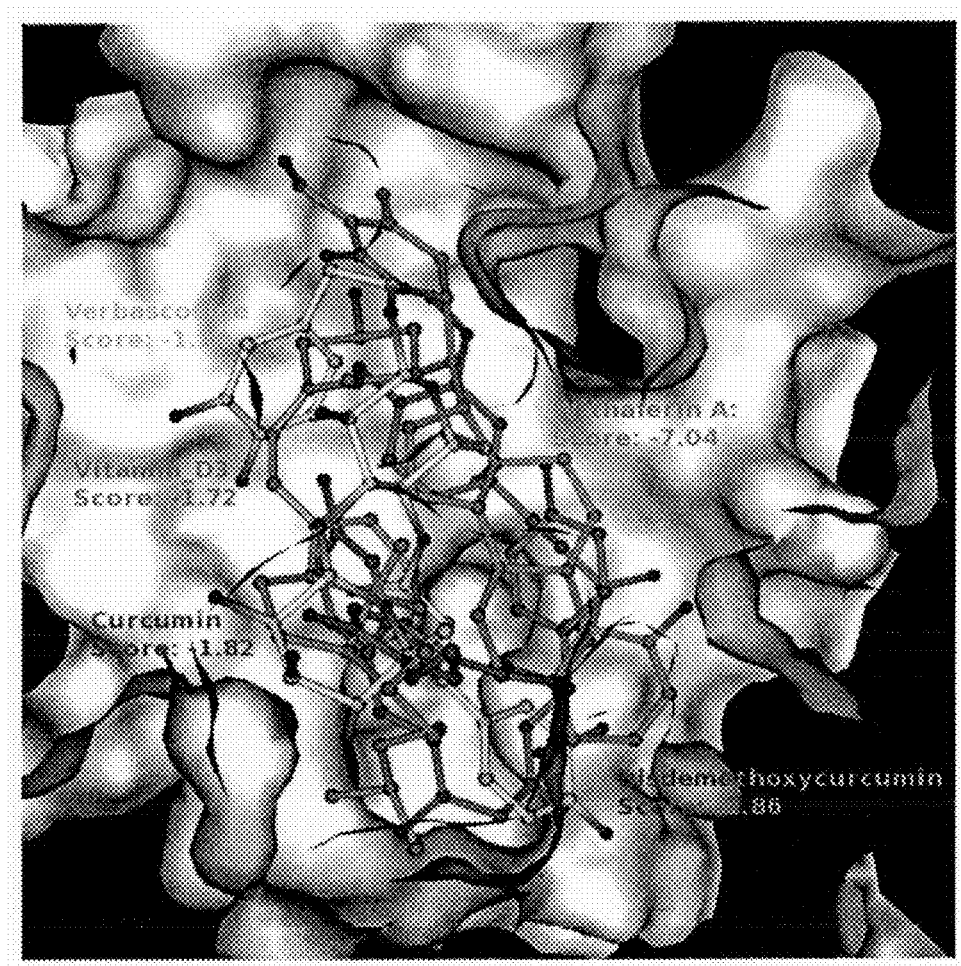

FIGS. 5A and 5B are critical to design compositions for suppressing/inhibiting the mammalian Target of Rapamycin.

Compositions

Compositions as described in the Tables below can module (a) gene expression, (b) epigenetic effects and (c) genomic stability.

TABLE 1A

Composition Of A Mixture Of Micronutrients - May Also Include Some Bioactive Compounds From Tables After This Table

| Chemicals | Unit | +/−50% | WT % |
|---|---|---|---|
| Pterostilbene (Nanoformulated)[1,2] | Mg | 200 | 4.89% |
| Resveratrol (Nanoformulated)[1,2] | Mg | 200 | 4.89% |

TABLE 1A-continued

Composition Of A Mixture Of Micronutrients - May Also Include Some Bioactive Compounds From Tables After This Table

|  | Unit | +/−50% | WT % |
|---|---|---|---|
| Minerals |  |  |  |
| Chromium Picolinate | Mg | 0.5 | 0.01% |
| Magnesium L-Threonate | Mg | 400 | 9.78% |
| Selenium (Selenomethionine) | Mg | 0.1 | 0.00% |
| Zinc (L-Opti) | Mg | 15 | 0.37% |
| Vanadium | Mg | 0.01 | 0.00% |
| Nucleotides |  |  |  |
| Nucleotides (DNA) | Mg | 400 | 9.78% |
| Nucleotides (RNA) | Mg | 40 | 0.98% |
| Vitamins |  |  |  |
| Vitamin $B_1$ (Thiamine) | Mg | 10 | 0.24% |
| Vitamin $B_3$ (Nicotinamide) | Mg | 400 | 9.78% |
| Vitamin $B_5$ | Mg | 200 | 4.89% |
| Vitamin $B_6$ (Pyritinol Or Pyridoxal 5'-Phosphate) | Mg | 20 | 0.49% |
| Vitamin $B_9$ (Folate) | Mg | 0.5 | 0.01% |
| Vitamin $B_{12}$ (Methylcobalamin) | Mg | 1 | 0.02% |
| Vitamin C | Mg | 200 | 4.89% |
| Vitamin $D_3$ (Cholecalciferol) | Mg | 0.25 | 0.01% |
| Vitamin $K_2$ | Mg | 2 | 0.05% |
| Other |  |  |  |
| Lactoferrin | Mg | 2000 | 48.91% |
| Total Weight | G | 4.09 | 100.00% |

Mixture of micronutrients contains about 35 billion cumulative (or each live probiotic bacterial component at 2.5 billion CFU) CFU of: *Lactobacillus acidophilus, Bifidobacterium lacti, Lactobacillus plantarum, Lactobacillus rhamnosus, Lactobacillus casei, Lactobacillus salivarius, Lactobacillus bulgaricus, Bifidobacterium breve, Lactobacillus paracasei, Lactococcus lactis, Streptococcus thermophilus, Lactobacillus brevis, Bifidobacterium bifidum* and *Bifidobacterium longum* can be added with composition in Table-1A.

Furthermore, live probiotic bacterial components can be encapsulated within a microparticulate system (e.g., chitosan-coated alginate microparticulate system).

TABLE 1B

Composition Of A Mixture Of Micronutrients - May Also Include Some Bioactive Compounds From Tables After This Table

|  | Unit | +/−50% | WT % |
|---|---|---|---|
| Botanicals |  |  |  |
| *Bacopa monnieri*[+] | Mg | 200 | 1.28% |
| *Emblica officinalis*[+] | Mg | 200 | 1.28% |
| *Vaccinium macrocarpon*[+] | Mg | 800 | 5.12% |
| *Withania somnifera*[+] | Mg | 200 | 1.28% |
| Chemicals |  |  |  |
| Acetyl-L-Carnitine | Mg | 200 | 1.28% |
| Alpha-R-Lipoic Acid | Mg | 20 | 0.13% |
| Beta carotene | Mg | 20 | 0.13% |
| Chlorogenic Acid | Mg | 200 | 1.28% |
| Citicoline (Or L-Alpha Glycerylphosphorylcholine) | Mg | 600 | 3.84% |
| Coenzyme $Q_{10}$ (Nanoformulated)[1,2] | Mg | 1000 | 6.40% |
| Curcumin (Nanoformulated)[1,2,3,4] | Mg | 200 | 1.28% |
| D-Ribose | Mg | 400 | 2.56% |
| Epigallocatechin Gallate | Mg | 200 | 1.28% |
| L-Arginine | Mg | 4000 | 25.62% |
| L-Glutathione (Or Ebselen Or N-Acetyl-L-Cysteine) | Mg | 200 | 1.28% |
| L-Theanine | Mg | 400 | 2.56% |
| Lutein | Mg | 10 | 0.06% |
| Phosphatidylserine | Mg | 200 | 1.28% |
| Pterostilbene (Nanoformulated)[1,2] | Mg | 200 | 1.28% |
| Pyrroloquinoline Quinone (PQQ) (Nanoformulated)[1,2] | Mg | 20 | 0.13% |
| Resveratrol (Nanoformulated)[1,2] | Mg | 200 | 1.28% |
| Touchi | Mg | 200 | 1.28% |
| Trehalose | Mg | 200 | 1.28% |
| Ubiquinol (Nanoformulated)[1,2] | Mg | 400 | 2.56% |
| Zeaxanthin | Mg | 2 | 0.01% |
| Minerals |  |  |  |
| Chromium Picolinate | Mg | 0.5 | 0.00% |
| Magnesium L-Threonate | Mg | 400 | 2.56% |
| Melatonin (Extended Release) | Mg | 3 | 0.02% |
| Omega 3-6-9 Acid (Including Decosahexanoic Acid) (Nanoformulated)[1] | Mg | 400 | 2.56% |
| Potassium | Mg | 400 | 2.56% |
| Selenium (Selenomethionine) | Mg | 0.1 | 0.00% |
| Zinc (L-Opti) | Mg | 15 | 0.10% |
| Zinc Sulfate | Mg | 250 | 1.60% |
| Vanadium | Mg | 0.01 | 0.00% |
| Nucleotides |  |  |  |
| Nucleotides (DNA) | Mg | 400 | 2.56% |
| Nucleotides (RNA) | Mg | 40 | 0.26% |
| Vitamins |  |  |  |
| Vitamin $B_1$ (Thiamine) | Mg | 10 | 0.06% |
| Vitamin $B_3$ (Nicotinamide) | Mg | 400 | 2.56% |
| Vitamin $B_5$ | Mg | 200 | 1.28% |
| Vitamin $B_6$ (Pyritinol Or Pyridoxal 5'-Phosphate) | Mg | 20 | 0.13% |
| Vitamin $B_9$ (Folate) | Mg | 0.5 | 0.00% |
| Vitamin $B_{12}$ (Methylcobalamin) | Mg | 1 | 0.01% |
| Vitamin C | Mg | 500 | 3.20% |
| Vitamin $D_3$ (Cholecalciferol) | Mg | 0.25 | 0.00% |
| Vitamin E | IU | 400 | 1.71% |
| Vitamin $K_2$ | Mg | 2 | 0.01% |
| Other |  |  |  |
| Lactoferrin | Mg | 2000 | 12.81% |
| Live *Lactobacillus plantarum* 299v | Billion | 10 | 0.00% |
| Total Weight | G | 15.61 | 100.00% |

800 mg of L-Tryptophan can be added with composition in Table-1B.

200 mg of passion fruit tea extract can be added with composition in Table-1B.

TABLE 1C

Composition Of A Mixture Of Micronutrients For Topical Use - May Also Include Some Bioactive Compounds From Tables Before & After This Table

|  | Unit | +/−50% | WT % |
|---|---|---|---|
| Botanicals |  |  |  |
| *Camellia sinensis* (Green Tea) Extract | Mg | 200 | 4.87% |
| *Daucus carota* Extract | Mg | 200 | 4.87% |
| *Emblica officinalis* Extract | Mg | 200 | 4.87% |
| *Hippophae rhamnoides* Oil | Mg | 200 | 4.87% |
| *Macrocystis pyrifera* Extract | Mg | 200 | 4.87% |
| *Prunus amygdalus dulcis* (Sweet Almond) Oil | Mg | 200 | 4.87% |
| *Solanum lycopersicum* | Mg | 200 | 4.87% |

TABLE 1C-continued

Composition Of A Mixture Of Micronutrients For
Topical Use - May Also Include Some Bioactive Compounds
From Tables Before & After This Table

|  | Unit | +/−50% | WT % |
|---|---|---|---|
| Chemicals |  |  |  |
| Acetyl Hexapeptide | Mg | 200 | 4.87% |
| Arbutin | Mg | 200 | 4.87% |
| Caffeine | Mg | 20 | 0.49% |
| Elastatropin | Mg | 200 | 4.87% |
| Haloxyl | Mg | 200 | 4.87% |
| Hyaluronic Acid | Mg | 200 | 4.87% |
| Hydroxytyrosol | Mg | 200 | 4.87% |
| Hydrolyzed Wheat Protein | Mg | 200 | 4.87% |
| Palmitoyl Pentapeptide-4 | Mg | 200 | 4.87% |
| Quercetin (Nanoformulated)[1,2] | Mg | 200 | 4.87% |
| Resveratrol (Nanoformulated)[1,2] | Mg | 200 | 4.87% |
| Superoxide Dismutase (Nanoformulated)[1,2] | Mg | 200 | 4.87% |
| Vitamins |  |  |  |
| Pyrroloquinoline Quinone (Nanoformulated)[1,2] | Mg | 20 | 0.49% |
| Vitamin B$_5$ | Mg | 200 | 4.87% |
| Vitamin E | IU | 400 | 6.49% |
| Total Weight | G | 4.11 | 100.00% |

About 200 mg of Argan oil or about 200 mg of Coconut (preferably mature coconut) oil or about 200 mg of Marula oil or about 200 mg Pomegranate (*Punica granatum*) seed oil or about 200 mg of Red Raspberry seed oil or about 600 mg of Turmeric oil or 600 mg of Winter Rose oil can be added with the topical composition (formulation) in Table-1C. About 200 mg of *Aloe vera* extract or about 200 mg of *Glycyrrhiza glabra* extract or about 200 mg of pine bark extract can be added with the topical composition (formulation) in Table-1C. About 100 mg of caviar extract or about 200 mg of silk fibroin can be added with the topical composition (formulation) in Table-1C.

About 200 mg of extract of stem cells of leaves of *Lycopersicon esculentum* or about 200 mg of extract of stem cells of *Malus domestica* can be added with the topical composition (formulation) in Table-1C. Furthermore, about 50 mg of a bioactive compound(s) based on naturally occurring antifreeze glycoproteins in Antarctic fish can be added with the topical composition (formulation) in Table-1C Regulatory proteins, called growth factors are biologically active molecules. Suitable amounts of growth factors (from stem cells) can be added. These growth factors can also be nanoformulated/nanoencapsulated (for repairing damaged skin). Fibroblasts are a type of cell found in the connective tissue, where fibroblasts produce proteins such as collagen, elastin and GAG, which are all critical to repairing skin density and the overall look/quality of the skin. Suitable amounts of fibroblasts can be added with the topical composition (formulation) in Table-1C.

Furthermore, activators of fibroblasts such as 1,3 beta glucan, *chlorella*, EGF, GHK-copper peptides, niacinamide, R-lipoic acid and retinaldehyde and/or the synergistic combination(s) of the above activators of fibroblasts can activate fibroblasts and supply nutrients to fibroblasts. Suitable amounts of activators of fibroblasts can be added with the topical composition (formulation) in Table-1C. Furthermore, the above activators of fibroblasts can be nanoformulated/nanoencapsulated. Fibroblast growth factors are critical for repairing damaged skin. Fibroblast growth factors can induce expression of Nrf2, which regulates the expression of proteins involved in the detoxification of reactive oxygen species (ROS). Suitable amounts of fibroblast growth factors can be also added with the topical composition (formulation) in Table-1C.

About 0.5% by weight of ebselen, a broad-spectrum antioxidant can be added with the topical composition (formulation) in Table-1C. The chemical structure of ebselen is given below.

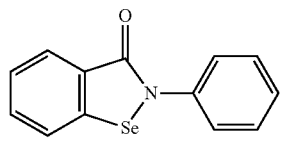 [SMILES: O=c1c2ccccc2[se]n1-c1ccccc1]

A suitable amount of selenohydantoin, an antioxidant and anticancer compound can be added with the topical composition (formulation) in Table-1C. Furthermore, a chemical derivative/structural analogue of selenohydantoin can also be utilized. The chemical structure of selenohydantoin is given below.

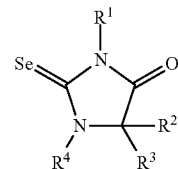

Zinc finger technology (ZFT) can be utilized to repair DNA damage and assist in the production of proteins and antioxidants within skin cells. A suitable amount of zinc finger technology can be added with the topical composition (formulation) in Table-1C.

Additionally, a nanoemulsion system/biodegradable substrate (e.g., silk)/silicone based polymer substrate with a high degree of stability can be utilized for transdermal delivery (via a patch/passive micropatch/active micropatch) of the topical composition (formulation) in Table-1C along with compositions described in previous paragraphs.

Furthermore, the topical composition (formulation) in Table-1C along with compositions described in previous paragraphs can be applied via silk fibroin nanoparticles or a silk fibroin based patch or a pressure sensitive transdermal patch (e.g., a pressure sensitive single-layer transdermal/multi-layer/reservoir transdermal patch) or the passive/active patch as described in later paragraphs

TABLE 1D

Composition Of A Mixture Of Micronutrients - May Also Include
Some Bioactive Compounds From Tables Before & After This Table

|  | Unit | +/−50% | WT % |
|---|---|---|---|
| Botanicals |  |  |  |
| *Boswellia serrata* Extract | Mg | 1000 | 12.62% |
| Cayenne Pepper | Mg | 200 | 2.52% |
| *Corydalis yanhusuo* Root Concentrate | Mg | 200 | 2.52% |
| *Curcuma longa* Root Extract | Mg | 200 | 2.52% |
| Salix (White Willow) Bark Extract | Mg | 200 | 2.52% |
| *Zingiber officinale* Root Concentrate | Mg | 200 | 2.52% |

TABLE 1D-continued

Composition Of A Mixture Of Micronutrients - May Also Include Some Bioactive Compounds From Tables Before & After This Table

|  | Unit | +/−50% | WT % |
|---|---|---|---|
| Chemicals |  |  |  |
| Chondroitin Sulfate | Mg | 1000 | 12.62% |
| Curcumin (Nanoformulated)[1,2] | Mg | 200 | 2.52% |
| Dehydrocorybulbine (DHCB) | Mg | 100 | 1.26% |
| Geinstein | Mg | 100 | 1.26% |
| Glucosamine Hydrochloride Or Glucosamine Sulfate | Mg | 2000 | 25.25% |
| Hyaluronic Acid | Mg | 100 | 1.26% |
| Methylsufonlymethane (MSM) | Mg | 1000 | 12.62% |
| S-Adenosyl methionine (SAM) | Mg | 200 | 2.52% |
| Sulforaphane | Mg | 400 | 5.05% |
| Minerals |  |  |  |
| Boron | Mg | 2 | 0.03% |
| Calcium | Mg | 500 | 6.31% |
| Copper | Mg | 1 | 0.01% |
| Magnesium | Mg | 100 | 1.26% |
| Manganese | Mg | 2 | 0.03% |
| Molybdenum | Mg | 0.1 | 0.00% |
| Zinc (L-Opti) | Mg | 15 | 0.19% |
| Vitamins |  |  |  |
| Vitamin B$_{12}$ (Methylcobalamin) | Mg | 1 | 0.01% |
| Vitamin C | Mg | 200 | 2.52% |
| Vitamin D | IU | 2000 | 0.00% |
| Total Weight | G | 7.92 | 100.00% |

TABLE 1E

Composition Of A Mixture Of Micronutrients - May Also Include Some Bioactive Compounds From Tables Before & After This Table

|  | Unit | +/−50% | WT % |
|---|---|---|---|
| Botanicals |  |  |  |
| *Boswellia serrata* Extract | Mg | 1000 | 12.95% |
| *Corydalis yanhusuo* Root Concentrate | Mg | 200 | 2.59% |
| *Curcuma longa* Root Extract | Mg | 200 | 2.59% |
| Salix (White Willow) Bark Extract | Mg | 200 | 2.59% |
| *Zingiber officinale* Root Concentrate | Mg | 200 | 2.59% |
| Chemicals |  |  |  |
| Chondroitin Sulfate | Mg | 1000 | 12.95% |
| Curcumin (Nanoformulated)[1,2] | Mg | 200 | 2.59% |
| Dehydrocorybulbine | Mg | 100 | 1.30% |
| Geinstein | Mg | 100 | 1.30% |
| Glucosamine Hydrochloride Or Glucosamine Sulfate | Mg | 2000 | 25.90% |
| Hyaluronic Acid | Mg | 100 | 1.30% |
| Methylsufonlymethane | Mg | 1000 | 12.95% |
| S-Adenosyl methionine | Mg | 200 | 2.59% |
| Sulforaphane | Mg | 400 | 5.18% |
| Minerals |  |  |  |
| Boron | Mg | 2 | 0.03% |
| Calcium | Mg | 500 | 6.48% |
| Copper | Mg | 1 | 0.01% |
| Magnesium | Mg | 100 | 1.30% |
| Manganese | Mg | 2 | 0.03% |
| Molybdenum | Mg | 0.1 | 0.00% |
| Zinc (L-Opti) | Mg | 15 | 0.19% |
| Vitamins |  |  |  |
| Vitamin B$_{12}$ (Methylcobalamin) | Mg | 1 | 0.01% |
| Vitamin C | Mg | 200 | 2.59% |
| Vitamin D | IU | 2000 | 0.00% |
| Total Weight | G | 7.72 | 100.00% |

TABLE 1F

Composition Of A Mixture Of Micronutrients - May Also Include Some Bioactive Compounds From Tables Before & After This Table

|  | Unit | +/−50% | WT % |
|---|---|---|---|
| Botanicals |  |  |  |
| *Boswellia serrata* Extract | Mg | 1000 | 13.30% |
| *Curcuma longa* Root Extract | Mg | 200 | 2.66% |
| Salix (White Willow) Bark Extract | Mg | 200 | 2.66% |
| *Zingiber officinale* Root Concentrate | Mg | 200 | 2.66% |
| Chemicals |  |  |  |
| Chondroitin Sulfate | Mg | 1000 | 13.30% |
| Curcumin (Nanoformulated)[1,2] | Mg | 200 | 2.66% |
| Dehydrocorybulbine | Mg | 100 | 1.33% |
| Geinstein | Mg | 100 | 1.33% |
| Glucosamine Hydrochloride Or Glucosamine Sulfate | Mg | 2000 | 26.59% |
| Hyaluronic Acid | Mg | 100 | 1.33% |
| Methylsufonlymethane | Mg | 1000 | 13.30% |
| S-Adenosyl methionine | Mg | 200 | 2.66% |
| Sulforaphane | Mg | 400 | 5.32% |
| Minerals |  |  |  |
| Boron | Mg | 2 | 0.03% |
| Calcium | Mg | 500 | 6.65% |
| Copper | Mg | 1 | 0.01% |
| Magnesium | Mg | 100 | 1.33% |
| Manganese | Mg | 2 | 0.03% |
| Molybdenum | Mg | 0.1 | 0.00% |
| Zinc (L-Opti) | Mg | 15 | 0.02% |
| Vitamins |  |  |  |
| Vitamin B$_{12}$ (Methylcobalamin) | Mg | 1 | 0.01% |
| Vitamin C | Mg | 200 | 2.66% |
| Vitamin D | IU | 2000 | 0.05% |
| Total Weight | G | 7.52 | 100.00% |

TABLE 1G

Composition Of A Mixture Of Micronutrients - May Also Include Some Bioactive Compounds From Tables Before & After This Table

|  | Unit | +/−50% | WT % |
|---|---|---|---|
| Botanicals |  |  |  |
| *Boswellia serrata* Extract | Mg | 1000 | 13.66% |
| Salix (White Willow) Bark Extract | Mg | 200 | 2.73% |
| *Zingiber officinale* Root Concentrate | Mg | 200 | 2.73% |
| Chemicals |  |  |  |
| Chondroitin Sulfate | Mg | 1000 | 13.66% |
| Curcumin (Nanoformulated)[1,2] | Mg | 200 | 2.73% |
| Dehydrocorybulbine (DHCB) | Mg | 100 | 1.37% |
| Geinstein | Mg | 100 | 1.37% |
| Glucosamine Hydrochloride Or Glucosamine Sulfate | Mg | 2000 | 27.32% |
| Hyaluronic Acid | Mg | 100 | 1.37% |
| Methylsufonlymethane | Mg | 1000 | 13.66% |
| S-Adenosyl methionine | Mg | 200 | 2.73% |
| Sulforaphane | Mg | 400 | 5.46% |
| Minerals |  |  |  |
| Boron | Mg | 2 | 0.03% |
| Calcium | Mg | 500 | 6.83% |
| Copper | Mg | 1 | 0.01% |
| Magnesium | Mg | 100 | 1.37% |
| Manganese | Mg | 2 | 0.03% |
| Molybdenum | Mg | 0.1 | 0.00% |
| Zinc (L-Opti) | Mg | 15 | 0.20% |

TABLE 1G-continued

Composition Of A Mixture Of Micronutrients - May Also Include Some Bioactive Compounds From Tables Before & After This Table

|  | Unit | +/−50% | WT % |
|---|---|---|---|
| Vitamins | | | |
| Vitamin $B_{12}$ (Methylcobalamin) | Mg | 1 | 0.01% |
| Vitamin C | Mg | 200 | 2.73% |
| Vitamin D | IU | 2000 | 0.00% |
| Total Weight | G | 7.32 | 100.00% |

TABLE 1H

Composition Of A Mixture Of Micronutrients - May Also Include Some Bioactive Compounds From Tables Before & After This Table

|  | Unit | +/−50% | WT % |
|---|---|---|---|
| Botanicals | | | |
| *Boswellia serrata* Extract | Mg | 1000 | 14.04% |
| *Zingiber officinale* Root Concentrate | Mg | 200 | 2.81% |
| Chemicals | | | |
| Chondroitin Sulfate | Mg | 1000 | 14.04% |
| Curcumin (Nanoformulated)[1,2] | Mg | 200 | 2.81% |
| Dehydrocorybulbine | Mg | 100 | 1.40% |
| Geinstein | Mg | 100 | 1.40% |
| Glucosamine Hydrochloride Or Glucosamine Sulfate | Mg | 2000 | 28.09% |
| Hyaluronic Acid | Mg | 100 | 1.40% |
| Methylsufonlymethane | Mg | 1000 | 14.04% |
| S-Adenosyl methionine | Mg | 200 | 2.81% |
| Sulforaphane | Mg | 400 | 5.62% |
| Minerals | | | |
| Boron | Mg | 2 | 0.03% |
| Calcium | Mg | 500 | 7.02% |
| Copper | Mg | 1 | 0.01% |
| Magnesium | Mg | 100 | 1.40% |
| Manganese | Mg | 2 | 0.03% |
| Molybdenum | Mg | 0.1 | 0.00% |
| Zinc (L-Opti) | Mg | 15 | 0.21% |
| Vitamins | | | |
| Vitamin $B_{12}$ (Methylcobalamin) | Mg | 1 | 0.01% |
| Vitamin C | Mg | 200 | 2.81% |
| Vitamin D | IU | 2000 | 0.00% |
| Total Weight | G | 7.12 | 100.00% |

TABLE 1I

Composition Of A Mixture Of Micronutrients - May Also Include Some Bioactive Compounds From Tables Before & After This Table

|  | Unit | +/−50% | WT % |
|---|---|---|---|
| Botanicals | | | |
| *Boswellia serrata* Extract | Mg | 1000 | 14.45% |
| Chemicals | | | |
| Chondroitin Sulfate | Mg | 1000 | 14.45% |
| Curcumin (Nanoformulated)[1,2] | Mg | 200 | 2.89% |
| Dehydrocorybulbine | Mg | 100 | 1.44% |
| Geinstein | Mg | 100 | 1.44% |
| Glucosamine Hydrochloride Or Glucosamine Sulfate | Mg | 2000 | 28.90% |
| Hyaluronic Acid | M | 100 | 1.44% |
| Methylsufonlymethane | Mg | 1000 | 14.45% |
| S-Adenosyl methionine | Mg | 200 | 2.89% |
| Sulforaphane | Mg | 400 | 5.78% |

TABLE 1I-continued

Composition Of A Mixture Of Micronutrients - May Also Include Some Bioactive Compounds From Tables Before & After This Table

|  | Unit | +/−50% | WT % |
|---|---|---|---|
| Minerals | | | |
| Boron | Mg | 2 | 0.03% |
| Calcium | Mg | 500 | 7.22% |
| Copper | Mg | 1 | 0.01% |
| Magnesium | Mg | 100 | 1.44% |
| Manganese | Mg | 2 | 0.03% |
| Molybdenum | Mg | 0.1 | 0.00% |
| Zinc (L-Opti) | Mg | 15 | 0.22% |
| Vitamins | | | |
| Vitamin $B_{12}$ (Methylcobalamin) | Mg | 1 | 0.01% |
| Vitamin C | Mg | 200 | 2.89% |
| Vitamin D | IU | 2000 | 0.00% |
| Total Weight | G | 6.92 | 100.00% |

TABLE 1J

Composition Of A Mixture Of Micronutrients - May Also Include Some Bioactive Compounds From Tables Before & After This Table

|  | Unit | +/−50% | WT % |
|---|---|---|---|
| Botanical | | | |
| *Boswellia serrata* Extract | Mg | 1000 | 14.66% |
| Chemicals | | | |
| Chondroitin Sulfate | Mg | 1000 | 14.66% |
| Curcumin (Nanoformulated)[1,2] | Mg | 200 | 2.93% |
| Geinstein | Mg | 100 | 1.47% |
| Glucosamine Hydrochloride Or Glucosamine Sulfate | Mg | 2000 | 29.32% |
| Hyaluronic Acid | Mg | 100 | 1.47% |
| Methylsufonlymethane | Mg | 1000 | 14.66% |
| S-Adenosyl methionine | Mg | 200 | 2.93% |
| Sulforaphane | Mg | 400 | 5.86% |
| Minerals | | | |
| Boron | Mg | 2 | 0.03% |
| Calcium | Mg | 500 | 7.33% |
| Copper | Mg | 1 | 0.01% |
| Magnesium | Mg | 100 | 1.47% |
| Manganese | Mg | 2 | 0.03% |
| Molybdenum | Mg | 0.1 | 0.00% |
| Zinc (L-Opti) | Mg | 15 | 0.22% |
| Vitamins | | | |
| Vitamin $B_{12}$ (Methylcobalamin) | Mg | 1 | 0.01% |
| Vitamin C | Mg | 200 | 2.93% |
| Vitamin D | IU | 2000 | 0.00% |
| Total Weight | G | 6.82 | 100.00% |

TABLE 1K

Composition Of A Mixture Of Micronutrients - May Also Include Some Bioactive Compounds From Tables Before & After This Table

|  | Unit | +/−50% | WT % |
|---|---|---|---|
| Botanical | | | |
| *Boswellia serrata* Extract | Mg | 1000 | 15.10% |
| Chemicals | | | |
| Chondroitin Sulfate | Mg | 1000 | 15.10% |
| Curcumin (Nanoformulated)[1,2] | Mg | 200 | 3.02% |
| Geinstein | Mg | 100 | 1.51% |

TABLE 1K-continued

Composition Of A Mixture Of Micronutrients - May Also Include Some Bioactive Compounds From Tables Before & After This Table

|  | Unit | +/−50% | WT % |
|---|---|---|---|
| Glucosamine Hydrochloride Or Glucosamine Sulfate | Mg | 2000 | 30.21% |
| Hyaluronic Acid | Mg | 100 | 1.51% |
| Methylsufonlymethane | Mg | 1000 | 15.10% |
| Sulforaphane | Mg | 400 | 6.04% |
| Minerals | | | |
| Boron | Mg | 2 | 0.03% |
| Calcium | Mg | 500 | 7.55% |
| Copper | Mg | 1 | 0.02% |
| Magnesium | Mg | 100 | 1.51% |
| Manganese | Mg | 2 | 0.03% |
| Molybdenum | Mg | 0.1 | 0.00% |
| Zinc (L-Opti) | Mg | 15 | 0.23% |
| Vitamins | | | |
| Vitamin $B_{12}$ (Methylcobalamin) | Mg | 1 | 0.02% |
| Vitamin C | Mg | 200 | 3.02% |
| Vitamin D | IU | 2000 | 0.00% |
| Total Weight | G | 6.61 | 100.00% |

500 mg of avocado soybean unsaponifiables (ASU) can be added to compositions in Table-1D through Table-1K.

300 mg of black tart cherry extract can be added to compositions in Table-1D through Table-1K.

300 mg of pine bark extract can be added to compositions in Table-1D through Table-1K.

TABLE 2A

Composition Of A Mixture Of Antioxidants - May Also Include Some Bioactive Compounds From Tables Before & After This Table

| Chemicals | Unit | +/−50% | WT % |
|---|---|---|---|
| Acetyl-L-Carnitine | Mg | 200 | 2.12% |
| Alpha-R-Lipoic Acid | Mg | 20 | 0.21% |
| Coenzyme $Q_{10}$ (Nanoformulated)[1,2] | Mg | 200 | 2.12% |
| D-Ribose | Mg | 400 | 4.25% |
| Epigallocatechin Gallate | Mg | 200 | 2.12% |
| Ferulic Acid | Mg | 200 | 2.12% |
| Hyaluronic Acid | Mg | 200 | 2.12% |
| Inositol Hexanicotinate | Mg | 2000 | 21.23% |
| Isothiocyanate Sulforaphane | Mg | 200 | 2.12% |
| L-Arginine | Mg | 4000 | 42.46% |
| L-Analyl-L-Glutamine | Mg | 200 | 2.12% |
| L-Glutamine | Mg | 200 | 2.12% |
| L-Glutathione (Or Ebselen Or N-Acetyl-L-Cysteine) | Mg | 200 | 2.12% |
| Pterostilbene (Nanoformulated)[1,2] | Mg | 200 | 2.12% |
| Quercetin (Nanoformulated)[1,2] | Mg | 200 | 2.12% |
| Resveratrol (Nanoformulated)[1,2] | Mg | 200 | 2.12% |
| Superoxide Dismutase* (Nanoformulated)[1,2] | Mg | 200 | 2.12% |
| Ubiquinol (Nanoformulated)[1,2] | Mg | 400 | 4.25% |
| Total Weight | G | 9.42 | 100.00% |

TABLE 2B

Additional Composition Of A Mixture Of Antioxidants - May Also Include Some Bioactive Compounds From Tables Before & After This Table

| Botanicals | Unit | +/−50% | WT % |
|---|---|---|---|
| *Aronia melanocarpa*[+] | Mg | 200 | 12.50% |
| *Citrus limonum*[+] | Mg | 200 | 12.50% |
| *Daucus carota*[+] | Mg | 200 | 12.50% |
| *Hibiscus* spp.[+] | Mg | 200 | 12.50% |
| *Malus domestica*[+] | Mg | 200 | 12.50% |
| *Ribes nigrum*[+] | Mg | 200 | 12.50% |
| *Sambucus nigra*[+] | Mg | 200 | 12.50% |
| *Vaccinium* spp.[+] | Mg | 200 | 12.50% |
| Total Weight | G | 1.60 | 100.00% |

TABLE 3A

Composition Of A Multi-Serve Antioxidant Liquid - May Also Include Some Bioactive Compounds From Tables Before & After This Table

|  | Unit | +/−50% | WT % |
|---|---|---|---|
| Botanicals | | | |
| *Actinidia chinenesis*[+] | G | 25 | 5.49% |
| *Ananas comosus*[+] | G | 25 | 5.49% |
| *Cocos nucifera*[+] | G | 350 | 76.88% |
| *Garcinia mangostana*[+] | G | 25 | 5.49% |
| *Litchi chinensis*[+] | G | 25 | 5.49% |
| *Vitis* spp.[+] | G | 0.75 | 0.16% |
| Chemicals | | | |
| Citicoline (Or L-Alpha Glycerylphosphorylcholine) | G | 0.75 | 0.16% |
| Coenzyme $Q_{10}$ (Nanoformulated)[1,2] | G | 0.75 | 0.16% |
| D-Ribose | G | 0.75 | 0.16% |
| L-Analyl-L-Glutamine | G | 0.75 | 0.16% |
| L-Theanine | G | 0.75 | 0.16% |
| Ubiquinol (Nanoformulated)[1,2] | G | 0.75 | 0.16% |
| Total Weight | G | 455.25 | 100.00% |

TABLE 3B

Composition Of A Single-Serve Antioxidant Liquid - May Also Include Some Bioactive Compounds From Tables Before & After This Table

|  | Unit | +/−50% | WT % |
|---|---|---|---|
| Chemicals | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.44% |
| D-Ribose | G | 0.25 | 0.05% |
| Gamma-Aminobutyric Acid | G | 0.25 | 0.05% |
| Inulin | G | 5 | 1.09% |
| L-Analyl-L-Glutamine | G | 0.25 | 0.05% |
| L-Theanine | G | 0.25 | 0.05% |
| Melatonin (Extended Release) | G | 0.002 | 0.00% |
| Omega 3-6-9 Acid (Including Decosahexanoic Acid) (Nanoformulated)[1] | G | 0.25 | 0.05% |
| Plant Sterol (Nanoformulated)[1] | G | 5 | 1.09% |
| Ubiquinol (Nanoformulated)[1,2] | G | 0.25 | 0.05% |
| Uridine | G | 0.25 | 0.05% |
| Sweeteners | | | |
| Erythritol | G | 10 | 2.18% |
| *Stevia rebaudiana*[+] | G | 0.025 | 0.01% |
| Trehalose | G | 0.25 | 0.05% |

TABLE 3B-continued

Composition Of A Single-Serve Antioxidant Liquid - May Also Include Some Bioactive Compounds From Tables Before & After This Table

| | Unit | +/−50% | WT % |
|---|---|---|---|
| Others | | | |
| Acidified Coconut Water (&/Or *Aloe Vera* Juice &/Or Filter Water) | G | 435 | 94.66% |
| Live *Lactobacillus plantarum* 299v | Billion | 10 | 0.00% |
| Total Weight | G | 459.52 | 100.00% |

TABLE 3C

Composition Of A Single-Serve Antioxidant Liquid - May Also Include Some Bioactive Compounds From Tables Before & After This Table

| | Unit | +/−50% | WT % |
|---|---|---|---|
| Botanicals | | | |
| *Aronia melanocarpa*[+] | G | 0.25 | 0.05% |
| *Citrus limonum*[+] | G | 0.25 | 0.05% |
| *Daucus carota*[+] | G | 0.25 | 0.05% |
| *Hibiscus* spp.[+] | G | 0.25 | 0.05% |
| *Malus domestica*[+] | G | 0.25 | 0.05% |
| *Ribes nigrum*[+] | G | 0.25 | 0.05% |
| *Sambucus nigra*[+] | G | 0.25 | 0.05% |
| *Vaccinium* spp.[+] | G | 0.25 | 0.05% |
| Chemicals | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.43% |
| D-Ribose | G | 0.25 | 0.05% |
| Gamma-Aminobutyric Acid | G | 0.25 | 0.05% |
| Inulin | G | 5 | 1.08% |
| L-Analyl-L-Glutamine | G | 0.25 | 0.05% |
| L-Theanine | G | 0.25 | 0.05% |
| Melatonin (Extended Release) | G | 0.002 | 0.00% |
| Omega 3-6-9 Acid (Including Decosahexaenoic Acid) (Nanoformulated)[1] | G | 0.25 | 0.05% |
| Plant Sterol (Nanoformulated)[1] | G | 5 | 1.08% |
| Ubiquinol (Nanoformulated)[1,2] | G | 0.25 | 0.05% |
| Uridine | G | 0.25 | 0.05% |
| Sweeteners | | | |
| Erythritol | G | 10 | 2.17% |
| *Stevia rebaudiana*[+] | G | 0.025 | 0.01% |
| Trehalose | G | 0.25 | 0.05% |
| Others | | | |
| Acidified Coconut Water (&/Or *Aloe Vera* Juice &/Or Filter Water) | G | 435 | 94.25% |
| Live *Lactobacillus plantarum* 299v | Billion | 10 | 0.00% |
| Total Weight | G | 461.52 | 100.00% |

TABLE 3D

Composition Of Botanicals - May Also Include Some Bioactive Compounds From Tables Before & After This Table

| | Unit | +/−50% | WT % |
|---|---|---|---|
| Botanicals | | | |
| *Chamomilla recutita* | Mg | 200 | 6.66% |
| *Humulus lupulus* | Mg | 200 | 6.66% |
| *Lavandula angustifolia* | Mg | 200 | 6.66% |
| *Melissa officinalis* | Mg | 200 | 6.66% |
| *Passiflora incarnate* | Mg | 200 | 6.66% |
| *Valeriana officinalis* | Mg | 200 | 6.66% |
| Chemicals | | | |
| Bromelain | Mg | 400 | 13.32% |
| Citicoline (Or L-Alpha Glycerylphosphorylcholine) | Mg | 200 | 6.66% |
| Gamma-Aminobutyric Acid | Mg | 200 | 6.66% |
| L-Theanine | Mg | 200 | 6.66% |
| L-Tryptophan | Mg | 800 | 26.64% |
| Melatonin (Extended Release) | Mg | 3 | 0.10% |
| Others | Unit | | |
| Live *Bifidobacterium longum* | Billion | 10 | 0.00% |
| Live *Lactobacillus helveticus* | Billion | 10 | 0.00% |
| Total Weight | G | 3.00 | 100.00% |

TABLE 3E

Composition Of A Mixture Of Electrolytes & Dextrose - May Also Include Some Bioactive Compounds From Tables Before & After This Table

| Nutrients | Unit Per 8 Fluid Oz |
|---|---|
| Sodium | 10.6 mEq |
| Potassium | 4.7 mEq |
| Chloride | 8.3 mEq |
| Zinc | 1.9 Mg |
| Dextrose | 5.9 G |

Smart Container

Suitable biodegradable material (e.g., silk/plant derived plastic material) can be used as a container.

Lignin (or lignen) is an integral complex chemical compound of the secondary cell walls of plants. A plant derived plastic can be based on lignin (or lignen) as a base material.

Furthermore, lignin (or lignen) can be integrated (multi-layered) with chitin (a biopolymer based on the N-acetyl-glucosamine monomer) and/or chitin's variant deacetylated counterpart chitosan and/or fibroin (a protein derived from silk) as a base material.

TABLE 4

Compositions Of A Biodegradable Plastic Material

| Compositions | Wt % Material A | Wt % Material B | Wt % Material C | Wt % Material D |
|---|---|---|---|---|
| 1 | 80% Lignin | 20% Chitin | | |
| 2 | 80% Lignin | 20% Chitosan | | |
| 3 | 80% Lignin | 10% Chitin | 10% Chitosan | |
| 4 | 80% Lignin | 20% Fibroin | | |
| 5 | 80% Lignin | 10% Chitin | 10% Fibroin | |
| 6 | 80% Lignin | 10% Chitosan | 10% Fibroin | |
| 7 | 80% Lignin | 10% Chitosan | 10% Fibroin | |
| 8 | 80% Lignin | 5% Chitosan | 5% Chitosan | 10% Fibroin |

A lens/an array of lenses (e.g., utilizing silk material) can be integrated on the interior wall of the container to detect the presence/growth of bacteria/microbes (e.g., bacteria/microbes in a liquid mixture).

Furthermore, the lens/array of lenses (e.g., utilizing silk material) can be integrated with a biological colony counter to estimate/count good/bad bacteria.

One-Dimensional/two-dimensional barcode/quick response (QR) codes and/or a radio frequency identification device (RFID) active/passive tag and/or a near-field communication (NFC) tag and/or an ultra-lower power consumption microprocessor (e.g., an Ambiqmicro ARM Cortex™-M3 microcontroller or an organic transistor based microprocessor or nano-scaled InAs XOI based microprocessor or Freescale 2 millimeters×2 millimeters KL02 chip-scale package (CSP) (chip-scale package with the components of a micro-scaled computer can be configured with a micro IP/light weight IP address) and/or a memory/storage component (e.g., a printed memristor on a flexible substrate) and a thin-film printed battery/miniature solar cell component can be integrated on an exterior label (covers only a segment of the container's exterior) to (a) deliver information about the product, (b) advertise (e.g., click to view more product (e.g., a drug) information linked with a website and/or click to receive a product coupon in near real-time/real-time), (c) interact (e.g., collective quorum vote on user liking/disliking of the product in near real-time/real-time) with a user's portable internet appliance (e.g., a smart phone/tablet personal computer) and (d) communicate with an inventory management system and/or smart shopping cart, wherein the smart shopping cart is configured (with a removable (about seven (7) inch) display device integrated with a near-field communication tag and a near-field communication reader) to determine the user's commercial identity/personality on the doorway entrance of the retailer.

Furthermore, the retail location can be enabled with sensors, augmented reality and computer vision (including self-learning computer vision) for enhanced experience of the user.

In another embodiment, a smart refrigerator containing (food) packages (wherein each package is integrated with a usage indicator microchip) can communicate (wirelessly) with an internet connected home gateway/storage subsystem. Thus, the home gateway/storage subsystem can communicate (wirelessly) with the user's portable internet appliance prior to any shopping.

The user's commercial identity/personality can be enhanced by a collection of inputs from statistically similar users in near real-time/real-time and these inputs can be analyzed by data mining, ANN (artificial neural networks), hierarchical cluster analysis and KNN (K-nearest neighbor analysis) and intelligent learning algorithm. These inputs can complement/enhance the user's commercial identity/personality.

Furthermore, these inputs can include the user's facial recognition profile (wherein a facial data is converted into a mathematical code or a pattern) to complement/enhance the user's commercial identity/personality.

The user experience can be further enhanced by artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

It should be noted that artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) can be enhanced by quantum computing or quantum computing based machine learning.

The exterior label can be integrated with thermochromic ink dot to indicate the temperature of the container.

The exterior label can be placed on a heat-dissipating thermally conducting flexible polymer film. Furthermore, the thermally conducting flexible polymer film can be integrated with a barrier thin-film (e.g., 100 nanometers thick alumina ($Al_2O_3$) fabricated/constructed, utilizing a low-temperature atomic layer deposition (ALD) process).

Humidity, oxygen and water can slowly diffuse into the container to degrade the liquid mixture over time. The barrier thin-film can prevent against humidity, oxygen and water.

The container can be suitably (about 15 degrees' centigrade hot-cold side temperature difference) heated or cooled by an array of (embedded superlattice based thin-film Peltier) thermoelectrics, herein the thermoelectrics can be integrated (by utilizing Lithographie-Galvanoformung-Abformung (LIGA), electroforming and microelectro-mechanical-system process) on the heat-dissipating thermally conducting flexible polymer film. The thermoelectrics covers only a section of the container's exterior.

Thermal resistance between the thermoelectrics and thermally conducting flexible polymer film is a critical parameter for an efficient heating and/or cooling.

The array of thermoelectrics can be electrically powered by an array of printed thin-film batteries/titanium dioxide solar cells (with porphyrin dyes).

TABLE 5

Composition Of A Mixture For Expression Of Beneficial NrF2 Protein - May Also Include Some Bioactive Compounds From Tables Before & After This Table (Except Table-4 and Table-6)

| Botanicals | Unit | +/−50% | WT % |
|---|---|---|---|
| Astragalus membranaceus[+] | Mg | 200 | 6.25% |
| Bacopa monnieri[+] | Mg | 200 | 6.25% |
| Camellia sinensis[+] (Black) | Mg | 200 | 6.25% |
| Camellia sinensis[+] (Green) | Mg | 200 | 6.25% |
| Curcuma longa[+] (Or A Curcuminoids Compound)[1,2,3,4] | Mg | 400 | 12.50% |
| Euterpe oleracea[+] | Mg | 200 | 6.25% |
| Hippophae rhamnoides[+] | Mg | 200 | 6.25% |
| Lycium barbarum[+] | Mg | 200 | 6.25% |
| Phyllanthus emblica[+] | Mg | 200 | 6.25% |
| Punica granatum[+] | Mg | 200 | 6.25% |
| Silybum marianum[+] | Mg | 200 | 6.25% |
| Tinospora cordifolia[+] | Mg | 200 | 6.25% |
| Vitis spp.[+] | Mg | 200 | 6.25% |
| Wasabia japonica[+] | Mg | 200 | 6.25% |
| Withania somnifera[+] | Mg | 200 | 6.25% |
| Total Weight | G | 3.20 | 100.00% |

Mitochondria are both generators of and targets for reactive molecular species. Therefore, oxidative stress is intimately linked with mitochondrial dysfunction. The abundant mitochondria in a human brain are major sites of generation and action of reactive oxygen species/reactive nitrogen species (RNS), since a human brain utilizes about 20% of the inspired oxygen and 90% of the consumed oxygen to produce energy during oxidative phosphorylation. Thus, a human brain is particularly sensitive to free radical damage/oxidative stress. Mitochondrial turnover is dependent on autophagy (meaning self-eating), which declines with age and is frequently dysfunctional in many neurodegenerative diseases (including Alzheimer's). Autophagy can engage in cross-talk with reactive oxygen species/reactive nitrogen species in both cell signaling and protein damage. The mammalian Target of Rapamycin is an autophagy pathway. The mammalian Target of Rapamycin pathway can function as an inhibitor of the initiation process of autophagy.

Alzheimer's, Cardiovascular and Type-2 Diabetes diseases have misfolded and they all have damaged proteins triggered by pathology at the molecular level. There are about 100,000 different proteins in a human body. After each protein is synthesized, it must be folded into the right shape to be functional. Mistakes can happen, that is why cells have sophisticated housekeeping mechanisms to repair or destroy poorly formed proteins before they can do any harm. Occasionally, a misfolded protein can evade these sophisticated housekeeping mechanisms and accumulates in sufficient quantities to clump together to damage/kill the cell.

One way to treat Alzheimer's, Cardiovascular and Type-2 Diabetes diseases, caused by misfolded proteins is to stimulate the housekeeping mechanisms by activating autophagy (or alternatively, suppressing/inhibiting the mammalian Target of Rapamycin).

As a central controller of cell growth and nutrient sensor, the mammalian Target of Rapamycin plays a key role in aging, Alzheimer's, Cardiovascular and Diabetes diseases.

Furthermore, AMPK up regulation (via bioactive compounds and/or bioactive molecules in *Momordica charantia*) activates autophagy via dual mechanisms involving not only by suppressing/inhibiting the mammalian Target of Rapamycin (in particular the mammalian Target of Rapamycin C1), but also by direct phosphorylation of ULK1 protein.

The bioactive compounds 100 and/or bioactive molecules 100A to suppress/inhibit the mammalian Target of Rapamycin can be encapsulated/caged in the nanoshell 120.

The nanoshell 120 decorated with a targeting ligand, wherein the targeting ligand can recognize/match/bind with adenosine receptors—thus allowing a human body's blood-brain barrier (BBB) to be opened for the passage of the nanoshell 120 to deliver the bioactive compounds 100 and/or bioactive molecules 100A to suppress/inhibit the mammalian Target of Rapamycin in a human brain.

TABLE 6

Molecular Docking Score With The Mammalian Target Of Rapamycin Utilizing Computational Chemistry Software
(Also Illustrated In FIG. 5A and 5B)

| Chemicals | Molecular Score |
| --- | --- |
| Rapamycin/Sirolimus (Known To Suppress/Inhibit The Mammalian Target Of Rapamycin) | −8.64 |
| Withaferin A | −7.04 |
| Cycloastragenol | −2.27 |
| Bisdemethoxycurcumin | −1.86 |
| Curcumin | −1.82 |
| Vitamin $D_3$ | −1.72 |
| Verbascoside | −1.13 |
| Momordin | −0.86 |
| SMER-28 | −0.71 |
| Resveratrol | −0.31 |
| Epigallocatechin gallate | −0.28 |
| Trehalose (Can Induce Autophagy Independent Of The Mammalian Target Of Rapamycin) | −0.25 |
| N,N-dimethylimidodicarbonimidic diamide (Metformin) | −0.11 |

Rapamycin can generate buildup of fatty acids and eventually an increase in insulin resistance leading to Type-2 Diabetes disease. But a combination of rapamycin and metformin can reduce insulin resistance and treat aging related diseases.

Furthermore, the combination of rapamycin and metformin can be enhanced in its efficacy and synergy by adding one or more chemicals (of suitable amount(s)): withaferin A, cycloastragenol, bisdemethoxycurcumin, curcumin, vitamin D3, verbascoside, momordin, SMER-28, resveratrol, epigallocatechin gallate and trehalose.

Alternatively, the above combination of rapamycin and metformin can be suitably replaced in its efficacy and synergy by one or more (of suitable amount(s)): withaferin A, cycloastragenol, bisdemethoxycurcumin, curcumin, vitamin $D_3$, verbascoside, momordin, SMER-28, resveratrol, epigallocatechin gallate and trehalose with metformin.

TABLE 7A

Composition Of A Mixture For Suppressing/Inhibiting The Mammalian Target Of Rapamycin - May Also Include Some Bioactive Compounds From Tables Before & After This Table

| | Unit | +/−50% | WT % |
| --- | --- | --- | --- |
| Botanical | | | |
| *Momordica charantia*+ Chemicals | Mg | 200 | 20.00% |
| Withaferin A (Or A Chemical Derivative Or A Structural Analog Of Withaferin A) (Nanoformulated)[1,2] | Mg | 400 | 40.00% |
| Withanolides (Or A Chemical Derivative Or A Structural Analog Of Withanolides) (Nanoformulated)[1,2] | Mg | 200 | 20.00% |
| Withanosides (Or A Chemical Derivative Or A Structural Analog Of Withanosides) (Nanoformulated)[1,2] | Mg | 200 | 20.00% |
| Total Weight | G | 1.00 | 100.00% |

TABLE 7B

Composition Of A Mixture For Suppressing/Inhibiting The Mammalian Target Of Rapamycin - May Also Include Some Bioactive Compounds From Tables Before & After This Table

| | Unit | +/−50% | WT % |
| --- | --- | --- | --- |
| Botanical | | | |
| *Momordica charantia*+ Chemicals | Mg | 200 | 12.50% |
| Bisdemethoxycurcumin (Nanoformulated)[1,2] | Mg | 200 | 12.50% |
| Curcumin (Nanoformulated)[1,2,3,4] | Mg | 200 | 12.50% |
| Cycloastragenol (Nanoformulated)[1,2] | Mg | 200 | 12.50% |
| Withaferin A (Or A Chemical Derivative Or A Structural Analog Of Withaferin A)[1,2] | Mg | 400 | 25.00% |
| Withanolides (Or A Chemical Derivative Or A Structural Analog Of Withanolides) (Nanoformulated)[1,2] | Mg | 200 | 12.50% |
| Withanosides (Or A Chemical Derivative Or A Structural Analog Of Withanosides) (Nanoformulated)[1,2] | Mg | 200 | 12.50% |
| Vitamin | | | |
| Vitamin $D_3$ (Cholecalciferol) | Mg | 0.06 | 0.00% |
| Total Weight | G | 1.60 | 100.00% |

TABLE 7C

Composition Of A Mixture For Suppressing/Inhibiting The Mammalian Target Of Rapamycin - May Also Include Some Bioactive Compounds From Tables Before & After This Table

|  | Unit | +/−50% | WT % |
|---|---|---|---|
| Botanical |  |  |  |
| *Momordica charantia*[+] | Mg | 200 | 7.66% |
| Chemicals |  |  |  |
| 6-Bromo-N-2-propenyl-4-quinazolinamine (SMER-28) | Mg | 10 | 0.38% |
| Bisdemethoxycurcumin (Nanoformulated)[1,2] | Mg | 200 | 7.66% |
| Curcumin (Nanoformulated)[1,2,3,4] | Mg | 200 | 7.66% |
| Cycloastragenol (Nanoformulated)[1,2] | Mg | 200 | 7.66% |
| Epigallocatechin gallate | Mg | 200 | 7.66% |
| Momordin | Mg | 200 | 7.66% |
| Resveratrol (Nanoformulated)[1,2] | Mg | 200 | 7.66% |
| Trehalose | Mg | 200 | 7.66% |
| Verbascoside | Mg | 200 | 7.66% |
| Withaferin A (Or A Chemical Derivative Or A Structural Analog Of Withaferin A) (Nanoformulated)[1,2] | Mg | 400 | 15.33% |
| Withanolides (Or A Chemical Derivative Or A Structural Analog Of Withanolides) (Nanoformulated)[1,2] | Mg | 200 | 7.66% |
| Withanosides (Or A Chemical Derivative Or A Structural Analog Of Withanosides) (Nanoformulated)[1,2] | Mg | 200 | 7.66% |
| Vitamin |  |  |  |
| Vitamin D$_3$ (Cholecalciferol) | Mg | 0.06 | 0.00% |
| Total Weight | G | 2.61 | 100.00% |

TABLE 7D

Composition Of A Mixture For Suppressing/Inhibiting The Mammalian Target Of Rapamycin - May Also Include Some Bioactive Compounds From Tables Before & After This Table

|  | Unit | +/−50% | WT % |
|---|---|---|---|
| Botanicals |  |  |  |
| *Cinnamomum zeylanicum*[+] | Mg | 200 | 6.67% |
| *Momordica charantia*[+] | Mg | 200 | 6.67% |
| *Vitis vinifera*[+] (e.g., Seed Extract) | Mg | 200 | 6.67% |
| Chemicals |  |  |  |
| Bisdemethoxycurcumin (Nanoformulated)[1,2] | Mg | 200 | 6.67% |
| Curcumin (Nanoformulated)[1,2,3,4] | Mg | 200 | 6.67% |
| Cycloastragenol (Nanoformulated)[1,2] | Mg | 200 | 6.67% |
| Epigallocatechin gallate | Mg | 200 | 6.67% |
| Momordin | Mg | 200 | 6.67% |
| N,N-dimethylimidodicarbonimidic diamide (Or Chemical Derivative Or Structural Analog Of N,N-dimethylimidodicarbonimidic diamide) | Mg | 200 | 6.67% |
| Proanthocyanidins | Mg | 200 | 6.67% |
| Resveratrol (Nanoformulated)[1,2] | Mg | 200 | 6.67% |
| Withaferin A (Or A Chemical Derivative Or A Structural Analog Of Withaferin A) (Nanoformulated)[1,2] | Mg | 400 | 13.33% |
| Withanolides (Or A Chemical Derivative Or A Structural Analog Of Withanolides) (Nanoformulated)[1,2] | Mg | 200 | 6.67% |
| Withanosides (Or A Chemical Derivative Or A Structural Analog Of Withanosides) (Nanoformulated)[1,2] | Mg | 200 | 6.67% |

TABLE 7D-continued

Composition Of A Mixture For Suppressing/Inhibiting The Mammalian Target Of Rapamycin - May Also Include Some Bioactive Compounds From Tables Before & After This Table

|  | Unit | +/−50% | WT % |
|---|---|---|---|
| Vitamin |  |  |  |
| Vitamin D$_3$ (Cholecalciferol) | Mg | 0.06 | 0.00% |
| Total Weight | G | 3.00 | 100.00% |

TABLE 8A

Composition Of A Mixture For Lowering The Risks Of Alzheimer's Disease - May Also Include Some Bioactive Compounds From Tables Before & After This Table

|  | Unit | +/−50% | WT % |
|---|---|---|---|
| Botanicals |  |  |  |
| *Bacopa monnieri*[+] | Mg | 200 | 2.01% |
| *Boswellia serrata*[+1] | Mg | 200 | 2.01% |
| *Camellia sinensis*[+] (Black) | Mg | 200 | 2.01% |
| *Camellia sinensis*[+] (Green) | Mg | 200 | 2.01% |
| *Cinnamomum zeylanicum*[+] | Mg | 200 | 2.01% |
| *Curcuma longa*[+] (Or A Curcuminoids Compound)[1,2,3,4] | Mg | 400 | 4.01% |
| *Emblica officinalis*[+] | Mg | 200 | 2.01% |
| *Mucuna pruriens*[+] | Mg | 200 | 2.01% |
| *Paeoniae alba*[+] | Mg | 200 | 2.05% |
| *Panax quinquefolius*[+] | Mg | 200 | 2.01% |
| *Polygala tenuifolia*[+] | Mg | 200 | 2.01% |
| *Rosmarinus officinalis*[+] | Mg | 200 | 2.01% |
| *Silybum marianum*[+] | Mg | 200 | 2.01% |
| *Vitis vinifera*[+] | Mg | 200 | 2.01% |
| *Withania somnifera*[+] | Mg | 200 | 2.01% |
| Chemicals |  |  |  |
| Acetylcholine (Or Choline Or Phosphatidyl Choline) | Mg | 200 | 2.01% |
| Alpha-R-Lipoic Acid | Mg | 20 | 0.20% |
| Aniracetam (Or Piracetam) | Mg | 200 | 2.01% |
| Caffeine | Mg | 20 | 0.20% |
| Citicoline (Or L-Alpha Glycerylphosphorylcholine) | Mg | 200 | 2.01% |
| Coenzyme Q$_{10}$ (Nanoformulated)[1,2] | Mg | 200 | 2.01% |
| DMAE (Dimethyl Amino Ethanol) | Mg | 200 | 2.01% |
| Epigallocatechin gallate | Mg | 200 | 2.01% |
| Fisetin | Mg | 200 | 2.01% |
| Huperzine A | Mg | 200 | 2.01% |
| L-Arginine | Mg | 200 | 2.01% |
| L-Carnosine | Mg | 200 | 2.01% |
| L-Dopa | Mg | 100 | 1.00% |
| L-Glutathione (Or Ebselen Or N-Acetyl-L-Cysteine) | Mg | 200 | 2.01% |
| L-Theanine | Mg | 200 | 2.01% |
| L-Tyrosine (Or M-Tyrosine Or N-Acetyl Tyrosine) | Mg | 200 | 2.01% |
| Melatonin (Extended Release) | Mg | 3 | 0.03% |
| N-Acetyl-L-Carnitine | Mg | 400 | 4.01% |
| Omega 3-6-9 Acid (Including Decosahexanoic Acid) (Nanoformulated)[1,2] | Mg | 200 | 2.01% |
| Picamilon | Mg | 200 | 2.01% |
| Phosphatidylserine | Mg | 200 | 2.01% |
| Pyrroloquinoline Quinone (Nanoformulated)[1,2] | Mg | 20 | 0.20% |
| Quercetin[1,2] | Mg | 200 | 2.01% |
| Resveratrol[1,2] | Mg | 200 | 2.01% |
| Tetramethylpyrazine (TMP) | Mg | 200 | 2.01% |
| Trehalose | Mg | 200 | 2.01% |
| Ubiquinol (Nanoformulated)[1,2] | Mg | 1000 | 10.03% |
| Uridine | Mg | 200 | 2.01% |
| Vinpocetine | Mg | 200 | 2.01% |

TABLE 8A-continued

Composition Of A Mixture For Lowering The Risks Of Alzheimer's Disease - May Also Include Some Bioactive Compounds From Tables Before & After This Table

| | Unit | +/−50% | WT % |
|---|---|---|---|
| Withaferin A (Or Chemical Derivative Or Structural Analog Of Withaferin A) (Nanoformulated)[1,2] | Mg | 400 | 4.01% |
| Mineral | | | |
| Magnesium L-Threonate | Mg | 400 | 4.01% |
| Vitamins | | | |
| Vitamin $B_{12}$ (Methylcobalamin) | Mg | 1 | 0.01% |
| Vitamin $D_3$ | Mg | 0.25 | 0.00% |
| Vitamin $K_2$ | Mg | 2.0 | 0.02% |
| Total Weight | G | 9.97 | 100.00% |

TABLE 8B

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Botanicals | | | |
| Bacopa monnieri[+] | Mg | 200 | 2.16% |
| Boswellia serrata[+1] | Mg | 200 | 2.16% |
| Chamomilla recutita | Mg | 200 | 2.16% |
| Cinnamomum zeylanicum[+] | Mg | 200 | 2.16% |
| Curcuma longa[+] (Or A Curcuminoids Compound)[1,2,3,4] | Mg | 400 | 4.33% |
| Humulus lupulus | Mg | 200 | 2.16% |
| Melissa officinalis | Mg | 200 | 2.16% |
| Passiflora incarnate | Mg | 200 | 2.16% |
| Silybum marianum[+] | Mg | 200 | 2.16% |
| Valeriana officinalis | Mg | 200 | 2.16% |
| Withania somnifera[+] | Mg | 200 | 2.16% |
| Chemicals | | | |
| Acetylcholine (Or Choline Or Phosphatidyl Choline) | Mg | 200 | 2.16% |
| Caffeine | Mg | 20 | 0.22% |
| Citicoline (Or L-Alpha Glycerylphosphorylcholine) | Mg | 200 | 2.16% |
| Coenzyme $Q_{10}$ (Nanoformulated)[1,2] | Mg | 200 | 2.16% |
| L-Glutathione (Or Ebselen Or N-Acetyl-L-Cysteine) | Mg | 200 | 2.16% |
| L-Theanine | Mg | 200 | 2.16% |
| L-Tyrosine (Or M-Tyrosine Or N-Acetyl Tyrosine) | Mg | 200 | 2.16% |
| Melatonin (Extended Release) | Mg | 3 | 0.03% |
| N-Acetyl-L-Carnitine | Mg | 400 | 4.33% |
| Omega 3-6-9 Acid (Including Decosahexanoic Acid) (Nanoformulated)[1,2] | Mg | 200 | 2.16% |
| Phosphatidylserine | Mg | 200 | 2.16% |
| Pyrroloquinoline Quinone (Nanoformulated)[1,2] | Mg | 20 | 0.22% |
| Quercetin (Nanoformulated)[1,2] | Mg | 200 | 2.16% |
| Resveratrol (Nanoformulated)[1,2] | Mg | 200 | 2.16% |
| Tetramethylpyrazine (TMP) | Mg | 200 | 2.16% |
| Trehalose | Mg | 200 | 2.16% |
| Ubiquinol (Nanoformulated)[1,2] | Mg | 1000 | 10.82% |
| Uridine | Mg | 200 | 2.16% |
| Withaferin A (Or Chemical Derivative Or Structural Analog Of Withaferin A) (Nanoformulated)[1,2] | Mg | 400 | 4.33% |
| Mineral | | | |
| Magnesium L-Threonate | Mg | 400 | 4.33% |

TABLE 8B-continued

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Vitamins | | | |
| Vitamin $B_{12}$ (Methylcobalamin) | Mg | 1 | 0.01% |
| Vitamin $D_3$ | Mg | 0.25 | 0.00% |
| Vitamin $K_2$ | Mg | 2.0 | 0.02% |
| Other | | | |
| Lactoferrin | Mg | 2000 | 21.63% |
| Total Weight | G | 9.25 | 100.00% |

[+1] *Boswellia serrata* can suppress/inhibit 5-lipoxygenase. A bioactive compound (e.g., 3-O-acetyl-11-keto-β-boswellic acid) of *Boswellia serrata*'s can be nanoformulated to improve its bioavailability.

TABLE 8C

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Botanicals | | | |
| Tinospora cordifolia[+] | Mg | 200 | 5.20% |
| Withania somnifera[+] | Mg | 200 | 5.20% |
| Chemicals | | | |
| Caffeine | Mg | 20 | 0.52% |
| Citicoline (Or L-Alpha Glycerylphosphorylcholine) | Mg | 400 | 10.40% |
| Curcumin (Nanoformulated)[1,2,3,4] | Mg | 200 | 5.20% |
| Decosahexanoic Acid | Mg | 400 | 10.40% |
| L-Glutathione (Or Ebselen Or N-Acetyl-L-Cysteine) | Mg | 200 | 5.20% |
| L-Theanine | Mg | 200 | 5.20% |
| Melatonin (Extended Release) | Mg | 3 | 0.03% |
| Pyrroloquinoline Quinone (Nanoformulated)[1,2] | Mg | 20 | 0.52% |
| Quercetin[1,2] | Mg | 200 | 5.20% |
| Ubiquinol | Mg | 1000 | 26.01% |
| Withaferin A (Or Chemical Derivative Or Structural Analog Of Withaferin A) (Nanoformulated)[1,2] | Mg | 400 | 10.40% |
| Mineral | | | |
| Magnesium L-Threonate | Mg | 400 | 10.40% |
| Vitamins | | | |
| Vitamin $D_3$ | Mg | 0.25 | 0.01% |
| Vitamin $K_2$ | Mg | 2.0 | 0.05% |
| Total Weight | G | 3.85 | 100.00% |

L-Theanine & melatonin combination for the night time dose, while L-Theanine and caffeine (or only caffeine) for the day time dose.

TABLE 8D

Additional Composition Of A Mixture For Lowering The Risks Of Alzheimer's Disease - May Also Include Some Bioactive Compounds From Tables Before & After This Table

|  | Unit | +/−50% | WT % |
|---|---|---|---|
| Botanicals |  |  |  |
| Bacopa monnieri[+] | Mg | 200 | 5.46% |
| Sceletium tortuosum[+] | Mg | 20 | 0.55% |
| Withania somnifera[+] | Mg | 200 | 5.46% |
| Chemicals |  |  |  |
| Caffeine | Mg | 20 | 0.55% |
| Citicoline (Or L-Alpha Glycerylphosphorylcholine) | Mg | 400 | 10.91% |
| Curcumin (Nanoformulated)[1,2,3,4] | Mg | 200 | 5.46% |
| Decosahexanoic Acid | Mg | 400 | 10.91% |
| L-Glutathione (Or Ebselen Or N-Acetyl-L-Cysteine) | Mg | 200 | 5.46% |
| Melatonin (Extended Release) | Mg | 3 | 0.08% |
| Oleocanthal (Or A Chemical Derivative Or A Structural Analog Of Oleocanthal) (Nanoformulated)[1,2] | Mg | 200 | 5.46% |
| Pyrroloquinoline Quinone (Nanoformulated)[1,2] | Mg | 20 | 0.55% |
| Ubiquinol | Mg | 1000 | 27.28% |
| Withaferin A (Or Chemical Derivative Or Structural Analog Of Withaferin A) (Nanoformulated)[1,2] | Mg | 400 | 10.91% |
| Mineral |  |  |  |
| Magnesium L-Threonate | Mg | 400 | 10.91% |
| Vitamins |  |  |  |
| Vitamin $D_3$ | Mg | 0.25 | 0.01% |
| Vitamin $K_2$ | Mg | 2.0 | 0.05% |
| Total Weight | G | 3.67 | 100.00% |

TABLE 8E

Additional Composition Of A Mixture For Lowering The Risks Of Alzheimer's Disease - May Also Include Some Bioactive Compounds From Tables Before & After This Table

| Chemicals | Unit | +/−50% | WT % |
|---|---|---|---|
| 4,5-Bis-(4-methoxyanilino)phthalimide | Mg | 20 | 6.78% |
| 6-Bromoindirubin-3'-oxime[2] | Mg | 10 | 3.39% |
| 6-Bromo-N-2-propenyl-4-quinazolinamine (SMER-28) | Mg | 10 | 3.39% |
| 3,6-Dibromo-α-[(phenylamino)methyl]-9H-carbazole-9-ethanol | Mg | 20 | 6.78% |
| Lithium (Lithium Orotate Or Lithium Chloride) | Mg | 5 | 1.69% |
| Sodium Phenylbutyrate[2] | Mg | 10 | 3.39% |
| Uric Acid (From Inosine: Hypoxanthine Ribose) | Mg | 20 | 6.78% |
| (+/−)-1-(1-Benzo[b]thien-2-ylethyl)-1-hydroxyurea | Mg | 200 | 67.80% |
| Total Weight | G | 0.29 | 100.00% |

TABLE 9

Composition Of A Mixture For Lowering The Risks Of Cardiovascular Disease - May Also Include Some Bioactive Compounds From Tables Before & After This Table

|  | Unit | +/−50% | WT % |
|---|---|---|---|
| Botanicals |  |  |  |
| Allium sativum[+] | Mg | 200 | 1.44% |
| Crataegus oxyacantha[+] | Mg | 200 | 1.44% |
| Inula racemosa[+] | Mg | 200 | 1.44% |
| Olea europaea[+] | Mg | 200 | 1.44% |
| Rauwolfia serpentina[+] | Mg | 200 | 1.44% |
| Terminalia arjuna[+] | Mg | 200 | 1.44% |
| Chemicals |  |  |  |
| Capsaicin (Or Capsinoid) | Mg | 200 | 1.44% |
| Chromium Polynicotinate | Mg | 0.2 | 0.00% |
| Cocoa Flavanols | Mg | 400 | 2.88% |
| Coenzyme $Q_{10}$ (Nanoformulated)[1,2] | Mg | 1000 | 7.19% |
| L-Arginine (Nanoformulated)[1,2] | Mg | 1000 | 7.19% |
| L-Glutathione (Or Ebselen Or N-Acetyl-L-Cysteine) | Mg | 200 | 1.44% |
| Plant Sterols (Nanoformulated)[1] | Mg | 5000 | 35.97% |
| Red Yeast Rice Extract | Mg | 2500 | 17.99% |
| Ubiquinol (Nanoformulated)[1,2] | Mg | 1000 | 7.19% |
| Mineral |  |  |  |
| Magnesium | Mg | 400 | 2.88% |
| Others |  |  |  |
| Coconut Oil | Mg | 1000 | 7.19% |
| Lactobacillus reuteri | Billion | 10 | 0.00% |
| Total Weight | G | 13.90 | 100.00% |

Table-9 can include 200 mg of *Commiphora mukul* extract.

TABLE 10A

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanicals |  |  |  |
| Andrographis paniculata[+] | Mg | 200 | 4.00% |
| Artemisia princeps[+] | Mg | 200 | 4.00% |
| Camellia sinensis[+] (Black) | Mg | 200 | 4.00% |
| Camellia sinensis[+] (Green) | Mg | 200 | 4.00% |
| Curulluma fimbrtara[+] | Mg | 200 | 4.00% |
| Cinnamomum zeylanicum[+] | Mg | 200 | 4.00% |
| Coccinia indica[+] | Mg | 800 | 16.00% |
| Irvingia gabonensis[+] | Mg | 200 | 4.00% |
| Lagerstroemia speciosa[+] (Leaf Extract) | Mg | 50 | 1.00% |
| Litchi chinensis[+] | Mg | 200 | 4.00% |
| Momordica charantia[+] | Mg | 200 | 4.00% |
| Salacia oblonga[+] | Mg | 800 | 16.00% |
| Chemicals |  |  |  |
| Beta Glucan | Mg | 200 | 4.00% |
| Chromium Polynicotinate | Mg | 0.2 | 0.0% |
| Chlorogenic Acid | Mg | 200 | 4.00% |

TABLE 10A-continued

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Nobiletin (Or 2000 Mg Naringenin) | Mg | 200 | 4.00% |
| Touchi | Mg | 1000 | 20.00% |
| Total Weight | G | 5.00 | 100.00% |

Chlorogenic acid (CHA) is an activator of calcineurin.

TABLE 10B

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanicals |  |  |  |
| *Andrographis paniculata*[+] | Mg | 200 | 2.63% |
| *Artemisia princeps*[+] | Mg | 200 | 2.63% |
| *Coccinia cordifolia*[+] | Mg | 200 | 2.63% |
| *Cordyceps sinensis*[+] | Mg | 200 | 2.63% |
| Green Coffee Bean Extract | Mg | 1200 | 15.79% |
| Lamon Variety Borlotto Bean Extract | Mg | 200 | 2.63% |
| *Paecilomyces hepiali* (Providing 70 mg Of Cordycepic Acid) | Mg | 1000 | 13.16% |
| *Momordica charantia*[+] | Mg | 200 | 2.63% |
| *Salacia oblonga*[+] | Mg | 800 | 10.53% |
| *Sorghum bicolor*[+] | Mg | 1000 | 13.16% |
| White Mulberry (Providing 1-deoxynojirinmycin 15 (DNJ) mg) Extract | Mg | 400 | 5.26% |
| Chemicals |  |  |  |
| Beta Glucan | Mg | 200 | 2.63% |
| Chlorogenic Acid | Mg | 200 | 2.63% |
| Cyanidin 3-glucoside (Nanoformulated)[1,2] | Mg | 400 | 5.26% |
| Phloridzin | Mg | 200 | 2.63% |
| Touchi | Mg | 1000 | 13.16% |
| Total Weight | G | 7.60 | 100.00% |

TABLE 10C

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanicals |  |  |  |
| *Coccinia cordifolia*[+] | Mg | 200 | 3.03% |
| *Cordyceps sinensis*[+] | Mg | 200 | 3.03% |
| Green Coffee Bean Extract | Mg | 1200 | 18.18% |
| Lamon Variety Borlotto Bean Extract | Mg | 200 | 3.03% |
| *Momordica charantia*[+] | Mg | 200 | 3.03% |
| *Salacia oblonga*[+] | Mg | 800 | 12.12% |
| *Sorghum bicolor*[+] | Mg | 1000 | 15.15% |
| White Mulberry (Providing 1-deoxynojirinmycin 15 (DNJ) mg) Extract | Mg | 400 | 6.06% |
| Chemicals |  |  |  |
| 4-(4-Hydroxyphenyl)butan-2-one (Nanoformulated)[1,2] | Mg | 400 | 6.06% |
| Beta Glucan | Mg | 200 | 3.03% |
| Chlorogenic Acid | Mg | 200 | 3.03% |
| Cyanidin 3-glucoside (Nanoformulated)[1,2] | Mg | 400 | 6.06% |
| Phloridzin | Mg | 200 | 3.03% |
| Touchi | Mg | 1000 | 15.15% |
| Total Weight | G | 6.60 | 100.00% |

TABLE 10D

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanicals |  |  |  |
| *Coccinia cordifolia*[+] | Mg | 200 | 7.02% |
| *Emblica officinalis*[+] | Mg | 200 | 7.02% |
| Green Coffee Bean Extract | Mg | 1200 | 42.11% |
| *Lagerstroemia speciosa*[+] | Mg | 50 | 1.75% |
| *Punica granatum* | Mg | 200 | 7.02% |
| *Syzygium cumini*[+] | Mg | 200 | 7.02% |
| Chemicals |  |  |  |
| 4-(4-Hydroxyphenyl)butan-2-one (Nanoformulated)[1,2] | Mg | 400 | 14.04% |
| Cyanidin 3-glucoside (Nanoformulated)[1,2] | Mg | 400 | 14.04% |
| Total Weight | G | 2.85 | 100.00% |

4-(4-Hydroxyphenyl)butan-2-one is raspberry ketone.
Green coffee bean extract has chlorogenic acid (CHA).

Explanation Of Notations {+, *, 1, 2, 3 and 4)

+ A component (meaning an extract or a powder or a bioactive compound or a bioactive molecule from any part of the specific plant)
* Found in *Citrullus vulgaris*[+]
1 Nanoformulated means nanoemulsion/nanodispersion/nanosuspension or nanoencapsulation
2 Chemically coupled with Triphenylphosphonium (TPP) or a chemical derivative of Triphenylphosphonium or a structural analog of Triphenylphosphonium
3 Higher bioavailability with black pepper (*Piper nigrum*) and/or vitamin $D_3$
4 FLLL-11 or FLLL-12 or GO-Y030 or GO-Y031 can replace curcumin

TABLE 11

Composition Of A Mixture Of Sugar Free Sweetener

|  | Unit | +/−50% | WT % |
|---|---|---|---|
| Botanical |  |  |  |
| *Stevia rebaudiana*[+] | Mg | 20 | 0.42% |
| Chemicals |  |  |  |
| Erythritol | Mg | 4500 | 95.34% |
| Trehalose | Mg | 200 | 4.24% |
| Total Weight | G | 4.72 | 100.00% |

TABLE 12A

Composition Of A Mixture Of Sugar Free Super-Sweetener

|  | Unit | +/−50% | WT % |
|---|---|---|---|
| Botanicals |  |  |  |
| *Capparis masaikai*[+] (Mabinlins Protein) | Mg | 5 | 0.11% |
| *Stevia rebaudiana*[+] | Mg | 20 | 0.42% |
| Chemicals |  |  |  |
| Erythritol | Mg | 4500 | 95.24% |
| Trehalose | Mg | 200 | 4.23% |
| Total Weight | G | 4.72 | 100.00% |

TABLE 12B

Composition Of A Mixture Of Sugar Free Super-Sweetener

|  | Unit | +/−50% | WT % |
|---|---|---|---|
| Botanicals |  |  |  |
| *Curculigo latifolia*[+] (Curculin Protein) | Mg | 5 | 0.11% |
| *Stevia rebaudiana*[+] | Mg | 20 | 0.42% |
| Chemicals |  |  |  |
| Erythritol | Mg | 4500 | 95.24% |
| Trehalose | Mg | 200 | 4.23% |
| Total Weight | G | 4.72 | 100.00% |

TABLE 12C

Composition Of A Mixture Of Sugar Free Super-Sweetener

|  | Unit | +/−50% | WT % |
|---|---|---|---|
| Botanicals |  |  |  |
| *Dioscoreophyllum cumminsii*[+] (Monellin Protein) | Mg | 2 | 0.04% |
| *Stevia rebaudiana*[+] | Mg | 20 | 0.42% |
| Chemicals |  |  |  |
| Erythritol | Mg | 4500 | 95.30% |
| Trehalose | Mg | 200 | 4.24% |
| Total Weight | G | 4.72 | 100.00% |

TABLE 12D

Composition Of A Mixture Of Sugar Free Super-Sweetener

|  | Unit | +/−50% | WT % |
|---|---|---|---|
| Botanicals |  |  |  |
| *Momordica grosvenorii*/ *Siraitia grosvenorii*[+] | Mg | 5 | 0.11% |
| *Stevia rebaudiana*[+] | Mg | 20 | 0.42% |
| Chemicals |  |  |  |
| Erythritol | Mg | 4500 | 95.24% |
| Trehalose | Mg | 200 | 4.23% |
| Total Weight | G | 4.72 | 100.00% |

TABLE 12E

Composition Of A Mixture Of Sugar Free Super-Sweetener

|  | Unit | +/−50% | WT % |
|---|---|---|---|
| Botanicals |  |  |  |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| Chemicals |  |  |  |
| Erythritol | Mg | 4500 | 95.14% |
| Trehalose | Mg | 200 | 4.23% |
| Total Weight | G | 4.73 | 100.00% |

TABLE 12F

Composition Of A Mixture Of Sugar Free Super-Sweetener

|  | Unit | +/−50% | WT % |
|---|---|---|---|
| Botanicals |  |  |  |
| *Stevia rebaudiana*[+] | Mg | 20 | 0.42% |
| *Synsepalum dulcificum*[+] (Miraculin Protein) | Mg | 5 | 0.11% |
| Chemicals |  |  |  |
| Erythritol | Mg | 4500 | 95.24% |
| Trehalose | Mg | 200 | 4.23% |
| Total Weight | G | 4.72 | 100.00% |

TABLE 12G

Composition Of A Mixture Of Sugar Free Super-Sweetener

|  | Unit | +/−50% | WT % |
|---|---|---|---|
| Botanicals |  |  |  |
| *Stevia rebaudiana*[+] | Mg | 20 | 0.42% |
| *Thaumatococcus daniellii*[+] (Thaumatin Protein) | Mg | 1 | 0.02% |
| Chemicals |  |  |  |
| Erythritol | Mg | 4500 | 95.32% |
| Trehalose | Mg | 200 | 4.24% |
| Total Weight | G | 4.72 | 100.00% |

TABLE 12H

Composition Of A Mixture Of Sugar Free Super-Sweetener

|  | Unit | +/−50% | WT % |
|---|---|---|---|
| Botanicals |  |  |  |
| *Dioscoreophyllum cumminsii*[+] (Monellin Protein) | Mg | 2 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| Chemicals |  |  |  |
| Erythritol | Mg | 4500 | 95.10% |
| Trehalose | Mg | 200 | 4.23% |
| Total Weight | G | 4.73 | 100.00% |

TABLE 12I

Composition Of A Mixture Of Sugar Free Super-Sweetener

|  | Unit | +/−50% | WT % |
|---|---|---|---|
| Botanicals |  |  |  |
| *Dioscoreophyllum cumminsii*[+] (Monellin Protein) | Mg | 2 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| *Synsepalum dulcificum*[+] (Miraculin Protein) | Mg | 5 | 0.11% |

TABLE 12I-continued

Composition Of A Mixture Of Sugar Free Super-Sweetener

|  | Unit | +/−50% | WT % |
|---|---|---|---|
| Chemicals |  |  |  |
| Erythritol | Mg | 4500 | 95.00% |
| Trehalose | Mg | 200 | 4.22% |
| Total Weight | G | 4.73 | 100.00% |

TABLE 12J

Composition Of A Mixture Of Sugar Free Super-Sweetener

|  | Unit | +/−50% | WT % |
|---|---|---|---|
| Botanicals |  |  |  |
| *Capparis masaikai*[+] (Mabinlins Protein) | Mg | 5 | 0.11% |
| *Dioscoreophyllum cumminsii*[+] (Monellin Protein) | Mg | 2 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| *Synsepalum dulcificum*[+] (Miraculin Protein) | Mg | 5 | 0.11% |
| Chemicals |  |  |  |
| Erythritol | Mg | 4500 | 94.90% |
| Trehalose | Mg | 200 | 4.22% |
| Total Weight | G | 4.74 | 100.00% |

TABLE 12K

Composition Of A Mixture Of Sugar Free Super-Sweetener

|  | Unit | +/−50% | WT % |
|---|---|---|---|
| Botanicals |  |  |  |
| *Curculigo latifolia*[+] (Curculin Protein) | Mg | 5 | 0.11% |
| *Dioscoreophyllum cumminsii*[+] (Monellin Protein) | Mg | 2 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| *Synsepalum dulcificum*[+] (Miraculin Protein) | Mg | 5 | 0.11% |
| Chemicals |  |  |  |
| Erythritol | Mg | 4500 | 94.90% |
| Trehalose | Mg | 200 | 4.22% |
| Total Weight | G | 4.74 | 100.00% |

TABLE 12L

Composition Of A Mixture Of Sugar Free Super-Sweetener

|  | Unit | +/−50% | WT % |
|---|---|---|---|
| Botanicals |  |  |  |
| *Capparis masaikai*[+] (Mabinlins Protein) | Mg | 1 | 0.02% |
| *Curculigo latifolia*[+] (Curculin Protein) | Mg | 1 | 0.02% |
| *Dioscoreophyllum cumminsii*[+] (Monellin Protein) | Mg | 2 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| *Synsepalum dulcificum*[+] (Miraculin Protein) | Mg | 5 | 0.11% |
| Chemicals |  |  |  |
| Erythritol | Mg | 4500 | 94.96% |
| Trehalose | Mg | 200 | 4.22% |
| Total Weight | G | 4.74 | 100.00% |

TABLE 12M

Composition Of A Mixture Of Sugar Free Super-Sweetener

|  | Unit | +/−50% | WT % |
|---|---|---|---|
| Botanicals |  |  |  |
| *Capparis masaikai*[+] (Mabinlins Protein) | Mg | 1 | 0.02% |
| *Curculigo latifolia*[+] (Curculin Protein) | Mg | 1 | 0.02% |
| *Dioscoreophyllum cumminsii*[+] (Monellin Protein) | Mg | 5 | 0.04% |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] | Mg | 20 | 0.42% |
| *Synsepalum dulcificum*[+] (Miraculin Protein) | Mg | 5 | 0.11% |
| Chemicals |  |  |  |
| Erythritol | Mg | 4500 | 94.90% |
| Trehalose | Mg | 200 | 4.22% |
| Total Weight | G | 4.74 | 100.00% |

[+] Means a component (meaning an extract or a powder or a bioactive compound or a bioactive molecule from any part of the specific plant).

TABLE 13A

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 0.92% |
| Curcumin/Nanoformulated Curcumin | Mg | 50 | 0.92% |
| Epigallocatechin Gallate | Mg | 50 | 0.92% |
| Inositol | Mg | 12.5 | 0.23% |
| L-Arginine | Mg | 4000 | 73.89% |
| Licoricidin | Mg | 50 | 0.92% |
| Licorisoflavan A | Mg | 50 | 0.92% |
| Resveratrol | Mg | 50 | 0.92% |
| Taurine | Mg | 50 | 0.92% |

TABLE 13A-continued

Composition Of A Mixture Of A Chewable/Soluble Strip For Health

| | Unit | +/−50% | WT % |
|---|---|---|---|
| Optional Botanicals | | | |
| Astragalus Root[5] | Mg | 200 | 3.69% |
| Licorice Root Extract-Deglycyrrhizinated | Mg | 200 | 3.69% |
| Magnolia Bark Extract | Mg | 50 | 0.92% |
| Tea Leaf (Green) Extract | Mg | 50 | 0.92% |
| Vitamins | | | |
| Biotin | Mg | 0.5 | 0.1% |
| Folate | Mg | 0.5 | 0.1% |
| Niacinimide | Mg | 200 | 3.69% |
| Vitamin $B_1$ | Mg | 25 | 0.46% |
| Vitamin $B_2$ | Mg | 25 | 0.46% |
| Vitamin $B_3$ | Mg | 25 | 0.46% |
| Vitamin $B_5$ | Mg | 50 | 0.92% |
| Vitamin $B_6$ | Mg | 25 | 0.46% |
| Vitamin $B_{12}$ | Mg | 0.01 | 0.00% |
| Vitamin C | Mg | 200 | 3.69% |
| Vitamin D | Mg | 0.1 | 0.00 |
| Other | | | |
| *Streptococcus salivarius* K12 | Billion | 10 | 0.00% |
| Total Weight | G | 5.41 | 100.00% |

TABLE 13B

Composition Of A Mixture Of A Chewable/Soluble Strip For Health

| | Unit | +/−50% | WT % |
|---|---|---|---|
| Chemicals | | | |
| Anhydrous Caffeine/Caffeine | Mg | 50 | 0.93% |
| Epigallocatechin Gallate | Mg | 50 | 0.93% |
| Inositol | Mg | 12.5 | 0.23% |
| L-Arginine | Mg | 4000 | 74.58% |
| Licoricidin | Mg | 50 | 0.93% |
| Licorisoflavan A | Mg | 50 | 0.93% |
| Resveratrol | Mg | 50 | 0.93% |
| Taurine | Mg | 50 | 0.93% |
| Optional Botanicals | | | |
| Astragalus Root[5] | Mg | 200 | 3.73% |
| Licorice Root Extract-Deglycyrrhizinated | Mg | 200 | 3.73% |
| Magnolia Bark Extract | Mg | 50 | 0.93% |
| Tea Leaf (Green) Extract | Mg | 50 | 0.93% |
| Vitamins | | | |
| Biotin | Mg | 0.5 | 0.01% |
| Folate | Mg | 0.5 | 0.01% |
| Niacinimide | Mg | 200 | 3.73% |
| Vitamin $B_1$ | Mg | 25 | 0.47% |
| Vitamin $B_2$ | Mg | 25 | 0.47% |
| Vitamin $B_3$ | Mg | 25 | 0.47% |
| Vitamin $B_5$ | Mg | 50 | 0.93% |
| Vitamin $B_6$ | Mg | 25 | 0.47% |
| Vitamin $B_{12}$ | Mg | 0.01 | 0.00% |
| Vitamin C | Mg | 200 | 3.73% |
| Vitamin D | Mg | 0.1 | 0.00% |
| Other | | | |
| *Streptococcus salivarius* K12 | Billion | 10 | 0.00% |
| Total Weight | G | 5.36 | 100.00% |

TABLE 13C

Composition Of A Mixture Of A Chewable/Soluble Strip For Health

| | Unit | +/−50% | WT % |
|---|---|---|---|
| Chemicals | | | |
| Anhydrous Caffeine/Caffeine | Mg | 50 | 0.94% |
| Inositol | Mg | 12.5 | 0.24% |
| L-Arginine | Mg | 4000 | 75.28% |
| Licoricidin | Mg | 50 | 0.94% |
| Licorisoflavan A | Mg | 50 | 0.94% |
| Resveratrol | Mg | 50 | 0.94% |
| Taurine | Mg | 50 | 0.94% |
| Optional Botanicals | | | |
| Astragalus Root[5] | Mg | 200 | 3.76% |
| Licorice Root Extract-Deglycyrrhizinated | Mg | 200 | 3.76% |
| Magnolia Bark Extract | Mg | 50 | 0.94% |
| Tea Leaf (Green) Extract | Mg | 50 | 0.94% |
| Vitamins | | | |
| Biotin | Mg | 0.5 | 0.01% |
| Folate | Mg | 0.5 | 0.01% |
| Niacinimide | Mg | 200 | 3.76% |
| Vitamin $B_1$ | Mg | 25 | 0.47% |
| Vitamin $B_2$ | Mg | 25 | 0.47% |
| Vitamin $B_3$ | Mg | 25 | 0.47% |
| Vitamin $B_5$ | Mg | 50 | 0.94% |
| Vitamin $B_6$ | Mg | 25 | 0.47% |
| Vitamin $B_{12}$ | Mg | 0.01 | 0.00% |
| Vitamin C | Mg | 200 | 3.76% |
| Vitamin D | Mg | 0.1 | 0.00% |
| Other | | | |
| *Streptococcus salivarius* K12 | Billion | 10 | 0.00% |
| Total Weight | G | 5.31 | 100.00% |

TABLE 13D

Composition Of A Mixture Of A Chewable/Soluble Strip For Health

| | Unit | +/−50% | WT % |
|---|---|---|---|
| Chemicals | | | |
| Anhydrous Caffeine/Caffeine | Mg | 50 | 3.81% |
| Inositol | Mg | 12.5 | 0.95% |
| Licoricidin | Mg | 50 | 3.81% |
| Licorisoflavan A | Mg | 50 | 3.81% |
| Resveratrol | Mg | 50 | 3.81% |
| Taurine | Mg | 50 | 3.81% |
| Optional Botanicals | | | |
| Astragalus Root[5] | Mg | 200 | 15.23% |
| Licorice Root Extract-Deglycyrrhizinated | Mg | 200 | 15.23% |
| Magnolia Bark Extract | Mg | 50 | 3.81% |
| Tea Leaf (Green) Extract | Mg | 50 | 3.81% |
| Vitamins | | | |
| Biotin | Mg | 0.5 | 0.04% |
| Folate | Mg | 0.5 | 0.04% |
| Niacinimide | Mg | 200 | 15.23% |
| Vitamin $B_1$ | Mg | 25 | 1.90% |
| Vitamin $B_2$ | Mg | 25 | 1.90% |
| Vitamin $B_3$ | Mg | 25 | 1.90% |
| Vitamin $B_5$ | Mg | 50 | 3.81% |
| Vitamin $B_6$ | Mg | 25 | 1.90% |
| Vitamin $B_{12}$ | Mg | 0.01 | 0.00% |
| Vitamin C | Mg | 200 | 15.23% |
| Vitamin D | Mg | 0.1 | 0.01% |

TABLE 13D-continued

Composition Of A Mixture Of A Chewable/Soluble Strip For Health

|  | Unit | +/−50% | WT % |
|---|---|---|---|
| Other |  |  |  |
| *Streptococcus salivarius* K12 | Billion | 10 | 0.00% |
| Total Weight | G | 1.31 | 100.00% |

TABLE 13E

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 3.96% |
| Inositol | Mg | 12.5 | 0.99% |
| Licoricidin | Mg | 50 | 3.96% |
| Licorisoflavan A | Mg | 50 | 3.96% |
| Taurine | Mg | 50 | 3.96% |
| Optional Botanicals |  |  |  |
| Astragalus Root[5] | Mg | 200 | 15.83% |
| Licorice Root Extract-Deglycyrrhizinated | Mg | 200 | 15.83% |
| *Magnolia* Bark Extract | Mg | 50 | 3.96% |
| Tea Leaf (Green) Extract | Mg | 50 | 3.96% |
| Vitamins |  |  |  |
| Biotin | Mg | 0.5 | 0.04% |
| Folate | Mg | 0.5 | 0.04% |
| Niacinimide | Mg | 200 | 15.83% |
| Vitamin $B_1$ | Mg | 25 | 1.98% |
| Vitamin $B_2$ | Mg | 25 | 1.98% |
| Vitamin $B_3$ | Mg | 25 | 1.98% |
| Vitamin $B_5$ | Mg | 50 | 3.96% |
| Vitamin $B_6$ | Mg | 25 | 1.98% |
| Vitamin $B_{12}$ | Mg | 0.01 | 0.00% |
| Vitamin C | Mg | 200 | 15.83% |
| Vitamin D | Mg | 0.1 | 0.01% |
| Other |  |  |  |
| *Streptococcus salivarius* K12 | Billion | 10 | 0.00% |
| Total Weight | G | 1.26 | 100.00% |

TABLE 13F

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 4.70% |
| Inositol | Mg | 12.5 | 1.18% |
| Licoricidin | Mg | 50 | 4.70% |
| Licorisoflavan A | Mg | 50 | 4.70% |
| Taurine | Mg | 50 | 4.70% |
| Optional Botanicals |  |  |  |
| Licorice Root Extract-Deglycyrrhizinated | Mg | 200 | 18.80% |
| *Magnolia* Bark Extract | Mg | 50 | 4.70% |
| Tea Leaf (Green) Extract | Mg | 50 | 4.70% |
| Vitamins |  |  |  |
| Biotin | Mg | 0.5 | 0.05% |
| Folate | Mg | 0.5 | 0.05% |
| Niacinimide | Mg | 200 | 18.80% |
| Vitamin $B_1$ | Mg | 25 | 2.35% |
| Vitamin $B_2$ | Mg | 25 | 2.35% |
| Vitamin $B_3$ | Mg | 25 | 2.35% |
| Vitamin $B_5$ | Mg | 50 | 4.70% |
| Vitamin $B_6$ | Mg | 25 | 2.35% |
| Vitamin $B_{12}$ | Mg | 0.01 | 0.00% |
| Vitamin C | Mg | 200 | 18.80% |
| Vitamin D | Mg | 0.1 | 0.01% |
| Other |  |  |  |
| *Streptococcus salivarius* K12 | Billion | 10 | 0.00% |
| Total Weight | G | 1.06 | 100.00% |

TABLE 13G

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 5.79% |
| Inositol | Mg | 12.5 | 1.45% |
| Licoricidin | Mg | 50 | 5.79% |
| Licorisoflavan A | Mg | 50 | 5.79% |
| Taurine | Mg | 50 | 5.79% |
| Optional Botanicals |  |  |  |
| *Magnolia* Bark Extract | Mg | 50 | 5.79% |
| Tea Leaf (Green) Extract | Mg | 50 | 5.79% |
| Vitamins |  |  |  |
| Biotin | Mg | 0.5 | 0.06% |
| Folate | Mg | 0.5 | 0.06% |
| Niacinimide | Mg | 200 | 23.16% |
| Vitamin $B_1$ | Mg | 25 | 2.89% |
| Vitamin $B_2$ | Mg | 25 | 2.89% |
| Vitamin $B_3$ | Mg | 25 | 2.89% |
| Vitamin $B_5$ | Mg | 50 | 5.79% |
| Vitamin $B_6$ | Mg | 25 | 2.89% |
| Vitamin $B_{12}$ | Mg | 0.01 | 0.00% |
| Vitamin C | Mg | 200 | 23.16% |
| Vitamin D | Mg | 0.1 | 0.01% |
| Other |  |  |  |
| *Streptococcus salivarius* K12 | Billion | 10 | 0.00% |
| Total Weight | G | 0.86 | 100.00% |

TABLE 13H

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 6.15% |
| Inositol | Mg | 12.5 | 1.54% |
| Licoricidin | Mg | 50 | 6.15% |
| Licorisoflavan A | Mg | 50 | 6.15% |
| Taurine | Mg | 50 | 6.15% |
| Optional Botanical |  |  |  |
| Tea Leaf (Green) Extract | Mg | 50 | 6.15% |
| Vitamins |  |  |  |
| Biotin | Mg | 0.5 | 0.06% |
| Folate | Mg | 0.5 | 0.06% |
| Niacinimide | Mg | 200 | 24.58% |

TABLE 13H-continued

Composition Of A Mixture Of A Chewable/Soluble Strip For Health

|  | Unit | +/−50% | WT % |
|---|---|---|---|
| Vitamin $B_1$ | Mg | 25 | 3.07% |
| Vitamin $B_2$ | Mg | 25 | 3.07% |
| Vitamin $B_3$ | Mg | 25 | 3.07% |
| Vitamin $B_5$ | Mg | 50 | 6.15% |
| Vitamin $B_6$ | Mg | 25 | 3.07% |
| Vitamin $B_{12}$ | Mg | 0.01 | 0.00% |
| Vitamin C | Mg | 200 | 24.58% |
| Vitamin D | Mg | 0.1 | 0.01% |
| Other |  |  |  |
| *Streptococcus salivarius* K12 | Billion | 10 | 0.00% |
| Total Weight | G | 0.81 | 100.00% |

TABLE 13I

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 6.55% |
| Inositol | Mg | 12.5 | 1.64% |
| Licoricidin | Mg | 50 | 6.55% |
| Licorisoflavan A | Mg | 50 | 6.55% |
| Taurine | Mg | 50 | 6.55% |
| Vitamins |  |  |  |
| Biotin | Mg | 0.5 | 0.07% |
| Folate | Mg | 0.5 | 0.07% |
| Niacinimide | Mg | 200 | 26.19% |
| Vitamin $B_1$ | Mg | 25 | 3.27% |
| Vitamin $B_2$ | Mg | 25 | 3.27% |
| Vitamin $B_3$ | Mg | 25 | 3.27% |
| Vitamin $B_5$ | Mg | 50 | 6.55% |
| Vitamin $B_6$ | Mg | 25 | 3.27% |
| Vitamin $B_{12}$ | Mg | 0.01 | 0.00% |
| Vitamin C | Mg | 200 | 26.19% |
| Vitamin D | Mg | 0.1 | 0.01% |
| Other |  |  |  |
| *Streptococcus salivarius* K12 | Billion | 10 | 0.00% |
| Total Weight | G | 0.76 | 100.00% |

TABLE 13J

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 6.55% |
| Inositol | Mg | 12.5 | 1.64% |
| Licoricidin | Mg | 50 | 6.55% |
| Licorisoflavan A | Mg | 50 | 6.55% |
| Taurine | Mg | 50 | 6.55% |
| Vitamins |  |  |  |
| Folate | Mg | 0.5 | 0.07% |
| Niacinimide | Mg | 200 | 26.21% |
| Vitamin $B_1$ | Mg | 25 | 3.28% |
| Vitamin $B_2$ | Mg | 25 | 3.28% |
| Vitamin $B_3$ | Mg | 25 | 3.28% |
| Vitamin $B_5$ | Mg | 50 | 6.55% |
| Vitamin $B_6$ | Mg | 25 | 3.28% |
| Vitamin $B_{12}$ | Mg | 0.01 | 0.00% |
| Vitamin C | Mg | 200 | 26.21% |
| Vitamin D | Mg | 0.1 | 0.01% |
| Other |  |  |  |
| *Streptococcus salivarius* K12 | Billion | 10 | 0.00% |
| Total Weight | G | 0.76 | 100.00% |

TABLE 13K

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 6.56% |
| Inositol | Mg | 12.5 | 1.64% |
| Licoricidin | Mg | 50 | 6.56% |
| Licorisoflavan A | Mg | 50 | 6.56% |
| Taurine | Mg | 50 | 6.56% |
| Vitamins |  |  |  |
| Niacinimide | Mg | 200 | 26.23% |
| Vitamin $B_1$ | Mg | 25 | 3.28% |
| Vitamin $B_2$ | Mg | 25 | 3.28% |
| Vitamin $B_3$ | Mg | 25 | 3.28% |
| Vitamin $B_5$ | Mg | 50 | 6.56% |
| Vitamin $B_6$ | Mg | 25 | 3.28% |
| Vitamin $B_{12}$ | Mg | 0.01 | 0.00% |
| Vitamin C | Mg | 200 | 26.23% |
| Vitamin D | Mg | 0.1 | 0.01% |
| Other |  |  |  |
| *Streptococcus salivarius* K12 | Billion | 10 | 0.00% |
| Total Weight | G | 0.76 | 100.00% |

TABLE 13L

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 8.89% |
| Inositol | Mg | 12.5 | 2.22% |
| Licoricidin | Mg | 50 | 8.89% |
| Licorisoflavan A | Mg | 50 | 8.89% |
| Taurine | Mg | 50 | 8.89% |
| Vitamins |  |  |  |
| Vitamin $B_1$ | Mg | 25 | 4.44% |
| Vitamin $B_2$ | Mg | 25 | 4.44% |
| Vitamin $B_3$ | Mg | 25 | 4.44% |
| Vitamin $B_5$ | Mg | 50 | 8.89% |
| Vitamin $B_6$ | Mg | 25 | 4.44% |
| Vitamin $B_{12}$ | Mg | 0.01 | 0.00% |
| Vitamin C | Mg | 200 | 35.55% |
| Vitamin D | Mg | 0.1 | 0.02% |
| Other |  |  |  |
| *Streptococcus salivarius* K12 | Billion | 10 | 0.00% |
| Total Weight | G | 0.56 | 100.00% |

TABLE 13M

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 9.30% |
| Inositol | Mg | 12.5 | 2.33% |
| Licoricidin | Mg | 50 | 9.30% |
| Licorisoflavan A | Mg | 50 | 9.30% |
| Taurine | Mg | 50 | 9.30% |
| Vitamins |  |  |  |
| Vitamin $B_2$ | Mg | 25 | 4.65% |
| Vitamin $B_3$ | Mg | 25 | 4.65% |
| Vitamin $B_5$ | Mg | 50 | 9.30% |
| Vitamin $B_6$ | Mg | 25 | 4.65% |
| Vitamin $B_{12}$ | Mg | 0.01 | 0.00% |
| Vitamin C | Mg | 200 | 37.20% |
| Vitamin D | Mg | 0.1 | 0.02% |
| Other |  |  |  |
| Streptococcus salivarius K12 | Billion | 10 | 0.00% |
| Total Weight | G | 0.54 | 100.00% |

TABLE 13N

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 9.75% |
| Inositol | Mg | 12.5 | 2.44% |
| Licoricidin | Mg | 50 | 9.75% |
| Licorisoflavan A | Mg | 50 | 2.44% |
| Taurine | Mg | 50 | 2.44% |
| Vitamins |  |  |  |
| Vitamin $B_3$ | Mg | 25 | 4.88% |
| Vitamin $B_5$ | Mg | 50 | 9.75% |
| Vitamin $B_6$ | Mg | 25 | 4.88% |
| Vitamin $B_{12}$ | Mg | 0.01 | 0.00% |
| Vitamin C | Mg | 200 | 39.02% |
| Vitamin D | Mg | 0.1 | 0.02% |
| Other |  |  |  |
| Streptococcus salivarius K12 | Billion | 10 | 0.00% |
| Total Weight | G | 0.51 | 100.00% |

TABLE 13O

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 10.25% |
| Inositol | Mg | 12.5 | 2.56% |
| Licoricidin | Mg | 50 | 10.25% |
| Licorisoflavan A | Mg | 50 | 10.25% |
| Taurine | Mg | 50 | 10.25% |
| Vitamins |  |  |  |
| Vitamin $B_5$ | Mg | 50 | 10.25% |
| Vitamin $B_6$ | Mg | 25 | 5.13% |
| Vitamin $B_{12}$ | Mg | 0.01 | 0.00% |
| Vitamin C | Mg | 200 | 41.02% |
| Vitamin D | Mg | 0.1 | 0.02% |
| Other |  |  |  |
| Streptococcus salivarius K12 | Billion | 10 | 0.00% |
| Total Weight | G | 0.49 | 100.00% |

TABLE 13P

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 11.43% |
| Inositol | Mg | 12.5 | 2.86% |
| Licoricidin | Mg | 50 | 11.43% |
| Licorisoflavan A | Mg | 50 | 11.43% |
| Taurine | Mg | 50 | 11.43% |
| Vitamins |  |  |  |
| Vitamin $B_6$ | Mg | 25 | 5.71% |
| Vitamin $B_{12}$ | Mg | 0.01 | 0.00% |
| Vitamin C | Mg | 200 | 45.70% |
| Vitamin D | Mg | 0.1 | 0.02% |
| Other |  |  |  |
| Streptococcus salivarius K12 | Billion | 10 | 0.00% |
| Total Weight | G | 0.44 | 100.00% |

TABLE 13Q

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 12.12% |
| Inositol | Mg | 12.5 | 3.03% |
| Licoricidin | Mg | 50 | 12.12% |
| Licorisoflavan A | Mg | 50 | 12.12% |
| Taurine | Mg | 50 | 12.12% |
| Vitamins |  |  |  |
| Vitamin $B_{12}$ | Mg | 0.01 | 0.00% |
| Vitamin C | Mg | 200 | 48.47% |
| Vitamin D | Mg | 0.1 | 0.02% |
| Other |  |  |  |
| Streptococcus salivarius K12 | Billion | 10 | 0.00% |
| Total Weight | G | 0.41 | 100.00% |

TABLE 13R

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 12.12% |
| Inositol | Mg | 12.5 | 3.03% |
| Licoricidin | Mg | 50 | 12.12% |
| Licorisoflavan A | Mg | 50 | 12.12% |
| Taurine | Mg | 50 | 12.12% |

TABLE 13R-continued

Composition Of A Mixture Of A Chewable/Soluble Strip For Health

|  | Unit | +/−50% | WT % |
|---|---|---|---|
| Vitamins |  |  |  |
| Vitamin C | Mg | 200 | 48.47% |
| Vitamin D | Mg | 0.1 | 0.02% |
| Other |  |  |  |
| Streptococcus salivarius K12 | Billion | 10 | 0.00% |
| Total Weight | G | 0.41 | 100.00% |

TABLE 13S

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 23.52% |
| Inositol | Mg | 12.5 | 5.88% |
| Licoricidin | Mg | 50 | 23.52% |
| Licorisoflavan A | Mg | 50 | 23.52% |
| Taurine | Mg | 50 | 23.52% |
| Vitamin |  |  |  |
| Vitamin D | Mg | 0.1 | 0.05% |
| Other |  |  |  |
| Streptococcus salivarius K12 | Billion | 10 | 0.00% |
| Total Weight | G | 0.21 | 100.00% |

TABLE 13T

Composition Of A Mixture Of A Chewable/Soluble Strip For Health

|  | Unit | +/−50% | WT % |
|---|---|---|---|
| Chemicals |  |  |  |
| Anhydrous Caffeine/Caffeine | Mg | 50 | 23.53% |
| Inositol | Mg | 12.5 | 5.88% |
| Licoricidin | Mg | 50 | 23.53% |
| Licorisoflavan A | Mg | 50 | 23.53% |
| Taurine | Mg | 50 | 23.53% |
| Other |  |  |  |
| Streptococcus salivarius K12 | Billion | 10 | 0.00% |
| Total Weight | G | 0.21 | 100.00% |

TABLE 13U

Composition Of A Mixture Of A Chewable/Soluble Strip For Health

|  | Unit | +/−50% | WT % |
|---|---|---|---|
| Chemicals |  |  |  |
| Inositol | Mg | 12.5 | 7.69% |
| Licoricidin | Mg | 50 | 30.77% |
| Licorisoflavan A | Mg | 50 | 30.77% |
| Taurine | Mg | 50 | 30.77% |

TABLE 13U-continued

Composition Of A Mixture Of A Chewable/Soluble Strip For Health

|  | Unit | +/−50% | WT % |
|---|---|---|---|
| Other |  |  |  |
| Streptococcus salivarius K12 | Billion | 10 | 0.00% |
| Total Weight | G | 0.16 | 100.00% |

TABLE 13V

Composition Of A Mixture Of A Chewable/Soluble Strip For Health

|  | Unit | +/−50% | WT % |
|---|---|---|---|
| Chemicals |  |  |  |
| Licoricidin | Mg | 50 | 33.33% |
| Licorisoflavan A | Mg | 50 | 33.33% |
| Taurine | Mg | 50 | 33.33% |
| Other |  |  |  |
| Streptococcus salivarius K12 | Billion | 10 | 0.00% |
| Total Weight | G | 0.15 | 100.00% |

TABLE 13W

Composition Of A Mixture Of A Chewable/Soluble Strip For Health

|  | Unit | +/−50% | WT % |
|---|---|---|---|
| Chemicals |  |  |  |
| Licoricidin | Mg | 50 | 50.00% |
| Licorisoflavan A | Mg | 50 | 50.00% |
| Other |  |  |  |
| Streptococcus salivarius K12 | Billion | 10 | 0.00% |
| Total Weight | G | 0.10 | 100.00% |

In formulations described in Table-13A through Table-13W, Licoricidin and Licorisoflavan A can prevent gum diseases. In formulations described in Table-13A through Table-13W, propolis extract of about 100 mg can be added. In formulations described in Table-13A through Table-13W, coffee and D-Ribose can be added in about 1:1 weight ratio.

In formulations described in Table-13A through Table-13W, L-Arginine Alpha Keto-Glutarate (AAKG) (about 4 grams+/−50%) can be added instead of L-Arginine. L-Arginine or L-Arginine Alpha Keto-Glutarate can be encapsulated in methocel, a micro-polymer hydrophilic ether matrix to control the release rate of L-Arginine or L-Arginine Alpha Keto-Glutarate.

In formulations described in Table-13A through Table-13W, *Astragalus* root[5] can be mixed with about 200 mg extract of *Agaricus subrufescens*, about 200 mg extract of *Cordyceps sinensis*, about 200 mg extract of *Ganoderma lucidum*, about 200 mg extract of *Grifola frondosa*, about 200 mg extract of *Hericium erinaceus*, about 200 mg extract of *Phallus indusiatus* and about 200 mg extract of *Phellinus linteus*.

In formulations described in Table-13A through Table-13W, about 200 mg of *Commiphora myrrha* powder can be added. In formulations described in Table-13A through Table-13W, about 200 mg of folic acid can be added.

In formulations described in Table-13A through Table-13W, about 200 mg of catalase, about 200 mg of glutathione peroxidase, about 1000 mg of L-Methionine, about 200 mcg of selenium amino acid complex (sodium selenite, L-selenomethionin and selenium-methyl L-selenocysteine) and about 200 mg superoxide dismutase can be added.

In formulations described in Table-13A through Table-13W, about 200 mg of *Emblica officinalis* extract can be added.

In formulations described in Table-13A through Table-13W, about 1000 mg of D-Aspartic acid, 100 mg of 3-Beta-Hydroxy-Urs-12-En-28-Oic acid, about 100 mg of 2-Phenyl-Di-Benzyl-Benzopyran-4 One, about 200 mg of extract of *Cordyceps sinensis*, about 400 mg of extract of *Trigonella foenum-graecum* with about 50% testofen and about 200 mg of *Panax ginseng* can be added.

In formulations described in Table-13A through Table-13W, inactive ingredients (malitol, sorbitol, gumbase, isomalt, calcium stearate, calcium pantothenate, flavor, gum Arabic, menthol, maltodextrin, acesulfame potassium, titanium dioxide, citric acid, malic acid, aspartame and glycerine) can be added.

TABLE 13X

Composition Of A Mixture Of Probiotics - May Also Include Some Bioactive Compounds From Tables Before & After This Table

|  | Unit | +/−50% | WT % |
|---|---|---|---|
| Chemicals |  |  |  |
| Bovine Colostrum | Mg | 500 | 20.00% |
| Lactoferrin | Mg | 2000 | 80.00% |
| Probiotics |  |  |  |
| Live *Lactobacillus acidophilus* | Billion | 10 | 0.00% |
| Live *Lactobacillus casei* | Billion | 10 | 0.00% |
| Live *Lactobacillus GG* | Billion | 20 | 0.00% |
| Live *Lactobacillus plantarum* 299v | Billion | 10 | 0.00% |
| Live *Lactobacillus rhamnosus* | Billion | 10 | 0.00% |
| Other |  |  |  |
| *S. salivarius* BLIS M18 | Billion | 10 | 0.00% |
| Total Weight | G | 2.50 | 100.00% |

TABLE 13Y

Composition Of A Mixture Of Chemicals, Vitamins & Minerals To Protect Against Aging - May Also Include Some Bioactive Compounds From Tables Before & After This Table

|  | Unit | +/−50% | WT % |
|---|---|---|---|
| Chemicals |  |  |  |
| Alpha Lipoic Acid | Mg | 200 | 2.07% |
| Apoaequorin | Mg | 20 | 0.21% |
| Beta-1,3 D Glucan | Mg | 600 | 6.20% |
| Choline (Coganzin) | Mg | 200 | 2.07% |
| Chrominum | Mg | 0.05 | 0.00% |
| CoQ10 | Mg | 200 | 2.07% |
| Curcumin | Mg | 200 | 2.07% |
| DHA | Mg | 400 | 4.14% |
| Folic Acid | Mg | 1 | 0.01% |
| Lactoferrin | Mg | 2000 | 20.68% |
| L-Glutamine | Mg | 600 | 6.20% |
| L-Theanin | Mg | 200 | 2.07% |
| L-Tyrosine | Mg | 600 | 6.20% |
| Melatonine | Mg | 3 | 0.03% |
| Nicotinamide Riboside | Mg | 200 | 2.07% |
| N-Acetyl-L-Cysteine | Mg | 800 | 8.27% |
| N-Acetyl Glucosamine | Mg | 800 | 8.27% |
| N-Acetyl-L-Carnitine | Mg | 800 | 8.27% |
| Phosphatidylserine | Mg | 200 | 2.07% |
| Pterostilbene | Mg | 200 | 2.07% |
| Quercetin | Mg | 200 | 2.07% |
| Resveratrol | Mg | 200 | 2.07% |
| Ubiquinol | Mg | 200 | 2.07% |
| Vitamins |  |  |  |
| Vitamin B12 | Mg | 1 | 0.01% |
| Vitamin C | Mg | 600 | 6.20% |
| Vitamin D3 | Mg | 0.25 | 0.00% |
| Vitamin E | Mg | 200 | 2.07% |
| Vitamin H | Mg | 0.1 | 0.00% |
| Mineral & Others |  |  |  |
| Selenium | Mg | 0.02 | 0.00% |
| Vanadyl Sulfate | Mg | 5 | 0.05% |
| Zinc Sulpfate | Mg | 40 | 0.41% |
| Total Weight | G | 9.70 | 100.00% |

TABLE 13Z1

Composition Of A Mixture Of Chemicals, Vitamins & Minerals To Protect Against Aging - May Also Include Some Bioactive Compounds From Tables Before & After This Table

|  | Unit | +/−50% | WT % |
|---|---|---|---|
| Chemicals |  |  |  |
| Alpha Lipoic Acid | Mg | 200 | 2.11% |
| Apoaequorin | Mg | 20 | 0.21% |
| Beta-1,3 D Glucan | Mg | 600 | 6.34% |
| Choline (Coganzin) | Mg | 200 | 2.11% |
| Chrominum | Mg | 0.05 | 0.00% |
| CoQ10 | Mg | 200 | 2.11% |
| Curcumin | Mg | 200 | 2.11% |
| DHA | Mg | 400 | 4.23% |
| Folic Acid | Mg | 1 | 0.01% |
| Lactoferrin | Mg | 2000 | 21.13% |
| L-Glutamine | Mg | 600 | 6.34% |
| L-Tyrosine | Mg | 600 | 6.34% |
| Nicotinamide Riboside | Mg | 200 | 2.11% |
| N-Acetyl-L-Cysteine | Mg | 800 | 8.45% |
| N-Acetyl Glucosamine | Mg | 800 | 8.45% |
| N-Acetyl-L-Carnitine | Mg | 800 | 8.45% |
| Phosphatidylserine | Mg | 200 | 2.11% |
| Pterostilbene | Mg | 200 | 2.11% |
| Quercetin | Mg | 200 | 2.11% |
| Resveratrol | Mg | 200 | 2.11% |
| Ubiquinol | Mg | 200 | 2.11% |
| Vitamins |  |  |  |
| Vitamin B12 | Mg | 1 | 0.01% |
| Vitamin C | Mg | 600 | 6.34% |
| Vitamin D3 | Mg | 0.25 | 0.00% |
| Vitamin E | Mg | 200 | 2.11% |
| Vitamin H | Mg | 0.1 | 0.00% |
| Mineral & Others |  |  |  |
| Selenium | Mg | 0.02 | 0.00% |
| Vanadyl Sulfate | Mg | 5 | 0.05% |
| Zinc Sulpfate | Mg | 40 | 0.42% |
| Total Weight | G | 9.50 | 100.00% |

TABLE 13Z2

Composition Of A Mixture Of Chemicals To Protect Against Aging - May Also Include Some Bioactive Compounds From Tables Before & After This Table

| Chemicals | Unit | +/−50% | WT % |
|---|---|---|---|
| Withaferin A (Or A Chemical Derivative/ Structural Analog Of Withaferin A) | Mg | 400 | 33.33% |
| Nicotinamide Riboside | Mg | 200 | 16.66% |
| Phosphatidylserine | Mg | 200 | 16.66% |
| Quercetin | Mg | 200 | 16.66% |
| Resveratrol | Mg | 200 | 16.66% |
| Total Weight | G | 1.20 | 100.00% |

TABLE 13Z3

Composition Of A Mixture Of Chemicals To Protect Against Aging - May Also Include Some Bioactive Compounds From Tables Before & After This Table

| Chemicals | Unit | +/−50% | WT % |
|---|---|---|---|
| Withaferin A (Or A Chemical Derivative/Structural Analog Of Withaferin A) | Mg | 400 | 40.00% |
| Nicotinamide Riboside | Mg | 200 | 20.00% |
| Phosphatidylserine | Mg | 200 | 20.00% |
| Quercetin | Mg | 200 | 20.00% |
| Total Weight | G | 1.00 | 100.00% |

TABLE 13Z4

Composition Of A Mixture Of Chemicals To Protect Against Aging - May Also Include Some Bioactive Compounds From Tables Before & After This Table

| Chemicals | Unit | +/−50% | WT % |
|---|---|---|---|
| Nicotinamide Riboside | Mg | 400 | 40.00% |
| Phosphatidylserine | Mg | 400 | 40.00% |
| Quercetin | Mg | 200 | 20.00% |
| Total Weight | G | 1.00 | 100.00% |

It should be noted that Nicotinamide Mononucleotide (NMN), a Nicotinamide Adenine Dinucleotide precursor can replace Nicotinamide Riboside. Nicotinamide Mononucleotide can also be nanoformulated.

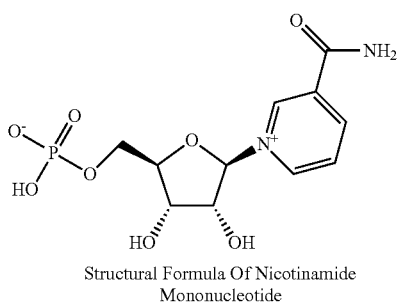 [SMILES: NC(=O)c1ccc[n+]([C@@H]2O[C@H](COP(=O)([O-])O)[C@@H](O)[C@H]2O)c1]

Structural Formula Of Nicotinamide Mononucleotide

Nanoemulsion/Nanodispersion/Nanosuspension

An oil dissolved bioactive compound 100 (e.g., curcumin in coconut oil) and an anti-solvent (e.g., water) are individually pressurized to collide head on at an extremely high velocity to form nanoemulsion/nanodispersion/nanosuspension of the (oil dissolved) bioactive compounds 100 (in the anti-solvent).

Furthermore, nanoparticles of the bioactive compounds 100 can be realized after evaporating the anti-solvent of nanoemulsion/nanodispersion/nanosuspension.

Furthermore, nanoemulsion/nanodispersion/nanosuspension/nanoparticle can enhance the efficacy and/or bioavailability of the bioactive compounds 100 at a lower concentration.

Targeted Delivery: Nanoencapsulation

Figure 6A:
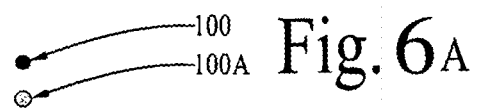
FIGS. 6A, 6B, 6C, 6D and 6E illustrate targeted delivery of bioactive compounds and/or bioactive molecules, utilizing a nanocarrier and/or a nanoshell.

FIG. 6A illustrates a bioactive compound 100 and a bioactive molecule 100A respectively.

Figure 6B:
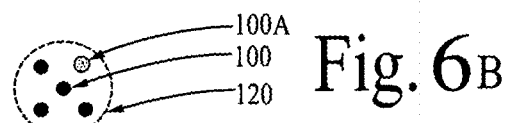
Figure 6C:
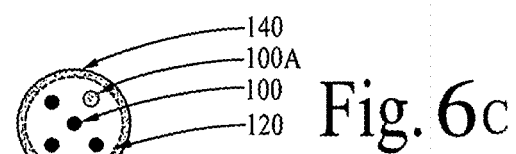
Figure 6D:
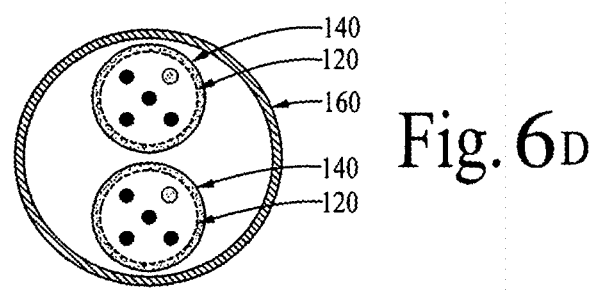

FIG. 6B illustrates the bioactive compound 100 and bioactive molecule 100A, which are encapsulated/caged in a nanoshell 120.

The size of the nanoshell 120 is about 25 nanometers to 115 nanometers in diameter and generally spherical in shape.

The nanoshell 120 can be biodegradable and less toxic.

By way of an example and not by way of any limitation, the nanoshell 120 can be a boron nitride nanotube, carbon nanotube, Cornell-dot, cubisome, dendrimer (including plant based dendrimer), deoxyribonucleic acid (DNA) origami nanostructure, exosome, fullerene $C_{60}$ (e.g., malonic acid derivative of $C_{60}$), gold nanoparticles (suitably coated), grapefruit-derived nanovector (GNV), hollow magnetic cage molecule (e.g., $Co_{12}C_6$, $Mn_{12}C_6$ and $Mn_{24}C_{18}$), iron nanoparticle, lipidoid, liposome, mesoporous silica, micelle, nanocrystal, niosome, polysebacic acid (PSA), polysilsesquioxane (PSQ), porous silicon photonic crystal, quantum dot, quantum dot capped with glutathione, ribonucleic acid (RNA) origami nanostructure, self-assembling peptide (or self-assembling protein), silk-fibroin nanoparticle, solid-lipid nanoparticle, spherical nucleic acid (SNA), synthasome, tubular/tetrahedral structure fabricated/constructed, utilizing DNA/RNA origami process, virus (e.g., tobacco mosaic virus), zein-plant protein and zeolite-1-nanocrystal.

A Cornell-dot consists of dye molecules encased in a chemically inert silica shell of about 5 nanometers in diameter.

Exosome contains RNAs. Cells communicate with each other by sending and receiving exosomes—thus an exosome can be viewed as a unit for cell-to-cell biological communication directly by surface expressed ligands or transferring molecules from the originating cells. For example, exosomes can carry material from the originating cancer cells to suppress the immune system and stimulate angiogenesis for the growth of cancer cells. Recipient cells act, utilizing RNAs—for example, protein manufacturing in the case of messenger RNA or repression of the expression of some genes in the case of microRNAs. Thus, exosomes (in their specific pathways) can be utilized as the nanoshell 120 to deliver RNA (e.g., a specific small interfering RNA) for therapeutic purposes.

Furthermore, an MRI contrast agent and/or molecular tag can be encapsulated/caged in the nanoshell 120—thus realizing a multifunctional nanoshell 120.

Monolayer coatings applied on the surface of gold nanoparticles can consist of a mix of hydrophobic and hydrophilic layers. Furthermore, additional functionalization (with ligand(s)) on the surface of gold nanoparticles can be applied to target a selective cell type. A mechanism allows gold nanoparticles to pass through a cell membrane and then seals the opening of the cell membrane, as soon as the gold nanoparticles enter into the selective cells. Harnessing of this cell-penetrating mechanism of suitably functionalized gold nanoparticles can be utilized as a way of delivering the bioactive compounds 100 and/or bioactive molecules 100A and/or biosensing molecules to the selective cell's interior, by binding the bioactive compounds 100 and/or bioactive molecules 100A and/or biosensing molecules with a monolayer of coating and/or additional functionalization. The biosensing molecules can detect/monitor a biomarker(s) to indicate an onset/decline of a disease.

Furthermore, the biosensing molecules can be embedded/integrated within a biodissolvable electronic circuit, which is generally fabricated/constructed by silicon nanowires and/or silk nanowires.

By way of an example and not by way of any limitation, the nanoshell 120 can be a combination of an artificial material and a biological material.

By way of an example and not by way of any limitation, the nanoshell 120, as a combination of an artificial inorganic/organic material and a natural biological material can be printed by three-dimensional self-assembly/nano-printing or four-dimensional (4-D) self-assembly/nano-printing, wherein an extra dimension of time in four-dimensional self-assembly/nano-printing may allow the nanoshell 120 to adapt/evolve/transform over time by an internal/external condition (e.g., pH and light).

Furthermore, a micelle can be fabricated/constructed, utilizing an aptamer, casein protein, epigallocatechin-3-O-gallate derivative (with vitamin E at the center of epigallocatechin-3-O-gallate derivative) and polymer.

By way of an example and not by way of any limitation, the nanocrystal can be a nanodiamond or nanohydroxyapatite. Hydroxyapatite is a form of calcium phosphate $Ca_{10}(PO_4)_6(OH)_2$.

Spherical nucleic acids are configured as a three-dimensional superlattice assembly on an inorganic nanoparticle (typically gold or silver). These three-dimensional superlattices can consist of functionalized and oriented nucleic acids-attached to the inorganic nanoparticle. Spherical nucleic acids can be core-filled with the above inorganic nanoparticle or core-less without the above inorganic nanoparticle. The strength/length of the programmable DNA bonds within the three-dimensional superlattice assembly can be adjusted by varying a DNA sequence and sequence length. The properties of spherical nucleic acids can be adjusted by varying nanoparticle size, shape and composition.

Linear nucleic acids cannot enter into cells, but spherical nucleic acids can enter into cells. Core-less spherical nucleic acids do not trigger an immune response. Thus, resulting in longer lifetime in a human body. Spherical nucleic acids can also cross a human body's blood-brain barrier and skin. Spherical nucleic acids can enable nucleic acid based and small interfering RNA based therapeutics. A DNA sequence can be matched to target genes for a different disease.

Synthasome is a spherical hollow nanoshell and it contains an aqueous solution for protecting the bioactive compounds 100 and/or bioactive molecules 100A. The synthasome has a nano-scaled channel(s) (e.g., a transmembrane protein channel) to permit or deny transport of the bioactive compounds 100 and/or bioactive molecules 100A across the synthasome membrane.

Furthermore, an appropriate synthetic polymer material can be utilized to customize the characteristics (e.g., control permeability, release rate and stability) of the synthasome membrane.

Furthermore, a specialized biodegradable and non-toxic theranostic (e.g., perfluorocarbon based polymer) based on as the nanoshell 120 can spontaneously form itself out of tailored polymers macromolecules.

The formation requires a balance between the polymers macromolecules' hydrophilic (capable of dissolving in water) and hydrophobic (not dissolvable in water) parts. The hydrophobic portion makes it possible to fill the nanoshell 120 with the bioactive compounds 100 and/or bioactive molecules 100A.

A relatively high concentration of the natural isotope 19F (fluorine) can make the theranostic nanoshell 120 clearly visible on high resolution images taken by magnetic resonance imaging. It is possible to obtain information about how the bioactive compounds 100 and/or bioactive molecules 100A are taken up by the cell and whether the treatment, utilizing the bioactive compounds 100 and/or bioactive molecules 100A are working or not.

Virus (e.g., Influenza A virus-IAV)-configured as harmless/non-infectious can act as a nanoshell 120. For example, Influenza A virus-IAV has eight (8) viral segments, encoding ten (10) major proteins. By eliminating two (2) viral segments, Influenza A virus-IAV can be made harmless/non-infectious. Thus, Influenza A virus-IAV as a nanoshell 120 can deliver the bioactive compounds 100 and/or bioactive molecules 100A.

Furthermore, Influenza A virus-IAV can also deliver either coding RNAs or noncoding RNAs or micro RNAs to treat a specific disease.

The interior surface of the nanoshell 120 can be electrically charged (e.g., an opposite electrical charge polarity with respect to the electrical charge polarity of the bioactive compounds 100 and/or bioactive molecules 100A to be encapsulated/caged in the nanoshell 120) to increase the encapsulation efficiency of the bioactive compounds 100 and/or bioactive molecules 100A.

The exterior surface of the nanoshell 120 can be electrically charged to increase the delivery efficiency of the bioactive compounds 100 and/or bioactive molecules 100A.

FIG. 6C illustrates the surface of the nanoshell 120, which can be coated with an optional protective (to protect from a human body's blood/biological fluid) functional surface 140.

By way of an example and not by way of any limitation, a biological fluid can generally mean blood plasma, blood serum, cerebrospinal fluid, saliva, tear and urine.

The optional protective functional surface 140 can be fabricated/constructed, utilizing a casein protein.

Optionally, the nanoshell 120 can be coated with an immune shielding (to protect from a human body's inherent immune surveillance) functional surface 180.

The nanoshell 120 can be coated with galactosamine sugar molecules.

The nanoshell 120 can be coated with mannose sugar molecules.

The nanoshell 120 can be coated with folic acid molecules.

Both galactosamine sugar and mannose sugar can accumulate selectively in the liver.

FIG. 6D illustrates the nanoshell 120, which can be further encapsulated/caged in a nanocarrier (e.g., an artificial cell, capsosome, DNA/RNA origami nanostructure, natural biopolymer chitosan and polyethylene glycol (PEG)) 160.

The DNA/RNA origami structure (nanostructure) with a lid that can stay locked until exposed to a DNA based key. The DNA/RNA origami structure (nanostructure) assembled with a lid which can be opened by a DNA/RNA strand displacement/chemical coupling with a specific functionalized oligonucleotide key (to chemically couple with a complementary oligonucleotide or external stimulus). The DNA/RNA origami structure (nanostructure) can offer unprecedented control over shape, size, mechanical flexibility and surface modification. The surfaces of the DNA/RNA origami structure (nanostructure) assembled with a lid can be fully addressable, allowing for the incorporation of multiple ligands/labels to chemically bind with a biomarker(s) for the detection of a disease(s) and delivery of bioactive compound(s)/molecule(s). For example, a DNA/RNA origami superstructure can include/integrate a cluster of many DNA/RNA origami structures (nanostructures), each DNA/RNA origami structure encapsulated/caged with its bioactive compound(s)/molecule(s) and programmed set of inputs(s) for the delivery of the bioactive compound(s)/molecule(s).

Furthermore, multiple inputs to the DNA/RNA origami structure (nanostructure) can be controlled by a basic principle of DNA/RNA computing (e.g., AND or NOR function) for the specific and simultaneous detection of the disease(s) and the controlled delivery of the bioactive compound(s)/molecule(s).

By way of an example and not by way of any limitation, utilizing a hybridization chain reaction, wherein cancer cells can be transfected with RNA transducers to recognize specific cancerous markers and induce PKR-mediated cancel cell death. Utilizing a cascade series of dynamic structures (e.g., metastable DNA hairpin motifs/DNAzymes/entropy driven strand displacement) to create DNA based molecular circuitries for point-of-care diagnosis. The magnitude and duration of the multiple inputs to the DNA/RNA origami structure (nanostructure) can also be programmed from a continuous delivery mode of the bioactive compound(s)/molecule(s) to a threshold-controlled delivery mode of bioactive compound(s)/molecule(s).

In addition to its well-known DNA's structural properties-A only binds T, G only binds C, one can predict the atomic-level structure of virtually any DNA origami nanostructure with remarkable accuracy.

Furthermore, because complementary DNA sequences recognize each other, short DNA strand can act as an accurate address label to direct a DNA origami structure to a specified cell location.

Furthermore, a DNA based sensor within the nanoshell 120 can recognize an RNA message produced because of a certain biological event—thus can trigger a release of RNA or DNA strands with therapeutic properties.

The size of the nanocarrier 160 is about 200 nanometers to 300 nanometers in diameter and generally spherical in shape.

The nanocarrier 160 can be biodegradable and less toxic.

To construct a capsosome, a polymer film (containing building blocks modified with cholesterol) is deposited onto small silica spheres. Liposomes (with an immune shielding functional surface 180) are anchored to the cholesterol. Subsequently, more polymer films are added and cross-linked by disulfide bridges. Finally, the small silica spheres are etched away.

Figure 6E:
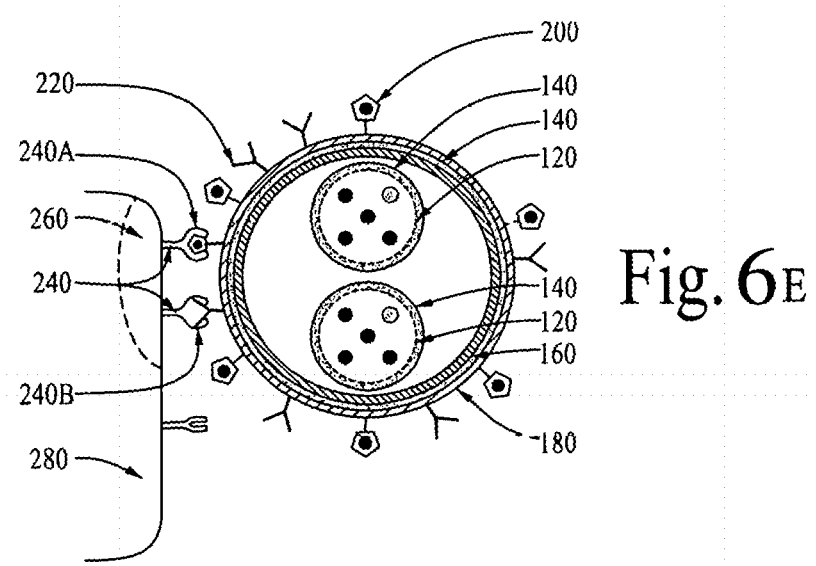

FIG. 6E illustrates the nanocarrier 160, which can be coated with the optional protective (to protect from a human body's blood/biological fluid) functional surface 140.

The nanocarrier 160 can be coated with an immune shielding (to protect from a human body's inherent immune surveillance) functional surface 180.

A human body's natural red blood/artificial red blood cell membrane can be utilized as an immune shielding functional surface 180.

Ligands and/or receptors or native lipids and/or proteins of purified & active leukocytes (from a human body's white blood cells) can be also utilized as an immune shielding functional surface 180

A polymer membrane (e.g., polyethylene glycol polymer/water-like polymer) can also be utilized as an immune shielding functional surface 180 instead of a human body's red blood cell membrane, or ligands and/or receptors or native lipids and/or proteins of purified & active leukocytes (from a human body's white blood cells).

Polyethylene glycol membrane is a low-toxicity polymer and it can also shield against hydrophobic and/or electrostatic interactions.

However, a human body's natural red blood/artificial red blood can be utilized as an immune shielding functional surface 180, along with (including) a polymer membrane.

However, ligands and/or receptors or native lipids and/or proteins of purified & active leukocytes (from a human body's white blood cells) can be utilized as an immune shielding functional surface 180, along with (including) a polymer membrane.

The extracellular space of a human brain is viscous and the viscosity can impede propagation of the nanoshell 120 in a human brain.

Considering the passage through a human body's blood-brain barrier and viscosity in the extracellular space of a human brain, a suitable diameter for propagation is estimated between 65 nanometers to 115 nanometers.

Thus, only the nanoshell 120 (without the nanocarrier 160) can be suitable for the passage through a human body's blood-brain barrier and extracellular space of a human brain.

Biological receptors 240 are located on cell 260 of tissue 280.

A first targeting ligand 200 (e.g., cobalamin/vitamin) can recognize/match/bind with specific biological receptors 240A of 240, located on cell 260 of tissue 280.

A second targeting ligand 220 (e.g., a specific antibody/aptamer) can recognize/match/bind with specific biological receptors 240B of 240, located on cell 260 of tissue 280.

Both targeting ligands 200 and 220 can be utilized as dual navigators toward the biological receptors 240A and 240B respectively.

Both the nanocarrier 160 and nanoshell 120 can break, when (a) the first targeting ligand 200 recognizes/matches/binds with the specific biological receptors 240A and (b) the second targeting ligand 220 recognizes/matches/binds with the specific biological receptors 240B.

Alternatively, both the nanocarrier 160 and nanoshell 120 can break under an external condition/response (e.g., pH and light).

Thus, the bioactive compounds 100 and/or bioactive molecules 100A can be delivered from the nanoshell 120 to the cell 260.

Example Applications of a Nanoshell (can be Decorated with a Human Body's Red Blood Cell Membrane & Polyethylene Glycol Membrane) with/without a Nanocarrier (can be Decorated with a Human Body's Red Blood Cell Membrane & Polyethylene Glycol Membrane)

Molecular Coupling/Reprogramming

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B (e.g., a messenger RNA aptamer). Upon passing through the nuclear pore, utilizing the second targeting ligand 220A that recognizes/matches/binds with the nuclear pore, the nanoshell 120 can be uncapped in the nucleus of the cell 260 itself, when the third targeting ligand 220B recognizes/matches/binds with a specific RNA (e.g., a messenger RNA).

The bioactive compounds 100 and/or bioactive molecules 100A can be delivered from the nanoshell 120 specifically to couple and/or edit and/or modulate the specific RNA (e.g., a messenger RNA)—thus enabling molecular coupling/reprogramming for specific disease prevention.

However, for a specific application of molecular coupling/reprogramming, only the nanoshell 120 (without the nanocarrier 160) can also be utilized.

Gene Text Editing by Zinc Fingers, a Class of DNA-Binding Proteins

A human genome has about 3 billion pairs of the chemical letters A, C, G, and T (adenine, cytosine, guanine, and thymine). Now to 3 billion letters for a single appearance of the word "CAT," and then replace a "C" with "T" to make the word "TAT." To enable this, one needs an enzyme that is both capable of precise recognition of a specific DNA sequence and outfitted with a scissor and paste to modify the chemical letters. One big unknown of the copy-paste editing strategy is any off-target effects that occur during fixing a defective or target gene, while it must not damage another gene.

Most gene therapy techniques use a virus to carry new genes into a cell, but cannot direct the virus to insert genes into a specific site.

But zinc fingers are a class of engineered DNA-binding proteins used by living cells to turn genes on and off. Each zinc finger recognizes a set of three letters, or bases, on the DNA molecule. Because the zinc fingers recognize specific sequences of DNA, they guide the control proteins to a specific site wherein the target gene begins. Thus, the zinc fingers can be utilized as a word processing system for cutting and pasting into a genetic text.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore, utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

The zinc fingers (with desired DNA template) can be delivered from the nanoshell 120 specifically to edit a specific gene for specific disease prevention.

Furthermore, the zinc fingers (with a desired DNA template) can be delivered from the nanoshell 120 specifically to genetically correct stem cells, prior to any use. This strategy can be used to generate genetically corrected, patient derived cells that could be transplanted without fear of a human body's immune-rejection.

However, for a specific application of genetic text editing, only the nanoshell 120 (without the nanocarrier 160) can also be utilized.

Gene Text Editing by Transcription Activator Like Effector Nucleases (TALENs)

The zinc fingers can snip away from a target site—thus, it may be a potentially serious safety problem.

Unlike the zinc fingers that bind to a group of three base pairs, TALENs can bind to individual nucleotides.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore, utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

Transcription activator like effector nucleases (with desired DNA template) can be delivered from the nanoshell 120 specifically to edit a specific gene for specific disease prevention.

Furthermore, transcription activator like effector nucleases (with a desired DNA template) can be delivered from the nanoshell 120 specifically to genetically correct stem cells, prior to any use. This strategy can be used to generate genetically corrected, patient derived cells that could be transplanted without fear of a human body's immune-rejection.

However, for a specific application of genetic text editing, only the nanoshell 120 (without the nanocarrier 160) can also be utilized.

Gene Text Editing by a Synthetic RNA

Challenges of zinc finger or TALEN nucleases are getting a high level of expression and persistence of the introduced DNA construct.

A synthetic RNA that encodes a gene-editing protein (e.g., transcription activator like effector nucleases) can be targeted to a specific gene.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore, utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

A synthetic RNA to encode a gene-editing protein (e.g., transcription activator like effector nucleases) (with desired DNA template) can be delivered from the nanoshell 120 specifically to edit a specific gene for specific disease prevention.

Furthermore, a synthetic RNA to encode a gene-editing protein (e.g., TALENs) (with a desired DNA template) can be delivered from the nanoshell 120 specifically to genetically correct stem cells, prior to any use. This strategy can be used to generate genetically corrected, patient derived stem cells that could be transplanted without fear of a human body's immune-rejection.

However, for a specific application of genetic text editing, only the nanoshell 120 (without the nanocarrier 160) can also be utilized.

Gene Text Editing by Cas9 Complexes with RNA

A DNA-cutting enzyme namely Cas9 complexed with a short 20-nucleotide segment of RNA (matching the target DNA segment) can be programmed to target a DNA sequence. Rather using a protein to target the desired DNA sequence, it uses RNA to guide the DNA-cutting enzyme namely Cas9 to the targeted the DNA sequence. This takes advantage of the natural pairing of RNA and DNA sequences. In order to recognize the target DNA, Cas9 requires the short sequence of "GG" in the target DNA adjacent to the site bound by the targeting RNA. The DNA-cutting enzyme namely Cas9 does not have to change for every DNA sequence to be targeted—one has to reprogram it with a different RNA transcript, which is easy to design and implement.

The nanoshell 120 (encapsulating/caging CRISPR-Cas9 system) can be encapsulated/caged in the nanocarrier 160. The nanocarrier 160 can be decorated with the first targeting ligand 200. The first targeting ligand 200 can recognize/match/bind with specific biological receptors 240A on the cell 260 to deliver the nanoshell 120 (encapsulating/caging CRISPR-Cas9 system) to the cell 260.

Alternatively, the nanoshell 120 (encapsulating/caging CRISPR-Cas9 system) can be decorated with a second targeting ligand 220A to recognize a nuclear pore. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system for gene editing. The second targeting ligand 220A can be a molecule also.

Alternatively, the nanoshell 120 (encapsulating/caging CRISPR-Cas9 system) can be decorated with the second targeting ligand 220A to recognize a nuclear pore and a third targeting ligand 220B. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system preciously for gene editing, when the third targeting ligand 220B recognizes/matches/binds with a specific DNA. The third targeting ligand 220B can be a molecule also.

However, just the nanoshell 120 (encapsulating/caging CRISPR-Cas9 system) can be decorated with the first targeting ligand 200 to recognize/match/bind with specific biological receptors 240A on the cell 260 to deliver CRISPR-Cas9 system.

Alternatively, just the nanoshell 120 (encapsulating/caging CRISPR-Cas9 system) can be decorated with the first targeting ligand 200 to recognize/match/bind with specific biological receptors 240A on the cell 260, the second targeting ligand 220A to recognize a nuclear pore. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system for gene editing.

Alternatively, just the nanoshell 120 (encapsulating/caging CRISPR-Cas9 system) can be decorated with the first targeting ligand 200 to recognize/match/bind with specific biological receptors 240A on the cell 260, the second targeting ligand 220A to recognize a nuclear pore and the third targeting ligand 220B. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system precisely for gene editing, when the third targeting ligand 220B recognizes/matches/binds with a specific DNA.

Alternatively, just the nanoshell 120 (in particular DNA/RNA origami structure (nanostructure) encapsulating/caging CRISPR-Cas9 system) can be decorated with the first targeting ligand 200 to recognize/match/bind with specific biological receptors 240A on the cell 260 to deliver CRISPR-Cas9 system.

Thus, CRISPR-Cas9 system delivered via the nanoshell 120, decorated with the targeting ligand 200 to recognize/match/bind with specific biological receptors 240A on cancer cells can be utilized to cut/edit a mutated DNA(s) causing cancer.

Similarly, CRISPR-Cas9 system delivered via the nanoshell 120, decorated with the targeting ligand 200 to recognize/match/bind with specific biological receptors 240A on HIV-infected cells can be utilized to cut/edit HIV DNA.

Alternatively, just the nanoshell 120 (in particular DNA/RNA origami structure (nanostructure) encapsulating/caging CRISPR-Cas9 system) can be decorated with the first targeting ligand 200 to recognize/match/bind with specific biological receptors 240A on the cell 260, the second targeting ligand 220A to recognize a nuclear pore. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system for gene editing.

Alternatively, just the nanoshell 120 (in particular DNA/RNA origami structure (nanostructure) encapsulating/caging CRISPR-Cas9 system) can be decorated with the first targeting ligand 200 to recognize/match/bind with specific biological receptors 240A on the cell 260, the second targeting ligand 220A to recognize a nuclear pore and the third targeting ligand 220B. Upon passing through the nuclear pore, utilizing the second targeting ligand 220A that recognizes/matches/binds with the nuclear pore, the nanoshell 120 can be uncapped in the nucleus of the cell 260 to deliver CRISPR-Cas9 system precisely for gene editing, when the third targeting ligand 220B recognizes/matches/binds with a specific DNA.

The engineered CRISPR-Cas9 system with RNA can be delivered from the nanoshell 120 specifically to activate or repress gene expression by modulating the transcription for specific disease prevention.

Cas9 does not have to change for every DNA sequence to be targeted—one has to reprogram it with a different RNA transcript, which is easy to design and implement.

Furthermore, the CRISPR-Cas9 can be replaced by the CRISPR-Cpf1. Cas9 requires two RNA molecules to cut DNA and Cpf1 needs just one RNA molecule. Both Cas9 and Cpf1 cut DNA at different places. Cas9 cuts both strands in a DNA molecule at a same position, leaving behind blunt ends and blunt ends can be repaired by sticking the two ends back together, in a repair process which can leave errors. However, Cpf1 cuts DNA in a different way, leaving one strand in a DNA molecule longer than the other—thus creating a sticky end.

Cas9 is an RNA-directed DNA-binding protein, guided by a single guide RNA. By inactivating its nuclease activity, coupling the protein to other effector domains and choosing an appropriate guide sequence, it can direct activities in a specific part of the genome. The nanoshell 120 (encapsulating/caging CRISPR-Cas9 system) can be decorated with the targeting ligand 200 to recognize/match/bind with specific biological receptors on stem cells (from pluripotent stem cells) to deliver CRISPR-Cas9 system into stem cells.

CRY2 and CIB1 are two plant proteins. In response to light, CRY2 undergoes a conformational change that allows it to interact with CIB1. In an optogenetic CRISPR-Cas9 system: CRY2 is fused to the transactivation domain (either p65 or VP64) and C1B1 is fused to dCas9—the deactivated Cas9 nuclease from CRISPR. The optogenetic CRISPR-Cas9 system can enable precise spatial and temporal control of cell behavior by light (e.g., blue light) and direct new DNA sequences for the dynamic regulation of endogenous genes. The nanoshell 120 (encapsulating/caging the optogenetic CRISPR-Cas9 system) can be decorated with targeting ligand 200 to recognize/match/bind with specific biological receptors on stem cells (from pluripotent stem cells) to deliver the optogenetic CRISPR-Cas9 system into stem cells by light.

The CRISPR-Cas9 or optogenetic CRISPR-Cas9 system can be inserted into stem cells via the nanoshell 120 to remove a key gene in a disease process and replace it with a beneficial gene that releases a biologic drug—thus-creating the engineered stem cells.

For example, the CRISPR-Cas9 or optogenetic CRISPR-Cas9 system can be inserted into stem cells via the nanoshell 120 to remove a key gene in the inflammatory process and replace it with a gene that releases a biologic drug (e.g., the tumor necrosis factor-alpha (TNF-alpha) inhibitor) to reduce inflammation via the engineered stem cells. Similarly, engineered stem cells can sense glucose and turn on insulin in response.

Example Applications of Gene Text Editing

HIV needs to latch onto a human body's white blood cell's CCR5 receptors to invade cells. However, a genetic mutation in a human body's white blood-cell's CCR5 receptor can prevent transmission of the HIV virus. Thus, gene editing can be utilized to disable the specific genes responsible for the production of CCR5 receptors.

Transcription Factor Control by Engineered CRISPR-Cas9 System with RNA

Transcription factors proteins can bind with specific DNA sequences in the gene's promoter region for either recruiting or blocking the enzymes needed to copy that gene into mRNA.

An engineered CRISPR-Cas9 system with RNA can act as a transcription factor, wherein Cas9 complexed with a short 20-nucleotides segment of RNA (matching the target DNA segment) can be programmed to target a DNA sequence, wherein Cas9 is disabled with a first protein to cut DNA after binding with DNA. Furthermore, the engineered CRISPR-Cas9 is embedded with a second protein (e.g., programmable oligomers), wherein the second protein can activate or repress gene expression by modulating the transcription.

Molecular Coupling to a Virus/Programmed Suicide of a Virus Infected Cell to Inhibit Virus Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell infected with a virus.

The nanoshell 120 can be decorated with the second targeting ligand 220 (e.g., an aptamer/protein kinase R (PKR) protein) which can recognize/match/bind with a single stranded RNA/double stranded RNA/double stranded DNA of a virus). The nanoshell 120 can be uncapped in the cell infected with the virus, when the second targeting ligand 220 recognizes/matches/binds with a single stranded RNA/double stranded RNA/double stranded DNA of the virus in the cell.

The bioactive compounds 100 and/or bioactive molecules 100A can be delivered from the nanoshell 120 to induce the cell infected with the virus for a programmed cell suicide (e.g., via apoptotic protease activating factor 1) to inhibit the multiplication/propagation of the virus.

However, for a specific application of molecular coupling to a virus/programmed suicide of a virus infected cell to inhibit virus multiplication/propagation, only the nanoshell 120 (without the nanocarrier 160) can be utilized.

Molecular Coupling to a Cancer Cell/Programmed Suicide of a Cancer Cell to Inhibit Cancer Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cancer cell to allow the nanoshell 120 to the cancer cell.

The nanoshell 120 can be decorated with the second targeting ligand 220 (e.g., a specific aptamer is designed to be complementary to an RNA sequence unique to a cancer cell). The nanoshell 120 can be uncapped in the cancer cell, when the second targeting ligand 220 recognizes/matches/ binds with an RNA sequence unique to a cancer cell.

The bioactive compounds 100 and/or bioactive molecules 100A can be delivered from the nanoshell 120 to induce a cancer cell 260 for a programmed cell suicide (e.g., via p53 pathway) to stop cancer multiplication/propagation.

For example, the bioactive compound 100, 2-(4-morpholinoanilino)-6-cyclohexylaminopurine, a small bioactive molecule can induce selectively cell death of a cancer cell.

For example, the bioactive compound 100, a Bax activator compound can bind directly and selectively to Bax for Bax activation. When activated, Bax damages the cell's mitochondria, releasing signals to self-destruct the cell and digest its pieces.

For example, the bioactive compound 100, Lomaiviticin A (or its chemical/structural analogue of Lomaiviticin A—e.g., Lomaiviticin aglycon), which can induce death of a cancer cell, by cleaving a cancer cell's double strands of its DNA structure. The three-dimensional structure and structure of Lomaiviticin A are given below.

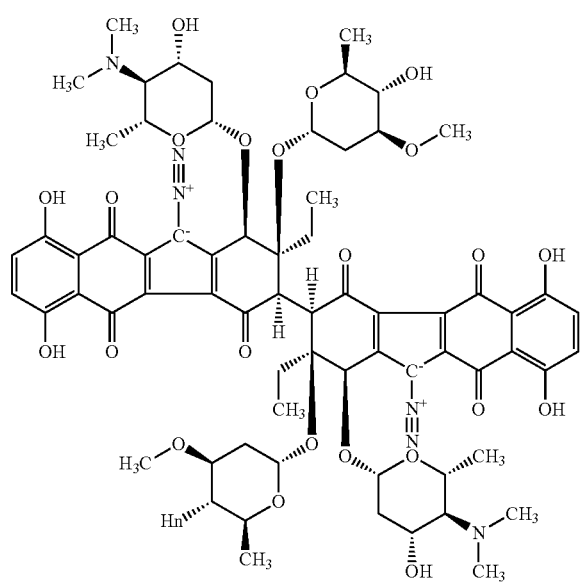

Structure Of Lomaiviticin A

For example, the bioactive compound 100, ironoxide nanoparticle or the bioactive molecule 100A aspirin (a COX inhibitor molecule) can activate immune cells (e.g., a tumor associated macrophage) to destroy a cancer cell.

For example, the bioactive compound 100 or the bioactive molecule 100A can be utilized to reprogram a corrupted/hijacked tumor associated macrophage by blocking its microRNA (e.g., Let-7 microRNA) to a human body's immune system.

For example, the bioactive compound 100 or the bioactive molecule 100A can be utilized to inhibit Focal Adhesion Kinase ("FAK") protein, which is often overproduced in a cancer cell to evade attacks by a human body's immune system.

Cancer cells often utilize immune checkpoint molecules (e.g., PD-L1) to deceive/evade an attack by a human body's immune system (e.g., T cells, one group of white blood cells). For example, the bioactive compound 100 (e.g., ipilimumab) or the bioactive molecule 100A (e.g., natural human antibody) can be utilized as a checkpoint inhibitor, which can block checkpoint molecules on a cancer cell or proteins (e.g., programmed death-1 (PD-1)) on T cells in order to remove the blinders that generally prevent T cells from recognizing a cancer cell.

However, for a specific application of molecular coupling to a cancer cell/programmed suicide of a cancer cell to inhibit cancer multiplication/propagation (e.g., utilizing extra copies of p53 protein), only the nanoshell 120 (without the nanocarrier 160) can be utilized.

Raising an amount of zinc via a bioactive compound (e.g., zinc metallochaperones) in a cancer cell can cause p53 protein to fold right back up and function normally. The recovered p53 protein can prompt apoptosis. A bioactive compound to raise zinc amount in a mutated p53 protein can be delivered by the nanoshell 120.

The addition of iron nanoparticles and/or anti-SIRPα antibodies (e.g., rituximab) to a tumor associated macrophage (TAM) can switch a tumor associated macrophage to attack a cancer cell. Iron nanoparticles can be delivered to a tumor associated macrophage by the nanoshell 120.

Molecular Coupling to Inhibit Insulin Degrading Enzyme

Normally about 50% of the insulin produced by the pancreas is immediately destroyed by the liver; but there may be a mechanism to regulate how much insulin enters into a human body's bloodstream. Insulin degrading enzyme is a protease, an enzyme that chops proteins or peptides into smaller pieces. If insulin degrading enzyme is inhibited, insulin can remain in a human body's blood stream longer. Insulin degrading enzyme is involved in a surprisingly wide range of important processes, including memory and cognition. Thus, insulin degrading enzyme inhibitors may have multiple therapeutic applications. Insulin degrading enzyme is a thiol-sensitive zinc-metallopeptidase.

A short-lived insulin degrading enzyme inhibitor, taken before a meal can be beneficial to manage Type-2 Diabetes disease.

By way of an example and not by way of any limitation, a bioactive compound $C_{21}H_{22}FN_3O_5S_2$ with the structural formula (as described below) can inhibit insulin degrading enzyme.

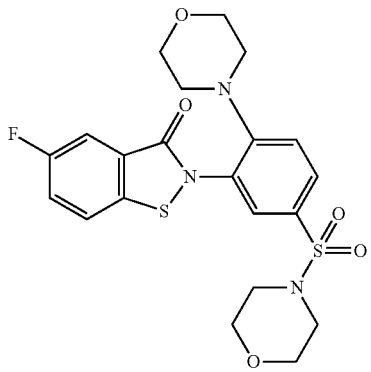

Structural Formula Of $C_{21}H_{22}FN_3O_5S_2$

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell.

The nanoshell 120 can be decorated with the second targeting ligand 220 (e.g., a specific aptamer is designed to bind with a specific target on insulin degrading enzyme). The nanoshell 120 can be uncapped in the cell, when the second targeting ligand 220 recognizes/matches/binds with the specific target of insulin degrading enzyme to deliver the bioactive compound such as, $C_{21}H_{22}FN_3O_5S_2$ to inhibit insulin degrading enzyme.

Molecular Coupling to Inhibit Insulin Degrading Enzyme Integrated with In-Vivo Gene Regulation by a Synthetic/Engineered Riboswitch Just as natural riboswitches can regulate gene expression in response to small-molecule ligands during transcription or translation, synthetic riboswitches can be engineered to repress or activate gene expression in a ligand-dependent fashion. A riboswitch can be turned on or off by a small molecule. Such riboswitch biosensors would provide spatial as well as temporal information regarding the levels of specific ligands in disease and the input information can be used to regulate cellular behavior for achieving therapeutic goals.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell. The nanoshell 120 can be decorated with the second targeting ligand 220 (e.g., a specific aptamer is designed to bind with a specific target on insulin degrading enzyme). The nanoshell 120 can be uncapped in the cell, when the second targeting ligand 220 recognizes/matches/binds with the specific target of insulin degrading enzyme to deliver the bioactive compound such as, $C_{21}H_{22}FN_3O_5S_2$ to inhibit insulin degrading enzyme and a riboswitch engineered to recognize glucose as its ligand and in response, the riboswitch engineered to recognize glucose as its ligand and in response, regulates the expression of insulin degrading enzyme gene in-vivo.

Example Applications of a Nanoshell (can be Decorated with a Human Body's Red Blood Cell Membrane & Polyethylene Glycol Membrane) without a Nanocarrier Collective Intelligence from Quorum Sensing of a Large Array of Smart Nanoshells DNA structure can assemble into a two-dimensional and/or a three-dimensional nanomechanical device. This two-dimensional and/or a three-dimensional nanomechanical device can be further integrated with (a) a targeting ligand (e.g., a specific aptamer/RNA) and a biocompatible nanosensor (e.g., an exosome) to act as a smart nanoshell 120. The smart nanoshell 120 can be activated by using a targeting ligand to deliver bioactive compounds 100 and/or bioactive molecules 100A.

Collective intelligence (e.g., swarm intelligence acquired from quorum sensing of the biocompatible nanosensors) of a large array of smart nanoshells 120s can be derived/utilized to predict the efficacy of the bioactive compounds 100 and/or bioactive molecules 100A for a treatment and/or to diagnose a disease and/or an array of diseases.

In many cases of, constrained applications, the nanoshell 120 (without the nanocarrier 160) coated with an immune shielding functional surface 180 can be utilized.

The nanoshell 120 (coated with a light sensitive layer or chemically coupled with wavelength converting nanoparticles) can be activated by a suitable wavelength from an external light source (e.g., an ultraviolet/visible/infrared light source) to deliver the bioactive compounds 100 and/or bioactive molecules 100A from the nanoshell 120 to the cell 260.

Alternatively, the nanoshell 120 (alternatively, configured with a magnetic nanoparticle) can be activated by a suitable external magnetic field to deliver the bioactive compounds 100 and/or bioactive molecules 100A from the nanoshell 120 to the cell 260.

A specific small interfering RNA can be designed to suppress/inhibit unwanted protein manufacturing in the cell 260. The specific small interfering RNA can be encapsulated/caged in the nanoshell 120. The nanoshell 120 decorated with a targeting ligand can deliver the specific small interfering RNA to suppress/inhibit specific unwanted protein manufacturing to the cell 260.

Molecular Coupling to a Virus/Programmed Death of a Virus Infected Cell to Inhibit Virus Multiplication/Propagation To sense an invading virus, a cell can use a pattern recognition receptor. The pattern recognition receptor can recognize/match/bind to a molecular signature, specific to the virus. This binding causes the pattern recognition receptors to change its structural shape. Thus, initiating a chain-reaction of a signal (regarding the virus) to the surrounding cells.

For example, one of these pattern recognition receptors is RIG-1, which can practically target all RNA viruses. In an absence of a virus, a molecular virus sensor of RIG-1 receptor is exposed, while the domain responsible for cell signaling is hidden out of reach of the signaling machinery.

But when the RIG-1 receptor detects a virus it changes its shape—waking up the cell signaling domains and triggering interferon production in the cell.

The changing shape of the RIG-1 receptor can be detected upon binding of the molecular virus sensor of the RIG-1 receptor with a molecular probe targeting ligand (e.g., a molecular beacon) wherein the molecular probe is configured with a suitable fluorophore.

The molecular probe (configured with a suitable fluorophore) targeting ligand can be decorated on the nanoshell 120.

Furthermore, the bioactive compounds 100 and/or bioactive molecules 100A for programmed cell suicide can be encapsulated/caged in/with an ultra-sensitive photolabile protecting group (PPG). The photolabile protecting group can be encapsulated/caged in the nanoshell 120.

Thus, in-vivo fluorescence can trigger a release of the bioactive compounds 100 and/or bioactive molecules 100A from the photolabile protecting group for programmed cell suicide (e.g., via apoptotic protease activating factor 1) of the virus infected cell to inhibit virus multiplication/propagation.

However, instead of the RIG-1 receptor, the nanoshell 120 can be decorated with a specific targeting ligand. The specific targeting ligand can recognize/match/bind with a single stranded RNA/double stranded RNA/double stranded DNA of a virus.

Molecular Coupling to a Virus/Programmed Death of a Virus Infected Cell to Inhibit Virus Multiplication/Propagation Utilizing DNA/RNA Origami Structure Smart Nanoshell The (DNA/RNA origami structure based) nanoshell 120 can be fabricated/constructed, inputting a list of DNA/RNA strands that can be mixed together, by utilizing DNA/RNA modeling software.

DNA/RNA modeling software can predict how DNA/RNA base pairs can bind/match together to create a particular DNA/RNA origami structure.

The (DNA/RNA origami structure based) nanoshell 120 can be decorated with a targeting ligand (e.g., a specific aptamer) to recognize/match/bind a target molecule in the signaling domain of the RIG-1 receptor, when the RIG-1 receptor changes its shape in the presence of a virus.

When the targeting ligand and target molecule recognize/match/bind in the signaling domain of the RIG-1 receptor, when the RIG-1 receptor changes its shape in the presence of a virus, the DNA strand can be configured to unzip, unlocking the (DNA/RNA origami structure based) nanoshell 120 and releasing the bioactive compounds 100 and/or bioactive molecules 100A for programmed cell suicide (e.g., via apoptotic protease activating factor 1) of a virus infected cell to inhibit virus multiplication/propagation.

However, instead of the RIG-1 receptor, the (DNA/RNA origami structure based) nanoshell 120 can be decorated with a specific targeting ligand. The specific targeting ligand can recognize/match/bind with a single stranded RNA/double stranded RNA/double stranded DNA of a virus.

To enhance specificity, two targeting ligands can be utilized, instead of one targeting ligand.

Thus, it would require two different matching signals in order to unzip the (DNA/RNA origami structure based) nanoshell 120.

Synthesis of Protein On-Demand

An amino acid, DNA/modified DNA (wherein the DNA/modified DNA encapsulated/caged in/with a photolabile protecting group) and a ribosome can be encapsulated/caged in the nanoshell 120.

For example, a nanosized hole in DNA can be drilled by an atomic beam to insert/delete a suitable atom or a molecule in order to fabricate/construct the modified DNA.

An incident light can activate the photolabile protecting group to synthesize a desired protein on-demand in-vitro and in-vivo. The nanoshell 120 can then deliver the desired protein directly to the cell 260. The desired protein can be utilized as a treatment against a disease.

Synthesis of Protein On-Demand by Synthetic Nucleotides

The natural genetic alphabet of DNA, the As, Cs, Gs, and Ts that writes the stories/book of life can be integrated (chemically bonded) with new compatible synthetic letters (e.g., $\alpha$ and $\beta$) to create a hybrid DNA (to write expanded stories/books of life). Furthermore, the hybrid DNA can be integrated (chemically bonded) with an importin protein(s). Importin is a type of protein that can transport its cargo hybrid DNA into the nucleus by binding to a specific recognition sequence, called the nuclear localization signal (NLS). Importin protein can bind with its cargo hybrid DNA in the cytoplasm, after which they are able to interact with the nuclear pore complex and pass through its channel. Once inside the nucleus, interaction with Ran-GTP causes a conformational change in the importin protein that causes it to dissociate from its cargo hybrid DNA. The nanoshell 120 decorated with a targeting ligand, wherein the targeting ligand can recognize/match/bind with specific receptors of a cell—thus allowing the cell membrane to be opened for the passage of the nanoshell 120 to deliver hybrid DNA integrated (chemically bonded) with an importin protein in cytoplasm and then ultimately into the nucleus.

Utilizing an artificial messenger RNA, hybrid DNA can manufacture useful protein(s)/protein(s)—on Demand, unknown to exist in nature, leading to a large number of amino acids and proteins. For example, adding just two (2) synthetic alphabets of DNA, one can manufacture one hundred seventy-two (172) amino acids with three (3) base pairs such as $\alpha\beta A$ or TG$\alpha$.

Furthermore, a hybrid DNA code can be used to build hybrid biological circuits (in cells) which may/may not interfere with the natural biological circuits.

Alzheimer's Disease

Shape and/or electrical polarity of the nanoshell 120 can be important parameters to suppress/inhibit Alzheimer's disease.

A tubular shaped nanoshell 120 can enhance/promote amyloid beta protein, increasing rate of decline in cognitive abilities in a human brain.

A negative electrical charged and tetrahedral shaped nanoshell 120 can distort and suppress/inhibit amyloid beta protein, significantly decreasing rate of decline in cognitive abilities in a human brain.

A specific small interfering RNA can be designed to suppress/inhibit unwanted protein manufacturing in the cell 260. A specific small interfering RNA can be encapsulated/caged in the nanoshell 120. The nanoshell 120 decorated with a targeting ligand, wherein the targeting ligand can recognize/match/bind with adenosine receptors—thus allowing a human body blood-brain barrier to be opened for the passage of the nanoshell 120 to deliver a specific small interfering RNA to suppress/inhibit unwanted protein manufacturing in a human brain.

Increased CD33 protein activity in microglia can impair amyloid beta protein. More CD33 proteins are on the cell surface of microglia; then more amyloid beta proteins-toxic amyloid beta plaques and damaging debris are in a human brain. Thus, reducing or silencing CD33 protein may be beneficial against Alzheimer's disease. The nanoshell 120 decorated with a targeting ligand, wherein the targeting ligand can recognize/match/bind with adenosine receptors—thus allowing a human body's blood-brain barrier to be opened for the passage of the nanoshell 120 to deliver a specific small interfering RNA to suppress/inhibit CD33 protein manufacturing in a human brain. However, it should be noted that a certain version of the CD33 gene may decrease CD33 protein activity in microglia.

Alzheimer's disease can be caused by a loss of synapses (between neurons) due to disintegration of tau protein, wherein tau protein can interact with amyloid beta protein.

Aging and/or poor autophagy can upregulate amyloid precursor protein cleaving enzyme: Bace1 ($\beta$-secretase-a molecular scissor).

Bace1 ($\beta$-secretase) can cut amyloid precursor protein to produce amyloid beta protein and another small fragment called AICD. Both amyloid beta protein and AICD can be linked to Alzheimer's disease. If Bace1 is acetylated via activation of ATase1 enzyme and ATase2 enzyme, then Bace1 can travel through the cell in a series of steps to produce amyloid precursor protein. If Bace1 is not acetylated, then Bace1 takes a different pathway toward degradation.

RanBP9 protein can push amyloid precursor protein at the cell (neuron cell) edge, wherein both Bace1 and presenilin complex ($\gamma$-secretase-a molecular scissor) can cut amyloid precursor protein to generate amyloid beta protein.

A potential prevention and/or treatment of Alzheimer's disease can be achieved by suppressing/inhibiting RanBP9 protein manufacturing. RanBP9 protein is encoded by RanBP9 gene.

Curcumin (e.g., a nanoformulated curcumin) can suppress/inhibit RanBP9 protein manufacturing in a human brain.

Cucurbitacin (e.g., Cucurbitacin E) can suppress/inhibit RanBP9 protein manufacturing in a human brain. Nanoformulated cucurbitacin can enhance the efficacy and/or bioavailability at a lower concentration.

Metformin (N,N-dimethylimidodicarbonimidic diamide) can suppress/inhibit RanBP9 protein manufacturing in a human brain.

An anticancer compound imatinib mesylate can suppress/inhibit RanBP9 protein manufacturing in a human brain. But imatinib mesylate cannot pass through a human body's blood-brain barrier Imatinib mesylate is 4-[(4-Methyl1-piperazinyl)methyl]-N-[4-methyl-3-[[4-(3-pyridinyl)-2-pyrimidinyl]amino]-phenyl]benzamide methanesulfonate and its structural formula is shown below:

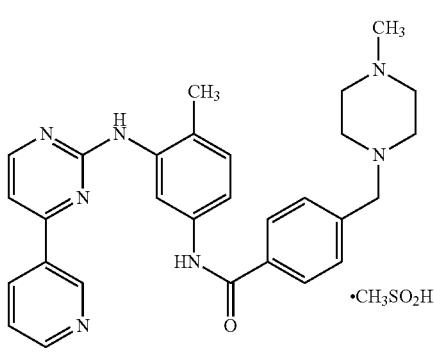

Structural Formula Of Imatinib mesylate

The molecular formula of Imatinib mesylate is $C_{29}H_{31}N7O$—$CH_4SO_3$ and its molecular weight is 589.7.

Imatinib mesylate can be encapsulated/caged in the nanoshell 120. The nanoshell 120 decorated with a targeting ligand, wherein the targeting ligand can recognize/match/bind with adenosine receptors—thus allowing a human body's blood-brain barrier to be opened for the passage of the nanoshell 120 to deliver imatinib mesylate to suppress/inhibit RanBP9 protein manufacturing in a human brain.

Nanoformulated imatinib mesylate can enhance the efficacy and/or bioavailability at a lower concentration.

Sodium phenylbutyrate can suppress/inhibit RanBP9 protein manufacturing in a human brain.

An anticancer compound dasatinib can suppress/inhibit RanBP9 protein manufacturing in a human brain.

The dasatinib is N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate and its structural formula is shown below:

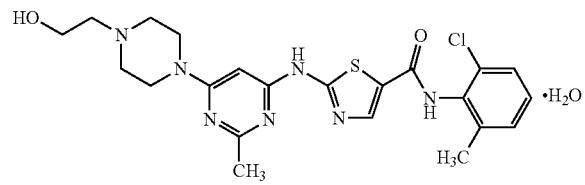

Structural Formula Of Dasatinib

The molecular formula of dasatinib is $C_{22}H_{26}ClN_7O_2S.H_2O$ and its molecular weight is 506.02 (monohydrate).

Nanoformulated dasatinib can enhance the efficacy and/or bioavailability at a lower concentration.

Dasatinib can be encapsulated/caged in the nanoshell 120. The nanoshell 120 decorated with a targeting ligand, wherein the targeting ligand can recognize/match/bind with adenosine receptors—thus allowing a human body's blood-brain barrier to be opened for the passage of the nanoshell 120 to deliver dasatinib to suppress/inhibit RanBP9 protein manufacturing in a human brain.

Affibody molecule (an engineered protein) can be encapsulated/caged in the nanoshell 120. The nanoshell 120 decorated with a targeting ligand, wherein the targeting ligand can recognize/match/bind with adenosine receptors—thus allowing a human body's blood-brain barrier to be opened for the passage of the nanoshell 120 to deliver affibody molecule to suppress/inhibit formation of amyloid beta protein in a human brain.

PARK7 gene (known as DJ-1) can protect cells (neurons) against oxidative damage. Sodium phenylbutyrate and/or a short protein fragment of non-mutated PARK7 can turn on PARK7 gene (known as DJ-1) to protect against oxidative damage.

Sodium phenylbutyrate and/or a short protein fragment of non-mutated PARK7 can be encapsulated/caged in the nanoshell 120. The nanoshell 120 decorated with a targeting ligand, wherein the targeting ligand can recognize/match/bind with adenosine receptors—thus allowing a human body's blood-brain barrier to be opened for the passage of the nanoshell 120 to deliver sodium phenylbutyrate and/or a short protein fragment of non-mutated PARK7 to protect against oxidative damage.

Glial cell line-derived neurotrophic factor (GDNF) protein can nourish dopamine neurons by activating survival and growth-promoting pathways inside the neurons of a human brain. But glial cell line-derived neurotrophic factor protein is limited in its ability to cross a human body's blood-brain barrier. The nanoshell 120 decorated with a targeting ligand, wherein the targeting ligand can recognize/match/bind with adenosine receptors—thus allowing a human body's blood-brain barrier to be opened for the passage of the nanoshell 120 to deliver glial cell line-derived neurotrophic factor protein to protect against damage of dopamine neurons.

Oleocanthal (its structural formula is shown below), a phenolic component of extra-virgin olive oil can reduce risk of Alzheimer's disease by clearing toxic amyloid beta protein from a human brain via up regulation of (a) P-glycoprotein (P-gp) and (b) low-density lipoprotein receptor-related protein (LRP1). P-glycoprotein and low-density lipoprotein receptor-related protein are major amyloid beta transport proteins at a human body's blood-brain barrier. However, the bioavailability of oleocanthal is unknown.

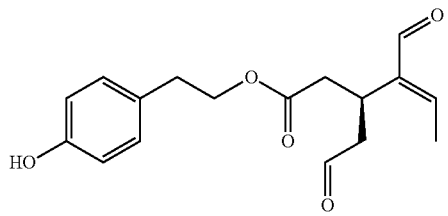

Structural Formula Of Oleocanthal

The nanoshell 120 decorated with a targeting ligand, wherein the targeting ligand can recognize/match/bind with adenosine receptors—thus allowing a human body's blood-brain barrier to be opened for the passage of the nanoshell 120 to deliver oleocanthal to protect against Alzheimer's disease.

The receptor for advanced glycation end products (RAGE) is a transporter of amyloid beta protein across a human body's blood-brain barrier into a human brain from the systemic circulation, while low-density lipoprotein receptor-related protein mediates transport of amyloid beta protein out of the brain. Accumulation of amyloid beta protein leading to Alzheimer's disease can be due to a relative distribution/ratio of receptor for advanced glycation end products protein and low-density lipoprotein receptor-related protein. However, the nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds 100 and/or bioactive molecules 100A and/or small interfering RNA to suppress/inhibit receptor for advanced glycation end products manufacturing to protect against Alzheimer's disease.

Stress/corticosteroid can cause the 5-lipoxygenase to overexpress and increase its levels which in turn increases the levels of the amyloid beta protein and tau protein. The nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds 100 and/or bioactive molecules 100A and/or small interfering RNA to suppress/inhibit 5-lipoxygenase protein manufacturing to protect against Alzheimer's disease.

Amyloid beta protein can injure synapses directly by inducing the release of excessive amounts of neurotransmitter glutamate from brain cells named astrocytes, located near neurons. Normal levels of glutamate can promote memory and learning, but excessive levels are very harmful. Excessive glutamate activates extrasynaptic receptors, designated as eNMDA receptors (N-methyl-D-aspartate). These eNMDA receptors can be hyperactivated—thus leading to synaptic loss. Memantine, a positively charged molecule can be easily repelled by positively diseased neurons; minimizing memantine's effectiveness, as it chemically binds with eNMDA receptors. Nitroglycerin can also bind eNMDA receptors. Nitroglycerin, isosorbide dinitrate and isosorbide mononitrate can convert into nitric oxide by mitochondrial aldehyde dehydrogenase and nitric oxide is a potent natural vasodilator. A combination of memantine and nitroglycerin (or isosorbide dinitrate or isosorbide mononitrate) can reduce excessive glutamate—thus protecting against Alzheimer's disease. Such a combination can include a chemical derivative or a structural analog of nitroglycerin (or isosorbide dinitrate or isosorbide mononitrate). Furthermore, the nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds: memantine and nitroglycerin (or isosorbide dinitrate or isosorbide mononitrate) to protect against Alzheimer's disease.

GLYX-13 (a small molecule) mimics an antibody and targets NMDA (N-methyl-Daspartate) receptors on neurons' surface. These NMDA receptors help control synaptic plasticity and neuro-chemical basis of learning, memory and depression. The nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds: GLYX-13 to protect against Alzheimer's disease.

Amyloid beta protein can bind with LilrB2 on neuron-cell surfaces—thus upregulating cofilin activity to destroy synapses' structural integrity. Furthermore, the nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds 100 and/or bioactive molecules 100A to protect against binding of amyloid beta protein binding with LilrB2.

Angiotensin-converting enzyme (ACE) is a naturally occurring enzyme that can have either detrimental or beneficial effects, depending on how and where it is active. Angiotensin-converting enzyme contributes to production of angiotensin II, a hormone that often causes blood vessels to narrow and blood pressure to rise; inhibiting the enzyme relaxes vessels and reduces pressure. But in the brain, high levels of angiotensin-converting enzyme quickly and efficiently lead an immune system response against beta-amyloid protein. Furthermore, the nanoshell 120 decorated with a targeting ligand, wherein the targeting ligand can recognize/match/bind with adenosine receptors—thus allowing a human body's blood-brain barrier to be opened for the passage of the nanoshell 120 to deliver bioactive compounds 100 and/or bioactive molecules 100A for overexpressing angiotensin-converting enzyme to protect against Alzheimer's disease.

Benzyl quinolone carboxylic acid (BQCA) and/or Benzoquinazoline-12 (BQZ-12) can be encapsulated/caged in a nanoshell 120 to protect against Alzheimer's disease.

Long-acting insulin derivative [2-sulfo-9fluroenyl-methoxycarbonyl]-3insulin can be encapsulated/caged in a nanoshell 120. The nanoshell 120 can be delivered for inhale via intranasal administration to protect against Alzheimer's disease.

Furthermore, intranasal administration can include stem cells to protect against Alzheimer's disease or other neurological diseases. Furthermore, intranasal administration can include engineered (engineered to express certain genes) stem cells to protect against Alzheimer's disease or other neurological diseases.

Cancer Disease

Bee venom contains a potent toxin called melittin that can poke holes in a cancer cell. However, large amounts of free melittin can also cause a lot of damage to healthy cells.

An assassin protein perforin can be a cancer's weapon of mass destruction. Perforin is encoded by the PRF1 gene. Perforin is expressed in T cells and natural killer (NK) cells. Interestingly, perforin resembles a cellular weapon employed by a bacterium (e.g., anthrax). Perforin has the ability to embed itself to form a pore in a cell-membrane. The pore by itself may be damaging to a cell and it enables the entry of a toxic enzyme granzyme B, which induces an apoptosis (a programmed suicide process) of a cancer cell.

The nanoshell 120 with melittin (its structural formula is shown below) can attack a cancer cell.

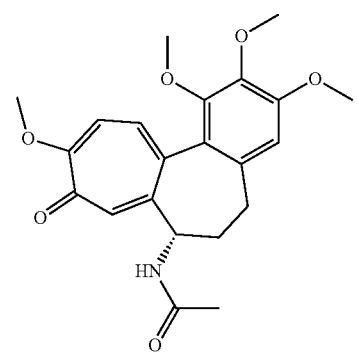

Structural Formula Of Melittin

The nanoshell 120 with both melittin and/or perforin can attack a cancer cell.

Cancer cells have a significantly increased rate of mitosis—thus cancer cells are significantly more vulnerable to toxic poisoning than are normal cells.

Colchicine is a toxic natural product and secondary metabolite, originally extracted from plants of the genus *Colchicum*. Colchicine only becomes active and detonates when in contact with an enzyme found in solid tumors sparing healthy tissue. The nanoshell 120 with colchicine at a low dose can attack a cancer cell.

The nanoshell 120 can collapse-enabling it to deliver encapsulated/caged small molecules/synthetic notch molecules to T cells for activation.

Alternatively, the nanoshell 120 can encapsulate/cage an encoding gene for chimeric antigen receptors/CARs and specifically deliver the encapsulated/caged encoding gene for converting T cells to CAR T cells. CAR T cells' action onto cancer cells can be also controlled by small molecules/synthetic notch molecules. Additionally, the nanoshell 120 can be coupled with nanoparticles to convert near-infrared light into visible blue light.

Alternatively, the nanoshell 120 encapsulating/caging a small interfering RNA to suppress liver receptor homolog 1 (LRH-1) to inhibit enormous glutamine metabolism of cancer cells.

Alternatively, the nanoshell 120 encapsulating/caging a small interfering RNA and/or a suitably charged (either positive polarity or negative polarity) small molecule and/or a notch signaling molecule and/or a small molecule to turn off a pyramid-shaped K-Ras molecular switch to inhibit growth of cancer cells. Additionally, the nanoshell 120 can be coupled with nanoparticles to convert near-infrared light into visible blue light.

Alternatively, the nanoshell 120 (e.g., fabricated/constructed by DNA origami) can encapsulate/cage an advanced encoding gene for advanced (consisting of a signaling domain(s)) chimeric antigen receptors (advanced CARs) and specifically deliver the encapsulated/caged advanced encoding gene for converting T cells to advanced CAR T cells. The advanced CAR T cells' action onto cancer cells can be also controlled by small molecules/synthetic notch molecules.

Additionally, checkpoint inhibitors, such as PD-1 inhibitors and/or anti-CTLA4 (anti-cytotoxic T-lymphocyte antigen 4) specific bioactive compounds 100 can also be integrated with T cells/CAR T cells/advanced CAR T cells.

The nanoshell 120 can be integrated with a targeting ligand (e.g., a specific antibody/aptamer) to bind specifically with a specific cancer cell. Such nanoshell 120 encapsulating/encaging lauric acid (a phase change material) as a carrier for a free radical generating compound(s) (e.g., an azo compound AIPH) can deliver the free radical generating compound(s), when a near-infrared laser heats up the nanoshell 120, causing lauric acid to melt and triggering the release of AIPH.

The nanoshell 120 can be integrated with a fluorescent probe molecule to illuminate cancer cells for locating purposes.

Alternatively, the fluorescent probe molecule can be chemically integrated with the targeting ligand.

The nanoshell 120 can be integrated with a photodynamic sensitizer molecule for detecting a specific cancer cell.

Alternatively, the nanoshell 120 can be integrated with a magnetic nanoparticle to guide the nanoshell 120 to a specific cancer cell by a magnetic field.

The nanoshell 120 can deliver the bioactive compounds 100 and/or bioactive molecules 100A to cancer cells (for therapy/treatment) under an external stimulus (e.g., pH).

Diabetes Disease

Long-acting insulin derivative [2-sulfo-9fluroenyl-methoxycarbonyl]-3insulin and leptin (or a chemical derivative/structural analog of leptin) can be encapsulated/caged in a pH responsive nanoshell 120. The pH responsive nanoshell 120 can be delivered for oral intake/inhale.

Long-acting insulin derivative [2-sulfo-9fluroenyl-methoxycarbonyl]-3insulin and oleoylethanolamide (OEA) (or a chemical derivative/structural analog of oleoylethanolamide) can be encapsulated/caged in a pH responsive nanoshell 120. The pH responsive nanoshell 120 can be delivered for oral intake/inhale.

Oleoylethanolamide (or a chemical derivative/structural analog of oleoylethanolamide) can be encapsulated/caged in a pH responsive nanoshell 120. The pH responsive nanoshell 120 can be delivered for oral intake/inhale.

A specific small interfering RNA can be designed to suppress/inhibit cryptochrome protein manufacturing. The specific small interfering RNA can be encapsulated/caged in the nanoshell 120. The nanoshell 120 can deliver the specific small interfering RNA to suppress/inhibit cryptochrome protein manufacturing.

Hearing Loss Disease

Free radicals can induce manufacturing of Bak, a protein. Bak protein can trigger suicide of cells (these cells do not regenerate like other cells in a human body) in the auditory portion of the inner ear.

The level of Bak protein can also increase with aging.

A specific small interfering RNA can be designed to suppress/inhibit Bak protein manufacturing. The specific small interfering RNA can be encapsulated/caged in the nanoshell 120. The nanoshell 120 can deliver the specific small interfering RNA (locally through the round window membrane (RWM) of the inner ear) to suppress/inhibit Bak protein manufacturing in a human ear.

Cochlear hair cell apoptosis (cell death)—a key factor in several forms of acute hearing loss, can be induced by p53 protein. However, an inhibition of p53 protein can be achieved by specific small interfering RNA. The specific small interfering RNA can be encapsulated/caged in the nanoshell 120. The nanoshell 120 can deliver the specific small interfering RNA (locally through the round window membrane of the inner ear) to suppress/inhibit p53 protein manufacturing in a human ear.

The administration of the bioactive compounds 100 and/or bioactive molecules 100A to treat hearing loss disease is through the permeation of the round window membrane. The ultra-fine structures of the round window membrane are not well known, but there are vesicles in the round window membrane, wherein clathrin and caveolin pathways may be involved in the transportation of the nanoshell 120 through round window membrane.

Mammalian hearing loss due to damage to auditory hair cells is normally irreversible. The Notch signaling pathway represents a critical component in the molecular circuits that control cell fate and plays a regulatory role in oxidative stress. But a partial recovery of auditory hair cells can be possible by inhibiting the Notch signaling pathway, utilizing (a) curcumin, (b) niclosamide (5-chloro-N-2-chloro-4-nitrophenyl)-2-hydroxybenzamide) and (c) a γ-secretase inhibitor.

Furthermore, the nanoshell 120 can be decorated with targeting ligands, which can bind to specific receptors on spiral ganglion cells (Trk-B receptors) and on the vasculature (the matrix metalloproteins, MMP2).

Brain-derived neurotrophic factor (BDNF) protein can also interact with Trk-B receptors.

Furthermore, cell entry of the nanoshell 120 can be facilitated by a viral-TAT peptide (e.g., TAT-Influenza-HA), binding of the nanoshell 120 with Trk-B receptors can be facilitated by brain-derived neurotrophic factor ligand and the nuclear pore complex entry of the nanoshell 120 can be facilitated by a nuclear targeting peptide.

Furthermore, brain-derived neurotrophic factor protein, Atoh1/Math1 gene (for growth of hair cells), a small interfering RNA designed to suppress/inhibit Bak protein manufacturing in a human ear) can be encapsulated/caged in the nanoshell 120.

Reactive oxygen species are involved in cisplatin-induced hearing loss. It depresses significantly the levels of antioxidant enzymes, superoxide dismutase, glutathione peroxidase, glutathione reductase, glutathione transferase and catalase—all antioxidants that protect cells from free radicals. Similarly, free radicals elevate the levels of products of lipid peroxidation, a process in which free radicals degrade the cell membrane. It also depletes the level of glutathione, another important antioxidant. When hair cells become damaged, glutamate (an excitatory neurotransmitter responsible for converting vibrational sounds into electrical signal) is produced in excessive amounts. Excessive amounts of glutamate can be toxic to neurons.

Coenzyme $Q_{10}$ (ubiquinol) can delay progression of hearing loss in patients with a genetic defect (7445A→G mitochondrial mutation). Although, supplementation with a single antioxidant may produce some beneficial effects in improving hearing disorders. However, a single antioxidant in a high oxidative environment can even act as a pro-oxidant.

The nanoshell 120 can deliver a synergistic combination of acetyl-L-carnitine, alpha-lipoic acid, glutathione, magnesium, n-acetylcysteine (NAC), 4-hydroxyphenyl N-tert-butyl nitrone/4-OHPBN nitrone and coenzyme $Q_{10}$ (ubiquinol) or ubiquinol (coenzyme $Q_{10}$) to reduce hearing loss.

Some photochemicals protect cells by disrupting established pathways by blocking activation of pro-inflammatory genes. Different photochemicals have different ways of interfering with toll-like receptors and nucleotide binding oligomerization domain containing proteins.

Furthermore, the nanoshell 120 can deliver a synergistic combination of curcumin and resveratrol and selenium (selenomethionine) to reduce hearing loss. Curcumin can undermine certain toll-like receptors when a specific part of curcumin's chemical structure-known as a beta unsaturated carboxyl group reacts with so-called sulfhydryl groups in toll-like receptors. Resveratrol can also interfere with molecules called TBK1 and RIP1. TBK1 and RIP1 convey signals to and from toll-like receptors. But when resveratrol interacts with TBK1 and RIP1, however, the effect is somewhat like a traffic light, which controls the flow of vehicles on a busy street.

Furthermore, the nanoshell 120 can deliver neurotrophin to reduce hearing loss.

Exposure to a high intensity noise can cause a decrease in total antioxidant capacity and an increase in nitric oxide. Increased nitric oxide can cause formation of peroxynitrite, which is very damaging to hair cells. The nanoshell 120 can deliver a combination of anticonvulsant zonisamide and glucocorticoid (e.g., methylprednisolone or betamethasone phosphate (BP)) to cochleae (cochleae is a Hopf oscillator acting as a nonlinear power amplifier, boosting weak signals much more than strong ones) over a sustained period of time to reduce hearing loss due to a high intensity noise.

Hepatitis B, Hepatitis C, HIV & Other Deadly Virus Based Diseases

Bee venom contains a potent toxin called melittin that can poke holes in the double-layered membranes indiscriminately of a virus (e.g., hepatitis B, hepatitis C and HIV). However, large amounts of free melittin can also cause a lot of damage to healthy cells.

In contrast, most anti-HIV drugs inhibit the virus's ability to replicate. But this anti-replication strategy does nothing to stop initial infection and some mutated strains of the virus have found ways around these drugs and reproduce anyway.

An assassin protein perforin can be a virus's weapon of mass destruction. Perforin is encoded by the PRF1 gene. Perforin is expressed in T cells and natural killer cells. Interestingly, perforin resembles a cellular weapon employed by a bacterium (e.g., anthrax). Perforin has an ability to embed itself to form a pore in a cell-membrane. The pore by itself may be damaging to a cell and it enables the entry of a toxic enzyme granzyme B, which induces an apoptosis (a programmed suicide process) of a diseased cell.

The nanoshell 120 with melittin can attack an essential part of the virus' (e.g., hepatitis B, hepatitis C and HIV) structure to destroy the virus.

The nanoshell 120 with melittin and perforin in combination can attack an essential part of the virus' (e.g., hepatitis B, hepatitis C and HIV) structure to destroy the virus.

The nanoshell 120 with a targeted small interfering RNA can attack an essential part of the virus' (e.g., hepatitis B, hepatitis C and HIV) structure to destroy the virus.

The nanoshell 120 a targeted small interfering RNA in combination with melittin can attack an essential part of the virus' (e.g., hepatitis B, hepatitis C and HIV) structure to destroy the virus.

The nanoshell 120 a targeted small interfering RNA in combination with perforin can attack an essential part of the virus' (e.g., hepatitis B, hepatitis C and HIV) structure to destroy the virus.

The nanoshell 120 a targeted small interfering RNA in combination with melittin and perforin can attack an essential part of the virus' (e.g., hepatitis B, hepatitis C and HIV) structure to destroy the virus.

Furthermore, the virus destroying strategy as cited in previous paragraphs can be generally utilized to destroy other deadly virus strains (e.g., Ebola). In the case of Ebola, a specific small interfering RNA is needed to silence the gene responsible for replication-polymerase L.

The nanoshell 120 can be decorated with a targeting ligand (e.g., a specific aptamer) to recognize/match/bind a target molecule in the signaling domain of a receptor (e.g., TIM-1) of Ebola virus.

When the targeting ligand and target molecule recognize/match/bind in the signaling domain of the receptor of Ebola virus, the nanoshell 120 can release the specific small interfering RNA to inhibit replication of polymerase L.

However, instead of the receptor, the nanoshell 120 can be decorated with a specific targeting ligand to recognize/match/bind with a negative stranded RNA based Ebola virus (which means the genome consists of one or more molecules of single stranded "antisense" RNA).

To enhance specificity, two targeting ligands can be utilized instead of one targeting ligand.

Thus, it would require two different matching signals in order to unzip the nanoshell 120.

Immune

An antigen/antibody generator can evoke the production of one or more antibodies. Each antibody binds to a specific antigen by way of an interaction similar to fit between a lock and a key. The antigen can originate from within a human body or external environment. The immune system can destroy or neutralize any antigen that is recognized as a foreign/potentially harmful invader.

The nanoshell 120 with specific antigen or an array of antigens can prevent immune-mediated diseases (e.g., Type-1 Diabetes disease). Insulin is destroyed in Type-1 Diabetes disease, because the autoimmune disease kills the beta cells producing that antigen. The nanoshell 120 with insulin can delay the onset or prevent Type-1 Diabetes disease.

The nanoshell 120 with myelin antigens can be engulfed by macrophages, a type of immune cell. Macrophages can then display the antigens on their cell surface. The nanoshell 120 with myelin antigens can inhibit the activity of myelin responsive T cells.

Inflammation

Reactive oxygen species can cause an inflammation in cardiovascular, hearing loss, infection and neurological diseases. An accumulation of reactive oxygen species can result in manifestation hydrogen peroxide ($H_2O_2$) or hypochlorous acid. Furthermore, an onset of reactive oxygen species related inflammation in cardiovascular, hearing loss, infection and neurological diseases can be approximately correlated with massive oxidative stress (thus, accumulation of hydrogen peroxide in the hair follicle), decreased antioxidant capacities including catalase, thioredoxin reductase and the repair mechanisms methionine sulfoxide reductases.

A synergistic combination of about 200 mg of catalase (or a chemical derivate or a structural analog of catalase or a pseudocatalase activated via sunlight), about 200 mg of glutathione peroxidase, about 1000 mg of L-methionine, about 100 mg of methionine sulfoxide reductase (MSR), about 200 mcg of selenium amino acid complex (sodium selenite, L-selenomethionin and selenium-methyl L-selenocysteine), about 200 mg superoxide dismutase and about 200 mg of *Emblica officinalis* extract can reduce damages due to free radicals and hydrogen peroxide in the hair follicle.

Hydrogen peroxide or hypochlorous acid sensitive nanoshell 120 can degrade in the presence of a minute amount of hydrogen peroxide or hypochlorous acid in order to deliver the bioactive compounds 100 and/or bioactive molecules 100A to reduce the inflammation in cardiovascular, hearing loss, infection and neurological diseases.

Inflammation in a human is an earlier indicator of Alzheimer's disease. A pathway involving TYROBP (an inflammatory gene) can interact with TREM2, a gene involved in Alzheimer's disease. TREM2-TYROBP pathway can play an initial role in driving Alzheimer's disease. Targeting TREM2-TYROBP pathway early on may delay/decrease risk of developing Alzheimer's disease.

TL1A protein takes part in driving the inflammation. The nanoshell 120 with the specific small interfering RNA can be utilized to block TL1A protein production.

Premature Aging (Progeria) Disease

A cellular instability leading to premature aging (Progeria) disease can be caused by toxic Lamin A protein. Toxic Lamin A protein is manufactured due to a mutation in the LMNA gene. A specific small interfering RNA can be designed to suppress/inhibit toxic Lamin A protein manufacturing. The nanoshell 120 can deliver the specific small interfering RNA to suppress/inhibit toxic Lamin A protein manufacturing.

Furthermore, Lamin A protein interacts with SUN 1 protein. The nanoshell 120 can deliver the specific small interfering RNA to suppress/inhibit SUN 1 protein manufacturing.

Protein Misfolding Disease

The complexity and dynamics of unfolded proteins can play a crucial role in aggregation, misfolding and subsequent diseases (e.g., Alzheimer's and Diabetes diseases).

Fragments of misfolded proteins can seed and then coerce/recruit normal protein to misfold and propagate various neurological diseases (e.g., Alzheimer's and Prion diseases) relentlessly. In the case of Alzheimer's disease, the proteins' individual amino acids can be assembled into strands, which stack into sheets that run the length of the entire structure. Those sheets can then group with increasing rigidity into protofilaments, filaments and finally mature and tough fibrils. Besides the intricate structure, many of the packing interactions are derived from the amyloid self-assembly process.

The reconfiguration dynamics of unfolded proteins may be governed by physics of thermodynamics. The reconfiguration dynamics can be measured by the rate of intramolecular diffusion (the diffusion rate of one part of a protein sequence with respect to another part).

The nanoshell 120 decorated with a first targeting ligand 200, wherein the first targeting ligand 200 can recognize/match/bind with adenosine receptors—thus allowing a human body's blood-brain barrier to be opened for the passage of the nanoshell 120 to deliver the bioactive compounds 100 and/or bioactive molecules 100A for prevention of aggregation/misfolding (e.g., bioactive compound nanocurcumin can prevent aggregation/misfolding on alpha-synuclein) by shifting the intramolecular diffusion rate out of the danger range.

Furthermore, the nanoshell 120 can be decorated with a second targeting ligand, wherein the second targeting ligand can recognize/match/bind with a suitable part of an aggregation-prone protein sequences. The nanoshell 120 can then deliver the bioactive compounds 100 and/or bioactive molecules 100A for prevention of protein aggregation/misfolding.

It is critical to prevent protein aggregation/misfolding at a very early stage of a neurological disease, so that the rogue protein may not be able to seed and then coerce/recruit normal protein to misfold and propagate a neurological disease.

Protozoan Infection

Natural artemisinin (from sweet wormwood plant/*Artemesia annua* L) can be an effective treatment against protozoan infection-*P. falciparum* malaria. When artemisinin comes in contact with high concentrations of iron (ferrous compounds generally found in protozoan infection-*P. falciparum* malaria), a chemical reaction is produced to create free radicals that attack cell membranes, breaking them apart and killing protozoan infection-*P. falciparum* malaria. Genes (e.g., encoding dehydrogenase enzymes) from *Artemesia annua* L can be inserted into suitable genes (with more rare words (codons) near the start of the genes) of bacterium/yeast to produce artemisinic acid, a precursor of synthetic artemisini. Artemisinic acid can be photochemically converted to artemisini. Similarly, bacterium/yeast can produce the anticancer compound taxol and the anti-HIV compound prostratin. It should be noted that synthetic OZ439 bioactive compound can be an alternative to artemisini.

Furthermore, the nanoshell 120 can be decorated with a targeting ligand, wherein the targeting ligand can recognize/match/bind with a suitable part of protozoan infection-*P. falciparum* malaria. The nanoshell 120 can then deliver the bioactive compounds (e.g., artemisini or OZ439) to treat against protozoan infection-*P. falciparum* malaria.

Superbug Infection

An antibiotic is a bioactive compound that kills/slows down the growth of bacteria by a mechanism like: (a) inhibiting the cell wall synthesis, (b) blocking DNA/RNA expression, (c) stopping the folic acid synthesis, (d) disrupting cell membrane permeability and arresting the central dogma of bacteria (DNA, RNA and protein synthesis) and (e) inhibiting the protein synthesis.

But superbugs embody a group of bacteria which contains several resistance genes which when expressed leads to development of antibiotic resistance by a mechanism like: (a) coding for specific enzymes which devastate antibiotics, (b) modifying the efflux pump which causes trans-shipment of antibiotic out of the bacterial cell, (c) modifying the configuration of target site so that antibiotics cannot bind with the bacterial cell and (d) production of alternative target (enzyme) to bind the antibiotics. In short, bacterial resistance is due to either transformation or transduction or conjugation.

For example, New Delhi metallo-beta-lactamase-1 (NDM-1) is a gene carried by bacteria, which is responsible for producing an enzyme, carbapenemase within the bacteria making them resistant to (almost all) the present antibiotics.

The nanoshell 120 can be coated with positively charged dimethyldecylammonium chitosan methacrylate. The interaction of positively charged dimethyldecylammonium chitosan methacrylate with the negatively charged bacterial cell wall can result in the disintegration of bacterial cell wall.

The nanoshell 120 can be decorated with the enzyme Lysostaphin, a natural enzyme and/or a compound configured for releasing nitric oxide and/or a compound configured for releasing reactive oxygen species and/or a compound configured for releasing reactive nitrogen species. Lysostaphin attacks the bacterial cell wall causing its slicing and disintegration. The reactive oxygen species and/or reactive nitrogen species can modify the essential protein in bacteria causing bacterial cell death.

With more and more antibacterials and antibiotics, strains of bacteria can evolve or mutate into superbugs, which are resistant to antibacterial drug(s). These drug resistant superbugs include CRE bacteria, clostridum difficile and methicillin-resistant *Staphylococcus aureus* (MRSA). Methicillin-resistant *Staphylococcus aureus* cells can grow to about 1 million cells in a day.

The nanoshell 120 can be decorated with a biomarker binder (e.g., an aptamer), which is very specific to a superbug. The nanoshell 120 (containing multivalent adhesion molecule 7 (MAM7) encapsulated/caged inside the nanoshell 120) with negatively charged electrical surface can be drawn to the positively charged cell surface of a superbug (e.g., methicillin-resistant *Staphylococcus aureus*), wherein multivalent adhesion molecule 7 can disable/disrupt adhesion of a superbug.

The nanoshell 120 can be decorated with a biomarker binder (e.g., an aptamer), which is very specific to a superbug. The nanoshell 120 (containing melittin from bee venom and/or an assassin protein perforin encapsulated/caged inside the nanoshell 120) with negatively charged electrical surface can be drawn to the positively charged cell surface of a superbug (e.g., methicillin-resistant *Staphylococcus aureus*).

Melittin and/or perforin can pierce through the cell membrane of the superbug. Thus, only the contents of the cell of the superbug are spilled out and the superbug is destroyed without harming any healthy cells.

An immune system called the CRISPR-Cas system is present in many bacteria. The CRISPR-Cas system protects a bacterium from an invader (e.g., a virus) by creating small strands of RNA called CRISPR-RNAs—matching the specific DNA sequences of the invader. When CRISPR RNAs find a match, the bacterium unleashes Cas proteins to cut the DNA of the invader. Conversely, a designer clustered regularly interspaced short palindromic repeats (CRISPR) RNAs can target DNA sequences in the bacterium, as a bacterium's CRISPR-Cas system attacks its own DNA, causing bacterium to suicide. The nanoshell 120 (containing a designer CRISPER RNAs-targeting DNA sequences in the bacterium, encapsulated/caged inside the nanoshell 120) can cause a superbug to suicide, without harming any healthy cells. Additionally, the nanoshell 120 can be decorated with a targeting ligand (e.g., a specific aptamer) to specifically bind with the particular superbug.

Diseases of Mind-Depression

Ketamine (with its structural formula is shown below) binds to and blocks a receptor in a human brain called NMDA receptor. Ketamine triggers both anesthetic and antidepressant effects.

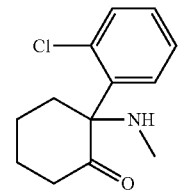

Structural Formula
Of Ketamine

Like an electroshock therapy, ketamine eases depression by blocking a neurotransmitter called glutamate from binding to the NMDA receptor on neurons.

Too much glutamate on the NMDA receptor, can lead to the opening of a calcium ion channel—thus releasing too much calcium downstream—thus affecting a brain chemical brain-derived neurotrophic factor protein.

Ketamine causes neurons to make more brain-derived neurotrophic factor protein, which increases connections between neurons in the brain. These connections can help the brain regulate emotions better and reset the background activity of a human brain.

Ketamine (used in the easing depression) can be delivered at an extremely low dose and over a longer period.

The nanoshell 120 decorated with a targeting ligand, wherein the targeting ligand can recognize/match/bind with adenosine receptors—thus allowing a human body's blood-brain barrier to be opened for the passage of the nanoshell 120 to deliver ketamine at an extremely low strength.

However, instead of NMDA receptor, the bioactive compounds 100 and/or bioactive molecules 100A can activate eEF2 protein to treat depression.

Psilocybin, a prodrug of psilocin (4-hydroxy-dimethyltryptamine) can also ease depression. Psilocybin can decrease cerebral blood flow (CBF) after its use.

The nanoshell 120 decorated with a targeting ligand, wherein the targeting ligand can recognize/match/bind with adenosine receptors—thus allowing a human body's blood-brain barrier to be opened for the passage of the nanoshell 120 to deliver psilocybin at an extremely low dose.

Alternatively, the nanoshell 120 decorated with a targeting ligand, wherein the targeting ligand can recognize/match/bind with adenosine receptors—thus allowing a human body's blood-brain barrier to be opened for the passage of the nanoshell 120 to deliver ibogain (derived from *Tabermanthe iboga*) at an extremely low dose.

Furthermore, there are about 100 trillion microbes in the gut. Leaky gut/displaced bacteria can activate inflammation and autoimmune response(s), which are responsible for onset of depression and fatigue.

Glutamine, N-accetylcysteine and zinc or combination of glutamine, N-accetylcysteine and zinc (L-Opti) can be encapsulated/caged in a nanoshell 120. The nanoshell 120 can deliver appropriate amounts of glutamine, N-accetylcysteine and zinc or combination(s) of glutamine, N-accetylcysteine and zinc to reduce inflammation and autoimmune response(s) for the leaky gut—thereby delaying the onset of depression and fatigue.

Reprogramming of an Epigenetic Marker

Changes in the epigenome do not change a gene's sequence, but rather its activity level. The environment (e.g., diet and exercise) can alter the epigenome, changing the activity level of genes to raise or lower the risk for developing a disease, but also appear to influence the epigenome of future generations. Epigenetic modifications can influence disease susceptibility, potentially lasting through several generations. Due to a phenomenon of genomic imprinting, maternal and paternal genomes are differentially marked and must be properly reprogrammed every time they pass through the germline. Many genes may be coated with methyl groups. When a cell divides, the cellular memory is passed on from one generation to the next generation.

Reprogramming refers to an erasure and/or a remodeling of epigenetic marks (e.g., DNA methylation) accumulated from previous generations.

Trichostatin A ($C_{17}H_{22}N_2O_3$) (with its structural formula is shown below) into a human brain can remove the methyl groups and behavioral deficits.

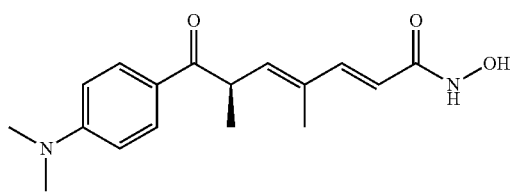

Structural Formula Of Trichostatin A

Trichostatin A has low-toxicity. To reduce toxicity of trichostatin A further, the nanoshell 120 decorated with a targeting ligand, wherein the targeting ligand can recognize/match/bind with adenosine receptors—thus allowing a human body's blood-brain barrier to be opened for the passage of the nanoshell 120 to deliver trichostatin A at an extremely low dose.

Delivery of Bioactive Compounds &/or Bioactive Molecules from a Nanoshell: A Nanoshell Configured with a Bacterium/Microbe/Genetically Engineered Microbe The nanoshell 120 can be configured with a harmless bacterium (e.g., *lactobacillus*)/microbe/genetically engineered microbe to deliver the bioactive compounds 100 and/or bioactive molecules 100A.

Delivery of Bioactive Compounds &/or Bioactive Molecules from a Nanoshell Configured with a Nanopump Prestin is a motor protein enabling direct voltage-to-force converter.

An engineered bacteria battery-M13 bacteriophage can translate mechanical energy into electrical energy. To improve the piezoelectric property of M13 bacteriophage, the outer protein layer of M13 bacteriophage can be engineered by adding appropriate molecules.

Furthermore, to amplify piezoelectric effect, multi-layers of engineered M13 bacteriophage can be utilized. Multi-layers of engineered M13 bacteriophage can then be sandwiched between two biocompatible electrodes to act as a battery, when stressed mechanically.

A thin-film battery/thin-film printed battery/biofuel battery/engineered bacteria battery coupled with prestin motor protein can be fabricated/constructed, as a nanopump (or as an array of nanopumps with networks of prestin motor proteins).

Alternatively, a thin-film battery/thin-film printed battery/biofuel battery/engineered bacteria battery coupled with phi29 DNA polymerase enzyme can be fabricated/constructed, as a nanopump (or as an array of nanopumps with an array of phi29 DNA polymerase enzymes).

A nanopump can generate a sustained mechanical wave in the nanoshell 120 to release/eject the bioactive compounds 100 and/or bioactive molecules 100A from the nanoshell 120.

Delivery of Bioactive Compounds &/or Bioactive Molecules from a Nanotube/Nanotube Configured with a Nanopump A nanotube (e.g., a boron nitride/carbon nanotube or a tubular/tetrahedral structure, fabricated/constructed, utilizing DNA/RNA origami process) can cross a cell membrane and enter the nuclei of the cell, while the cell may not recognize the nanotube as an unfriendly intruder. The nanotube can be biodegradable and less toxic.

The uptake of the bioactive compounds 100 and/or bioactive molecules 100A from a solution into the nanotube can be achieved by van der Waals attraction between the nanotube and the bioactive compounds 100 and/or bioactive molecules 100A.

The nanotube's exterior surface can be coated with (a) an optional protective (to protect from a human body's blood/biological fluid) functional surface and (b) an immune shielding (to protect from a human body's inherent immune surveillance) functional surface.

Furthermore, the nanotube's exterior surface can be decorated with a targeting ligand to recognize/match/bind with specific biological receptors on the cell to allow aft entry of the nanotube to the cell.

Therefore, the bioactive compounds 100 and/or bioactive molecules 100A can be delivered to the cell with unprecedented accuracy and efficiency.

Prestin is a motor protein enabling direct voltage-to-force converter. A thin-film battery/thin-film printed battery/biofuel battery/engineered bacteria battery coupled with prestin motor protein can be fabricated/constructed, as a nanopump (or as an array of nanopumps with networks of prestin motor proteins).

Alternatively, a thin-film battery/thin-film printed battery/biofuel battery/engineered bacteria battery coupled with phi29 DNA polymerase enzyme can be fabricated/constructed, as a nanopump (or as an array of nanopumps with an array of phi29 DNA polymerase enzymes).

A nanopump can generate a sustained mechanical wave in the nanotube to release/eject the bioactive compounds 100 and/or bioactive molecules 100A from the nanotube.

Targeted Delivery to Mitochondria

The mitochondria are the power plants of cells. Mitochondria generate most of the cell's supply of adenosine triphosphate (ATP). Adenosine triphosphate is used as a source of chemical energy.

While mitochondria are present in all cells, in some cells, because of their size and purpose—it is necessary to transport mitochondria at proper positions within the cell to maintain proper function of the cell.

For example, neurons have a complex cellular structure of a main cell body and enormous arms of axons and dendrites that fan out from the cell core and transmit signals to adjoining cells via synapses at their termini.

Thus, the supply chain to mitochondria is very long. Mitochondria are also constantly cycling throughout the neuron. Neurons can transport mitochondria (some mitochondria are stationary/fixed, while other mitochondria are mobile) down the enormous arms of axons and dendrites at proper positions to provide other parts of the cell with energy, help with the transmission of signals and maintenance of the cellular health.

Additionally, at any given time about half of the mobile mitochondria in the neurons are returning to the cell to be recycled/replenished.

One interesting property of mitochondria is that they have their own DNA. Mitochondrial DNA is different from chromosomal/nuclear DNA. First, it exists as a simple plasmid (a DNA loop) than the chromosomal/nuclear DNA. Second, most repair mechanisms to correct chromosomal/nuclear DNA are missing from mitochondrial DNA. Thus, relatively unprotected/unrepairable mitochondrial DNA can suffer about 10 times more damage than chromosomal/nuclear DNA.

Mitochondrial electron transport is not perfect. Even under ideal mitochondrial conditions, some electrons can leak from the electron transport chain. These leaking electrons can interact with oxygen to produce superoxide radicals.

Furthermore, with mitochondrial dysfunction, leakage of electrons can increase significantly.

The close proximity of mitochondrial DNA to the flux of superoxide radicals (or hydroxyl radicals) and the lack of mitochondrial protection/repair mechanism can lead to mitochondrial dysfunction.

Many diseases can be related to mitochondrial dysfunction—thus an ability to transport the bioactive compounds 100 and/or bioactive molecules 100A to mitochondria specifically can be beneficial.

Furthermore, the disruptive changes to mitochondria can occur, when both amyloid beta protein and tau protein (rather truncated version of tau protein, not regular version of tau protein) are present together and the disruptive changes are: (a) about 30% remaining electrical potential (but 100% electrical potential is needed to produce energy efficiently), (b) abnormal mitochondria clumping, (c) fragmentation of mitochondria, (d) incorrect control of calcium level and (e) release of (toxic) free radicals.

Triphenylphosphonium can pass through and accumulate several hundred folds in mitochondrial matrix.

The bioactive compounds 100 and/or bioactive molecules 100A can be chemically coupled with triphenylphosphonium/chemical derivative of triphenyl phosphonium/structural analog of triphenylphosphonium to enhance an uptake of the bioactive compounds 100 and/or bioactive molecules 100A in mitochondria.

Passive Micropatch

Figure 7A:
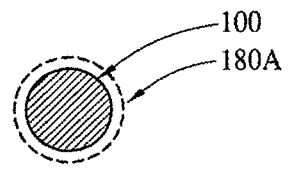

FIG. 7A illustrates an expanded view of a negative electrical charged surface 180A on the bioactive compound 100.

Figure 7B:
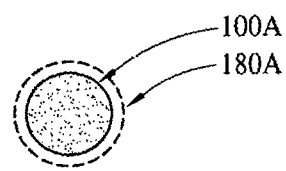

FIG. 7B illustrates an expanded view of a negative electrical charged surface 180A on the bioactive molecule 100A.

Figure 7C:
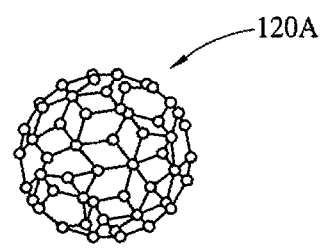

FIG. 7C illustrates an expanded view of a nanocrystal 120A.

Figure 7D:
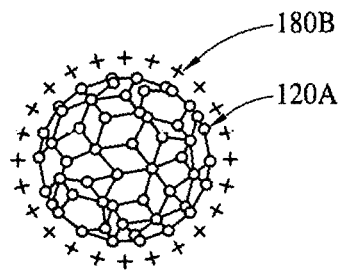

FIG. 7D illustrates an expanded view of a positive electrical charged surface 180B on the nanocrystal 120A.

The charge conjugation can increase the encapsulation efficiency and/or delivery efficiency of the bioactive compounds 100 and/or bioactive molecules 100A.

Figure 7E:

FIG. 7E illustrates an expanded view of a fluorophore (e.g., a quantum dot fluorophore) 120B. Furthermore, the fluorophore 120B can be a dye (e.g., ATTO/Alexa Fluor 488 dye or photostable diarylmethylene-bridged naphthophosphole P-oxide dye) based fluorophore or a fluorescent protein.

With a quantum dot fluorophore, the size of the bandgap can be controlled by varying the diameter of the quantum dot. Larger diameter (e.g., 10 nanometers in diameter) quantum dot fluorophore will have a smaller bandgap—thus the larger diameter quantum dot fluorophore will fluoresce in the red part of the optical spectrum. Conversely, smaller diameter (e.g., 5 nanometers in diameter) quantum dot fluorophore will have a larger bandgap—thus the smaller diameter quantum dot fluorophore will fluoresce in the blue part of the optical spectrum.

Figure 7F:
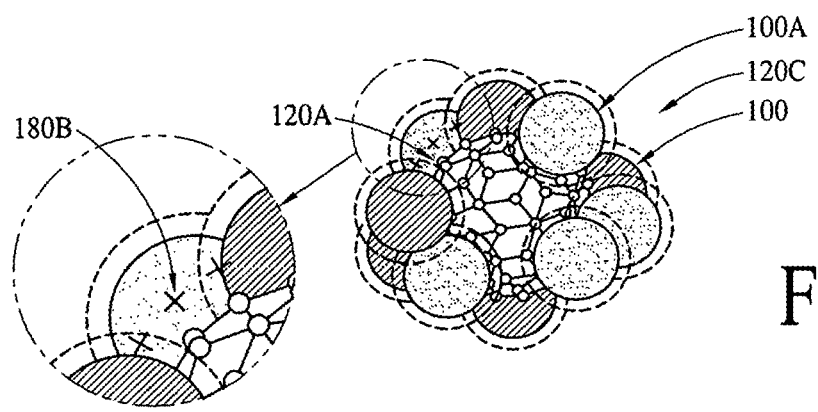

FIG. 7F illustrates 120C, wherein the negative electrical charged bioactive compounds 100 and/or bioactive molecules 100A are surrounded by a cluster of the positive electrical charged nanocrystals 120A.

Figure 7G:
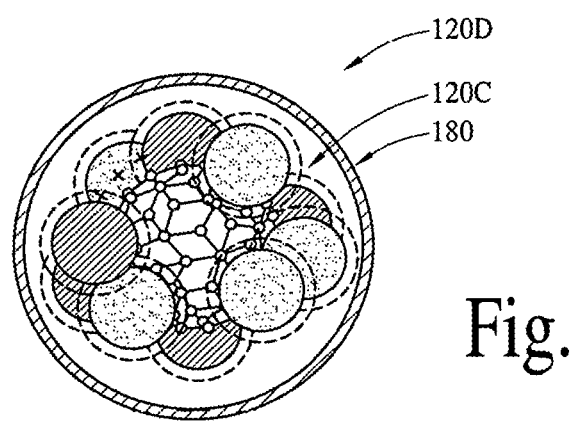

FIG. 7G illustrates 120D, wherein 120C is chemically bonded with the immune shielding functional surface 180.

Figure 7H:
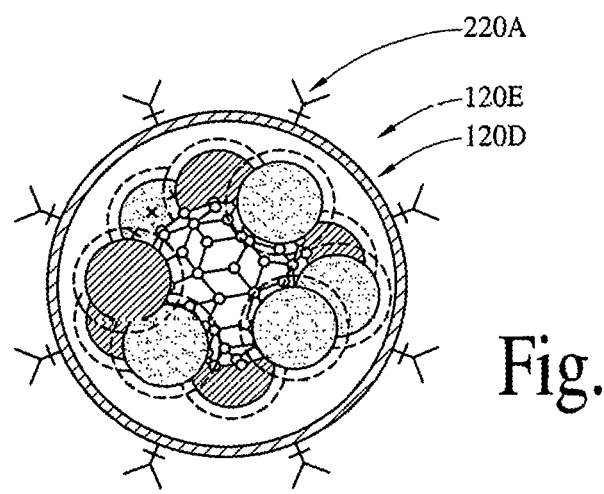

FIG. 7H illustrates 120E, wherein 120D can be chemically bonded with a specific targeting ligand 220A.

FIG. 7I illustrates 120F, wherein 120E is optionally chemically bonded with the fluorophore 120B.

The above nanoassembly 7I can be utilized for targeted delivery of the bioactive compounds 100 and/or bioactive molecules 100A.

FIG. 7J illustrates a microelectromechanical systems reservoir 300.

The microelectro-mechanical-system reservoir 300 can be fabricated/constructed, utilizing liquid-crystal polymers/polyimide/silicon/silk/SU-8 resin/other suitable material.

Figure 7:
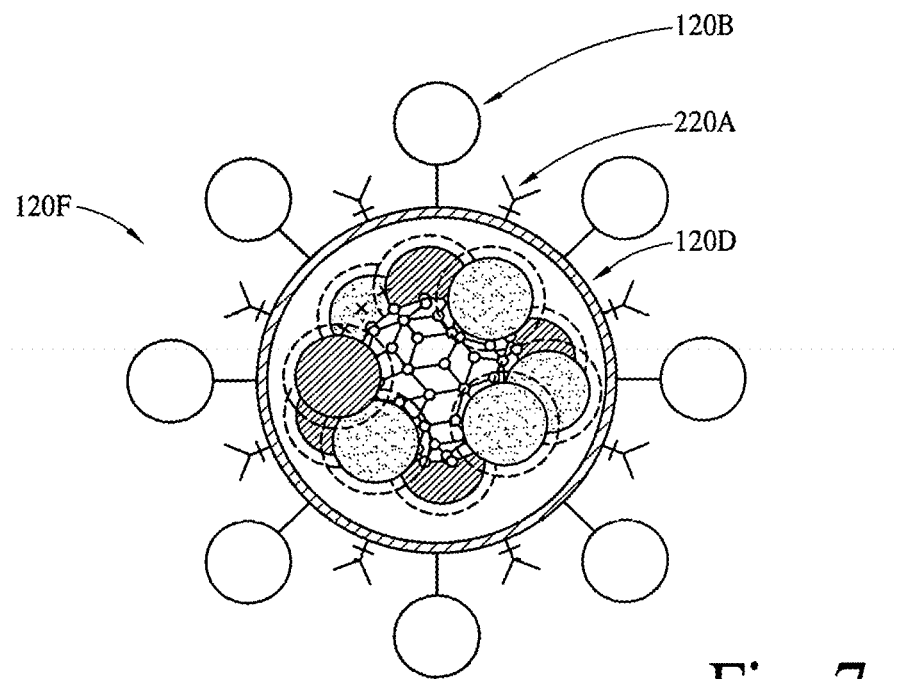
Figure 7:
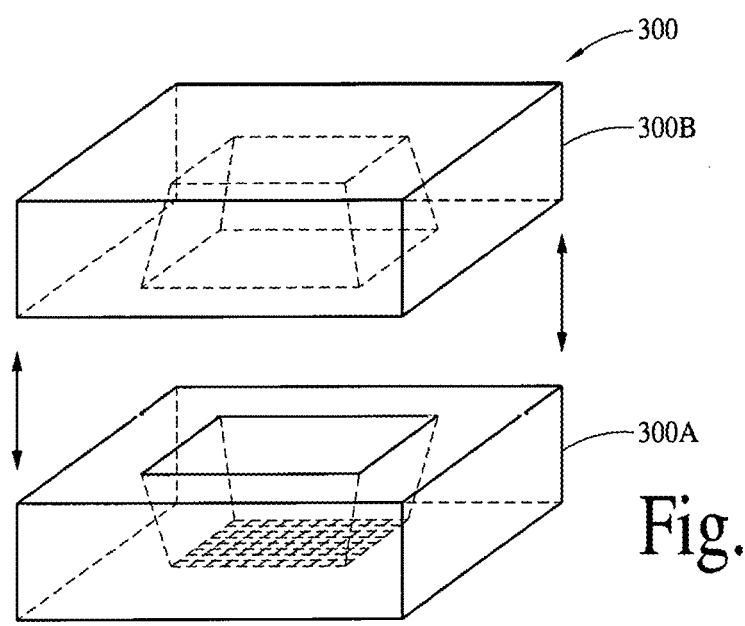
Figure 7K:
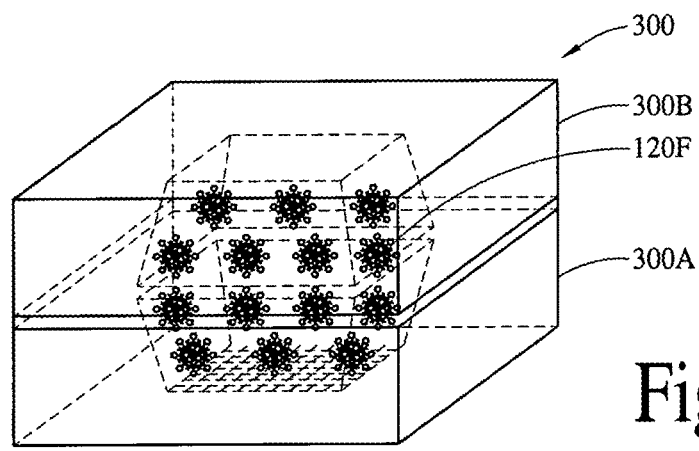

FIG. 7K illustrates 120Fs. 120Fs are inserted/caged in the microelectro-mechanical-system reservoir 300.

Figure 7L:
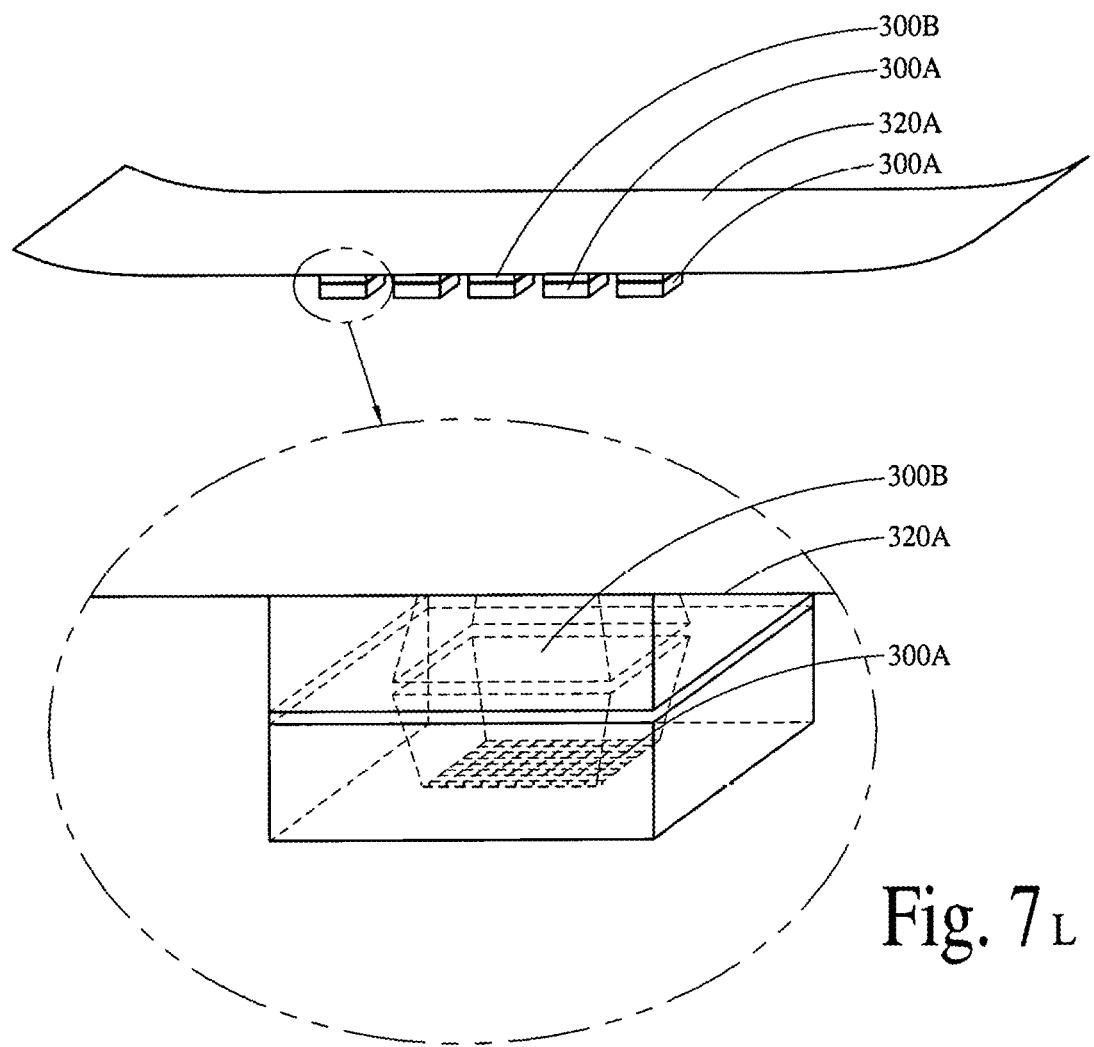

FIG. 7L illustrates the top surface 300B of the microelectro-mechanical-system reservoir 300. 300B can be attached onto a non-porous adhesive top thin-film 320A.

The porous bottom surface of the microelectro-mechanical-system reservoir 300 is 300A. 300A can be attached onto a biological transport medium (e.g., skin) for delivery of the bioactive compounds 100 and/or bioactive molecules 100A.

Thus, a long-term passive micropatch (about 15 millimeters$^2$ in area) (with the porous bottom surface of the microelectro-mechanical-system reservoir) can be fabricated/constructed for the delivery of the bioactive compounds 100 and/or bioactive molecules 100A.

The porous bottom surface of the microelectro-mechanical-system reservoir 300 is 300A. The porous bottom surface of (the microelectro-mechanical-system reservoir 300) 300A can be attached onto a nanoporous membrane (e.g., a nanoporous membrane of titanium dioxide nanotubes or a carbon nanomembrane), then onto a biological transport medium for delivery of the bioactive compounds 100 and/or bioactive molecules 100A.

Thus, a long-term passive micropatch (about 15 millimeters$^2$ in area) (with the porous bottom surface of the microelectro-mechanical-system reservoir and nanoporous membrane) can be fabricated/constructed for the delivery of the bioactive compounds 100 and/or bioactive molecules 100A.

Figure 7M:
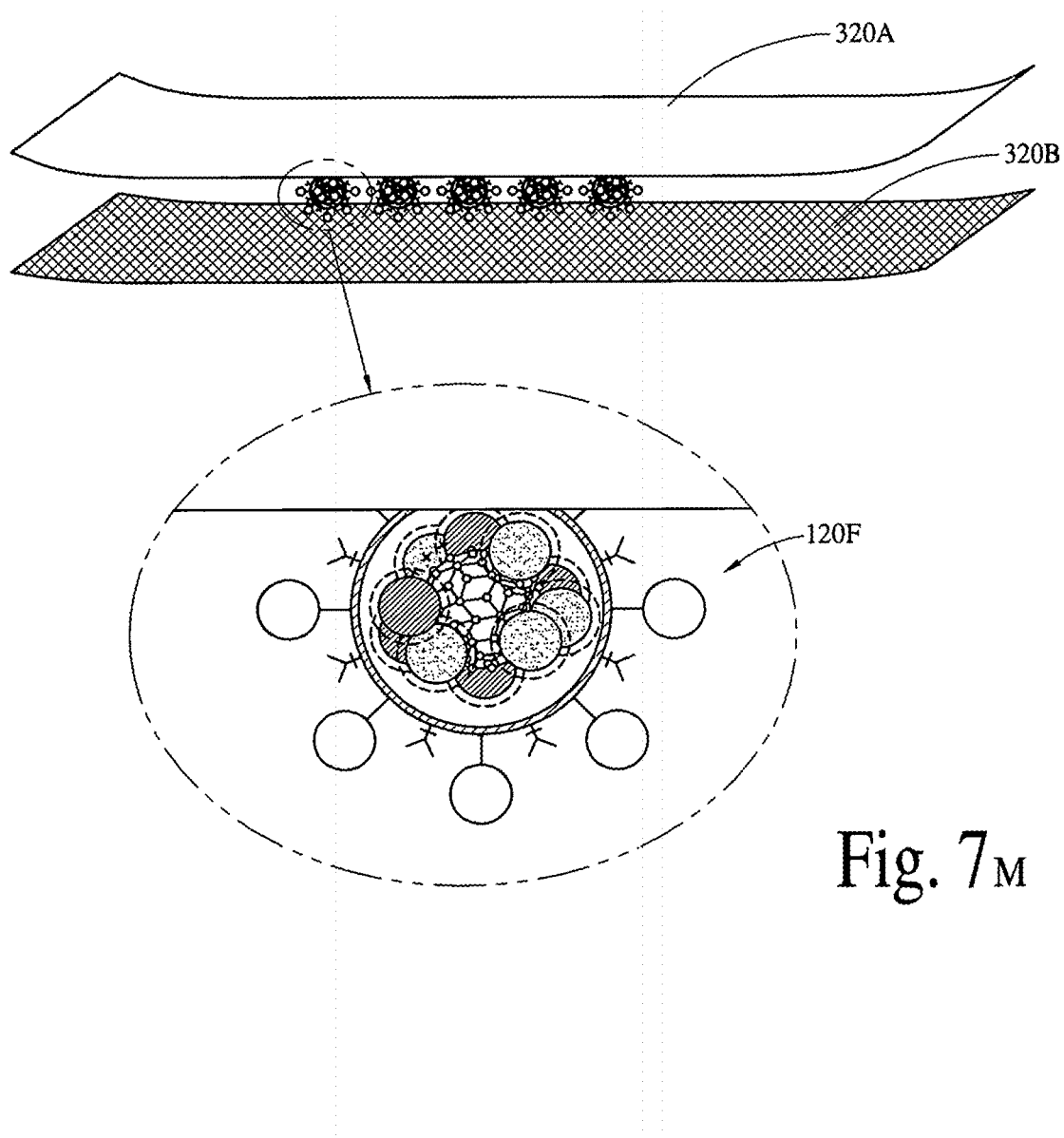

FIG. 7M illustrates 120F bonded directly between a non-porous top (adhesive) thin-film 320A and a porous bottom (adhesive) thin-film 320B. The porous bottom (adhesive) thin-film 320B can be attached onto a biological transport medium.

The non-porous top (adhesive) thin-film 320A can utilize chitin (a biopolymer based on the N-acetyl-glucosamine monomer) and/or chitin's variant deacetylated counterpart chitosan and/or fibroin (a protein derived from silk) as a base material/protective coating material for the non-porous top (adhesive) thin-film 320A.

Thus, a short-term passive micropatch (about 15 millimeters$^2$ in area) with the porous bottom (adhesive) thin-film 320B can be fabricated/constructed for the delivery of the bioactive compounds 100 and/or bioactive molecules 100A.

Furthermore, a specific vaccine can be preserved by drying in sugar. Then the sugar-dried vaccine can be fabricated/constructed, as an array of dissolvable microneedles. Such an array of dissolvable microneedles can be embedded with the porous bottom (adhesive) thin-film 320B, for the instant delivery of the vaccine.

Passive Micropatch of Porous Nanofiber Mesh

Electrospinning uses an electric field to catapult a charged fluid jet through air to create very fine nanometer-scale fibers (e.g., biocompatible material/material mixtures of alginate and/or chitin and/or fibroin) and it can be manipulated to control the material's solubility, strength and geometry.

A nanofiber mesh can be stretched to physically block a human body's blood/biological fluid and/or deliver the bioactive compounds 100 and/or bioactive molecules 100 through the nanofiber mesh.

The nanofiber mesh can incorporate many fibers with variable properties to deliver the bioactive compounds 100 and/or bioactive molecules 100 through the nanofiber mesh at different delivery rates to increase the potency. The nanofiber mesh can be used on or in a human body.

Two-Dimensional Array of Nanosized Wells of a Porous Material, as an Alternative to A Microelectro-Mechanical-System Reservoir Alternatively, a two-dimensional array of nanosized wells of a suitable porous material (e.g., porous hydrogel/porous silicon/silicate based polymer nanocomposite) containing the bioactive compounds 100 and/or bioactive molecules 100A (or indirectly, utilizing nanocrystals, wherein the nanocrystals encapsulate/cage the bioactive compounds 100 and/or bioactive molecules 100A) can replace the above microelectro-mechanical-system reservoir 300 in both the long-term/short-term passive micropatch.

The two-dimensional array of nanosized wells of the suitable porous material thin-film can be fabricated/constructed, utilizing lithography (e.g., phase mask/electron beam lithography) and inductively-coupled plasma (ICP) etching/focused ion beam etching.

The two-dimensional array of nanosized wells of the suitable porous material thin-film can be functionalized with peptide nucleic acid (PNA) probes to target distinguishing different bacterial strains (e.g., *S. aureus* and *E. coli*).

Furthermore, the two-dimensional array of nanosized wells of the suitable porous material thin-film can be functionalized with peptide nucleic acid probes to target simultaneous identification of resistant and non-resistant *E. coli*, causing urinary tract infections.

Smart Porous Thin-Film, as an Alternative to a Microelectro-Mechanical-System Reservoir A smart thin-film (e.g., a composite-gel) can regulate permeability in response to an external stimulus.

The smart thin-film can contain an ordered array of nanochannels. Furthermore, the ordered array of nanochannels can contain an ordered array of magnetic polystyrene latex particles.

The magnetic polystyrene latex particle can change its size in response to an external stimulus (e.g., temperature). Expansion/contraction of the magnetic polystyrene latex particles can affect the permeability of the smart porous thin-film from on state to off state.

Thus, a controlled transport and/or a tunable transport of the bioactive compounds 100 and/or bioactive molecules 100A can be achieved, by utilizing the suitable smart porous material thin-film.

Thus, in addition to delivering the bioactive compounds 100 and/or bioactive molecules 100A, utilizing the long-term/short-term passive micropatch, other bio/health sensors to monitor vital health parameters (e.g., blood sugar and heart rate) can be integrated with the long-term/short-term passive micropatch.

An example of a bio/health sensor integrated with the long-term/short-term passive micropatch is in-situ blood sugar measurement. Blood sugar measurement can involve an electrochemical reaction activated by an enzyme. Glucose oxidase can be convert glucose into hydrogen peroxide and other chemicals—thus their concentrations can be measured with a miniature potentiostat or nanosized potentiostat as a biosensor for calculating the glucose level in sweat. Furthermore, the bio/health sensor can be integrated with an analog signal to a digital signal converter (ADC) circuit.

Wibree, Bluetooth, Wi-Fi and near-field communication can be integrated with the long-term/short-term passive micropatch. Furthermore, ultrathin/bare-die electronic components, processor(s), sensors, light emitting diodes, photodetectors on the substrate of the long-term/short-term passive micropatch can be flexibly interconnected to detect/measure for example, blood flow dynamics, pressure wave velocity (a measure of blood pressure variation) and level of oxygenation in a human blood. Additionally, by injecting tiny heat pulses, the long-term/short-term passive micropatch can measure a human skin's thermal conductivity (related to hydration level). Such substrate of the long-term/short-term passive micropatch is biocompatible and preferably is flexible/stretchable.

The long-term/short-term passive micropatch can be integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Thus, the bio/health sensor integrated with the long-term/short-term passive micropatch can deliver the bioactive compounds 100 and/or bioactive molecules 100A, utilizing the long-term/short-term passive micropatch.

Example Applications of a Passive Micropatch

7M can be utilized as a passive micropatch to deliver a compound, drug, molecule (e.g., a micro RNA and small interfering RNA) and protein.

7M can be utilized as a passive micropatch to deliver an antibiotic bioactive compound.

Furthermore, an antibiotic bioactive compound can be integrated with magnesium oxide nanoparticles, self-assembling peptides (e.g., RADA16-I) and silver nanoparticles.

7M can be utilized as a passive micropatch to deliver the preprogrammed release of an array of growth factors for wound healing. Furthermore, the growth factors for wound healing can be photo activated/modulated (by a small quantity of reactive molecular species), utilizing a laser/an array of lasers of suitable wavelength and intensity. Furthermore, after a wound, epidermal cells can replicate and move into the area of a wound to close it up and start the healing process. This causes ionic/free radical concentrations to shift, a change that generates subtle but characteristic electrical fields. The fields can be detected by sensor arrays-printed onto the passive micropatch itself, wherein the passive micropatch can be fabricated/constructed on a flexible/stretchable substrate (e.g., manufactured by MC10 company).

7M can be utilized as a passive micropatch to deliver sildenafil.

7M can be utilized as a passive micropatch to deliver testosterone.

7M can be utilized as a passive micropatch to deliver luric acid and/or an isolated active protein from the *Propionibacterium acnes* phages for treatment against acne.

*Propionibacterium acnes* phages, (a family of harmless viruses that live on a human skin) are naturally programmed to kill the *Propionibacterium acnes*, a bacterium that triggers acne.

Furthermore, 7M can be utilized as a passive micropatch to deliver a mixture of suitable oils and/or luric acid and/or an isolated active protein from the *Propionibacterium acnes* phages for treatment against acne.

7M can be utilized as a passive micropatch to deliver rivastigmine for treatment against Alzheimer's disease.

7M can be utilized as a passive micropatch to deliver rotigotine for treatment against Parkinson's disease.

7M can be utilized as a passive micropatch (as a transplant passive micropatch) to deliver insulin-producing stem cells (by manipulating both the Wnt and Notch signals. Wnt enhances self-renewal of adult pancreatic stem cells and inhibiting Notch signaling increases production of insulin) or cells against Type 1 Diabetes disease. The passive micropatch may also contain protein and immune suppressing bioactive compound to allow the insulin-producing cells/stem cells to successfully graft, survive and function within a human body.

β-cell replication is difficult to control in a human body. A decrease in the function of θβ-cells late in life is the main cause of Type 2 Diabetes disease. Betatrophin, a liver hormone stimulates β-cell replication with remarkable efficiency. 7M can be utilized as a passive micropatch to deliver betatrophin.

7M can be utilized as a passive micropatch to deliver a nanoshell 120 decorated with a targeting ligand, wherein the targeting ligand can recognize/match/bind with adenosine receptors—thus allowing a human body's blood-brain barrier to be opened for the passage of the nanoshell 120 to deliver oxytocin ("the love hormone). The oxytocin hormone may help build a long-lasting love.

A constant and low dose of psilocybin can calm the psychological turbulence of people afflicted with a number of conditions, including depression and/or alcohol addiction. 7M can be utilized as a passive micropatch to deliver a nanoshell 120 decorated with a targeting ligand, wherein the targeting ligand can recognize/match/bind with adenosine receptors—thus allowing a human body's blood-brain barrier to be opened for the passage of the nanoshell 120 to deliver psilocybin.

Bacteria outnumber human cells about ten to one. A human body has a complex network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking. Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

7M can be utilized as a passive micropatch to deliver a pro-quorum sensing compound.

7M can be utilized as a passive micropatch to deliver an anti-quorum sensing compound. Such anti-quorum compounds are called disaccharide derivatives and they mimic a class of natural molecules known as rhamnolipids, which are produced and secreted by the bacterium itself. Such compounds have the potential to inhibit horizontal gene transfer, the process by which bacteria share genetic information, such as the ability to be drug-resistant.

7M can be utilized as a passive micropatch to deliver multivalent adhesion molecule 7 (MAM7) to disable/disrupt adhesion of bacteria.

7M can be utilized as a passive micropatch to deliver melittin and/or perforin to protect against Hepatitis B.

7M can be utilized as a passive micropatch to deliver melittin and/or perforin to protect against Hepatitis C.

7M can be utilized as a passive (vaginal) micropatch to deliver melittin and/or perforin to protect against HIV. However, the passive (vaginal) micropatch (to deliver melittin and/or perforin) can be coated with super hydrophilic nanoparticle to prevent breakage.

7M can be utilized to deliver granulocyte macrophage colony-simulating factor (GMC-SF), which can reprogram a human body's immune system to attack cancer cells.

7M can be integrated/impregnated with cell penetrating peptides. Cell penetrating peptides (e.g., IMT-P8/various fomulations of IMT-P8) can transport a bioactive compound/bioactive molecule/nanoparticle/nucleic acid/peptide/protein/small molecule/small interfering RNA through human skin.

Active Micropatch Integrated with an Electrically Controlled Layer

The porous bottom thin-film 320B can be composed of electrically charged (an opposite electrical charge polarity with respect to the electrical charge polarity of nanocrystals 120A) pigmented layers. Electrically charged pigmented layers can hold (an opposite electrical charge polarity) electrically charged nanocrystals 120A by an electrostatic field.

By applying a voltage (about a few millivolts from a thin-film printed battery), the electrically charged pigmented layers can disintegrate.

Thus, the bioactive compounds 100 and/or bioactive molecules 100A can be delivered in a variable quantity from the electrically charged nanocrystals 120A.

Active Micropatch Integrated with an Electrically Controlled Layer & a Smart Porous Thin-Film The porous bottom thin-film 320B can be composed of a smart thin-film. A smart thin-film (e.g., a composite-gel) can regulate permeability in response to an external stimulus. The smart thin-film can contain an ordered array of nanochannels. Furthermore, the ordered array of nanochannels can contain an ordered array of magnetic polystyrene latex particles. The magnetic polystyrene latex particle can change its size in response to an external stimulus (e.g., temperature). Expansion/contraction of the magnetic polystyrene latex particles can affect the permeability of the smart porous thin-film from an on state to an off state.

Thus, a controlled transport and/or a tunable transport of the bioactive compounds 100 and/or bioactive molecules 100A can be achieved, by utilizing the smart porous material thin-film.

Thus, in addition to delivering the bioactive compounds 100 and/or bioactive molecules 100A, utilizing the active micropatch, other bio/health sensors to monitor vital health parameters (e.g., blood sugar and heart rate) can be integrated with the active micropatch.

An example of a bio/health sensor integrated with the active micropatch is in-situ blood sugar measurement. Blood sugar measurement can involve an electrochemical reaction activated by an enzyme. Glucose oxidase can convert glucose into hydrogen peroxide and other chemicals—thus their concentrations can be measured with a miniature potentiostat or nanosized potentiostat as a biosensor for calculating the glucose level in sweat. Furthermore, the bio/health sensor can be integrated with an analog signal to a digital signal converter circuit.

Wibree, Bluetooth, Wi-Fi and near-field communication can be integrated with the active micropatch. Furthermore, ultrathin/bare-die electronic components, processor(s), sensors, light emitting diodes, photodetectors on the substrate of the active micropatch can be flexibly interconnected to detect/measure for example, blood flow dynamics, pressure wave velocity (a measure of blood pressure variation) and level of oxygenation in a human blood. Additionally, by injecting tiny heat pulses, the active micropatch can measure human skin's thermal conductivity (related to hydration level). Such substrate of the active micropatch is biocompatible and preferably flexible/stretchable. Furthermore, thin-film digital/source-gated transistor based circuits, as an artificial skin can be integrated with the active micropatch for on-demand delivery of the bioactive compounds 100 and/or bioactive molecules 100A.

The active micropatch integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Thus, the bio/health sensor integrated with the active micropatch can enable active (actively controlled via closed loop measurement) delivery of the bioactive compounds 100 and/or bioactive molecules 100A, utilizing the active micropatch.

An active micropatch can be placed (attached and/or implanted) on or in (meaning within) a human body Example Applications of an Active Micropatch Integrated with Electrically Controlled Layer NAD is a key molecule that coordinates activities between the cell's nuclear genome and the mitochondrial genome. With aging, levels of NAD decline. Without sufficient NAD, SIRT1 cannot keep tabs on HIF-1. Levels of HIF-1 can escalate and begin wreaking havoc on the cross-genome communication. Over time, this loss of communication reduces the cell's ability to make energy and signs of ageing related diseases become apparent. By administering an endogenous compound (that cells can transform into NAD) such as, plasma NAD metabolites-nicotinamide mononucleotide, one could restore cross-genome communication, if the endogenous compound was administered early enough, prior to excessive mutation accumulation. An active micropatch can be utilized to deliver an endogenous compound (that cells can transform into NAD) to delay onset of ageing related diseases.

An active micropatch can be utilized to deliver a compound, drug and molecule (e.g., a micro RNA and small interfering RNA.

An active micropatch can be utilized to deliver an antibiotic bioactive compound.

Furthermore, an antibiotic bioactive compound can be integrated with magnesium oxide nanoparticles, self-assembling peptides (e.g., RADA16-I) and silver nanoparticles.

An active micropatch can be utilized to deliver the preprogrammed release of an array of growth factors for wound healing. Furthermore, the growth factors for wound healing can be photo activated/modulated (by a small quantity of reactive molecular species), utilizing a laser/an array of lasers of suitable wavelength and intensity. Furthermore, after a wound, epidermal cells can replicate and move into the area of a wound to close it up and start the healing process. This causes ionic/free radical concentrations to shift, a change that generates subtle but characteristic electrical fields. The fields can be detected by sensor arrays-printed onto the active micropatch itself, wherein the active micropatch can be fabricated/constructed on a flexible/stretchable substrate (e.g., manufactured by MC10 company).

An active micropatch can be utilized to deliver sildenafil.

An active micropatch can be utilized to deliver testosterone.

An active micropatch can be utilized to deliver luric acid and/or an isolated active protein from the *Propionibacterium acnes* phages for treatment against acne.

An active micropatch can be utilized to deliver rivastigmine for treatment against Alzheimer's disease.

An active micropatch can be utilized to deliver rotigotine for treatment against Parkinson's disease.

An active micropatch (as a transplant active micropatch) can be utilized to deliver insulin-producing stem cells (by manipulating both the Wnt and Notch signals. Wnt enhances self-renewal of adult pancreatic stem cells and inhibiting Notch signaling increases production of insulin) or cells against Type 1 Diabetes disease. The active micropatch may also contain protein and immune suppressing bioactive compounds to allow the insulin-producing cells/stem cells to successfully graft, survive and function within a human body.

β-cell replication is difficult to control in a human body. A decrease in the function of β-cells late in life is the main cause of Type 2 Diabetes disease. Betatrophin, a liver hormone stimulates β-cell replication with remarkable efficiency. An active micropatch can be utilized to deliver betatrophin.

An active micropatch can be utilized to deliver a nanoshell 120 decorated with a targeting ligand, wherein the targeting ligand can recognize/match/bind with adenosine receptors—thus allowing a human body's blood-brain barrier to be opened for the passage of the nanoshell 120 to deliver oxytocin ("the love hormone"). The oxytocin hormone may help build a long-lasting love.

A constant and low dose of psilocybin can calm the psychological turbulence of people afflicted with a number of conditions, including depression and alcohol addiction. An active micropatch can be utilized to deliver a nanoshell 120 decorated with a targeting ligand, wherein the targeting ligand can recognize/match/bind with adenosine receptors— thus allowing a human body's blood-brain barrier to be opened for the passage of the nanoshell 120 to deliver psilocybin.

Bacteria outnumber human cells ten to one. A human body has a complex molecular network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking. Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

An active micropatch can be utilized to deliver a pro-quorum sensing compound.

An active micropatch can be utilized to deliver an anti-quorum sensing compound. Such anti-quorum compounds are called disaccharide derivatives and they mimic a class of natural molecules known as rhamnolipids, which are produced and secreted by the bacterium itself. Such compounds have the potential to inhibit horizontal gene transfer, the process by which bacteria share genetic information, such as the ability to be drug-resistant.

An active micropatch can be utilized as a passive micropatch to deliver multivalent adhesion molecule 7 (MAM7) to disable/disrupt adhesion of bacteria.

An active micropatch can be utilized to deliver granulocyte macrophage colony-simulating factor (GMC-SF), which can reprogram a human body's immune system to attack the cancer cells.

Active Micropatch of Three-Dimensional Porous Graphene Scaffold/Foam

A three-Dimensional porous graphene scaffold/foam can be synthesized by chemical vapor deposition (CVD) using a Ni foam template. The three-dimensional porous graphene scaffold/foam can serve as a biocompatible container, when it is coated with laminin/matrix proteins.

The three-dimensional porous graphene scaffold/foam, as an active micropatch (e.g., a transdermal patch) can be electrically controlled by polyaniline (PANi) hydrogel electrodes and a thin-film battery/thin-film printed battery/biofuel battery/DNA solar cell.

A biofuel battery has a paste with two carbon nanotubes, wherein one carbon nanotube is mixed with glucose oxidase and the other carbon nanotube is mixed with glucose and polyphenol oxidase. Current is delivered to the biofuel battery's circuit via a platinum wire inserted into the paste. The biofuel battery is wrapped in a biocompatible material to prevent any leaking.

A DNA based solar cell incorporates metal atoms and other chemicals to mimic the efficient mechanisms bacteria used to derive energy from the sunlight.

Silicon/polymer nanowires (about 50 nanometers to 100 nanometers in diameter) for stable electronic sensors are more electrically sensitive than metal electrodes. These stable electronic sensors can be embedded in the three-dimensional porous graphene scaffold/foam to monitor electrical activity—thus enabling how living cells and/or stem cells would respond to specific bioactive compounds 100 and/or bioactive molecules 100A.

Example Applications of an Active Micropatch of Three-Dimensional Porous Graphene Scaffold/Foam Nitric mono oxide (NO) is a short-lived, gaseous signaling free radical molecule, produced in cells. Once released into a human body's bloodstream, it signals in a human body to perform certain functions such as vasodilatation opening up the blood vessels and capillaries to increase blood flow and deliver oxygen and critical nutrients throughout a human body at the time it needs them most.

Controlled amounts of nitric mono oxide gas can be beneficial for health. Nitric mono oxide can remain stable and trapped within the three-dimensional porous graphene scaffold/foam.

The three-dimensional porous graphene scaffold/foam, utilizing graphene/polyaniline hydrogel electrodes and a thin-film battery/thin-film printed battery/biofuel battery/engineered bacteria battery can act as an active micropatch for nitric mono oxide.

Trapped nitric mono oxide can be released in a controlled manner, utilizing graphene/polyaniline hydrogel electrodes and a thin-film battery/thin-film printed battery/biofuel battery/engineered bacteria battery.

Furthermore, chitosan can be added to the three-dimensional porous graphene scaffold/foam for increasing an antimicrobial killing action. Controlled amounts of nitric mono oxide gas can be beneficial for wound healing.

The three-dimensional porous graphene scaffold/foam, utilizing graphene/polyaniline hydrogel electrodes and a thin-film battery/thin-film printed battery/biofuel battery/engineered bacteria battery, as an active micropatch can deliver adipose-derived stem cells (ADSC) for wound healing.

Furthermore, the three-dimensional porous graphene foam, utilizing graphene/polyaniline hydrogel electrodes and a thin-film battery/thin-film printed battery/biofuel battery/engineered bacteria battery, as an active micropatch can deliver neural stem cells.

Furthermore, the three-dimensional porous graphene foam, utilizing graphene/polyaniline hydrogel electrodes and a thin-film battery/thin-film printed battery/biofuel battery/engineered bacteria battery and silicon nanowire sensors, as an active micropatch can deliver neural stem cells with embedded silicon nanowire sensors (configured to monitor specific biochemical functions) and specific bioactive compounds 100 and/or bioactive molecules 100A.

Active Micropatch of Three-Dimensional Porous Graphene Scaffold/Foam Coupled with A Porous Nanomembrane & Nanopump The three-dimensional porous graphene scaffold/foam can be integrated with an atomically thick (about 1 nanometer thick) porous nanomembrane (e.g., a carbon nanomembrane), wherein the atomically thick porous nanomembrane is attached on a human body.

The three-dimensional porous graphene scaffold/foam integrated with the atomically thick porous nanomembrane can be activated by a thin-film battery/thin-film printed battery/biofuel battery/engineered bacteria battery coupled with phi29 DNA polymerase enzyme as a nanopump (or as an array of nanopumps with an array of phi29 DNA polymerase enzymes) to deliver the bioactive compounds 100 and/or bioactive molecules 100A across the porous nanomembrane, wherein the atomically thick porous carbon nanomembrane is attached on a human body.

Active Micropatch of Three-Dimensional Porous Epoxy Scaffold/Foam

A three-dimensional porous epoxy scaffold/foam (e.g., hydrogel scaffold/foam), as an active (implantable) micropatch can serve as a biocompatible container for living cells and/or stem cells and/or bioactive compounds 100 and/or bioactive molecules 100A. The three-dimensional porous epoxy scaffold/foam, as an active (implantable) micropatch can be electrically controlled with boron-doped diamond electrodes and a thin-film battery/thin-film printed battery/biofuel battery/engineered bacteria battery.

Boron-doped conducting diamond-like material can be grown on a silicon dioxide ($SiO_2$) substrate by chemical vapor deposition at about 900-degrees' centigrade. Boron-doped conducting diamond-like material can be bonded on a polymer substrate and then lifted off from the silicon dioxide substrate by hydrofluoric (HF) acid. Thus, a boron-doped conducting diamond-like material can act as an interface electrode for any biological application.

Silicon/polymer nanowires (about 50 nanometers to 100 nanometers in diameter) for stable electronic sensors are more electrically sensitive than metal electrodes. These stable electronic sensors can be embedded in the three-dimensional porous epoxy scaffold/foam to monitor electrical activity—thus enabling how living cells and/or stem cells would respond to specific bioactive compounds 100 and/or bioactive molecules 100A.

Example Applications of an Active Micropatch of Three-Dimensional Porous Epoxy Scaffold/Foam Nitric mono oxide is a short-lived, gaseous signaling free radical molecule, produced in cells. Once released into a human body's bloodstream, it signals a human body to perform certain functions such as vasodilatation opening up the blood vessels and capillaries to increase blood flow and deliver oxygen and critical nutrients throughout a human body at the time it needs them most.

Controlled amounts of nitric mono oxide gas can be beneficial for health. Nitric mono oxide can remain stable and trapped within the three-dimensional porous epoxy scaffold/foam.

The three-dimensional porous epoxy scaffold/foam, utilizing boron-doped diamond electrodes and a thin-film battery/thin-film printed battery/biofuel battery/engineered bacteria battery can act as an active micropatch. Trapped nitric mono oxide can be released in a controlled manner, utilizing boron-doped diamond electrodes and thin-film battery/thin-film printed battery/biofuel battery/engineered bacteria battery.

Chitosan can be added to the three-dimensional porous epoxy scaffold/foam for increasing an antimicrobial killing action. Controlled amount of nitric mono oxide gas can be beneficial for wound healing.

Furthermore, the three-dimensional porous epoxy scaffold/foam, utilizing boron-doped diamond electrodes and a thin-film battery/thin-film printed battery/biofuel battery/engineered bacteria battery, as an active micropatch can deliver adipose-derived stem cells for wound healing.

Furthermore, the three-dimensional porous epoxy foam, utilizing boron-doped diamond electrodes and a thin-film battery/thin-film printed battery/biofuel battery/engineered bacteria battery, as an active micropatch can deliver neural stem cells.

Furthermore, the three-dimensional porous epoxy foam, utilizing boron-doped diamond electrodes, a thin-film battery/thin-film printed battery/biofuel battery/engineered bacteria battery and silicon nanowire sensors, as an active micropatch can deliver neural stem cells with embedded silicon nanowire sensors (configured to monitor specific biochemical functions) and specific bioactive compounds 100 and/or bioactive molecules 100A.

Active Micropatch of Three-Dimensional Porous Epoxy Scaffold/Foam Coupled with A Porous Nanomembrane & Nanopump The three-dimensional porous epoxy scaffold/foam can be integrated with an atomically thick (about 1 nanometer thick) porous nanomembrane (e.g., a carbon nanomembrane), wherein the atomically thick porous nanomembrane is attached on a human body.

The three-dimensional porous epoxy scaffold/foam integrated with the atomically thick porous nanomembrane can be activated by a thin-film battery/thin-film printed battery/biofuel battery/engineered bacteria battery coupled with phi29 DNA polymerase enzyme as a nanopump (or an array of nanopumps of phi29 DNA polymerase enzymes) to deliver the bioactive compounds 100 and/or bioactive molecules 100A across the porous nanomembrane, wherein the atomically thick porous nanomembrane is attached on a human body.

Active Micropatch of Three-Dimensional Porous Scaffold/Foam of Other Material Matrix

TABLE 14A

Compositions Of A Scaffold

| Compositions | Wt % Material A | Wt % Material B | Wt % Material C | Wt % Material D |
|---|---|---|---|---|
| 1 | 80% Hydrogel | 20% Chitin | | |
| 2 | 80% Hydrogel | 20% Chitosan | | |
| 3 | 80% Hydrogel | 20% Fibroin | | |
| 4 | 80% Hydrogel | 10% Chitin | 10% Chitosan | |
| 5 | 80% Hydrogel | 10% Chitin | 10% Fibroin | |
| 6 | 80% Hydrogel | 10% Chitosan | 10% Fibroin | |
| 7 | 80% Hydrogel | 10% Chitin | 10% PGLA | |
| 8 | 80% Hydrogel | 10% Chitosan | 10% PGLA | |
| 9 | 80% Hydrogel | 10% Fibroin | 10% PGLA | |
| 10 | 70% Hydrogel | 10% Chitin | 10% Fibroin | 10% PGLA |
| 11 | 70% Hydrogel | 10% Chitosan | 10% Fibroin | 10% PGLA |

TABLE 14B

Compositions Of A Scaffold Integrated With Various Nanowire Field Effect Transistors

| Compositions From Table-14A | Integrated With An Array Of Nanowire Field Effect Transistors |
|---|---|
| 1 | Nanowire$^{P1}$/Nanowire$^{P2}$/Nanowire$^{P3}$/Nanowire$^{e}$/Nanowire$^{c}$ |
| 2 | Nanowire$^{P1}$/Nanowire$^{P2}$/Nanowire$^{P3}$/Nanowire$^{e}$/Nanowire$^{c}$ |
| 3 | Nanowire$^{P1}$/Nanowire$^{P2}$/Nanowire$^{P3}$/Nanowire$^{e}$/Nanowire$^{c}$ |
| 4 | Nanowire$^{P1}$/Nanowire$^{P2}$/Nanowire$^{P3}$/Nanowire$^{e}$/Nanowire$^{c}$ |
| 5 | Nanowire$^{P1}$/Nanowire$^{P2}$/Nanowire$^{P3}$/Nanowire$^{e}$/Nanowire$^{c}$ |
| 6 | Nanowire$^{P1}$/Nanowire$^{P2}$/Nanowire$^{P3}$/Nanowire$^{e}$/Nanowire$^{c}$ |
| 7 | Nanowire$^{P1}$/Nanowire$^{P2}$/Nanowire$^{P3}$/Nanowire$^{e}$/Nanowire$^{c}$ |
| 8 | Nanowire$^{P1}$/Nanowire$^{P2}$/Nanowire$^{P3}$/Nanowire$^{e}$/Nanowire$^{c}$ |
| 9 | Nanowire$^{P1}$/Nanowire$^{P2}$/Nanowire$^{P3}$/Nanowire$^{e}$/Nanowire$^{c}$ |
| 10 | Nanowire$^{P1}$/Nanowire$^{P2}$/Nanowire$^{P3}$/Nanowire$^{e}$/Nanowire$^{c}$ |
| 11 | Nanowire$^{P1}$/Nanowire$^{P2}$/Nanowire$^{P3}$/Nanowire$^{e}$/Nanowire$^{c}$ |

Nanowire$^{P1}$ field effect transistor is a polymer nanowire field effect transistor (optionally coated with a lipid layer).

Nanowire$^{P2}$ field effect transistor is an engineered protein nanowire field effect transistor (optionally coated with a lipid layer). An engineered protein based field effect transistor can be fabricated/constructed, utilizing a suitable material decorated on engineered protein (e.g., a three-dimensional ball and spike engineered protein-synthesized by a fusion of both Dps and gp5c genes).

Nanowire$^{P3}$ field effect transistor is a proton nanowire field effect transistor (optionally coated with a lipid layer). A natural biopolymer chitosan/melanin based proton field effect transistor incorporates a polymer substrate as a gate, a gate oxide insulator film, a source metal thin-film and a drain metal thin-film for proton current.

Nanowire$^z$ field effect transistor is a zinc oxide wire nanowire field effect transistor (optionally coated with a lipid layer).

Nanowire$^C$ field effect transistor is a carbon nanotube nanofiber field effect transistor (optionally coated with a lipid layer).

Compositions as described in Table-14B can enable merging biology and electronics to monitor a biological function/parameter of a cell/stem cell.

A three-dimensional porous scaffold/foam of various mixtures as illustrated by Table-14A and Table-14B can be fabricated/constructed, utilizing electrospinning/three-dimensional printing process.

Active Micropatch of Porous Nanofiber Mesh Electrically Connected with Nanofiber Field Effect Transistors A porous nanofiber mesh can be electrically connected with nanofiber field effect transistors (e.g., polymer field effect transistor/zinc oxide field effect transistor) to monitor electrical activity—thus enabling how living cells and/or stem cells would respond to specific bioactive compounds 100 and/or bioactive molecules 100A. Furthermore, the nanofiber field effect transistor can be coated/integrated with a lipid layer.

Active Micropatch Integrated with Microelectro-Mechanical-System Reservoirs & Microneedles A passive delivery of the bioactive compounds 100 and/or bioactive molecules 100A is generally limited by low permeability (of the bioactive compounds 100 and/or bioactive molecules 100A) in a biological transport medium.

Figure 7N:
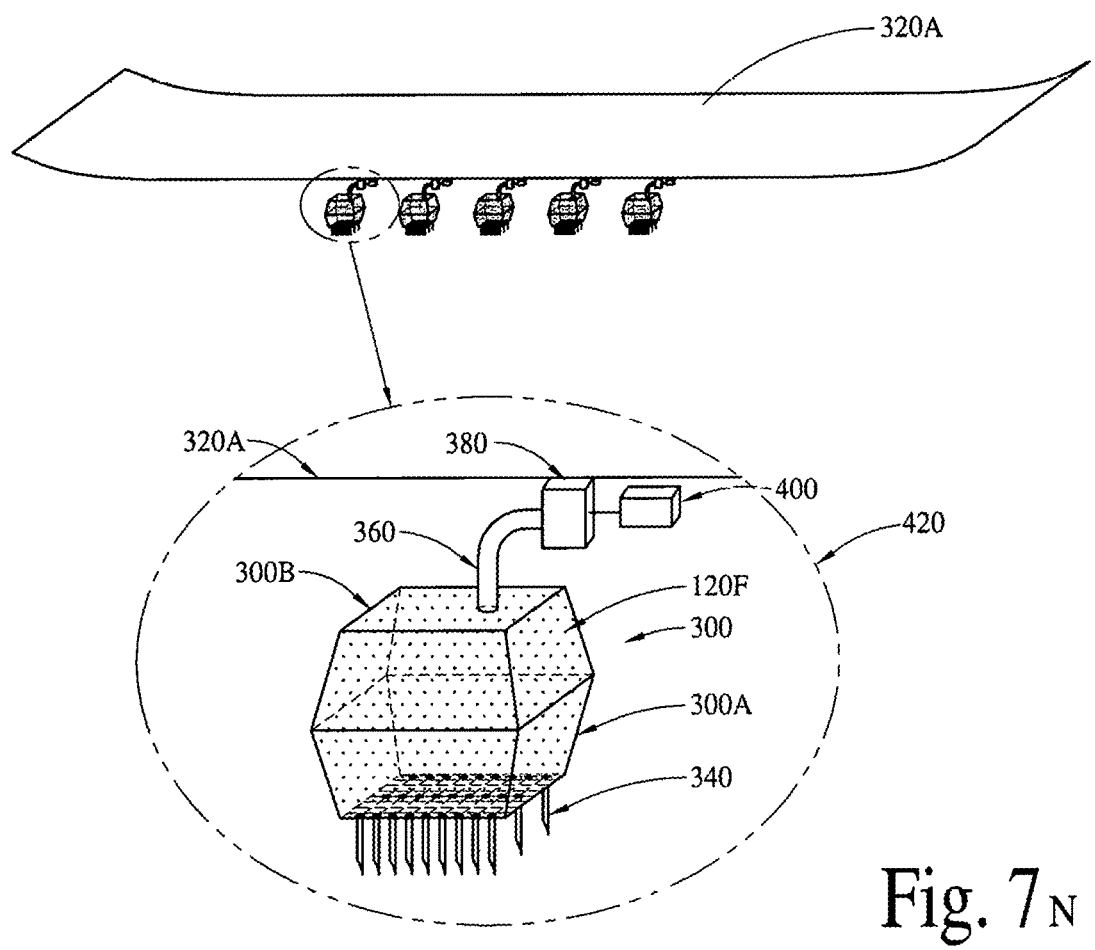
FIG. 7N illustrates a programmable/active (via a micropatch and microelectro-mechanical-system reservoir(s) integrated with needles) delivery of bioactive compounds and/or bioactive molecules, utilizing thin-films, nanocrystals, hydrogel, microelectro-mechanical-system reservoirs and micropumps.

FIG. 7N illustrates a thin-film 320A attached with a microelectro-mechanical-system microassembly as 420.

The microelectro-mechanical-system microassembly 420 illustrates the microelectro-mechanical-system reservoirs 300 with monolithically integrated microneedles 340, utilizing a microflow tube 360.

The microflow tube 360 can be connected to a micropump 380.

The micropump 380 can be powered by an electrical power providing component 400. The electrical power providing component 400 can be a thin-film battery/thin-film printed battery/biofuel battery/engineered bacteria battery.

The microelectro-mechanical-system reservoir 300 can be fabricated/constructed, utilizing liquid-crystal polymers/polyimide/silicon/silk/SU-8 resin/other suitable material.

The microelectro-mechanical-system reservoir 300 can be monolithically integrated with the microneedles 340.

The microneedle 340 is biocompatible and about 450 microns long with an internal hole-diameter of about 45 microns.

The microneedle 340 can be fabricated/constructed, utilizing liquid-crystal polymers/polyimide/silicon/silk/SU-8 resin/other suitable material.

The microneedle 340 can be coated with carbon nanotubes, wherein the carbon nanotubes are integrated with the enzyme Lysostaphin. Lysostaphin is a natural enzyme, which attacks the bacterial cell wall causing its slicing and disintegration.

The microneedle 340 can be coated with positively charged dimethyldecylammonium chitosan methacrylate. The interaction of positively charged dimethyldecylammonium chitosan methacrylate with the negatively charged bacterial cell wall can result in the disintegration of the bacterial cell wall.

Furthermore, the microneedle 340 can be coated with polyvinyl alcohol integrated with nitric oxide releasing nanoparticle and/or reactive oxygen species releasing nanoparticle and/or reactive nitrogen species releasing nanoparticle and/or silver oxide nanoparticle and/or titanium oxide nanoparticle and/or zinc oxide nanoparticle against bacterial infection.

Furthermore, the microneedle 340 can be coated with poly(ethylene glycol)-poly(lactic acid) (PEG-PLA) nanoparticle with silver carbene complexes (SCCs) to act as a controlled release system against bacterial infection.

The microelectro-mechanical-system microassembly is indicated as 420.

Thus, a long-term active micropatch (about 15 millimeters$^2$ in area) can be fabricated/constructed for the delivery of the bioactive compounds 100 and/or bioactive molecules 100A from the nanoassembly 120F in the microelectro-mechanical-system reservoirs 300.

Alternatively, a hydrogel contains up to 99.7% water and 0.3% cellulose polymers by weight, wherein the polymers are held by cucurbiturils. Cucurbiturils are methylene-linked macrocyclic molecules made of glycoluril [=C4H2N4O2=] monomers. The oxygen atoms are located along the edges of the band and are tilted inwards, forming a partly enclosed cavity.

The hydrogel can protect the bioactive compounds 100 and/or bioactive molecules 100A for about six (6) months.

The hydrogel (embedded with the bioactive compounds 100 and/or bioactive molecules 100A) can be utilized in the microelectro-mechanical-system reservoirs 300 with the nanoassembly 120F.

The hydrogel (embedded with the bioactive compounds 100 and/or bioactive molecules 100A) can be utilized in the microelectro-mechanical-system reservoirs 300 without the nanoassembly 120F.

Bee venom contains a potent toxin called melittin that can indiscriminately poke holes in the double-layered membranes of a virus (e.g., hepatitis B, hepatitis C and HIV). However, large amounts of free melittin can cause a lot of damage to healthy cells. The nanoshell 120 can attack an essential part of the virus' structure. Furthermore, melittin-loaded nanoshell 120 can be also effective in killing cancer cells.

The hydrogel embedded with melittin can be utilized in the microelectro-mechanical-system reservoirs 300 without the nanoassembly 120F.

Alternatively, a long-term active micropatch (about 15 millimeters' in area) can be fabricated/constructed for the delivery of the bioactive compounds 100 and/or bioactive molecules 100A from the hydrogel (embedded with the bioactive compounds 100 and/or bioactive molecules 100A e.g., melitin) in the microelectro-mechanical-system reservoirs 300.

Furthermore, the bioactive compounds 100 and/or bioactive molecules 100A can be utilized directly in the microelectro-mechanical-system reservoirs 300 without the nanoassembly 120F for a long-term active micropatch.

Thus, in addition to delivering the bioactive compounds 100 and/or bioactive molecules 100A, utilizing the long-term active micropatch, other bio/health sensors to monitor vital health parameters (e.g., blood sugar and heart rate) can be integrated with the long-term active micropatch.

An example of a bio/health sensor integrated with the long-term active micropatch is in-situ blood sugar measurement. Blood sugar measurement can involve an electrochemical reaction activated by an enzyme. Glucose oxidase can convert glucose into hydrogen peroxide and other chemicals—thus their concentrations can be measured with a miniature potentiostat or nanosized potentiostat as a biosensor for calculating the glucose level in sweat. Furthermore, the bio/health sensor can be integrated with an analog signal to a digital signal converter circuit.

Wibree, Bluetooth, Wi-Fi and near-field communication can be integrated with the long-term active micropatch. Furthermore, ultrathin/bare-die electronic components, processor(s), sensors, light emitting diodes, photodetectors on the substrate of the long-term active micropatch can be flexibly interconnected to detect/measure for example, blood flow dynamics, pressure wave velocity (a measure of blood pressure variation) and level of oxygenation in a human blood. Additionally, by injecting tiny heat pulses, the long-term active micropatch can measure a human skin's thermal conductivity (related to hydration level). Such substrate of the long-term active micropatch is biocompatible and preferably is flexible/stretchable. Furthermore, thin-film digital/source-gated transistor based circuits, as an artificial skin can be integrated with the long-term active micropatch for on-demand delivery of the bioactive compounds 100 and/or bioactive molecules 100A.

The long-term active micropatch can be integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Thus, the bio/health sensor integrated with the long-term active micropatch can enable active (actively controlled via closed loop measurement) delivery of the bioactive compounds 100 and/or bioactive molecules 100A, utilizing the long-term active micropatch.

The long-term active micropatch can be placed (attached and/or implanted) on or in (meaning within) a human body Example Applications of an Active Micropatch Integrated with Microelectro-Mechanical-System Reservoirs & Microneedles NAD is a key molecule that coordinates activities between the cell's nuclear genome and the mitochondrial genome. With aging, levels of NAD decline. Without sufficient NAD, SIRT1 can not keep tabs on HIF-1. Levels of HIF-1 can escalate and begin wreaking havoc on the cross-genome communication. Over time, this loss of communication reduces the cell's ability to make energy and signs of aging related diseases become apparent. By administering an endogenous compound (that cells can transform into NAD) such as, plasma NAD metabolites-nicotinamide mononucleotide, one could restore cross-genome communication, if the endogenous compound was administered early enough, prior to excessive mutation accumulation. 7N can be utilized to deliver an endogenous compound (that cells can transform into NAD) to delay onset of aging related diseases.

7N can be utilized as an active micropatch to deliver multivalent adhesion molecule 7 (MAM7) to disable/disrupt adhesion of bacteria.

7N can be utilized as an active micropatch to deliver a liquid drug (e.g., immunoglobulin).

7N can be utilized as an active micropatch to deliver a liquid nanoemulsified drug.

7N can be utilized as an active micropatch to deliver insulin/long acting insulin/smart insulin.

7N can be utilized as an active micropatch to deliver insulin/long acting insulin/smart insulin from the nanoshell 120. For example, the nanoshell 120 can be made of water-fearing molecules (pointing inward) and water-loving molecules (pointing outward). The nanoshell 120 can encapsulate insulin molecules/long acting insulin molecules/smart insulin molecules. The external surface of the nanoshell 120 can be coupled with an enzyme to convert glucose into gluconic acid. In the presence of excess glucose, the enzyme (converting glucose into gluconic acid) creates a lack of oxygen and causes water-loving molecules (pointing outward) to collapse-enabling the delivery of insulin/long acting insulin/smart insulin at a suitable external condition.

In another example, the nanoshell 120 (fabricated/constructed by DNA origami) can be decorated with an aptamer/engineered riboswitch based (excess) glucose sensor. In the presence of excess glucose, the nanoshell 120 can collapse-enabling the delivery of insulin/long acting insulin/smart insulin at a suitable external condition.

Smart insulin can be Ins-PBA-F, which can consist of a long-acting insulin derivative that has a chemical moiety with phenylboronic acid added at one end. Under normal condition, smart insulin can bind with serum proteins (circulating in blood). In the presence of excess glucose, it can bind with phenylboronic acid to release Ins-PBA-F.

7N can be utilized as an active micropatch to deliver insulin/long acting insulin/smart insulin with leptin.

7N can be utilized as an active micropatch to deliver both insulin and glucagon (which lowers the risk of insulin overdose).

7N can be utilized as an active micropatch to deliver both insulin with leptin and glucagon.

7N can be utilized as an active micropatch to deliver exenatide.

7N can be utilized as an active micropatch to deliver specific micro RNA.

7N can be utilized as an active micropatch to deliver specific small interfering RNA.

Figure 7O:
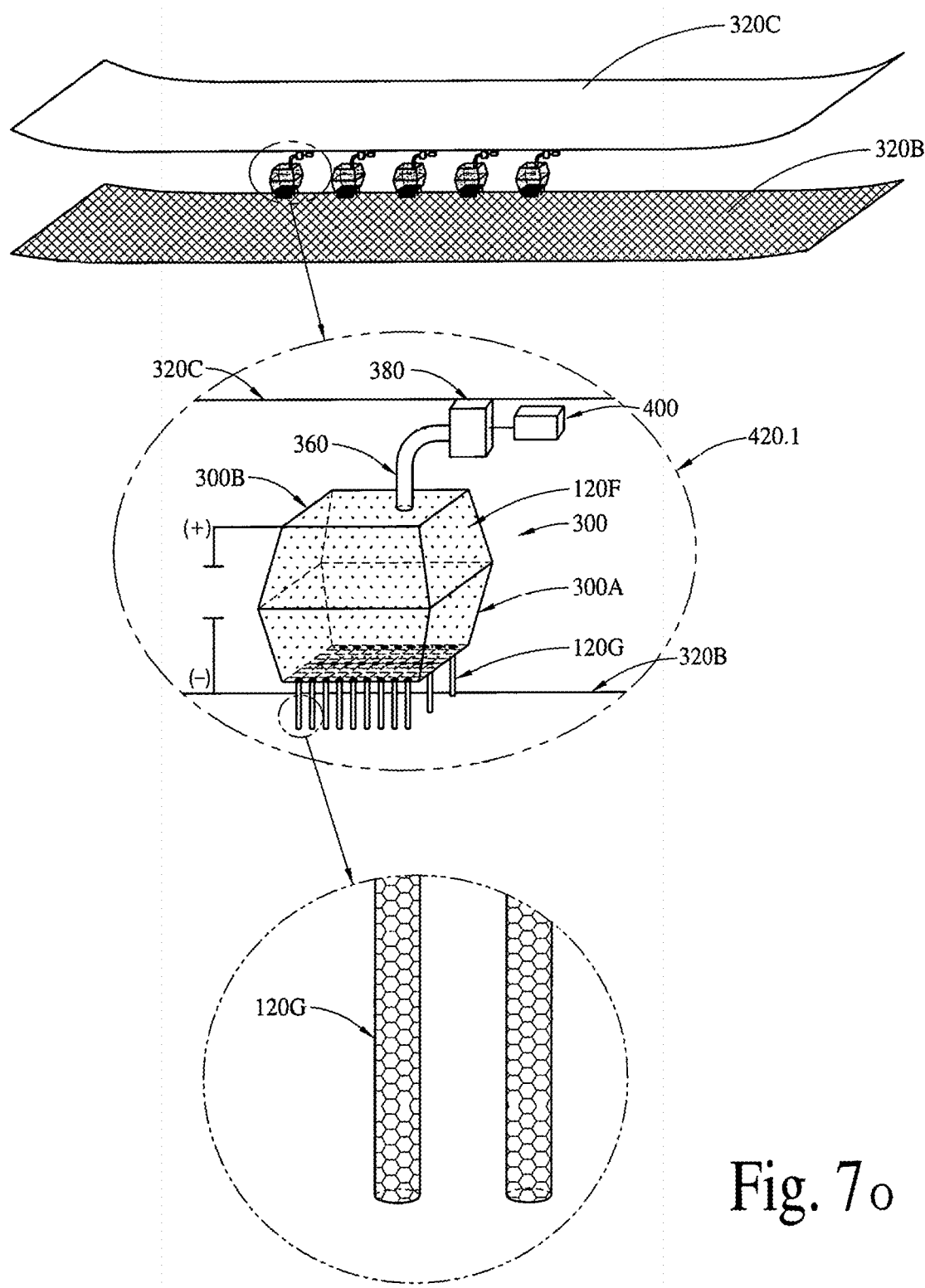
FIG. 7O illustrates a programmable/active (via a micropatch and microelectro-mechanical-system reservoir(s) integrated with nanotubes) delivery of bioactive compounds and/or bioactive molecules, utilizing thin-films, nanocrystals, hydrogel, microelectro-mechanical-system reservoirs and micropumps.

7N can be utilized to deliver granulocyte macrophage colony-simulating factor, which can reprogram a human body's immune system to attack cancer cells.
Active Micropatch Integrated with Microelectro-Mechanical-System Reservoirs & Nanotubes FIG. 7O illustrates a conducting thin-film 320C attached with the microelectro-mechanical-system reservoirs 300.

Furthermore, the microelectro-mechanical-system reservoirs 300, with integrated/bonded nanotubes (e.g., a boron nitride/carbon nanotube or a tubular structure fabricated/constructed, utilizing DNA/RNA origami process) 120G, utilizing a microflow tube 360, can be connected to a micropump 380. The microelectro-mechanical-system reservoirs microassembly is indicated as 420.1.

The micropump 380 can be powered by an electrical power providing component 400. The electrical power providing component 400 can be a thin-film battery/thin-film printed battery/biofuel battery/engineered bacteria battery.

Thus, a long-term active micropatch (about 15 millimeters$^2$ in area) can be fabricated/constructed for the delivery of the bioactive compounds 100 and/or bioactive molecules 100A from the nanoassembly 120F.

Alternatively, a long-term active micropatch (about 15 millimeters$^2$ in area) can be fabricated/constructed for the delivery of the bioactive compounds 100 and/or bioactive molecules 100A from the hydrogel (embedded with the bioactive compounds 100 and/or bioactive molecules 100A) in the microelectro-mechanical-system reservoirs 300.

Furthermore, the bioactive compounds 100 and/or bioactive molecules 100A can be utilized directly within the microelectro-mechanical-system reservoirs 300 without the nanoassembly 120F.

The nanotubes 120G can be further integrated/bonded with the porous bottom thin-film 320B.

By applying a voltage (about millivolts from a thin-film battery/thin-film printed battery/biofuel battery/engineered bacteria battery) between 320C and the nanostructure membrane 120G, the bioactive compounds 100 and/or bioactive molecules 100A can be delivered in a variable quantity according to the required dose/need.

Wibree, Bluetooth, Wi-Fi and near-field communication can be integrated with 7O. Furthermore, ultrathin/bare-die electronic components, processor(s), sensors, light emitting diodes, photodetectors on the substrate of 7O can be flexibly interconnected to detect/measure for example, blood flow dynamics, pressure wave velocity (a measure of blood pressure variation) and level of oxygenation in a human blood. Additionally, by injecting tiny heat pulses, 7O can measure a human skin's thermal conductivity (related to hydration level). Such substrate of 7O is biocompatible and preferably is flexible/stretchable. Furthermore, thin-film digital/source-gated transistor based circuits, as an artificial skin can be integrated with 7O for on-demand delivery of the bioactive compounds 100 and/or bioactive molecules 100A.

7O can be integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTH-CARE EXPERIENCE", filed on Jun. 1, 2016 and the entire contents of this US Non-Provisional Patent Application are incorporated herein.

7O can be placed (attached and/or implanted) on or in (meaning within) a human body.

Example Applications of an Active Micropatch Integrated with Microelectro-Mechanical-System Reservoirs & Nanotubes NAD is a key molecule that coordinates activities between the cell's nuclear genome and the mitochondrial genome. With aging, levels of NAD decline. Without sufficient NAD, SIRT1 can not keep tabs on HIF-1. Levels of HIF-1 can escalate and begin wreaking havoc on cross-genome communication. Over time, this loss of communication reduces the cell's ability to make energy and signs of aging related diseases become apparent. By administering an endogenous compound (that cells can transform into NAD) such as, plasma NAD metabolites-nicotinamide mononucleotide, one could restore cross-genome communication, if the endogenous compound was administered early enough, prior to excessive mutation accumulation. 7O can be utilized to deliver an endogenous compound (that cells can transform into NAD) to delay onset of aging related diseases.

7O can be utilized as an active micropatch to deliver multivalent adhesion molecule 7 (MAM7) to disable/disrupt adhesion of bacteria.

7O can be utilized as an active micropatch to deliver a liquid drug (e.g., immunoglobulin).

7O can be utilized as an active micropatch to deliver a nanoformulated liquid drug.

7O can be utilized as an active micropatch to deliver insulin/long acting insulin/smart insulin.

7O can be utilized as an active micropatch to deliver insulin/long acting insulin/smart insulin from the nanoshell 120. For example, the nanoshell 120 can be made of water-fearing molecules (pointing inward) and water-loving molecules (pointing outward). The nanoshell 120 can encapsulate insulin molecules/long acting insulin molecules/smart insulin molecules. The external surface of the nanoshell 120 can be coupled with an enzyme to convert glucose into gluconic acid. In the presence of excess glucose, the enzyme (converting glucose into gluconic acid) creates a lack of oxygen and causes water-loving molecules (pointing outward) to collapse-enabling the delivery of insulin/long acting insulin/smart insulin at a suitable external condition.

In another example, the nanoshell 120 (fabricated/constructed by DNA origami) can be decorated with an aptamer/engineered riboswitch based (excess) glucose sensor. In the presence of excess glucose, the nanoshell 120 can collapse-enabling the delivery of insulin/long acting insulin/smart insulin at a suitable external condition.

Smart insulin can be Ins-PBA-F, which can consist of a long-acting insulin derivative that has a chemical moiety with phenylboronic acid added at one end. Under normal conditions, smart insulin can bind with serum proteins (circulating in blood). In the presence of excess glucose, it can bind with phenylboronic acid to release Ins-PBA-F.

7O can be utilized as an active micropatch to deliver insulin/long acting insulin/smart insulin with leptin.

7O can be utilized as an active micropatch to deliver both insulin and glucagon (which lowers the risk of insulin overdose).

7O can be utilized as an active micropatch to deliver both insulin with leptin and glucagon.

7O can be utilized as an active micropatch to deliver exenatide.

7O can be utilized as an active micropatch to deliver specific micro RNA.

7O can be utilized as an active micropatch to deliver specific small interfering RNA.

Figure 8:
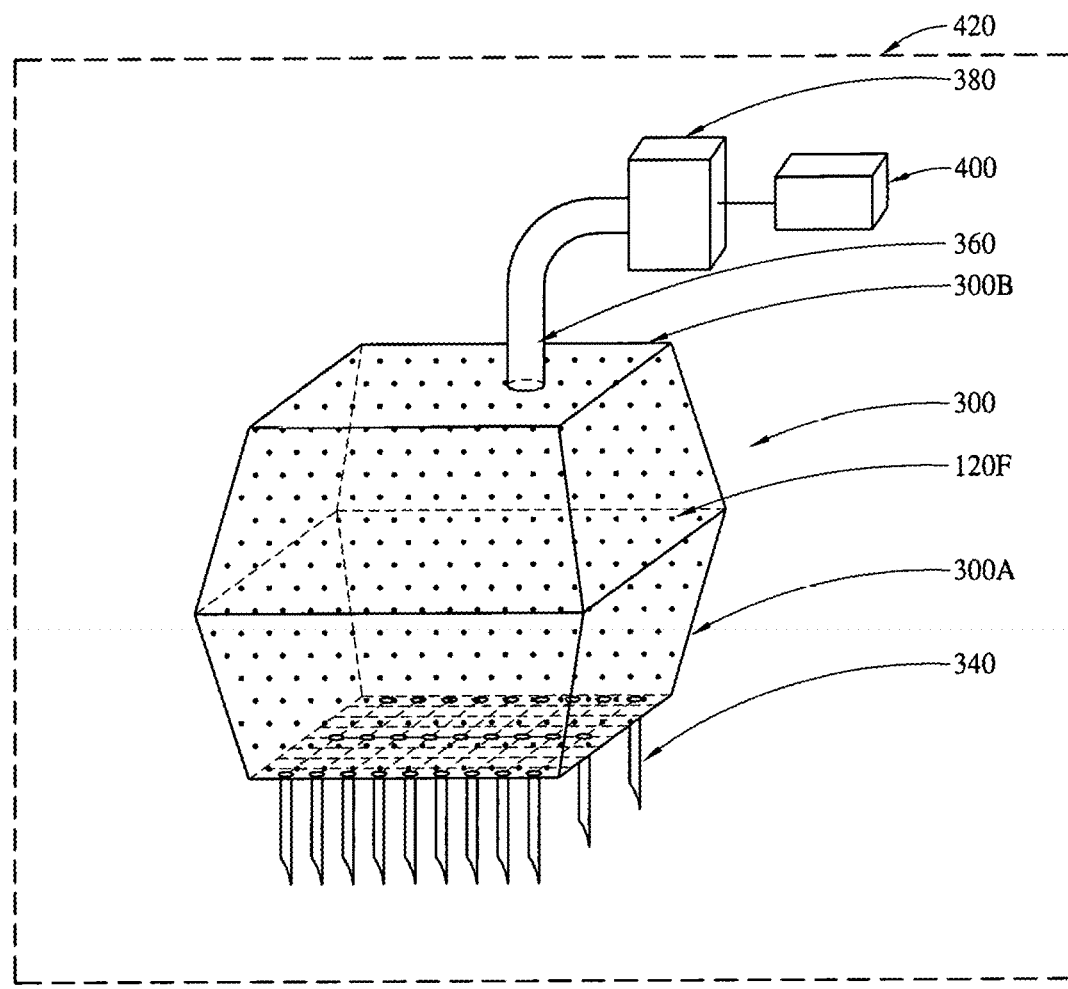
FIG. 8 illustrates a programmable/active (via a micropatch and microelectro-mechanical-system reservoir(s) integrated with needles) delivery of bioactive compounds and/or bioactive molecules, utilizing a microelectro-mechanical-system reservoir and a micropump.

FIG. 8 illustrates the microelectro-mechanical-system reservoir 300 with 120Fs dispersed in a liquid medium. 120Fs can encapsulate/cage the bioactive compounds 100 and/or bioactive molecules 100A.

However, the bioactive compounds 100 and/or bioactive molecules 100A can be dispersed directly (via a liquid medium) in the microelectro-mechanical-system reservoir 300, without the need for 120F.

The microelectro-mechanical-system reservoir 300 is about 1 millimeter in total thickness.

The microelectro-mechanical-system reservoir 300 can be monolithically integrated with the microneedle(s) 340 at the bottom surface 300A of the microelectro-mechanical-system reservoir 300.

The microneedle 340 is biocompatible and about 450 microns long with an internal hole-diameter of about 45 microns.

The microneedle 340 can be fabricated/constructed, utilizing liquid-crystal polymers/polyimide/silicon/silk/SU-8 resin/other suitable material.

The microelectro-mechanical-system reservoir 300 can be connected to a microflow tube 360, which is connected to a micropump 380.

The micropump 380 can be powered by an electrical power providing component 400. The electrical power providing component 400 can be a thin-film battery/thin-film printed battery/biofuel battery/engineered bacteria battery.

Such a microelectro-mechanical-system biomodule 420 can be utilized to achieve a higher permeability (of the bioactive compounds 100 and/or bioactive molecules 100A) through a biological transport medium for long-term programmable/active delivery of the bioactive compounds 100 and/or bioactive molecules 100A.

Alternatively, a microelectro-mechanical-system biomodule 420 can be utilized to achieve a higher permeability (of the bioactive compounds 100 and/or bioactive molecules 100A) through a biological transport medium for a long-term programmable/active delivery of the bioactive compounds 100 and/or bioactive molecules 100A, utilizing a hydrogel.

The hydrogel embedded with the bioactive compounds 100 and/or bioactive molecules 100A can be utilized in the microelectro-mechanical-system reservoirs 300.

Wibree, Bluetooth, Wi-Fi and near-field communication can be integrated with the microelectro-mechanical-system biomodule 420. Furthermore, ultrathin/bare-die electronic components, processor(s), sensors, light emitting diodes, photodetectors with the microelectro-mechanical-system biomodule 420 can be flexibly interconnected to detect/measure for example, blood flow dynamics, pressure wave velocity (a measure of blood pressure variation) and level of oxygenation in a human blood. Additionally, by injecting tiny heat pulses, the microelectro-mechanical-system biomodule 420 can measure human skin's thermal conductivity (related to hydration level). The microelectro-mechanical-system biomodule 420 is biocompatible and preferably is flexible/stretchable. Furthermore, thin-film digital/source-gated transistor based circuits, as an artificial skin can be integrated with the microelectro-mechanical-system biomodule 420 for on-demand delivery of the bioactive compounds 100 and/or bioactive molecules 100A.

The microelectro-mechanical-system biomodule 420 can be integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

The microelectro-mechanical-system biomodule 420 can be placed (attached and/or implanted) on or in (meaning within) a human body.

Array of Fluidic Containers/Zero-Mode Waveguides (ZMG)

A zero-mode waveguide is a fluidic container that guides light into a volume, which is small in all dimensions compared to the wavelength of the incident light.

With an exception of a zero-mode waveguide, by way of an example and not by way of any limitation, a fluidic container can generally mean a fluidic capillary (including a microcapillary/nanocapillary) or a fluidic well (including a microwell/nanowell) or a fluidic cavity (including a microcavity/nanocavity) or a fluidic channel (including a microchannel/nanochannel or a recessed substrate/surface or a planar substrate/surface, utilizing one or more suitable materials (e.g., an insulator, a semiconductor-including a two-dimensional crystal material (e.g., graphene) and a metal) of suitable thicknesses to contain/propagate fluid.

Additionally, a fluidic container/zero-mode waveguide can be integrated with a flow cell (containing an aqueous solution).

It should be noted that a multilayer of suitable materials with each layer of a specifc material/thickness can enable a metamaterial based substrate. Furthermore, a one-dimensional/two-dimensional periodic ordered structure in a multilayer of suitable materials with each layer of a specific material/thickness can enable a photonic crystal based substrate.

Figure 9A:
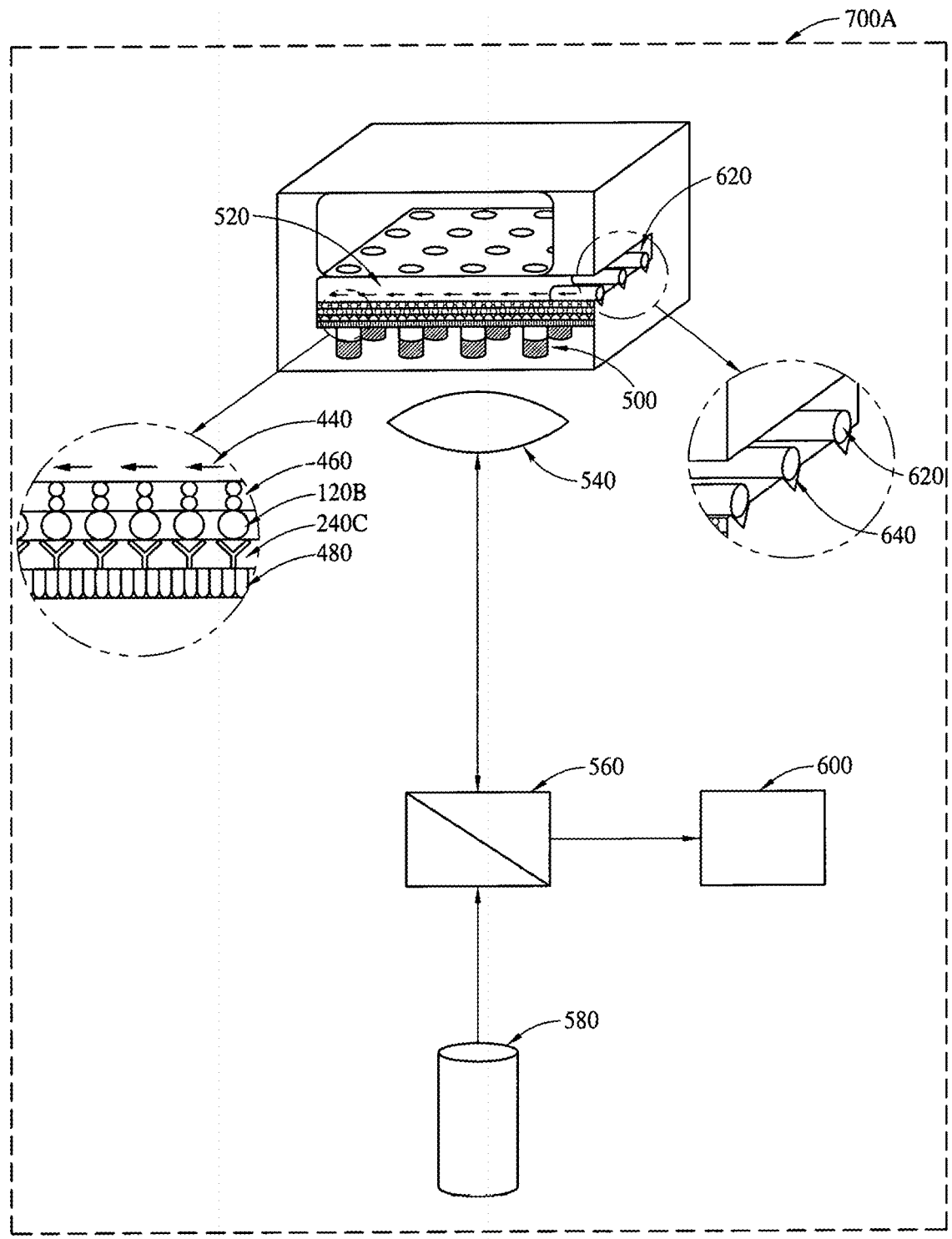
FIGS. 9A, 9B, 9C and 9D illustrate an array of photonic crystal cavities based integrated optical diagnostic biomodule to detect a disease specific biomarker/an array of disease specific biomarkers.

Array of Photonic Crystal Cavities Based Optical Diagnostic Biomodule for Detection of A Disease Specific Biomarker/an Array of Disease Specific Biomarkers FIG. 9A illustrates an array of photonic crystal cavities 500 based optical diagnostic biomodule 700A for detection of a disease specific biomarker 460 (in a human body's blood/biological fluid 440 which can be propagated through a fluidic channel 620 to a fluidic cavity 520).

The disease specific biomarker 460 can chemically bind with the disease specific biomarker binder 240C, wherein the disease specific biomarker binder 240C can chemically bind with the fluorophore 120B on an optional biomolecular interface layer 480, within the array of photonic crystal cavities (fabricated/constructed, utilizing both low index materials and high index materials) 500.

By way of an example and not by way of any limitation, the disease specific biomarker 460 can be a disease predicting biomarker (e.g., higher concentration of fetuin-A protein in a human body's blood can indicate an increased risk of Diabetes disease or higher lever of C-reactive protein (CRP) protein or lactate dehydrogenase (LDH) protein in a human body's blood can indicate an increased risk of heart attack or higher level of carcinoembryonic antigen (CEA) indicate an increased risk of heart attack).

An incident light from a microelectro-mechanical-system enabled wavelength tunable surface emitting vertical cavity laser 580 can be split through an optical beam splitter 560, collimated by a lens 540, absorbed by the fluorophore 120B.

Reference incident emission from the microelectro-mechanical-system enabled wavelength tunable surface emitting vertical cavity laser 580 and the fluorescence emission wavelength can be measured by a spectrophotometer 600.

By way of an example and not by way of any limitation, the spectrophotometer 600 can be an array of charged-coupled detectors (CCD)/echelle gratings based demultiplexer/microspectrophotometer-on-a-chip/photonic crystal/planar lightwave circuit based demultiplexer/silicon nanowire waveguide based demultiplexer spectrophotometer. The spectrophotometer 600 can also be a quantum dot spectrophotometer, which generally utilizes hundreds of quantum dot material based filters, wherein each quantum dot material based filter is designed for a specific set of wavelengths of light. The quantum dot filters can be printed onto a thin-film (on top of a photodetector (e.g., charge-coupled devices)).

700A can be scaled to an array of disease specific biomarkers 460, an array of disease specific biomarker binders 240C and an array of fluorophores 120B with distinct fluorescence emission wavelengths. A direct correlation exists between the fluorescence emission wavelength and the diameter of a quantum dot fluorophore.

Microspectrophotometer-On-A-Chip

The penetration depth of photons in silicon depends upon wavelength of photons. The shorter wavelength photons can be absorbed in top thin-films, while the longer wavelength photons travel some distance, before they can be absorbed in bottom thin-films.

A pixel of a microspectrophotometer-on-a-chip has vertically stacked detection material thin-film (e.g., silicon) and wavelength tunable optical filters (utilizing a combination of non-absorbing dielectric thin-films and resistor thin-films configured with thermo-optic semiconductor thin-films).

A two-dimensional array of the pixels can constitute a microspectrophotometer-on-a-chip, as the spectrophotometer 600.

Alternatively, the spectrophotometer 600 can be based on a cascaded configuration of coarse arrayed waveguide gratings coupler (AWG), fine arrayed waveguide gratings coupler and an array of photodetectors. Alternatively, the spectrophotometer 600 can be based on a cascaded configuration of coarse arrayed waveguide gratings coupler, fine arrayed waveguide gratings coupler, an array of ring-resonators and an array of photodetectors.

However, an ultra-compact spectrophotometer (as the spectrophotometer 600) can be realized, by utilizing photonic crystal (PC) based coarse arrayed waveguide gratings coupler and photonic crystal based fine arrayed waveguide gratings coupler.

Microelectro-Mechanical-System Biomodule to Draw/Propagate Blood

Figure 9B:
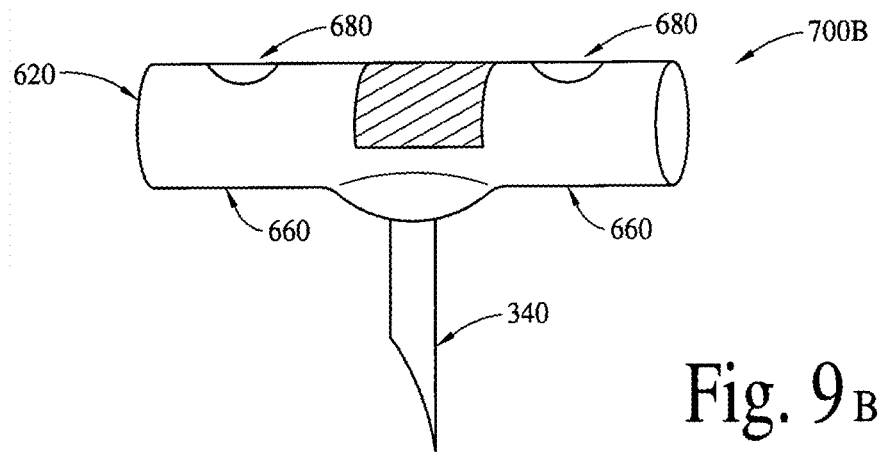

FIG. 9B illustrates a microelectro-mechanical-system biomodule 700B to draw blood/biological fluid 440 from a human, utilizing a microneedle 340, which can be monolithically integrated with a micromachined (voltage deflectable) membrane 660, a membrane sensor 680 and a fluidic channel 620.

The microneedle 340 can be electrically powered and programmed to draw a human's blood/biological fluid 440 at a periodic interval of time.

Furthermore, the microelectro-mechanical-system biomodule 700B can include an array of microneedles 340, an array of micromachined membranes 660, an array of membrane sensors 680 and an array of fluidic channels 620.

Furthermore, an array of fluidic channels 620 can be placed onto an array of precise silicon/ceramic v-grooves 640.

The array of precise silicon/ceramic v-grooves 640 can be enclosed within a precisely machined connector (not shown in FIG. 9B).

The precisely machined connector can be attached precisely/detached from the microelectro-mechanical-system biomodule for drawing/propagating a human body's blood/biological fluid 440.

Figure 9C:
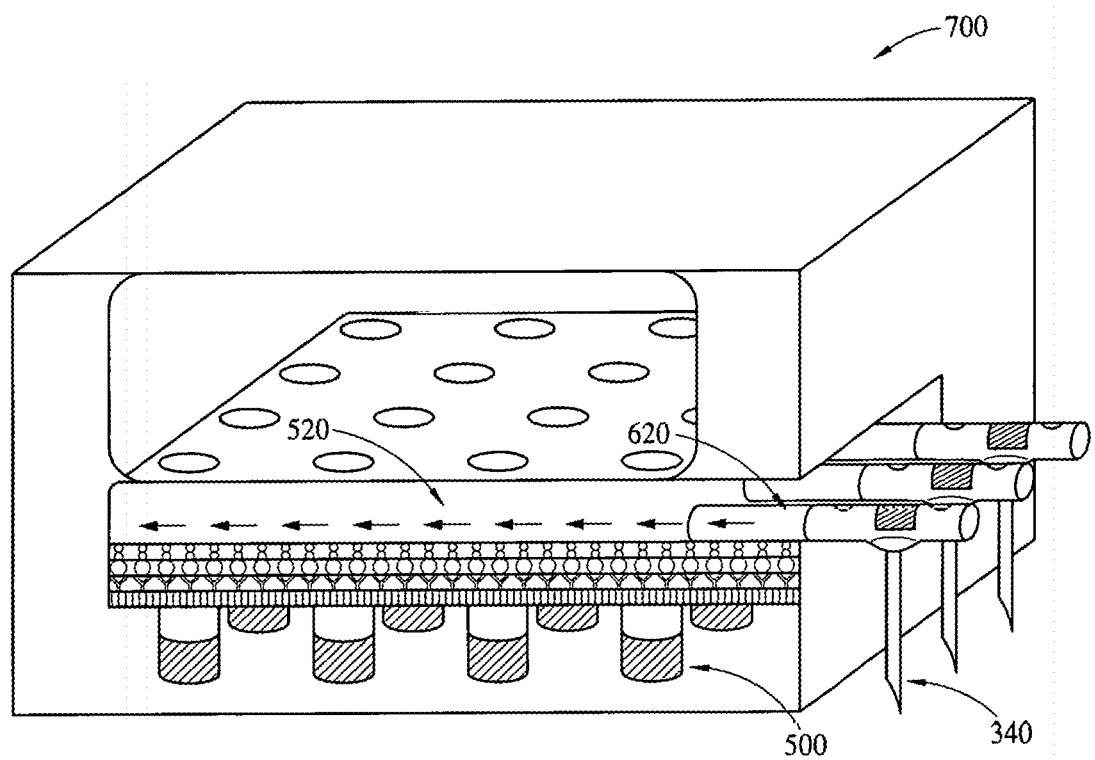

Array of Photonic Crystal Cavities Based Integrated Optical Diagnostic Biomodule for Detection of a Disease Specific Biomarker/an Array of Disease Specific Biomarkers FIG. 9C illustrates an array of photonic crystal cavities based integrated optical diagnostic biomodule 700.

Stokes Shift to Detect a Disease Specific Biomarker/an Array of Disease Specific Biomarkers The Stokes Shift is the difference between the absorption wavelength and fluorescence emission wavelength.

Figure 9D:
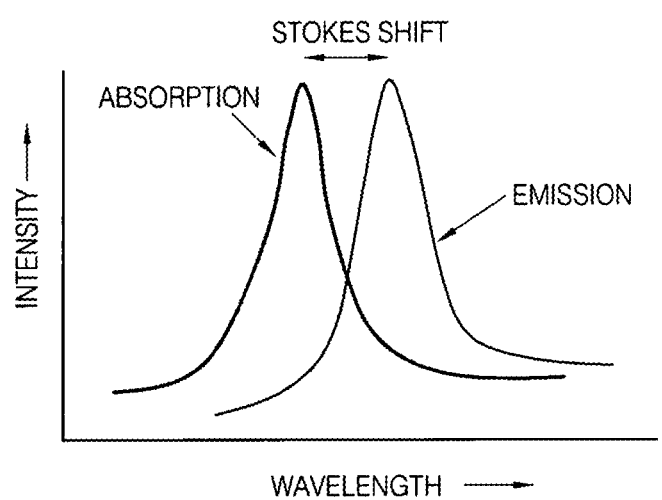

FIG. 9D illustrates the Stokes Shift due to binding of a disease specific biomarker 460 with a disease specific biomarker binder 240C.

The Stokes Shift can be utilized to detect the presence of a disease specific biomarker/an array of disease specific biomarkers.

Figure 10A:
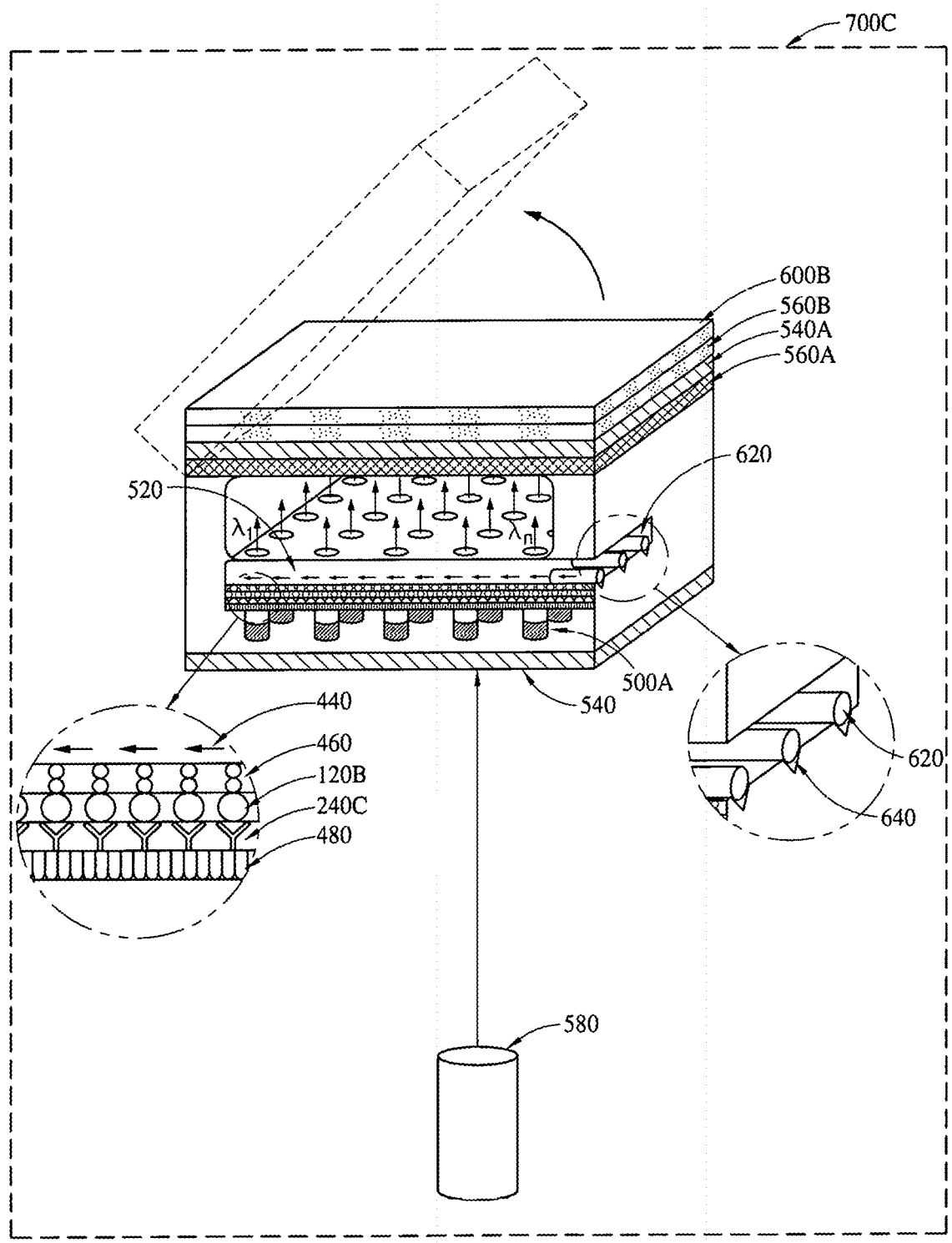
FIGS. 10A, 10B, 10C and 10D illustrate (an array of fluid containers based) integrated optical diagnostic biomodules (various embodiments) to detect a disease specific biomarker/an array of disease specific biomarkers.

Array of Fluidic Containers Based Optical Diagnostic Biomodule for Detection of a Disease Specific Biomarker/an Array of Disease Specific Biomarkers FIG. 10A illustrates an array of fluidic containers 500A based optical diagnostic biomodule 700C for detection of a disease specific biomarker 460 (in a human body's blood/biological fluid 440, which can be propagated through a fluidic channel 620 to a fluidic cavity 520).

The disease specific biomarker 460 can chemically bind with a disease specific biomarker binder 240C, wherein the disease specific biomarker binder 240C can chemically bind with the fluorophore 120B, on an optional biomolecular interface layer 480, within the array of fluidic containers 500A.

Furthermore, the top optical assembly can be removed to allow a direct access to fill the array of fluidic containers 500A with a human body's blood/biological fluid 400.

Furthermore, a particular biological fluid can be considered as gold nanoparticles chemically bonded with DNAzyme (DNAzyme, a synthetic DNA enzyme that can cleave a nucleic acid molecule) in liquid form. When a disease gene is introduced, the DNA can be cleaved from the gold nanoparticles, turning the liquid red in color The array of fluidic containers 500A is optically transparent to the incident light. The incident light from a microelectro-mechanical-system enabled wavelength tunable surface emitting vertical cavity laser 580 can be collimated by a lens 540, absorbed by the fluorophore 120B.

The fluorophore 120B can exist within each container of fluidic containers 500A. The fluorophore 120B can be a dye based fluorophore or a quantum dot fluorophore or a fluorescent protein.

700C can be scaled to an array of disease specific biomarkers 460, an array of disease specific biomarker binders 240C and an array of fluorophores 120B with distinct fluorescence emission wavelengths.

Fluorescence emission can propagate through a first optical filter (not to transmit the incident wavelength from the microelectro-mechanical-system enabled wavelength tunable surface emitting vertical cavity laser 580) 560A, an array of lenses 540A and an array of second optical filters 560B, then finally be detected by an array of light detectors 600B.

By way of an example and not by way of any limitation, the light detector 600B can be a charge-coupled detector/electron multiplying charge-coupled detector (EMCCD)/intensified charge-coupled detector (ICCD)/back illuminated high quantum efficiency complementary metal-oxide-semiconductor (CMOS) detector/color-complementary metal-oxide-semiconductor detector, wherein a complementary metal-oxide-semiconductor detector pixel can be integrated with a transparent polyimide light collecting lens and a color (blue, green and red) selective optical filter.

A color selective optical filter can be a wavelength tunable optical filter (utilizing a combination of non-absorbing dielectric thin-films and resistor thin-films configured with thermo-optic semiconductor thin-films).

Furthermore, the light detector 600B can be based on a single photon detector(s) (e.g., single photon avalanche diode (SPAD) detector). A single photon avalanche diode detector is a reverse biased avalanche photodiode (APD), which is biased above the avalanche breakdown voltage in the Geiger mode.

Microelectro-Mechanical-System Biomodule to Draw/Propagate Blood

Figure 10B:
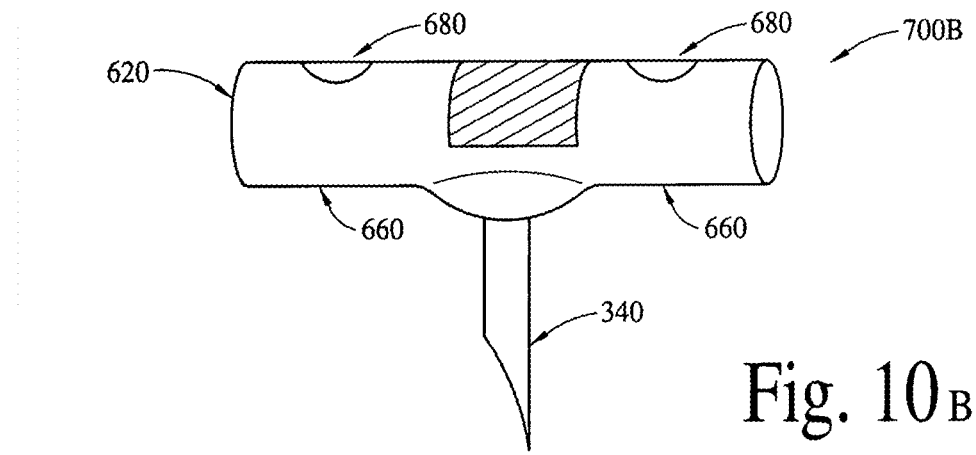

FIG. 10B illustrates a microelectro-mechanical-system biomodule 700B to draw blood/biological fluid 440 from a human, utilizing a microneedle 340, which can be monolithically integrated with a micromachined (voltage deflectable) membrane 660, a membrane sensor 680 and a fluidic channel 620.

The microneedle 340 can be electrically powered and programmed to draw a human's blood/biological fluid 440 at a periodic interval of time.

Furthermore, the microelectro-mechanical-system biomodule 700B can include an array of microneedles 340, an array of micromachined membranes 660, an array of membrane sensors 680 and an array of fluidic channels 620.

Furthermore, an array of fluidic channels 620 can be placed onto an array of precise silicon/ceramic v-grooves 640.

The array of precise silicon/ceramic v-grooves 640 can be enclosed within a precisely machined connector (not shown in FIG. 10B).

The precisely machined connector can be attached precisely/detached from the microelectro-mechanical-system biomodule for drawing/propagating a human body's blood/biological fluid 440.

Figure 10C:
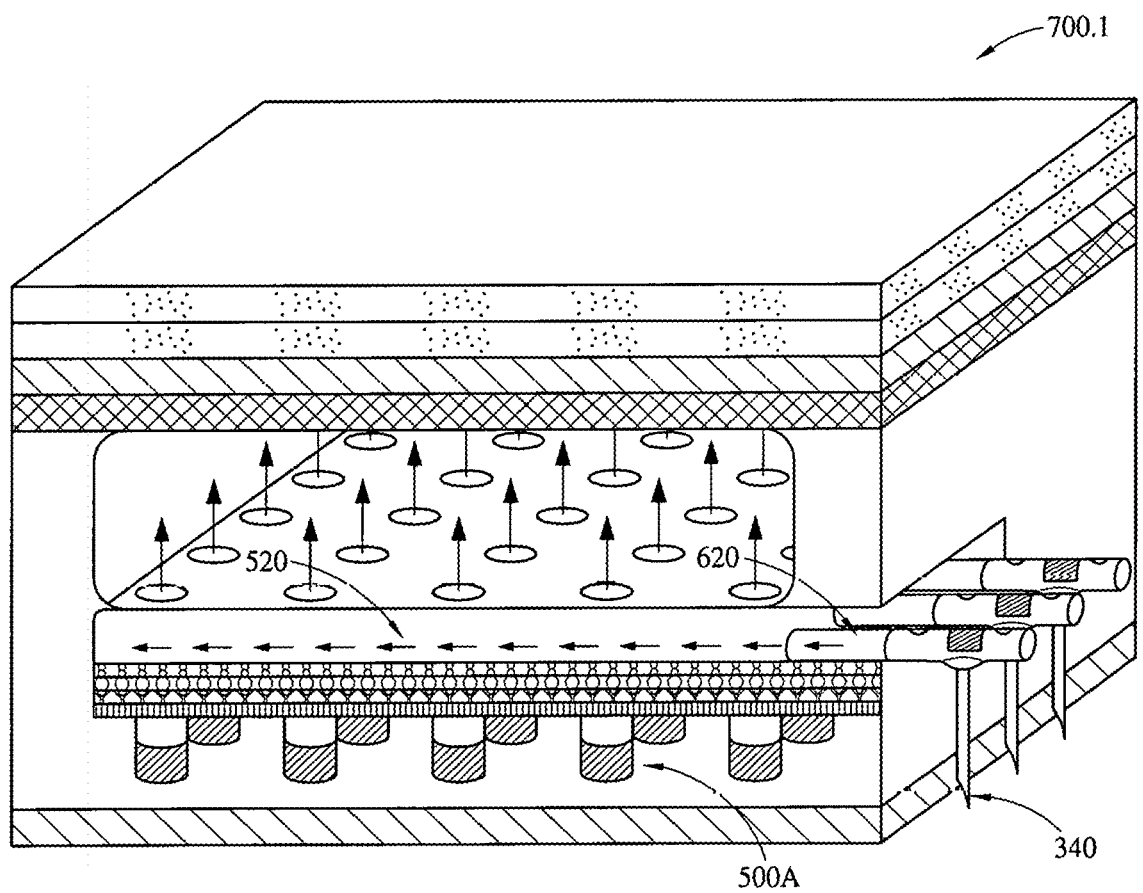

Array of Fluidic Containers Based Optical Integrated Diagnostic Biomodule for Detection of a Disease Specific Biomarker/an Array of Disease Specific Biomarkers FIG. 10C illustrates an array of fluidic containers based integrated optical diagnostic biomodule 700.1.

Stokes Shift to Detect a Disease Specific Biomarker/an Array of Disease Specific Biomarkers The Stokes Shift is the difference between the absorption wavelength and fluorescence emission wavelength.

Figure 10D:
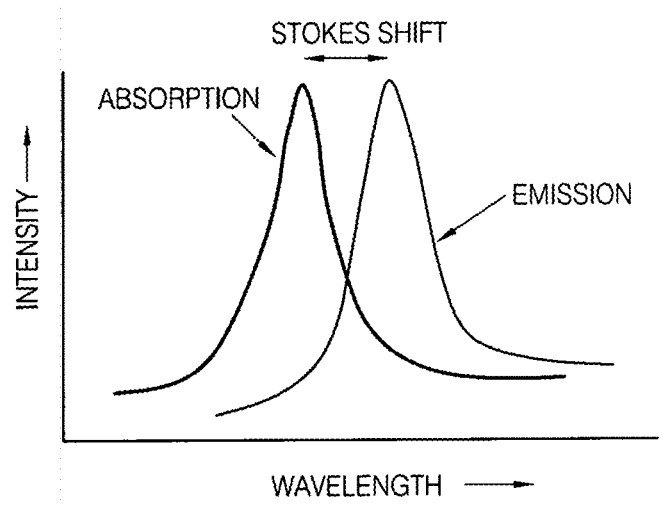

FIG. 10D illustrates the Stokes Shift due to binding of a disease specific biomarker 460 with a disease specific biomarker binder 240C.

The Stokes Shift can be utilized to detect the presence of a disease specific biomarker/an array of disease specific biomarkers.

Figure 11A:
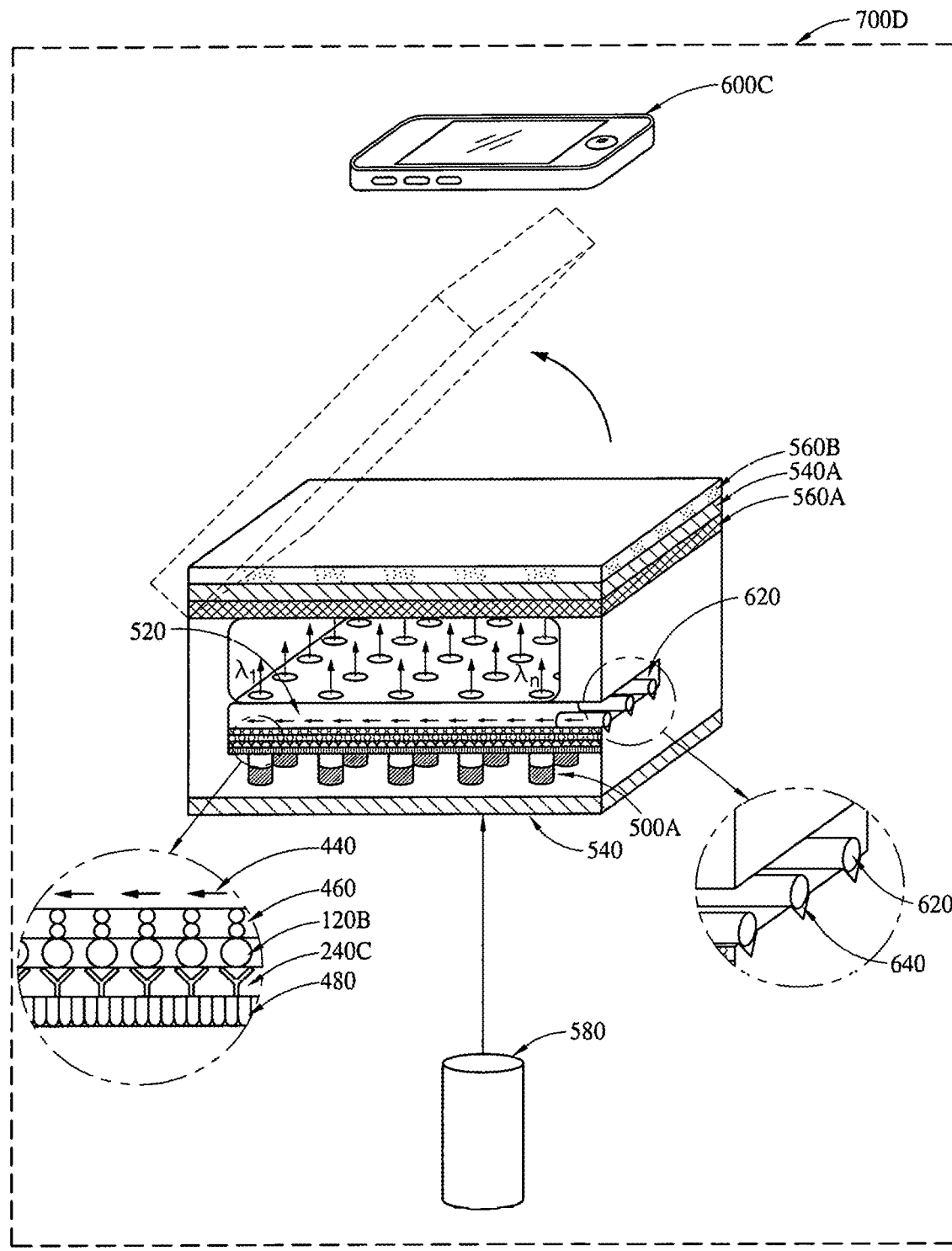
FIGS. 11A, 11B, 11C and 11D (an array of fluid containers based) illustrate integrated optical diagnostic biomodules (various other embodiments) to detect a disease specific biomarker/an array of disease specific biomarkers.
Figure 11:
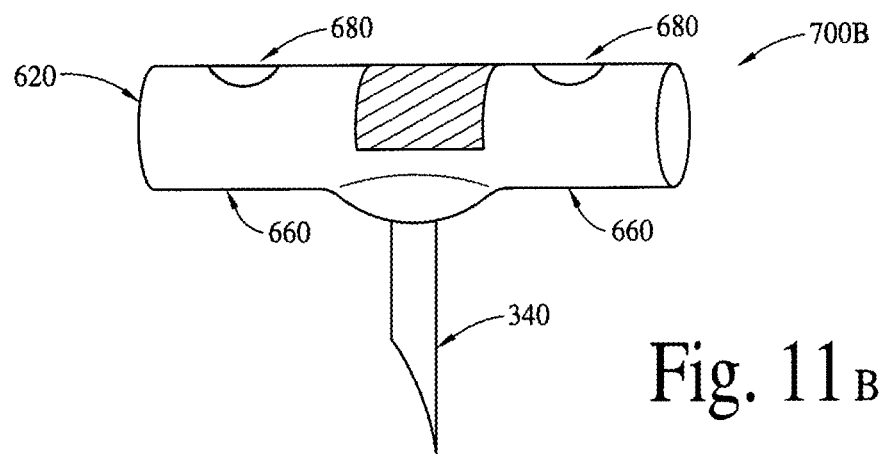
Figure 11:
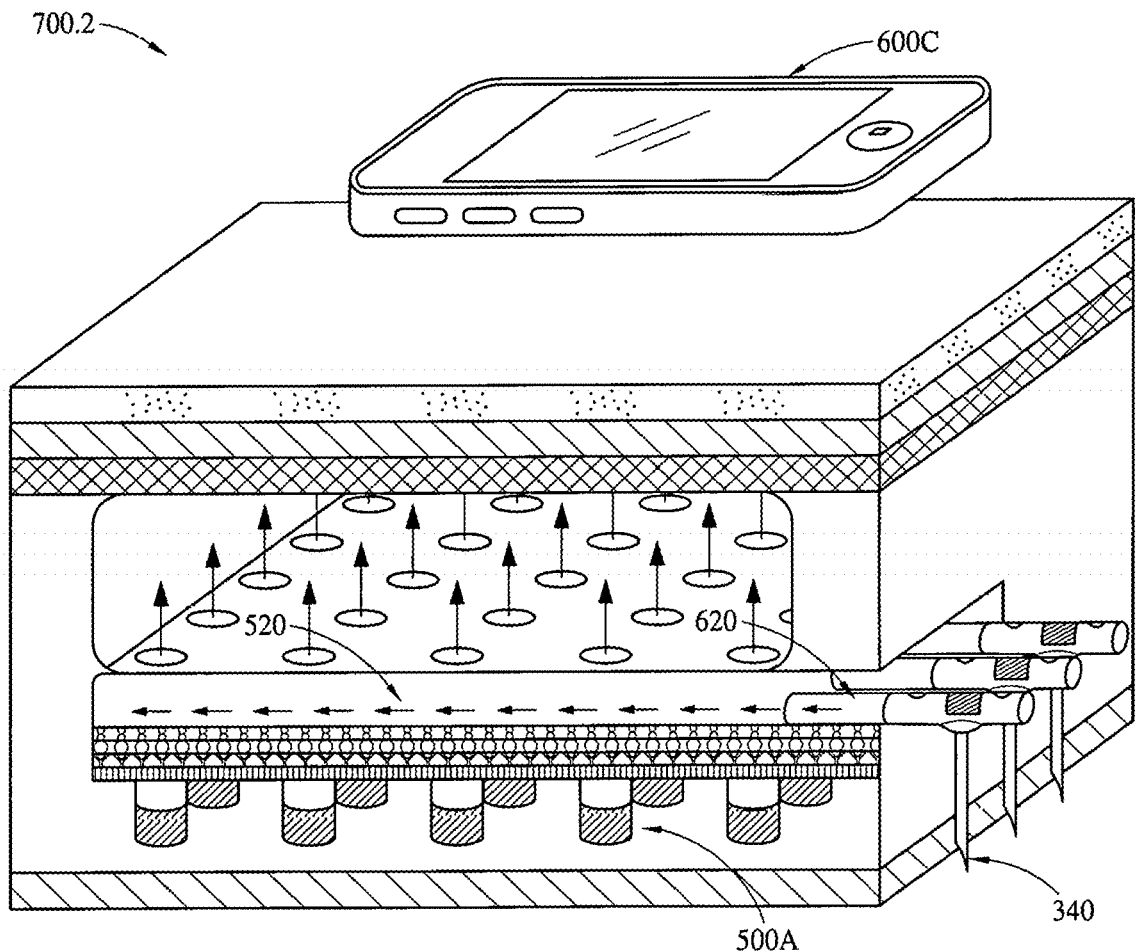

Array of Fluidic Containers Optical Diagnostic Biomodule (Configured by a Camera of A Portable Internet Appliance) for Detection of a Disease Specific Biomarker/an Array of Disease Specific Biomarkers FIG. 11A illustrates an array of fluidic containers 500A based optical diagnostic biomodule 700D, configured by a camera (optionally integrated with a color image processing algorithm) 600C of the portable internet appliance. This configuration can replace the array of light detectors 600B. The camera (of the portable internet appliance) can enable quantitative fluorescence based measurement for a real-time application, utilizing the camera as a photodetector and the portable internet appliance's microprocessor. Furthermore, A surface plasmon enhanced fluorescence microscope (detecting less than 100 fluorophores per diffraction limited spot) can be realized by utilizing the camera of the portable internet appliance and Kretschmann illumination configuration, where a linearly polarized laser beam (filtered by a linear polarizer) optically excites an ultra thin-film (e.g., 30 nanometers) coated fluidic container (e.g., a planar quartz substrate) through a glass prism at an illumination angle of about 58 degrees angle.

Furthermore, the top optical assembly can be removed to allow a direct access to fill the array of fluidic containers 500A with a human body's blood/biological fluid 440.

700D can be scaled to an array of disease specific biomarkers 460, an array of disease specific biomarker binders 240C and an array of fluorophores 120B with distinct fluorescence emission wavelengths.

Microelectro-Mechanical-System Biomodule to Draw/Propagate Blood

FIG. 11B illustrates a microelectro-mechanical-system biomodule 700B to draw blood/biological fluid 440 from a human, utilizing a microneedle 340, which can be monolithically integrated with a micromachined (voltage deflectable) membrane 660, a membrane sensor 680 and a fluidic channel 620.

The microneedle 340 can be electrically powered and programmed to draw a human's blood/biological fluid 440 at a periodic interval of time.

Furthermore, the microelectro-mechanical-system biomodule 700B can include an array of microneedles 340, an array of micromachined membranes 660, an array of membrane sensors 680 and an array of channels 620.

Furthermore, an array of fluidic containers 620 can be placed onto an array of precise silicon/ceramic v-grooves 640.

The array of precise silicon/ceramic v-grooves 640 can be enclosed within a precisely machined connector (not shown in the FIG. 11B).

The precisely machined connector can be attached precisely/detached from the microelectro-mechanical-system biomodule for drawing/propagating a human body's blood/biological fluid 440.

Array of Fluidic Containers Based Optical Integrated Diagnostic Biomodule (Configured by a Camera of a Portable Internet Appliance) for Detection of a Disease Specific Biomarker/an Array of Disease Specific Biomarkers FIG. 11C illustrates an array of fluidic containers based integrated optical diagnostic biomodule (configured by a camera of the portable internet appliance) 700.2.

Stokes Shift to Detect a Disease Specific Biomarker/an Array of Disease Specific Biomarkers The Stokes Shift is the difference between the absorption wavelength and fluorescence emission wavelength.

Figure 11D:
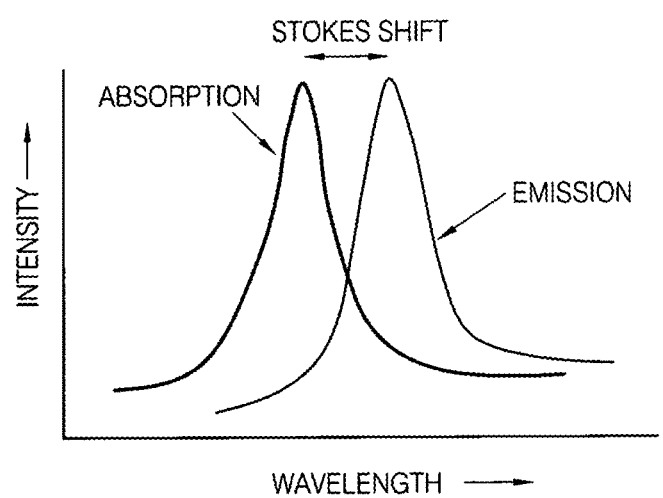

FIG. 11D illustrates the Stokes Shift due to binding of a geo biomarker 460 with a disease specific biomarker binder 240C.

The Stokes Shift can be utilized to detect the presence of a disease specific biomarker/an array of disease specific biomarkers.

Figure 12A:
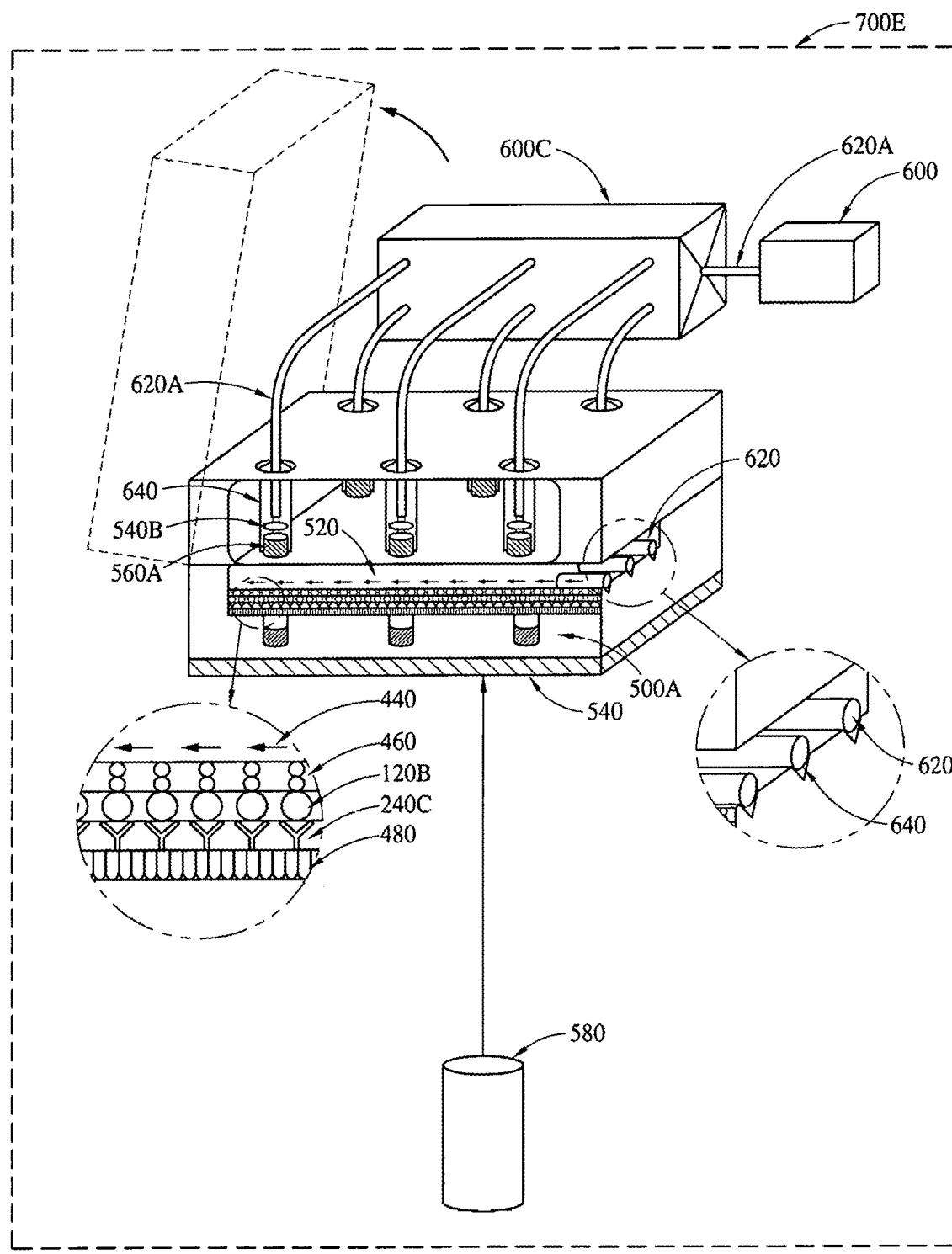
FIGS. 12A, 12B and 12C illustrate (an array of fluid containers based) illustrate integrated optical diagnostic biomodules (various other embodiments) to detect a disease specific biomarker/an array of disease specific biomarkers.

Array of Fluidic Containers Based Optical Diagnostic Biomodule (Configured by an Array of Optical Fibers & a N×1 Optical Switch) for Detection of a Disease Specific Biomarker/An Array Of Disease Specific Biomarkers FIG. 12A illustrates an array of fluidic containers 500A based optical diagnostic biomodule 700E, configured by an array of optical fibers 620A and a N×1 optical switch 600C.

FIG. 12A illustrates an array of fluidic containers based optical diagnostic biomodule 700E for detection of a disease specific biomarker (in a human body's blood/biological fluid 440, which can be propagated through a fluidic channel 620 to a fluidic cavity 520).

The disease specific biomarker 460 can chemically bind with a disease specific biomarker binder 240C, wherein the disease specific biomarker binder 240C can chemically bind with a fluorophore 120B, on an optional biomolecular interface layer 480 within the array of fluidic containers 500A.

Furthermore, the top optical assembly can be removed to allow direct access to fill the array of fluidic containers 500A with a human body's blood/biological fluid.

An incident light from a microelectro-mechanical-system enabled wavelength tunable surface emitting vertical cavity laser 580 can be collimated by a lens 540, absorbed by the fluorophore 120B.

Fluorescence emission can propagate through an array of optical filters (not to transmit the incident wavelength from the laser 580) 560A, an array of focusing lenses 540B and an array of multi-mode/single-mode optical fibers 620A to the N×1 multi-mode/single-mode optical switch 600C and a spectrophotometer 600.

Furthermore, the array of optical fibers 620A can be attached onto an array of precise silicon/ceramic v-grooves 640.

The array of optical fibers 620A can be replaced by an array of optical waveguides (not shown in FIG. 12A).

N×1 multi-mode/single-mode optical switch 600C can be replaced by an ultra-fast N×1 optical switch based on metamaterial (not shown in FIG. 12A) to detect the presence of a disease specific biomarker/an array of disease specific biomarkers rapidly.

A N×1 multi-mode/single-mode optical switch 600C can be replaced by an ultra-fast N×1 optical switch based on (Pb,La)(Zr,Ti)O$_3$ or LiNbO$_3$ waveguide, when the ultra-fast optical switch is incorporating an (a) input-output 3-dB coupler and (b) a Mach-Zehnder (MZ) modulator.

Alternatively, the N×1 multi-mode/single-mode optical switch 600C can be replaced by an ultra-fast N×1 optical switch based on vanadium dioxide. A directional coupler (e.g., silicon-on-insulator (SOI) waveguide directional coupler) with vanadium dioxide (VO$_2$) thin-film can be utilized as a fast optical switch, when the vanadium dioxide thin-film is excited by a mode locked laser (e.g., a mode locked microelectro-mechanical-system tunable vertical cavity surface emitting semiconductor laser at 1550 nanometers excitation wavelength) with an light intensity about 2 mJ/cm$^2$ to 4 mJ/cm$^2$ and a light pulse width of about 2 picoseconds to 4 picoseconds) with an integrated focusing lens to focus the excitation light beam to a spot the size of 4.5 microns by 4.5 microns. Instead of a focusing lens, curved second order gratings can be utilized for vertically coupling/focusing onto the vanadium dioxide thin-film. Furthermore, instead of a classical focusing lens, surface plasmon polariton (SPPs) based nanofocussing waveguide (as illustrated in FIG. 19O) can be utilized for vertically coupling/focusing onto the vanadium dioxide thin-film. For example, a nano-scaled waveguide (rectangular tapered to a point) of an insulating material, wherein the nano-scaled waveguide is coated/ deposited with an ultra thin-film of gold can focus a light beam onto an approximate size of 25 nanometers by 100 nanometers, due to the surface plasmon polaritons effect.

Upon excitation by the mode locked laser onto the vanadium dioxide thin-film, the vanadium dioxide thin-film undergoes a semiconductor to metal phase transition/switching and the optical properties of the directional coupler can be rapidly changed, such that the optical signal (as the input) at the upper branch of the directional coupler is shifted (as the output) to the lower branch of the directional coupler. The vanadium dioxide thin-film has an area of about 0.01 microns$^2$ to 0.16 microns$^2$ with thickness in the range of 25 nanometers to 30 nanometers. The vanadium dioxide thin-film is formed about 25 nanometers to 100 nanometers away from the straight middle section of the directional coupler. The vanadium dioxide thin-film can be fabricated by electron beam evaporation or laser assisted electron beam evaporation or RF magnetron sputtering or molecular beam epitaxy or atomic layer deposition. Alternatively, vanadium dioxide nanoparticles (with diameter in the range of 25 nanometers to 50 nanometers) can be utilized, instead of the vanadium dioxide thin-film. Furthermore, vanadium(III) oxide (V$_2$O$_3$) thin-film/nanoparticles can also be utilized, instead of the vanadium dioxide thin-film/nanoparticles respectively.

In another embodiment, a fast-optical switch-fabricated/ constructed as: integrated (a) 3-dB input-output coupler and (b) a Mach-Zehnder type device (with electrodes on vanadium dioxide/vanadium(III) oxide thin-film, in intimate proximity to two arms of Mach-Zehnder type device) can be activated electrically for a semiconductor to metal phase transition/switching, without any optical excitation.

The semiconductor to metal phase transition/switching in the vanadium dioxide/vanadium(III) oxide can be realized below 0.2 picoseconds time, under optical excitation or electrical activation. Thus, the silicon-on-insulator vanadium dioxide/vanadium(III) oxide silicon photonics platform can enable a new class of ultrafast silicon photonic devices (e.g., optical limiters, optical logic gates and optical memories).

With the combination of an electrical activation (preferably voltage) and an optical excitation to the vanadium dioxide/vanadium(III) oxide thin-film, a high density optical memory can be realized, wherein optical excitation is based on an array of vertically aligned nanolasers and surface plasmon polaritons nanofocusing lens. Alternatively, vanadium dioxide/vanadium(III) oxide nanoparticles (about 50 nanometers in diameter) deposited on an array of nanowires lasers/light emitting diodes can be utilized. For example, vanadium dioxide/vanadium(III) oxide nanoparticles deposited on an array of gallium nitride nanowires light emitting diodes can be utilized. Furthermore, gallium nitride nanowires light emitting diodes can be electrically powered by zinc oxide nanowires. Complementary metal-oxide semiconductor processing element can be integrated with zinc oxide nanowires nanogenerator/nanobattery. However, any material with both semiconducting and piezoelectric properties can replace gallium nitride-zinc oxide combination.

Faster optical switching time can be obtained by scaling/ segmenting vanadium dioxide thin-film to a smaller area and/or by optical activation (e.g., ultrashort pulse laser activation) rather than an electrical activation. Other chemical compositions of vanadium oxide and doped compositions of vanadium oxide can be utilized to enable a higher performance optical switch.

Various permutations and combinations of graphene/graphene quantum dots with vanadium oxide/vanadium oxide quantum dots can be utilized to enable even higher performance optical switch. The process of fabricating/constructing graphene layer consists of dispersing a graphene oxide (GO) solution in a micropipette, depositing the solution locally and then reducing the graphene oxide to graphene by thermal or chemical treatment.

Furthermore, a particular phase change material-Ag$_4$In$_3$Sb$_{67}$Te$_{26}$ can switch between a disordered amorphous phase A and another disordered amorphous phase B in a sub-picosecond time-scale, when excited by picosecond electrical pulses (e.g., about 500 kV/cm peak field strength at a repetition rate of about 30 Hz for about 30 seconds). Such phase change switching occurs at lower electric field strength/energy level and can enable an ultra-high speed optical switch (as switching from the disordered amorphous phase B to the disordered amorphous phase A back requires an application of a short burst of heat, which can be provided electrically/optically).

Following permutations and combinations of graphene/ graphene quantum dots with Ag$_4$In$_3$SboTe$_{26}$/ Ag$_4$In$_3$Sb$_{67}$Te$_{26}$ thin-film/quantum dots can be utilized to enable even a higher performance optical switch.

The optical switch can be integrated with a log 2N demultiplexer, which generally integrates rectangular shaped periodic frequency filters in series, wherein the rectangular shaped periodic frequency filters can be formed in one dimensional photonic crystal on a ridge waveguide.

Flip-chip bonding packaging was developed as an alternative to wire-bonding. In flip-chip bonding, components are flipped upside-down and placed on an array of solder bumps that form the connection between circuitry and package. The optical switch can be packaged, utilizing flip-chip bonding on a precise silicon optical bench substrate.

Fiber can be aligned passively with precise metal alignment pins seated into v-grooves on the precise silicon optical bench substrate. The precise metal alignment pins are mated with a pluggable optical fiber connector integrated with a molded plastic lens.

In another embodiment, an ultra-fast N×1 optical switch based on metamaterial can be fabricated/constructed, utilizing an array of nanostructured elements, wherein each nanostructured element can be actuated by electrostatic forces on pairs of parallel flexible strings of nanoscale membrane. Electrically reconfigurable metamaterial element changes the transmission and reflection spectra of the metamaterial.

In another embodiment, an ultra-fast N×1 Bose-Einstein condensate based optical switch can be realized, utilizing an array of single-mode/multi-mode waveguides on the left-hand side and a single-mode/multi-mode waveguide on the right-hand side, wherein both the array of single-mode/multi-mode waveguides on the left-hand side and the single-mode/multi-mode waveguide on the right-hand side are optically coupled with polariton Bose-Einstein condensate.

Short-lived room temperature polariton Bose-Einstein condensate can be created through interaction of a laser light (bouncing back and forth within multiple dielectric thin-films) and a luminescent polymeric thin-film of about 30 nanometers in thickness. The luminescent polymeric thin-film is embedded within multiple dielectric thin-films, wherein the multiple dielectric thin-films is then illuminated from the bottom (of the multiple dielectric thin-films, each dielectric thin-film is about 40 nanometers in thickness) by a vertical surface emitting laser or an in-plane laser integrated with a suitable 45-degrees angle mirror and a focusing lens.

Furthermore, an ultra-fast N×N Bose-Einstein condensate based optical switch can be realized, by utilizing an array of single-mode/multi-mode waveguides on the right-hand side instead of just one single-mode/multi-mode waveguide on the right-hand side.

700E can be scaled to an array of disease specific biomarkers 460, an array of disease specific biomarker binders 240C and an array of fluorophores 120B with distinct fluorescence emission wavelengths.

Microelectro-Mechanical-System Biomodule to Draw/Propagate Blood

Figure 12B:
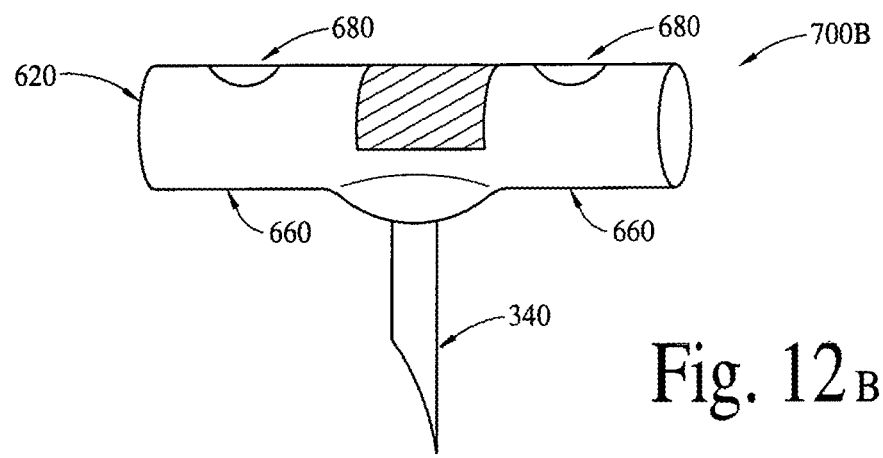

FIG. 12B illustrates a microelectro-mechanical-system biomodule 700B to draw blood/biological fluid 440 from a human, utilizing the microneedle 340, which can be monolithically integrated with a micromachined (voltage deflectable) membrane 660, a membrane sensor 680 and a fluidic channel 620.

A microneedle 340 can be electrically powered and programmed to draw a human's blood/biological fluid 440 at a periodic interval of time.

Furthermore, the microelectro-mechanical-system biomodule 700B can include an array of microneedles 340, an array of micromachined membranes 660, an array of membrane sensors 680 and an array of fluidic channels 620.

Furthermore, an array of fluidic channels 620 can be placed onto an array of precise silicon/ceramic v-grooves 640.

The array of precise silicon/ceramic v-grooves 640 can be enclosed within a precisely machined connector (not shown in the FIG. 12B).

The precisely machined connector can be attached precisely/detached from the microelectro-mechanical-system biomodule for drawing/propagating a human body's blood/biological fluid 440.

Light Incident at Side of an Array of Fluidic Containers

In FIGS. 10A, 11A and 12A light from the microelectro-mechanical-system enabled wavelength tunable surface emitting vertical cavity laser 580 can be incident at the side of the array of fluidic containers 500A.

Light Source Integrated with a Plasmonic Optical Nanoantenna

A plasmonic optical nanoantenna may incorporate two triangular shaped gold configurations, wherein each triangular shaped gold configuration is about 75 nanometers long and facing directly across from each other in the shape of a miniature bowtie.

The plasmonic optical nanoantenna can squeeze an incident light from the microelectro-mechanical-system enabled wavelength tunable surface emitting vertical cavity laser 580 into 25 nanometers or less gap, separating the two gold triangular configurations—thus resulting in an intense (about thousand times more intense than the light from the microelectro-mechanical-system enabled wavelength tunable surface emitting vertical cavity laser 580) speck of light.

Nanolaser, as a Light Source

For miniaturization, in conjunction with an array of nano-scaled fluidic containers, a nanolaser/an array of nanolasers can be utilized, instead of a microelectro-mechanical-system enabled wavelength tunable surface emitting vertical cavity laser/an array of microelectro-mechanical-system enabled wavelength tunable surface emitting vertical cavity lasers 580.

By way of an example and not by way of any limitation, the structure of a metal-insulator-semiconductor-insulator-metal (MISIM) semiconductor nanolaser (operating at room temperature) with a rectangular cross-section cavity can consist of a metal organic chemical vapor deposited (MOCVD) rectangular pillar of InP/InGaAs/InP protected on all four sides of the rectangular pillar with a thin silicon nitride insulating layer.

The InP/InGaAs/InP layer stack can form a waveguide, largely confining the optical field in a vertical direction. The above rectangular pillar is then encapsulated in silver metal from all four sides as well as from the top forming a rectangular cavity in horizontal directions.

The n-contact is silver metal and the p-side contact is connected to an external electric source via p-type InGaAsP contact layer underneath the rectangular pillar.

Focusing Light onto a Nanosized Spot

A nano-scaled waveguide (rectangular tapered to a point) of an insulating material, wherein the nano-scaled waveguide is coated/deposited with an ultra thin-film of gold can focus a light beam onto an approximate size of 25 nanometers by 100 nanometers, due to the surface plasmon polaritons effect.

Fluorescent or Raman signal light can also propagate in a reverse direction from the point of the nano-scaled tapered device for further analysis.

Light Source Coupled with an Array of Micromirrors

A programmable microelectro-mechanical-system mirror chip can be utilized to divert light of varying wavelengths of the incident light from a microelectro-mechanical-system enabled wavelength tunable surface emitting vertical cavity laser 580 at ultra-high speed and with micrometer-accuracy to the bottom of each fluidic container (for example in FIG. 12A) from a single light source—thus it will eliminate the need for an array of microelectro-mechanical-system enabled wavelength tunable surface emitting vertical cavity lasers 580.

A programmable microelectro-mechanical-system mirror chip may consist of a large array of individual miniature micromirrors which can each be tilted separately and virtually in a continuous way. By controlling the deflection of all mirrors to distribute the angle of incidence and the intensity of the light with up to 1,000 changes per second over the entire area can be realized.

This particular configuration can enable one to analyze one fluid container at a time—thus reducing any optical cross-talk.

Figure 12C:
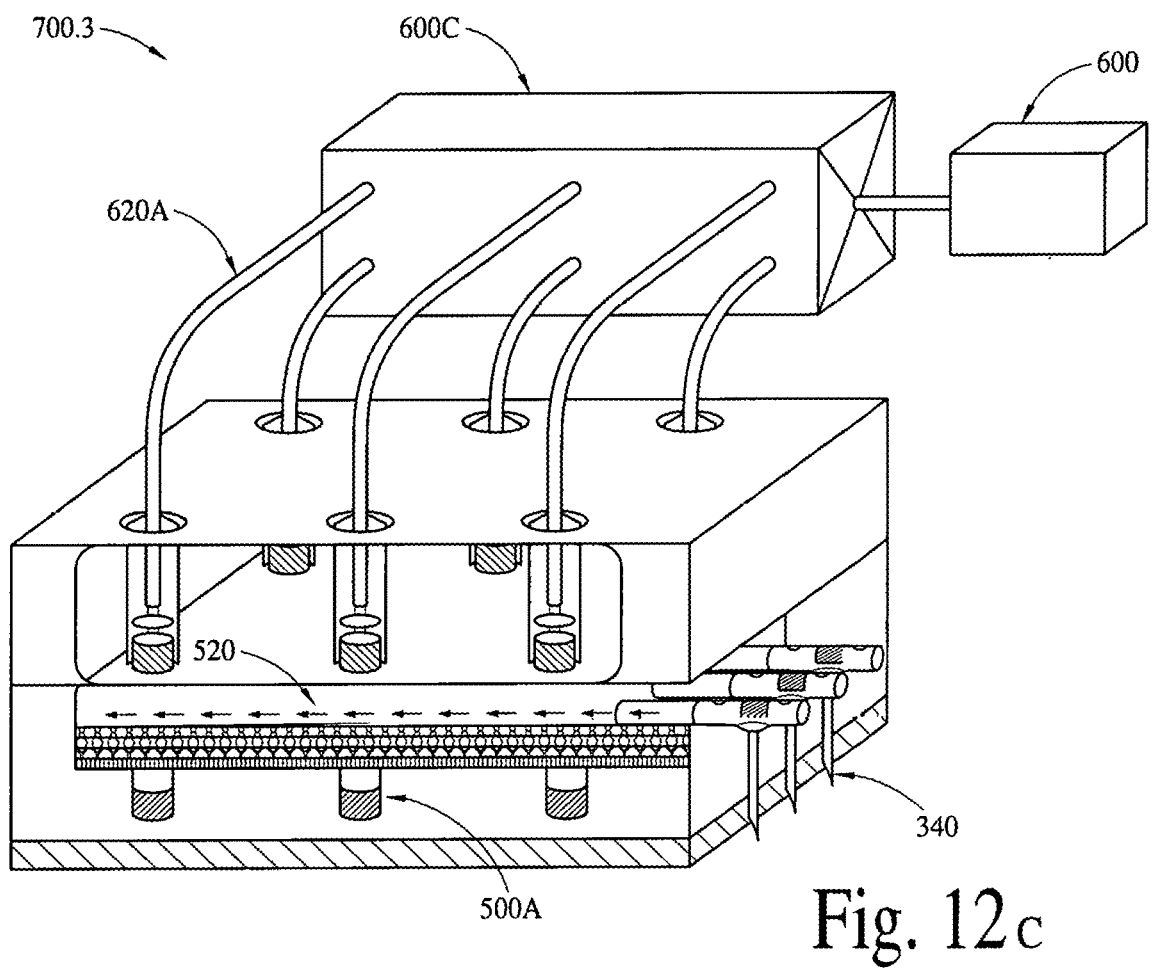

Array of Fluidic Containers Based Optical Integrated Diagnostic Biomodule (Configured by an Array of Optical Fibers & a N×1 Optical Switch) for Detection of a Disease Specific Biomarker/an Array of Disease Specific Biomarkers FIG. 12C illustrates an array of fluidic containers based integrated optical diagnostic biomodule 700.3 (configured by an array of optical fibers 620A and a N×1 optical switch 600C).

Array of Fluidic Containers Based Optical Integrated Diagnostic Biomodule (Configured by an Array of Optical Fibers, a N×1 Optical Switch & Multiplexing of Biomarker Binders) for Detection of a Disease Specific Biomarker/an Array of Disease Specific Biomarkers FIG. 12D illustrates an array of specialized fluidic containers 500A$_1$, containing a human body's blood/biological fluid 440 with an array of disease specific biomarkers 460.

500A$_2$ is an enclosure for the array of specialized fluidic containers 500A$_1$. 500A$_3$ is an array of microsized/nanosized mesh tubes. 500A$_4$ is a removable holder.

The array of microsized/nanosized mesh tubes 500A$_3$ can contain a biomarker binder assembly 240C$_1$ and biomarker binder assembly 240C$_2$.

Figure 12E:
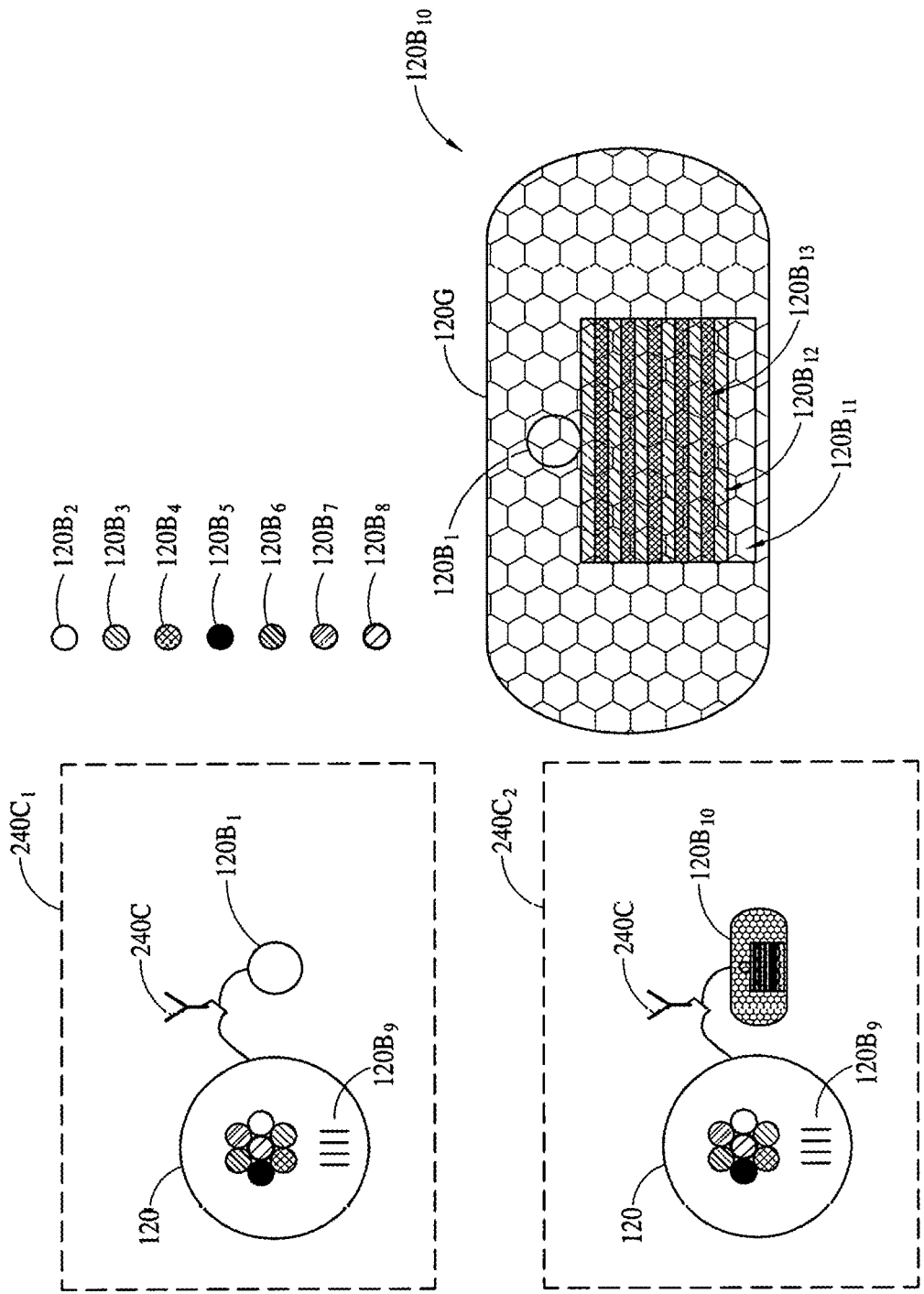

FIG. 12E illustrates the biomarker binder assembly 240C$_1$. 240C$_1$ can integrate the biomarker binder 240C, nanoshell 120 and fluorophore 120B$_1$.

The nanoshell 120 can have printed (by electroplating/laser induced direct printing/soft lithography) metal barcode patterns of alternating reflective gold/silver/nickel/platinum metal 120B$_9$ on it.

The stripe width of the metal barcode patterns can be controlled by the amount of current passed during the electroplating process.

The nanoshell 120 can also encapsulate/cage about six (6) quantum dot fluorophores 120B$_2$, 120B$_3$, 120B$_4$, 120B$_5$, 120B$_6$ and 120B$_7$, wherein each quantum dot fluorophore has a unique fluorescence color based on the diameter of the quantum dot fluorophore.

Furthermore, the intensity of each fluorophore's unique florescence emission colors can be varied.

The nanoshell 120 can also encapsulate/cage a paramagnetic nanoparticle (e.g., an iron oxide nanoparticle ($Fe_3O_4$)) 120B$_8$.

FIG. 12E also illustrates the biomarker binder assembly 240C$_2$. 240C$_2$ can integrate the biomarker binder 240C, nanoshell 120 and nanotube assembly 120B$_{11}$.

The nanotube assembly 120B$_{11}$ can consist of a nanotube (e.g., a boron nitride/carbon nanotube or a tubular structure fabricated/constructed, utilizing DNA/RNA origami process) 120G. The nanotube 120G can encapsulate/cage at least one quantum dot fluorophore 120B$_1$ on alternating thin-films of titanium dioxide dielectric (about 15-30 nanometers in thickness) 120B$_{12}$ and metal silver 120B$_{13}$ (about 5-10 nanometers in thickness) on a biochemically functional glass/plastic substrate 120B$_{11}$.

Figure 12F:
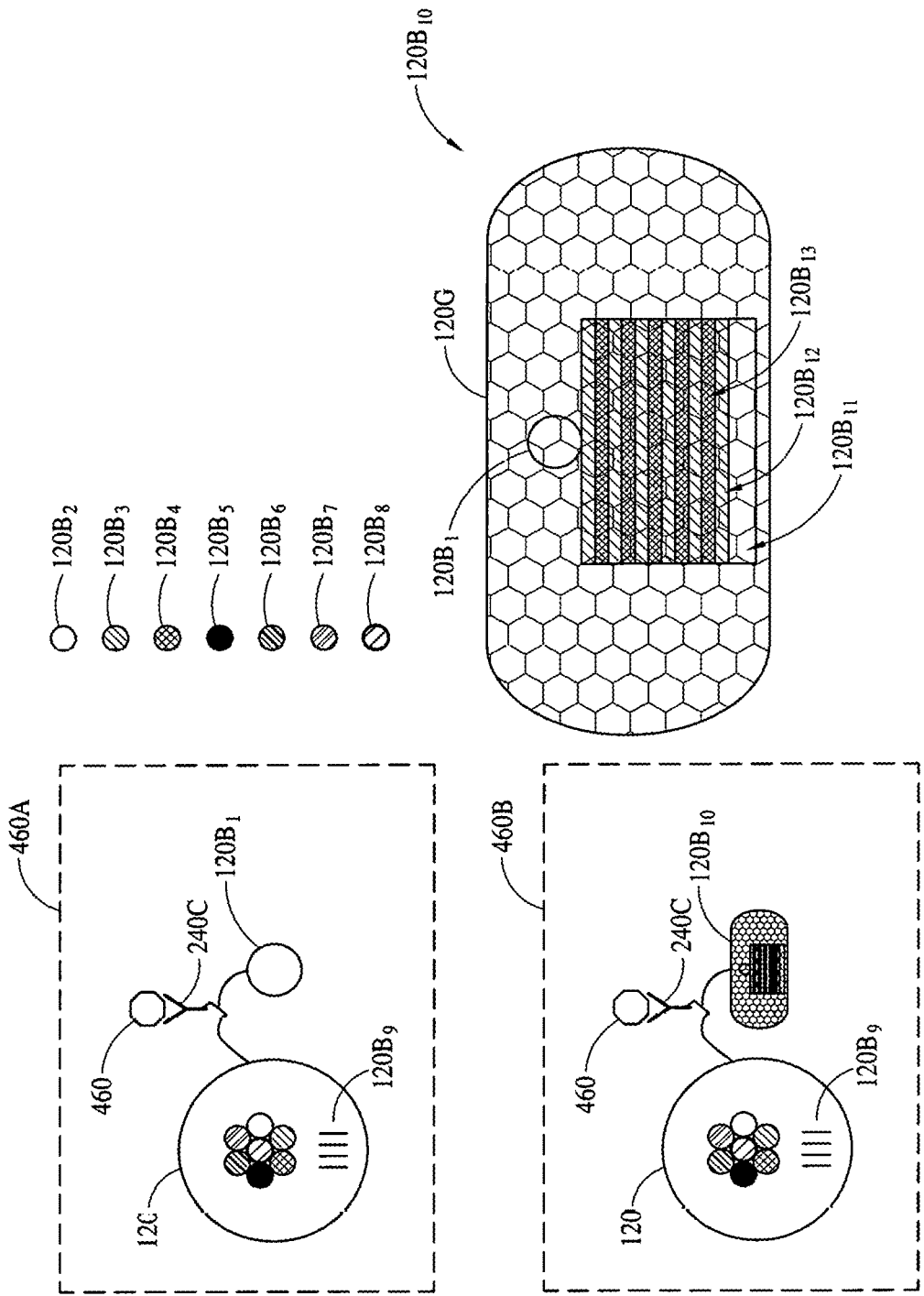

FIG. 12F illustrates the biomarker binder assembly 240C$_1$, chemically bonded with a biomarker 460 and an entire biomarker binder assembly-biomarker combination is represented as 460A.

FIG. 12F illustrates the biomarker binder assembly 240C$_2$, chemically bonded with a biomarker 460 and an entire biomarker binder assembly-biomarker combination is represented as 460B.

Figure 12G:
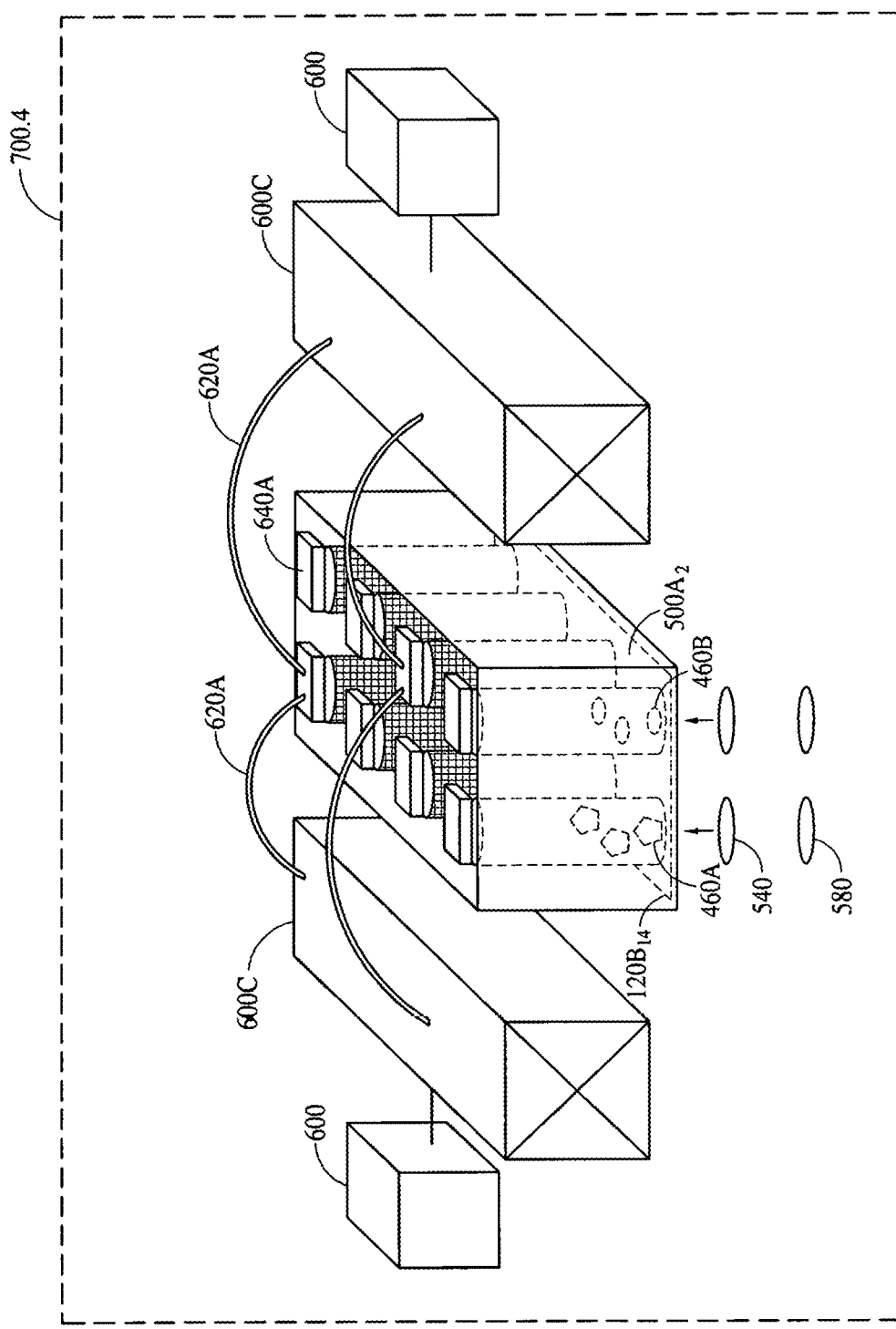

FIG. 12G illustrates an optical diagnostic biomodule 700.4 to determine fluorescence of 460A and 460B upon being magnetically pulled down by an optically transparent magnetic substrate 120 B$_{14}$ and then excited by an array of microelectro-mechanical-system enabled wavelength tunable surface emitting vertical cavity lasers 580 and collimated by an array of lenses 540.

An assembly 640A integrates suitable optical filters, suitable lenses and two (2) optical fibers 620A on precise silicon/ceramic v-grooves.

At one instance, utilizing wavelength $\lambda=\lambda_1$ from the microelectro-mechanical-system enabled wavelength tunable surface emitting vertical cavity laser 580, transmission of wavelength $\lambda=\lambda_1$ through a metal barcode pattern, further propagated through a suitable optical filter, suitable lens and optical fiber 620A is then multiplexed by the N×1 multimode/single-mode optical switch 600C and analyzed by the spectrophotometer 600.

Any suitable image processing software can be utilized to resolve any misorientated metal barcode pattern.

At another instance, utilizing wavelength $\lambda=\lambda_2$ from the microelectro-mechanical-system enabled wavelength tunable surface emitting vertical cavity laser 580, a fluorescence spectrum of the entire biomarker binder assembly-biomarker combination 460A/460B, is propagated through a suitable optical filter, suitable lens and optical fiber 620A, then multiplexed by the N×1 multi-mode/single-mode optical switch 600C and analyzed by the spectrophotometer 600.

The array of optical fibers 620A can be replaced by an array of optical waveguides (not shown in FIG. 12G).

Furthermore, an array of optical waveguides and lenses can be integrated (by a monolithic and/or a hybrid process) on silica on silicon substrate.

One million optical barcodes can be realized, utilizing six (6) unique fluorescent emission colors and ten (10) intensity levels for each unique fluorescent emission color.

Furthermore, one million optical barcodes can be also enhanced in conjunction with reflective metal barcode patterns. The reflective metal barcode patterns indicate a digital barcode.

Up to 2 million or more disease specific biomarkers 460 per specialized fluidic container 500A$_1$ (or generally referred as, the array of fluidic containers) can be identified, utilizing a combination of optical barcode multiplexing and metal barcode multiplexing. Data from 2 million or more disease specific biomarkers 460 can be a large dataset—Big Data. Analysis of Big Data is described in later paragraphs.

For example, considering 19,599 genes in a human body can, in turn produce about 200,000 types of RNA. Each RNA strand can encode up to 200,000 proteins-resulting in 40 billion proteins in a human body. Furthermore, there are millions of patients worldwide—thus mathematical/statistical analysis tools of the Big Data are needed (which are discussed in later paragraphs).

Three-Dimensional Protruded Optical Nanoantenna on a Horizontal Plane/Substrate

FIGS. 12H-12O illustrate eight distinct embodiments (examples) of a three-dimensional protruded optical nanoantenna. FIG. 12H illustrates a three-dimensional protruded optical nanoantenna incorporating a nano-scaled star. FIG. 12I illustrates a three-dimensional protruded optical nanoantenna incorporating two nano-scaled triangles facing each other. 12J illustrates a three-dimensional protruded optical nanoantenna incorporating two nano-scaled rods facing each other. FIG. 12K illustrates a three-dimensional protruded optical nanoantenna incorporating a nano-scaled triangle. FIG. 12L illustrates a three-dimensional protruded optical nanoantenna incorporating two nano-scaled spheres facing each other. FIG. 12M illustrates a three-dimensional protruded optical nanoantenna incorporating two nano-scaled v-shapes facing each other. FIG. 12N illustrates a three-dimensional protruded optical nanoantenna incorporating two nano-scaled complex shapes facing each other. FIG. 12N illustrates a three-dimensional protruded optical nanoantenna incorporating two nano-scaled squares with sharp tips facing each other. By way of an example and not by way of any limitation, a three-dimensional protruded optical nanoantenna should not be confined to the above eight distinct embodiments (examples). A three-dimensional protruded optical nanoantenna can be fabricated/constructed in thin-film metal (e.g., aluminum/gold/silver) or thin-film metal nitride. Furthermore, the thin-film metal can be poly-crystalline or single crystalline in structure. A three-dimensional protruded optical nanoantenna fabricated/constructed in single crystalline thin-film metal may give rise to higher performance three-dimensional protruded optical nanoantenna.

For example, thin-film gold may be a good choice for an optical excitation in red wavelength region and thin-film silver may be a good choice for an optical excitation in blue-green wavelength region. Thus, a specific choice of material of a three-dimensional protruded optical nanoantenna can depend on an optical excitation wavelength.

A three-dimensional protruded optical nanoantenna in thin-film metal/metal nitride can be coated with a monolayer of a two-dimensional material (e.g., graphene/graphene oxide/boron nitride (BN)).

Alternatively, a three-dimensional protruded optical nanoantenna can be fabricated/constructed on a monolayer of a two-dimensional material (e.g., graphene/graphene oxide/boron nitride) or transition metal dichalcogenide (e.g., tungsten disulfide ($WS_2$))/carbon 60/conducting nanotube (e.g., carbon nanotube).

It should be noted that non-essential areas of above monolayer beyond the three-dimensional protruded optical nanoantenna may be etched off to eliminate electrical shorting.

A three-dimensional protruded optical nanoantenna is less than 250 nanometers in maximum dimension and the gap of a three-dimensional protruded optical nanoantenna (as illustrated in FIGS. 12I, 12J, 12L, 12M, 12N and 12O) can be at 25 nanometers or less than 25 nanometers.

It should be noted that a higher performance three-dimensional protruded optical nanoantenna can be realized, if the gap of a three-dimensional protruded optical nanoantenna (as illustrated in FIGS. 12I, 12J, 12L, 12M, 12N and 12O) is less than 25 nanometers and/or the height of a three-dimensional protruded optical nanoantenna (as illustrated in FIGS. 12I, 12J, 12L, 12M, 12N and 12O) can be increased (e.g., 30 nanometers) with respect to a substrate (e.g., a quartz substrate) by etching into the substrate.

Furthermore, three-dimensional protruded optical nanoantennas can be also embedded with a supported phospholipid membrane (phospholipid membrane is fluid at room temperature). This can enable mobile molecules of interest within the bilayer membrane to enter the hot-spot regions of the three-dimensional protruded optical nanoantennas via diffusion.

Nano-Scaled Lithography

Helium ion beam lithography (HIBL) on hydrogen-silesquioxane (HSQ) resist can be utilized to create a nanoimprinting lithography (NIL) template. Then, followed by development of hydrogen-silesquioxane resist and surface treatment of anti-sticking layer on hydrogen-silesquioxane. The nanoimprinting lithography template (anti-sticking surface treated hydrogen-silesquioxane resist) can be utilized to nanoimprint a dimension in an ultra violet wavelength (UV) curable nanoimprinting resist at 25 nanometers or less than 25 nanometers. These steps are illustrated in FIG. 12P1.

FIG. 12P2 illustrates an alternative method to fabricate a dimension at 25 nanometers or less than 25 nanometers, wherein the etched pattern is subjected to ion (e.g., helium ion) bombardment. Such ion bombardment can cause the gaps within the etched pattern to shrink laterally and the reduced gaps within the etched pattern can now be utilized as a mask to fabricate a dimension at 25 nanometers or less than 25 nanometers.

FIG. 12P3 illustrates another alternative method to fabricate a dimension at 25 nanometers or less than 25 nanometers, wherein gold (Au) thin-film and a cover metal thin-film are patterned by a first electron beam (e-beam) lithography and liftoff, followed by reflow/oxidation of the cover metal thin-film (e.g., titanium (Ti)/chromium (Cr)) and a second electron beam lithography and liftoff of gold (Au) thin-film. Further wet etching/removal of the cover metal thin-film can be utilized to fabricate a dimension at 25 nanometers or less than 25 nanometers.

Additionally, utilizing an ultra thin (e.g., 10 nanometers thick) single layer hydrogen-silesquioxane as an electron beam negative resist or double layers of hydrogen-silesquioxane negative resist/polymethyl methacrylate (PMMA) positive resist (on a substrate) a dimension at 25 nanometers or less than 25 nanometers can be fabricated by electron beam lithography.

ZEP, an electron beam positive resist and calixarene, as an electron beam negative resist can be utilized to fabricate a dimension at 25 nanometers or less than 25 nanometers.

For reducing electron charging due to non-conducting substrate, an ultra thin-layer of conducting polymer or about 30 nanometers of gold can be deposited on the above electron beam resist.

Positioning Fluorophore (Coupled with a Biomarker Binder) at a Defined Spot on a Horizontal Plane/Substrate To significantly enhance the fluorescence signal from the array of fluidic containers/zero-mode waveguides, it may be necessary to position the fluorophore (coupled with a biomarker binder) at a specified spot with respect to a substrate.

FIG. 12Q1 illustrates a configuration method 1 to position a fluorophore (coupled with a biomarker binder) on a defined spot of a substrate, wherein the defined spot of such a substrate is defined by an opening of an electron beam resist. The defined spot is a biotinylated surface. For example, a biomarker binder A (e.g., an antibody) can be streptavidin labeled. The streptavidin labeled biomarker binder A can be attached to the biotinylated defined spot of such a substrate. In a sandwich structure, a second biomarker binder B with a fluorophore can be utilized to attach with a biomarker (e.g., antigen).

FIG. 12Q2 illustrates a configuration method 2 to position a fluorophore (coupled with a biomarker binder) on a defined spot of a substrate, wherein the defined spot of such a substrate is defined by an opening of an electron beam resist. The spot is functionalized with primary amines, using an aminosilane regent and then reacted to create a maleimaide activated surface for attracting with sulfhydryl groups of the modified biomarker binder A. In a sandwich structure, a second biomarker binder B with a fluorophore can be utilized to attach with a biomarker.

FIG. 12Q3 illustrates a configuration method 3 to position a fluorophore (coupled with a biomarker binder) on a defined spot of a substrate, wherein the defined spot of such a substrate is defined by an opening of an electron beam resist. The spot is functionalized with a molecule α, as shown below:

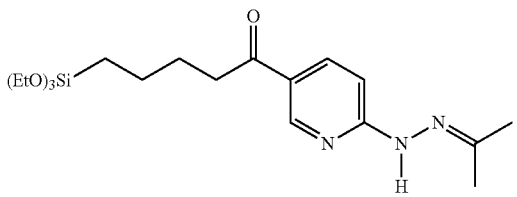

Then the biomarker binder A is attached with a molecule β, as shown below:

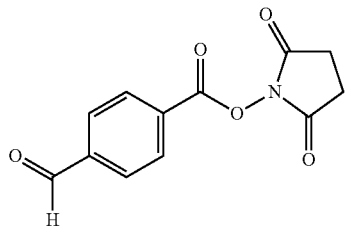 [SMILES: O=Cc1ccc(C(=O)ON2C(=O)CCC2=O)cc1]

In a sandwich structure, a second biomarker binder B with a fluorophore can be utilized to attach with a biomarker. Alternatively, the molecule β chemically coupled with (3-aminopropyl)triethoxysilane molecule to conjugate on the substrate and a molecule, as shown below

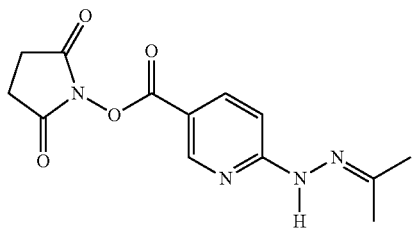 [SMILES: CC(C)=NNc1ccc(C(=O)ON2C(=O)CCC2=O)cn1]

can be chemically coupled with the biomarker binder A and this rearrangement may be necessary for process compatibility with electron beam lithography.

FIG. 12Q4 illustrates a configuration method 4 to position a fluorophore (coupled with a biomarker binder) on a defined spot of a substrate, wherein the defined spot of such a substrate is defined by an opening of an electron beam resist. The spot of the substrate is functionalized with a DNA/RNA origami surface, which has a diameter of about 100 nanometers. A single DNA/RNA strand on a DNA/RNA origami surface can be chemically coupled with a biomarker binder A via a complementary single DNA/RNA strand on the biomarker binder A. The fabrication/construction will be a surface treatment (e.g., by oxygen plasma and/or HMDS treatment), followed by electron beam lithography placement of DNA/RNA origami surface, which can couple with biomarker binder A.

Alternatively, a DNA/RNA origami surface can be chemically coupled with functional (chemical) binding sites (e.g., with maleimide) for a biomarker binder A.

Furthermore, stability of the above DNA/RNA origami surface can be increased if the DNA/RNA origami surface is dry or in a solution containing 5 millimolar concentration of magnesium ions (from $MgCl_2$) or 500 millimolar concentration of sodium ions (from $NaCl_2$).

FIG. 12Q5 illustrates a configuration method 5 to position a fluorophore (coupled with a biomarker binder) on a defined spot of a substrate, wherein the defined spot of such a substrate is defined by an opening of an electron beam resist. Configuration method 5 is similar to configuration 4 (as illustrated in FIG. 12Q4), except the above DNA/RNA origami surface can be chemically coupled by two opposing conducting nanotubes (e.g., single-walled/multi-walled carbon nanotubes or boron nitride nanotubes).

Additionally, above two opposing conducting nanotubes can be replaced by two opposing carbon nanospheres or two opposing metal (e.g., aluminum/gold/silver) nanoparticles or two opposing metal nanorods.

FIG. 12Q6 a configuration method 6 to position a fluorophore (coupled with a biomarker binder) on a defined spot of a substrate, wherein the defined spot of such a substrate is defined by an opening of an electron beam resist. The spot of the substrate is functionalized with a single DNA/RNA strand, which can be chemically coupled with a biomarker binder A via a complementary single DNA/RNA strand on the biomarker binder A.

Furthermore, about 1 wt % to 2 wt % DNA with CH3(CH2)15N(CH3)3.Cl (hexadecyltrimethylammonium chloride) in butanol solution can be utilized as a direct electron beam lithography resist with functional (chemical) binding sites (e.g., with maleimide) for a biomarker binder A.

In many cases, there can be an electrically isolated metalized spot/nano-scaled spot instead of a spot of a substrate, wherein the electrically isolated metalized spot/nano-scaled spot is defined by an opening of an electron beam resist. The electrically isolated metalized spot/nano-scaled spot can be functionalized with self-assembled monolayers of 11-mercaptoundecanoic acid, which can be chemically coupled with a biomarker binder A.

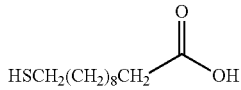

In many cases, there can be a spot/nano-scaled spot of titanium dioxide instead of a spot of a substrate, wherein the spot/nano-scaled spot of titanium dioxide is defined by an opening of an electron beam resist. The spot/nano-scaled spot of titanium dioxide can be functionalized with monolayers of alkane phosphates, which can be chemically coupled with a biomarker binder A. In a sandwich structure, a second biomarker binder B with a fluorophore can be utilized to attach with a biomarker (e.g., antigen).

Alternatively, there can be a spot/nano-scaled spot of a substrate, wherein other areas can be covered by silicon nitride—thus reducing the need for two-step electron beam lithography. Alternatively, there can be a spot/nano-scaled spot of aluminum oxide instead of a spot/nano-scaled spot of a substrate, wherein the spot/nano-scaled spot of aluminum oxide is defined by an opening of an electron beam resist. The spot/nano-scaled spot of aluminum oxide can be functionalized by monolayers of phosph(on)ate, which can be chemically coupled with a biomarker binder A. In a sandwich structure, a second biomarker binder B with a fluorophore can be utilized to attach with a biomarker (e.g., antigen).

A substrate surface coated with about 10 nanometers thick $Nb_2O_5/TiO_2$ can be patterned by electron beam lithography. Such patterned substrate can be dipped into an aqueous solution of poly(L-lysine) grafted poly(ethylene glycol) on which a controlled amount of poly(ethylene glycol) chains are functionalized, which can be chemically coupled with a biomarker binder A. Furthermore, an electron beam resist can be removed without damaging poly(L-lysine) grafted poly(ethylene glycol) layer. In a sandwich structure, a second biomarker binder B with a fluorophore can be utilized to attach with a biomarker.

It should be noted that the second biomarker binder B can be the same as the first biomarker binder A in some cases.

The height of an antibody can be shortened by either papain/pepsin enzyme.

Furthermore, a single aptamer/wavelength-shifting aptamer/aptamer sensor/aptamer beacon/molecular beacon, as a biomarker binder can replace a relatively taller (e.g., 30 nanometers) sandwich structure incorporating two antibodies, as biomarker binders.

Aptamer Sensor/Molecular Beacon

FIG. 12R1 illustrates an example of an aptamer sensor as a biomarker binder, which consists of two chemical components. The first chemical component is a DNA/RNA based aptamer section as a biomarker binder to chemically couple with a biomarker. The second chemical component is a DNA/RNA based aptamer section to chemically couple with a fluorophore, which is sensitive to its environment. Upon binding of the first chemical component with a biomarker, the aptamer sensor fluoresces.

FIG. 12R2 illustrates an example of a molecular beacon, as a biomarker binder, having self-complementary ends in a stem-loop structure (e.g., a hairpin structure) in its native dark state. Upon binding with a biomarker, a quencher is separated and the molecular beacon fluoresces.

FIG. 12R3 illustrates chemically coupled three distinct biomarker binders (e.g., antibody/synthetically designed antibody/aptamer aptamer) A, B and C, wherein the distinct biomarker binder B and the distinct biomarker binder C are then chemically coupled with a plus ligation arm of short sequences of a biological material (e.g., oligonucleotides) and a minus ligation arm of short sequences of a biological material (e.g., oligonucleotides) respectively. Thus, generating a randomly coiled single stranded structure composed of hundreds of copies of a biological material, relying on the proximity extension array method (which may require some temperature cycling). Thus, subsequently leading to covalently hybridization of fluorescent or enzyme-labeled biological material. Furthermore, the proximity extension array method can be replaced by a rolling circle amplification (RCA) method (which may require some temperature cycling). The rolling circle amplification method generates a localized signal via an isothermal amplification of a circle of the biological material. Thus, subsequently leading to covalently hybridization of fluorescent or enzyme-labeled biological material.

Fluorophore (Coupled with a Biomarker Binder) Positioned Relative to a Three-Dimensional Protruded Structure on a Horizontal Plane/Substrate FIG. 12S1 illustrates positioning a fluorophore (coupled with a biomarker binder) at a defined spot within three-dimensional protruded circular gratings (of thin-film metal/thin-film metal nitride) by a configuration 1/configuration 2/configuration 3/configuration 4/configuration 5/configuration 6. This arrangement is denoted as $\Omega_1$.

Similarly, FIG. 12S2 illustrates positioning a fluorophore (coupled with a biomarker binder) at a defined spot within two opposing three-dimensional protruded triangles (of thin-film metal/thin-film metal nitride) by a configuration 1/configuration 2/configuration 3/configuration 4/configuration 5/configuration 6. This arrangement is denoted as $\Omega_2$.

Similarly, FIG. 12S3 illustrates positioning a fluorophore (coupled with a biomarker binder) at a defined spot within two opposing three-dimensional protruded conducting nanotubes by a configuration 1/configuration 2/configuration 3/configuration 4/configuration 5/configuration 6. This arrangement is denoted as $\Omega_3$.

Similarly, FIG. 12S4 illustrates positioning a fluorophore (coupled with a biomarker binder) at a defined spot within two opposing three-dimensional protruded conducting spheres of a two-dimensional material by the configuration 1/configuration 2/configuration 3/configuration 4/configuration 5/configuration 6. This is denoted as $\Omega_4$.

Similarly, FIG. 12S5 illustrates positioning a fluorophore (coupled with a biomarker binder) at a defined spot on a sharp metalized tip by a configuration 1/configuration 2/configuration 3/configuration 4/configuration 5/configuration 6. This arrangement is denoted as $\Omega_5$.

Similarly, FIG. 12S6 illustrates positioning a fluorophore (coupled with a biomarker binder) at a defined spot on a sharp metalized tip by a configuration 1/configuration 2/configuration 3/configuration 4/configuration 5/configuration 6, wherein the sharp metalized tip is on a metal (e.g., aluminum/silver/gold) metal nanoparticle. This arrangement is denoted as $\Omega_6$.

Similarly, FIG. 12S7 illustrates positioning a fluorophore (coupled with a biomarker binder) at a defined spot on a sharp metalized tip by a configuration 1/configuration 2/configuration 3/configuration 4/configuration 5/configuration 6, wherein the sharp metalized tip is placed within the gap of two opposing three-dimensional protruded triangles (of thin-film metal/thin-film metal nitride). This arrangement is denoted as $\Omega_7$. It should be noted that other optical nanoantenna with a gap can also be utilized.

FIG. 12T1 illustrates a nano-scaled open box (having a maximum dimension less than about 400 nanometers) to enclose/cage a three-dimensional protruded optical nanoantenna as illustrated in FIGS. 12H-12O.

FIG. 12T2 illustrates a nano-scaled closed box (having a maximum dimension less than about 400 nanometers) to enclose/cage a three-dimensional protruded optical nanoantenna as illustrated in FIGS. 12H-12O.

FIG. 12U1 illustrates a metamaterial structure incorporating alternating thin-film of metal (of about 15 nanometers in thickness) and thin-film of insulator/semiconductor (of about 30 nanometers in thickness). The upper most thin-film of metal is separated by a layer of nanoholes (e.g., of diameter less than 250 nanometers), wherein the nanoholes can act as gratings.

Alternatively, nanoholes can be replaced by two-dimensional gratings as illustrated in FIG. 12U2.

Enhancement of Fluorescent Signal

Light is a wave. Thus, an optical nanoantenna can amplify light waves in the same way as a television and/or a mobile phone captures radio waves. Two gold nanoparticles (about 40 nanometers in diameter) and a fluorophore (e.g., a quantum dot fluorophore) bonded to a synthetic biological material (e.g., a single stand of DNA) of about 25 nanometers or less in length can act as an optical nanoantenna. The fluorophore can act as a quantum source, supplying the optical nanoantenna with photons.

Generation of Raman Signal

In FIGS. 12A and 12G, the function of the disease specific biomarker binder 240C can be enhanced by a dielectric (e.g., silica) sphere (about 50 nanometers in diameter).

The dielectric sphere can be encapsulated/caged in a thin metal (e.g., gold), wherein the thin metal is coupled with the biomarker binder (e.g., a specific antibody/aptamer) 240C to bind with the disease specific biomarker 460.

When light from the microelectro-mechanical-system enabled wavelength tunable surface emitting vertical cavity laser 580 is incident on the above silica sphere, it can shift a characteristic Raman signal (Raman Shift) upon chemically binding with the disease specific biomarker 460.

Measurement of Raman Shift

Measurements of Raman Shift can require a high-performance laser module. But a Raman sensor can utilize the microelectro-mechanical-system enabled wavelength tunable surface emitting vertical cavity laser 580 to scan over a narrow band of Raman Shift via a suitable wavelength tunable optical filter.

Surface-Enhanced Raman Scattering/Spectroscopy (SERS) Surface-Enhanced Resonance Raman Scattering/Spectroscopy (SERRS)

If the bottom of the microsized/nanosized mesh tubes 500A$_3$ (FIG. 12D) is atomically rough, then the disease specific biomarker 240C can be identified by surface-enhanced Raman scattering/spectroscopy or alternatively by surface-enhanced Resonance Raman scattering/spectroscopy.

Electron-beam lithographically patterned and ion beam etched (about) 25 nanometers pitch surface gratings of metal thin-film (about 2 to 5 nanometers in thickness) deposited by a low-temperature atomic layer deposition process on porous silicon substrate can be utilized as a reproducible atomically rough surface.

Surface-enhanced Raman scattering/spectroscopy is a surface-sensitive analytical technique that can enhance Raman scattering by a factor of $10^{10}$.

One disadvantage of surface-enhanced Raman scattering/spectroscopy is spectral interpretation. The signal enhancement is so dramatic that even weak Raman bands (unnoticeable in conventional Raman scattering/spectroscopy) can appear in surface-enhanced Raman scattering/spectroscopy.

Some trace contaminants can contribute unwanted peaks in surface-enhanced Raman scattering/spectroscopy. Furthermore, chemical interactions with metal surfaces, certain strong peaks (noticeable in conventional Raman scattering/spectroscopy) might not appear in surface-enhanced Raman scattering/spectroscopy.

Because of the above complications in surface-enhanced Raman scattering/spectroscopy, surface-enhanced Resonance Raman scattering/spectroscopy can integrate both the surface-enhancement and the Raman resonance—thus the Raman signal intensity can be as high as $10^{14}$ and the Raman spectra can be easier to interpret.

Enhancement of Raman Signal

A Raman nanoprobe (e.g., a single-walled carbon nanotube) encapsulating/caging dye molecules, can enhance enhancement of the Raman signal, wherein the nanotube can suppress unwanted fluorescence. The nanotube can be 1 nanometer in diameter and 300 nanometers in length, encapsulating/caging about 500 to 1000 dye molecules.

Addition of Three-Dimensional Protruded Structure(s) in Each Fluidic Container to Enhance Fluorescence Signal To enhance the fluorescence signal, a single/one-dimensional/two-dimensional array of three-dimensional protruded structures of (a) a single crystalline/polycrystalline thin-film of metal (e.g., aluminum/gold/silver)/metal nitride or (b) two-dimensional material (e.g., germanene/graphene/phosphorene/silicone/stanene) or (c) conducting nanotubes (e.g., a single-walled/multi-walled carbon nanotube) or (d) sharp tips or (e) Mie-Type resonators can be fabricated/constructed/bonded at/near the bottom of each fluidic container of the array of fluidic containers 500A. The thickness of the single crystalline/polycrystalline thin-film metal is less than 250 nanometers. The geometrical shape or a dimension(s) (e.g., height/depth) of the three-dimensional protruded structure or the pitch/gap of the one-dimensional/two-dimensional array of the three-dimensional protruded structures can be varied for maximum enhancement of the fluorescence signal.

Example: Three-Dimensional Protruded Structure (Atomic Force Microscopy (AFM) Like Sharp Tip)

To enhance the fluorescence signal, a single/one-dimensional/two-dimensional array of three-dimensional protruded atomic force microscopy like sharp tips (e.g., FIG. 12S5/12S6) of a single crystalline/polycrystalline thin-film of metal or a semiconductor can be fabricated/constructed/bonded at/near the bottom of each fluidic container of the array of fluidic containers 500A. The sharpness and/or radius curvature of the three-dimensional protruded atomic force microscopy like sharp tip and/or pitch/gap/duty cycle of the one-dimensional/two-dimensional array of the three-dimensional protruded atomic force microscopy like sharp tips can be varied for maximum enhancement of the fluorescence signal Example: Three-Dimensional Protruded Structure (Grating)

To enhance the fluorescence signal, three-dimensional protruded linear gratings/circular gratings of a single crystalline/polycrystalline thin-film metal/thin-film metal nitride/two-dimensional material can be fabricated/constructed/bonded at/near the bottom of each fluidic container of the array of fluidic containers 500A. The geometrical shape or a dimension(s) (e.g., height/depth) of the three-dimensional protruded linear/circular gratings and/or pitch/gap/duty cycle of the one-dimensional/two-dimensional array of the three-dimensional protruded linear/circular gratings can be varied for maximum enhancement of the fluorescence signal Example: Three-Dimensional Protruded Structure (Optical Nanoantenna)

To enhance the fluorescence signal, a single/one-dimensional/two-dimensional array of three-dimensional protruded optical nanoantennas (FIGS. 12H-12O) of a single crystalline/polycrystalline thin-film metal/thin-film metal nitride/two-dimensional material can be fabricated/constructed/bonded at/near the bottom of each fluidic container of the array of fluidic containers 500A. The typical thickness of the single crystalline/polycrystalline thin-film metal is less than 250 nanometers. The geometrical shape or a dimension(s) (e.g., height/depth and/or gap) of the three-dimensional protruded optical nanoantenna and/or pitch/gap/duty cycle of the one-dimensional/two-dimensional array of the three-dimensional protruded optical nanoantenna can be varied for maximum enhancement of the fluorescence signal. The maximum dimension of the three-dimensional optical nanoantenna is less than 250 nanometers.

Example: Three-Dimensional Protruded Structure (Optical Nanoantenna with Atomic Force Microscopy Like Sharp Tip)

To enhance the fluorescence signal, a single/one-dimensional/two-dimensional array of three-dimensional protruded optical nanoantennas of a single crystalline/polycrystalline thin-film metal/thin-film metal nitride/two-dimensional material, wherein each single three-dimensional protruded optical nanoantenna is fabricated/constructed/coupled with an atomic force microscopy like sharp tip e.g., FIG. 12S7 can be fabricated/constructed/bonded at/near the bottom of each fluidic container of the array of fluidic containers 500A. The typical thickness of the single crystalline/polycrystalline thin-film metal is less than 250 nanometers. The geometrical shape or a dimension(s) (e.g., height/depth and/or gap) of the three-dimensional protruded optical nanoantenna and/or pitch/gap/duty cycle of the one-dimensional/two-dimensional array of the three-dimensional protruded optical nanoantenna can be varied for maximum enhancement of the fluorescence signal. The maximum dimension of the three-dimensional optical nanoantenna is less than 250 nanometers.

Example: Three-Dimensional Protruded Structure (Optical Nanoantenna with a Two-Dimensional Material)

As an example, by fabricating/constructing a one atom thick/monolayer of a two-dimensional material at least on top (a) each nano-scaled triangle (FIG. 12 I), (b) each nano-scaled rod (FIG. 12J), (c) each nano-scaled sphere (FIG. 12L) and (d) each nano-scaled square with sharp tip (FIG. 12N), further enhancement of the fluorescence signal can be realized with a single/one-dimensional/two-dimensional array of three-dimensional protruded optical nanoantennas of a single crystalline/polycrystalline thin-film metal/thin-film metal nitride.

Example: Three-Dimensional Protruded Structure (Optical Nanoantenna with a Thin-Film of Room Temperature Topological Insulator)

A topological insulator is insulator inside or through the bulk, but is conducting around its surfaces/edges. Surface states of a topological insulator are protected by time-reversal symmetry. In contrast to an ordinary insulator, such surface states of a topological insulator are delocalized on the surface and are immune to imperfections in contrast to ordinary insulators.

As an example, by fabricating/constructing an ultra thin-film (e.g., about 5 nanometers to 50 nanometers in thickness) of a room temperature topological insulator (e.g., bismuth selenide ($Bi_2Se_3$)) at least on top of (a) each nano-scaled triangle (FIG. 12I), (b) each nano-scaled rod (FIG. 12J), (c) each nano-scaled sphere (FIG. 12L) and (d) each nano-scaled square with sharp tip (FIG. 12N), further enhancement of the fluorescence signal can be realized with a single/one-dimensional/two-dimensional array of three-dimensional protruded optical nanoantennas of a single crystalline/polycrystalline thin-film metal/thin-film metal nitride/two-dimensional material.

Example: Three-Dimensional Protruded Structure (Optical Nanoantenna with a Nanoparticle of Room Temperature Topological Insulator)

As an example, by fabricating/constructing a nanoparticle (e.g., about 2 nanometers to 10 nanometers in diameter) of a room temperature topological insulator (e.g., bismuth selenide ($Bi_2Se_3$)) at least on top of (a) each nano-scaled triangle (FIG. 12I), (b) each nano-scaled rod (FIG. 12J), (c) each nano-scaled sphere (FIG. 12L) and (d) each nano-scaled square with sharp tip (FIG. 12N), further enhancement of the fluorescence signal can be realized with a single/one-dimensional/two-dimensional array of three-dimensional protruded optical nanoantennas of a single crystalline/polycrystalline thin-film metal/thin-film metal nitride/two-dimensional material. Such a nanoparticle of a (room temperature) topological insulator of about 10 nanometers in diameter can be fabricated/constructed by electron beam lithography/reactive ion etching or colloidal lithography.

Example: Three-Dimensional Protruded Structure (Optical Nanoantenna of Room Temperature Topological Insulator)

It should be noted that a room temperature topological insulator can also replace each nano-scaled triangle (FIG. 12I), (b) each nano-scaled rod (FIG. 12J), (c) each nano-scaled sphere (FIG. 12L) and (d) each nano-scaled square with sharp tip (FIG. 12N).

Example: Three-Dimensional Protruded Structure (Metamaterial)

To enhance the fluorescence signal, a single/one-dimensional/two-dimensional array of a three-dimensional protruded hyperbolic metamaterial surface ($\infty_1$) (e.g., FIGS. 12U1-12U2) with nanoholes/gratings can be fabricated/constructed/bonded at/near the bottom of each fluidic container of the array of fluidic containers 500A. The pitch/gap/duty cycle of the one-dimensional/two-dimensional array of the three-dimensional protruded hyperbolic metamaterial surface with nanoholes/gratings can be varied for maximum enhancement of the fluorescence signal.

Example: Three-Dimensional Protruded Structure (Photonic Crystal)

A photonic crystal is an artificial periodic arrangement of a low-refractive index dielectric material and a high-refractive index dielectric material in two/three-dimensions. To enhance the fluorescence signal or Raman signal, a single/one-dimensional/two-dimensional array of photonic crystals can be fabricated/constructed/bonded at/near the bottom of each fluidic container of the array of fluidic containers 500A. The refractive indices of the dielectric materials or dimension (e.g., height/depth) of the photonic crystal or the pitch/gap/duty cycle of the one-dimensional/two-dimensional array of photonic can be varied for maximum enhancement of the fluorescence signal.

One-Dimensional/Two-Dimensional Array of Fluidic Containers for Diagnostic System The fluidic container can be fabricated/constructed to an approximate volume of 45 femtoliter to 55 femtoliter (which can have a depth of about 3 microns) and the fluidic container can be integrated/mechanically coupled with a flow cell (containing an aqueous solution of biological interest).

The side walls of a 45 femtoliter to 55 femtoliter fluidic container can be passivated/functionalized with a polymeric molecule X (e.g., polyethylene glycol or polyvinylphosphonic acid (PVPA)). The bottom of a 45 femtoliter to 55 femtoliter fluidic container can be passivated/functionalized with silane/α-X or silane/α-X-biotin, wherein molecule α is described below:

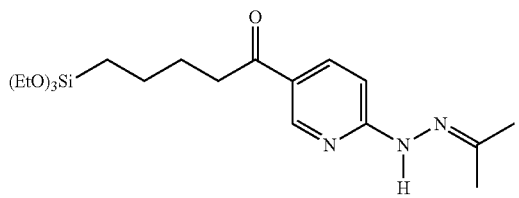

Addition of Three-Dimensional Protruded Structure(s) in Each Zero-Mode Waveguide to Enhance Fluorescence Signal The previously discussed embodiments to enhance fluorescence signal, utilizing just one single three-dimensional protruded structure can be applied for maximum enhancement of the fluorescence signal in each zero-mode waveguide.

Figure 12V:
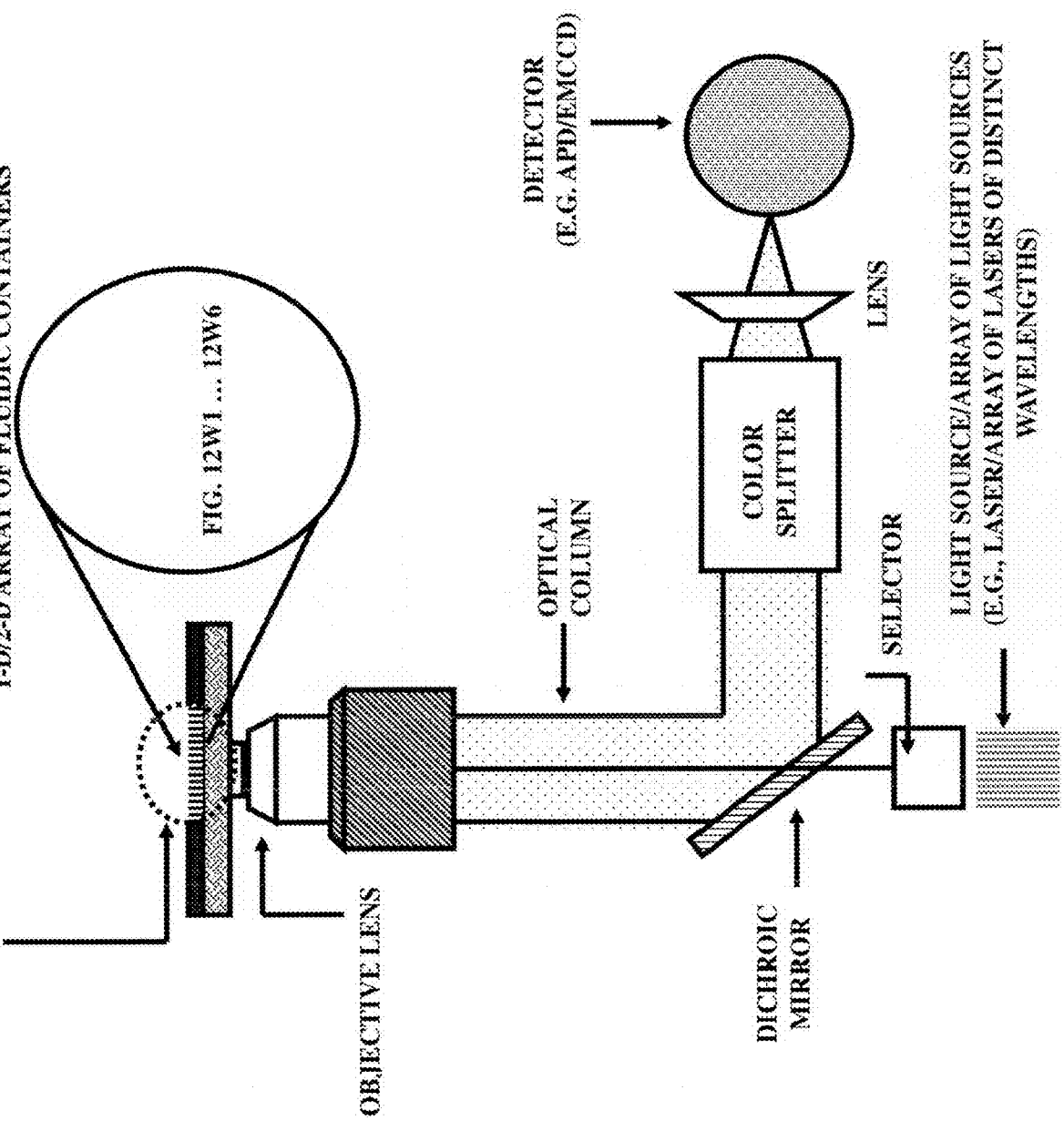
FIG. 12V illustrates an embodiment of an optical diagnostic biomodule, utilizing a one-dimensional (1-D)/two-dimensional (2-D) array of fluidic containers, incorporating various embodiments of three-dimensional protruded structures.

Summary and Applications of Optical Diagnostic Biomodule (FIG. 12V)

FIG. 12V illustrates an embodiment of an optical diagnostic biomodule for detecting a biomarker or plurality of biomarkers, wherein the biomarker or the plurality of biomarkers indicate either the presence or absence of a disease or an infection or a biological agent, or plurality of diseases or infections or biological agents. The optical diagnostic biomodule (as in FIG. 12V) can include an array of fluidic containers, wherein each fluidic container of the array of fluidic containers can include:

(a) a substrate of the fluidic container can include one or more materials (or one or more layers of materials, which can be insulating or semiconducting (including a two-dimensional material) or metallic, but optically suitable/transparent), wherein the fluidic container can include one or more first biomarker binders or one or more second biomarker binders, wherein more than one the first biomarker binder is either similar or distinct, wherein more than one the second biomarker binder is either similar or distinct, wherein the one first biomarker binder is coupled with a first fluorophore (which also includes, but is not limited to a quantum dot fluorophore/fluorescent protein/noble metal atom nanocluster (a cluster of less than one hundred (100) noble metal atoms (e.g., silver (Ag) atoms)/Mie-type resonator based fluorophore) or a first photoswitchable fluorophore, wherein the fluidic container includes one or more three-dimensional protruded structures (they can be fabricated/constructed on insulating spots to avoid any electrical shorting), wherein the first fluorophore or the first photoswitchable fluorophore is positioned horizontally relative (e.g., at 25 nanometers or less than 25 nanometers with respect to the one three-dimensional protruded structure as in FIG. 12K or alternatively in some cases at 25 nanometers or less than 25 nanometers with respect to an open space/gap of the one single three-dimensional protruded structure as in 12L) to the one three-dimensional protruded structure or the one second biomarker binder (or the one second biomarker may be coupled with a second fluorophore or second photoswitchable fluorophore in some cases) is positioned relative (e.g., at 25 nanometers or less than 25 nanometers with respect to the one three-dimensional protruded structure as in FIG. 12K or alternatively in some cases, at 25 nanometers or less than 25 nanometers with respect to an open space/gap of the one single three-dimensional protruded structure as in 12L) to the one three-dimensional protruded structure, wherein the dimension or shape of the one three-dimensional protruded structure is varied for maximum enhancement of fluorescence emission, wherein more than the one three-dimensional protruded structure is spaced or arranged in a one-dimensional array or in a two-dimensional array, wherein a pitch or a gap or a duty cycle of the one-dimensional array or the two-dimensional array of three-dimensional protruded structures is varied for maximum enhancement of the fluorescence emission, (b) a light source of a particular wavelength or light sources of distinct wavelengths directed at the fluidic container for inducing the fluorescence emission due to the interaction of the one first biomarker binder (which is coupled with the fluorophore or the photoswitchable fluorophore) with a biomarker or the one second biomarker binder with a biomarker and (c) a device for detecting the fluorescence emission from the fluidic container.

The substrate of the fluidic container (as in FIG. 12V) can include a periodic structure of one or more materials.

The fluidic container (as in FIG. 12V) can include one or more sudden/abruptly constricted fluid containers (e.g., fluid channels). The diameter of the sudden/abruptly constricted fluid container is typically about 25% to 75% smaller than the diameter of cell/stem cell/T cell. During a passage through the (planar) sudden/abruptly constricted fluid container at a high speed, wherein a temporary tiny opening in the cell/stem cell/T cell membrane is formed, without any permanent damage to the cell/stem cell/T cell. This configuration can be utilized to (a) inject bioactive compounds 100 and/or bioactive molecules 100A or (b) the nanoshell 120 to synthesize protein on-demand (as discussed earlier) or (c) the nanoshell 120 to deliver the CRISPR-Cas9 or optogenetic CRISPR-Cas9 system into cell/stem cell/T cell to analyze the effectiveness of the bioactive compounds 100 and/or bioactive molecules 100A and/or synthesized protein on-demand.

The first biomarker binder can be selected from the group consisting of: an isolated antibody, a synthetically designed antibody, an aptamer, a wavelength-shifting aptamer and a synthetically designed protein, wherein the synthetically designed protein has a binding site to bind with the biomarker.

The first biomarker binder can be a nano-scaled synthetically designed biomolecular circuit, wherein the nano-scaled synthetically designed biomolecular circuit can include (i) a synthetically designed riboswitch or (ii) a DNA sequence of adenine (A), thymine (T), guanine (G) and cytosine (C) or (iii) a DNA sequence of adenine (A), thymine (T), guanine (G) cytosine (C) and a synthetic molecule or (iv) an RNA sequence or (v) a programmable synthetically designed DNA-targeting-cleaving enzyme (may be coupled with a nanoparticle (of diameter less than the nanoshell)) or (vi) a programmable synthetically designed RNA-targeting-cleaving enzyme (may be coupled with a nanoparticle (of diameter less than the nanoshell)). The nano-scaled synthetically designed biomolecular circuit can include a synthetically designed biological logic circuit.

The first biomarker binder can include a nanoshell, wherein the nanoshell is decorated with a cleavable biological material, wherein the cleavable biological material is cleaved from a diseased cell or a decorated diseased cell, wherein the nanoshell may be coupled with a nanoparticle (of diameter less than the nanoshell).

The first biomarker binder can include a synthetically designed exosome-specific biomarker binder to couple with a molecule (e.g., small RNAs, including miRNA, Y-RNA, piwi-RNA and tRNA) of an exosome.

The second biomarker binder can be an aptamer beacon or a molecular beacon or a noble metal atom nanocluster beacon (a cluster of less than one hundred (100) noble metal atoms (e.g., silver (Ag) atoms) coupled with a biological material (e.g., DNA/RNA) fluoresce upon binding with a complementary biological material (e.g., DNA) or a synthetically designed riboswitch beacon. The aptamer beacon or the molecular beacon or the noble metal atom nanocluster beacon or the synthetically designed riboswitch beacon can include a synthetically designed biological logic circuit.

The second biomarker binder can be coupled or functionalized (e.g., via a lipid-functional-spacer construct, which is commercially available from Kode Biotech or via an aptamer) on a nanostructural element (e.g., a single-walled carbon nanotube/multi-walled carbon nanotube/boron nitride nanotube) of diameter less than 5 nanometers. The second biomarker binder may be coupled or functionalized with a synthetic biological material (e.g., a single stand of DNA), wherein the synthetic biological material is further coupled with two gold nanoparticles (about 40 nanometers in diameter). The nanostructural element can be electrically conducting. The nanostructural element can have a point defect (e.g., a point defect realized by an electrochemical method, as discussed in later paragraphs). Alternatively, the second biomarker binder may be coupled or functionalized at the point defect of the nanostructural element, which can be electrically coupled with a field effect transistor (e.g., as in FIG. 13C/13D/13E).

The second biomarker binder can be an aptamer sensor, wherein the aptamer sensor includes a first chemical segment to couple with the biomarker and a second chemical segment to couple with a second fluorophore or a second photoswitchable fluorophore.

The second biomarker binder can include both a first isolated antibody and a second isolated antibody, wherein the first isolated antibody or the second isolated antibody can be coupled with a second fluorophore or a second photoswitchable fluorophore. The first isolated antibody can be distinct from the second isolated antibody and they can couple with distinctly different epitopes.

The second biomarker binder can include both a first synthetically designed antibody and a second synthetically designed antibody, wherein the first synthetically designed antibody or the second synthetically designed antibody can be coupled with a second fluorophore or a second photoswitchable fluorophore. The first synthetically designed antibody can be distinct from the second synthetically designed antibody and they can couple with distinctly different epitopes. Furthermore, the first synthetically designed antibody or the second synthetically designed antibody can be arranged in three-dimension.

The three-dimensional protruded structure in the fluidic container can be an optical nanoantenna or a three-dimensional protruded structure/construct of a two-dimensional material or a conducting nanotube or a sharp tip or a hyperbolic metamaterial surface. The open gap within the optical nanoantenna is typically 25 nanometers or less than 25 nanometers.

The optical nanoantenna can include a room temperature stable topological insulator or a two-dimensional material or a nanoparticle. The hyperbolic metamaterial surface can include nanoholes or gratings.

It should be noted that the DNA sequence or RNA sequence or programmable synthetically designed DNA-targeting-cleaving enzyme specifically targeted to an infection or a biological agent can be attached to a microsphere/nanosphere. By way of an example and not by way of any limitation, a biological agent can be *Bacillus anthracis/Yersinia pestis/Francisella tularensis/Brucella melitensis/Clostridium botulinum/Vaccinia* virus/*Bacillus thuringiensis kurstaki*.

Furthermore, coated/painted/decorated/functionalized cells/disease cells in-vivo can be realized by a lipid-functional-spacer construct, which is commercially available from Kode Biotech.

It should be noted that coupling in previous paragraph could mean physical coupling and/or chemical coupling.

The optical diagnostic biomodule in FIG. 12V can be passivated/functionalized with:
first passivating molecules (e.g., polyethylene glycol) on side walls of each fluidic container and/or,
second capturing molecules (e.g., silane-polyethylene glycol and/or biotin) at or near the bottom of each fluidic container. The second capturing molecules are capable of capturing (e.g., binding/chemically binding/coupling/chemically coupling) with target molecules of interest for fluorescence and/or,
third binding molecules, positioned near or within the open spaces between the three-dimensional protruded structures (e.g., the open space within the single optical nanoantenna, as illustrated in FIG. 12J) at or near the bottom of each fluidic container to bind with a biomarker binder within the open space of the three-dimensional protruded structure.

Each fluidic container can be excited by an incident beam from a laser/laser array of distinct wavelengths. The incident laser can be selected and propagated by a dichroic mirror (or a beam splitter) via an optical column and objective lens. The optical column can be positioned with respect to each fluidic container by a precision mechanical stage. Similarly, the fluorescence emission can be propagated by the objective lens, optical column, dichroic mirror, color splitter and lens. The fluorescence emission is collected/detected by a photodetector. Furthermore, instead of a laser, a light source can be a two-dimensional material based light source (e.g., FIG. 12Z1). Utilizing a first laser (from the laser array) and a second laser (from the laser array) simultaneously, a beam of the first laser can be shaped like an open toroidal shape by altering the optical properties of the pupil plane of the objective lens (e.g., integrating diffractive optical elements with objective lens) and this can enable turning on fluorescence of the fluorophores only in the exact center (spot) of the open toroidal shaped area (turning off fluorescence of the fluorophores in other areas). Moreover, when the fluorophores are photoswitchable, then a subset of photoswitchable fluorophores within the exact center (spot) of the open toroidal shaped area can be activated—there by significantly enhancing resolution of the fluorescence observation.

The optical diagnostic biomodule in FIG. 12V incorporating the light source, wherein the light source can include a coherent light source or a light source, incorporating a two-dimensional material (e.g., FIG. 12Z1) for inducing the fluorescence emission in each fluidic container.

The optical diagnostic biomodule in FIG. 12V incorporating the light source, wherein the light source can include a first coherent light source and a second coherent light source, wherein a beam of the first coherent light source is approximately an open toroidal shaped, wherein the first coherent light source and the second coherent light source are activated simultaneously for inducing the fluorescence emission on a spot in each fluidic container.

The optical diagnostic biomodule in FIG. 12V incorporating the device for detecting fluorescence, wherein the device for detecting fluorescence can include a quantum dot spectrophotometer or a charged-coupled detector or an electron multiplying charged-coupled detector or a complementary metal-oxide-semiconductor detector or a back illuminated complementary metal-oxide-semiconductor detector or a single photon detector for detecting the fluorescence emission from in each fluidic container.

The optical diagnostic biomodule in FIG. 12V can include an optical fiber or an optical waveguide, which is optically coupled with each fluidic container for propagating the fluorescence emission.

The optical diagnostic biomodule in FIG. 12V can include a lens, optically coupled with the optical fiber or the optical waveguide, which is optically coupled with each fluidic container for propagating the fluorescence emission.

The optical diagnostic biomodule in FIG. 12V can include a N (inputs)×1 (output) optical switch, optically coupled with the optical fiber or the optical waveguide, which is optically coupled with each fluidic container for propagating the fluorescence emission.

Various types of fluidic containers are illustrated in Figures in 12W1-12W6.

FIG. 12W1 illustrates a two-dimensional array of recessed surfaces on a rigid/flexible substrate (e.g., glass/bendable glass), wherein each recessed surface has a two-dimensional array of three-dimensional protruded structures (e.g., three-dimensional protruded optical nanoantennas).

FIG. 12W2 illustrates a two-dimensional array of recessed surfaces on a rigid/flexible substrate, wherein each recessed surface has a two-dimensional array of three-dimensional protruded structures-generally represented by $\Omega_x$ where x=1 (FIG. 12S1 for $\Omega_1$), 2 (FIG. 12S2 for $\Omega_2$), 3 (FIG. 12S3 for $\Omega_3$), 4 (FIG. 12S4 for $\Omega_4$), 5 (FIG. 12S5 for $\Omega_5$), 6 (FIG. 12S6 for $\Omega_6$) and 7 (FIG. 12S7 for $\Omega_7$).

FIG. 12W3 illustrates a two-dimensional array of recessed surfaces on a rigid/flexible substrate, wherein each recessed surface has a two-dimensional array of three-dimensional protruded structures of metamaterial structures.

Furthermore, the one-dimensional array of recessed surfaces can be utilized instead of the two-dimensional array of recessed surfaces.

FIGS. 12W4, 12W5, 12W6 are similar to FIG. 12W1, FIG. 12W2, FIG. 12W3 respectively, except the recessed surfaces are replaced by vertically aligned fluidic containers.

Summary Of Optical Diagnostic Biomodule (FIG. 12X1)

FIG. 12X1 illustrates an embodiment of an optical diagnostic biomodule which is similar (including passivation by first molecules, second molecules and third molecules) to the optical diagnostic biomodule in FIG. 12V, except it incorporates a zero-mode waveguide, a flow cell. It should be noted that all zero-mode waveguides can be optically excited.

It should be noted that coupling in previous paragraph could mean physical coupling and/or chemical coupling.

Furthermore, coated/painted/decorated/functionalized cells/disease cells in-vivo can be realized by a lipid-functional-spacer construct, which is commercially available from Kode Biotech.

The zero-mode waveguide can be wet cleaned with acetone and isopropanol, dried in nitrogen gas and cleaned in oxygen gas or in mixture of 90% (in volume) oxygen gas with 10% (in volume) argon gas or in mixture of 90% oxygen gas (in volume)/10% nitrogen gas (in volume) or in mixture of oxygen gas (90% in volume)/nitrogen gas (5% in volume)/argon gas (5% in volume).

The zero-mode waveguide can be passivated/functionalized with:

first passivating molecules Xs (e.g., polyethylene glycol or polyvinylphosphonic acid (PVPA)) on the side walls of each zero-mode waveguide and/or, for example, the polymeric molecule X in aqueous solution (volume of 50 mL to 250 mL) can be electrochemically deposited onto the walls of the zero-mode waveguide by a two-electrode electrochemical cell or a three-electrode (e.g., working electrode, counter electrode and reference electrode) electrochemical cell (e.g., manufactured by Gamry Instruments).

second capturing molecules (e.g., silane/α-X or silane/α-X-biotin at or near the bottom of each zero-mode waveguide, wherein molecule α is described below:

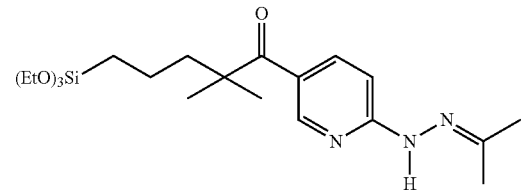

The second capturing molecules are capable of capturing (e.g., binding/chemically binding/coupling/chemically coupling) with target molecules for single molecule fluorescence and/or, third binding molecules, positioned near or within the open spaces between the three-dimensional protruded structures (e.g., the open space within the single optical nanoantenna, as illustrated in FIG. 12J) at or near the bottom of each zero-mode waveguide to bind with a biomarker binder within the open space of the three-dimensional protruded structure.

The array of zero-mode waveguides can be optically excited in parallel and the array of zero-mode waveguides should be monitored continuously for detection of fluorescence, as the incorporation of biomarkers into a zero-mode waveguide is a random stochastic process. Thus, it requires a high-power laser (e.g., 10 W), as each zero-mode waveguide is to be optically excited close to saturation. Integrating diffractive optical elements (e.g., binary phase gratings) on the optical (laser) excitation side of the substrate of the array of zero-mode waveguides, the excitation efficiency of the laser can be increased significantly. The binary phase grating is a special case of one-dimensional Damman grating with a duty cycle of 50% within a period. However, the substrate of the array of zero-mode waveguides needs to be thinner (e.g., 25 microns to 50 microns) for a depth of binary phase grating at a range of 500 nanometers, while the grating pitch and width of grating teeth can be suitably varied for a particular thickness of the substrate of the array of zero-mode waveguides.

All zero-mode waveguides (simultaneously) (or each zero-mode waveguide sequentially) can be excited by an incident beam from a laser/laser array of distinct wavelengths. The incident laser can be selected and propagated by a dichroic mirror (or a beam splitter) via an optical column and objective lens. The optical column can be positioned with respect to each fluidic container by a precision mechanical stage. Similarly, the fluorescence emission can be propagated by the objective lens, optical column, dichroic mirror, color splitter and lens. The fluorescence emission is collected/detected by a photodetector. Furthermore, instead of a laser, a light source can be a two-dimensional material based light source (e.g., FIG. 12Z1). Utilizing a first laser (from the laser array) and a second laser (from the laser array) simultaneously, a beam of the first laser can be shaped like an open toroidal shape by altering the optical properties of the pupil plane of the objective lens (e.g., integrating diffractive optical elements with objective lens) and this can enable turning on fluorescence of the fluorophores only in the exact center (spot) of the open toroidal shaped area (turning off fluorescence of the fluorophores in other areas). Moreover, when the fluorophores are photoswitchable, then a subset of photoswitchable fluorophores within the exact center (spot) of the open toroidal shaped area can be activated—thereby significantly enhancing resolution of the fluorescence observation.

It should be noted that optically exciting each zero-mode waveguide sequentially has an advantage, utilizing an optical nanofiber/optical nanowaveguide with an optical switch.

The optical diagnostic biomodule as illustrated in FIG. 12X1 can include diffractive optical elements to increase excitation efficiency of the light source or the array of light sources.

Each fluidic container in the optical diagnostic biomodule in FIG. 12V/12X1 can include magnesium acetate. Magnesium acetate can be utilized to increase a tiny amount of a nucleic acid (as a biomarker) in the plasma, upon temperature cycling by a heating device. Furthermore, a metal alloy slab of Invar (a nickel iron alloy) can be sandwiched between the heater and each fluidic container. Additionally, a temperature control circuitry can also be integrated.

The optical diagnostic biomodule in FIG. 12V/12X1 can include a microfluidic device/nanofluidic device/flow cell. Such a microfluidic/nanofluidic device can be utilized to reduce or eliminate various washing steps (utilizing PBS solution and/or Tween-20) for consumer applications and separation of plasma from a human's blood.

The optical diagnostic biomodule in FIG. 12V/12X1 can include a device or an apparatus to isolate exosomes from a biological fluid and to isolate molecules of the exosomes, wherein the device or the apparatus to isolate the exosomes can include a separator module of exosomes-attached magnetic beads or a nano-scaled filter to filter the exosome from the biological fluid; as described in detail in later paragraphs.

Device fabrication of the optical diagnostic biomodule in FIG. 12V/12X1 can generally include these steps: (a) fabrication of an array of spots (of one or more three-dimensional protruded structures) on a substrate (e.g., quartz) by electron beam lithography and reactive ion etching, (b) fabrication of an array of photoresist columns (e.g., considering suitable geometry for the optical diagnostic biomodule in FIG. 12V/12X1) covering the array of spots, (c) blanket deposition of a suitable material (e.g., a metal) of suitable thickness and (d) removal of the suitable material over the array of photoresist columns.

Bioinformatics analysis of molecular components and proteins by the optical diagnostic biomodule in 12V/12X1 can generate a large set of Data—Big Data. Analysis of Big Data is described in latter paragraphs.

FIG. 12X2 illustrates an optical nanoantenna (indicated by $\infty$) in each zero-mode waveguide of the array of zero-mode waveguides.

FIG. 12X3 illustrates a metamaterial surface (indicated by $\infty_1$) in each zero-mode waveguide of the array of zero-mode waveguides, wherein the metamaterial surface is integrated with a two-dimensional array of nanoholes/gratings.

FIG. 12X4 illustrates a metalized sharp tip (indicated by $\infty_2$) in each zero-mode waveguide of the array of zero-mode waveguides.

FIG. 12X5 illustrates details of the metalized sharp tip (indicated by $\infty_2$). The sharp tip is created by wet etching on a thin (e.g., 10 microns in thickness) silicon substrate with <100> crystal orientation and the sharp tip can be metalized. The top surface of silicon substrate has 2.5 nanometers thick silicon dioxide dielectric (by atomic layer deposition). The metalized sharp tip (indicated by $\infty_2$) is to enhance the fluorescence emission in each zero-mode waveguide of the array of zero-mode waveguides.

FIG. 12X6 illustrates a metalized sharp tip integrated with a metal nanoparticle (indicated by $\infty_3$) in each zero-mode waveguide of the array of zero-mode waveguides.

FIG. 12X7 illustrates details of the metalized sharp tip integrated with a metal nanoparticle (indicated by $\infty_3$). The metalized sharp tip integrated with the metal nanoparticle indicated by $\infty_3$) is to enhance the fluorescence emission in each zero-mode waveguide of the array of zero-mode waveguides.

FIG. 12X8 illustrates a metalized sharp tip integrated with an optical nanoantenna (indicated by $\infty_4$) in each zero-mode waveguide of the array of zero-mode waveguides.

FIG. 12X9 illustrates a metalized sharp tip integrated with an optical nanoantenna (indicated by $\infty_4$) in each zero-mode waveguide of the array of zero-mode waveguides. It should be noted that any optical nanoantenna with a gap can be utilized.

FIG. 12X10 illustrates details of the critical process steps of imprint lithography/nanoimprinting lithography, depending on the dimension to be printed on a substrate.

In FIG. 12X12, step A is to create a silicon template, step B is to deposit a suitable material, step C is to apply adhesive and peel and step D is to fabricate/construct an array of zero-mode waveguides/nanoholes.

Figure 12Y:
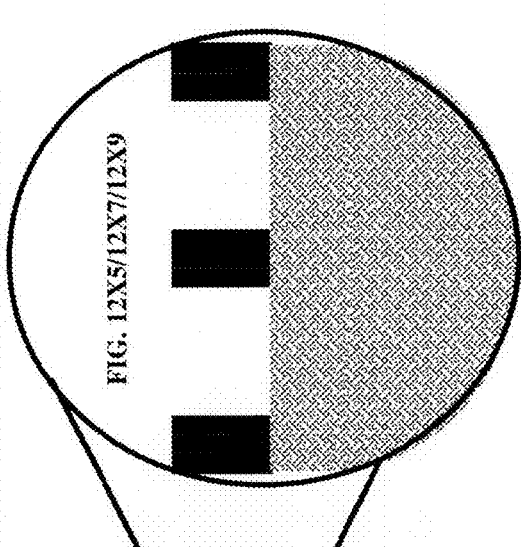
FIG. 12Y illustrates an embodiment of an optical diagnostic biomodule, utilizing a one-dimensional/two-dimensional array of fluidic containers/zero-mode waveguides, wherein each fluidic container/zero-mode waveguide can include a sharp tip (a sharp tip of various configurations).

The embodiment of an optical diagnostic biomodule in FIG. 12Y is similar to 12X1 (including a flow cell), except each fluidic container/zero-mode waveguide has a metalized sharp tip. There are various configurations of the metalized sharp tip. Such configurations are previously illustrated in FIG. 12X5, FIG. 12X7 and FIG. 12X9.

The optical diagnostic biomodule in FIG. 12X1 can enable single molecule DNA sequencing, sensors for interactions between biological molecules including DNA-DNA or protein-protein interactions, enzyme activity assays, metabolomic profiling and biological activity in real-time and with single-molecule resolution.

12Z1 illustrates a tunable light source. By way of an example and not by way of any limitation, the substrate can be either heavily doped p-type silicon or n-type silicon. Boron nitride thin-film is deposited by chemical vapor deposition on the above substrate. The thickness of boron nitride is less than 250 nanometers. Two-dimensional surface gratings of about or less than 10 nanometers in pitch can be fabricated/constructed in boron nitride thin-film and then followed by deposition of a two-dimensional material (e.g., graphene). Upon electrical excitation, a two-dimensional material will emit a visible light. The wavelength of the emitted visible light can be tuned by varying strength of electrical excitation (e.g., voltage).

However, if two-dimensional surface gratings of about 100 nanometers to 200 nanometers in pitch can be fabricated/constructed in boron nitride thin-film and followed by deposition of a two-dimensional material (e.g., graphene), then a tunable (by varying strength of electrical excitation) terahertz emission source can be realized.

The optical diagnostic biomodule as illustrated in FIG. 12X1 or 12Y can be utilized for detection of a biomarker, a single molecule analysis (by fluorescence emission) and DNA/RNA sequencing for diseases/infections.

For example, a biomarker binder (e.g., a specific monoclonal antibody) targeted for *Plasmodium falciparum* histidine-rich protein-2 biomarker in the blood/biological fluid can be used to detect early onset of a specific type of malaria (infection). Biomarker binders targeted for biomarkers such as NCAM, CRP, SAP, IP-10, ferritin, TPA, 1-309, and MIG in the blood/biological fluid can be used to detect early onset of a specific type of tuberculosis (infection).

FIG. 12Z2 illustrates a light source/tunable light source in the visible spectrum, utilizing a two-dimensional material, wherein a two-dimensional material surface can be functionalized as a biomarker binder. Additionally, utilizing either dip-pen nanolithography (DPN) or microchannel cantilever spotting (μCS) on a small area of the two-dimensional material/surface can be patterned in nanometer resolution to functionalize as a biomarker binder(s)/biological/chemical sensor(s). Furthermore, a three-dimensional array of a biomarker binder can also be utilized to enhance sensitivity to detect a disease.

Furthermore, a particular two-dimensional material-graphene's ability to form chemical bonds can be turned on or tuned off based on what is underneath graphene. When silicon dioxide is underneath graphene, it is reactive when exposed to certain biomarkers/chemicals. But when boron nitride is underneath graphene, it is not reactive when exposed to certain biomarkers/chemicals. An array of materials (e.g., an array of boron nitride and silicon dioxide) underneath graphene can be utilized by an array of sensors to detect a trace amount of biomarkers/chemicals.

FIG. 12Z3 illustrates a nano optical fiber, which consists of a first region of a single mode optical fiber, followed by a second adiabatically tapered region and a third nano optical fiber region. The tip of the nano optical fiber can be fabricated/constructed with a flat mirror/spherical mirror/silicon waveguide for efficient optical coupling. Instead of bulk optics, an array of nano optical fibers can be utilized as a conduit for the incident and fluorescence light in zero-mode waveguide. Furthermore, the array of nano optical fibers can be connected to inputs of a N×1 optical switch 600 and the output of the optical switch can be connected to the detector or a spectrophotometer. This configuration can enable faster analysis.

Terahertz Analysis

Terahertz absorption constants can vary linearly with red blood cell concentrations in whole blood for quantitative analysis of human blood/infected blood (e.g., blood infected with malaria parasites). Super paramagnetic nanoparticles/nanobeads functionalized with a disease specific biomarker binder can be introduced in human blood/infected blood to chemically bind/couple with a disease specific biomarker. Super paramagnetic nanoparticles/nanobeads functionalized with a disease specific biomarker binder chemically binding/coupling with a disease specific biomarker can form a cluster. Thus, magnetic property of human blood/infected blood can be altered and the altered magnetic property of human blood/infected blood can be analyzed by (a) quantifying refractive index and absorption coefficient in terahertz or (b) terahertz time domain spectroscopy. Furthermore, utilizing terahertz time domain spectroscopy and total internal reflection method, wherein amplitude of an attenuated total internal reflection of terahertz signal through human skin can increase with an increased glucose concentration in blood increase—thus enabling non-invasive real-time measurement of blood glucose concentration in blood. Terahertz imaging can be also integrated with a film/nano-composite film to make human skin transparent to terahertz, when a measurement is initiated. This ensures consistent readings across all people independent of age, skin type and color. The refractive index and absorption coefficient of cancer (e.g., skin, breast and colon cancer) tissue in terahertz are higher in comparison to a normal tissue due to higher water content and structural changes in cancer tissue. Terahertz imaging can be highly sensitive to water concentration. Thus, it can help detect an early cancer, before it is sensitive to other imaging methods.

Additionally, detection by terahertz imaging can be enhanced by artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

It should be noted that artificial intelligence (including self-learning artificial intelligence), computer vision (including self-learning computer vision), data mining, fuzzy/neuro-fuzzy logic, machine vision (including self-learning machine vision) natural language processing, neural networks (including self-learning neural networks), pattern recognition, reasoning modeling and self-learning (including evidence based self-learning) can be enhanced by quantum computing or quantum computing based machine learning.

Terahertz imaging (e.g., terahertz pulse imaging, terahertz time domain spectroscopy and terahertz continuous wave spectroscopy) can be utilized to render real-time imaging during surgery to avoid cutting off healthy tissues and exclude leaving cancer tissues in a patient's body. Terahertz imaging can be also utilized to distinguish between soft tissue and hard tissue. Terahertz pulse imaging can be used to provide valuable diagnostic information pertaining to enamel, dentine and cavity. Different types of biomolecules leave distinctive molecular spectral fingerprints in the terahertz region and this property enables both in-vitro and in-vivo measurements of small biomolecules. By obtaining both frequency and time domain information, terahertz imaging can enhance detection of cancer/inflammation and provide sharper imaging and in-vitro/in-vivo molecular fingerprinting/molecular imaging. A terahertz camera can enable label-free detection of reactions/interactions of small molecules with proteins—thus enabling high speed non-destructive imaging for drug discovery.

Example Application of Terahertz Analysis & On-Demand In-Situ Delivery of Insulin Utilizing terahertz time domain spectroscopy and total internal reflection method, wherein amplitude of an attenuated total internal reflection of terahertz signal of human skin can increase with increased glucose concentration in blood increase—thus enabling non-invasive real-time measurement of blood glucose concentrations in blood. Such primary data can be utilized to deliver the smart nanoshells 120s (encapsulating/caging insulin/long acting insulin) from the active micropatch (e.g., as described in FIG. 7N). These smart nanoshells 120s will only release encapsulated/caged insulin/long acting insulin, when the glucose level in blood is high in-situ (a secondary data). Details of the smart nanoshells 120s have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

For example, the smart nanoshell 120 can be made of water-fearing molecules (pointing inward) and water-loving molecules (pointing outward). The smart nanoshell 120 can encapsulate insulin molecules/long acting insulin molecules. The external surface of the smart nanoshell can be coupled with an enzyme to convert glucose into gluconic acid. In the presence of excess glucose, the enzyme (converting glucose into gluconic acid) creates a lack of oxygen and causes water-loving molecules (pointing outward) to collapse-enabling the delivery of insulin/long acting insulin/smart insulin at a suitable external condition.

In another example, the smart nanoshell 120 (fabricated/constructed by DNA origami) can be decorated with an aptamer/engineered riboswitch based (excess) glucose sensor. In the presence of excess glucose, the smart nanoshell 120 can collapse-enabling the delivery of insulin/long acting insulin/smart insulin at a suitable external condition.

Smart insulin can be Ins-PBA-F, which can consist of a long-acting insulin derivative that has a chemical moiety with phenylboronic acid added at one end. Under normal conditions, smart insulin can bind with serum proteins (circulating in blood). In presence of excess glucose, it can bind with phenylboronic acid to release Ins-PBA-F.

It should be noted that both terahertz analysis and on-demand in-situ delivery of insulin from the active micropatch (e.g., as described in FIG. 7N) can be integrated with a bio/health sensor or a wearable device. Details of a wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Integration of Two-Dimensional Material Based Light Source with Negatively Charged Atomic Nitrogen Vacancy (NV) Color Center(s) in Diamond Negatively charged atomic nitrogen vacancy color centers are point defects in a diamond lattice with unique properties in ultra sensitive high resolution magnetometry. Although a single (negatively charged) nitrogen vacancy color center in a diamond lattice is useful for high spatial resolution, highest sensitivity can be realized, by utilizing a diamond lattice incorporating many atomic (negatively charged) nitrogen vacancy color centers. A single (negatively charged) nitrogen vacancy color center can carry a spin that is very sensitive to magnetic fields owing to the Zeeman-Effect and the optical rate of emission depends on the single (negatively charged) nitrogen vacancy color center's spin state. The (negatively charged) nitrogen vacancy color center can be highly spin polarized via laser irradiation. It can exhibit extraordinarily long coherence times at room temperature (about 1 millisecond in Carbon 12 enriched sample).

In order to create (negatively charged) nitrogen vacancy color centers in a diamond lattice, a nitrogen containing crystal can be irradiated with high-energy electrons. After irradiation, the crystal contains vacancies that migrate towards nitrogen atoms forming (negatively charged) nitrogen vacancy color centers in a diamond lattice.

A diamond substrate with (negatively charged) nitrogen vacancy color centers just below (within a few nanometers) the top surface can be fabricated/constructed. The diamond substrate can be integrated (fabricated/constructed) with a microwave stripline for microwave excitation (e.g., at 2.869 GHz). Alternatively, microwave excitation can be applied via an antenna.

A biological material with a magnetic property/spin can be placed on top of the diamond substrate (integrated with the microwave stripline) with (negatively charged) nitrogen vacancy color centers just below (within a few nanometers) the top surface.

Furthermore, the diamond substrate (with the biological material with a magnetic property/spin) can be placed on top of the two-dimensional material based light source (as discussed in previous paragraphs) for excitation at a suitable wavelength (e.g., at 532 nanometers) and red-shifted fluorescence emission (fluoresce in a manner proportional to the strength of the biological material's own magnetic field) in wavelength range of 600 to 800 nanometers can be detected by an avalanche photodetector/single photon detector. Microwave excitation is amplitude modulated and changes to red-shifted fluorescence emission are measured in conjunction with (a) microwave modulation and (b) applied magnetic field. Thus, red-shifted fluorescence emission can be used to map minute magnetism of the biological material.

Furthermore, a light source (e.g., a light emitting diode/laser) of a suitable optical intensity can replace the two-dimensional material based light source.

Additionally, a pair of bias magnets and nano positioning stage (e.g., a PZT stage) can be utilized to map the biological material with a magnetic property/spin in high resolution. Alternatively, a laser instead of the two-dimensional material based light source can be utilized.

For angstrom resolution, a scanning probe (e.g., an atomic force microscope tip) integrated with a single (negatively charged) nitrogen vacancy color center in diamond lattice (just below the surface) can be utilized. Since, a function of a biological material (e.g., protein/neurons/stem cells) is closely related to its structure, one can estimate/derive a relationship between them.

Example Application for Detection of Malaria

As the malaria parasite consumes a human's red blood cells, it leaves a residue of insoluble malaria pigment/byproduct hemozoin (heme polymer) in the infected blood. Hemozoin contains iron particles. Hemozoin is either diamagnetic or super paramagnetic, depending on its oxygenated or deoxygenated form. But generally, hemozoin is considered super paramagnetic. It has a magnetic permeability constant $\mu = \sim 4585$ at $-20°$ C. and $\mu = \sim 3845$ at about $+20°$ C. Under an applied magnetic field, hemozoin induces an optical dichroism, which is a function of its concentration. Precise measurement of this optical dichroism can be utilized to detect malaria infection.

Alternatively, a diamond substrate (with (negatively charged) nitrogen vacancy color centers just below (within a few nanometers) the top surface) with hemozoin (in diluted blood of an infected human) on top of the diamond substrate can be excited at a wavelength of 532 nanometers and red-shifted fluorescence emission (fluoresce in a manner proportional to the strength of the hemozoin's own magnetic field) in wavelength range of 600 to 800 nanometers can be detected by a single photon detector. The diamond substrate integrated (fabricated/constructed) with a microwave stripline for microwave excitation. Additionally, a pair of bias magnets can be utilized. Thus, red-shifted fluorescence emission can be used to map minute magnetism of hemozoin (hence detection of malaria).

Example Application for Contrast Enhancement in Magnetic Resonance Imaging (MRI) of Cancer Magnetic resonance imaging can see inside a human body in detail without invasive surgery. A suitable contrast enhancement agent can enhance this imaging method. For example, the pH of cancer microenvironment is about 6.5 to 6.8 (compared to the pH of a human blood which is 7.4). The nanoshell 120/nanocarrier 160 can be fabricated/constructed to be pH sensitive. The particular pH sensitive nanoshell 120/nanocarrier 160 can encapsulate/cage manganese ions and nanodiamonds. The particular pH sensitive nanoshell 120/nanocarrier 160 can break in a pH range of the cancer microenvironment—thus increasing contrast in magnetic resonance imaging. Additionally, the nanodiamonds can be conjugated with gadolinium(III), wherein the gadolinium (III) concentration can be varied to realize the highest contrast enhancement in magnetic resonance imaging and the nanodiamonds can be functionalized with a cancer specific biomarker binder(s) to bind with a cancer specific biomarker(s).

Example Application for Contrast Enhancement in Magnetic Resonance Imaging of Cancer & In-Situ Destruction Of Cancer Cells The particular pH sensitive multifunctional nanoshell 120/nanocarrier 160 can encapsulate/cage manganese ions, nanodiamonds and gold nanoparticles. The particular pH sensitive nanoshell 120/nanocarrier 160 can break in a pH range of the cancer microenvironment—thus increasing contrast in magnetic resonance imaging. By heating the gold nanoparticles with a laser of a suitable wavelength, cancer cells can be destroyed and the subsequent rise in temperature can be reordered in the spin frequency of nanodiamonds. Additionally, the nanodiamonds can be conjugated with gadolinium(III), wherein gadolinium(III) concentration can be varied to realize the highest contrast enhancement in magnetic resonance imaging and also the nanodiamonds can be functionalized with a cancer specific biomarker binder(s) to bind with a cancer specific biomarker(s). Alternatively/additionally, a magnetic imaging system can be integrated with a positron emission tomography system to detect cancer cells and a computer controlled focused beam of x-ray and/or proton beam can be utilized to destroy cancer cells.

Example Application for Contrast Enhancement in Hybrid Magnetic Resonance Imaging & Fluorescence Imaging Of Cancer The nanoshell 120/nanocarrier 160 can be fabricated/constructed to be pH sensitive. The particular pH sensitive nanoshell 120 can encapsulate/cage manganese ions and fluorescent nanodiamonds (about 50-100 nanometers in maximum dimension). The particular pH sensitive nanoshell 120/nanocarrier 160 can break in a pH range of the cancer microenvironment—thus increasing contrast in magnetic resonance imaging. Additionally, the fluorescent nanodiamonds can be conjugated with gadolinium(III), wherein gadolinium(III) concentration can be varied to realize the highest contrast enhancement in magnetic resonance imaging and also the fluorescent nanodiamonds can be functionalized with a cancer specific biomarker binder(s) to bind with a cancer specific biomarker(s).

In fluorescent nanodiamonds, the nitrogen vacancy color centers in the diamond lattice provide fluorescence. Unlike quantum dots/organic dyes, these nitrogen vacancy color centers do not photobleach/photoblink. Upon laser excitation, extremely stable fluorescence emission from nitrogen vacancy color centers of fluorescent nanodiamonds can be detected by a photodetector (e.g., an avalanche photodetector). Thus, enabling hybrid magnetic resonance and fluorescence imaging in a cancer environment. Details of such fluorescence detection have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Example Application for Contrast Enhancement in Hybrid Magnetic Resonance Imaging, Fluorescence Imaging of Cancer & In-Situ Destruction of Cancer Cells by Light Excitation The particular pH sensitive multifunctional nanoshell 120/nanocarrier 160 can encapsulate/cage manganese ions, fluorescent nanodiamonds and gold nanoparticles/gold nanorods. The particular pH sensitive nanoshell 120/nanocarrier 160 can break in a pH range of the cancer microenvironment—thus increasing contrast in magnetic resonance imaging. By heating the gold nanoparticles/gold nanorods with a laser source of a suitable wavelength, cancer cells can be destroyed and the subsequent rise in temperature can be reordered in the spin frequency of fluorescent nanodiamonds. Additionally, the fluorescent nanodiamonds can be conjugated with gadolinium(III), wherein the gadolinium (III) concentration can be varied to realize the highest contrast enhancement in magnetic resonance imaging and also the fluorescent nanodiamonds can be functionalized with a cancer specific biomarker binder(s) to bind with a cancer specific biomarker(s). Alternatively/additionally, a magnetic imaging system can be co-integrated with a positron emission tomography system to detect cancer cells and a computer controlled focused beam of x-ray and/or proton beam can be utilized to destroy cancer cells.

Example Application for Contrast Enhancement in Hybrid Magnetic Resonance Imaging, Fluorescence Imaging of Cancer & In-Situ Destruction of Cancer Cells by Light Excitation The particular pH sensitive multifunctional nanoshell 120/nanocarrier 160 can encapsulate/cage manganese ions, fluorescent nanodiamonds and gold nanoparticles/gold nanorods. A hairpin DNA structure can be covalently conjugated on the surface of gold nanoparticles/gold nanorods and cancer destroying drug molecules (e.g., camptothecin/doxorubicin/paclitaxel molecules) can be intercalated into the adjacent base pairs of hairpin DNA structures. The particular pH sensitive nanoshell 120/nanocarrier 160 can break in a pH range of the cancer microenvironment—thus increasing contrast in magnetic resonance imaging. Upon visible light excitation (e.g. at 532 nanometers, at plasmonic resonance wavelength of gold nanoparticles/gold nanorods) the generated photothermal response assists the rapid release of cancer destroying drug molecules from the surface of gold nanoparticles/gold nanorods can result in enhanced antitumor activity. Additionally, the fluorescent nanodiamonds can be conjugated with gadolinium(III), wherein gadolinium (III) concentrations can be varied to realize the highest contrast enhancement in magnetic resonance imaging and also the fluorescent nanodiamonds can be functionalized with a cancer specific biomarker binder(s) to bind with a cancer specific biomarker(s). Alternatively/additionally, a magnetic imaging system can be integrated with a positron emission tomography system to detect cancer cells and a computer controlled focused beam of x-ray and/or proton beam can be utilized to destroy cancer cells.

The particular pH sensitive multifunctional nanoshell 120/nanocarrier 160 can encapsulate/cage manganese ions, fluorescent nanodiamonds, gold nanoparticles/gold nanorods and upconverting nanoparticles. A hairpin DNA structure can be covalently conjugated on the surface of gold nanoparticles/gold nanorods and cancer destroying drug molecules (e.g., camptothecin/doxorubicin/paclitaxel molecules) can be intercalated into the adjacent base pairs of hairpin DNA structures. The particular pH sensitive nanoshell 120/nanocarrier 160 can break in a pH range of the cancer microenvironment—thus increasing contrast in magnetic resonance imaging. Upon visible light excitation (e.g. at 532 nanometers, at plasmonic resonance wavelength of gold nanoparticles/gold nanorods) the generated photothermal response assists the rapid release of cancer destroying drug molecules from the surface of gold nanoparticles/gold nanorods can result in enhanced antitumor activity. Furthermore, upon infrared light excitation, the light sensitive upconverting nanoparticle can generate localized reactive oxygen species to destroy cancer cells. Additionally, the fluorescent nanodiamonds can be conjugated with gadolinium(III), wherein gadolinium(III) concentrations can be varied to realize the highest contrast enhancement in magnetic resonance imaging and also the fluorescent nanodiamonds can be functionalized with a cancer specific biomarker binder(s) to bind with a cancer specific biomarker(s). Alternatively/additionally, a magnetic imaging system can be integrated with a positron emission tomography system to detect cancer cells and a computer controlled focused beam of x-ray and/or proton beam can be utilized to destroy cancer cells.

By Way of an Example and not by Way of any Limitation, an Exosome as a Disease Specific Biomarker A disease specific biomarker 460 can indicate the progression of a disease. Exosome (40 nanometers to 100 nanometers in diameter) and microvesicle (>100 nanometers to 1000 nanometers in diameter) are small vesicles that are shed by cells periodically. On an average, each exosome contains only 1 to 10 RNA molecules, wherein each RNA molecule has an average of 100 nucleotides. However, taking into account that exosomes are present in very high numbers in body fluids (typically $>10^9$ per mL), as a population they are capable of inducing significant biological effects.

An exosome and/or a microvesicle carry messenger RNAs, micro-RNAs and signaling proteins. An exosome contains RNAs or other molecules. Cells communicate with each other by sending and receiving exosomes—thus an exosome can be viewed as a unit for cell-to-cell biological communication (molecular Twitter) directly by surface expressed ligands or transferring molecules from the originating cells. For example, exosomes can carry material from the originating cancer cells to suppress the immune system and stimulate angiogenesis for the growth of cancer cells.

An exosome and/or a microvesicle can be isolated from a human body's blood/biological fluid by ultracentrifugation and filtration. An exosome can contain many types of molecules such as: small RNAs, including miRNA, Y-RNA, piwi-RNA and tRNA. The circulating level, origination and message transported by an exosome and/or a microvesicle can be utilized as a disease specific biomarker 460. A specific microRNA in an exosome and/or a microvesicle isolated from a disease specific blood can be elevated compared to an exosome and/or a microvesicle isolated from non-disease specific blood. Thus, microRNA analysis within an exosome and/or a microvesicle can be utilized to predict a patient-specific disease, before any clinical symptoms occur.

Relevant properties of an exosome and/or a microvesicle are size, size distribution, density, morphology, composition and zeta potential. Furthermore, an exosome and/or a microvesicle as a disease specific biomarker can be selectively qualified and/or quantified by a disease specific biomarker binder, wherein the disease specific biomarker binder is coupled with a fluorophore (e.g., a quantum dot fluorophore) or a photoswitchable fluorophore.

By Way of an Example and not by Way of any Limitation, a Glycoprotein as a Disease Specific Biomarker Elusive glycoprotein can form when a sugar molecule(s) is attached to a protein. The glycoprotein in the biological fluid/blood can indicate a disease (including a cancer). A nano-scaled polymer can be utilized to chemically couple with a sugar molecule to indentify the glycoprotein.

By Way of an Example and not by Way of any Limitation, Engineered Nanoparticles/Nanosensors Attached with a Disease Specific Enzyme(s)/Protein(s)/mRNA Fragment(s) as a Disease Specific Biomarker Binder Injected engineered nanoparticles/nanosensors in a human body can attach with a disease specific enzyme(s)/protein(s)/fragment(s) of mRNA(s). Such engineered nanoparticles/nanosensors attached with a disease specific enzyme(s)/protein(s)/mRNA(s) fragment(s) can be found in blood/biological fluid. For example, p24-a protein related to HIV infection and endoproteases enzymes related to various cancers can be identified as biomarkers.

By Way of an Example and not by Way of any Limitation, an Antibody or Aptamer/Aptamer Sensor or Synthetic/Engineered Riboswitch or Molecular Beacon/Riboswitch Beacon as a Disease Specific Biomarker Binder A disease specific biomarker binder 240C can be a specific antibody/synthetic antibody/aptamer/aptamer beacon/molecular beacon/synthetic or an engineered riboswitch/synthetic or an engineered ribowitch beacon.

A synthetic antibody is a supramolecular form aptamer component containing one or more functional groups (e.g., amino acids, fatty acids, carbohydrates, small organics and/or metals) into a unique orientation. The order and proximity of these functional groups can play a role in enhanced functionalities ranging from higher affinities and specificities.

There are DNA aptamers or RNA aptamers or XNA aptamers or peptide aptamers. DNA/RNA/XNA aptamers generally consist of short strands of oligonucleotides. Peptide aptamers generally consist of a short variable peptide domain, attached at both ends to a protein scaffold.

Furthermore, an aptamer can be a (fluorescence) wavelength-shifting aptamer, wherein upon binding a (fluorescence) wavelength-shifting aptamer switches fluorescence wavelength from one wavelength to another wavelength. Thus, a (fluorescence) wavelength-shifting aptamer can reduce background signals in a human body's blood/biological fluid.

A molecular beacon is looped like a hairpin. The loop-like hairpin can contain a molecular probe sequence, which is complementary to a disease specific nucleic acid molecule. The molecular beacon can be chemically coupled with a fluorophore at one end and a non-fluorescent quencher at the other end.

Furthermore, in addition to molecular quenchers, many nanomaterials (e.g., graphene oxide) also possess excellent quenching efficiency.

Upon binding to the disease specific nucleic acid molecule, the molecular probe sequence undergoes a spontaneous conformational reorganization, which removes the fluorophore from the vicinity of the quencher and restores its fluorescence.

Optionally, the molecular beacon can be chemically coupled with two (2) or more fluorophores/quantum dot fluorophores, assembled/fabricated/constructed, utilizing the tip of an atomic force microscope.

Furthermore, the molecular beacons chemically coupled with fluorophores (each fluorophore has a distinct fluorescence emission) can be utilized as an array of disease specific biomarkers.

Similar to the molecular beacon, a synthetic/engineered riboswitch beacon can be chemically coupled with a fluorophore at one end and a non-fluorescent quencher at the other end.

Furthermore, each synthetic/engineered riboswitch can be designed with a synthetically designed biological logic circuit wherein the output of one synthetic or engineered riboswitch can activate/deactivate another downstream synthetic or engineered riboswitch with a synthetically designed biological logic circuit. This can enable one to answer whether biological fluid/blood contains a biomarker A and biomarker B, but not a biomarker C.

By Way of an Example and not by Way of any Limitation, Molecular Three-Dimensional Self-Assembly of Biomarker Binder Utilizing a molecular self-assembly process, a three-dimensionally organized (e.g., an array) biomarker binder (e.g., an antibody/aptamer/riboswitch) can be fabricated/constructed in a suitable polymer matrix (e.g., poly(N-isopropylacrylamide)) to enable improved sensitivity. The biomarker binder and polymer matrix can repel each other, so that the biomarker binders can arrange themselves in a structure/configuration that minimizes chemical interactions between them.

Array of Fluidic Containers Sudden/Abruptly Constricted Fluid Channels Based Optical Integrated Diagnostic Biomodule (Configured by an Array of Optical Fibers, a N×1 Optical Switch & Multiplexing of Biomarker Binders) for Detection of a Disease Specific Biomarker/an Array of Disease Specific Biomarkers A way to inject a large molecule, nanoshell 120, protein/viral protein and RNA (from a micro reservoir/microelectromechanical-system reservoir) into a cell/stem cell/T cell is by squeezing the cell/stem cell/T cell through a (planar) sudden/abruptly constricted fluid channel. During such a passage through the (planar) sudden/abruptly constricted (about 25% to 75% smaller than the diameter of cell/stem cell/T cell) fluid channel at a high speed, a temporary tiny opening in the cell/stem cell/T cell membrane is formed, without any permanent damage to the cell/stem cell/T cell.

The above configuration can be utilized to (a) inject bioactive compounds 100 and/or bioactive molecules 100A or (b) the nanoshell 120 to synthesize protein on-demand (as discussed earlier) or (c) the nanoshell 120 to deliver the CRISPR-Cas9 or optogenetics CRISPR-Cas9 system into cell/stem cell/T cell (as discussed earlier) to analyze the effectiveness of the bioactive compounds 100 and/or the bioactive molecules 100A and/or synthesized protein on-demand. An amino acid, DNA/modified DNA (wherein DNA/modified DNA encapsulated/caged in/with a photolabile protecting group) and a ribosome can be encapsulated/caged in the nanoshell 120. An incident light can activate the photolabile protecting group to synthesize a desired protein on-demand in-vitro and in-vivo in the nanoshell 120.

The above configuration can be utilized to inject a viral protein into immune cells to analyze the effectiveness of the viral protein. The above configuration can be also utilized to inject a protein to differentiate stem cells (into specialized tissues) to analyze the effectiveness of the protein.

For injecting and/or analyzing an array of large molecules, nanoshells 120, proteins/viral proteins and RNAs into a diversity of different cells/stem cells, a cascaded configuration of an array of (planar) sudden/abruptly constricted fluid channels can be utilized.

For example, an array of fluid containers based integrated optical diagnostic biomodule 700.3/700.4 can be further integrated by an array of (planar) sudden/abruptly constricted fluid channels, wherein each (planar) sudden/abruptly constricted fluid channel in a horizontal plane is connected/coupled with each fluid container.

A fluid container or a zero-mode waveguide can be integrated by an array of (planar) sudden/abruptly constricted fluid channels.

Array of Liquid Core Ring Resonators Sudden/Abruptly Constricted Fluid Channels Based Optical Integrated Diagnostic Biomodule for Detection of a Disease Specific Biomarker/an Array of Disease Specific Biomarkers Optionally a cascaded configuration (for injecting an array of large molecules, nanoshells 120, proteins/viral proteins and RNAs one after another in a cascaded manner into a diversity of different cells/stem cells) of an array of (planar) sudden/abruptly highly constricted fluidic channels can be integrated with an array of liquid core optical ring resonators.

Each liquid core optical ring resonator has a fluidic container, whose circular cross section forms a ring resonator. A human body's blood/biological fluid can be passed through the liquid core optical ring resonator capillary, while a waveguide arranged perpendicularly to the fluidic container configured to deliver/couple light into a human body's blood/biological fluid core optical ring resonator wall evanescently via a presence of the evanescent field of the whispering gallery mode.

The liquid core optical ring resonator and the whispering gallery mode derive its sensitivity from monitoring frequency shift, induced by binding (of a biomarker with a biomarker binder) at the sites of highly confined field intensities.

Furthermore, the field intensity can be amplified by excitation of plasmon resonances in a nanoparticle layer/layer of an array of plasmonic optical nanoantennas attached to a fluorophore.

By way of an example and not by way of any limitation, a plasmonic optical nanoantenna can consist of two triangular pieces of gold, each about 75 nanometers long, whose tips face directly across from each other in the shape of a miniature bowtie.

One method to increase the sensitivity is to implement a reference measurement in a proximate liquid core optical ring resonator capillary.

Another method to increase the sensitivity is by pushing more light for more light-matter interaction or by reducing the wall thickness and/or fabricating concentric rings.

In-Situ DNA Microarray Chip with Dual Array of Micromirrors to Determine Suitability of Bioactive Compounds &/or Bioactive Molecules for Treating a Disease/an Array of Diseases As before, an array of miniature mirrors to pattern/deflect light via a combination of a shutter and a lens to the bottom of each fluidic container (for example in FIG. 12A) from a single light source. This particular configuration can enable the analysis of each fluidic container at a time.

Furthermore, each fluidic container (for example in FIG. 12A) with a flat rectangular bottom can be coupled to an optical fiber (and DNA synthesizer as well).

The array of micromirrors (as virtual masks) can reflect/focus the desired pattern of light (e.g., ultraviolet light/nitrogen laser beam onto the flat rectangular bottom via a combination of a shutter and lens-including a metamaterial negative refractive index optical superlens) with individually addressable mirrors controlled by a computer. Each micromirror is individually controlled and it can rock on its angle about 2 milliseconds time scale.

A metamaterial negative refractive index optical superlens can be fabricated/constructed, utilizing nanoscale patterns (e.g., photonic crystals).

However, a metamaterial negative refractive index optical superlens for ultraviolet light can be fabricated/constructed, utilizing alternating nanometer-thick layers of silver (Ag) and titanium dioxide ($TiO_2$)—This type of design has a stack of strongly coupled waveguides sustaining backward waves, the metamaterial exhibits a negative index of refraction to incoming light, regardless of its angle of propagation.

Furthermore, the computer also controls the delivery of chemicals. The light can cleave a photo-labile protecting group at the precise location wherein the next nucleotide is to be coupled. The desired pattern of light can be coordinated with the DNA synthesizer, such that there are 385,000 to 4.2 million unique probes on a DNA microarray chip.

Such a DNA microarray chip in fluidic container can enable a suitability measurement of bioactive compounds 100 and/or bioactive molecules 100A in treating a disease.

Electrical Diagnostic Biomodule for Detection of a Disease Specific Biomarker/an Array of Disease Specific Biomarkers Graphene is a two-dimensional crystal with a high carrier mobility and low noise. It has the ideal properties to be an excellent component of electrical circuits. Graphene epitaxially grown on silicon carbide (SiC) substrate can be suitable for production of electrical circuits.

Graphane is a graphene variant, wherein hydrogen atoms are attached to the carbon lattice in insulating layers.

Graphyne is a one-atom-thick sheet of carbon that resembles graphene, except that its two-dimensional framework (of atomic bonds) contains triple bonds in addition to double bonds.

Graphyne has a graphene-like electronic structure resulting in effectively massless electrons due to Dirac Cones. All electrons are travelling at roughly the same speed (about 0.3 percent of the speed of light). This uniformity leads to conductivity greater than copper.

Graphyne can be utilized as a semiconductor practically as-is, rather than requiring noncarbon dopant atoms to be added as a source of electrons, as noncarbon dopants are required for graphene. Furthermore, structures of graphyne crystals allow electrons to flow in one direction.

Molybdenite ($MoS_2$) is also a two-dimensional crystal with a natural bandgap. It can be suitable for production of electrical circuits.

Figure 13A:
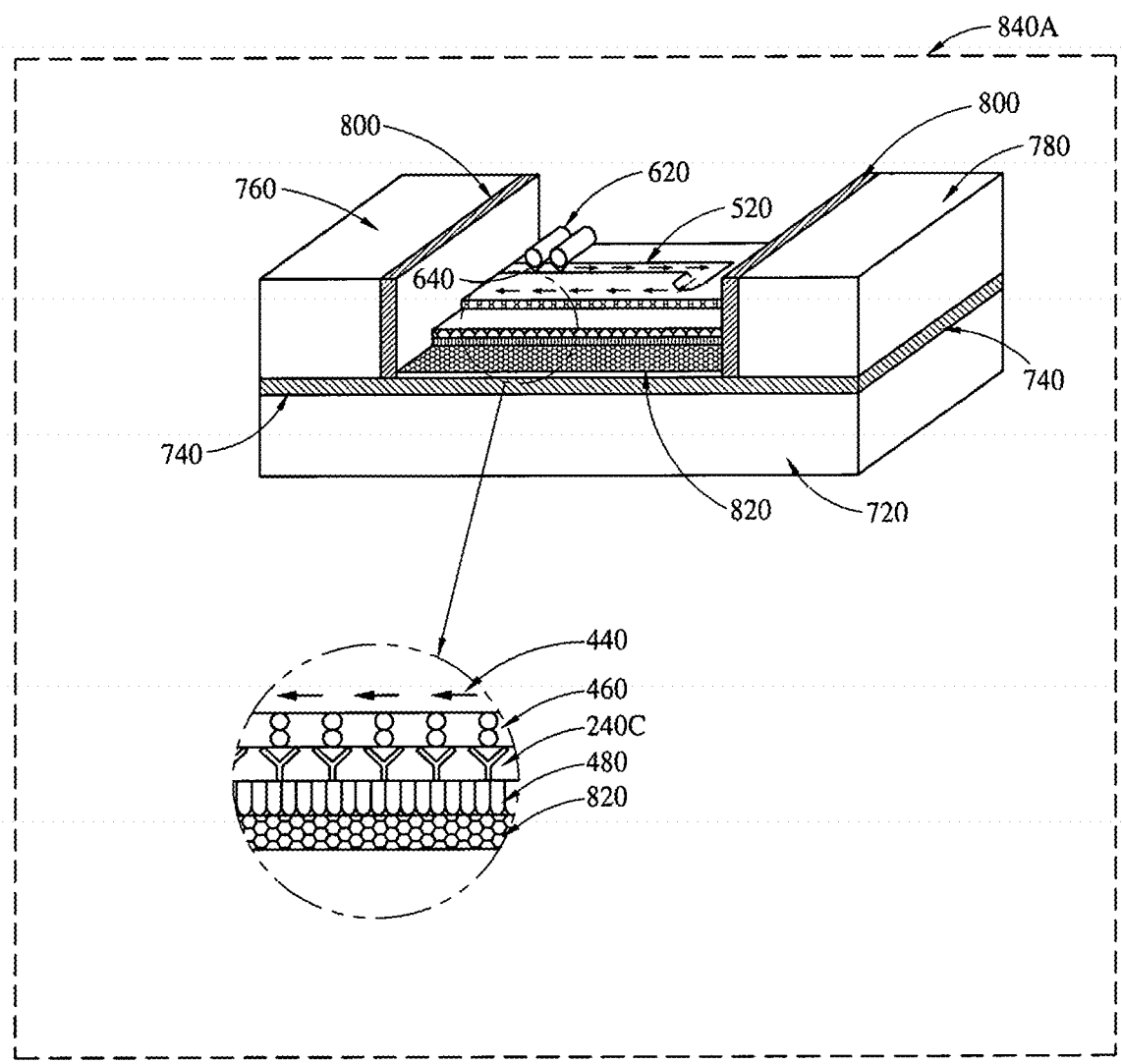
FIGS. 13A, 13B and 13C illustrate (a two-dimensional crystal based field effect transistor based integrated electrical diagnostic biomodules (various embodiments) to detect a disease specific biomarker/an array of disease specific biomarkers.

FIG. 13A illustrates an electrical diagnostic biomodule 840A based on changes in electrical characteristics of a two-dimensional crystal based field effect transistor (e.g., graphene or molybdenite) due to a disease specific biomarker 460 (in a patient's biological fluid 440) which can be propagated through a fluidic channel 620 to a fluidic cavity 520).

The disease specific biomarker 460 can chemically bind with a disease specific biomarker binder 240C on the optional biomolecular interface layer 480 on a single layer of the two-dimensional crystal substrate 820.

The field effect transistor can integrate: a semiconductor substrate as a gate 720, a gate oxide insulator thin-film 740, a source metal thin-film 760, a drain metal thin-film 780, a polymeric insulator thin-film 800 and a two-dimensional crystal substrate 820.

Furthermore, graphene's ability to form chemical bonds can be turned on or turned off based on what is underneath the graphene. When silicon dioxide is underneath graphene, it is reactive when exposed to certain biomarkers/chemicals. But when boron nitride is underneath graphene, it is not reactive when exposed to certain biomarkers/chemicals. An array of materials (e.g., an array of boron nitride and silicon dioxide) underneath graphene can be utilized with an array of sensors to detect a trace amount of biomarkers/chemicals.

Microelectro-Mechanical-System Biomodule to Draw/Propagate Blood

Figure 13B:
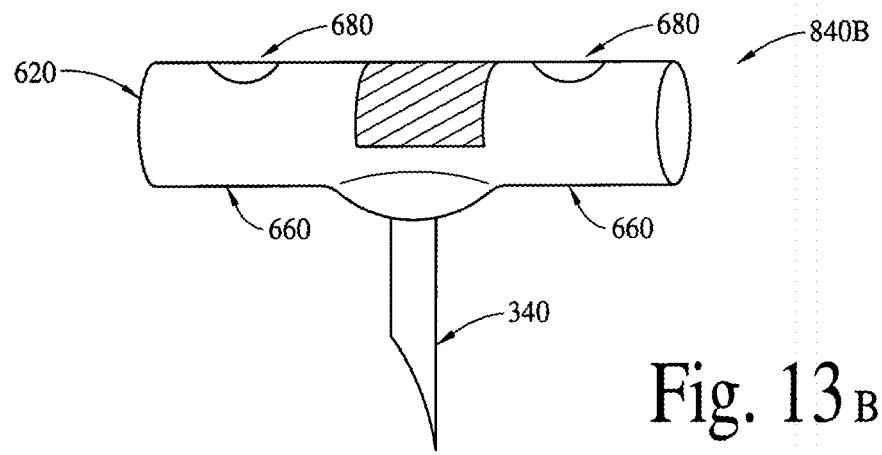

FIG. 13B illustrates a microelectro-mechanical-system biomodule 700B to draw blood from a patient, utilizing the microneedle 340, which can be monolithically integrated with a micromachined (voltage deflectable) membrane 660, a membrane sensor 680 and a fluidic channel 620.

A microneedle 340 can be electrically powered and programmed to draw the patient's blood at a periodic interval of time.

Furthermore, the microelectro-mechanical-system biomodule 700B can include an array of microneedles 340, an array of micromachined membranes 660, an array of membrane sensors 680 and an array of fluidic channels 620.

Furthermore, an array of fluidic channels 620 can be placed onto an array of precise silicon/ceramic v-grooves 640.

The array of precise silicon/ceramic v-grooves 640 can be enclosed within a precisely machined connector (not shown in the FIG. 13B).

The precisely machined connector can be attached precisely/detached from the microelectro-mechanical-system biomodule for drawing/propagating the patient's blood.

Figure 13C:
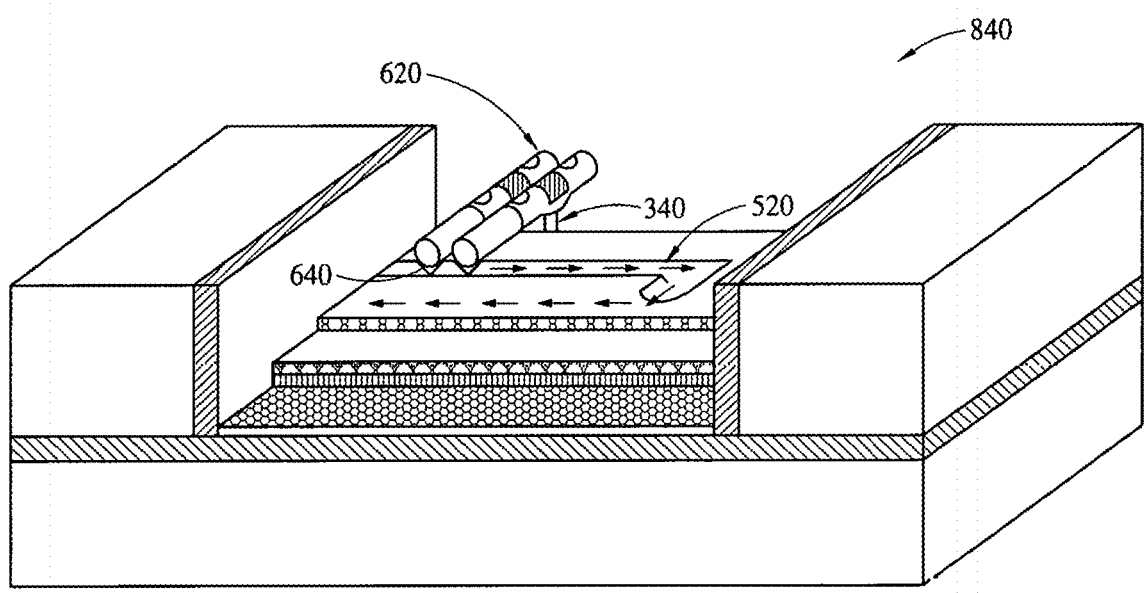

An Integrated Two-Dimensional Crystal Field-Effect Transistor Based Electrical Diagnostic Biomodule for Detection of a Disease Specific Biomarker/an Array of Disease Specific Biomarkers FIG. 13C illustrates an integrated two-dimensional crystal field-effect transistor based electrical diagnostic biomodule 840.

Engineered Protein Based Field-Effect Transistor to Replace Two-Dimensional Crystal Field-Effect Transistor Furthermore, the two-dimensional crystal field-effect transistor can be replaced by an engineered protein based field-effect transistor. The engineered protein based field-effect transistor can be fabricated/constructed, utilizing a suitable material decorated on engineered protein (e.g., a three-dimensional ball and spike engineered protein-synthesized by a fusion of both Dps and gp5c genes).

Figure 13D:
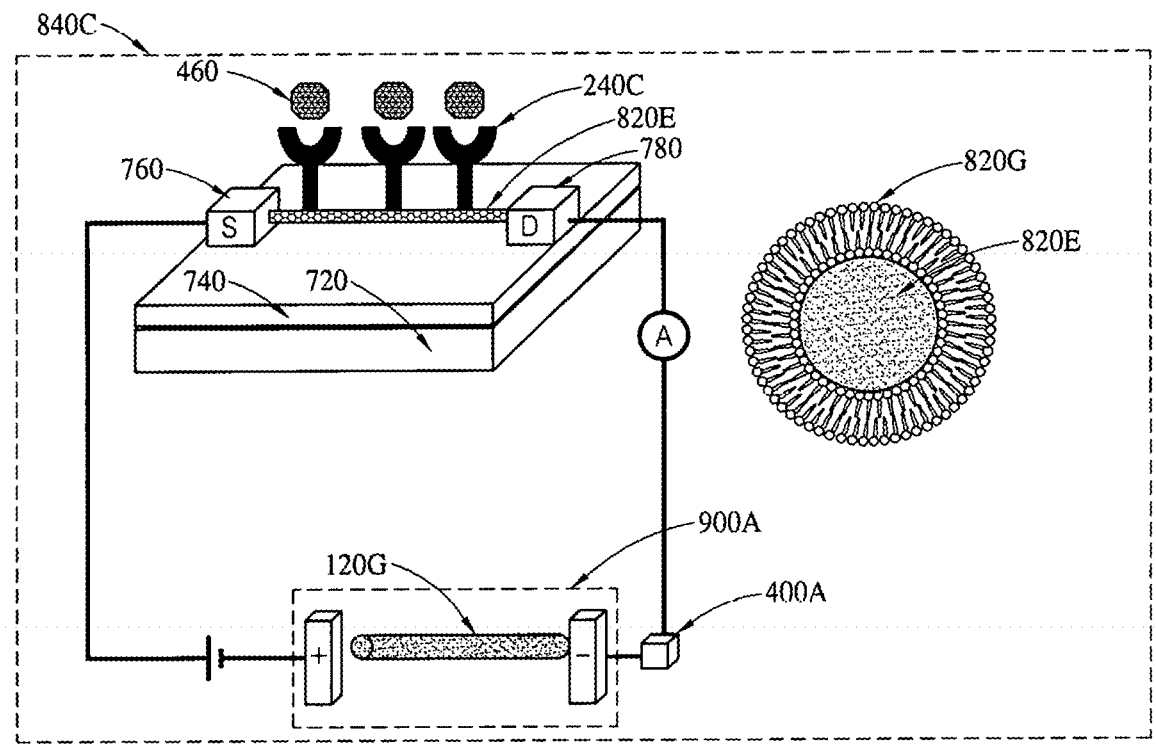
FIG. 13D illustrates chitosan/melanin based proton field effect transistor ($H^+$ FET) integrated with a lipid layer and a nanotransmitter to detect a disease specific biomarker/an array of disease specific biomarkers.

Proton Based Field-Effect Transistor Decorated with a Lipid Layer to Replace Two-Dimensional Crystal Field-Effect Transistor FIG. 13D illustrates a proton field-effect transistor and it incorporates a semiconductor substrate as a gate 720, a gate oxide insulator thin-film 740, a source metal thin-film 760, a drain metal thin-film 780 for proton current and a nanowire 820E.

Palladium hydride contacts can replace the source metal or drain metal. The chitosan/melanin based nanowire 820E (connecting the source metal thin-film 760 and the drain metal thin-film 780) can be decorated with a lipid layer (a double wall of oil molecules, that biological cells utilizes to separate its inside from its outside environment) 820G. The lipid layer 820G can be decorated with a disease specific biomarker binder 240C.

The disease specific biomarker binder 240C can chemically bind with a disease specific biomarker 460—thus it can change the electrical characteristics of the proton field-effect transistor 820E.

Furthermore, the proton field-effect transistor can be integrated with a nanotube (e.g., a boron nitride/carbon/tubular structure nanotube, fabricated/constructed by DNA/RNA origami process) 120G based nanoradio transmitter with a nanoantenna 900A.

The nanotube 120G based nanoradio transmitter with the nanoantenna 900A can be electrically powered by a nanobattery 400A.

A miniaturized non-rechargeable lithium battery can replace the nanobattery 400A.

Glucose fuel cells (fabricated/constructed on a silicon substrate with integrated platinum catalyst to strip electrons from glucose) can replace the nanobattery 400A.

M13 bacteriophage can translate mechanical energy into electrical energy. To improve the piezoelectric property of M13 bacteriophage, the outer protein layer of M13 bacteriophage can be engineered by adding appropriate molecules. Furthermore, to amplify the piezoelectric effect, multi-layers of engineered M13 bacteriophage can be utilized. Multi-layers of engineered M13 bacteriophage can then be sandwiched between two biocompatible electrodes to act as a battery, when stressed mechanically (e.g., by a cardiac cycle).

Similarly, prestin protein can convert tiny vibrations into a voltage output. Each prestin protein is only capable of making nanowatts of electricity. Many prestin proteins can be sandwiched between two biocompatible electrodes to act as a battery, when stressed mechanically (e.g., by a cardiac cycle).

Furthermore, in melanin based electrical circuits both electron and proton can be utilized. A chitosan/melanin based proton field-effect transistor integrated with the nanoradio transmitter with a nanoantenna 900A and the nanobattery 400A can be indicated as 840C.

Figure 13E:
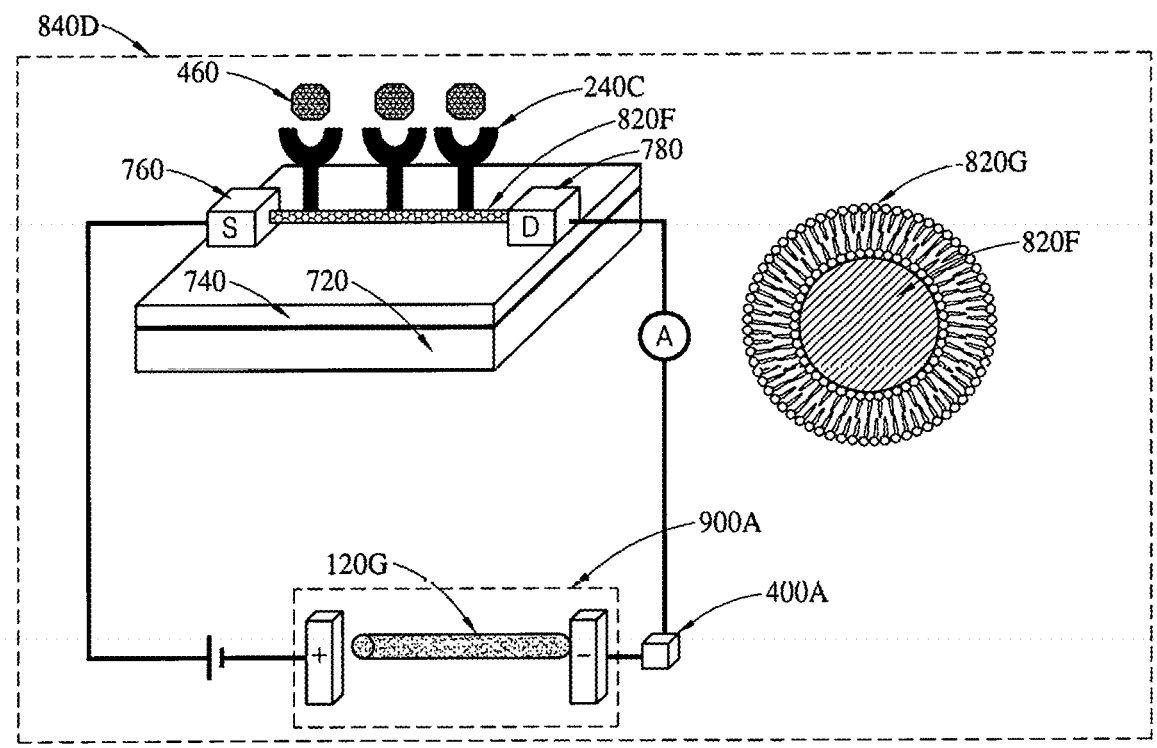
FIG. 13E illustrates a silicon nanowire based field effect transistor integrated with a lipid layer and a nanotransmitter to detect a disease specific biomarker/an array of disease specific biomarkers.

Silicon Nanowire Based Field-Effect Transistor Decorated with a Lipid Layer to Replace Two-Dimensional Crystal Field-Effect Transistor FIG. 13E illustrates a similar configuration as 13D except that a silicon nanowire replaces the chitosan/melanin nanowire.

A silicon nanowire field-effect transistor 820F integrated with the nanotube 120G based nanoradio transmitter, the nanoantenna 900A and the nanobattery 400A can be indicated as 840D.

Furthermore, the silicon substrate of silicon nanowire field-effect transistor 820F can also be replaced by just melanin or a conducting polymer.

A nanoantenna printed on a biocompatible material (e.g., silk) can be placed in (within) a human body such that any change in current flow in the nanoantenna can induce a change in the radio transmitter placed on a human body.

Furthermore, device configurations, as illustrated in FIG. 13D or 13E can be integrated with an organic semiconductor circuit. A shape memory polymer can be laminated and cured on the organic semiconductor circuit or on the device, as illustrated in FIG. 13D or 13E.

Interface Electrode

Boron-doped conducting diamond-like material can be grown on a silicon dioxide substrate by a chemical vapor deposition process at about 900 degrees' centigrade.

Boron-doped conducting diamond-like material can be bonded on a polymer substrate and then lifted off from the silicon dioxide substrate by hydrofluoric acid.

Thus, a boron-doped conducting diamond-like material can act as an interface electrode for any biological application.

It should be noted an implantable (within a human body) miniature diagnostic biomodules 840C and 840D can be rendered nonfunctional due to biofouling, because of a triggered immune response.

A thermoresponsive material can contract and expand in response to changes in temperature. Thus, the implantable (within a human body) miniature diagnostic biomodule can be coated with a biocompatible thermoresponsive material (e.g., hydrogel). By increasing the temperature of the biocompatible thermoresponsive material, the thermoresponsive material contracts, as proteins and cells are dislodged from the coated surface of the thermoresponsive material. When the heat is removed, the thermoresponsive material can return to its normal state. This heating/cooling process can be repeated until the implantable (within a human body) miniature diagnostic biomodule is cleaned from biofouling.
Detection of a Disease Specific Biomarker/an Array of Disease Specific Biomarkers & Programmable/Active Delivery of Bioactive Compounds/Bioactive Molecules in Near Real-Time/Real-Time If 840C/840D detects an abnormal level of a disease specific biomarker 460, then the nanoradio transmitter with the nanoantenna 900A can transmit the information so that a microelectro-mechanical-system reservoir can enable a programmable/active delivery of the bioactive compounds 100 and/or bioactive molecules 100A in near real-time/real-time via a dynamic closed feedback loop.

Furthermore, an array of 840C/840D can be utilized instead of a single 840C/840D.

Nanostructure Based Diagnostic Biomodule for Label-Free Detection of a Disease Specific DNA/Protein or an Array of Disease Specific DNAs/Proteins A probe DNA can be attached to a lipid layer on a nanostructure (e.g., carbon nanotube/boron nanotube), utilizing an electrochemical functionalization. The lipid layer can be replaced by a suitable polymer layer. Alternatively, the nanostructure can be decorated by a lipid-functional-spacer construct, which is commercially available from Kode Biotech.

In particular, the nanostructure can be decorated by a lipid-functional-spacer construct at a single point defect (e.g., fabricated/constructed by electrochemical oxidation/electrochemical etching/atomic force microscopy based nanolithography) of the nanostructure. Alternatively, the nanostructure can be decorated by an aptamer, utilizing the DNA origami fabrication process at a single point defect of the nanostructure. The detection can be based on a unique impedance measurement technique coupled to a field effect transistor device, when a complementary target DNA binds with a probe DNA or a probe DNA at the single point defect. Alternatively, a probe DNA can be replaced by a disease specific designer protein. A disease specific designer protein has a leave-one-out configuration, wherein each protein has an omitted segment to create a binding site to fit a protein for a specific disease.

In addition to a unique impedance measurement technique coupled to a field effect transistor device by electrical method, the nanostructure can naturally fluoresce in its native state (e.g., prior to a complementary target DNA binding with a probe DNA), when excited by light (e.g., light from a laser or a light source, utilizing a two-dimensional material (e.g., graphene) as described in FIG. 12Z1), but fluorescence emission from the nanostructure will change from its non-native state (e.g., upon binding complementary target DNA with a probe DNA). This change in fluorescence emission can be utilized for detection of disease specific DNAs and/or proteins and this change in fluorescence emission can be enhanced by integration of one or more three-dimensional protruded structures and/or photonic crystals.

Furthermore, a particular two-dimensional material-graphene's ability to form chemical bonds can be turned on or tuned off based on what is underneath the graphene. When silicon dioxide is underneath graphene, it is reactive when exposed to certain biomarkers/chemicals. But when boron nitride is underneath graphene, it is not reactive when exposed to certain biomarkers/chemicals. An array of materials (e.g., an array of boron nitride and silicon dioxide) underneath graphene can be utilized by an array of sensors to detect a trace amount of biomarkers/chemicals.

Furthermore, an array of nanostructures can be utilized instead of a single nanostructure for label-free detection of an array of disease specific DNAs and/or proteins by an electrical and/or optical method. The nanostructures (on a distinct semiconductor substrate (e.g., silicon) for electrical method and on another distinct substrate (e.g., quartz) for optical method) can be integrated with a complementary metal-oxide semiconductor integrated circuit and/or a microfluidic device/nanofluidic device/flow cell. However, it should be noted that a transparent semiconductor substrate can minimize the need for two distinct substrates. Such an array of nanostructures can enable the detection of bacterial infection via quorum sensing (which allows bacteria to communicate with each other to coordinate their gene expression), disease specific biomarkers, engineered cells'/stem cells' expression of therapeutic proteins (e.g., as obtained through a (planar) sudden/abruptly constricted fluid channel in cell/stem cell/T cell), neural functions and viral infection.

Nanohole Based Diagnostic Biomodule for Detection of a Disease Specific Biomarker/an Array of Disease Specific Biomarkers Four (4) molecules, when chemically bonded together that make up the structural units of DNA are: adenine (A), cytosine (C), guanine (G) and thymine (T). A segment of a DNA strand can be a gene.

Four (4) molecules, when chemically bonded together that make up the structural units of RNA are: adenine (A), cytosine (C), guanine (G) and uracil (U).

Figure 14A:
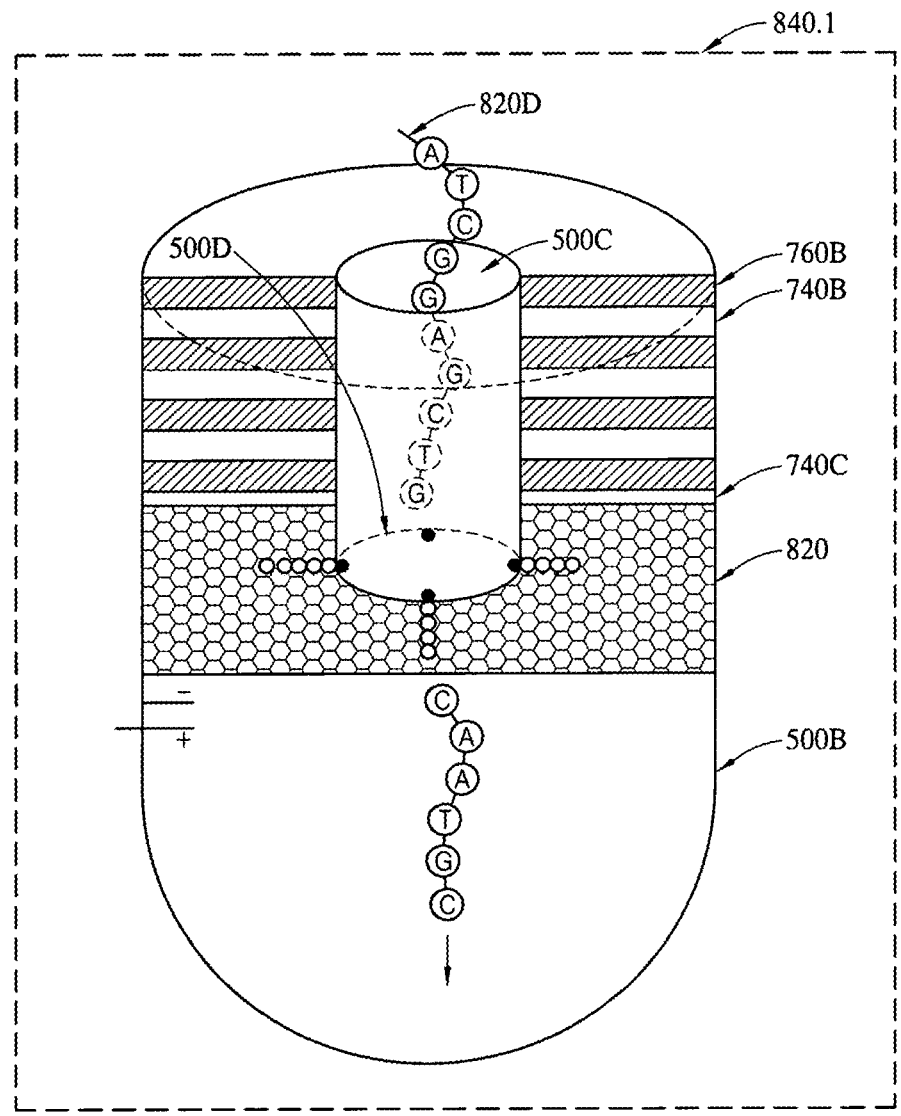
FIGS. 14A and 14B illustrate a nanohole based single molecule DNA/RNA sequencing electrical diagnostic biomodule to detect a disease specific biomarker/an array of disease specific biomarkers (by measuring an alteration/elimination of a single molecule of a single stranded DNA/RNA).

FIG. 14A illustrates a nanotunnel 500C. The nanotunnel 500C can be fabricated/constructed, utilizing a low-temperature atomic layer deposition process on an atomically thick substrate.

Multi-layers of dielectrics 740B and metals 760B are embedded in the nanotunnel 500C.

A nanohole 500D is about 1.5 nanometers in diameter. The nanohole 500D can be fabricated/constructed just below the nanotunnel 500C.

Through an amazing coincidence, the graphene layer's thickness is about 3.35A° or 0.335 nanometers, which exactly fits the gap between two DNA/RNA molecules. Hence, the nanohole 500D can be fabricated/constructed from atomically thick graphene.

Alternatively, the nanohole 500D can also be fabricated/constructed, utilizing two-dimensional material like molybdenum disulfide.

Alternatively, the nanohole 500D can also be fabricated/constructed, utilizing a tunable self-assembly material $Ni_3(HITP)_2$, which is a combination of nickel and an organic compound: HITP (2,3,6,7,10,11-hexaiminotriphenylene). $Ni_3(HITP)_2$ has graphene's perfectly hexagonal honeycomb crystal structure. Furthermore, multiple thin-layers of $Ni_3(HITP)_2$ naturally form perfectly aligned stacks, with the openings at the centers of the hexagons of about 2 nanometers. Since, $Ni_3(HITP)_2$ has a natural bandgap, electronic circuits can also be fabricated/constructed.

Alternatively, the nanohole 500D can also be fabricated/constructed, utilizing the DNA/RNA origami process on the same atomically thick substrate. The DNA/RNA origami structure can be fabricated/constructed into an accurately controlled size/shape of the nanohole 500D.

The nanohole 500D has four (4) embedded tunneling metal electrodes 820A. The four (4) embedded tunneling electrodes 820A are metal (e.g., gold nanoparticle based) tunneling electrodes. The four (4) embedded tunneling metal electrodes 820A can be fabricated/constructed, utilizing the DNA/RNA origami process.

Optionally, the tips of the tunneling metal electrodes 820A can have ultrasharp apexes with radii of curvatures of less than 1 nanometer. Electromagnetic fields are enhanced at the tip of the ultrasharp tunneling metal electrodes 820, when they are irradiated with laser light. Electromagnetic field enhancement can lead to an amplification of signals to enable even single molecule detection. The ultrasharp tunneling metal electrodes 820 can enable field enhancement of $10^{11}$ and lateral resolution less than 0.2 nanometers to identify/distinguish a single molecule of the single stranded DNA/RNA 820D by laser induced Raman spectroscopy. The ultrasharp tunneling metal electrodes 820 can be coated with a monolayer of diamond thin-film for contamination-free operation, stability and reliability.

The DNA origami process is a template for the design and fabrication of nano-scaled structures. One can engineer selected staple strands on a DNA origami structure with site-specific attachment of gold nanoparticles to fabricate conducting nanowires from the DNA origami nanostructure.

Similarly, the RNA origami template can replace the DNA origami template.

By way of an example and not by way of any limitation, the DNA/RNA origami structure with site-specific attachment of gold nanoparticles can act as a tunneling metal electrode.

Furthermore, polythiophene, a light emitting diode (LED) polymer molecule can be chemically bonded/attached/integrated with the tunneling metal electrode or chemically bonded/attached/integrated with the tip of the tunneling metal electrode.

Figure 14B:
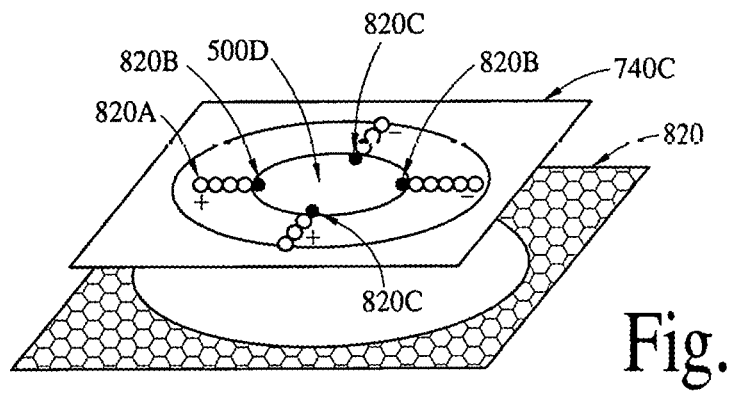

FIG. 14B illustrates a set of two (2) embedded tunneling metal electrodes 820A diametrically positioned as opposite to each other.

FIG. 14B also illustrates another set of two (2) embedded tunneling metal electrodes 820A diametrically positioned as opposite to each other.

The nanohole 500D can be mechanically supported on a larger (about 2 nanometers in diameter) nanohole in an atomically thick dielectric 740C.

The dielectric 740C can be fabricated/constructed, utilizing a low-temperature atomic layer deposition process.

The larger (about 2 nanometers in diameter) nanohole in the dielectric 740C can be fabricated/constructed, utilizing electron beam lithography and focused ion beam etching.

Furthermore, the larger nanohole (about 2 nanometers in diameter) in the dielectric 740C can be mechanically supported on fabricated/constructed on an atomically thick two-dimensional crystal (e.g., graphene, molybdenum sulfide and phosphorene) membrane 820.

The nanohole 740C can be mechanically supported by two (2) atomically thick two-dimensional crystals (e.g., a combination of graphene and phosphorene, or a combination of molybdenum sulfide and phosphorene, or a combination of graphene and molybdenum sulfide).

Alternatively, the nanohole 740C can be fabricated/constructed directly onto the atomically thick two-dimensional crystal membrane 820, which can be further supported by another atomically thick two-dimensional crystal membrane.

It should be noted that molybdenum sulfide is different from other semiconductor materials, because it can be grown in layers of one atom thickness, without compromising its properties. In sharp contrast to graphene, which is a semimetal with no bandgap by nature, molybdenum sulfide monolayers offer an attractive semiconductor option due to a direct bandgap of 1.8 eV. Molybdenum sulfide monolayers are a better candidate than graphene for many electronic and photonic devices. Thus, a molybdenum sulfide monolayer deposited on a suitable substrate can be utilized for (a) an electronics circuit (e.g., an electronics circuit to measure transverse tunneling currents preciously), (b) tunneling electrodes and (c) a nanohole (fabricated/constructed, utilizing electron beam lithography and focused ion beam etching) for identifying molecules in a single stranded DNA/RNA 820D, wherein the substrate in the nanohole area is removed/etched back—further simplifying fabrication/construction of a nanohole based diagnostic biomodule for detection of a disease specific biomarker (e.g., a gene mutation)/an array of disease specific biomarkers.

Unlike graphene, phosphorene is a natural semiconductor. Thus, a phosphorene monolayer deposited on a suitable substrate can be utilized for (a) an electronics circuit (e.g., an electronics circuit to measure transverse tunneling currents preciously), (b) tunneling electrodes and (c) a nanohole (fabricated/constructed, utilizing electron beam lithography and focused ion beam etching) for identifying molecules in a single stranded DNA/RNA 820D, wherein the substrate in the nanohole area is removed/etched back—further simplifying fabrication/construction of a nanohole based diagnostic biomodule for detection of a disease specific biomarker (e.g., a gene mutation)/an array of disease specific biomarkers.

Furthermore, the nanohole in the atomically thick two-dimensional crystal membrane 820 is about 2 nanometers in diameter, which can be optionally integrated with tunnel junctions.

Furthermore, the nanohole in the atomically thick two-dimensional crystal membrane 820 is about 2 nanometers in diameter, which can be optionally integrated with a nanotransistor(s), as described in FIG. 13C, FIG. 13D and FIG. 13E, built on top of the atomically thick two-dimensional crystal membrane 820.

Furthermore, the nanohole in the atomically thick two-dimensional crystal membrane 820 is about 2 nanometers in diameter, which can be optionally integrated with a nanotransistor(s) such as graphene nanoribbon transistor, built on top of the atomically thick two-dimensional crystal membrane 820.

The atomically thick two-dimensional crystal membrane 820 can be a metallic graphene nanoribbon with zigzag edges or metallic chiral graphene nanoribbon or wires made of a two-dimensional topological insulator.

The nanohole 500D can be electrically connected to the atomically thick two-dimensional crystal membrane 820 for reliable electrical contact.

Alternatively, the nanohole 500D can be electrically connected to an atomically thick (about 1 nanometer thick) porous carbon nanomembrane/silicon nitride nanomembrane for reliable electrical contact instead of the atomically thick two-dimensional crystal membrane 820.

A single stranded DNA/RNA 820D can be pulled down through the nanotunnel 500C and nanohole 500D by a vertical electrical field, as the DNA/RNA 820D is electrically charged.

A four-point-probe measurement of transverse tunneling currents (of about $3A°$ long single molecule of the single stranded DNA/RNA 820D) through the nanotunnel 500C and nanohole 500D can electrically identify each single molecule of the single stranded DNA/RNA 820D.

Tunneling is confined to tiny distances such that a tunnel junction can identify about $3A°$ long single molecule (e.g., adenine (A), cytosine (C), guanine (G) and thymine (T) of the single stranded DNA) of the single stranded DNA/RNA 820D at a time without interference from other molecules.

Because of extreme sensitivity requirements in the measurement of transverse tunneling currents, tiny vibrations can severely degrade a tunneling signal.

A tiny voltage bias between the tunneling metal electrodes can enable polythiophene, a light emitting diode (LED) polymer molecule to emit light (e.g., light of red wavelength), which can be detected by a nano-scaled detector (e.g., a detector based on graphene/molybdenum sulfide heterostructure or a detector based on nano-scaled three-dimensional structure or a nanogap detector based on colloidal quantum dot).

Variations in optical intensity detection can also identify the approximately $3A°$ long single molecule (e.g., adenine (A), cytosine (C), guanine (G) and thymine (T) of the single stranded DNA) of the single stranded DNA/RNA 820D at a time without interference from other molecules.

Additionally, current (surrounding the nanohole 560D) through the atomically thick two-dimensional crystal membrane 820 can be also measured, as a single stranded DNA/RNA 820D can be pulled down through the nanotunnel 500C and nanohole 500D by a vertical electrical field, as a DNA/RNA 820D is electrically charged.

A large electric field is needed to push the single stranded DNA/RNA 820D through the nanohole 500D, but the same large electric field can also push single stranded DNA/RNA 820D too rapidly through the nanohole 500D—thus reducing the ability of four embedded tunneling metal electrodes 820A' to sense/read individual molecules in single stranded DNA/RNA, utilizing the four-point-probe measurement of transverse tunneling currents.

However, the pulling speed of the single stranded DNA/RNA 820D can be reduced by traversing the single stranded DNA/RNA 820D through an alternating electric field generated by multi-layers of dielectrics 740B and metals 760B, embedding/surrounding the nanotunnel 500C.

The single stranded DNA/RNA can be chemically coupled to a magnetic nanoparticle to push the single stranded DNA/RNA by a magnetic field in the opposite upward direction with respect to the downward electric field.

Furthermore, the pulling speed of the single stranded DNA/RNA 820D can be reduced by chemically coupling phi29 DNA polymerase enzyme with the single stranded DNA/RNA or to the magnetic nanoparticle.

The tug-of-war between the electric field and the magnetic field (oppositely orientated with respect to each other) can be optimized to reduce the velocity of the single stranded DNA/RNA—thus allowing four embedded tunneling metal electrodes 820A' the ability to sense/read individual molecules in the single stranded DNA/RNA, utilizing the four-point-probe measurement of transverse tunneling currents.

Furthermore, a piezoelectric thin-film (e.g., zinc oxide or gallium nitride thin-film) can be deposited intimately surrounding the nanohole 500D. The piezoelectric thin-film can be deposited by the atomic layer deposition process. The piezoelectric thin-film physically can strain in response to an electric field—thus adjusting approximately the diameter of the nanohole 500D in-situ for reducing the velocity of the single stranded DNA/RNA 820D.

A molecule can either be right-handed (D) or left-handed (L). This property is called chirality. A chiral molecule can recognize/transfer information that has the same chirality (same handedness, L to L or D to D) and discriminate the molecule of different chirality (L to D and D to L).

The diametrically opposite first set of two (2) embedded tunneling electrodes 820A, wherein each embedded tunneling electrode is chemically configured with a recognition molecule 820B such that, the recognition molecule 820B for adenine (A) can effectively clutch adenine (A) of the single stranded DNA/RNA 820D.

The diametrically opposite second set of two (2) embedded tunneling electrodes 820A, wherein each embedded tunneling electrode is chemically configured with a recognition molecule 820C such that, the recognition molecule 820C for guanine (G) can effectively clutch guanine (G) of the single stranded DNA/RNA 820D.

Furthermore, an additional change in edge conduction current can be measured when the single stranded DNA/RNA 820D is pushed through the nanohole in the atomically thick two-dimensional crystal membrane 820.

The atomically thick two-dimensional crystal membrane 820 can be a metallic graphene nanoribbon with zigzag edges (ZGNR) or metallic chiral graphene nanoribbon or wires made of a two-dimensional topological insulator.

Nanohole Integrated with a Suitable Functional/Fluorescent Molecule & a Nanoantenna for Single Molecule Fluorescence/Single Molecule Raman Spectroscopy Furthermore, the single stranded DNA/RNA 820D can be also configured (at a sub-nanometer precision by dip pen lithography) with suitable functional/fluorescent molecules—thus improving the sensitivity and reliability of the molecular identification of the single stranded DNA/RNA 820D.

The nanohole 500D can be integrated (utilizing dip pen lithography) with a suitable functional fluorescent molecule.

Furthermore, the proximity or vicinity of the nanohole 500D can be integrated with a plasmonic optical nanoantenna, for single molecule fluorescence or single molecule Raman spectroscopy, when the single stranded DNA/RNA 820D is also appropriately decorated with suitable functional molecules.

By way of an example and not by way of any limitation, a plasmonic optical nanoantenna can consist of two triangular pieces of gold, each about 75 nanometers long, whose tips face directly across from each other in the shape of a miniature bowtie.

Furthermore, the plasmonic optical nanoantenna can be integrated with a lens based on metamaterial.

It may not be necessary to uniquely identify all four (4) molecules for some applications. A binary conversion of molecular sequence (e.g., A or T=0, and G or C/U=1) can be utilized to identify a disease specific biomarker and/disease specific genomic alteration/elimination in the single stranded DNA/RNA 820D.

Furthermore, statistics enhanced repeated four-point-probe measurements of transverse tunneling currents can reliably identify each single molecule of the single stranded DNA/RNA 820D—thus detecting an alteration/elimination of a single molecule in the single stranded DNA/RNA 820D, without need of PCR and Sanger sequencing.

Furthermore, such a two-dimensional array of the nanotunnels 500C and the nanoholes 500D can sequence many single stranded DNA/RNA 820D in parallel.

Sequencing of DNA/RNA can generate Big Data.

Analysis of Big Data Related to Biology

Big Data can be converted into a smaller data set, utilizing linear simplification and/or signal clustering, as the underlying data has geometrical structures and patterns (repeated over time). Furthermore, signal clustering can be categorized and weighted for importance. Alternatively, topological data analysis or Bayesian analysis coupled with Markov chain Monte Carlo methods can be utilized for analysis of Big Data. Analysis of Big Data can be coupled with an augmented intelligence modeling algorithm and/or predictive modeling for a disease/an array of diseases. Furthermore, analysis of Big Data in an unstructured format can also be realized by a cloud based machine learning/deep learning neural networks based learning/relearning interactive expert cognitive computer, utilizing a natural language. Furthermore, analysis of Big Data can be coupled with an intelligent learning set of instructions. An intelligent learning set of instructions can include: artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

It should be noted that artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) can be enhanced by quantum computing or quantum computing based machine learning.

At the heart of a quantum computer is a quantum bit (qubit)—a basic unit of information analogous to a classical bit 0/1 represented by a transistor in a classical computer. The qubit is exponentially more powerful than the classical bit 0/1, because of its two unique properties: it can represent both 1 and 0 at the same time. But for qubit to be useful, it must achieve both quantum superposition (like being in two physical states simultaneously) and quantum entanglement (like what happens to one qubit can instantly affect the other qubit, even when they are physically separated) and these two unique properties can be easily upset by a slightest disturbance (e.g., a material defect/vibration/fluctuating electric fields/noise). Therefore, qubits are extremely susceptible to error, without operating at an extremely low temperature. A quantum computer enhanced machine learning algorithm is an approach that enables a quantum computer to learn/relearn and to make predictions—by combining machining learning with quantum computation. A quantum computer enhanced machine learning algorithm can be compiled on one or more microprocessors, or one or more neural network based microprocessors and downloaded onto the quantum computer-classical computer interface for execution.

Details of the intelligent learning set of instructions have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

By utilizing biostatistics, data mining algorithms (e.g., a topological data mining algorithm), genomics, proteomics, augmented intelligence modeling algorithm and/or predictive modeling algorithm, a set of primary predictive genes/proteins for a specific disease may be determined.

The nanohole based diagnostic biomodule (including the two-dimensional array of the nanotunnels 500C and two-dimensional array of nanoholes 500D) for detection of a disease specific biomarker/an array of disease specific biomarkers is identified as 840.1.

Furthermore, 840.1 is integrated with a suitable port to input/drop a DNA/RNA sample and 840.1 can connect to the USB port of a personal computer for displaying and analyzing the DNA/RNA sample. The ability to correlate a patient's DNA with a specific disease treatment can be beneficial.

Nanohole Based Diagnostic Biomodule for Application to Personalized Medicine

Most treatments today rely on clinical data taken from average patients. However, the individual response to different drugs can vary remarkably even to the point where an effective dose tolerated by one individual could be completely ineffective or even toxic to another.

In many cases, this can be due to the Cytochrome P450 (CYP450) family of proteins which is responsible for the metabolism of most drugs into active forms and/or forms that can be excreted from the body. The CYP450 family of proteins is not large, but different people can express different members of the family and/or express the same members at different levels. Knowing this information is the first step towards delivering personalized medicine—thus drug doses can be tailored to the individual. The sequencing of a human genome, identification of gene families (such as CYP450) and a greater understanding of the genetics behind responses to drugs may allow delivery of personalized medicine.

The nanohole based diagnostic biomodule 840.1 can rapidly and reliably analyze samples from a patient to determine the presence of specific genetic sequences which predisposing them to disease or sensitivity to specific bioactive compounds and/or bioactive molecules and/or drugs and also the levels and types of proteins that they are producing (such as CYP450 family members).

The nanohole based diagnostic biomodule 840.1 can include a first device to isolate an exosome (wherein this first device can include a magnetic bead and/or a nano-scaled filter to filter one or more exosomes) and a second device to separate a molecular component(s) within the exsosome. Details of the first device and second device are described in later paragraphs.

Nanohole Based Diagnostic Biomodule for Application to Epigenetic Factors

If genome/genes are the blueprint of life, the epigenome is life's Etch-a-sketch. Our lives are little more than a checklist of various genes on a genetic scantron sheet that can be turned on or off. The regulation of gene expression is controlled by multiple mechanisms, such as the sequence-specific binding of transcription factors to DNA, epigenetic signals and a dynamic chromatin state. Epigenome is responsible for the determination of the cell type and cell activity. Epigenetic regulation of genes acquired during early development is inherited not only during cell division (mitotic inheritance), but it can be passed on from one generation to the next (meiotic inheritance), but how long these changes persist remains unclear. Epigenetic changes, like so many vital biological processes, fall to human bodies to deal with. Genes become epigenetically set to deal with conditions (e.g., diet, lifestyle and stress) and then pass that on to the next generation. Epigenetics holds great promise in the area of personalized medicine. When human eats, his/her metabolism changes, but food doesn't change a cell's genome. Instead, food modulates the epigenome, the molecular markers on the chromatin that influence gene expression by affecting how tightly DNA is wrapped around its protein scaffolding.

Epigenetic factors (guided by molecular architect piRNAs) traverse the static genome and turn the genes on or off. The staggering number of potential combinations of active and inactive genes explains why a relatively small number of genes can carry out such a wide range of functions. If a cell has ever turned on a gene in the past, the piRNA will recognize it and allow it to be expressed.

But if a gene has not been active in a cell before, the piRNA will set the silencing mechanism into action so it remains off. The silencing or lack of silencing is permanent. If the piRNA doesn't silence a gene the first time it encounters it, it won't ever silence it. And if it silences it once, then every time that gene appears in the future, the system will turn it off.

Several types of cancers can be triggered when the wrong kinds of piRNAs guide epigenetic factors to activate the wrong genes. Blocking the action of these piRNAs should become a new opportunity to treat cancers.

Epigenetic mechanisms involve adding chemical tags to DNA or the proteins it is wrapped around. Changes to the cell's environment cause the chemical tags to be added or removed. These epigenetic markers are passed on to daughter cells when the original cell divides in two. Mapping the epigenome—all the chemical modifications to the DNA and its protein scaffolding that are used to switch genes on and off throughout an organism's life is critical and can be achieved by the nanohole based diagnostic biomodule 840.1.

Differences in the epigenetic markers carried on a genome may also explain some of the differences between apparently identical individuals, due to diet, lifestyle and stress.

A connectivity brain scan (measures water diffusion in a human brain) can map the strength of neural connections and how information is routed in a human brain to estimate risk factors for neurological diseases (e.g., Alzheimer's disease). Furthermore, the above connectivity scan can be correlated with a gene sequencing to determine a genetic error for Alzheimer's disease.

Figure 14C:
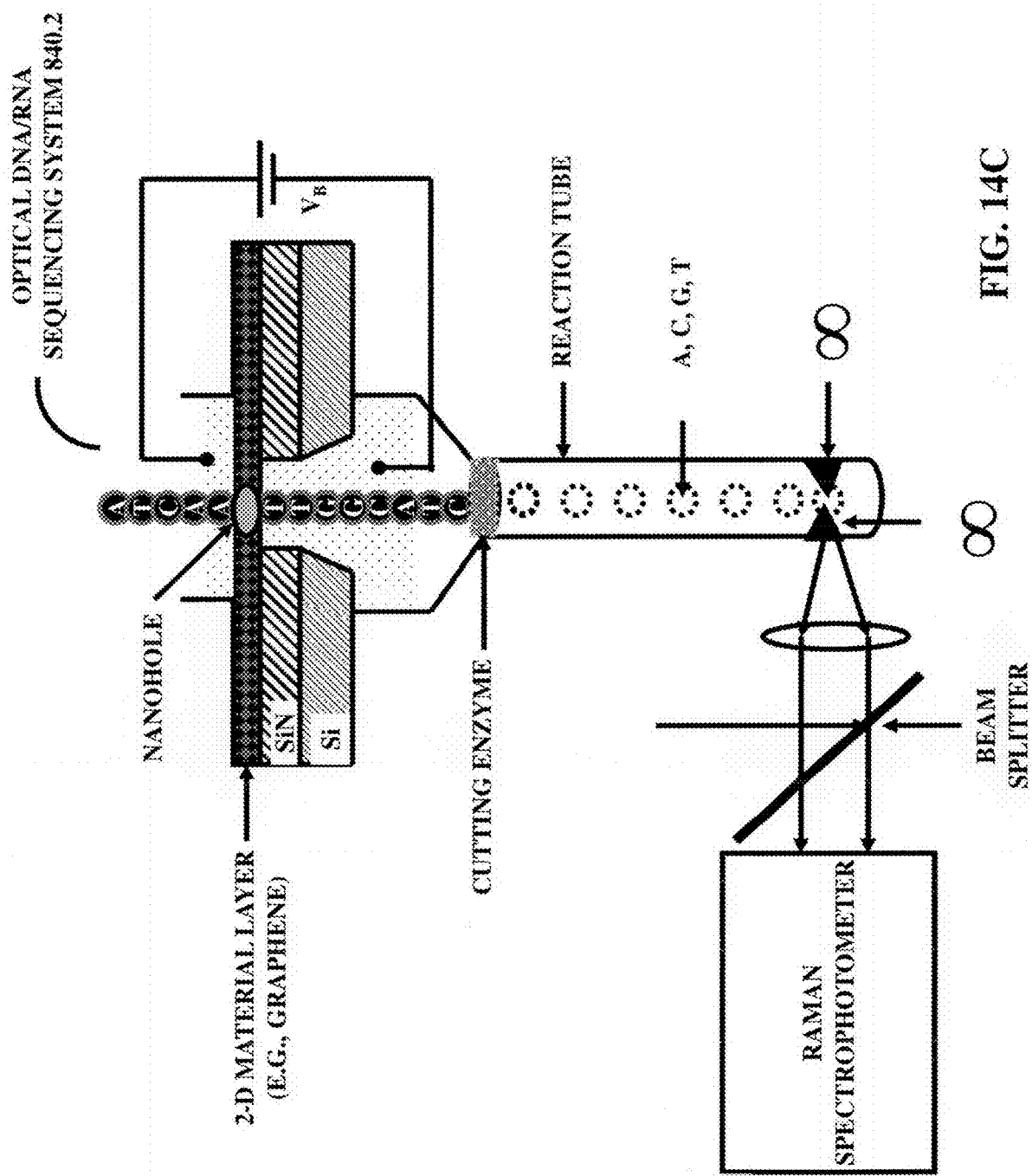
FIGS. 14C-14G illustrate a nanohole based single molecule DNA/RNA sequencing optical diagnostic biomodule.
Figure 14E:
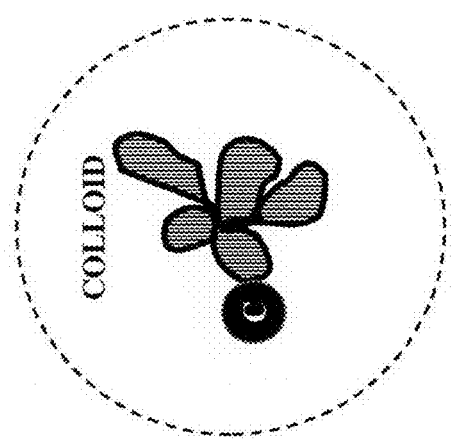
Figure 14G:
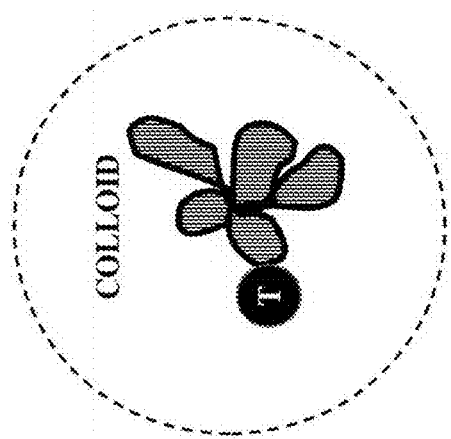
Figure 14D:
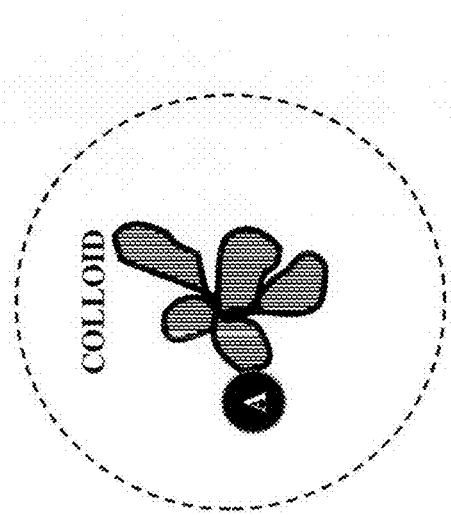
Figure 14F:
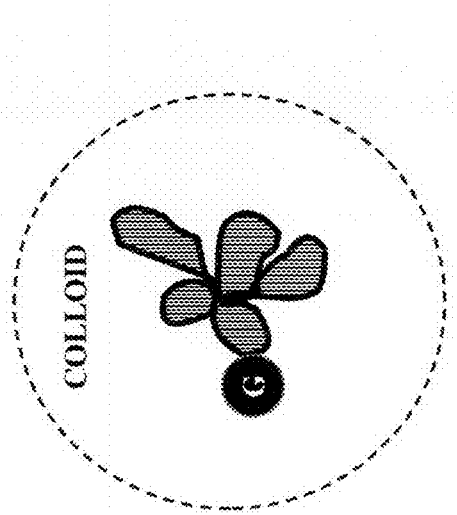

Alternatively, FIG. 14C illustrates another DNA/RNA sequencing system 840.2, wherein DNA/RNA can be pulled through a nanohole on an angstrom thin membrane (the angstrom thin membrane is mechanically supported by silicon nitride and/or silicon membrane). The angstrom thin membrane can be fabricated/constructed in a two-dimensional material. In case of DNA, upon passing through the nanohole, a cutting enzyme (e.g., utilizing CRISPR-Cas9) can cut nucleotides A, C, G and T of DNA in a reaction tube. Then, each nucleotide (chemically coupled with a colloidal molecule) passes through a specific reaction zone of the reaction tube and then it is identified by an ultrasensetitive Raman spectrophotometer.

Additionally, a Raman nanoprobe can be chemically coupled with nucleotides A, C, G and T of DNA to enhance the Raman signal. For example, a Raman nanoprobe can be a nanotube (e.g., a single-walled carbon nanotube) encapsulating/caging dye molecules, can enhance enhancement of the Raman signal, wherein the nanotube can suppress unwanted fluorescence signals. The nanotube can be 1 nanometer in diameter and 300 nanometers in length, encapsulating/caging about 500 to 1000 dye molecules.

Additionally, at the zone of Raman measurement, an optical nanoantenna(s) can be fabricated/constructed to enhance the Raman signal. The optical nanoantenna(s) can be also embedded with a supported phospholipid membrane (phospholipid membrane is fluid at room temperature). This can enable mobile nucleotides (e.g., adenine (A), cytosine (C), guanine (G) and thymine (T)) within the bilayer membrane to enter the hot-spot region(s) of the optical nanoantenna(s) via diffusion and can therefore be measured by an ultrasensetitive Raman spectrophotometer.

The DNA/RNA sequencing system 840.2 can be utilized also for exome sequencing. In case of RNA, RNA-targeted Cas9 (RCas9) with CRISPR can be utilized to cut RNA molecule.

The optical biomodule in FIG. 14C can include a first device to isolate an exosome (wherein this first device can include a magnetic bead and/or a nano-scaled filter to filter one or more exosomes) and a second device to separate a molecular component(s) within the exsosome. Details of the first device and second device are described in later paragraphs. Bioinformatic analysis of molecular components within exosomes can generate a large set of Data—Big Data. The analysis of Big data is described in previous paragraphs.

FIGS. 14D-14G illustrate chemically coupling to cut nucleotides A, C, G and T of the DNA with a colloidal molecule respectively.

Figure 14H:
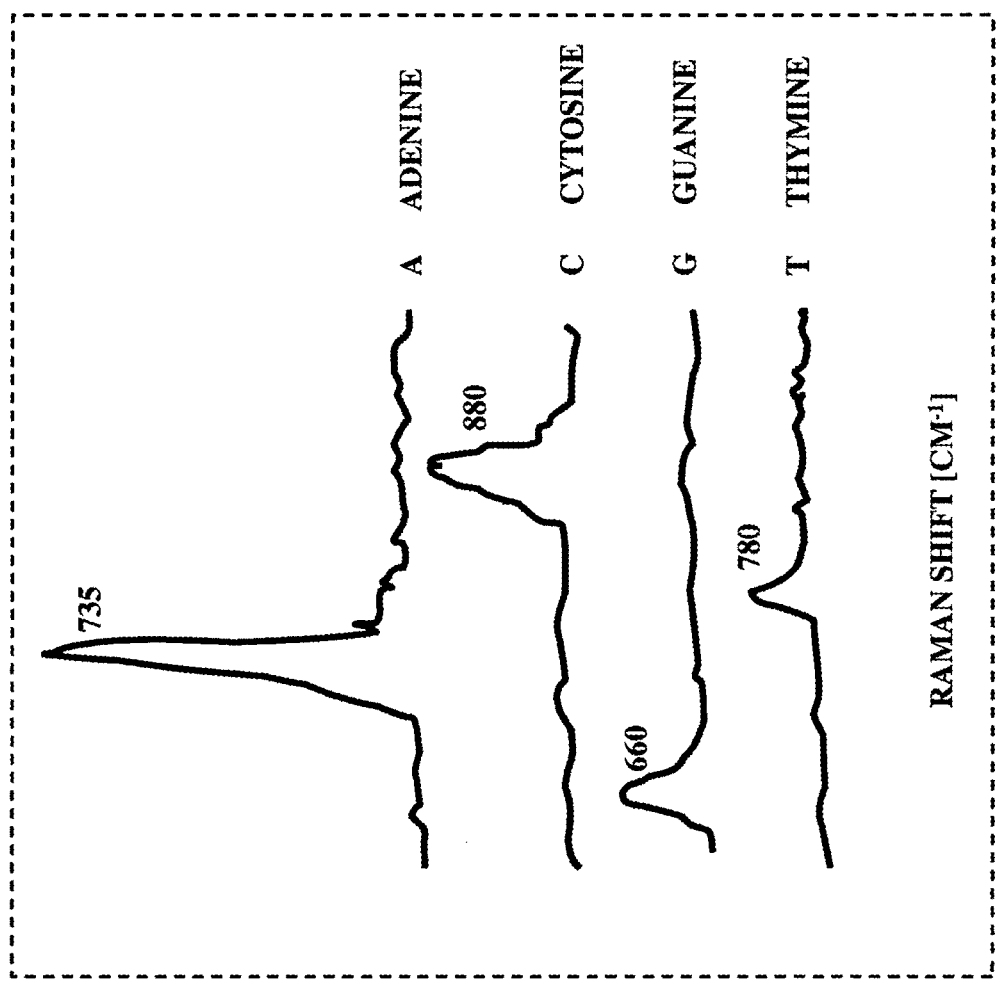
FIG. 14H illustrates Raman shift spectrum of nucleotides A, C, G and T of the DNA respectively.

FIG. 14H illustrate the Raman shift spectrum of nucleotides A, C, G and T of the DNA respectively.

Figure 14I:
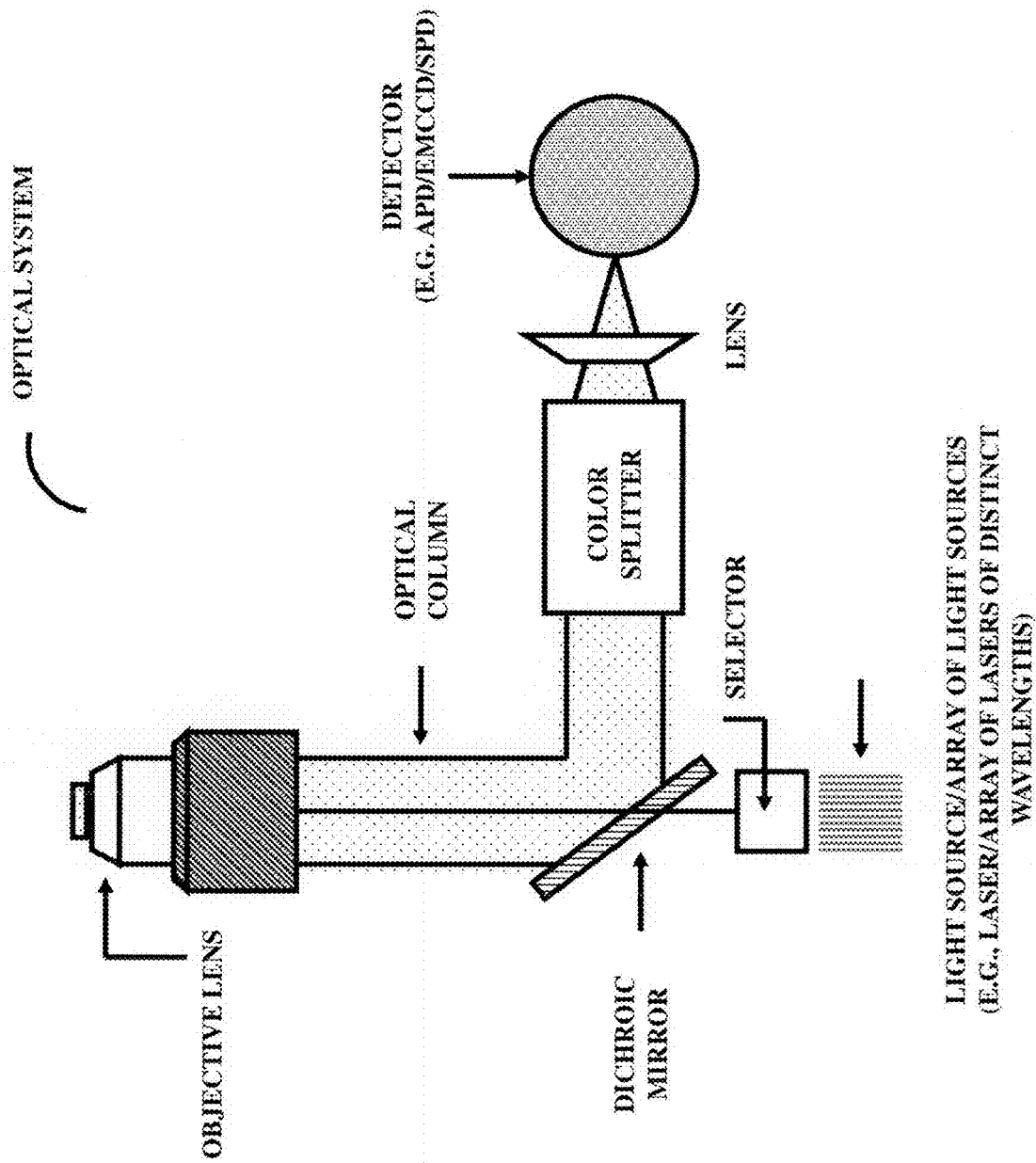
FIGS. 14I-14J illustrate another embodiment of a nanohole based single molecule DNA/RNA sequencing optical diagnostic biomodule.
Figure 14J:
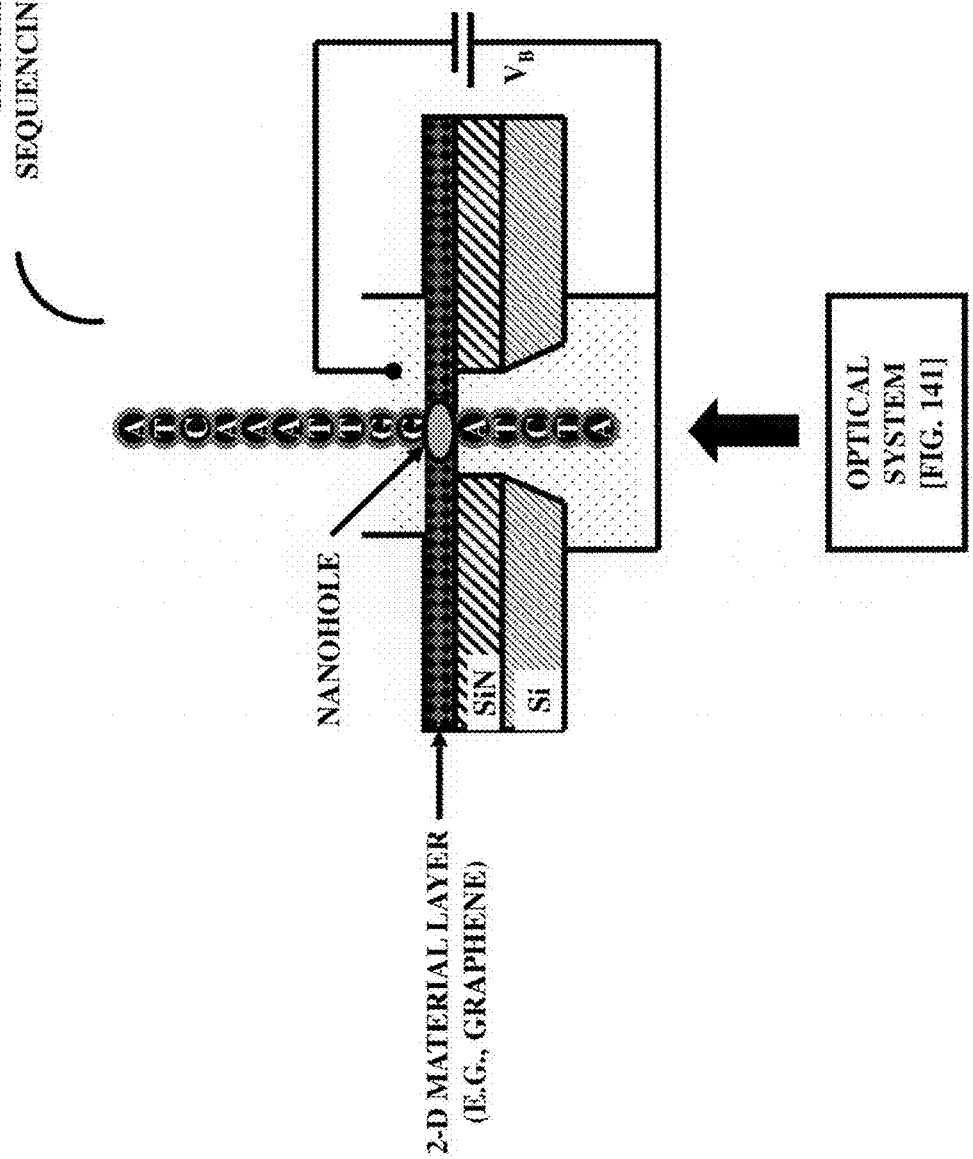

FIGS. 14I-14J illustrate another nanohole based single molecule DNA/RNA sequencing optical diagnostic biomodule 840.3. FIG. 14I illustrates an optical system for excitation by laser and detection of light. FIG. 14J illustrates another DNA/RNA sequencing system 840.3, wherein DNA/RNA can be pulled through a nanohole on an angstrom thin membrane (the angstrom thin membrane is mechanically supported by silicon nitride and/or silicon membrane). The angstrom thin membrane can be fabricated/constructed in a two-dimensional material. In case of DNA, DNA passing through the nanohole, nucleotides A, C, G and T of DNA are excited in a time sequence (e.g., 0 millisecond, 45 milliseconds, 90 milliseconds, 180 milliseconds and 360 milliseconds) by the optical system and the respective optical signal is measured by a detector (as illustrated in FIG. 14I). The DNA/RNA sequencing system 840.3 can be utilized also for exome sequencing.

Figure 14K:
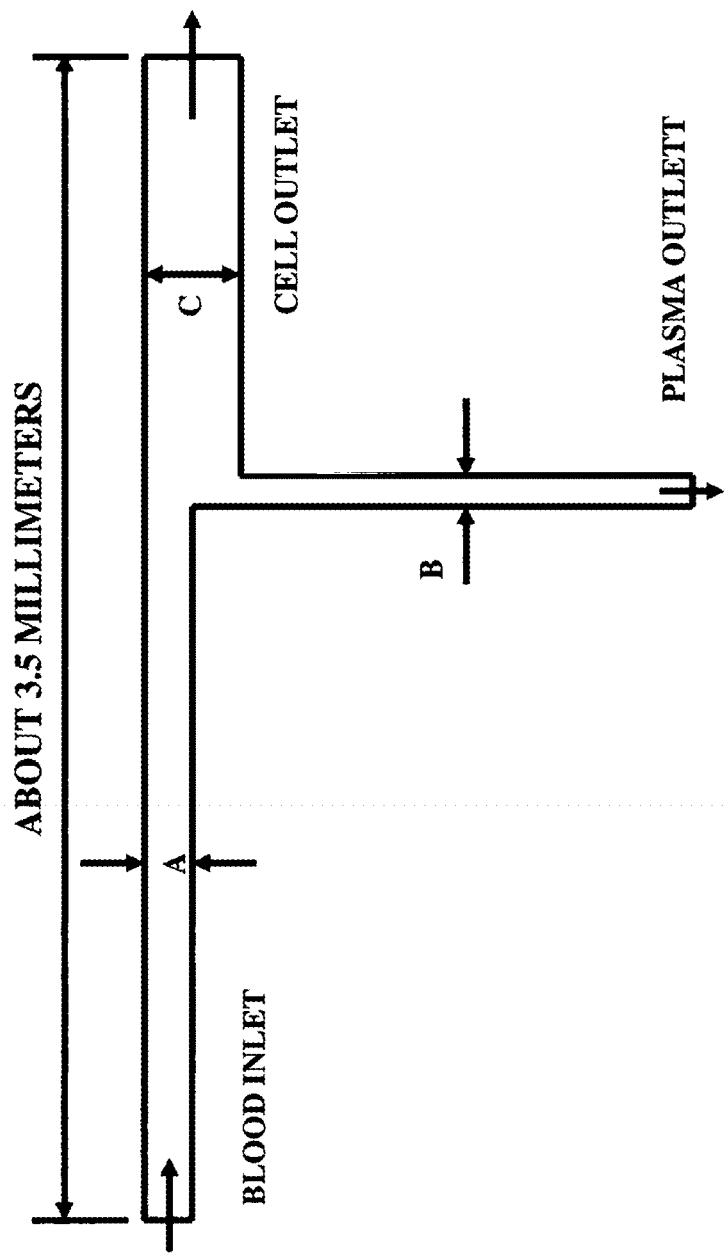
FIGS. 14K-14L illustrate two microfluidic waveguide configurations to separate (blood) plasma from blood.

FIG. 14K illustrates a microfluidic waveguide configuration to separate (blood) plasma from blood via an inlet/outlet.

Figure 14L:
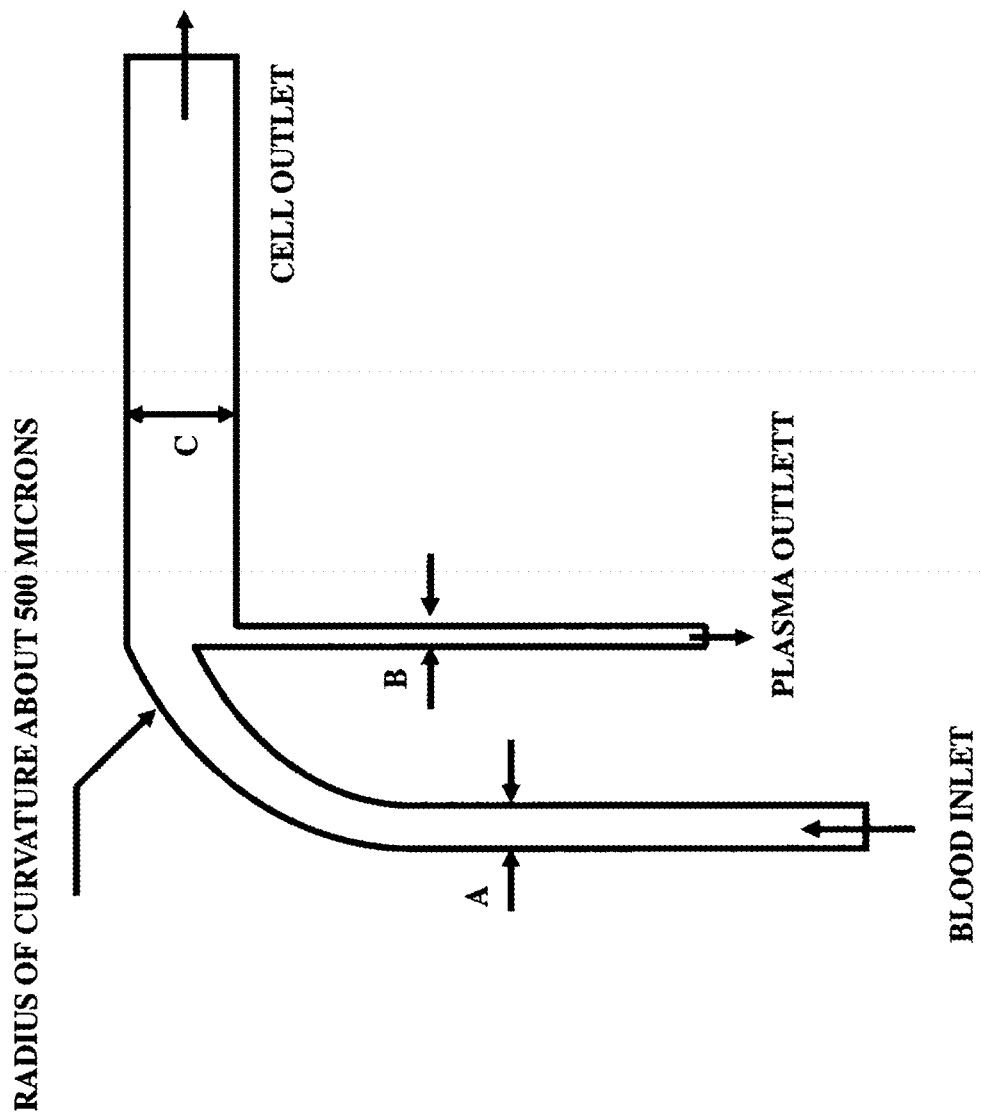

FIG. 14L illustrates another microfluidic waveguide configuration to separate (blood) plasma from blood via an inlet/outlet.

FIG. 14M illustrates a portable diagnostic device, which can be coupled with a machine learning/deep learning neural networks based (with learning/relearning configuration) healthcare application ("app") on the portable internet appliance 1600.

Figure 14N:
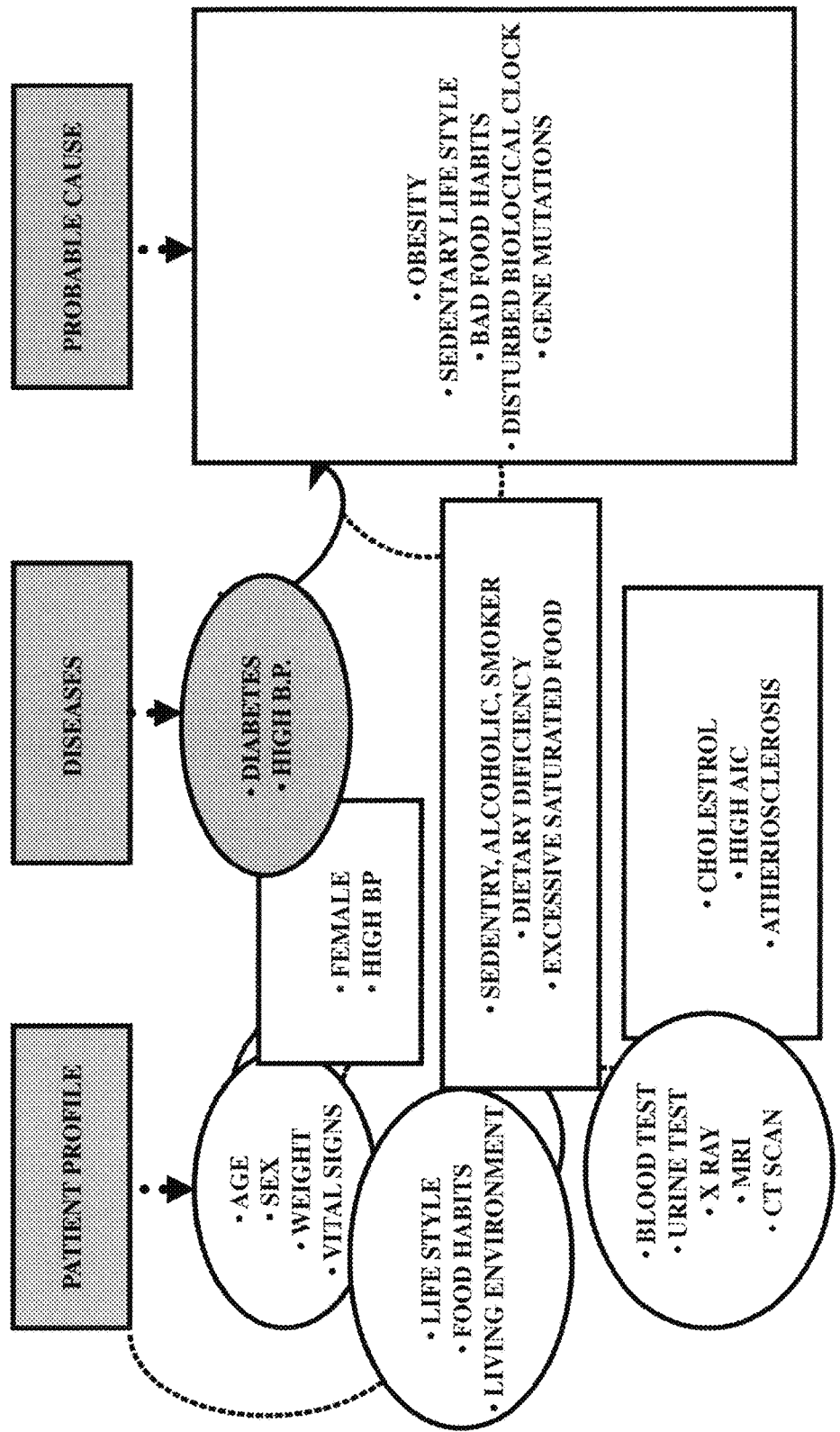
FIG. 14N illustrates an example application ("App") related to consumer healthcare.

FIG. 14N illustrates an example of a machine learning/deep learning neural networks based (with learning/relearning configuration) healthcare application on the portable internet appliance 1600.

Furthermore, the machine learning/deep learning neural networks based (learning/relearning) healthcare application on the portable internet appliance 1600 can be wirelessly connected to a cloud based expert system, which has the significant computing power of a supercomputer or a quantum computer.

Plasmonic Microhole/Nanohole Based Diagnostic Biomodule for Detection of a Disease Specific Biomarker/an Array of Disease Specific Biomarkers Furthermore, the nanohole based diagnostic biomodule (including the two-dimensional array of the nanotunnels 500C and two-dimensional array of nanoholes 500D) for detection of a disease specific biomarker/an array of disease specific biomarkers identified as 840.1 can be integrated with a plasmonic microhole/nanohole based diagnostic biomodule for validation.

A plasmonic microhole/nanohole based diagnostic biomodule can be fabricated/constructed with an array of microholes/nanoholes on a metal foil/metalized thin-film/metalized ultra thin-film, wherein the light from the bottom of the metal foil/metalized thin-film/metalized ultra thin-film can set plasmons to work on the surface and wherein each microhole/nanohole is coated with a different disease biomarker binder. Plasmons trap so much energy around each microhole/nanohole that they can convert more light on the top of the metal foil/metalized thin-film/metalized ultra thin-film. If a disease biomarker from a human body's blood/biological fluid binds with a respective disease biomarker binder, then it will attenuate the light intensity of an incident light beam (e.g., a laser beam).

Optionally, each microhole/nanohole can be decorated with a synthetic DNA strand designed to bind with a specific disease (e.g., a specific cancer) cell from a human body's blood/biological fluid. If the specific disease cell from a human body's blood/biological fluid binds with the respective synthetic DNA strand, then it will attenuate the light intensity. Furthermore, captured disease cells can be separated/squeezed into a petri dish. Then various bioactive compounds 100 and/or bioactive molecules 100A or drugs can be added to the separated/squeezed disease cells to evaluate the most effective treatment for the specific disease.

Figure 15A:
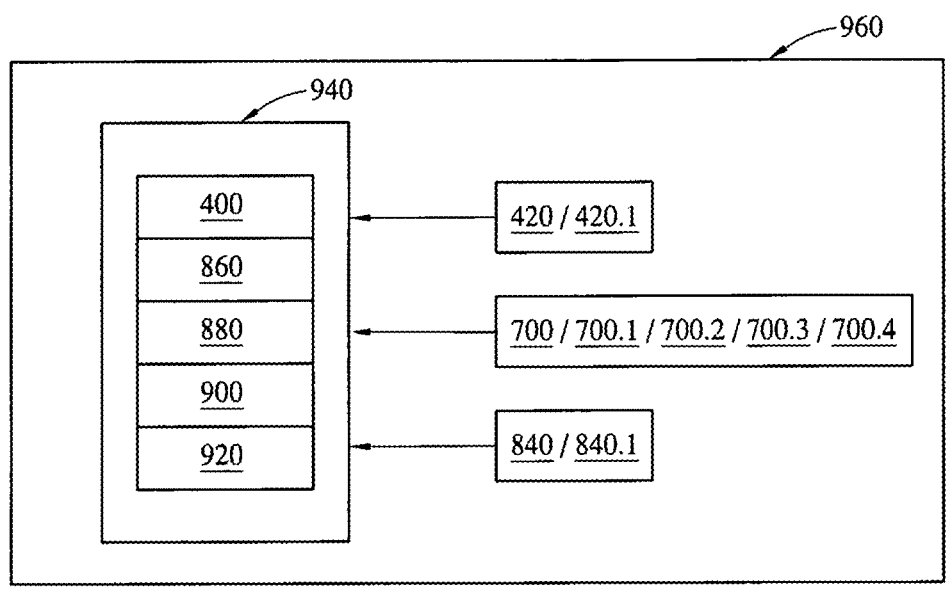
FIG. 15A illustrates integrated bioelectronics subsystems (various embodiments) to detect a disease specific biomarker/an array of disease specific biomarkers and deliver (programmable/active) bioactive compounds and/or bioactive molecules.

Bioelectronics Subsystem for Detection of a Disease Specific Biomarker/an Array of Disease Specific Biomarkers & Programmable/Active Delivery of Bioactive Compounds &/or Bioactive Molecules in Near Real-Time/Real-Time FIG. 15A illustrates an integrated bioelectronics subsystem 960 for detection of a disease specific biomarker/an array of disease specific biomarkers and programmable/active delivery of bioactive compounds 100 and/or bioactive molecules 100A in near real-time/real-time.

The integrated bioelectronics subsystem 960 at least can include (a) a microelectro-mechanical-system biomodule 420/420.1, (b) an integrated optical diagnostic biomodule 700.1/700.2/700.3/700.4, (c) an integrated electrical diagnostic biomodule 840/840.1 and (d) an electronic module 940.

Furthermore, the electronics module 940 can be fabricated/constructed on a flexible/bendable/stretchable substrate by lifting off the electronics circuit layer from a rigid semiconductor substrate and then bonding/connecting, the lifted off electronics circuit layer on nanoribbons of wires mounted onto a lightweight and stretchable membrane, wherein the wires can bend, twist and stretch, while maintaining their functionality.

The integrated bioelectronics subsystem 960 can stick to the biological transport medium (e.g., skin) via the van der Waals force, without the need of an adhesive.

Thus, the integrated bioelectronics subsystem 960 can be removed easily from the biological transport medium.

The electronics module 940 can integrate: (a) an electrical power providing component 400, (b) a microprocessor component 860, (c) a memory/data storage component 880, (d) a wireless (radio) transceiver component 900 and (e) an embedded operating system algorithm 920.

By way of an example and not by way of any limitation, the wireless (radio) transceiver component 900 can be configured with Wibree, Bluetooth, Wi-Fi and near-field communication.

Other bio/health sensors to monitor vital health parameters (e.g., blood sugar and heart rate) can be integrated with the electronics module 940 to monitor vital health parameters (e.g., blood sugar and heart rate).

Silicon-On-Insulator as an Integration Platform Substrate for the Integrated Bioelectronics Subsystem 960

For fabricating/constructing a compact bioelectronics subsystem 960 optical components/electronics circuitry components can be attached (including flip-chip bonding on metalized thermal bumps integrated with thin-film solder) on silicon-on-insulator as an integration platform substrate.

Printed Electronics Over a Three-Dimensional Structure for Miniaturization/Manufacturing of the Integrated Bioelectronics Subsystem 960

An aerosol jet can atomize nanoparticle based print materials into microscopic droplets. These microscopic droplets can be focused, utilizing a sheath of gas into a precise jet stream by a nozzle.

The nozzle can be placed about 5 millimeters away from a surface/irregular shaped surface.

Both the nozzle and a container securing the surface/irregular shaped surface can be manipulated through different angles to print (size smaller than 0.01 millimeters wide) on a three-dimensional structure.

Higher levels of miniaturization and manufacturing can be realized, utilizing printed electronics (e.g., aerosol nanoparticle jet to print an antenna, electronics circuitry, radio frequency component and sensor).

Furthermore, printed electronics can print a section of the integrated bioelectronics subsystem 960 over a three-dimensional structure, instead of assembling many discrete components.

However, printed electronics can be extended to any substrate of any material of any shape.

For example, resting arms of a wheel chair can be printed with various bio/health sensors to monitor vital health parameters (e.g., blood pressure, blood sugar, heart rate, % oxygen in blood and weight) and low-power wireless sensors (e.g., Wibree, Bluetooth, Wi-Fi and near-field communication) to transmit such vital health parameters to a portable internet appliance for statistical analysis, then eventually to a healthcare professional.

Alternatively, fiber-reinforced composite/thermoplastic composite can be utilized to reduce the weight of the wheel chair. Alternatively, a nanocomposite material can include carbon nanotubes (single-walled/multi-walled) and/or graphene (or graphene like nanostructual material e.g., graphene flakes) and a poly vinyl alcohol (PVA) binder matrix, can be utilized to reduce the weight of the wheel chair. Carbon nanotubes (single-walled/multi-walled) and/or graphene (or graphene like nanostructual material e.g., graphene flakes) can form an interconnected network within the poly vinyl alcohol binder matrix. In case of the combination of carbon nanotubes and graphene (or graphene like nanostructual material e.g., graphene flakes), the strength of the nanocomposite material can be varied by changing the weight ratio (from 0.1 to 1) of carbon nanotubes (single-walled/multi-walled) to graphene (or graphene like nanostructual material e.g., graphene flakes). Alternatively, a material matrix (of either carbon fiber or polyacrilonitrile nanofiber) can be added with 1 wt % to 10 wt % graphene (or graphene like nanostructual material e.g., graphene flakes) and/or 1 wt % to 10 wt % nanotubes (e.g., boron nitride/carbon (single-walled/multi-walled)) to form a nanocomposite. Such a nanocomposite can be utilized to reduce the weight of the wheel chair.

Furthermore, DuPont Kevlar with the addition of (1 wt % to 10 wt %) carbon fiber and/or (1 wt % to 20 wt %) carbon nanotubes (single-walled/multi-walled) and/or (1 wt % to 20 wt %) graphene (or graphene like nanostructual material e.g., graphene flakes) can be utilized to reduce the weight (and increase strength) of the wheel chair/other tools. Alternatively, DuPont Kevlar with the addition of (1 wt % to 10 wt %) carbon fiber and/or (1 wt % to 20 wt %) carbon nanotubes (single-walled/multi-walled) and/or (1 wt % to 20 wt %) graphene (or graphene like nanostructual material e.g., graphene flakes) and/or (1 wt % to 30 wt %) natural silk/synthetic silk can be utilized to reduce the weight (and increase strength) of the wheel chair/other tools. Alternatively, DuPont HPF resins with the addition of (1 wt % to 10 wt %) carbon fiber and/or (1 wt % to 20 wt %) carbon nanotubes (single-walled/multi-walled) and/or (1 wt % to 20 wt %) graphene (or graphene like nanostructual material e.g., graphene flakes) can be utilized in fabricating/constructing other components/tools. Alternatively, DuPont HPF resins with the addition of (1 wt % to 10 wt %) carbon fiber and/or (1 wt % to 20 wt %) carbon nanotubes (single-walled/multi-walled) and/or (1 wt % to 20 wt %) graphene (or graphene like nanostructual material e.g., graphene flakes) and/or (1 wt % to 30 wt %) natural silk/synthetic silk can be utilized in fabricating/constructing other components/tools.

The integrated bioelectronics subsystem 960 can communicate with an integrated intelligent expert algorithm. The integrated intelligent expert algorithm can be located at a cloud based data storage unit or a cloud based server, wherein the cloud based data storage unit or the cloud based server can be configured with additional hardware and/or software to spill out volumes of wrong data, in the event of a memory-access-pattern security breach.

The integrated intelligent expert algorithm can include a first set of intelligent learning instructions of artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) for diseases/treatments.

It should be noted that artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) can be enhanced by quantum computing or quantum computing based machine learning.

The integrated intelligent expert algorithm can include a second set of intelligent learning instructions of algorithm-as-a-service, patients' behavior/nutrition modeling, physical search algorithm and software agent Furthermore, the integrated intelligent expert algorithm can include: statistical analysis (e.g., Student t-test, ANOVA (analysis of variance) and Chi-Square), data mining, ANN (artificial neural network), hierarchical cluster analysis, KNN (K-nearest neighbor analysis) and performance analysis (e.g., specificity, sensitivity and accuracy).

Furthermore, the intelligent expert algorithm can be complemented by a collection of inputs (including identification of images) from healthcare professionals. The inputs from the healthcare professionals can be in near real-time/real-time. These inputs can complement/enhance the intelligent expert algorithm.

Figure 15B:
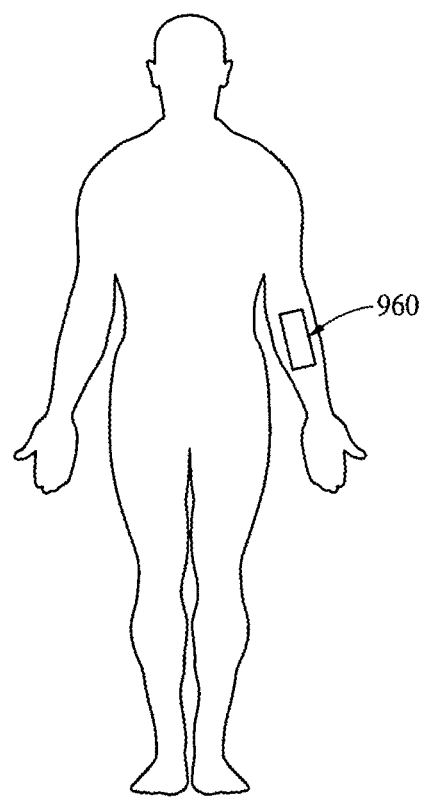
FIG. 15B illustrates a near real-time/real-time application of the wearable integrated bioelectronics subsystem.

FIG. 15B illustrates a near real-time/real-time application of a wearable integrated bioelectronics subsystem of 960.

The above bioelectronics subsystem 960 can enable near real-time/real-time measurement of a disease specific biomarker and instantaneous programmable/active delivery of the bioactive compounds 100 and/or bioactive molecules 100A in near real-time/real-time (via a dynamic closed feedback loop).

The above bioelectronics subsystem 960 can enable near real-time/real-time measurement of a disease specific biomarker and delayed programmable/active delivery of the bioactive compounds 100 and/or bioactive molecules 100A in near real-time/real-time (via a dynamic closed feedback loop), utilizing a remote wireless command from a healthcare professional.

Rapid Point-of-Care Detection of a Disease/an Array of Diseases by a DNAzyme/an Array of DNAzymes on a Substrate/Membrane with an Array of Plasmonic Optical Nanoantennas Gold nanoparticles absorb light. The wavelength of absorption depends on whether the nanoparticles are separated or aggregated. The difference in color can be seen with the naked eye. A powder of individual particles appears red, but when the powder aggregates, it appears blue-violet in color. The difference in color can be seen with a naked eye.

DNAzyme is a synthetic DNA molecule that can enzymatically split another nucleic acid molecule.

Gold nanoparticles chemically bonded with DNAzyme in a powder/solution form on a membrane/paper/polymer substrate. Furthermore, gold nanoparticles chemically bonded with DNAzyme may be preserved by drying in sugar for an extended period of time.

When a disease specific gene from a human body's blood/biological fluid/synheric biological circuit is introduced, the DNA can be cleaved from the gold nanoparticles, turning the color of the membrane/paper/polymer substrate red in color.

The membrane/paper/polymer substrate can have many strips. Each strip is configured with a disease specific DNAzyme to test a disease specific gene.

Furthermore, each separate strip of the membrane/paper/polymer substrate can be integrated with an array of large numbers (e.g., billions) of plasmonic optical nanoantennas to significantly enhance the change in color.

Rapid Point-of-Care Detection of a Disease/an Array of Diseases by a Designer Protein/an Array of Designer Proteins on a Substrate/Membrane with an Array of Plasmonic Optical Nanoantennas A membrane/paper/polymer substrate can have many strips/fluid cavities. Each strip/fluid cavity is configured with a disease specific designer protein or a synthetic biomolecular circuit or a biomarker binder (e.g., a DNAzyme) to test a specific disease.

A disease specific designer protein has a leave-one-out configuration, wherein each protein has an omitted segment to create a binding site to fit to a disease specific protein.

For example, a synthetic designed-in protein analogous to an abnormal protein (produced by mutated BRCA1 gene or BRCA2 gene) has a leave-one-out configuration to create a binding site to detect the breast cancer disease. The above example can be applied to an array of synthetic designed-in proteins analogous to abnormal proteins (produced by mutated BRCA1 gene or BRCA2 gene). Other mutations as single nucleotide polymorphisms (SNP) in pieces of chromosomes may be linked to a higher breast cancer disease risk with an abnormal BRCA1 gene or BRCA2 gene.

The disease specific design protein can be integrated with a fluorescent protein (e.g., Green Fluorescent Protein (GFP)) or a fluorophore (e.g., fluorophore based on quantum dot).

Furthermore, each separate strip/fluid cavity of the membrane/paper/polymer substrate can be integrated with an array of large numbers of three-dimensional protruded structures (e.g. plasmonic optical nanoantennas or sharp tips) to significantly enhance the fluorescence (when activated by a light source) upon binding with the specific disease protein, to fit at the binding site of the designer protein with the specific leave-one-out configuration.

Early Point-of-Care Detection of a Disease with Exosomes and Three-Dimensional Protruded Structures Serum can be separated from blood. Serum can be mixed and incubated at 4° C. with System Bio Exoquick and further centrifuged and filtered to isolate exosomes. Furthermore, to obtain embedded proteins and RNAs within the exosomes, a suitable chemical (e.g., System Bio company's Micro SeraMir) can break the membrane of exosomes. Isolation of exosomes can be automated by a robotic tool.

A disease specific designer protein (integrated with a fluorescent protein or a fluorophore) has a leave-one-out configuration, wherein each protein has an omitted segment to create a binding site to fit a disease specific protein, which was once caged within the exosomes.

Similarly, a disease specific aptamer (integrated with a fluorescent protein or a fluorophore) can bind with a disease specific mRNA, which was once caged within the exosomes.

Light scattering and/or reflected fluorescence can detect/quantify disease specific proteins and/or mRNAs, which were once gaged within the exosomes.

Plasmonic optical nanoantennas can be integrated with a fluorescent protein or a fluorophore to enhance fluorescence. Alternatively, fluorescence can be magnified with an array of large numbers of three-dimensional protruded structures (e.g. plasmonic optical nanoantennas or sharp tips) at or near the bottom floor of the fluid chamber, containing specific proteins and/or mRNAs and/or piRNAs which were once caged within the exosomes.

Measurement of fluorescence can be performed by the optical diagnostic biomodule 700A (FIG. 9A), or 700C (FIG. 10A) or 700D (FIG. 11A) or 700E (FIG. 12A) or as illustrated in FIGS. 12V/12X1/12Y.

Early Point-of-Care Detection of a Disease with Exosomes, Microfluidic-Photonics Circuit (MPC) and Three-Dimensional Protruded Structures Alternatively, in the first part, a microfluidic-photonics circuit chip can take blood samples at inlets. The microfluidic-photonics circuit chip consists of a set of chambers molded in poly(dimethylsiloxane) (PDMS). The microfluidic-photonics circuit chip is degassed via vacuum prior to its use and the absorption of gas by poly(dimethylsiloxane) provides the mechanism for actuating and metering the flow of fluid in the microfluidic channels and chambers.

In a second part, the microfluidic-photonics circuit chip can use tiny microfluidic channels of 30 microns in diameter underneath the inlets to separate the serum from the blood, by utilizing laws of microscale physics. The serum moves through the microfluidic-photonics circuit chip via a process called degas-driven flow.

Superparamagnetic nanoparticles of iron oxide can be synthesized with a positive electrical charge to bond onto the membrane surface of exosomes (exosomes are found within a human body's blood/biological fluid) of negative electrical charge due to electrostatic interactions. In a third part, the microfluidic-photonics circuit chip can be integrated with a magnet. Exposure to a magnetic field can separate superparamagnetic nanoparticles of iron oxide bonded with exosomes.

Alternatively, a third part of the microfluidic-photonics circuit chip can be integrated with a nanosieve/nanomembrane (e.g., a carbon nanomembrane) of about 100 nanometers pore diameter to filter only exosomes.

Furthermore, a suitable chemical (e.g., System Bio company's Micro SeraMir) can be added in a fourth part of the microfluidic-photonics circuit chip to break the membranes of exosomes to obtain embedded RNAs and proteins within the exosomes.

The fourth part of the microfluidic-photonics circuit has a disease specific aptamer (integrated with a fluorescent protein or a fluorophore) to bind with a disease specific mRNA, which was once caged within the exosomes.

Furthermore, the fourth part of the microfluidic-photonics circuit chip has a disease specific designer protein (integrated with a fluorescent protein or a fluorophore) with a leave-one-out configuration, wherein each protein has an omitted segment to create a binding site to fit with a disease specific protein, which was once caged within the exosomes.

Light scattering and/or reflected fluorescence can detect/quantify disease specific mRNAs and/or proteins which were once caged within the exosomes.

Plasmonic optical nanoantennas can be integrated with the fluorescent protein or the fluorophore (e.g., quantum dot fluorophore) to enhance fluorescence.

Alternatively, the fourth part of the microfluidic-photonics circuit has an array (e.g., billions) of large numbers of three-dimensional protruded structures (e.g. plasmonic optical nanoantennas or sharp tips) at or near the bottom floor of the fourth part of the microfluidic-photonics circuit to enhance fluorescence.

In one instance, a modified microfluidic-photonics circuit chip without separating the serum from a human body's blood can be utilized—thus the serum separation part is not needed. In this instance, the first part of the modified microfluidic-photonics circuit chip can contain a large array of nickel coated superparamagnetic nanoparticles iron oxide/nickel coated magnetic beads to detect malaria, as nickel chemically binds with a protein namely histidine-rich protein 2, produced by malaria in a human body's blood. It should be noted that face-centered tetragonal phase FePt alloy based magnetic bead can be as small as 3 nanometers.

The large array of nickel coated superparamagnetic nanoparticles iron oxide/nickel coated magnetic beads chemically bonded with histidine-rich protein 2 (produced by malaria) can be isolated by a magnet in the second part of the modified microfluidic-photonics circuit chip.

In the third part of the modified microfluidic-photonics circuit chip, contaminants on nickel coated superparamagnetic nanoparticles iron oxide/nickel coated magnetic beads chemically bonded with histidine-rich protein 2 (produced by malaria) can be washed.

The fourth part of the modified microfluidic-photonics circuit chip contains a suitable salt solution to bind with nickel—thus histidine-rich protein 2 (produced by malaria) that can be detached.

The fifth part of the modified microfluidic-photonics circuit has a disease specific aptamer (integrated with a fluorescent protein or a fluorophore) to bind with histidine-rich protein 2 (produced by malaria).

Alternatively, in the fifth part of the modified microfluidic-photonics circuit chip has a malaria disease specific designer protein (integrated with a fluorescent protein or a fluorophore) with a leave-one-out configuration, wherein malaria disease specific designer protein has an omitted segment to create a binding site to fit with histidine-rich protein 2 (produced by malaria).

Light scattering and/or reflected fluorescence can detect/quantify histidine-rich protein 2 (produced by malaria).

Plasmonic optical nanoantennas can be integrated with the fluorescent protein or the fluorophore (e.g., quantum dot fluorophore) to enhance fluorescence.

Alternatively, the fifth part of the modified microfluidic-photonics circuit has an array of large numbers of three-dimensional protruded structures (e.g. plasmonic optical nanoantennas or sharp tips) at or near the bottom floor of the fifth part of the modified microfluidic-photonics circuit to enhance fluorescence.

In another instance, a modified microfluidic-photonics circuit chip without separating the serum from a human body's blood can be utilized—thus the serum separation part is not needed. In this instance, the first part of the modified microfluidic-photonics circuit chip can contain a large array of silica coated superparamagnetic nanoparticles iron oxide/silica coated magnetic beads to detect tuberculosis, as silica chemically binds with the DNA of tuberculosis.

The large array of silica coated superparamagnetic nanoparticles iron oxide/silica coated magnetic beads chemically bonded with the DNA of tuberculosis can be isolated by a magnet in the second part of the modified microfluidic-photonics circuit chip.

In the third part of the modified microfluidic-photonics circuit chip, contaminants on silica coated superparamagnetic nanoparticles iron oxide/silica coated magnetic beads chemically bonded with the DNA of tuberculosis can be washed.

In The fourth part of the modified microfluidic-photonics circuit has the tuberculosis specific aptamer (integrated with a fluorescent protein or a fluorophore) to bind with the DNA of tuberculosis.

Plasmonic optical nanoantennas can be integrated with the fluorescent protein or the fluorophore (e.g., the quantum dot fluorophore) to enhance fluorescence.

Light scattering and/or reflected fluorescence can detect/quantify the DNA of tuberculosis.

Alternatively, the fourth part of the modified microfluidic-photonics circuit has an array of large numbers of three-dimensional protruded structures (e.g. plasmonic optical nanoantennas or sharp tips) to enhance fluorescence.

Similarly, nickel coated superparamagnetic nanoparticles iron oxide ($Fe_3O_4$)/nickel coated magnetic beads, coupled with one or more sepsis-specific biomarker binders can filter sepsis from a human's blood and filtered (sepsis free) human blood can be resupplied to a human.

X-Ray Fluorescence Diagnostic Biomodule Utilizing an Array of Microcapillaries & an Array of Miniature X-Ray Sources An array of microcapillaries containing a biological sample can be excited by an array of miniature x-ray sources (powered by the portable electrical power providing component) to induce x-ray fluorescence in the biological sample for various elemental concentrations related to a disease.

Furthermore, multiple DNAs and/or protein biomarkers can be detected based on characteristic x-ray fluorescence.

The array of sharp tips of a pyroelectric crystal (e.g., lithium niobate/lithium tantalite) can be fabricated/constructed on a thin-film resistor. The array of sharp tips can be capped with a metal thin-film. The metal thin-film emits x-rays when bombarded by electrons emitted by the sharp tips.

The x-ray fluorescence can be detected by an array of silicon drift detectors. Due to the unique process/fabrication technology of the silicon drift detectors, the leakage current of the silicon drift detectors is low such that the silicon drift detectors can be operated with a moderate cooling, provided by a single stage thermoelectric cooler (TEC)/microrefrigerator.

Furthermore, a high-efficiency nanostructure $50 A°$ thick $Sb_2Te_3/10 A°$ thick $Bi_2Te_3$ based thin-film superlattices miniature thermoelectric cooler/microrefrigerator (about 1 millimeter×3 millimeters in size) can be utilized to cool the array of silicon drift detectors.

However, significant thermoelectric cooler/microrefrigerator efficiency can be gained by fabricating a quantum wire/quantum dot, transitioning from a two-dimensional superlattice.

Retinal Contact Lens Biomodule Subsystem for Detection of a Disease Specific Biomarker/an Array of Disease Specific Biomarkers & Programmable/Active Delivery of Bioactive Compounds &/or Bioactive Molecules in Near Real-Time/Real-Time Specific proteins (e.g., protein biomarkers of Alzheimer disease) can accumulate in the retina. These specific proteins can be utilized to diagnose a disease specific biomarkers/an array of disease specific biomarkers in near real-time/real-time.

Figure 16A:
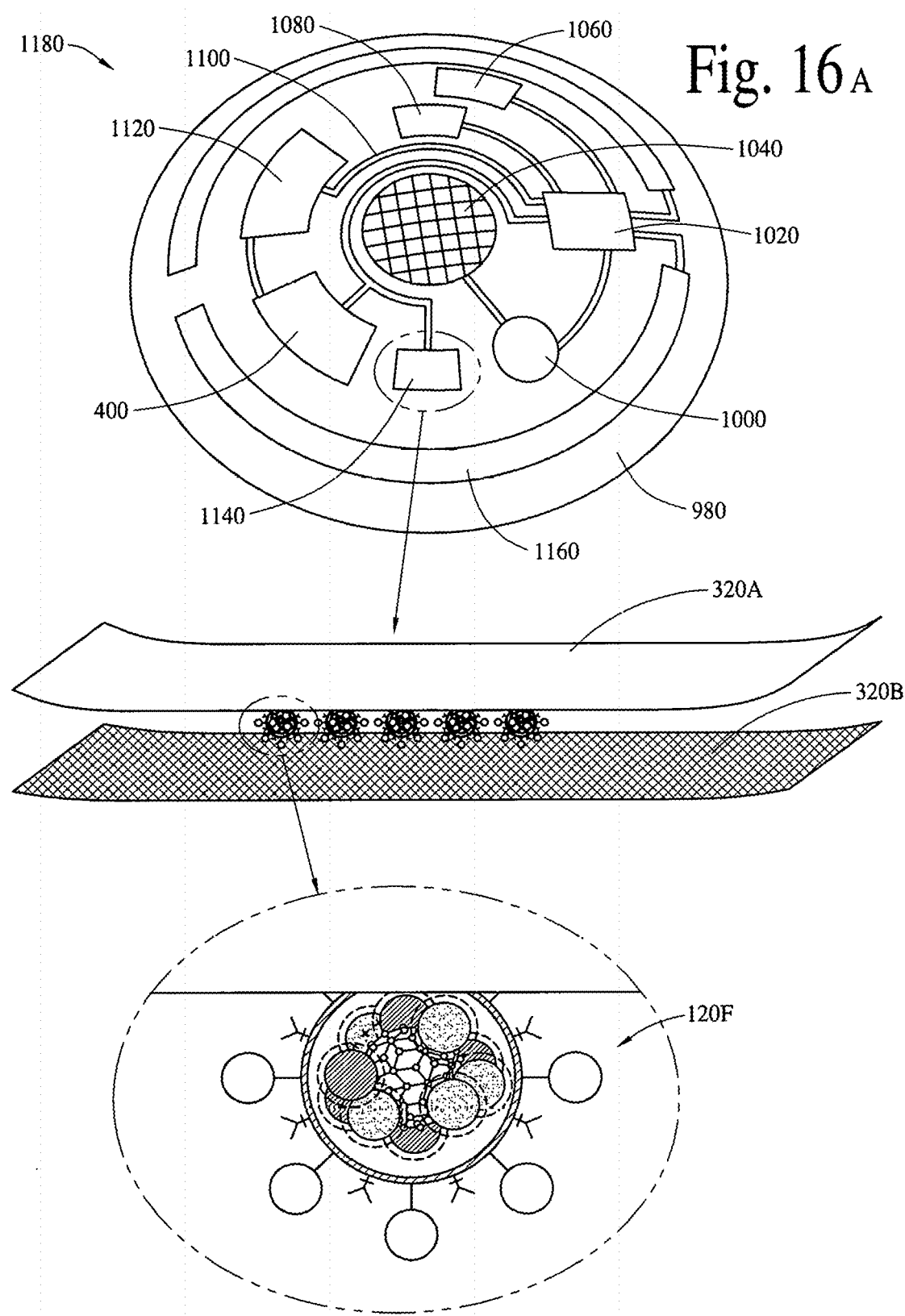
FIG. 16A illustrates a retinal contact lens subsystem to detect a disease specific biomarker/an array of disease specific biomarkers and deliver (programmable/active) bioactive compounds and/or bioactive molecules.

FIG. 16A illustrates a retinal contact lens biomodule subsystem 1180 on a biocompatible frame 980.

The biocompatible frame 980 can be fabricated/constructed, utilizing liquid-crystal polymers/polyimide/silica/silicon/silk/SU-8 resin/other suitable material.

Furthermore, if needed, the biocompatible frame 980 can be coated with a fluorinated silicon material to protect against water and/or oil.

The retinal contact lens biomodule subsystem 1180 can integrate: (a) a control circuitry component 1000, (b) an array of display pixels 1020, (c) an array of microlenses 1040, (d) a biosensor component 1060, (e) a biosensor read-out component 1080, (f) a solar cell component 1120, (g) a micropatch component 1140, (h) a low-power wireless (radio) transmitter (with an antenna) component 1160 and (g) an electrical power providing component (e.g., a printed thin-film battery or an array of glucose fuel cells) 400, utilizing a connecting electrical contact layer 1100.

Example of a biosensor component 1060: Blood sugar measurement can involve an electrochemical reaction activated by an enzyme. Glucose oxidase can convert glucose into hydrogen peroxide and other chemicals—thus their concentrations can be measured with a miniature potentiostat or nanosized potentiostat as a biosensor for calculating the glucose level in tears. Furthermore, the biosensor component 1060 can be integrated with an analog signal to a digital signal converter circuit.

A glucose fuel cell consists of a platinum catalyst that strips electrons from glucose-mimicking the activity of cellular enzymes that break down glucose to generate adenosine triphosphate.

Multi-layers of positive electrical charged ferritin protein, separated by a layer of nanocrystals, from multi-layers of negative electrical charged ferritin protein—sandwiched between two (2) transparent metal electrodes on a biocompatible substrate (e.g., silk) can act as the solar cell component 1120.

Furthermore, the micropatch component 1140, can consist of porous nanoshells or nanodiamonds to deliver timolol maleate (which is commonly used in eye drops) to manage glaucoma.

Printed Electronics Over a Three-Dimensional Structure for Miniaturization/Manufacturing of the Retinal Contact Lens Biomodule Subsystem Printed electronic technology or three-dimensional printing can print a section of the retinal contact lens biomodule subsystem 1180 over a three-dimensional structure, instead of assembling many discrete components. Higher levels of miniaturization and manufacturing can be realized, utilizing printed electronics (e.g., aerosol nanoparticle jets to print an antenna, electronics circuitry, radio frequency component and sensor) or three-dimensional printing.

The retinal contact lens biomodule subsystem 1180 can be fabricated/constructed by lifting off the electronics circuit layer from a rigid semiconductor substrate and then bonding/connecting, the lifted off electronics layer on nanoribbons of wires mounted onto a lightweight and stretchable membrane, wherein the wires can bend, twist and stretch, while maintaining their functionality.

Furthermore, the micropatch components 1140 can integrate a microelectro-mechanical-system reservoir to store the bioactive compounds 100 and/or bioactive molecules 100A for a sustained delivery. The above retinal contact lens biomodule subsystem 1180 can enable near real-time/real-time measurement of a disease specific biomarker and programmable/active delivery of the bioactive compounds 100 and/or bioactive molecules 100A in near real-time/real-time (via a dynamic closed feedback loop).

Figure 16B:
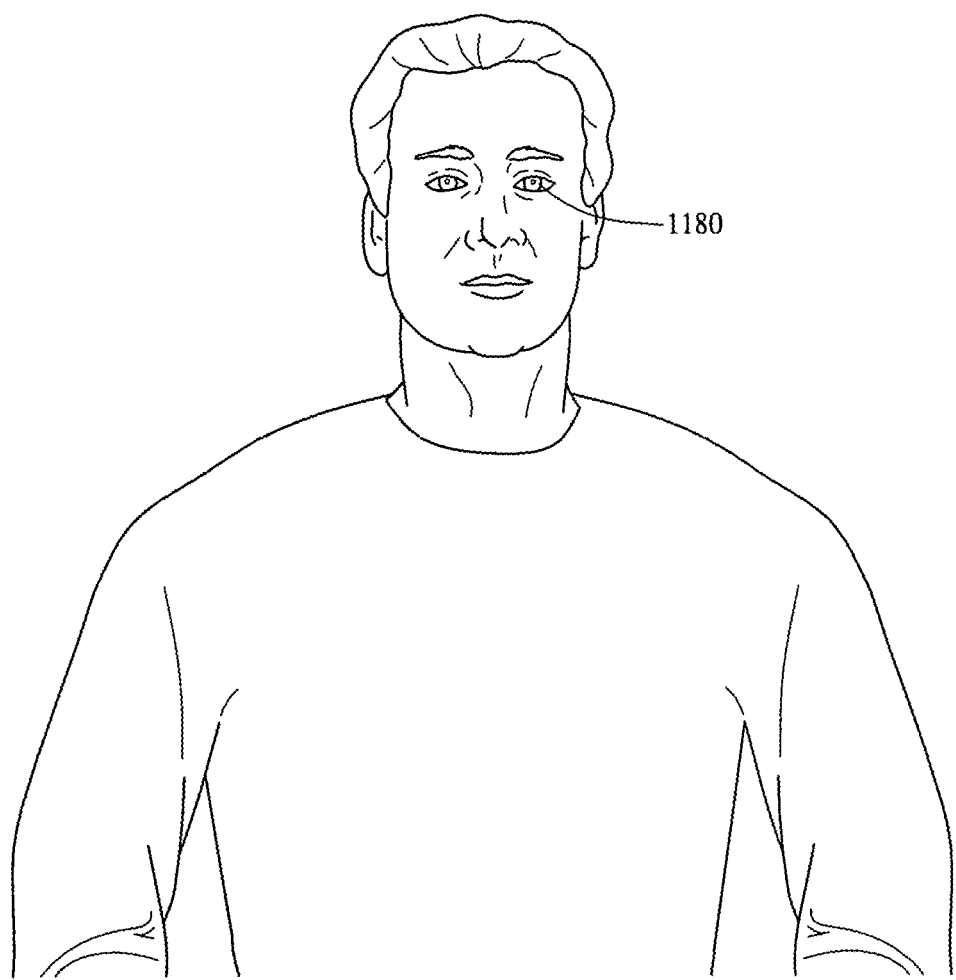
FIG. 16B illustrates a near real-time/real-time application of the wearable retinal contact lens subsystem in FIG. 16A.

FIG. 16B illustrates a near real-time/real-time application of a wearable retinal contact lens biomodule subsystem 1180.

Near Real-Time/Real-Time Wearable Integrated Bioelectronics Subsystem, as an Augmented Reality Personal Assistant FIGS. 17A, 17B, 17C, 17D and 17E illustrate a near real-time/real-time wearable bioelectronics subsystem 1580.

FIG. 17A illustrates a near real-time/real-time wearable subsystem 1540 with a bifocal retinal contact lens 1180A on a biocompatible frame 980.

The bifocal retinal contact lens 1180A on the biocompatible frame 980 has two (2) different focal lengths—one contact lens can focus foreground light into the middle of the pupil, while the other contact lens can focus the background light onto the edge of the pupil. Furthermore, the bifocal retinal contact lens 1180A can be embedded with optical nanostructures to achieve higher optical performances.

The biocompatible frame 980 can be fabricated/constructed, utilizing liquid-crystal polymers/polyimide/silica/silicon/silk/SU-8 resin/other suitable material.

Furthermore, if needed, the biocompatible frame 980 can be coated with a fluorinated silicon material to protect against water and/or oil.

The bifocal retinal contact lens 1180A can be fabricated/constructed, utilizing liquid-crystal polymers/polyimide/silica/silicon/silk/SU-8 resin/other suitable material. Furthermore, a photochromic transparent nanoemulsion polymer material can be used, which has an ability to block glare by darkening immediately in strong sunlight and to revert back to transparency in normal sunlight. The photochromic transparent nanoemulsion polymer material also can offer ultraviolet-blocking ability, high water content, oxygen permeability and suitable mechanical properties.

Furthermore, the bifocal retinal contact lens 1180A on the biocompatible frame 980 can optionally integrate (a) a biosensor component 1060, (b) biosensor read-out component 1080 and (c) a micropatch component 1140 to enable near real-time/real-time measurement of a disease specific biomarker and programmable/active delivery of the bioactive compounds 100 and/or bioactive molecules 100A in near real-time/real-time (via a dynamic closed feedback loop).

A common cause of blindness is when a retina is damaged by diseases that kill the photoreceptors and/or destroy the circuits that create the coded neural pulses. But often these diseases do not damage the output cells. The bifocal retinal contact lens 1180A on the biocompatible frame 980 can integrate (a) an artificial retina system which can consist of an array of thin-film electrodes (in a biocompatible package) for stimulating the retina, a visual processing unit, a miniature video camera and a transmitter mounted on an eye glass frame. The array of the thin-film electrodes should conform to the curvature of the retina. Thus, the array of thin-film electrodes should be fabricated/constructed on flexible polymers.

An artificial retina can require high-density electrical interconnects between the array of the thin-film electrodes and a biocompatible package.

The high-density electrical interconnects can be fabricated/constructed, utilizing an array of carbon fibers (about 10 microns in diameter), wherein each carbon fiber is coated with chemicals to prevent moisture, ionic and biological contamination from causing failure/damage of the carbon fiber.

The high-density electrical interconnects can be insulated/hermetically sealed in a biocompatible package (e.g., fabricated/constructed, utilizing polycrystalline diamond material) to prevent moisture, ionic and biological contamination from causing failure of the artificial retina.

The high-density electrical interconnects (integrated with the bifocal retinal contact lens 1180A) can convert/transform the electrochemical signals of eyes to digital signals of a local microprocessor/super-processor (including a graphical processing unit) 1320 and vice-a-versa.

Similarly, the high-density electrical interconnects integrated with a neural converter chip (which can be implanted in a human brain) to convert/transform electrochemical signals of a human brain to digital signals for coupling with a local microprocessor/super-processor (including a graphical processing unit) 1320 and/or coupling with one or more artificial neural network based neural processors in a cloud server and vice versa.

A light pattern incident to the artificial retina can be converted into a set of mathematical equations/codes of electrical patterns. An encoder chip can convert a general light pattern (incident on a retina) into a set of mathematical equations/codes of an electrical pattern.

A miniaturized projector-decoder chip can convert the above electrical pattern into a modified coded light pattern to drive the light-sensitive proteins (these light-sensitive proteins can be delivered by the nanoshell 120 and/or by gene therapy in the ganglion cells) to the modified light pattern to a human brain, which understands the stream of coded light patterns to translate into meaningful images.

Furthermore, an encoder circuit, a decoder circuit and a biocircuit (a biocircuit fabricated/constructed, utilizing DNA, RNA and a protein to respond to biological signals) can be integrated in the biocompatible package.

Alternatively, a retinal implant microchip can be used below the fovea (area of sharpest vision in the retina). The retinal implant microchip is approximately 3 millimeters×3 millimeters in area and 50 microns in thickness. The retinal implant microchip has about 1500 pixels, wherein each pixel has an area of about 75 microns×75 microns. An array of photocells (e.g., a light dependant resistor/light dependant phototransistor), an amplifying circuit, a stimulation electrode, an encoder circuit and a decoder circuit are integrated with each pixel. The photocells absorb the light entering the eye, transforming the light into electrical signals. The retinal implant microchip can be electrically powered by a subdermal coil behind the ear. The subdermal coil can be electrically powered by a battery via transdermal inductive transmission.

Furthermore, in the case of blindness caused by destroyed photoreceptors, suitable light sensitive proteins can be delivered by the nanoshell 120 and/or by gene therapy, so that sensitive proteins can chemically bind with remaining bipolar cells, wherein the bipolar cells are located below the destroyed photodetectors. These suitable light sensitive proteins can interact with an array of nano-scaled cameras to communicate with the ganglion cells for restoring vision, at least in a limited way. By way of an example and not by way of any limitation, Light Harvesting Complex II proteins of spinach can be utilized as suitable light sensitive protein.

Additionally, interactions of photons (of various wavelengths) with light sensitive protein(s) chemically bonded with cells (e.g., neurons) can be utilized to model treatment (with bioactive compounds 100 and/or bioactive molecules 100A) efficiency for various diseases (e.g., neurological diseases).

FIG. 17B illustrates a power unit 400, a storage/memory component 880, a wireless transceiver (e.g., a radio/millimeter wave (including 60 GHz)/terahertz band) with an antenna 900, a control circuitry component 1000, a microphone 1200, a scrolling audio recording buffer 1220, a camera (e.g., a holographic camera/three-dimensional computational image camera, utilizing a light-field camera, capturing intensity and arrival angles of light rays) with a built-in sensor 1240, a location determination component (e.g., an indoor positioning system (IPS)/global positioning system (GPS)) 1260 and a first PCS component (a PCS is an integration of a projector, a camera and an emotion sensor/eye motion/gesture/touch sensor) component 1280 embedded in the eye glass frame.

Furthermore, Broadcom's BCM4752 chipset can support an indoor positioning system with Bluetooth, Wi-Fi and near-field communication.

The powering unit 400 can be a nanobattery or a wireless enabled powering unit.

Figure 17C:
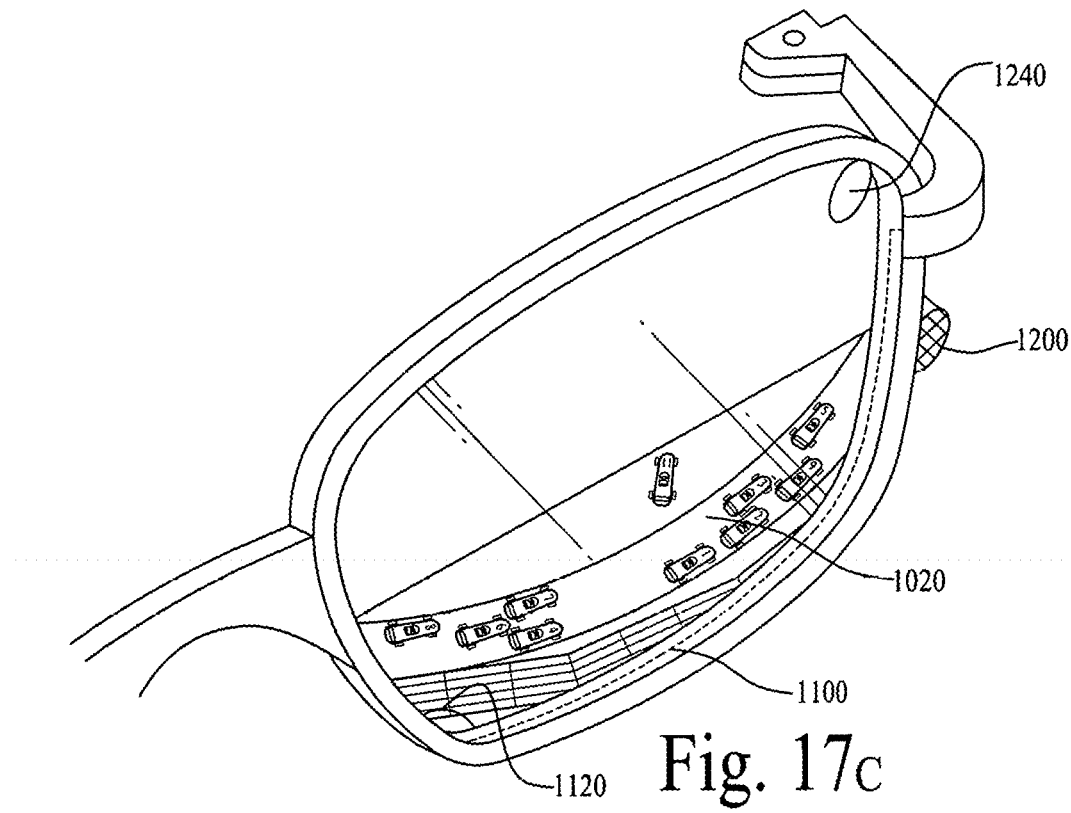

FIG. 17B also illustrates an array of display pixels (e.g., pixels of liquid-crystal display (LCD)/light emitting display (LED)/organic light emitting display (OLED)/quantum dots based display) 1020 covering about half of the eye glass, displaying an instant live action (e.g., a live surgery or a car race illustrated as in FIG. 17C) or a physical environment, an electrical contact layer/thread (e.g., super-strong electrically conducting DuPont Aracon-made of Kevlar clothing fiber) 1100, a solar cell component 1120 on the corners of the eye glasses (optionally the solar cell component 1120 can be located anywhere on the frame, rather than on the corners of the eye glasses), an integrated eye tracking sensor and decoder 1300, at the enter of the eye glass frame.

Light emitting diode/organic light emitting diode display/quantum dots based display is limited to a few pixels, but liquid-crystal displays can permit a larger surface.

A spherical curved liquid-crystal display based on an array of display pixels 1020 can enable text, images, videos and other visuals on the spherical curved liquid-crystal display.

Furthermore, liquid-crystal display based on an array of display pixels 1020 can be an array of three-dimensionally configured liquid-crystal display pixels. Details of three-dimensionally configured liquid-crystal display pixels are described in later paragraphs.

The display/display pixels 1020 (including three-dimensionally configured liquid-crystal display pixels) can be integrated with an array of sensors, such sensors can be fabricated/constructed (e.g., optically sensing waveguides) by a femtosecond laser. Utilizing a femtosecond laser module, a two-dimensional/three-dimensional optically sensing waveguide(s) can be fabricated/constructed at various depths of the display substrate. For example, such sensors can enable detection of a near real-time/real-time image or an environment near the user's location. The substrate of the display incorporating display pixels 1020 can be integrated with a metamaterial surface (utilizing many optical nano-antennas) to enable a three-dimensional/holographic display. Details of a three-dimensional/holographic display/real-time holographic display (with micro-scaled pixels) have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

The display incorporating display pixels 1020 can be integrated with (a) a transparent/semi-transparent image sensor (e.g., transparent/semi-transparent sensor based on graphene), (b) a transparent/semi-transparent microprocessor based on nanowires (e.g., zinc oxide nanowires), (c) a transparent/semi-transparent memory and (d) a transparent/semi-transparent battery/solar cell. It should be noted that the transparent/semi-transparent image sensor, transparent/semi-transparent microprocessor, transparent/semi-transparent memory and transparent/semi-transparent battery/solar cell are not needed in some cases, unless they are fabricated/constructed/packaged directly on the display incorporating display pixels 1020.

An ultrafast transparent/semi-transparent memory of graphene oxide-titanium oxide dual-layer memory cell (about 25 nanometres long and 4 nanometres thick) can be utilized.

The display can be integrated with transparent/semi-transparent solar cell (e.g., $CH_3NH_3PbI_3-xClx$ perovskite based solar cell, utilizing indium tin oxide (ITO) or fluorine-doped tin oxide (FTO) and gold or graphene electrode). Furthermore, the transparent/semi-transparent solar cell can be integrated with vanadium dioxide nanoparticles/thin-film for both electricity generation and electricity saving. Additionally, a transparent luminescent solar concentrator device of organic molecules can be utilized to absorb invisible wavelengths of light (e.g., ultraviolet and/or near infrared) and then to concentrate at the edge of the transparent luminescent solar concentrator device, wherein an array of strips of photovoltaic solar cells can convert solar energy to electricity. Details of such configuration been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Furthermore, a perovskite containing both inorganic materials (iodine and lead) and an organic material (methylammonium) can boost solar to electric conversion efficiency.

Additionally, the transparent/semi-transparent microprocessor can be integrated with an array of transparent/semi-transparent sensors (e.g., transparent vanadium dioxide/bismuth ferrite based sensors). Such transparent/semi-transparent sensors integrated with the transparent/semi-transparent microprocessor can sense, manipulate and respond quickly, because either feedback or feed forward control is integrated within one integrated system-on-chip.

A graphene (with both source metal and drain metal on graphene, graphene is fabricated/constructed on silicon carbide) based field effect phototransistor can be utilized to detect a change in electric field, caused by light, interacting with an undoped silicon carbide substrate (with back gate metal). An array of pixels of graphene based field effect transistors can be utilized for an ultrasensitive camera sensor, which can be integrated with a see-through display (e.g., an organic light-emitting display) incorporating display pixels 1020.

The thin-film transistor (TFT) located at each display pixel 1020 can control an image at each display pixel 1020 of the display. However, the thin-film transistor can also have a light sensing circuitry to sense the light reaching the pixels 1020 of the display from its surroundings—thus enabling the possibility of new user experience with the display pixel 1020 of the display. Furthermore, the display incorporating the display pixels 1020 can enable a dual-view to show entirely two separate scenes simultaneously. Both light sensing display pixels and dual-view display have been described/disclosed in U.S. Non-Provisional patent application Ser. No. 13/448,378 entitled "SYSTEM AND METHOD FOR MACHINE LEARNING BASED USER APPLICATION", filed on Apr. 16, 2012 and the entire contents of this US Non-Provisional Patent Application are incorporated herein.

Thus, the display incorporating the display pixels 1020 can be integrated with (a) dual-view to show entirely two separate scenes simultaneously and/or, (b) a light sensing circuitry to sense the light reaching the pixels 1020 of the display and/or, (c) a solar cell and/or, (d) a camera sensor and/or, (e) a sensor and/or, (f) a transparent/semi-transparent microprocessor and/or, (g) a transparent/semi-transparent memory and/or (h) a network of photonic integrated circuits (as described in later paragraphs), wherein (b), (c), (d), (e), (f) and (g) can be connected by a small area electrical interconnect and optical interconnect or by an electro-optical interconnect (the electro-optical interconnect can be realized by plurality of semiconductor fibers (a semiconductor fiber consists of depositing/laser recrystallizing an amorphous semiconductor material into core of silica fiber for propagation of both light and electricity).

Additionally, the display incorporating display pixels 1020 can be integrated with a partially reflective multi-layer thin-film coating to see-through/view-through. The display pixels 1020 can be touch-sensitive. Details of see-through/view-through configuration have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

The display incorporating display pixels 1020 can be integrated with a vanadium dioxide thin-film thermochromic device, when it is activated by either voltage or temperature.

Alternatively, the glass material for the display pixels 1020 can be replaced by a super-strong, scratch-resistant and bendable (about 0.5 millimeters in thickness) plastic. The plastic has a fingerprint proof material layer at the front and a polymer hardening material layer at the back.

Alternatively, thin-film transistor-organic light emitting diode (TFT-OLED) display pixels 1020 can enable text, images, videos and other visuals on the spherical curved thin-film transistor-organic light emitting diode display pixels 1020.

Furthermore, thin-film transistor can be either organic transistor based or carbon nanotube based. Carbon nanotube based thin-film transistor can be fabricated/constructed by the gravure printing method, where a plastic substrate is mounted onto a cylindrical drum, which rolls it over a flat surface that serves as a patterned mask of holes filled with inks made of the desired materials. The gravure printing method can be processed at a relatively low temperature, making it suitable with a plastic substrate. The gravure printing method can be utilized to fabricate/construct various sensors/micro-scaled sensors/nano-scaled sensors. Thus, each thin-film transistor-organic light emitting diode display pixel 1020 can be integrated or embedded with a sensor/micro-scaled sensor/nano-scaled sensor.

The display pixel related circuits using conventional thin-film transistors are slow for any real-time tasks. But graphene conducts electricity faster than silicon. By chemically flaking graphene, filtering it and using N-Methylpyrrolidone, transparent graphene based display pixel related circuits can be printed through a conventional inkjet printer.

FIG. 17B also illustrates a second PCS component 1280 and the microprocessor/super-processor (including a graphical processing unit) 1320 comprised or connected or electrically/wirelessly coupled with an operating system algorithm 920 on the right frame. The system operating algorithm 920 can be located at the storage/memory component 880 or in a cloud based data storage unit to interact with the local microprocessor/super-processor (including a graphical processing unit) 1320.

Furthermore, various embodiments of (a) displays/holographic displays, (b) viewing/partial viewing configurations and (c) system-on-chips (including neural networks based system-on-chips) related to the near real-time/real-time wearable subsystem 1540 have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

The above system-on-chip can be a neural learning processor (either electrical or photonics based) and it can replace the microprocessor/super-processor (including a graphical processing unit) 1320 and also enable cognitive/neural like computing for learning or relearning.

Furthermore, it should be noted that the above cognitive/neural like computing for learning or relearning can be enhanced by an intelligent learning algorithm 1460 (stored in a storage/memory component 880 or at a cloud based data storage unit or a cloud based server) and/or augmented by an implanted neural converter chip to convert/transform electrochemical signals of a human brain to digital signals of a local microprocessor/super-processor (including a graphical processing unit) 1320 and vice-a-versa.

Furthermore, the operating system algorithm 920 can be integrated with a voice recognition/editing algorithm 1340, a voice-to-text conversion algorithm 1360, an algorithm to decipher and understand a sound 1380, a gesture (to interpret body movements by embedded sensors in a peripheral device (e.g., a stylus/body wear)) a recognition algorithm 1400, a face/emotion recognition algorithm 1420, a pattern recognition algorithm 1440, an intelligent learning algorithm 1460 and a software agent 1480.

The intelligence from the intelligent learning algorithm 1460 can be coupled with a data mining algorithm and a predictive modeling algorithm. Both the data mining algorithm and predictive modeling algorithm can reside in a cloud based data storage unit to interact with the intelligent learning algorithm 1460.

Additionally, the voice recognition/editing algorithm 1340, the voice-to-text conversion algorithm 1360, the algorithm to decipher and understand a natural language/sound 1380, the algorithm to understand gesture (to interpret body movements by embedded sensors in a peripheral device (e.g., a stylus/body wear)) 1400, the face/emotion recognition algorithm 1420, the pattern recognition algorithm 1440, the intelligent learning algorithm 1460 and the software agent 1480 can reside at the storage/memory component 880 or in a cloud based data storage unit to interact with the local microprocessor/super-processor (including a graphical processing unit) 1320 and derive intelligence synthesized from vast amounts of data patterns.

It should be noted that the intelligent learning algorithm 1460 can include or couple with artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning), stored in a cloud based data storage unit/cloud based server to interact with the local microprocessor/super-processor (including a graphical processing unit) 1320 and derive intelligence synthesized from vast amounts of data patterns It should be noted that artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) can be enhanced by quantum computing or quantum computing based machine learning based algorithm, stored in a cloud based data storage unit/cloud based server.

Additionally, many components can be integrated within a plastic/polymer layer (e.g., super-strong electrically conducting DuPont Aracon—made of Kevlar clothing fiber).

Figure 17D:
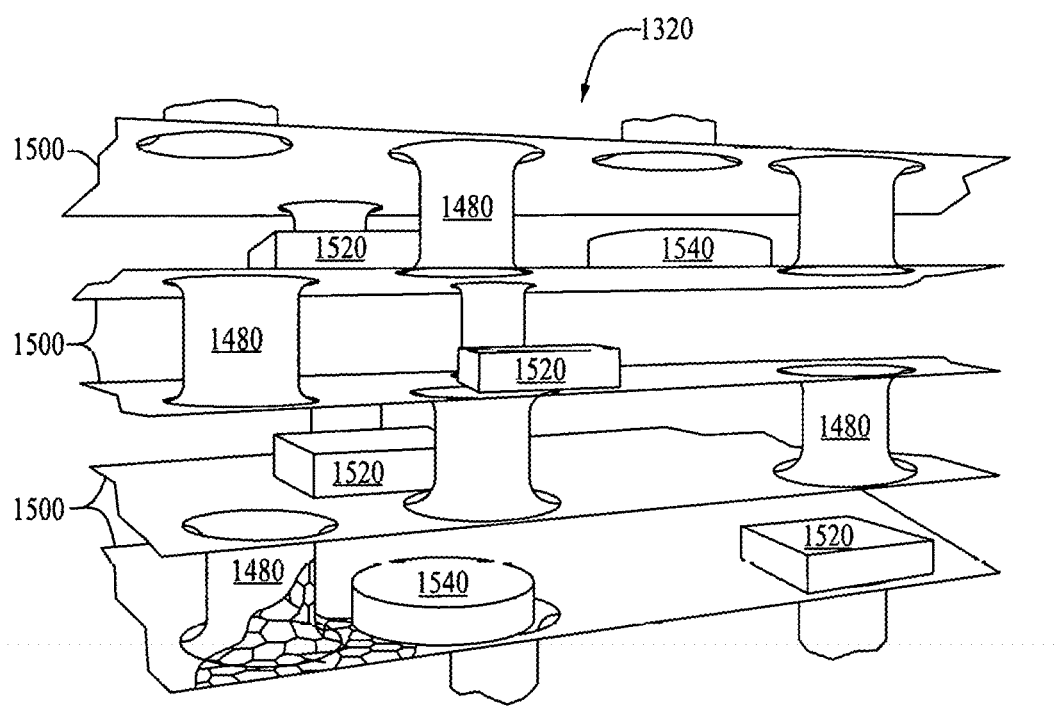

As illustrated in FIG. 17D, stacking circuits of the microprocessor/super-processor (including a graphical processing unit) 1320 in three-dimension can be achieved by utilizing a large array of vertical nanotubes (e.g., a boron nitride/carbon nanotubes) 1480 and a horizontal frame 1500 of a two-dimensional material (e.g., graphene/molybdenum disulphide) or silicene with an electrical circuit 1520 and memristor 1540—thus substantially eliminating interconnected wires.

For example, memristor 1540 can be fabricated/constructed, as silver/amorphous-silicon/poly-silicon structure. Furthermore, a particular phase change material-$Ag_4In_3Sb_{67}Te_{26}$ can switch between a disordered amorphous phase A and another disordered amorphous phase B in a sub-picosecond time-scale, when excited by picosecond electrical pulses (e.g., about 500 kV/cm peak field strength at a repetition rate of about 30 Hz for about 30 seconds). Such phase change switching occurs at lower electric field strength/energy level and such ultra-fast phase switching can enable an ultra-high speed non-volatile memristor(s) (as switching from the disordered amorphous phase B to the disordered amorphous phase A back requires an application of a short burst of heat, which can be provided electrically/optically).

Furthermore, a large array of vertical nanotubes (e.g., boron nitride/carbon nanotube) grown on a two-dimensional material-graphene interface chemically bonded on a diamond substrate can act as a chip-to-chip interconnect, as well as a heat sink.

Alternatively, the vanadium dioxide or vanadium(III) oxide based optical switch can be utilized as a chip-to-chip interconnect. Details of an embodiment of a chip-to-chip interconnect have been illustrated in FIG. 21A of U.S. Non-Provisional patent application Ser. No. 13/448,378 entitled "SYSTEM & METHOD FOR MACHINE LEARNING BASED USER APPLICATION", filed on Apr. 16, 2012 and have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Stacking circuits of the microprocessor/super-processor (including a graphical processing unit) 1320 in a three-dimensional configuration can be achieved, by utilizing droplets of nanoparticle-infused liquid, thus-substantially eliminating interconnect wires.

Furthermore, stacking circuits of the microprocessor/super-processor (including a graphical processing unit) 1320 in a three-dimensional configuration can be also achieved by DNA/RNA template wires for a nano-scaled circuit board—thus substantially eliminating interconnect wires.

The bifocal retinal contact lens 1180A and some components of a device 1560 can be integrated on a common biocompatible substrate. The bifocal retinal contact lens 1180A with the device 1560 is a near real-time/real-time wearable integrated bioelectronics subsystem 1580.

The near real-time/real-time wearable integrated bioelectronics subsystem 1580 can couple or integrate with a nano-scaled system. Such a nano-scaled system can include: (a) a nanoprocessor (e.g., molybdenum disulphide nanoprocessor), (b) a nanomemory/nanostorage (e.g., a memristor 1540 based nanomemory/nanostorage), (c) a nanoradio transceiver with a nanoantenna (e.g., graphene based nanoantenna) and (d) a nanosensor, wherein the nanoprocessor and nanomemory are wirelessly connected for data bus by the nanoradio transceiver with the nanoantenna. A nanobattery or a wireless enabled powering unit can electrically power the nano-scaled system. Details of the nano-scaled system have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Furthermore, the near real-time/real-time wearable integrated bioelectronics subsystem 1580 can assist in memory recollection for patients with Alzheimer's disease.

FIGS. 17A, 17B, 17C, 17D and 17E illustrate the near real-time/real-time wearable integrated bioelectronics subsystem 1580, which can act as an augmented reality personal assistant to (a) eavesdrop on a user's communication (e.g., an e-mail/text/image/sensing/viewing), (b) search the internet with or without (anonymously) the user's input and (c) then recommend a solution to the user's need (utilizing the intelligent learning algorithm 1460, integrated with a predictive modeling algorithm) in near real-time/real-time.

Furthermore, the camera with a sensor 1240 is configured to track the user's hands for sensing; when the user touches anything, along with the microphone 1200 to capture the user's voice for spoken commands.

The integrated eye tracking sensor and decoder 1300 can be configured to detect a radio frequency identification/near-field communication tag or recognize an optical identification (e.g., a barcode/quick response code).

Furthermore, the integrated eye tracking sensor and decoder 1300 can be configured to communicate with other sensors (e.g., bio/health sensors) in near real-time/real-time.

For example, the integrated eye tracking sensor and decoder 1300 of the near real-time/real-time integrated bioelectronics wearable subsystem 1580, as an augmented reality personal assistant can detect the user's eye position to pinpoint an item/person that the user is focused on.

The integrated eye tracking sensor and decoder 1300 can then read an item/person in the user's field of view and convert/record the reading into a text/image/holographic image as a location based near real-time/real-time snapshot/holographic snapshot of the contextual world around the user.

Additionally, an indoor positioning system can track/map how and where the user spends his/her time both online and offline and if these times are happy or sad. Furthermore, an indoor positioning system can link location, payment pattern and personal analytics of the user in near real-time/real-time or depicting the user's daily life in near real-time/real-time ("social graph"). It should be noted that social graph is synonymous with personal analytics.

The near real-time/real-time wearable integrated bioelectronics subsystem 1580, as an augmented reality personal assistant (integrated with an indoor positioning system) is with the user all the time and it already contains a host of personal information/data/preference and it can manage daily aspects of the user's life, utilizing an intelligent web portal ("social wallet"). Details of a social wallet have been described/disclosed in U.S. Non-Provisional patent application Ser. No. 13/448,378 entitled "SYSTEM & METHOD FOR MACHINE LEARNING BASED USER APPLICATION", filed on Apr. 16, 2012 and the entire contents of this US Non-Provisional Patent Application are incorporated herein.

For example, by eavesdropping on the user's communication, the near real-time/real-time wearable integrated bioelectronics subsystem 1580, as an augmented reality personal assistant can anticipate the user's need for emergency healthcare and then recommend the fastest route to the emergency section of a nearby hospital by synthesizing data (anonymously searching the internet) regarding traffic, road and weather condition. If the user is about to go to the emergency section of a nearby hospital, but another healthcare facility is cheaper with a special offer, the near real-time/real-time wearable integrated bioelectronics subsystem 1580, as an augmented reality personal assistant can alert the user. Again, this can be achieved passively, without giving away the user's location.

Furthermore, the near real-time/real-time wearable integrated bioelectronics subsystem 1580, as an augmented reality personal assistant can enable the user to share location based near real-time/real-time snapshots/holographic snapshots of the contextual world around the user—a way of viewing the world through someone else's eyes on his/her way to a place/event.

Figure 17E:
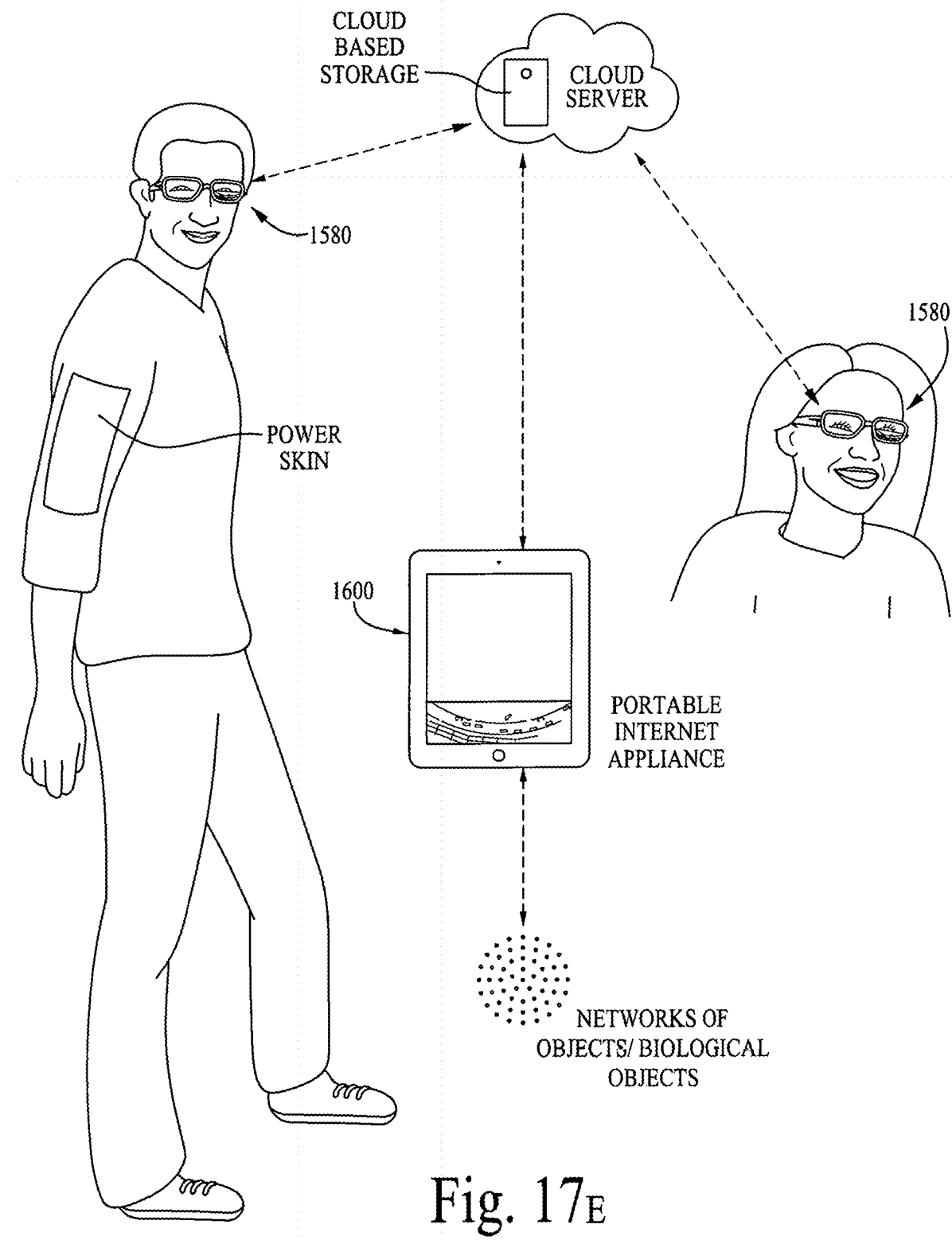
FIG. 17E illustrates interactions of a near real-time/real-time wearable bioelectronics subsystem, as an augmented reality personal assistant with another near real-time/real-time wearable bioelectronics subsystem, as an augmented reality personal assistant and a portable internet appliance via a cloud based data storage unit.

FIG. 17E illustrates a power skin with a thin-film printed battery or a textile nanogenerator, integrated with a textile supercapacitor (for energy storage).

Prestin protein is found in the outer hair cells of a human ear. Prestin can convert tiny vibrations into a voltage. To increase conductivity, a microbe (e.g., a bacterium Pili) can act as a conducting nanowire to transfer electrons generated by prestin. Each protein is capable of making nanowatts of electricity, but an array of prestin proteins can charge a battery. Furthermore, networks of the prestin proteins can construct a nanogenerator on the power skin, so that the user's natural movements can generate electrical power. The user's natural movements can generate electrical power in an embedded textile battery (e.g., piezoelectric zinc oxide nanowires woven in textile-fibers). Annealed (at about 125° C.)/self-assembled (aqueous-dried) thin-film of electrically conducting vanadium pentoxide ($V_2O_5$) fibers (with ions incorporated between the vanadium pentoxide fibers) can be utilized as a suitable electrically conducting fiber electrode for the power skin. The electrical properties and mechanical properties of annealed (at about 125° C.)/self-assembled (aqueous-dried) thin-film of electrically conducting vanadium pentoxide fibers can vary according to the amount of water content. A direct synthesis of multi-layer graphene and porous carbon woven composite films by chemical vapor deposition on Ni gauze templates can be achieved. The composite films integrate the dual advantages of graphene and porous carbon, having not only the excellent electrical properties and flexibility of graphene, but also the porous characteristics of amorphous carbon. The multi-layer graphene/porous carbon woven fabric film can enable a textile supercapacitor.

Furthermore, the power skin can be integrated with a component to detect a radio frequency identification/near-field communication tag or to recognize an optical identification (e.g., a barcode/quick response code).

The near real-time/real-time wearable integrated bioelectronics subsystem 1580, as an augmented reality personal assistant can (a) determine the location of the user, (b) upload near real-time/real-time snapshots/holographic snapshots of the contextual world around the user to a cloud based data storage unit and (c) instantly share location based near real-time/real-time snapshots/holographic snapshots of the contextual world around the user's near real-time/real-time wearable integrated bioelectronics subsystem 1580, as an augmented reality personal assistant with another user's near real-time/real-time wearable integrated bioelectronics subsystem 1580, as an augmented reality personal assistant and/or another user's portable internet appliance, wherein the portable internet appliance can be connected with an object/an array of objects, wherein the object is fabricated/constructed with at least a sensor and a wireless transmitter.

Additionally, the components of the object can be packaged by a redistributive chip packaging (RCP) method.

The near real-time/real-time wearable integrated bioelectronics subsystem 1580, as an augmented reality personal assistant can enable a pay-per-gaze advertising model that involves billing an advertiser, if the user looks at an ad online or offline, while wearing the near real-time/real-time wearable integrated bioelectronics subsystem 1580.

Furthermore, the near real-time/real-time wearable integrated bioelectronics subsystem 1580, as an augmented reality personal assistant can enable a pay-per-interact advertising model that involves billing an advertiser, if the user interacts with an ad online or offline, while wearing the near real-time/real-time wearable integrated bioelectronics subsystem 1580.

The near real-time/real-time wearable integrated bioelectronics subsystem 1580, as an augmented reality personal assistant can enable an application (e.g., navigation, photo capture and sharing information). Thus, a surgeon can have a patient's vital information in front of his/her eyes, while operating on the patient.

The near real-time/real-time wearable integrated bioelectronics subsystem 1580, as an augmented reality personal assistant can enable the user to interact with virtual items, as the camera with a built-in sensor 1240 is configured to track hands for sensing; when the user touches anything along with the microphone 1200 to capture the user's voice for spoken commands in a natural language.

Furthermore, the near real-time/real-time wearable bioelectronics subsystem 1580, as an augmented reality personal assistant can be integrated with a headset to block out all external light—thus enabling a high-definition image (in front of the user's eyes) for an immersive experience. The headset can be synchronized with the near real-time/real-time wearable bioelectronics subsystem 1580 to track the user's head movement and/or eye movement. For example, the near real-time/real-time wearable bioelectronics subsystem 1580 can be utilized for e-mails, text messages, Facebook/Twitter updates, tweets, appointments & incoming phone calls, breaking news, weather, stock data, sports results, real-time feedback on action sports, turn by turn directions, aid for hearing impaired, translations when talking in different languages, patient's body data to a surgeon, remote training for surgery, teleprompter for public speaking, subtitles at the movies (for hearing impaired and/or for different languages), teaching/discovery, details about art in a museum, social graph/personal analytics and gaming.

A blockchain is a global distributed ledger/database running on millions of devices and open to anyone, involving not just information but anything of value. In essence, it is a shared trusted public ledger that everyone can inspect, but which no single user controls. A blockchain creates distributed documentation of (outputs/transactions) in the form of a digital ledger available on a network of computers. When a transaction happens, the users propose a record to the ledger. Records are bundled into blocks (groups for processing), and each block receives a unique fingerprint derived from the records it contains. Each block can include the fingerprint of the prior block, creating a robust chain of title. It's very easy to verify the integrity of the entire chain, and nearly impossible to falsify historic records. In summary, a blockchain is a public ledger of transactions which critically provides trust based upon mathematics, rather than human relationships or institutions. Furthermore, a blockchain can be a public blockchain or a consortium blockchain or a private blockchain.

FIG. 17E illustrates interactions/communications/couplings of the near real-time/real-time wearable bioelectronics subsystem 1580, as an augmented reality personal assistant with (a) another near real-time/real-time wearable bioelectronics subsystem, as an augmented reality personal assistant and (b) the portable internet appliance 1600 via a cloud based data storage unit. It should be noted that the near real-time/real-time wearable bioelectronics subsystem 1580, as an augmented reality personal assistant can directly interact/communicate/couple with the portable internet appliance 1600 and/or the near real-time/real-time wearable bioelectronics subsystem 1580, as an augmented reality personal assistant via the internet for sharing snapshots/holographic snapshots (e.g., images/videos) of the surrounding contextual world. The user may color enhance/edit/geotag/personalize (e.g., personalize with emoji/emoticon) snapshots/holographic snapshots by utilizing an algorithm(s). For example, the user is watching the 2016 NBA final game between the Cleveland Cavaliers v. Golden State Warriors, the user (along with his/her personalized social graph and/or social geotag of geographical data (latitude & longitude) with videos, photographs, websites, e-mails and status updates) may color enhance/edit/geotag/personalize the near real-time/real-time snapshots/holographic snapshots of Lebron James blocking the shot of the Golden State Warriors' Andre Iguodala like "unbelievable—superman/batman performance of Lebron James" by either text input or text command in natural language or voice command in natural language from the near real-time/real-time wearable bioelectronics subsystem 1580, as an augmented reality personal assistant or from the portable internet appliance 1600.

Furthermore, the near real-time/real-time wearable bioelectronics subsystem 1580, as an augmented reality personal assistant can be also electrically or wirelessly coupled with networks of objects/biological objects, which can couple with a blockchain to manage their outputs/interactions. Networks of objects/biological objects can enable a highly distributed global grid, wherein blockchain enabled transactions can be negotiated by one or more machine learning/deep learning neural networks based learning/re-learning algorithms and can be executed for self-executing and self-enforcing smart contracts. These transactions can be verified by the many near real-time/real-time wearable bioelectronics subsystem 1580s, as an augmented reality personal assistants. Biological programming (e.g., editing a gene of a specific cell for a specific function) is a biological transaction, which can be provisioned, regulated and supported by a blockchain. For example, networks of objects/biological objects can report to a blockchain, when it detects a problem. The problem can trigger a set of instructions (e.g., calling/paying for repairman/doctor) for solving the specific problem, even before the user knows anything is wrong.

The near real-time/real-time wearable bioelectronics subsystem 1580, as an augmented reality personal assistant with an internet connection, real-time location data, personal information/profile, appointments/calendar, chats/e-mails (or eavesdropping on chats/e-mails/conversations in a natural language in near real-time/real-time), payment/purchase history and a changing social graph (of the user) can anticipate what information the user may/will need based on context and past behavior—thus to provide it, before they have even asked for it. For example, spontaneously and predictively suggesting that the user should stay in the hotel room, because of heavy traffic in the downtown of a city (where the hotel is located) and offer personalized suggestions for a dinner in the hotel.

The near real-time/real-time wearable bioelectronics subsystem 1580, as an augmented reality personal assistant with an internet connection, real-time location data, personal information/profile, appointments/calendar, chats/e-mails (or eavesdropping on chats/e-mails in near real-time/real-time), payment/purchase history and a changing social graph (of the user) can eavesdrop on the user's communication, utilizing (a) an intelligent learning algorithm and/or (b) an algorithm for understanding communication, wherein the intelligent learning algorithm and/or the algorithm for understanding communication can be stored in the storage/memory component 880 or a cloud based data storage unit.

In connection with (a) another near real-time/real-time wearable bioelectronics subsystem 1580, as an augmented reality personal assistant and (b) the portable internet appliance via a cloud based data storage unit, the near real-time/real-time wearable bioelectronics subsystem 1580, as an augmented reality personal assistant with an internet connection, real-time location data, personal information/profile, appointments/calendar, chats/e-mails (or eavesdropping on chats/e-mails/conversations in a natural language in near real-time/real-time), payment/purchase history and a changing social graph (of the user) can anticipate what information the user may/will need based on context and past behavior—thus to provide it, before they have even asked for it. For example, spontaneously and predictively suggesting that the user buy a new dress with particular details (e.g., matching colors), prior to a job interview and offer personalized suggestions for the new dress.

Furthermore, the near real-time/real-time wearable bioelectronics subsystem 1580, as an augmented reality personal assistant can detect what's going on in a photo or video, live in real-time, making it possible to suggest contextual choice recommendations for that particular situation, when the near real-time/real-time wearable bioelectronics subsystem 1580, as an augmented reality personal assistant communicates with an unified algorithm, wherein the unified algorithm can include artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

Furthermore, a location-sensing system, utilizing sensors (which are capable of area sensing, depth sensing and motion tracking), computer vision (including self learning computer vision), machine vision (including self-learning machine vision), image processor and/or the microprocessor/super-processor (including a graphical processing unit) 1320 can enable the near real-time/real-time wearable bioelectronics subsystem 1580, as an augmented reality personal assistant near real-time/real-time comprehension of space and motion for learning/remembering/mapping areas around the near real-time/real-time wearable bioelectronics subsystem 1580, as an augmented reality personal assistant. It should be noted that the system-on-chips (including neural networks based system-on-chips) described/disclosed in U.S. Non-Provisional patent application Ser. No. 14/999,601 entitled "SYSTEM AND METHOD OF AMBIENT/PER- VASIVE USER/HEALTHCARE EXPERIENCE", filed on Jun. 1, 2016 can replace the above microprocessor/superprocessor (including a graphical processing unit) 1320 and also enable cognitive/neural like computing and the entire contents of this US Non-Provisional Patent Application are incorporated herein.

For example, a virtual reality game (e.g., Pokémon Go) can appear in close proximity and really interact with its environment/landscape in a realistic way, rather than hovering just in the air. An artist is livestreaming a performance, which can be watched by the near real-time/real-time wearable bioelectronics subsystem 1580, as an augmented reality personal assistant. The artist can receive compensation, when his performance is linked with a blockchain. Similarly, a virtual reality game can be linked with a blockchain for compensation/locating a suitable affinity group, when the virtual reality game is played.

As an example, the near real-time/real-time wearable bioelectronics subsystem 1580, as an augmented reality personal assistant can be utilized for (a) augmenting digital information atop the real world (e.g., directions over the street in front of the user) or (b) adding a digital object onto the real world (e.g., a virtual post-it note/graffiti on a museum wall) or (c) enhancing a real object/real event with reviews/edits/social recommendations or (d) creating an instant social graph (personal analytics) of the user with user location, user selfie (may also utilize depth sensing technology) and user instant activities. Such social graphs can be shared with other users in real-time/near real-time.

The near real-time/real-time wearable bioelectronics subsystem 1580, as an augmented reality personal assistant can include an active optical waveguide device that can estimate eye aberrations of the user and project an aberration corrected image into the eyes of the user. Such an optical waveguide device can be (a) decorated with optical nanoantennas (e.g., FIG. 12K) on top of the optical waveguide and/or (b) integrated with an actively tunable optical material (e.g., a phase change material GST ($Ge_2Sb_2Te_5$) or a phase transition material vanadium dioxide.

The near real-time/real-time wearable bioelectronics subsystem 1580, as an augmented reality personal assistant can include a network of photonic integrated circuits on silicon nitride thin-film or benzocyclobutene (BCB) polymer deposited/lifted off on the substrate (e.g., glass) of the display, incorporating display pixels 1020. The network of photonic integrated circuits includes waveguides, wherein the waveguides are optically coupled with light (light from quantum dot red/green/blue light emitting diodes or lasers or two-dimensional material based light sources, as in 12Z2). A section of the photonic integrated circuit can include about 100 pixels (e.g., an array of ten pixels by ten pixels), wherein each pixel can have an array of dielectric Mie-type resonators to project an image into the eyes of the user. For example, 50 titanium dioxide nanopillars (each titanium dioxide nanopillar is about 250 nanometers in diameter, about 150 nanometers apart in center-to-center) can be utilized as dielectric Mie-type resonator arrays to project an image into the eyes of the user. However, an electrically activated optically tunable material (e.g., samarium nickelate ($SmNiO_3$) or vanadium dioxide) or ferroelectric material (e.g., barium strontium titanate (BST)) can be utilized instead of titanium dioxide for active control of light propagation/image into the eyes of the user.

In another embodiment, on top of the substrate (e.g., glass) of the display incorporating display pixels 1020, a network of silicon nitride waveguides can be fabricated/constructed. The network of silicon nitride waveguides can route light (e.g., light from quantum dot red/green/blue light emitting diodes or lasers or two-dimensional material based light sources, as in 12Z2). Above the silicon nitride waveguides, a layer (about 1 micron in thickness) of an electrically activated optically tunable material can be fabricated/constructed. On top of the electrically activated optically tunable material, there are transparent/niobium electrodes, integrated with tiny openings in the electrodes to allow light (which is guided via silicon nitride waveguides) to pass through. Beneath the tiny openings in the electrodes, the waveguides break into a series of sequential ridges, which can act as diffraction gratings to direct light down through the holes and concentrate the light into a beam narrow enough toward an eye/retina. Alternatively, a hologram/pair of holograms coupled with one or more waveguides can be utilized to direct the light into a beam narrow enough toward an eye/retina.

Furthermore, the integration of a surface normal light modulator (e.g., graphene based surface normal spatial light modulator (SLM)) with the diffraction gratings) can enable the eye to receive light in time-varying intensities.

Additionally, the photonic integrated circuit in silicon nitride thin-film or benzocyclobutene polymer deposited/lifted off on the substrate of the display with an array of v-shaped metal resonators an enable holograms over the substrate of display, incorporating display pixels 1020, when light sources are generally lasers/quantum-dot lasers.

Additionally, a two-dimensional array of Mie-type resonators (e.g., silicon nanodisks of about 500 nanometers in diameter at about 750 nanometers apart-center of one silicon nanodisk to next one) embedded in liquid-crystals on a glass substrate, wherein the glass substrate is integrated on a transparent semiconductor (e.g., amorphous indium gallium zinc oxide/IGZO). The upper electrode on liquid-crystals is a transparent electrode (e.g., indium tin oxide). By applying voltage, liquid-crystal molecules orient perpendicular to Mie-resonators—thus, interacting with incoming light beams to enable an electrically tunable dynamic display/hologram, depending on the orientation of liquid-crystal molecules.

Alternatively, a topological insulator (e.g., $Sb_2Te_3$)/artificial topological insulator (e.g., utilizing alternating layers of topological and standard insulators) can have a low refractive index on the surface and an ultra-high refractive index in bulk. A thin-film/stretchable film (e.g., poly(dimethylsiloxane) film) of the topological insulator/artificial topological insulator can modulate the phase of light (from a fast-direct laser writing (DLW) system) to give three-dimensional depth, as in holograms. It should be noted that a stretchable film can also switch between images.

Furthermore, the photonic integrated circuit in silicon nitride thin-film or benzocyclobutene polymer deposited/lifted off on the substrate of the display with an array of dielectric/semiconductor (e.g., AiGaAs) metamaterial Mie-type resonators (about 500 nanometers in diameter, 200 nanometers in depth and 3 to 5 microns in pitch) can be utilized to convert infrared light to visible light, directly in line of sight.

Additionally, it should be noted that all components/devices and/or application examples and/or embodiments of the portable internet appliance 1600 can be utilized with the near real-time/real-time wearable bioelectronics subsystem 1580, as an augmented reality personal assistant.

It should be apparent that one or more features of the portable internet appliance 1600 (as discussed later) can be combined with one or more features of the near real-time/real-time wearable bioelectronics subsystem 1580.

In particular, the near real-time/real-time wearable bio-electronics subsystem 1580, as an augmented reality personal assistant can be integrated/co-packaged with (a) system-on-chip/learning neural processor (either electrical or photonic), (b) interconnection within the system-on-chip, (c) Terahertz band transceiver, (d) tunable/graphene/metamaterial based antenna, (e) software-defined radio, (f) 360-degrees spherical camera, (g) ultrathin/lensless/multi-spectral band camera, (h) sensor integrated with multi-spectral band camera, (i) three-dimensional video conferencing subsystem, (j) embedded configuration of projector, camera & sensor, (k) embedded configuration of projector, camera, sensor & microprocessor/system-on-chip, (l) embedded configuration of display, camera, sensor & microprocessor/system-on-chip, (m) sensor-system-on-chip, (n) personal awareness assistant module, (o) solar cell, (p) wireless charging, (q) ultrathin display and (r) ultrathin battery, as described below in connection with the portable internet appliance 1600.

Portable Internet Appliance

Details of the portable internet appliance 1600 have been described/disclosed in U.S. Non-Provisional patent application Ser. No. 12/238,286 entitled, "PORTABLE INTERNET APPLIANCE", filed on Sep. 25, 2008; "SYSTEM & METHOD FOR MACHINE LEARNING BASED USER APPLICATION", filed on Apr. 16, 2012 and "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

The portable internet appliance 1600 is about 125 millimeters long, 75 millimeters wide and 20 millimeters thick. It has a microprocessor (e.g., Intel's x86 based Medfield or Qualcomm's ARM based Snapdragon 800 or Nvidia Tegra) and a system operating algorithm (stored in a data storage component of the portable internet appliance 1600) which can be electrically connected/coupled/interacted with: (a) a memory component, (b) a data storage component, (c) an IP address stored in the memory component, (d) an internet security algorithm (internet firewall/spyware/user-specified security control and authentication), (e) a touch/multi-touch sensitive foldable/stretchable/split/wrap-around display, wherein at least one section of the display is integrated with a component such as PCS 1280/DCS 1285 and alternatively, a touch/multi-touch sensitive stretchable/split/wrap-around display, wherein at least the back side of the display is integrated with a solar cell component to collect residual back reflected light, (f) two (2) high definition (HD) (e.g., one giga pixel) multi-spectral band visible/near-infrared/infrared/three-dimensional image capturing cameras (two (2) cameras-one camera for video chat and another camera for photography, however, a 180-degrees angle rotating camera is also suitable), (g) a video conferencing system-on-chip (integrated with a dynamic video compression module—the video compression module could be either an electronic module and/or an algorithm), (h) a surround sound component (e.g., a micro-electrical-mechanical-systems based silicon microphone component Analog ADMP 401 or an equivalent component from akustica), (i) a personal area network (PAN) wireless transceiver module (e.g., Wibree/Bluetooth/Wi-Fi/ultra-wideband/millimeter wave (including 60 GHz)/terahertz band with antenna(s) or a software-defined radio with a tunable antenna), (j) near-field communication to enable the following: product/service discovery/initiation, peer-to-peer exchange/transfer/share/transaction, machine-to-machine exchange/transfer/share/transaction, remote access of a system/terminal and access authentication, (k) DASH 7 wireless transceiver (DASH 7 is an inexpensive instant-on, long range, low power P2P wireless communications standard for applications requiring modest bandwidth like text messages, sensor readings, or source and operates on a single, global frequency 433 MHz. Unlike Wi-Fi, DASH 7 operates at a radio frequency which provides for both long range (up to 1 Km) and excellent indoor signal propagation. Dash 7 is a complement to near-field communication, driven by a combination of sensing function with wireless transmission), (l) a location measurement component (e.g., an electronic compass/indoor positioning system/global positioning system with antenna(s)), (m) a radio frequency identification/one-dimensional/two-dimensional barcode/quick response codes reader, (n) a communication wireless transceiver module (e.g., WiMax/LTE) with antenna(s)/metamaterial antenna(s) or a software-defined radio with a tunable antenna/tunable metamaterial antenna), (o) a sensor based communication component (e.g., low-power radio frequency identification presence tag that can announce a user's identity and location or can communicate to turn on the temperature of a home or can text the user's wife what things she might need from the grocery store on the way back from the user's office or can text the nearest Starbucks for the user's favorite coffee, as the user's car approaches the nearest Starbucks or the nearest Starbucks can text an electronic coupon to the user for purchasing the user's favorite coffee, as the user/user's car approaches the nearest Starbucks), (p) a biometric component (e.g., finger print/retina scan sensor), (q) a time-shift module (e.g., the user's favorite live basketball game can be recorded to be watched at a later time), (r) a place-shift module (e.g., the user's favorite live basketball game is configured to be watched anywhere, irrespective of the user's location), (s) a personal awareness assistant module, (t) a first algorithm for content (voice, video and data)—over-IP—thus the first algorithm for content over-IP via an ambient Wi-Fi/WiMax network, can disrupt a traditional carrier controlled cellular business model, (u) a second algorithm of a voice-to-text-to-voice conversion algorithm, (v) a third algorithm including one or more of the following: a voice recognition/editing algorithm, a hand-writing recognition algorithm, an image authentication algorithm, a facial recognition algorithm and a biometric recognition algorithm (e.g., a heartbeat/voice signature can validate the user depositing an image of a check/banknote via digital banking), (w) a fourth algorithm for rendering intelligence (e.g., artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning)), (x) a fifth algorithm for evidence based learning, hypothesis generation and natural language processing, (y) a sixth algorithm for a voice activated search engine configured by natural language processing, as a digital personal assistant, (z) a seventh algorithm including one or more of the following: algorithm-as-a-service, behavior modeling (e.g., if the user prefers to watch basketball games-such behavior patterns can be analyzed statistically with a predictive modeling algorithm for sending a basketball ticket related coupon to the user), physical search algorithm (e.g., the portable internet appliance 1600 can scan/tag a product physically/directly to search-product manufacturer, product price, product availability, product reviews and store locations/distribution centres of the product) and a semi-autonomous or autonomous software agent (e.g., a semi-autonomous or autonomous software agent can search the internet with/without the user's input to find any useful information for the user or for the preferences/behavior patterns of the user)—it should be noted that the semi-autonomous or autonomous software agent can be algorithmically coupled/integrated with the sixth algorithm for voice activated search engine (aa) an electrical powering component (e.g., a battery), (ab) a solar cell component, (ac) a supercapacitor (e.g., a graphene based supercapacitor) to store electrical power, (ad) a lab-on-chip/biosensor, (ae) an ionized gas cloud based cooling component for the microprocessor/system-on-chip and (af) a fixed/reconfigurable outer case/package, wherein the portable internet appliance 1600 can morph into a smaller form factor (e.g., a size of a multi-purpose programmable smart card/wristwatch-style device).

System-On-Chip of Portable Internet Appliance

A first system-on-chip integrates: (a) a digital microprocessor based on planar transistors/three-dimensional transistors/spin-transistors; (b) memory; (c) a graphic processor; and (d) chip-to-chip optical interconnect. Details of an optical interconnect have been described/disclosed in U.S. Non-Provisional patent application Ser. No. 13/448,378 entitled "SYSTEM & METHOD FOR MACHINE LEARNING BASED USER APPLICATION", filed on Apr. 16, 2012 and the entire contents of this US Non-Provisional Patent Application are incorporated herein.

Additionally, the digital microprocessor in the first system-on-chip can integrate a VLSI Electronic IC with memristors elements (e.g., silver/amorphous-silicon/poly-silicon structure) for neural like processing based on electrical inputs (e.g., current/voltage). This can be referred as an electrical neural learning processor.

Additionally, the digital microprocessor in the first system-on-chip can integrate a VLSI Photonic IC (a photonic flip-flop based on two multi-wavelength ring lasers coupled with one SOA or plasmonic lasers with a metallic cavity) for ultrafast information processing.

Both the VLSI Photonic IC (VLSI-PIC) and VLSI Electronic IC (VLSI-EIC) can be fabricated/constructed by co-integration epitaxy of III-V material on silicon.

A second system-on-chip integrates the first system-on-chip and an embedded internet firewall.

A third system-on-chip integrates the second system-on-chip and an embedded spyware.

A fourth system-on-chip integrates the third system-on-chip and a user-specific security control/authentication.

A fifth system-on-chip integrates the fourth system-on-chip and a personal area network wireless component (e.g., Wibree/Bluetooth/near-field communication/Wi-Fi/ultra-wideband/millimeter wave (including 60 GHz)/terahertz band).

Additionally, a sixth system-on-chip can integrate the fifth system-on-chip and a photonic neural learning processor, wherein the photonic neural learning processor (can be useful for machine learning and/or image/pattern recognition and/or Big Data analysis) can be fabricated/constructed for example, utilizing a cascaded configuration of interferometers (e.g., Mach-Zehnder type interferometers), 3-db couplers and waveguide based phase shifters. Heat applied to the waveguide base phase shifter(s) can direct light beams to change its shape. It should be noted that interferometer(s) and/or waveguide based phase shifter(s) can be fabricated/constructed, utilizing a phase change/phase transition material for faster response to an external stimulus (e.g., heat or voltage) and/or integrated with saturable absorbers (e.g., graphene integrated saturable absorber). To reduce thermal cross-talk between the heating elements, thermal isolation trenches can be fabricated/constructed between the heating elements. It should be noted that the photonic neural processor can be a standalone subsystem. Furthermore, various embodiments of system-on-chips/neural networks based system-on-chips have been described/disclosed described in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein. Such a system-on-chip/neural networks based system-on-chip can replace the microprocessor/super-processor and enable cognitive/neural like computing.

Interconnection within a System-On-Chip of Portable Internet Appliance

Connecting circuits (chip-to-chip) within a system-on-chip can be achieved by an optical interconnect. Details of an optical interconnect have been described/disclosed in U.S. Non-Provisional patent application Ser. No. 13/448,378 entitled "SYSTEM & METHOD FOR MACHINE LEARNING BASED USER APPLICATION", filed on Apr. 16, 2012 and entire contents of this US Non-Provisional Patent Application are incorporated herein.

As illustrated in FIG. 17D, stacking of circuits within a system-on-chip can be realized, by utilizing an array of vertical nanotubes (e.g., boron nitride/multi-walled carbon nanotubes) and a horizontal frame of a two-dimensional material (e.g. graphene/molybdenum disulphide) or silicone—thus substantially eliminating interconnected wires.

Terahertz Band Transceiver of Portable Internet Appliance

It should be noted that a terahertz band transceiver can be based on silicon-germanium heterojunction bipolar transistors (HBTs) or a hybrid silicon-germanium and gallium nitride based device enhanced with graphene.

Tunable Antenna & Software-Defined Radio of Portable Internet Appliance

A tunable radio-frequency carbon nanotube cavity can tune in between 2 GHz and 3 GHz. By merging many antennas, utilizing a tunable carbon nanotube cavity and an analog/digital converter, a software-defined radio can be fabricated/constructed.

Graphene or Metamaterial Based Antenna of Portable Internet Appliance

A graphene based antenna can enable faster wireless connection. Graphene based antennas can be fabricated/constructed, utilizing an array of strips of graphene material (about 10 to 100 nanometers width and 1 micron in length). Transmission and reception at a terahertz band can occur at these dimensions. Electromagnetic waves in the terahertz band can interact with plasmonic waves of electrons at the surface of the array of strips of graphene material to send and/or receive data.

360-Degrees Angle Spherical Camera of Portable Internet Appliance

A spherical 360-degrees angle image can be generated by shooting images in four directions (left, right, up and down) centering on a spherical camera with two super-wide-angle lenses at once. Incident light from the super-wide-angle lenses are reflected by a prism mirror (at 90-degrees angle with respect to each other) and received by two image sensors. Two images obtained with two image sensors are thus synthesized to generate a complete spherical image.

Lensless Camera of Portable Internet Appliance

A lensless camera has: (a) an array of liquid-crystal devices that allows light to pass through, (b) a red-green-blue photoelectric sensor and (c) a microprocessor to control the array of liquid-crystal devices and to process the data that is received from red-green-blue photoelectric sensor. To create an image, the array of liquid-crystal devices is placed between an item (to be imaged) and the single pixel sensor. The microprocessor sends signals to the array of liquid-crystal devices causing a few liquid-crystals in the array of liquid-crystal devices to allow light to pass through, each serves as a tiny optical aperture. The liquid-crystals in the array of liquid-crystal devices can be chosen by a random number generator and the end result is just a speckled pattern. The photoelectric sensor can capture the light that is allowed to pass through the liquid-crystals in the array of liquid-crystal devices and send the data to the microprocessor. To create a single picture, multiple image-captures can be taken with different random patterns generated on the array of liquid-crystal devices. The data from all of the image-captures can be processed at the microprocessor afterwards and the result is a single photograph. The more image-captures are taken, the higher is the resolution of the final image.

In another embodiment, a lensless camera can be fabricated/constructed, utilizing the principle of an insect's compound eye/light field optics with over 200 photodiodes, wherein each photodiode is placed just below a microlens, wherein each microlens is configured to capture 40 by 40 pixels. The resulting image can be electronically focused/processed into a three-dimensional image afterwards.

Three-Dimensional Video Conferencing of Portable Internet Appliance

An array of (at least four) front-facing cameras can provide stereo views and motion parallax (apparent difference in a direction of movement produced relative to its environment). Each camera can create a low dynamic range depth map. However, an array of cameras can create a high dynamic range depth map. Thus, the portable internet appliance 1600 can enable three-dimensional video conferencing.

Multi-Spectral Band Camera of Portable Internet Appliance

Nano-scaled lithography (e.g., phase mask/electron beam lithography) and reactive ion/plasma etching of two gold electrodes can be utilized to electrically contact on graphene.

Graphene can be chemically functionalized with an array of quantum dots/nanocrystals. Quantum dots/nanocrystals can be arranged according to their size and the specific wavelength of the spectrum to be absorbed.

Silicon (Si) quantum dots/nanocrystals can be tuned in visible wavelength range. Lead-sulphide (PbS) quantum dots/nanocrystals can be tuned in short-wavelength infrared (SWIR) and near-infrared (NIR) ranges.

The above graphene device chemically functionalized with quantum dots/nanocrystals can act like a transistor and the carrier density in the graphene can be changed by varying the gate voltage.

Graphene functionalized with an array of quantum dots/nanocrystals can act as a multi-spectral band (visible/near-infrared/infrared) photodetector/camera pixel.

In another embodiment, graphene quantum dots can trap light-generated electron particles for a much longer time, resulting in a much stronger electric signal to be processed into an image. Furthermore, graphene quantum dots themselves can be utilized to fabricate/construct a multi-spectral band camera. Fabrication of graphene quantum dots can be as follows: a monolayer graphene can be mechanically exfoliated on an ultrathin silicon dioxide/silicon substrate. The graphene photodetector can be fabricated/constructed (by photolithography and lift-off process) into a field effect transistor structure with a source metal electrode, a drain metal electrode and a gate terminal (the gate terminal is at the bottom of the silicon substrate). A nano-scaled sacrificial metal can be deposited on the graphene by electron beam evaporation and then the nano-scaled sacrificial metal can be wet etched to form graphene quantum dots of various sizes on the ultrathin silicon substrate.

Sensor Integrated with Multi-Spectral Band Camera of Portable Internet Appliance A multi-spectral band (visible/near-infrared/infrared) camera can be integrated with a sensor. The sensor can track what the user touches or sees. The sensor can capture the user's voice for spoken commands with the microphone (of the personal awareness assistant module of the portable internet appliance 1600).

Embedded Configuration of Projector, Camera & Sensor of Portable Internet Appliance The portable internet appliance 1600 can be integrated with a projector, a camera and a sensor/an array of sensors (e.g., an array of touch-sensitive sensors) in an embedded configuration (of a projector, a camera and a sensor/an array of sensors) for blurring between reality, virtual reality and augmented reality for an enhanced mixed reality experience. If a user can enlarge a portion of an image by gently touching the screen to enlarge, the projected image will make the same response.

A rear projector can be based on Texas Instrument's Digital Light Processor projector chip. A typical Texas Instrument's Digital Light Processor projector chip contains up to 8 million micromirrors. Each micromirror can be tilted at a rate of 10,000 times per second to reflect light to create a precise digital image on a surface.

Instead of Texas Instrument's Digital Light Processor projector chip, a rear projector can be fabricated/constructed, utilizing a tiltable single crystal mirror (of about 1 millimeter in diameter) or a microelectro-mechanical-system based scanning mirror. The tiltable single crystal mirror or a microelectro-mechanical-system based scanning mirror deflects a color (blue, green and red) of light beam from a microelectro-mechanical-system enabled wavelength tunable surface emitting vertical cavity laser, by rapidly switching the angle of orientation—thus building pixel by pixel.

Furthermore, a rear projector can be fabricated/constructed, utilizing the principle of an insect's compound eye/light field optics with hundreds of light emitting diodes, wherein each light emitting diode is placed just below a microlens.

A PCS component 1280 is an embedded integration of a projector, a camera and an emotion sensor/eye motion/gesture/touch sensor (e.g., an emotion sensor can be fabricated/constructing, utilizing analysis of facial expressions by an algorithm(s) and a camera/infrared camera viewing the user's facer and a touch sensor can be fabricated/constructed, utilizing a large array of zinc oxide nanowire based transistors).

Figure 18A:
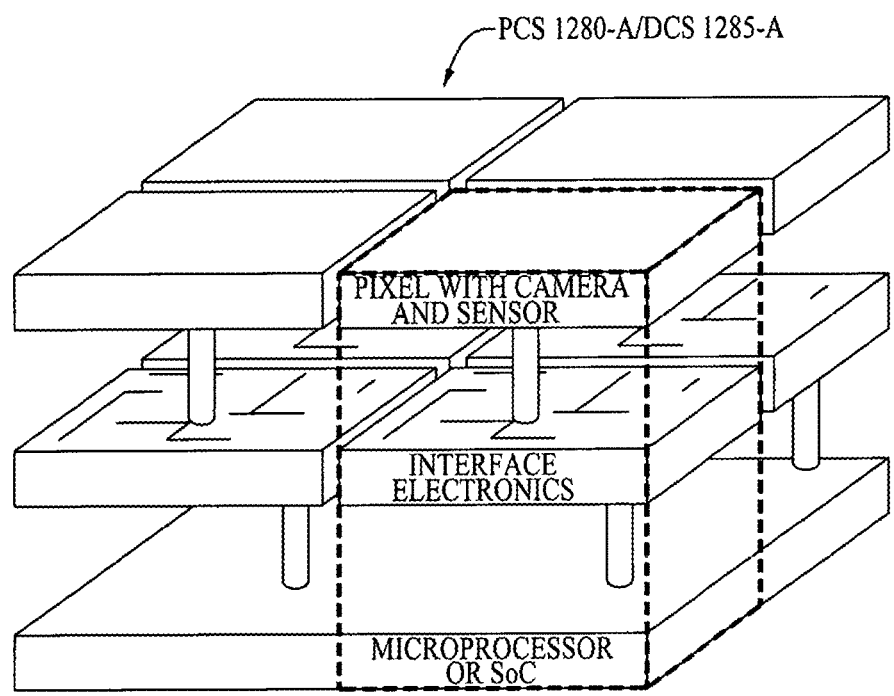
FIG. 18A illustrates a display configuration of the portable internet appliance.

FIG. 18A illustrates a display configuration with a horizontal space sharing and vertical three-dimensional stacking of PCS component 1280/1285-A and a DCS component 1285/1285-A of the portable internet appliance 1600.

Furthermore, in some cases, it may be suitable to replace the projector of the PCS component 1280 with a display pixel. A DCS component 1285 is an embedded integration of a display, a camera and an emotion sensor/eye motion/gesture/touch sensor. Optionally, such an embedded integration can be limited to an array of display pixels.

The integrated PCS component 1280 or integrated DCS 1285 can display, record visual information and sense without an external video capture device, while the user is sitting in front of it.

Embedded Configuration of Projector, Camera, Sensor & Microprocessor/System-On-Chip of Portable Internet Appliance The PCS component 1280-A is an embedded integration of a projector, a camera and an emotion sensor/eye motion/gesture/touch sensor and a microprocessor or first/second/third/fourth/fifth system-on-chip.

Embedded Configuration of Display, Camera, Sensor & Microprocessor/System-On-Chip of Portable Internet Appliance The DCS 1285-A is an embedded integration of a display, a camera and an emotion sensor/eye motion/gesture/touch sensor and a microprocessor or the first/second/third/fourth/fifth system-on-chip.

The display itself can have embedded integration of an array of sensors, such sensors can be fabricated/constructed (e.g., optically sensing waveguides) by a femtosecond laser. Utilizing a femtosecond laser module, a two-dimensional/three-dimensional optically sensing waveguide(s) can be fabricated/constructed at various depths of the display substrate.

The display itself can have embedded integration of (a) a transparent image sensor based on graphene, (b) a transparent microprocessor based on nanowires (e.g., zinc oxide nanowires) and (c) a transparent battery.

The display itself can have embedded integration of a transparent solar cell (e.g., $CH_3NH_3PbI_3$-xClx perovskite based solar cell, utilizing indium tin oxide (ITO) or fluorine-doped tin oxide (FTO) and gold or graphene electrodes).

Furthermore, the above transparent solar cell can be integrated with vanadium dioxide thin-film/nanoparticles for both electricity generation and electricity saving.

Additionally, the transparent microprocessor can have embedded integration of an array of transparent sensors (e.g., transparent vanadium dioxide sensors). Such transparent sensors integrated with the transparent microprocessor can sense, manipulate and respond quickly, because either feedback or feed forward control is integrated within one integrated system-on-chip.

Furthermore, the display itself can be integrated with a vanadium dioxide thin-film thermochromic device, when it is activated by either voltage or temperature.

The integrated PCS component 1280-A or integrated DCS 1285-A can display, record visual information, sense and process data/information without an external video capture device, while the user sits in front of it.

Split Display/Wrap-Around/Foldable-Stretchable Display/Dual Displays Of Portable Internet Appliance The portable internet appliance 1600 can have a split display, wherein one section of the display is a high pixel density-high brightness liquid-crystal display/organic light emitting display and wherein the other section of the display is based on a component, such as PCS 1280/DCS 1285.

Alternatively, the portable internet appliance 1600 can have a wrap-around display or dual displays, wherein one display is a high pixel density-high brightness liquid-crystal display/organic light emitting display and wherein another display is integrated with a component such as PCS 1280/DCS 1285.

The display can be reconfigured for at least two (2) different sizes, utilizing a foldable/stretchable display, which can be fabricated/constructed, utilizing a graphene sheet and/or an organic light-emitting diode (OLED) connecting/coupling/interacting with a printed organic transistor or carbon nanotube based thin-film transistor and a rubbery conductor (e.g., a mixture of a carbon nanotube/gold conductor and a rubbery polymer) with a touch/multi-touch sensor.

Furthermore, a foldable/stretchable display can be fabricated/constructed, utilizing an array of flexible polymer waveguides/multi-mode plastic fibers, wherein the input of each flexible polymer waveguide/multi-mode plastic fiber can be integrated with a high brightness light source and the output of the above flexible polymer waveguide/multi-mode plastic fiber can be integrated with a high brightness white phosphor thin-film and a dense matrix of blue, green and red thin-film filters or tunable thin-film filters.

Various spatial arrangements of the flexible polymer waveguide/multi-mode plastic fiber, high brightness light source, high brightness white phosphor thin-film and thin-film filters/tunable thin-film filters are possible.

Touch Sensitive Interactive Three-Dimensional Liquid-Crystal Display of Portable Internet Appliance The display of the portable internet appliance 1600 can be a thin-film-transistor liquid-crystal three-dimensional liquid-crystal display. A thin-film-transistor liquid-crystal display is an active-matrix liquid-crystal display, a special variant of a liquid-crystal display that utilizes thin-film transistor technology to improve image qualities (e.g., contrast and addressability). Thin-film transistors are tiny switching thin-film transistors/capacitors-arranged in a matrix on a glass substrate. To address a particular pixel, the proper row is switched on and then a charge is sent down to the proper column. Since all of the other rows that the column intersects are turned off, only the capacitor at the designated display pixel receives the specified charge. The capacitor is able to hold the specified charge until the next refresh cycle. With the controlled amount of voltage supplied to a liquid-crystal, the liquid-crystal can untwist only enough to allow some light to pass through.

Instead of a liquid-crystal material, a polymer stabilized liquid-crystal/photoreactive polymer stabilized liquid-crystal material can be utilized.

Additionally, utilizing plasma enhanced chemical vapor deposition (PECVD) and electron beam lithography, an array of vertical nanotubes (e.g., multi-walled carbon nanotubes at about 2 to 5 microns apart) can be fabricated/constructed on a glass substrate. The array of vertical nanotubes can act as an array of vertical microlens-electrodes of variable focal lengths, controlled by an applied voltage. Furthermore, the array of vertical nanotubes, as an array of vertical microlens-electrodes of variable focal lengths can be switched on or off by an applied voltage.

Alternatively, an array of vertical nanowires (e.g., zinc oxide nanowires) can be utilized instead of an array of vertical nanotubes. Additionally, an array of vertical nanowires can be fabricated/constructed by spin-on-nano-printing method.

Currently, due to larger pixel size, the field of view of the three-dimensional liquid-crystal display is limited. Vertical nanotubes/nanowires based three-dimensional liquid-crystal display incorporating of millions of nano-scaled pixels can produce three-dimensional liquid-crystal display with a wider field view.

Additionally, these nano-scaled pixels can be tuned by integrating with millions of micromirrors, wherein each micromirror can be activated by a microelectro-mechanical-system actuator (e.g., Texas Instrument's Digital Light Processor projector chip).

A polymer stabilized liquid-crystal/photoreactive polymer stabilized liquid-crystal material integrated with an array of vertical nanotubes/nanowires can enable a three-dimensional liquid-crystal display, where a hologram can be changed dynamically in real-time.

Furthermore, a polymer stabilized liquid-crystal/photoreactive polymer stabilized liquid-crystal material integrated with (a) an array of vertical nanotubes/nanowires and (b) an array of micromirrors (wherein each micromirror is activated by a microelectro-mechanical-system actuator) can enable a three-dimensional tunable liquid-crystal display, where a hologram can be changed dynamically in real-time.

Furthermore, the above three-dimensional liquid-crystal display can be touch/multi-touch sensitive.

The above touch/multi-touch sensitive three-dimensional liquid-crystal display can be a foldable/stretchable/split/wrap-around display.

The above touch/multi-touch sensitive three-dimensional liquid-crystal display can be an interactive display.

Sensor-System-On-Chip (S-SoC) of Portable Internet Appliance

The portable internet appliance 1600 can be integrated with a sensor-system-on-chip. The sensor-system-on-chip integrates (a) a sensor/an array of sensors, (b) microcontroller/microprocessor and (c) a low-power radio. The sensor/array of sensors can be aware, always on, intelligent, intuitive (e.g., utilizing fuzzy logic based instructions) and wirelessly connected with other sensors. Furthermore, the sensor-system-on-chip can be embedded with the portable internet appliance.

Personal Awareness Assistant Module of Portable Internet Appliance

The personal awareness assistant module can include: a second microprocessor component, a second memory component, a microphone component and a scrolling audio recording buffer component. Furthermore, the personal awareness assistant module can also include: a second data storage component and a second camera component.

The personal awareness assistant module can be always on. It can passively listen to what the user says in a natural language and can respond to particular contexts and situations. For example, the user can hear about a product on the radio and then the user can create a reminder by speaking to the personal awareness assistant module. The portable internet appliance 1600 can then enable further purchasing of the product at a later time.

For example, when the user is introduced to a person, the personal awareness assistant module can automatically recognize the person and may take a low-resolution photo. Once the personal awareness assistant module collects the information, it can automatically categorize the information into a pre-designated database with audio, digital image, time/date stamp and indoor positioning/outdoor positioning location. Because the data is stored contextually, information retrieval can be straightforward. A simple voice command inquiry, such as whom did I meet on Apr. 15, 2009 at 12 p.m.?, enables the personal awareness assistant module to bring up the appropriate information about that specific person. Thus, the portable internet appliance 1600 (integrated with the personal awareness assistant module) is context-aware.

Furthermore, the voice recognition/editing algorithm can enhance the capability of the personal awareness assistant module. Additionally, a face/emotion recognition algorithm can enhance the capability of the personal awareness assistant module.

Solar Cell Component of Portable Internet Appliance

The solar cell can be a quantum dot-nanowire-plasmon solar cell/an array of microscopic solar cells integrated with an array of refractive microlenses.

By way of an example and not by way of any limitation, typical photovoltaic material can be copper indium gallium diselenide/CdS/CdTe/graphene/organic material/crystalline silicon/polycrystalline silicon. Furthermore, monolithically integrated lattice matched, bangdgap-optimized and current matched multi junctions of III-V semiconductor materials can be used, wherein each junction containing a p-n junction and tuned to a particular spectrum of light, reducing losses and thereby increasing efficiency.

An organic material with squaraine dye coating is based on the principle of Förster resonance energy transfer (FRET) mechanism, wherein extra energy can migrate from one molecule to another molecule over a relatively longer distance. Squaraine dye broadens the spectral absorption of the sunlight.

In singlet-exciton fission, an arriving photon from the sunlight can generate two (2) excitons (excited states) yielding two (2) electrons. Pentacene generates two (2) excitons (excited states) yielding two (2) electrons in a narrow visible spectrum of the sunlight. However, pentacene (an organic dye) and/or other materials for singlet-exciton fission in another spectrum of the sunlight can be integrated via coating or wafer stacking/bonding (wafer stacking/bonding is useful, when the material is not suitable for coating) for enhanced electron generation.

The top surface or back surface of the photovoltaic material (e.g., copper indium gallium diselenide/CdS/CdTe/graphene/organic material/crystalline silicon/polycrystalline silicon/monolithically integrated multi junctions of III-V semiconductor materials) can be integrated with a singlet-exciton fission material or an array of singlet-exciton fission materials, depending on the configuration of the solar cell component.

Furthermore, photovoltaic material can be integrated (e.g., doped) with a light sensitive compound/protein.

Furthermore, photovoltaic material can be integrated with a light trapping structure or an optical metamaterial based light trapping structure for light collection from many incident angles. The light trapping structure or an optical metamaterial based light trapping structure can be deposited directly onto the photovoltaic material. Alternatively, the light trapping structure or an optical metamaterial based light trapping structure can be deposited on a suitable substrate and stacked/bonded (e.g., Soitec company's smart stacking layer transfer technology for processed wafers).

Unlike conventional solar cells, electrical contacts can run below the light trapping structure.

Graphene based photovoltaic material can be fabricated/constructed as follows: an ultrathin graphene sheet can be fabricated/constructed, by depositing carbon atoms in the form of graphene on nickel (thin-film substrate) from methane gas.

Additionally, transition metal dichalcogenides (TMDC) or aerographite (a synthetic foam consisting of a porous interconnected network of tubular carbon) monolayers can be sandwiched between/within two layers of graphene. Transition metal dichalcogenides or aerographite monolayers can act as very efficient light absorbers.

Furthermore, an array of vertical/vertically ordered plasmonic nanostructures of metal can be directly fabricated/constructed on the top surface of graphene. The plasmonic nanostructures of metal can enhance local electromagnetic fields in graphene by coupling incoming light with electrons on the surface of the metal.

Furthermore, instead of an array of vertical/vertically ordered plasmonic nanostructures of metal, nanowires of indium gallium arsenide (InGaAs) can be grown on the top surface of graphene by van der Waals epitaxy induced phase segregation.

Alternative to an array of vertical/vertically ordered nanowires integrated on the top surface of the photovoltaic material, the top surface of the photovoltaic material can have an array of vertical nanowires (e.g., zinc oxide nanowires) to concentrate rays of sunlight into a very small area of each nanowire by a factor of about ten (10) at a given wavelength of the sunlight. Because the diameter of a vertical nanowire is smaller than the wavelength of sunlight, it can cause resonances in the intensity of the sunlight in and around nanowires to produce concentrated sunlight, at a much higher conversion efficiency of the sunlight.

Furthermore, the top surface of the array of vertical/vertically ordered nanowires or vertical nanowires can be integrated with an array of colloidal deposited/self-assembled variable sized quantum dots. These variable sized quantum dots can absorb the sunlight over a much wider range of wavelengths. These variable sized quantum dots can be arranged according to their size and according to the specific wavelength of the solar spectrum that is absorbed. Thus, the harvesting of the sunlight's power (absorption) is increased.

Furthermore, instead of colloidal deposited/self-assembled variable sized quantum dots, an ultra thin-film of silicon nanoparticles (1 to 3 nanometers) can be deposited, forming a transparent layer of silicon nanoparticles. Large voltage enhancement with a dramatic increase in power ranging from as much as 60-70% in the ultraviolet-blue (UV) spectrum using these silicon nanoparticles and a significant boost in power by as much as 10% in the visible light spectrum can be obtained.

Instead of an array of plasmonic nanostructures of metal, an array of metamaterial structures of multi-layered metal-dielectric thin-film can be directly fabricated/constructed on the top surface of graphene.

A protective film can be deposited over the graphene and nickel (thin-film substrate on which graphene was grown) and dissolved in a suitable acid.

The unprotected back surface of graphene can be suitably coated with pentacene and then it can be attached to a flexible polymer sheet. Instead of a single layer, several layers of graphene (wherein each layer of graphene is protected on a flexible polymer sheets) can act as an efficient graphene photovoltaic material.

Furthermore, an array of plasmonic optical nanoantennas at the substrate (of the quantum dot-nanowire-plasmon solar cell) can be fabricated/constructed to enhance both light trapping and spectral efficiency.

Furthermore, sunlight can be collected by a micro-reflector and directed at a very specific angle into an array of thin-film optical filters (or nano-scaled optical filters), wherein each thin-film optical filter (or each nano-scaled optical filter) is configured to transmit a spectral band/slice of sunlight spectrum to illuminate a spectrum-matching quantum dot-nanowire-plasmon solar cell (out of an array of quantum dot-nanowire-plasmon solar cells).

Each quantum dot-nanowire-plasmon solar cell is fabricated/constructed, utilizing a different photovoltaic material, wherein each photovoltaic material is coated with pentacene. Such a configuration of an array of quantum dot-nanowire-plasmon solar cells of different photovoltaic materials coated with pentacene coating can significantly increase efficiency of the solar cell.

An alternative embodiment of the solar cell, a three-dimensional solar cell can be fabricated/constructed, by depositing a photovoltaic material: CdS/CdTe/polycrystalline silicon or alternatively, roll-to-roll processing of a photovoltaic material: (e.g., graphene/organic material) on an array of vertical cubes.

Each vertical cube can consist of a large array of nanotubes (e.g., carbon nanotubes). The nanotubes are grown on a bottom metal pattern (the bottom metal film is deposited, photolithographically patterned and reactive ion-plasma etched on a substrate).

By way of an example and not by way of any limitation, a photovoltaic material such as polycrystalline silicon can be deposited on the array of cubes. Then pentacene can be deposited on the top surface of the polycrystalline silicon.

The top surface of the photovoltaic material can have an array of vertical nanowires (e.g., zinc oxide nanowires) to concentrate rays of sunlight into a very small area of each nanowire by a factor of about ten (10) at a given wavelength of the sunlight. Because the diameter of a vertical nanowire is smaller than the wavelength of sunlight, it can cause resonances in the intensity of the sunlight in and around nanowires to produce concentrated sunlight, at a much higher conversion efficiency of the sunlight.

Furthermore, the top surface of the array of vertical nanowires can be integrated with an array of colloidal deposited/self-assembled variable sized quantum dots. These variable sized quantum dots can absorb the sunlight over a much wider range of wavelengths. These variable sized quantum dots can be arranged according to their size and according to the specific wavelength of the solar spectrum that is absorbed. Thus, the harvesting of the sunlight's power (absorption) is increased.

Furthermore, instead of colloidal deposited/self-assembled variable sized quantum dots, an ultra thin-film of silicon nanoparticles (1-3 nanometers) can be deposited, forming a transparent layer of silicon nanoparticles. Large voltage enhancement with a dramatic increase in power ranging from as much as 60-70% in the ultraviolet-blue spectrum using these silicon nanoparticles and a significant boost in power by as much as 10% in the visible light spectrum can be obtained.

Furthermore optionally, an array of plasmonic optical nanoantennas at the substrate can be fabricated/constructed to enhance both light trapping and spectral efficiency of the three-dimensional solar cell.

The photovoltaic material on the array of cubes is then encapsulated with a transparent top electrode (e.g., indium tin oxide/graphene)—thus forming the three-dimensional solar cell.

Furthermore, the three-dimensional solar cell can be a microscopic solar cell. The microscopic solar cell is about 0.25 millimeters to 1 millimeter in diameter and about 10 times thinner than the conventional solar cell.

Other Design Considerations of Portable Internet Appliance

The portable internet appliance 1600 can be dramatically thinner, by utilizing (a) a metamaterial based camera, (b) an ultrathin display and (c) an ultrathin battery Ultrathin Camera Of Portable Internet Appliance An ultrathin camera based on metamaterial can enable light to pass through a two-dimensional array of gold metamaterial elements. The two-dimensional array of gold metamaterial elements can be fabricated/constructed, utilizing electron beam lithography on a 60 nanometers thick silicon wafer.

Ultrathin Display of Portable Internet Appliance

An ultrathin photonic crystal display can be constructed by optically pumping different sized photonic crystals, wherein each photonic crystal can emit blue or green or red light based on a photonic crystal's inherent diameter. An optical pump can be generated (from an optical emission) by electrical activation of semiconductor quantum-wells. Blue, green and red light can be multiplexed to generate white light. Details of such a quantum dot based display have been described/disclosed in DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION, U.S. Pat. No. 8,548,334, Issued on Oct. 1, 2013 and the entire contents of this US Non-Provisional Patent Application are incorporated herein.

Ultrathin Battery Of Portable Internet Appliance

An ultrathin organic battery utilizes push-pull organic molecules, wherein after an electron transfer process, two positively charged molecules are formed which are repelled by each other like magnets. By installing a molecular switch an electron transfer process can proceed in an opposite direction. Thus, forward and backward switching of an electron flow can form a basis of an ultrathin, light weight and power efficient organic battery.

Wireless Charging of Portable Internet Appliance

The portable internet appliance 1600 can be electrically charged via a resonant electromagnetic inductive coupling energy transfer without any physical wire.

Authentication by Portable Internet Appliance

The portable internet appliance 1600 can be integrated into a miniature Raman spectrophotometer. The miniature arrayed waveguide gratings Raman spectrophotometer can be inserted into the USB port of the portable internet appliance 1600. The Raman spectrophotometer can authenticate a product by scanning the product in Raman multispectral mode for molecular vibrational spectrum. For example, the Raman spectrophotometer can authenticate a check/banknote, wherein the check/banknote is integrated with a nano-scaled barcode. The nano-scaled barcode can be an array of a unique combination of fluorescent nanoparticles. Furthermore, each fluorescent nanoparticle/Raman tag (as described in previous paragraph) can be embedded with an optical nanoantenna to increase the Raman signal, if needed. The fluorescent nanoparticles/Raman tags with embedded nanoantenna can be caged within a bit larger nanocontainer (e.g., a boron nitride nanotube/carbon nanotube). Thus, the miniature Raman spectrophotometer can enable product authentication.

Biological Lab-On-A Chip of Portable Internet Appliance

A biological lab-on-a-chip is a module that integrates a few bio-analytical functions on a single chip to perform point-of-care disease diagnostics. For example, a miniature biological lab-on-a-chip module manufactured by Ostendum can be integrated (by inserting into an electro-mechanical cavity of the portable internet appliance 1600) into the portable internet appliance 1600 to perform point-of-care disease diagnostics reliably, quickly and economically. Such a lab-on-a-chip analysis can be transmitted from the portable internet appliance 1600 to a physician and/or a hospital for an interpretation without human input.

In addition, holographic images of the complete gene sequence of the user can be stored in the portable internet appliance 1600 to enable a physician/surgeon to design a personalized medical treatment.

Ionized Gas Cloud Based Cooling Component of Portable Internet Appliance

Many algorithms, as discussed above can consume significant electrical power due to computational complexities. Alternatively, many algorithms can be processed at a secure remote/cloud based data storage unit/server. Details of an ionized gas cooling component for the microprocessor or system-on-chip have been described/disclosed in U.S. Non-Provisional patent application Ser. No. 13/448,378 entitled "SYSTEM & METHOD FOR MACHINE LEARNING BASED USER APPLICATION", filed on Apr. 16, 2012 and the entire contents of this US Non-Provisional Patent Application are incorporated herein.

An ionized gas cloud based cooling component has an array of negative voltage biased nano-scaled tips (e.g., nano-scaled tips can be fabricated/constructed, utilizing boron nanotube/carbon nanotube/amorphous diamond/tungsten), wherein each nano-scaled tip is placed just below a micro-scaled hole (e.g., about 50-100 microns in diameter) of positive voltage biased surface (e.g., tungsten/two-dimensional crystal material (e.g., graphene)). Electrons emitted from the negative voltage biased array of nano-scaled tips can escape through the array of micro-scaled holes and ionize the gas molecules within the boundaries of a heat sink (e.g., aluminum/silicon/copper/carbon nanotube/carbon nanotube-copper composite/diamond). By switching the voltage polarity of the heat sink, a moving ionized gas cloud can disperse/dispose the heat from the system-on-chip.

However, it is desirable that an array of nano-scaled tips emit electrons at a much lower voltage (e.g., at 5 volts). An array of nano-scaled tungsten tips can be fabricated/constructed, utilizing a tungsten substrate. The array of nano-scaled tungsten tips can be surrounded by an insulator. The array of nano-scaled tungsten tips can be decorated with a monolayer(s) of material(s)—in particular a monolayer of diamond, deposited by low temperature electron cyclotron resonance chemical vapor deposition or a monolayer of gold deposited by radio frequency magnetron sputtering to enable electron emission at much lower voltage (e.g., at 5 volts) through the micro-scaled hole, which is fabricated/constructed, utilizing tungsten material.

Fixed or Reconfigurable Outer Case/Package of Portable Internet Appliance

The outer case/package of the portable internet appliance 1600 can be fabricated/constructed, utilizing a biodegradable material as described in the Table-15.

TABLE 15

Compositions Of A Biodegradable Plastic Material For Portable Internet Appliance

| Compositions | Wt % Material A | Wt % Material B | Wt % Material C | Wt % Material D |
|---|---|---|---|---|
| 1 | 80% Lignin | 20% Chitin | | |
| 2 | 80% Lignin | 20% Chitosan | | |
| 3 | 80% Lignin | 10% Chitin | 10% Chitosan | |
| 4 | 80% Lignin | 20% Fibroin | | |
| 5 | 80% Lignin | 10% Chitin | 10% Fibroin | |
| 6 | 80% Lignin | 10% Chitosan | 10% Fibroin | |
| 7 | 80% Lignin | 10% Chitosan | 10% Fibroin | |
| 8 | 80% Lignin | 5% Chitosan | 5% Chitosan | 10% Fibroin |

The aluminum/magnesium alloys have small building blocks-called nanocrystal grains and crystal defects. Nanocrystal grains with crystal defects are mechanically stronger than perfect aluminum/magnesium crystals.

The outer case/package of the portable internet appliance 1600 can be constructed from a nano-engineered aluminum/magnesium alloy or a liquid metal alloy or a carbon fiber/carbon nanotube-polymer composite material (carbon fiber/carbon nanotubes embedded within injection mold of a molten polymer) or a carbon fiber/carbon nanotube-polymer composite material with magnesium metal.

Furthermore, an antenna can be constructed from a carbon fiber embedded with a conducting polymer or metal.

The outer case/package of the portable internet appliance 1600 can be fabricated/constructed, utilizing a suitable material matrix with an array of shape memory changing material wires (e.g., shape memory changing polymer wires).

Furthermore, the shape memory changing material matrix can be added with 1 wt % to 10 wt % graphene (or 1 wt % to 10 wt % graphene like nanostructural material) and/or 1 wt % to 10 wt % nanotubes (e.g., boron nitride/carbon) to form a nanocomposite.

Additionally, carbon nanotubes (by stamping onto the shape memory changing material matrix/nanocomposite) can serve as a scaffold for growing zinc oxide nanostructure. Zinc oxide is a piezoelectric semiconductor material (it generates an electric potential after a mechanical motion). Zinc oxide nanostructures are nearly transparent and they can be used for touch-sensitive active matrix arrays on top a display matrix.

Furthermore, the above nanocomposite can be integrated (e.g., multi-layered/mixed) with (a) lignin (or lignen) and/or (b) chitin (a biopolymer based on the N-acetyl-glucosamine monomer) and/or (c) chitin's variant deacetylated counterpart chitosan and/or (d) fibroin (a protein derived from silk).

For flexibility/stretchability, a nanotube (e.g., carbon nanotube) based microprocessor can be embedded in a flexible/stretchable substrate, which has both conductive and non-conductive regions.

By way of an example and not by way of any limitation, a flexible substrate can be hydrogel/chitosan/fibroin/poly(lactic-co-glycolic acid embedded with regions of nanotubes or a suitable combination of chitosan, fibroin and poly(lactic-co-glycolic acid) embedded with regions of nanotubes or a suitable combination of hydrogel, chitosan, fibroin and poly(lactic-co-glycolic acid) embedded with regions of nanotubes.

By way of an example and not by way of any limitation, a flexible substrate of hydrogel/chitosan/fibroin/poly(lactic-co-glycolic acid embedded with regions of nanotubes) or a suitable combination of chitosan, fibroin and poly(lactic-co-glycolic acid embedded with regions of nanotubes) or a suitable combination of hydrogel, chitosan, fibroin and poly(lactic-co-glycolic acid embedded with regions of nanotubes) can act as a flexible/stretchable sensor.

The portable internet appliance 1600 can be flexible and stretchable, when it is integrated with a flexible electrophoretic plastic display, flexible transparent electronics chipset, printed battery (e.g., Zn—MnO$_2$ printed battery) and zinc oxide nanowire based solar cell component (photosensitive dye molecules can be anchored to an array of zinc oxide nanowires to fabricate/construct a solar cell component).

Other Algorithms of Portable Internet Appliance in Healthcare

The portable internet appliance 1600 can include an algorithm for interpreting a user's communication in a natural language, wherein the algorithm for interpreting communication in a natural language is stored in a local data storage unit of the portable internet appliance 1600 or a cloud based data storage unit. The portable internet appliance 1600 can include an algorithm for generating social graph/personal analytics, wherein the algorithm for social graph/personal analytics generation is stored in a local data storage unit of the portable internet appliance 1600 or a cloud based data storage unit.

Example Applications of Portable Internet Appliance in Healthcare

A biosensor (integrated with a low-power wireless transceiver such as Broadcom's BCM20732) can measure a user's heart rhythm. The lab-on-chip (integrated with a low-power wireless transceiver such as Broadcom's BCM20732) can measure the user's cardiovascular rhythm pattern(s). Both the biosensor and lab-on-chip can transmit data to the portable internet appliance 1600.

The portable internet appliance 1600 can compare the newly measured data with previously stored data of the user and if the newly measured data is significantly abnormal, the portable internet appliance 1600 can immediately communicate (indicating the location and condition of the user) with the user's personal physician and/or directly communicate with 911 emergency without the user input.

Figure 18B:
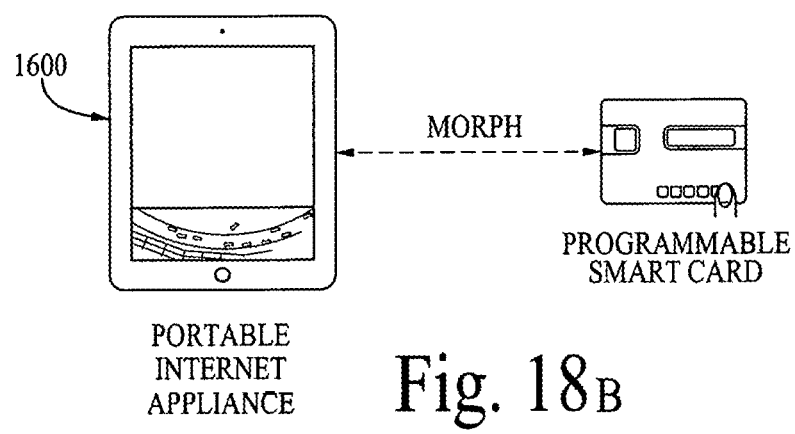
FIG. 18B illustrates how the portable internet appliance can be morphed into a small form factor.

FIG. 18B illustrates how the portable internet appliance 1600 can be morphed into a small form factor (multi-purpose) programmable smart card. Additionally, a smart card can contain a nanotube (e.g., boron nitride/carbon) based microprocessor.

Figure 18C:
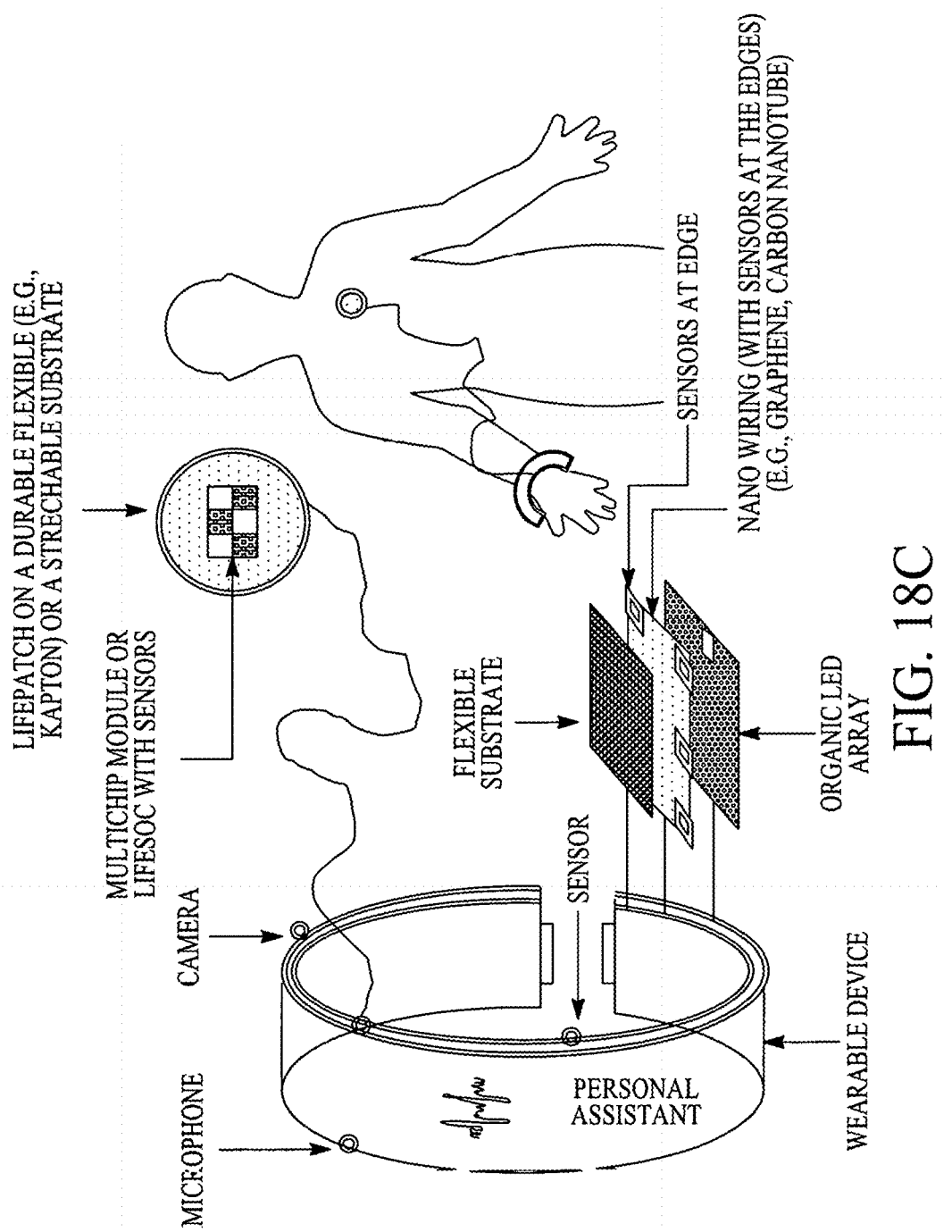
FIG. 18C illustrates how the portable internet appliance can be connected with a standalone wearable device.

Furthermore, a stand-alone wristwatch-style device as illustrated in FIG. 18C can be wirelessly tethered to the portable internet appliance 1600. The standalone wristwatch-style device can be fabricated/constructed, utilizing a wraparound display on a flexible substrate (e.g., DuPont Kapton or Corning Willow glass).

Organic light emitting diodes that do not need backlighting, are brighter with a wider viewing angle and better color contrast and organic light emitting diodes can be printed on the flexible substrate.

Furthermore, the above flexible substrate can be integrated with a microprocessor, memory/data storage, a sensor/an array of sensors (e.g., bio/health sensors), a low-power radio and a thin-film battery.

The stand-alone wristwatch-style device can be integrated with an image sensor based on graphene. Additionally, the stand-alone wristwatch-style device can be integrated with a microphone for voice activation to enable the user's voice instructions and/or authentication.

Furthermore, the standalone wristwatch-style device can pull relevant information (e.g., an appointment calendar, e-mail, twitter notification and short picture chat) from the portable internet appliance 1600, so the user can absorb information with a mere glance and can interact/communicate with the portable internet appliance 1600.

As illustrated in FIG. 18C, the stand-alone wristwatch-style device can be connected (by wire or wirelessly) with a Lifepatch of an array of bio/health sensors (e.g., a sensor for blood pressure/blood sugar/heart rate/oxygen level).

Figure 18D:
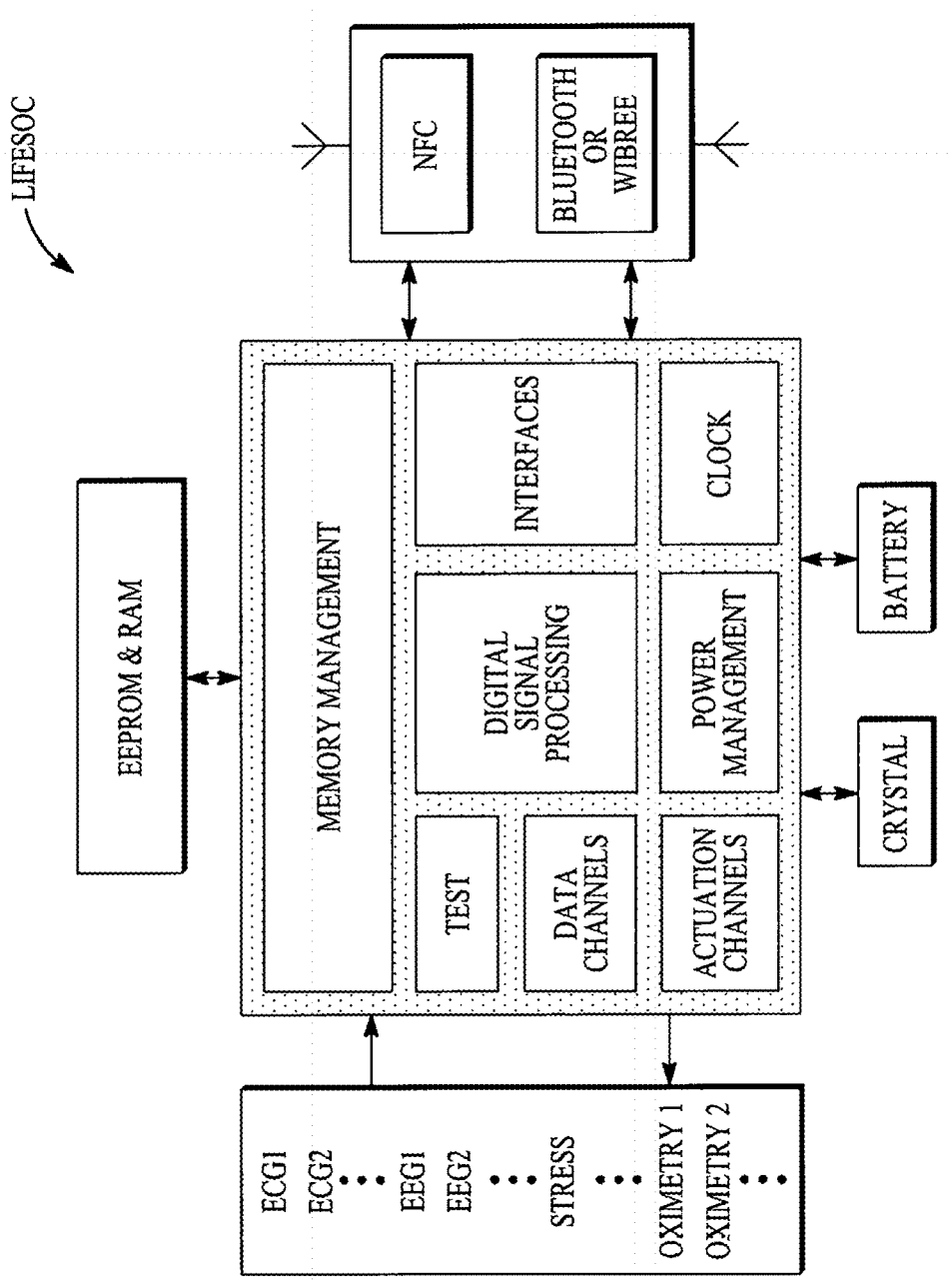
FIG. 18D illustrates a block diagram of a LifeSoC for the Lifepatch.

FIG. 18D illustrates a block diagram of a LifeSoC for the Lifepatch. LifeSoC has digital signal processing, memory management and power management capabilities; wherein LifeSoC is interfacing with various bio/health sensors (e.g., blood pressure, ECG, EEG, skin hydration, stress and oximetry) and low power wireless devices (e.g., Wibree/Bluetooth) and near-field communication. Furthermore, LifeSoC can be fabricated/constructed on a flexible/stretchable substrate.

Figure 18E:
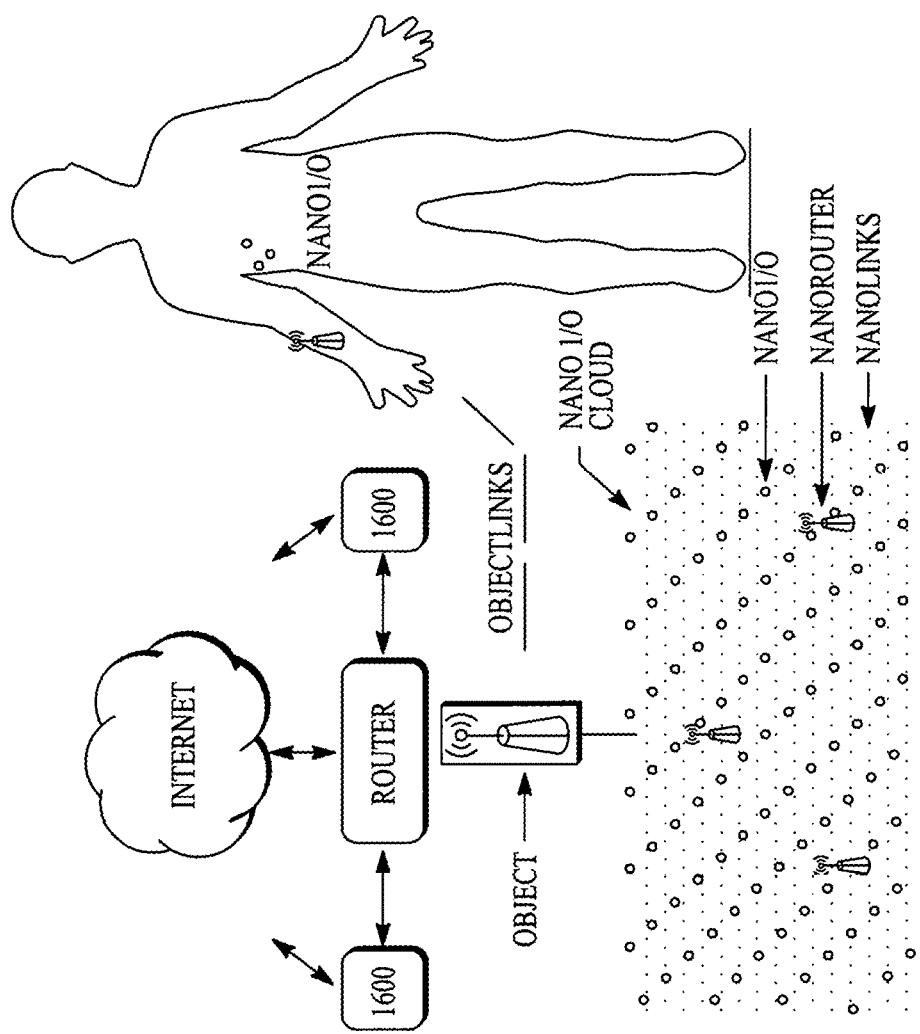
FIG. 18E illustrates how nano I/Os (e.g., sensors on or within a human body), nanorouters and objects can connect/communicate with other nanoI/Os, nanorouters and objects in a ubiquitous/pervasive manner with the internet.

FIG. 18E illustrates how a nanoI/O connects/communicates with other nanoI/Os via nanolinks. An array of nanoI/Os connects/communicates with a nanorouter via nanolinks. The nanorouter or the array of nanorouters connects/communicates with an object. The object or the array of objects connects/communicates with a router via objectlinks. The router or the array of routers connects/communicates with portable internet appliances 1600 via the internet. Such interactions as described in FIG. 18E can enable real-time tracking of consumer behavior, real-time awareness (of health/environment), real-time sensor-driven decision analytics and complex autonomous systems.

Figure 18F:
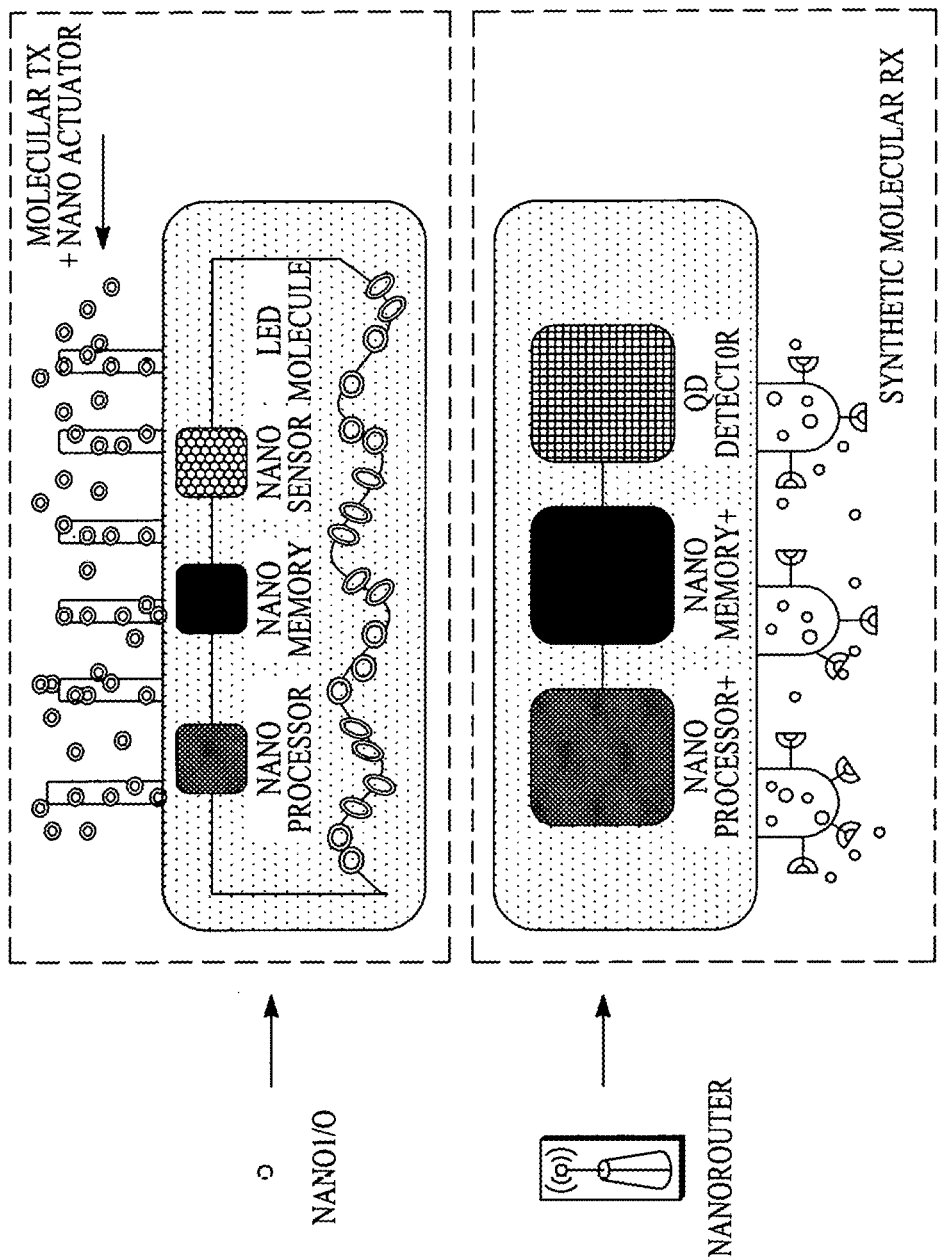
FIG. 18F illustrates a nanoI/O and a nanorouter.

FIG. 18F illustrates a block diagram of a nanoI/O and a block diagram of a nanorouter. The nanoI/O integrates a nano-scaled processor (nanoprocessor), a nano-scaled memory (nanomemory), a nano-scaled sensor (nanosensor), a nano-scaled actuator enabled molecular transmitters and a single molecule organic (e.g., polythiophene) light emitting diode. It should be noted that the single molecule organic light emitting diode and/or an array of nano-scaled actuator enabled molecular (e.g., pheromone) transmitters, can be activated upon the nanosensor's signal.

The nanoprocessor, nanomemory and nanosensor can be fabricated/constructed on silicon with nanopillars of non-silicon semiconductor materials (e.g., gallium arsenide, gallium nitride and indium phosphide on silicon) and nanowires connecting between nanopillars of non-silicon semiconductor materials.

Furthermore, the nanoprocessor can be fabricated/constructed as an array of nanowire transistors/switches. The array of nanowire transistors/switches can be nonvolatile. Nonvolatile nanowire transistors/switches can remember when no electrical power is applied to nonvolatile nanowire transistors/switches—thus enabling extremely low electrical power consumption.

Furthermore, nonvolatile nanowire transistors/switches can integrate memristors enabling neuron-like analog or learning nanoprocessor.

Nanomemory cells can be fabricated/constructed of molybdenum disulphide with graphene in a two-dimensional hetrostructure, where molybdenum disulphide acts as a channel in intimate contact with graphene electrodes in field-effect transistor configurations.

Alternatively, bistable rotaxane molecule based crossbar nanomemory cells can be fabricated/constructed, wherein a nanomemory cell consists of two perpendicular layers of nanowires, providing voltage, reading and writing information in bistable rotaxane molecule. A bistable rotaxane is a dumbbell-shaped molecule of a rod section and terminated by two stoppers, further encircled by a ring. The bistable rotaxane molecule can act as an electrical switch by incorporating two different recognition sites for the ring and the ring sits preferentially at one of the two recognition sites. The bistable rotaxane molecule can act as an electrical switch, provided the ring can be induced to move from one recognition site to the other recognition site and then reside there for minutes. The bistable rotaxane molecules can be electrically switched at a very modest voltage from an off (low conductivity) state to an on (high conductivity) state.

The nanorouter integrates a nanoprocessor+ (a bit more powerful than nanoprocessor), nanomemory+ (a bit more powerful than nanomemory), molecular receivers with synthetic receptors and a quantum dot detector (e.g., a nanogap quantum dot detector). Light and/or molecules (e.g., pheromone) transmitted by a nanoI/O can be detected by a quantum dot detector and an array of synthetic molecular receptors respectively.

The signals received by the nanorouter from nanoI/Os are similar to quorum sensing.

It should be noted that a nanoprocessor++ is a bit more powerful than a nanoprocessor+ and a nanomemory++ is a bit more powerful than a nanomemory+.

Figure 18G:
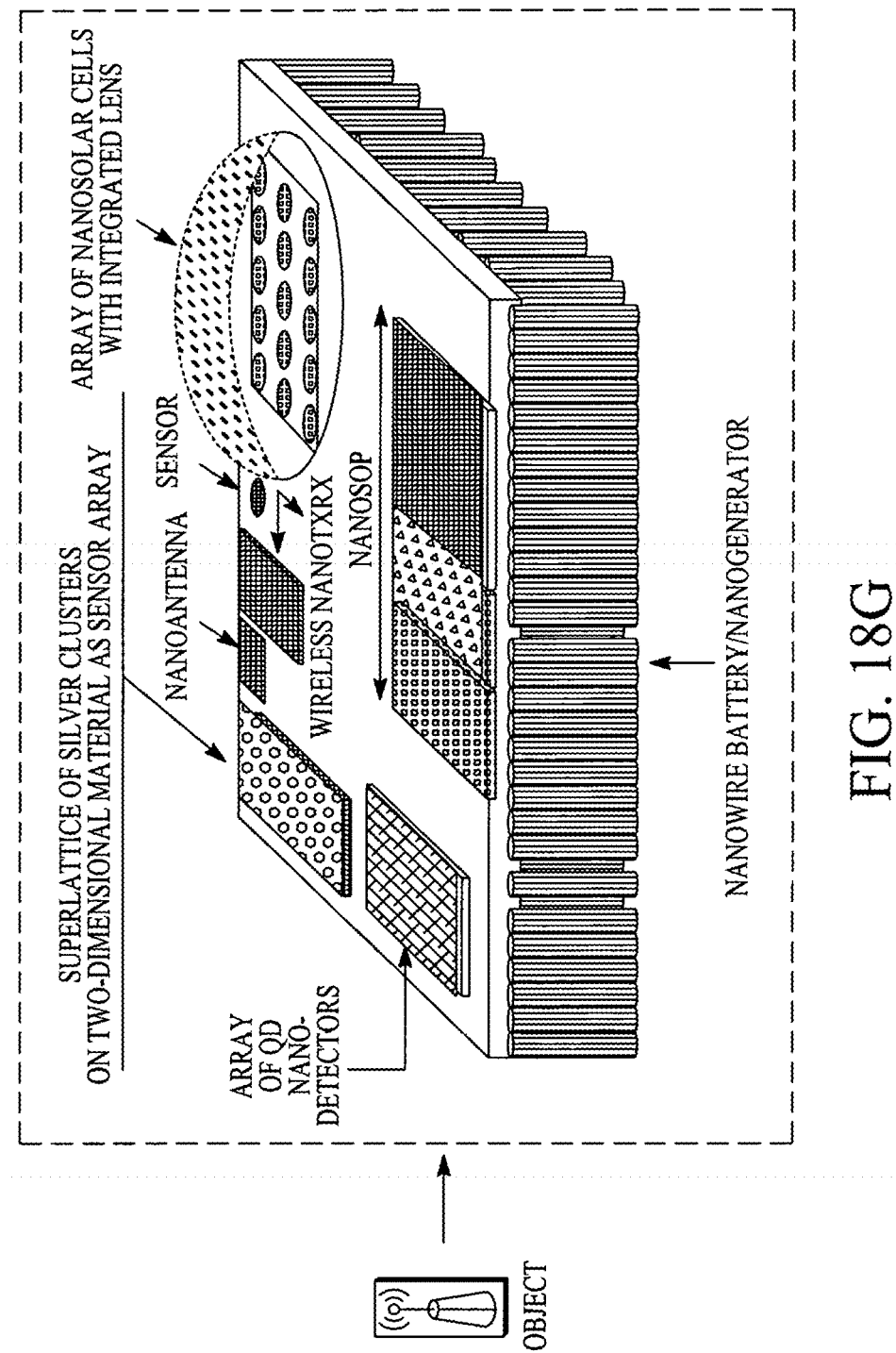
FIGS. 18G and 18H illustrate various configurations of an object.

FIG. 18G illustrates a configuration of an object, which is a nano-scaled system-on-package (SoP) of a nanoprocessor++, a nanomemory++, a nanostorage for tiny instructions (which can be either embedded in the nanostorage at the very onset or wirelessly transmitted/reconfigured to be stored in the nanostorage at a later time), a wireless nanotransceiver (e.g., a terahertz band nanotransceiver based on silicon-germanium heterojunction bipolar transistors or a hybrid silicon-germanium and gallium nitride based device enhanced with graphene), a nanoantenna (e.g., graphene based nanoantenna), an array of quantum dot nanodetectors, an array of nano-scaled solar cells (e.g., a nanoassembly of gold nanoparticles with organic porphyin molecules) as nanosolar cells integrated with a nano-scaled lens to capture sunlight, a nano-scaled sensor, an array of self-assembled superlattices of silver clusters on a two-dimensional material (e.g., graphene) as an array of molecular sensors and a nanowire battery (e.g., piezoelectric zinc oxide nanowires based nanogenerator).

Furthermore, the nanosolar cells can be three-dimensional nanosolar cells. An array of three-dimensional nanosolar cells (each nanosolar cell is about 5 microns by 5 microns in area, 100 microns tall and separated from each other at about 10 microns) can utilize a silicon substrate, as the nanosolar cells' bottom electrode. A thin-film of iron is deposited and patterned on the silicon wafer by photolithography. Vertically aligned multi-walled carbon nanotubes can be seeded and grown on the patterns of thin-film of iron, utilizing 700 degrees' centigrade chemical vapor deposition with hydrocarbon gases, wherein the carbon and hydrogen are separated. Upon formation of arrays of vertical carbon nanotubes, a p-type photovoltaic layer (e.g., cadmium telluride (CdTe)) and an n-type photovoltaic layer (e.g., cadmium sulfide) can be conformally grown by molecular beam epitaxy (MBE).

In singlet-exciton fission, an arriving photon from the sunlight can generate two (2) excitons (excited states) yielding two (2) electrons. Pentacene generates two (2) excitons (excited states) yielding two (2) electrons in a narrow visible spectrum of the sunlight. Pentacene and/or other suitable materials for singlet-exciton fission in another spectrum of the sunlight can be integrated via coating or wafer stacking/bonding (wafer stacking/bonding is useful, when the material is not suitable for coating) for enhanced electron generation.

A thin-film of conducting transparent indium tin oxide/graphene layer can act as the top electrode.

Furthermore, a photovoltaic material can be integrated (e.g., doped) with a light sensitive compound/protein.

Furthermore, a photovoltaic material can be integrated with a light trapping structure or an optical metamaterial based light trapping structure for light collection from many incident angles. The light trapping structure or an optical metamaterial based light trapping structure can be deposited directly onto the photovoltaic material. Alternatively, the light trapping structure or an optical metamaterial based light trapping structure can be deposited on a suitable substrate and stacked/bonded (e.g., Soitec company's smart stacking layer transfer technology for processed wafers).

A nanostorage device for instructions in the form of write-once-read-many times can be fabricated/constructed of a DNA based memory cell, which is DNA embedded with silver nanoparticles sandwiched between two transparent electrodes. An incident ultraviolet light (through one of the transparent electrodes) can cause the silver atoms to nanocluster for data encoding. When a low voltage is applied through the electrodes to ultraviolet-irradiated DNA, only a low current is able to pass through the memory cell. This corresponds to the off state. But, when the applied voltage exceeds a certain threshold, an increased current is able to pass through the memory cell—this corresponding to the on state. It is reversible from the off state to the on state. Once the memory cell is turned on, it stays on, no matter what voltage is applied to the memory cell.

A self-assembled superlattice consists of silver clusters, wherein each silver cluster has a core of 44 silver atoms. Thirty-three molecules of mercaptobenzoic acid (p-MBA) can be utilized to protect the silver clusters. Mercaptobenzoic acid molecules are attached to the silver atoms by sulfur atoms. By compressing the self-assembled superlattice, the hydrogen bonds attached to the p-MBA molecules, rotate about 25-degrees angle and return to their original position—creating a molecular gear machine.

By integrating conductive polymers with the self-assembled superlattice of silver clusters on a substrate of a two-dimensional material, the self-assembled superlattice of silver clusters can be utilized as molecular sensors.

DNA nanostructures preferentially attached to lithographically patterned binding/assembly sites can be utilized as a nanoprinted circuit board (nanoPCB) to fabricate/construct a nanoI/O, a nanorouter and an object by sticking nano-scaled components of the nanoI/O or the nanorouter or the object.

Figure 18H:
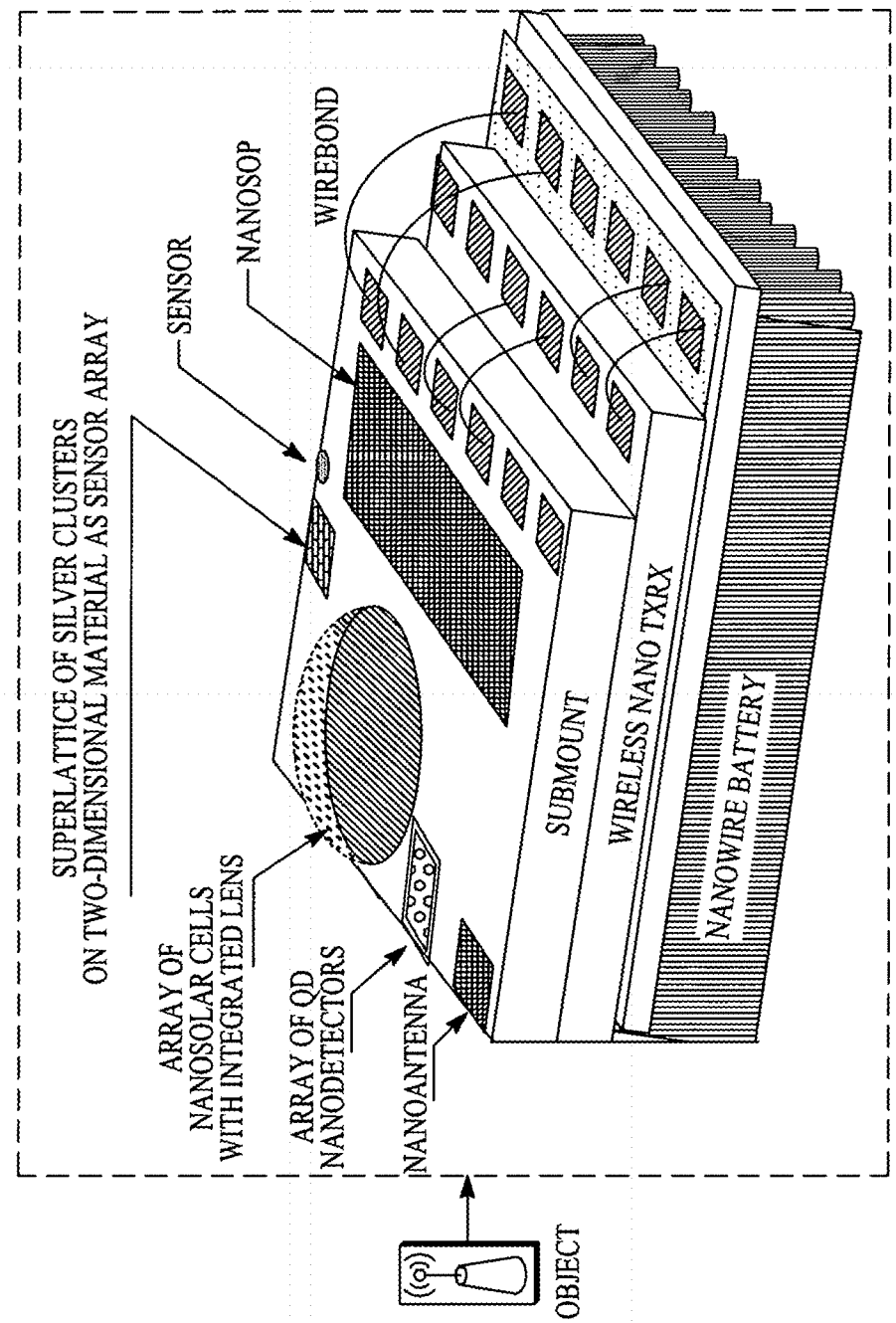

FIG. 18H illustrates another configuration of the object, wherein the stacked package is realized by a standard microelectronics packaging method.

The object can be encapsulated for protection from the environment. Furthermore, ambient backscattering of existing wireless signal(s) can enable an object as a sensor to communicate with another object as a sensor without an electrical powering device.

The object can sense/measure/coordinate its actions via a shared language (e.g., AllJoyn or Message Queue Telemetry Transport (MQTT)). AllJoyn provides a universal software framework. Message Queue Telemetry Transport is an open message protocol. Collective intelligence (e.g., swarm intelligence) can be derived from inputs of networks of objects/biological objects.

Example Applications of Portable Internet Appliance for Point-of-Care Detection of a Disease/an Array of Diseases The portable internet appliance 1600 can be suitably integrated with a photonics-lab-on chip for point-of-care detection of a disease/an array of diseases.

Various embodiments of a photonics-lab-on-chip are illustrated in FIGS. 19A, 19B, 19C, 19D, 19E, 19F, 19G, 19H, 19I and 19J.

Figure 19A:
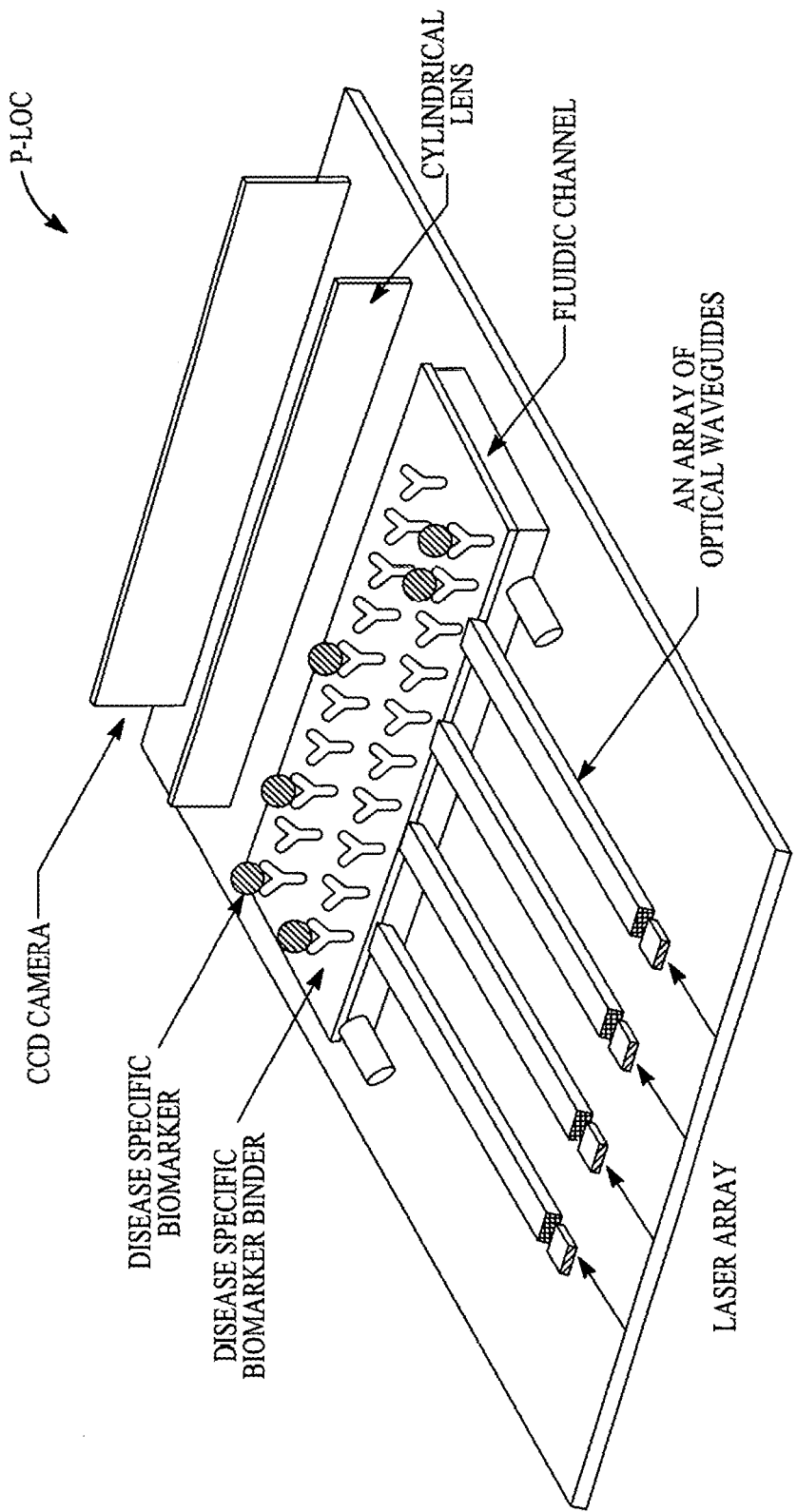
FIGS. 19A, 19B, 19C, 19D, 19E, 19F, 19G, 19H, 19I and 19J illustrate various (block diagram) embodiments of a photonics-lab-on chip (P-LOC).

In FIG. 19A an array of light sources (e.g., an edge emitting distributed feedback (DFB) wavelength tunable laser or a microelectro-mechanical-system enabled wavelength tunable surface emitting vertical cavity laser-integrated with a 45-degrees angle mirror) is guided via an array of optical waveguides.

The array of optical waveguides is connected with a fluidic channel, which contains disease specific fluorescent biomarker binders to chemically bind with disease specific biomarkers in a human body's blood/biological fluid. A fluorescent biomarker binder is a biomarker, which is chemically coupled with a fluorophore or a photoswitchable fluorophore.

Furthermore, each fluorescent biomarker binder can be integrated or coupled with a three-dimensional protruded structure (e.g., an optical antenna) to enhance fluorescence significantly.

The fluidic channel is optically connected with a cylindrical lens to collimate the output fluorescent beam to an array of charged-coupled detectors based cameras for spectrum analysis.

Figure 19B:
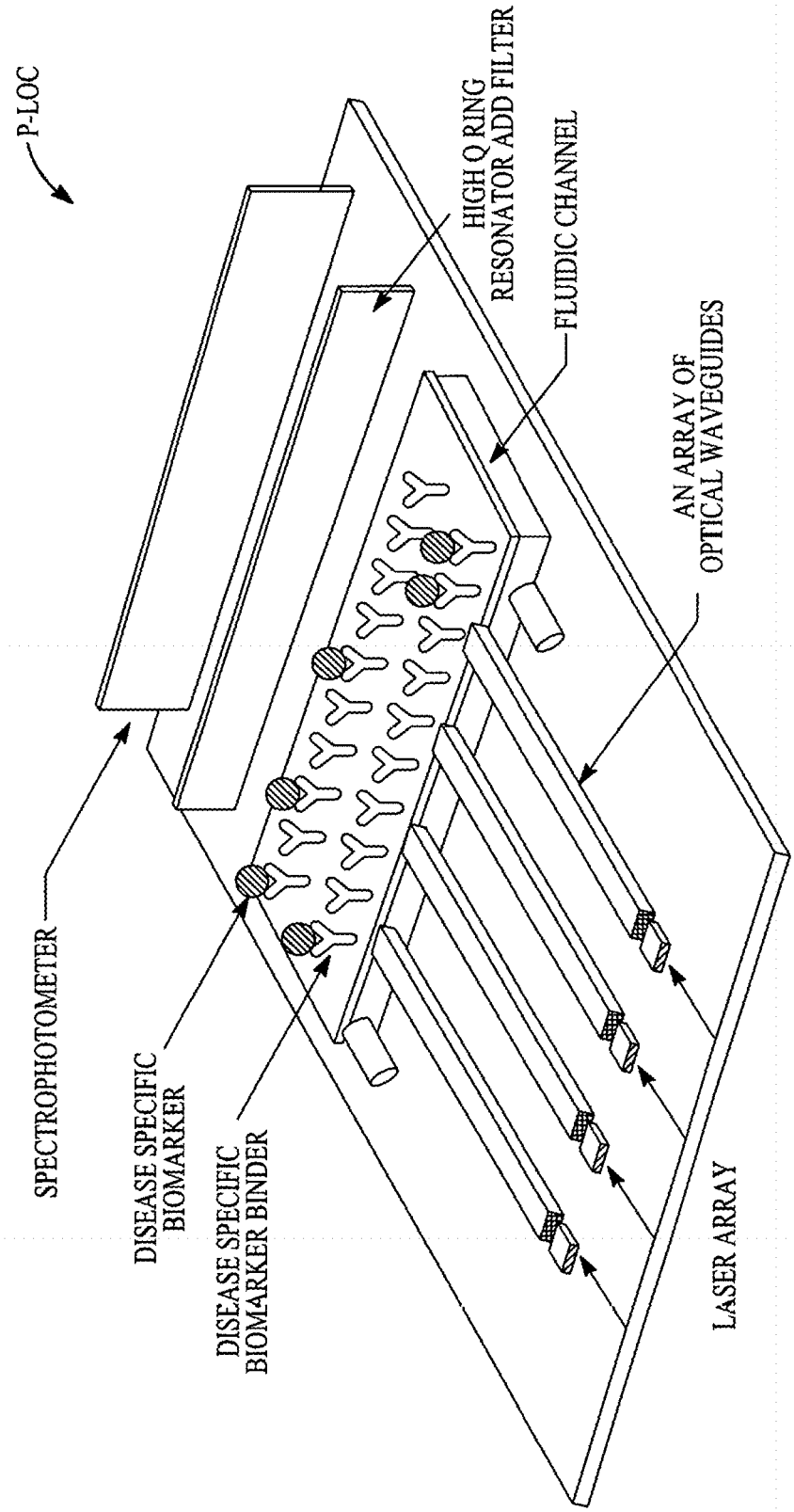

Alternatively, in FIG. 19B, the cylindrical lens can be replaced by an array of high Q ring resonator based add filters. The outputs of the high Q ring resonators based add filters can be combined at one port. This combined port can be the input of a high-resolution spectrophotometer for spectrum analysis.

Figure 19C:
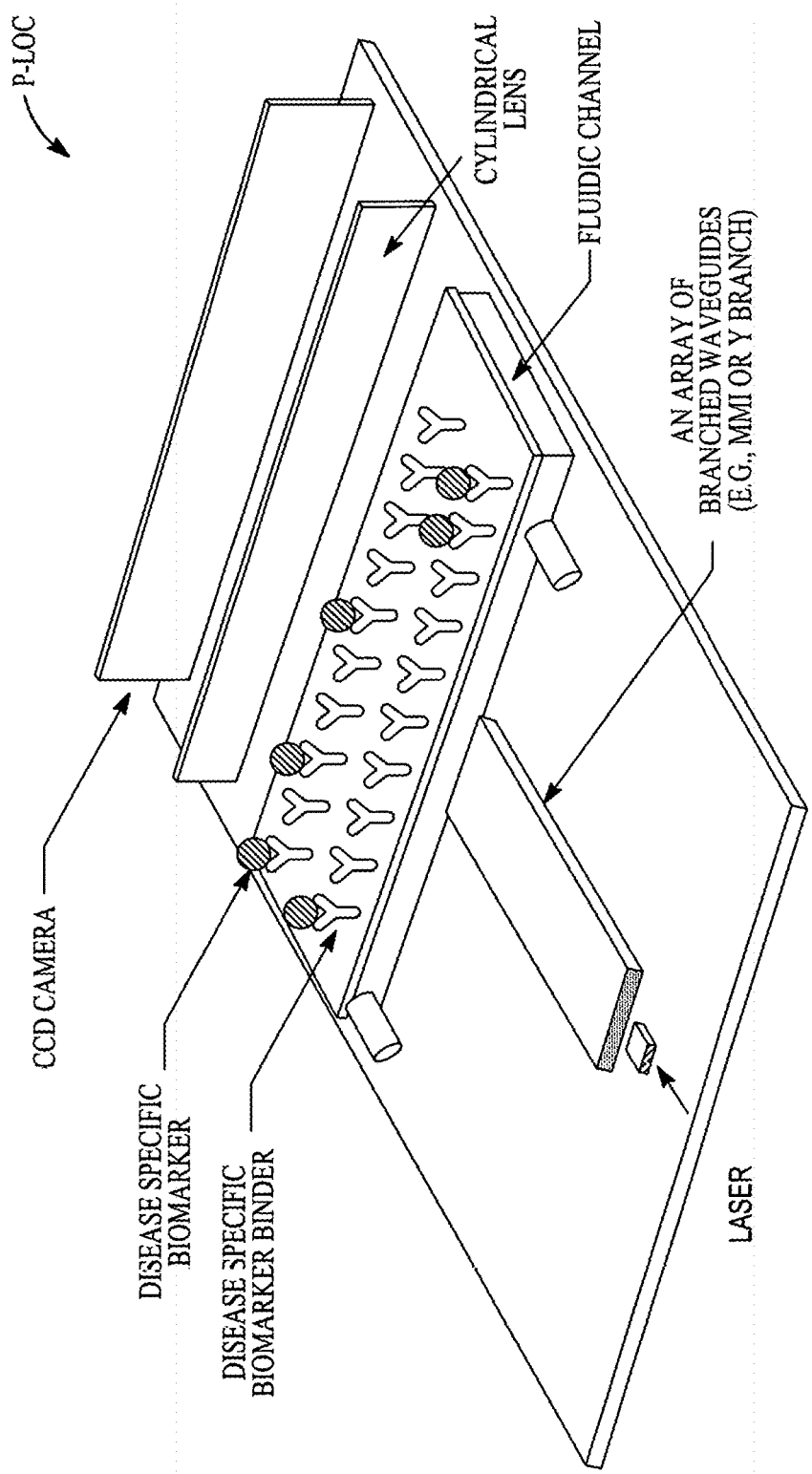

In FIG. 19C, a light source is guided via an array of optical waveguides (e.g., MMI/Y-branched waveguides). The array of optical waveguides is connected with a fluidic channel, which contains disease specific fluorescent biomarker binders to chemically bind with disease specific biomarkers in a human body's blood/biological fluid.

Furthermore, each fluorescent biomarker binder can be integrated with an optical antenna to enhance fluorescence significantly.

The fluidic channel is optically connected with a cylindrical lens to collimate the output fluorescent beam to an array of charged-coupled detectors based cameras for spectrum analysis.

Figure 19D:
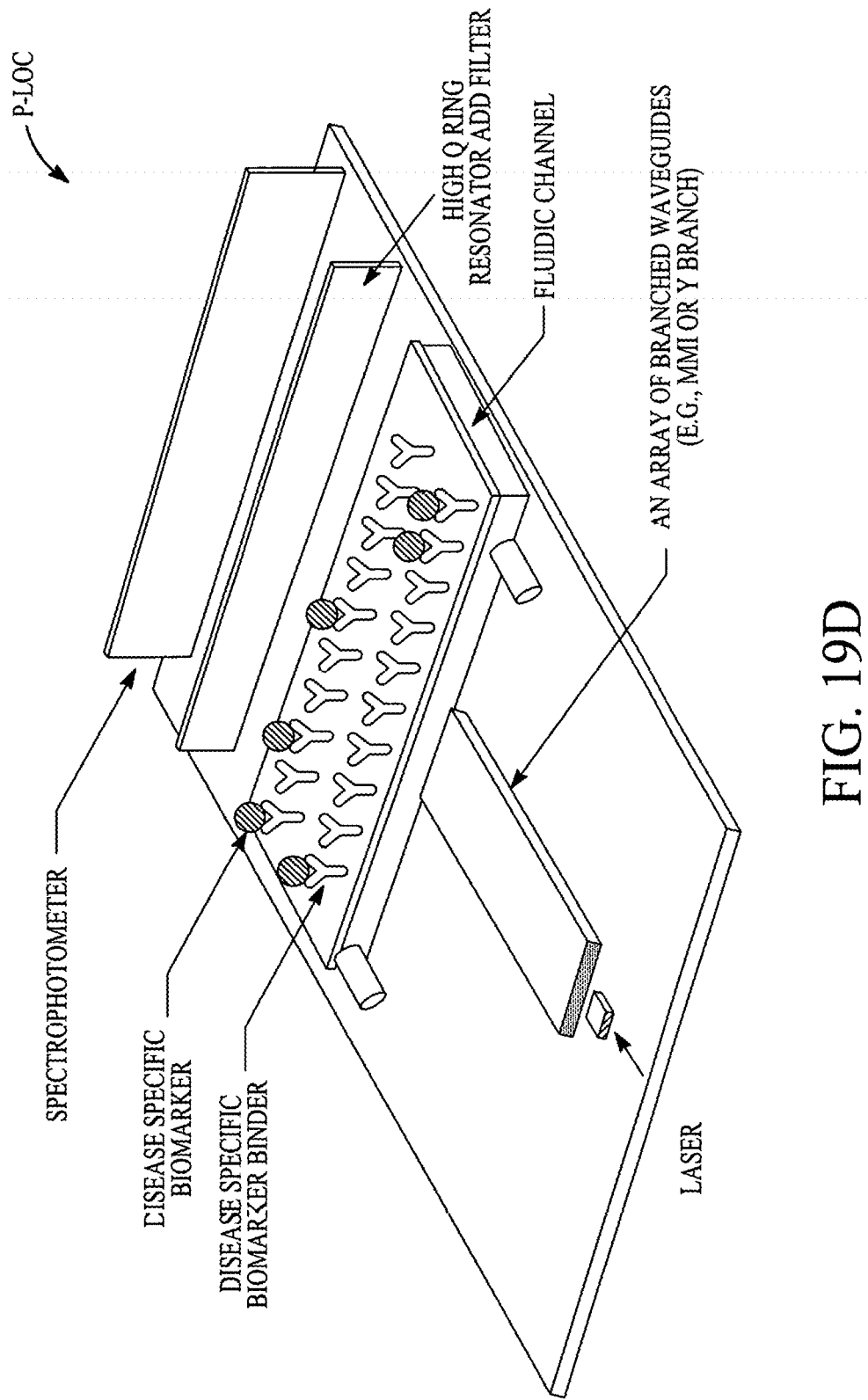

Alternatively, in FIG. 19D, the cylindrical lens can be replaced by an array of high Q ring resonator based add filters. The outputs of the ring resonators based add filters can be combined at one port. This combined port can be the input of a high-resolution spectrophotometer for spectrum analysis.

By way of an example and not by way of any limitation, a high-resolution spectrophotometer can be echelle gratings based demultiplexer/microspectrophotometer-on-a-chip/photonic crystal/planar lightwave circuit based demultiplexer/microring resonator based/silicon nanowire waveguide based demultiplexer spectrophotometer.

Alternatively, a high-resolution spectrophotometer can be a Fourier-transform (FT) Michelson-type arrayed waveguide gratings spectrophotometer. The spectral resolution of the Fourier-transform Michelson-type arrayed waveguide gratings spectrophotometer can be increased by inserting a triangular photonic bandgap waveguide section into the waveguide array. Furthermore, the Fourier-transform Michelson-type arrayed waveguide gratings spectrophotometer can be fabricated/constructed by two interleaved arrayed waveguide gratings that produce interference fringes with different spacing for different wavelengths.

Figure 19E:
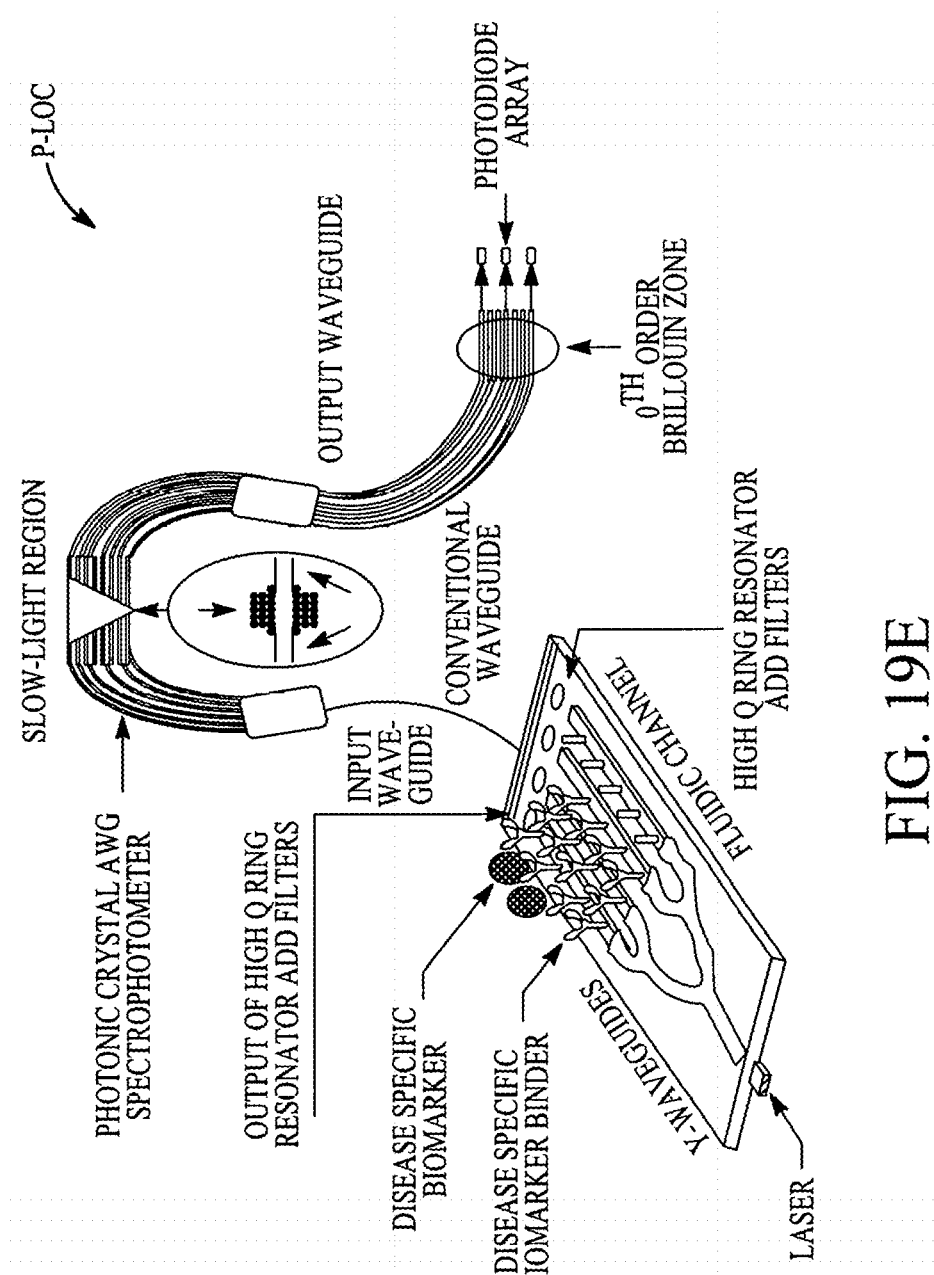

FIG. 19E illustrates a specific embodiment of 19D. Y-branched optical waveguides are connected to an array of fluidic channels, wherein each fluidic channel contains disease specific fluorescent biomarker binders to chemically bind with disease specific biomarkers in a human body's blood/biological fluid. Furthermore, any branched optical waveguides (e.g., MMI waveguide) can function instead of Y-branched optical waveguides.

Furthermore, each fluorescent biomarker binder can be integrated with an optical antenna to enhance fluorescence significantly.

Laser light propagating through Y-branched optical waveguides can induce fluorescence signals in the array of fluidic channels. The fluidic channels are separated spatially enough to reduce fluorescence related cross-talk from one fluidic channel with another fluidic channel. Fluorescence from each fluidic channel is picked up by a suitable high Q ring-resonator filter and multiplexed/combined at the exit port of the ring-resonator filter device, which is coupled with the Fourier-transform Michelson-type arrayed waveguide gratings spectrophotometer/an array of photodiodes for spectrum analysis.

However, it should be noted that a ring resonator based spectrophotometer/an array of photodiodes can be utilized for spectrum analysis.

Figure 19F:
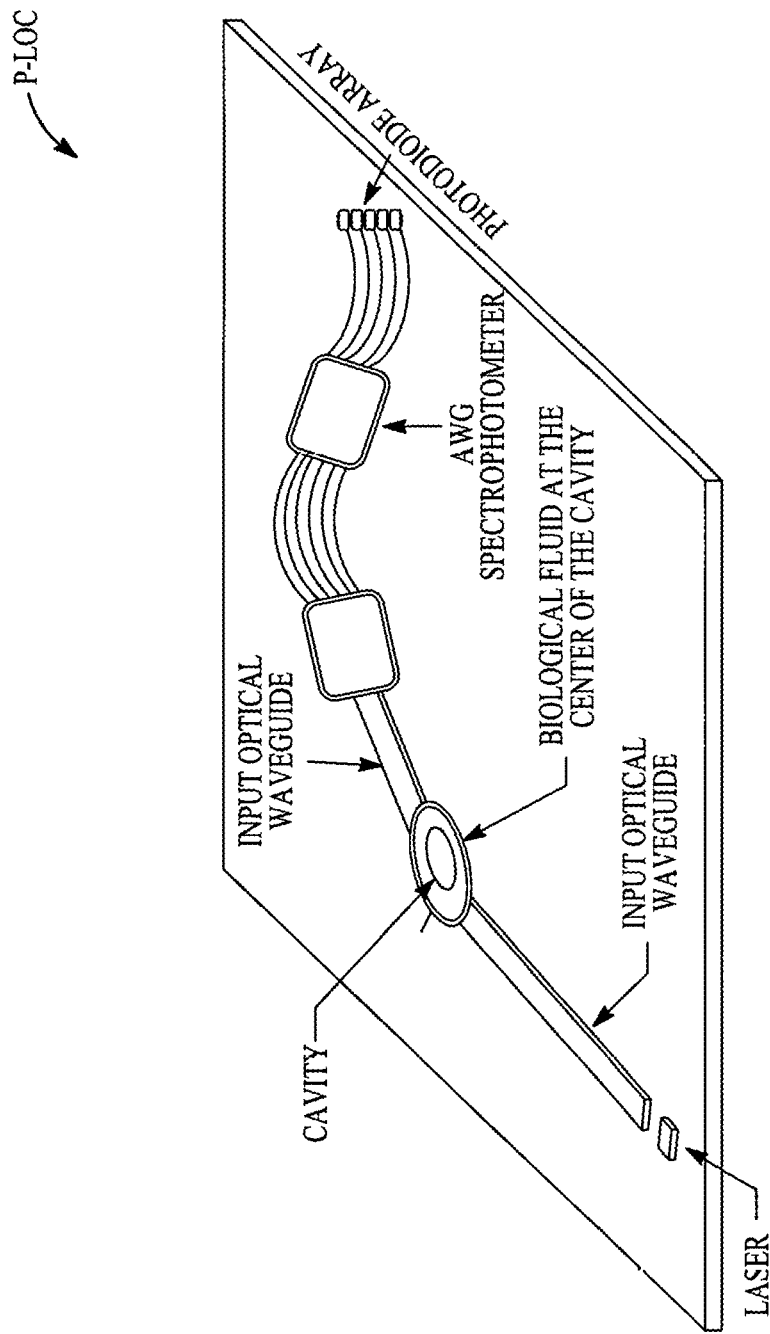

FIG. 19F illustrates a planar design of a photonics-lab-on chip. The planar design has a fluid cavity which contains a human body's blood/biological fluid and disease specific fluorescent biomarker binders to chemically bind with disease specific biomarkers in a human body's blood/biological fluid.

The fluid cavity is optically connected by an input optical waveguide and an output optical waveguide. The input optical waveguide is connected with an optical excitation source (e.g., a laser). The output optical waveguide is connected to an arrayed waveguide gratings spectrophotometer and an array of photodiodes for spectrum analysis.

Figure 19G:
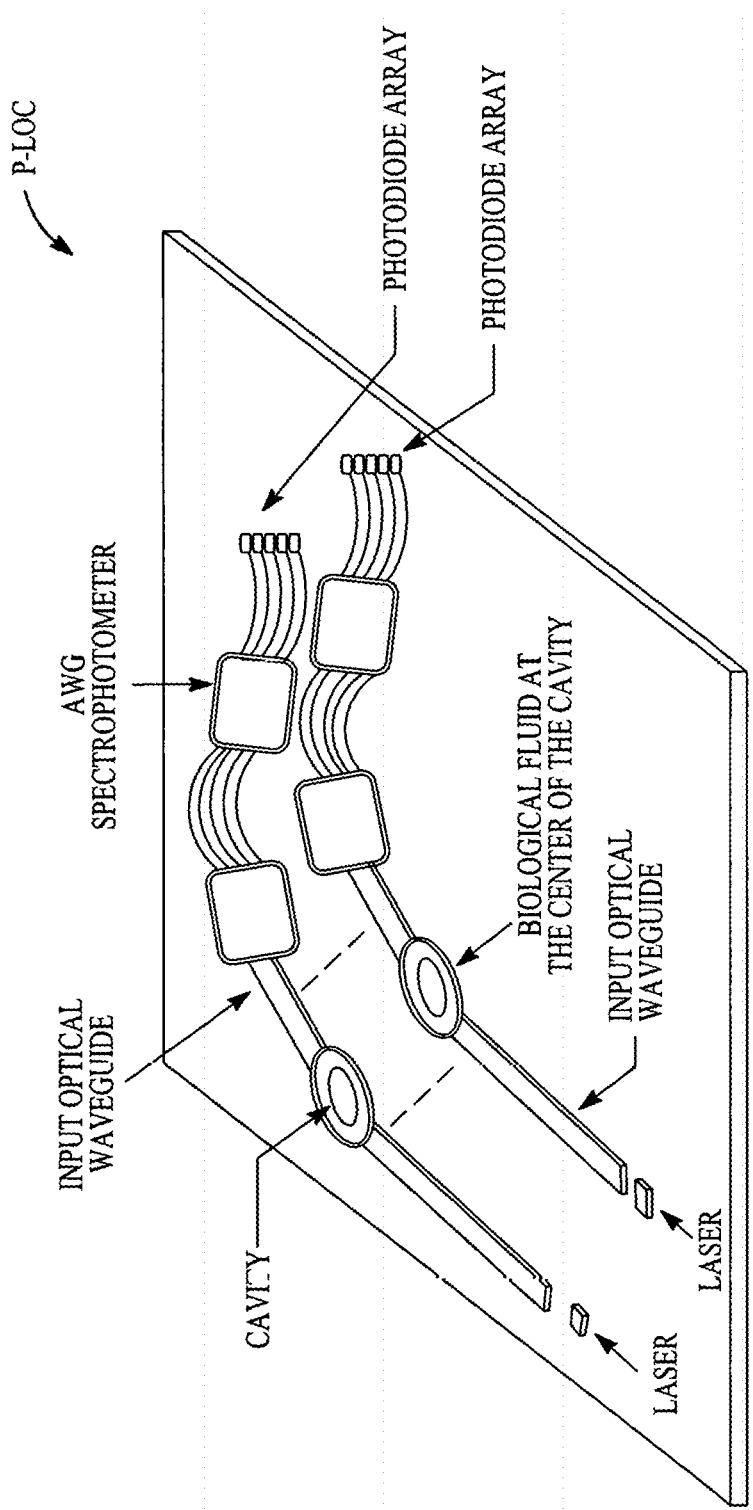

The planar design in FIG. 19F can be scaled to an array of fluid cavities, an array of input optical waveguides, an array of output optical waveguides, an array of arrayed waveguide gratings spectrophotometers and multiple arrays of photodiodes. The scaled version of the planar design is illustrated in FIG. 19G.

Figure 19H:
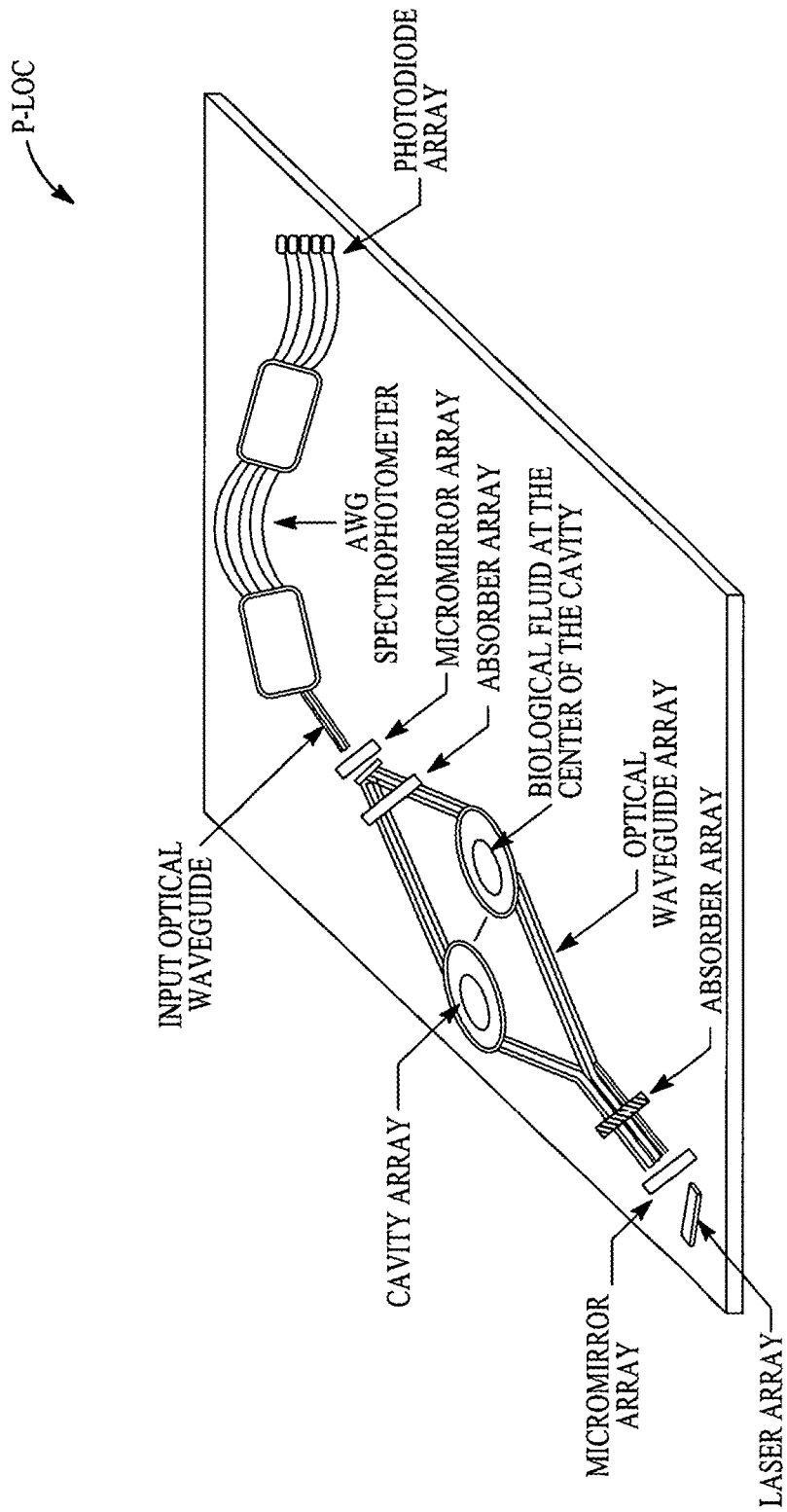

Alternatively, as illustrated in FIG. 19H just one arrayed waveguide gratings spectrophotometer/an array of photodiodes can be utilized in conjunction with an array of lasers, an array of micromirrors, an array of absorbers, an array of optical waveguides, an array of fluid cavities-containing a human body's blood/biological fluid and disease specific fluorescent biomarker binders to chemically bind with disease specific biomarkers in a human body's blood/biological fluid.

Figure 19I:
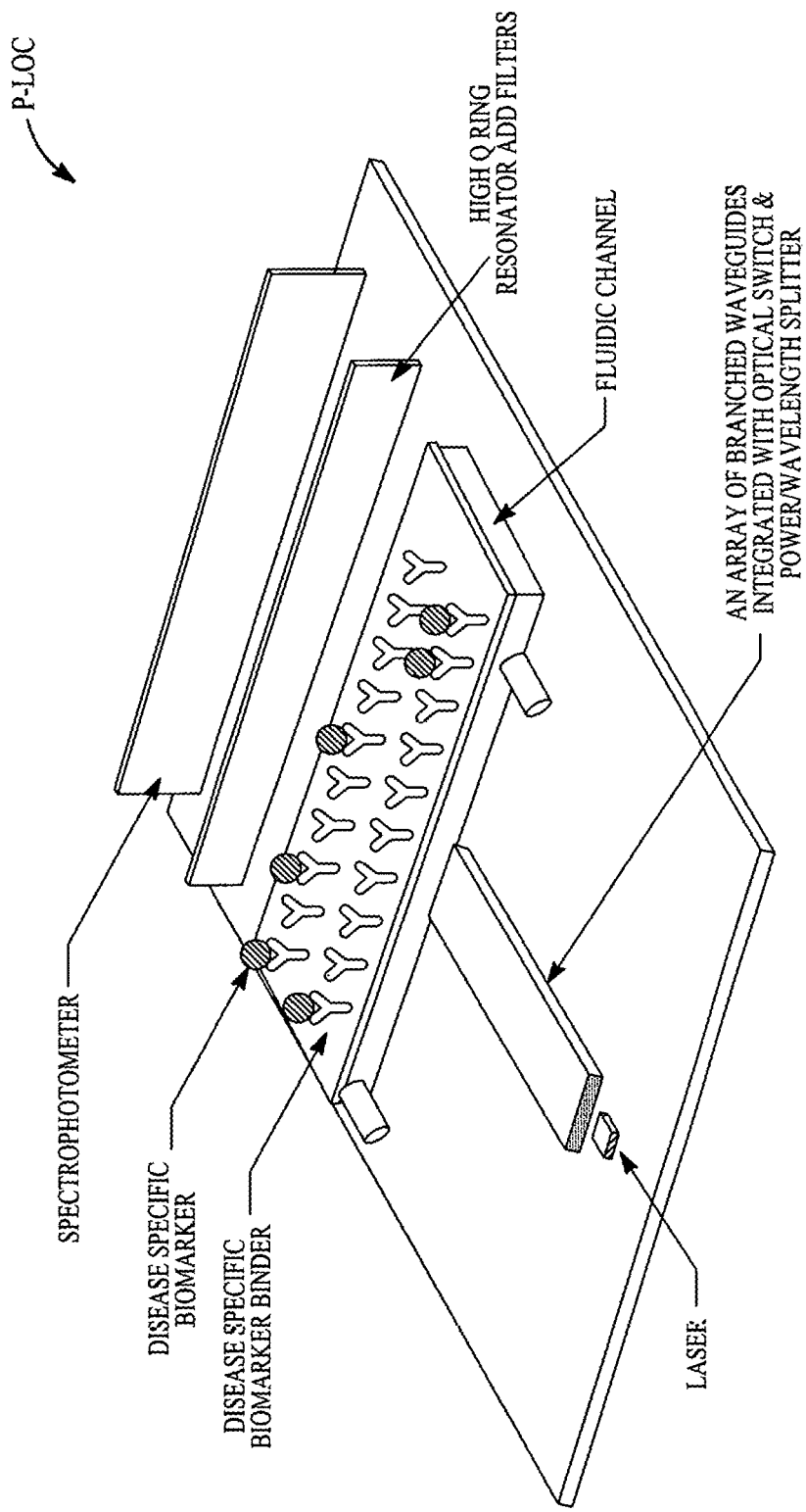

FIG. 19I illustrates another embodiment of 19D, wherein an array of branched optical waveguides is replaced by an array of optical waveguides, integrated with an optical switch and a power/wavelength splitter.

Figure 19J:
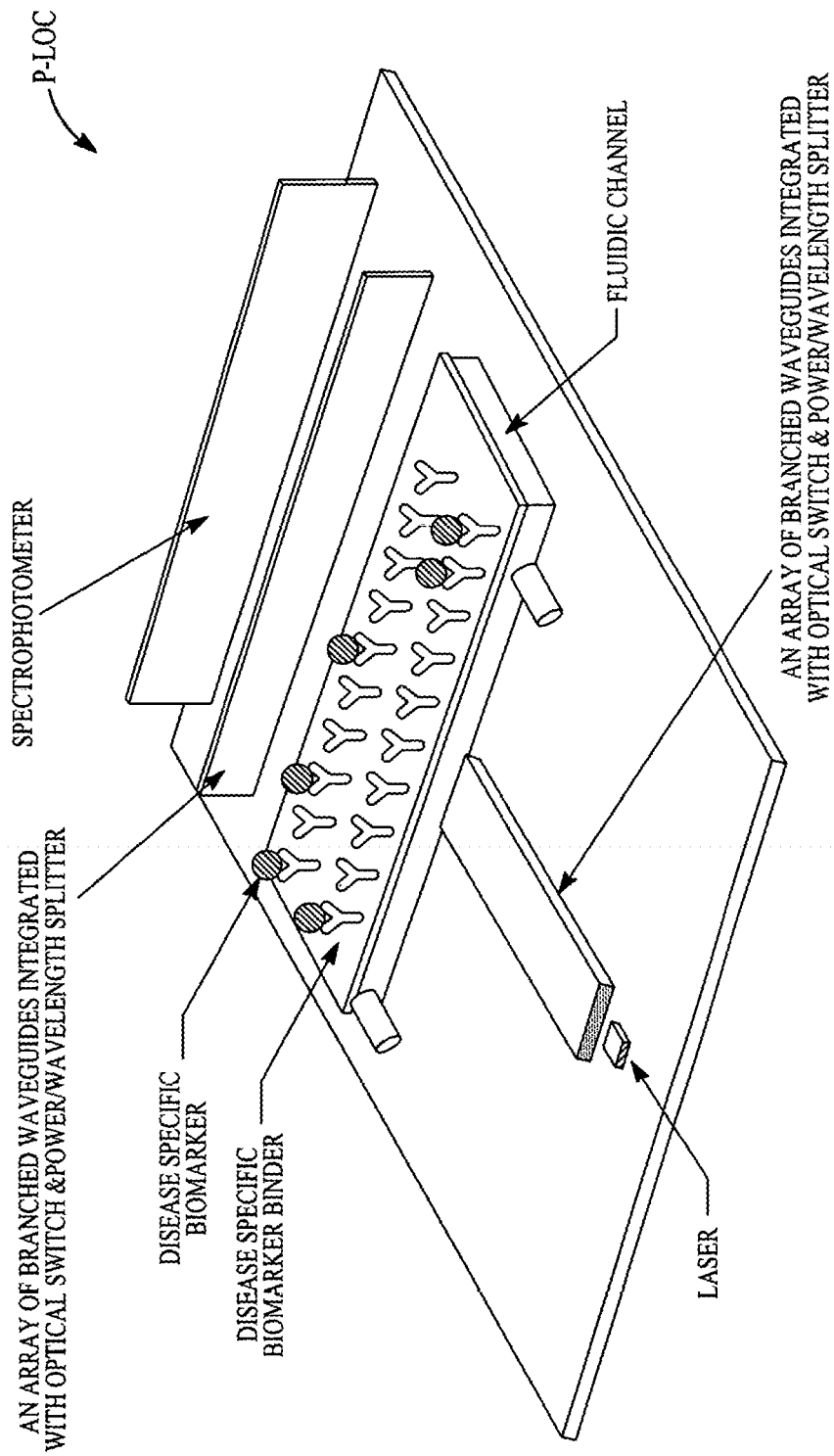

FIG. 19J illustrates another embodiment of 19I, wherein an array of high Q ring resonator based add filters is also replaced by an array of optical waveguides, integrated with an optical switch and a power/wavelength splitter.

Additionally, a metamaterial waveguide (e.g., a hyperbolic waveguide) of alternating ultra thin-films of semiconductors and/or insulators and metals can be fabricated/constructed to absorb each wavelength of light, at slightly different places in a vertical direction.

Additionally, various devices can be connected by a multi-optical fiber connector, making the fluid/cavity section(s) containing a human body's blood/biological fluid disposable.

Alternatively, optical fibers can be aligned passively with precise metal alignment pins seated into v-grooves on a precise silicon optical bench substrate. The precise metal alignment pins can be utilized top mate with a pluggable optical fiber connector integrated with a molded plastic lens.

Figure 19K:
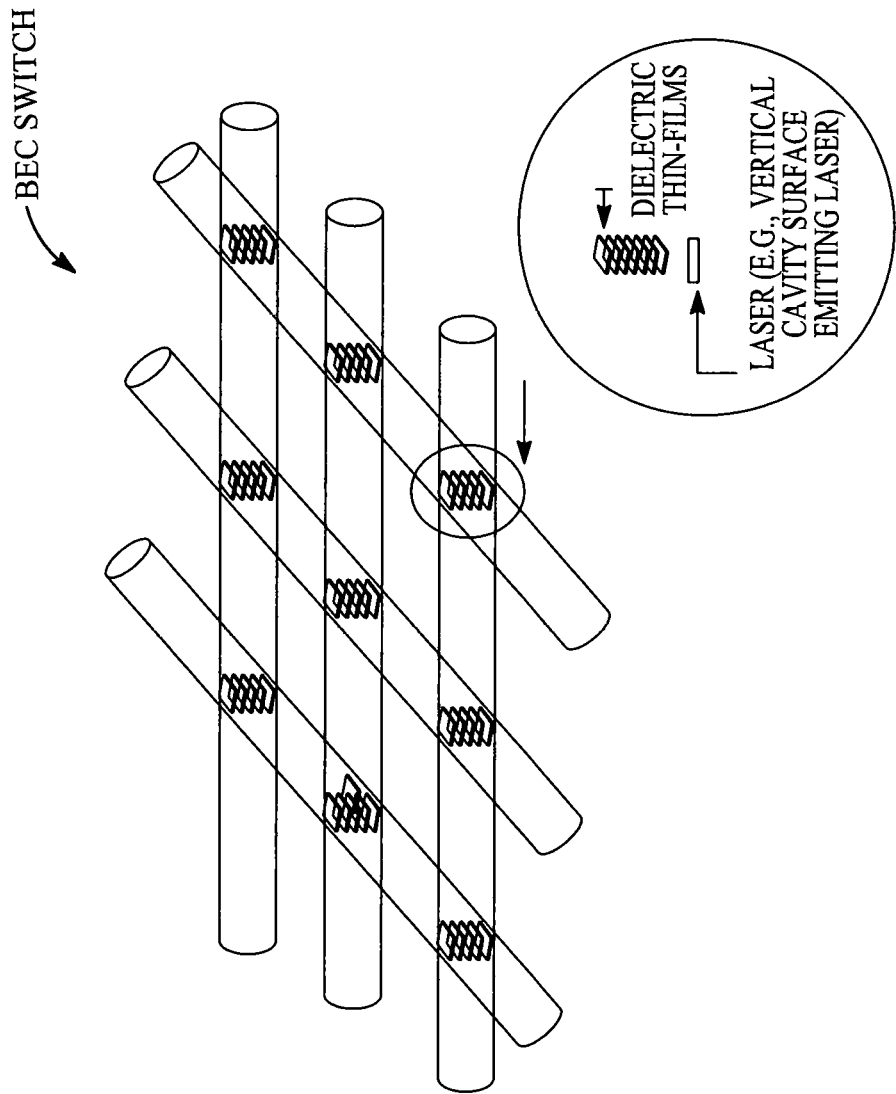
FIG. 19K illustrates a specific embodiment of Bose-Einstein condensate (BCE) based ultrafast optical switch for applications in biology.

FIG. 19K illustrates an embodiment of an ultra-fast Bose-Einstein condensate based ultra-fast optical switch for applications in biology. An ultra-fast N×N Bose-Einstein condensate based optical switch can be realized, utilizing an array of single-mode/multi-mode waveguides on the left-hand side and an array of single-mode/multi-mode waveguides on the right-hand side, wherein the array of single-mode/multi-mode waveguides on the left-hand side and the array of single-mode/multi-mode waveguides on the right-hand side are optically coupled with polariton Bose-Einstein condensate. Short-lived room temperature polariton Bose-Einstein condensate can be created through the interaction of a laser light (bouncing back and forth within multiple dielectric thin-films) and a luminescent polymeric thin-film of about 30 nanometers in thickness. The luminescent polymeric thin-film is embedded within multiple dielectric thin-films, wherein the multiple dielectric thin-films is then illuminated from the bottom (of the multiple dielectric thin-films, each dielectric thin-film is about 40 nanometers in thickness) by a vertical surface emitting laser or an in-plane laser integrated with a mirror and a lens.

Figure 19L:
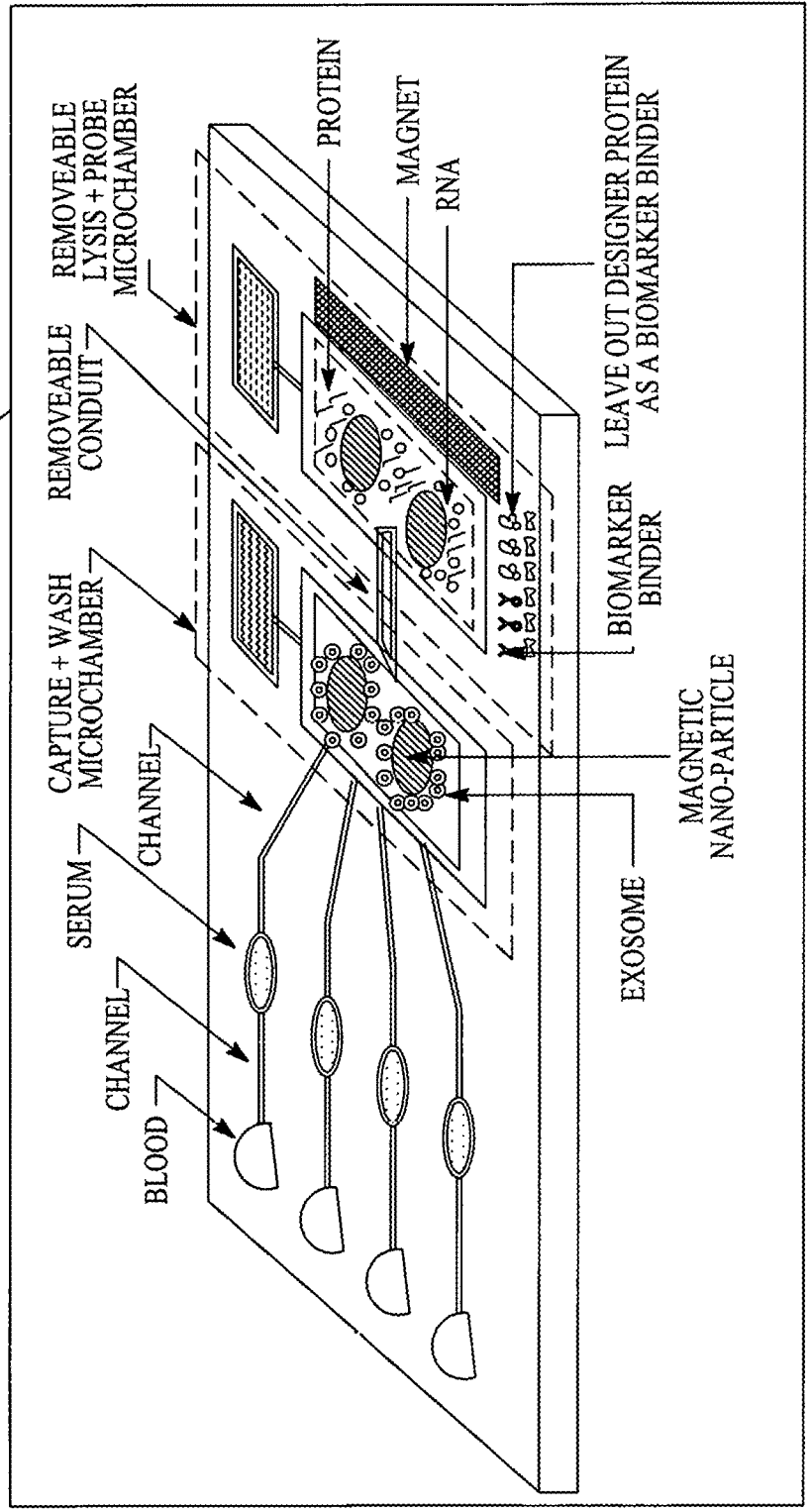
FIGS. 19L, 19M and 19N illustrate an integrated device to obtain various RNAs and proteins within exosomes from a human body's blood.
Figure 19M:
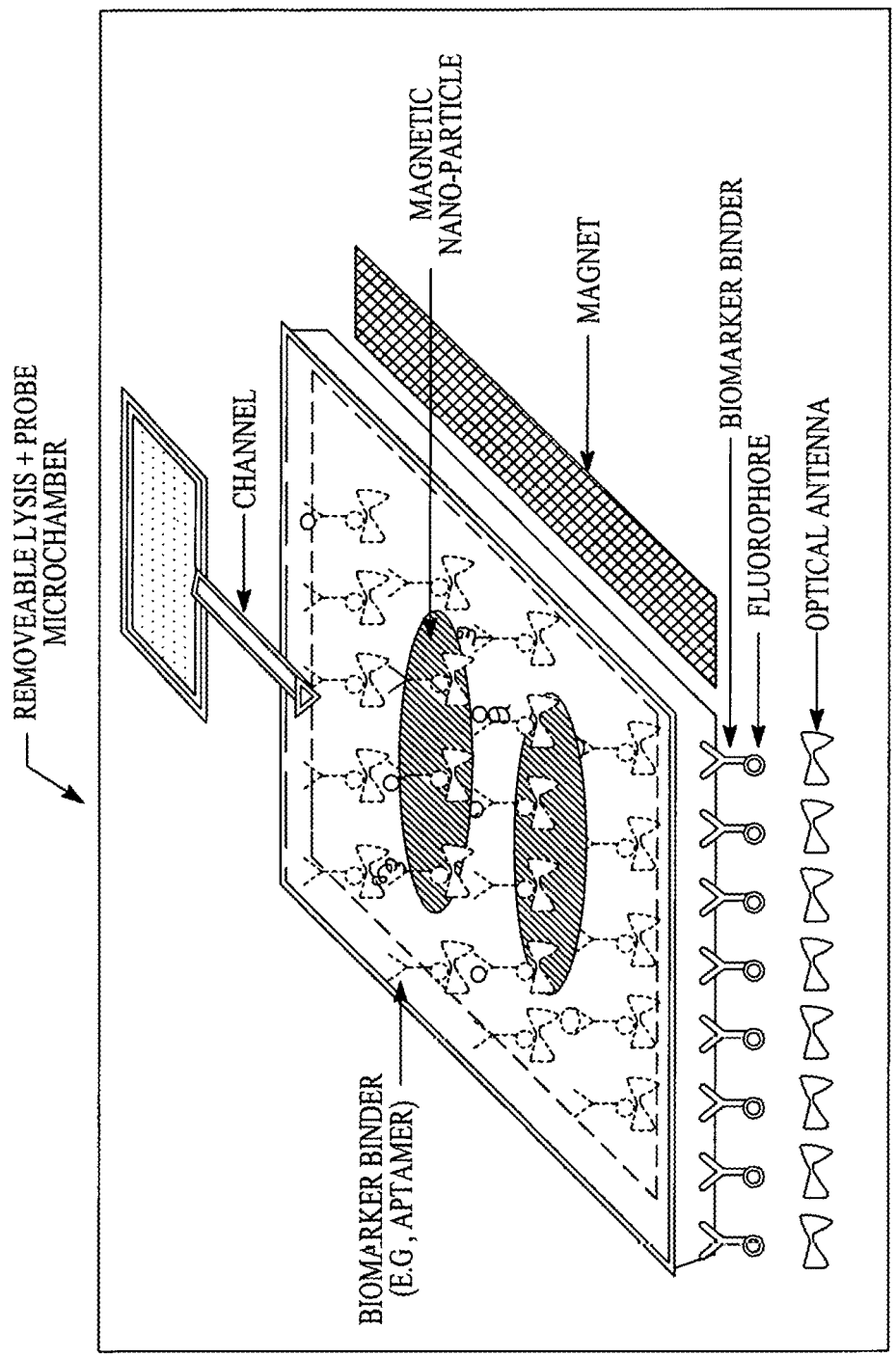
Figure 19N:
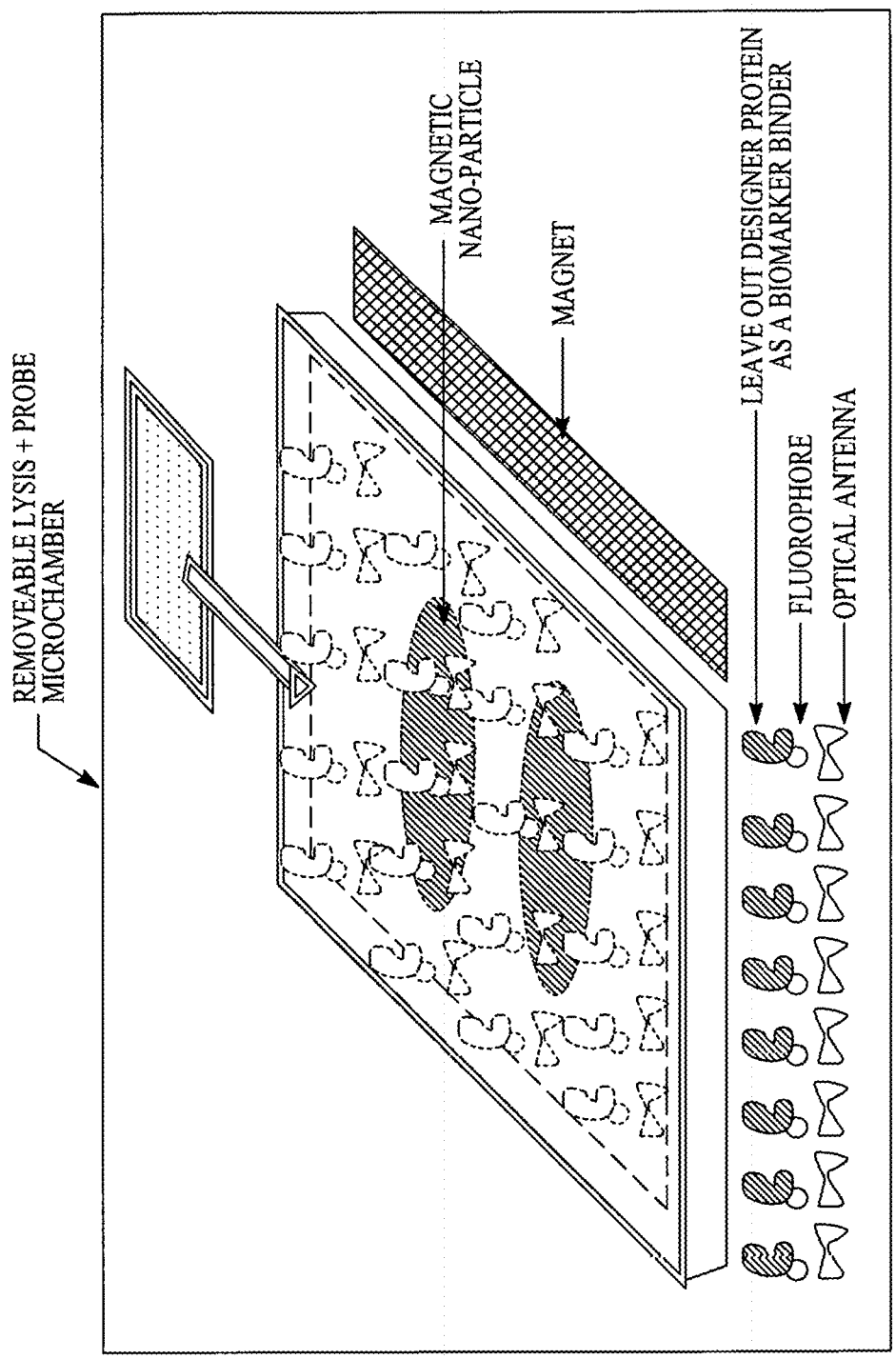
Figure 190:
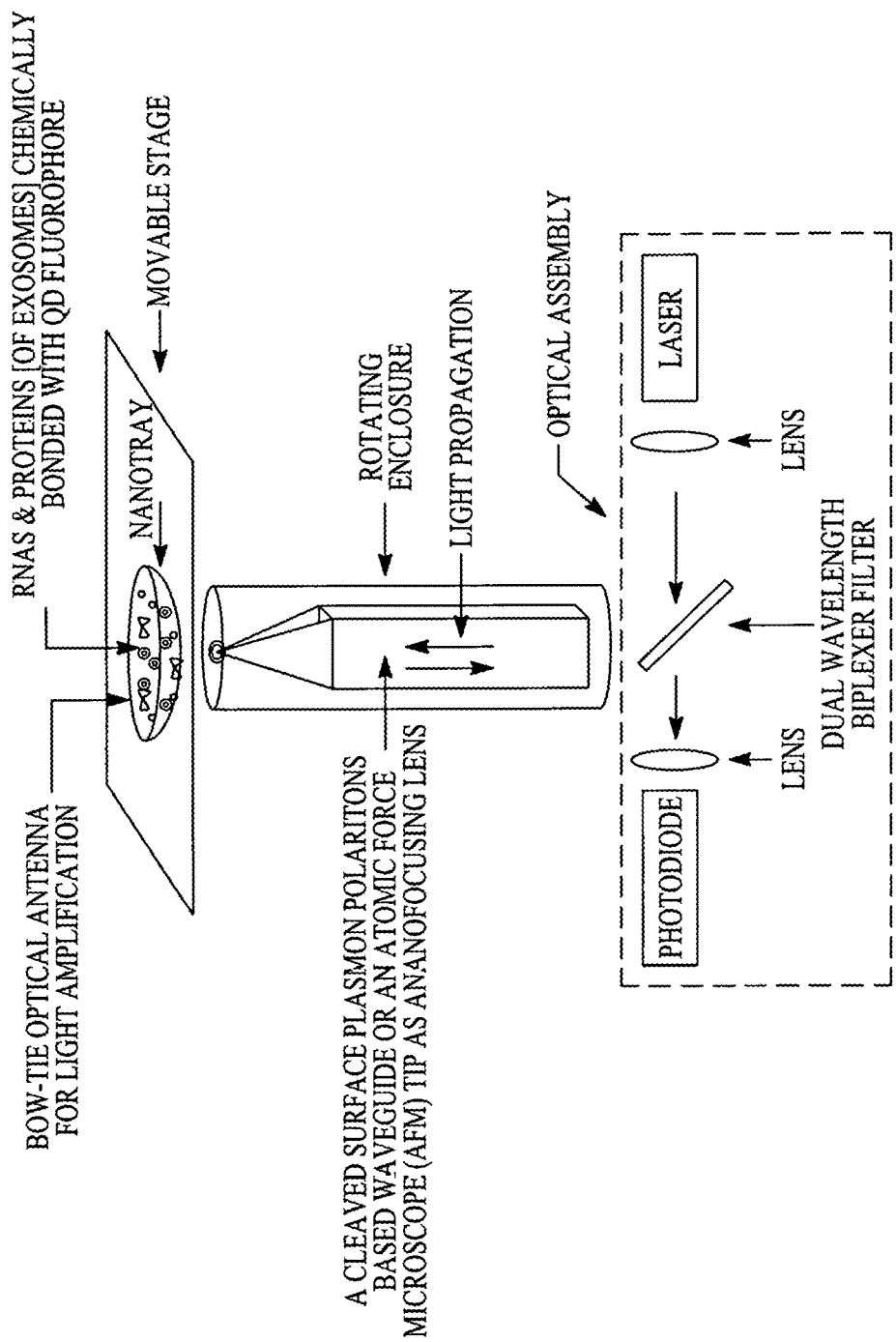

FIGS. 19L, 19M and 19N illustrate an integrated device to obtain native molecular components (e.g., DNA/mRNA/miRNA/piRNA/rRNA/tRNA) and proteins—as biomarkers, which were once caged within exosomes from a human body's blood/biological fluid. These native molecular components can be representative of the cell of origin.

FIG. 19L illustrates a biochemical chamber to obtain native biological molecular components and/or proteins—as the biomarkers, which were once caged within exosomes.

The biochemical chamber can be molded in poly(dimethylsiloxane). The biochemical chamber is degassed via vacuum prior to its use and the absorption of gas by poly(dimethylsiloxane) provides the mechanism for actuating and metering the flow of fluid in the microfluidic channels and between various parts of the biochemical chamber. The biochemical chamber can take in a human body's blood at inlets. The biochemical chamber can use tiny microfluidic channels of 30 microns in diameter underneath the inlets to separate the serum from a human body's blood, by utilizing laws of microscale physics. The serum moves through the biochemical chamber via a process called degas-driven flow.

Superparamagnetic nanoparticles iron oxide can be synthesized with a positive electrical charge to bond onto the membrane surface of exosomes (within a human body's blood/biological fluid) of negative electrical charge due to electrostatic interactions. Capture of exosomes by superparamagnetic nanoparticles iron oxide can be realized in Capture+Wash Microchamber. The biochemical chamber can be integrated with a magnet. Exposure to a magnetic field can separate superparamagnetic nanoparticles iron oxide bonded with exosomes.

Alternatively, the biochemical chamber can be integrated with a nanosieve/nanomembrane (e.g., a carbon nanomembrane) of about 100 nanometers pore diameter to filter exosomes—this is not illustrated in the Lysis+Probe Microchamber of the FIG. 19L.

Alternatively, the biochemical chamber can be integrated with a nanofilter (e.g., a carbon nanomembrane) of about 100 nanometers pore diameter to filter exosomes. For example, a nanofilter can be graphene based nanofilter. Nanoholes in graphene-a hexagonal array of carbon atoms can be fabricated/constructed in a two-stage process. First, a graphene sheet is bombarded with gallium ions or helium ions, which disrupt the carbon bonds. Second, the graphene sheet is etched in an oxidizing solution that reacts strongly with the disrupted carbon bonds-producing a nanohole at each spot where the gallium ions or helium ions struck. By controlling how long the graphene sheet is left in the oxidizing solution, one can control the average size of the nanoholes.

Alternatively, the biochemical chamber can be integrated with a biological probe, wherein a modified first end (e.g., the first end is modified with one/two lipid tail(s)) of the biological probe can chemically bind/couple/attach with an exosome, wherein a second end of the biological probe containing a biotin molecule, wherein the biotin molecule can chemically bind/couple/attach with an avidin molecule, attached on a surface modified magnetic bead (e.g., a magnetic bead of 300-500 nanometers in diameter). Capture of exosomes by the biological probe is realized in Capture+Wash Microchamber.

The Lysis+Probe Microchamber is removable. Furthermore, a suitable chemical (e.g., System Bio company's Micro SeraMir) can be added in the removable Lysis+Probe Microchamber to break the membrane of exosomes to obtain embedded a disease specific molecular components and/or proteins—as the biomarkers, which were once caged within the exosomes.

The removable Lysis+Probe Microchamber has a disease specific aptamer (integrated with a fluorescent protein/fluorophore/photoswitchable fluorophore) to bind with a-disease specific molecular components and/or proteins, which were once caged within the exosomes.

The removable Lysis+Probe Microchamber has a disease specific designer protein (integrated with a fluorescent protein/fluorophore/photoswitchable fluorophore) with a leave-one-out configuration, wherein each protein has an omitted segment to create a binding site to fit a disease specific protein, which was once caged within the exosomes.

The removable Lysis+Probe Microchamber has a disease specific synthetically designed biomarker binder (e.g., an aptamer or a synthetically designed biological sensor for nucleic acid/synthetically designed gene circuit) integrated with a fluorescent protein/fluorophore/photoswitchable fluorophore to fit with a disease specific native molecular component—as the biomarkers, which were once caged within the exosomes.

FIG. 19M illustrates an embodiment of the removable Lysis+Probe Microchamber with a biomarker binder (integrated with a fluorescent protein/fluorophore/photoswitchable fluorophore).

FIG. 19N illustrates an embodiment of the removable Lysis+Probe Microchamber with a biomarker binder such as a designer protein (integrated with a fluorescent protein/fluorophore/photoswitchable fluorophore). The designer protein is a leave-one-out configuration, wherein each protein has an omitted segment to create a binding site to fit a disease specific protein, which was once caged within the exosomes.

One or more three-dimensional protruded structures can be integrated with the fluorescent protein/fluorophore/photoswitchable fluorophore to enhance fluorescence.

Alternatively, the removable Lysis+Probe Microchamber has an array of three-dimensional protruded structures at or near the bottom of the Removable Lysis+Probe Microchamber to enhance fluorescence.

The one three-dimensional protruded structure can include generally a thin-film, wherein the thin-film can include a single crystalline structure metal or a polycrystalline structure metal or a metal nitride, wherein a dimension or shape of the one three-dimensional protruded structure is varied for maximum enhancement of the fluorescence emission, wherein more than the one three-dimensional protruded structure is spaced or arranged in a one-dimensional array or in a two-dimensional array, wherein the one-dimensional array or two-dimensional array is a systematic arrangement of similar three-dimensional protruded structures, wherein a pitch or a gap or a duty cycle of the one-dimensional array of the three-dimensional protruded structures is varied for maximum enhancement of the fluorescence emission, wherein a pitch or a gap or a duty cycle of the two-dimensional array of the three-dimensional protruded structures is varied for maximum enhancement of the fluorescence emission, wherein the fluorescent protein/fluorophore/photoswitchable fluorophore is positioned at a specified location with respect to the one three-dimensional protruded structure, as described in previous paragraphs.

The fluidic channel as described in FIGS. 19A, 19B, 19C, 19D, 19E, 19I and 19J can be replaced with the removable Lysis+Probe Microchamber, as described in either FIG. 19M or FIG. 19N.

The cavity, as described in FIGS. 19F, 19G and 19H, can be replaced with the removable Lysis+Probe Microchamber, as described in either FIG. 19M or FIG. 19N.

The optical diagnostic biomodule described in FIGS. 12V, 12X1 and 12Y can be utilized to detect the fluorescence emission, identifying specific native molecular components and/or proteins—as the biomarkers. The optical diagnostic biomodule described in FIGS. 14C and 14J can be also utilized to detect DNA sequencing (which can be also utilized for exome sequencing and RNA sequencing), identifying specific native molecular components, as the biomarkers.

The electrical diagnostic biomodule described in FIG. 14A can be utilized to detect DNA sequencing (which can be also utilized for exome sequencing and RNA sequencing), identifying specific native molecular components, as the biomarkers.

Alternatively, a femtosecond laser (as a single machining tool) can be utilized to fabricate/construct three-dimensional optical waveguides and fluidic channels of the photonics-lab-on chip. Thus, the photonics-lab-on chip can be utilized for point-of-care detection of a disease/an array of diseases.

FIG. 19O illustrates (both in top view and cross-sectional view) a nanoscope for detecting various RNAs and proteins within exosomes from a human body's blood/biological fluid. A specific RNA and/or protein can bind with a specific aptamer, wherein the aptamer is chemically coupled with a quantum dot fluorophore. An incident light from a laser, collimated by a lens and transmitted through an optical filter, then focused onto a nanotray containing exosomes, by surface plasmon polaritons based a nanofocusing waveguide lens.

Alternatively, an atomic force microscopy tip with high resolution optics (100×, resolving power ≤400 nanometers) can be utilized as a nanofocusing waveguide lens.

The bottom of the nanotray can be integrated with an array of gold nanoantennas for light amplification. The nanotray can be mounted on a movable stage.

The nanofocusing waveguide lens is fabricated/constructed, utilizing amorphous silicon dioxide. The waveguide is coated with an ultra thin-film of gold. The nanofocusing waveguide lens is about 5 microns long and rectangular in shape tapering to a point at one end. Because the nanofocusing waveguide lens concentrates light into a nanosized point, it can create a high-resolution map of RNAs and proteins within exosomes. The nanofocusing waveguide lens is mounted and enclosed within a rotating enclosure.

Fluorescence light can also travel in the reverse/opposite direction through the nanofocusing waveguide lens, then through the optical filter, the lens and the photodiode. Thus, collecting light through the narrow point can turn the nanofocusing waveguide lens into a high resolution nanoscope.

However, it should be noted that FIG. 19O illustrates the nanoscope in a vertical configuration. Other configurations (e.g., an upright or an inverted or a planar configuration) of the nanoscope are possible, without departing from the scope and spirit of this nanoscope.

Figure 19P:
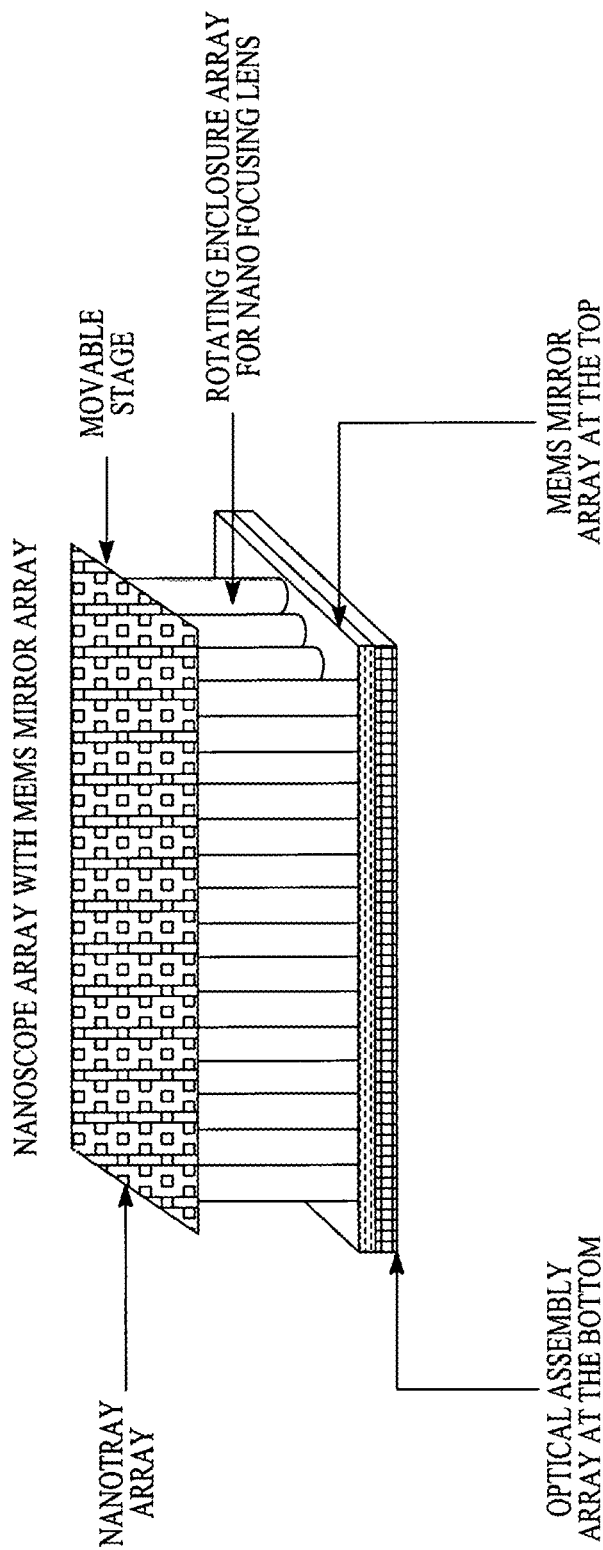
FIG. 19P illustrates an array of nanoscopes for detecting various RNAs and proteins within exosomes from a human body's blood.

FIG. 19P illustrates an array of nanoscopes enabled by microelectro-mechanical-system mirror array (e.g., Texas Instrument's Digital Light Processor projector chip) and rotating array of enclosures for nanofocusing waveguide lens.

Figure 19Q:
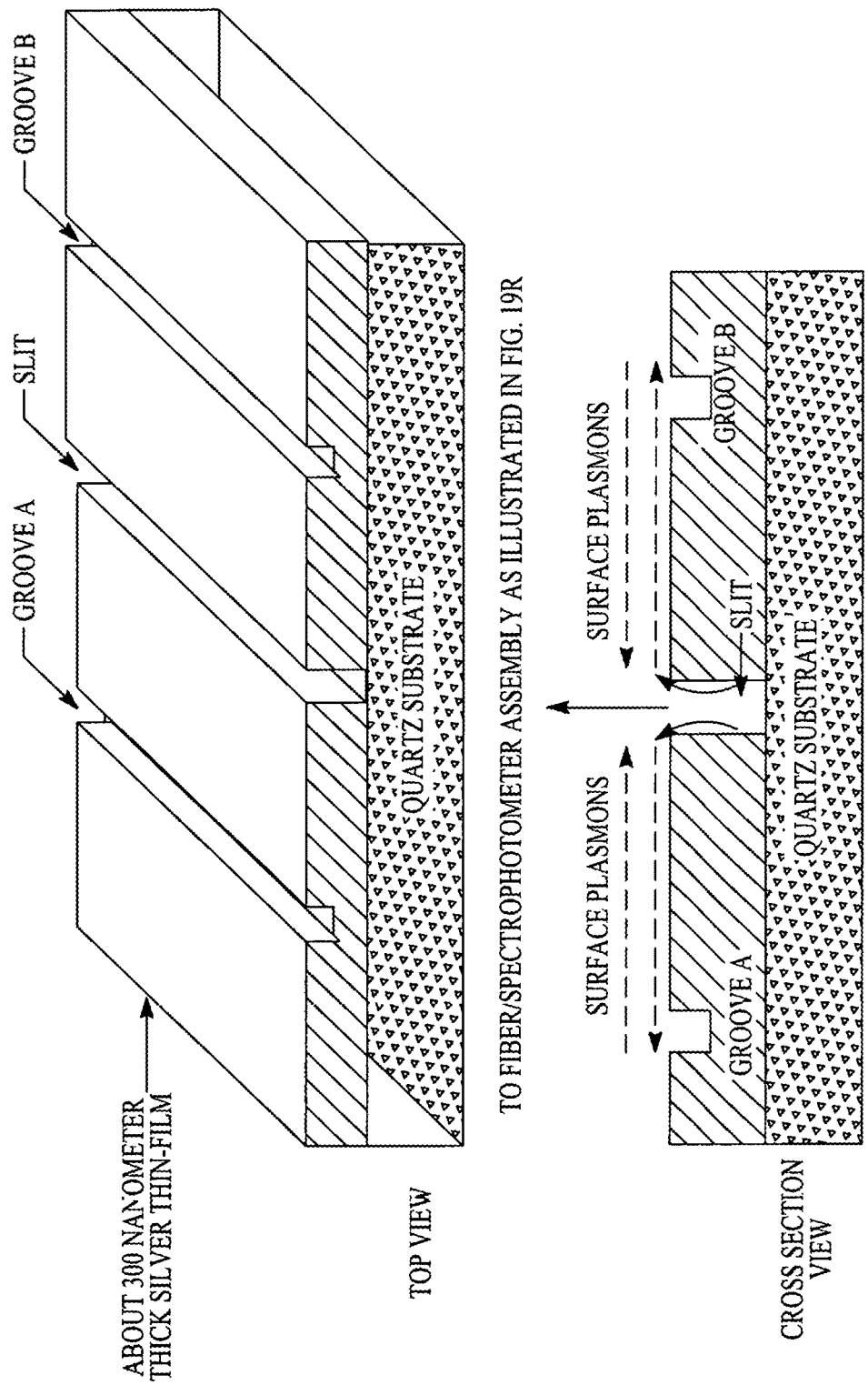
FIG. 19Q illustrates a plasmonic interferometer for detecting various RNAs and proteins within exosomes from a human body's blood.

FIG. 19Q illustrates a plasmonic interferometer for detecting various RNAs and proteins within exosomes from a human body's blood/biological fluid. A quartz substrate coated with a thin-film of silver (about 300 nanometers in thickness). Fabricated/constructed in silver thin-film is a nano-scaled plasmonic interferometer, wherein the nano-scaled plasmonic interferometer has a center slit (about 100 nanometers in depth and 30 microns in length) with a groove (about 70 nanometers in depth, 130 nanometers in width and 30 microns in length) on each side of the groove. When light (e.g., light from a narrow-band light source) is shone through the quartz substrate, the groove causes a wave of free electrons in the silver thin-film, a surface plasmon polariton to propagate toward the center slit. Those waves interfere with light that passes through the center slit. A sensitive spectrophotometer/optical fiber assembly (as described in the FIG. 19R) can be utilized to measure the patterns of interference generated by the grooves and slit. When a human body's blood/biological fluid is deposited on the above nano-scaled plasmonic interferometer; the light and the surface plasmon waves propagate through a human body's blood/biological fluid before they interfere with each other—thus altering the interference pattern detected by a sensitive spectrophotometer.

Furthermore, by adjusting the distance between the grooves and center slit, the above nano-scaled plasmonic interferometer can be calibrated to detect the signature of a disease specific biomarker and/or bioactive compound and/or bioactive biomolecule with high sensitivity in an extremely small volume of a human body's blood/biological fluid.

For example, a first enzyme-glucose oxidase can chemically react with glucose (from a human blood/biological fluid) to generate hydrogen peroxide. A second enzyme-horseradish peroxidase can chemically react with hydrogen peroxide to generate resorufin. Both reactions can be facilitated by microfluidic channels. Resorufin is a colored liquid, which can absorb/emit red light. Thus, the above nano-scaled plasmonic interferometer can be calibrated to detect the signature of resorufin, as a measure of glucose concentration in a human body's blood/biological fluid.

Furthermore, thousands of nano-scaled plasmonic interferometers can be fabricated in the thin-film of silver, wherein each nano-scaled plasmonic interferometer can be calibrated to detect only the signature of a disease specific biomarker and/or bioactive compound and/or bioactive biomolecule with high sensitivity in an extremely small volume of a human body's blood/biological fluid without any need of a fluorophore.

Figure 19R:
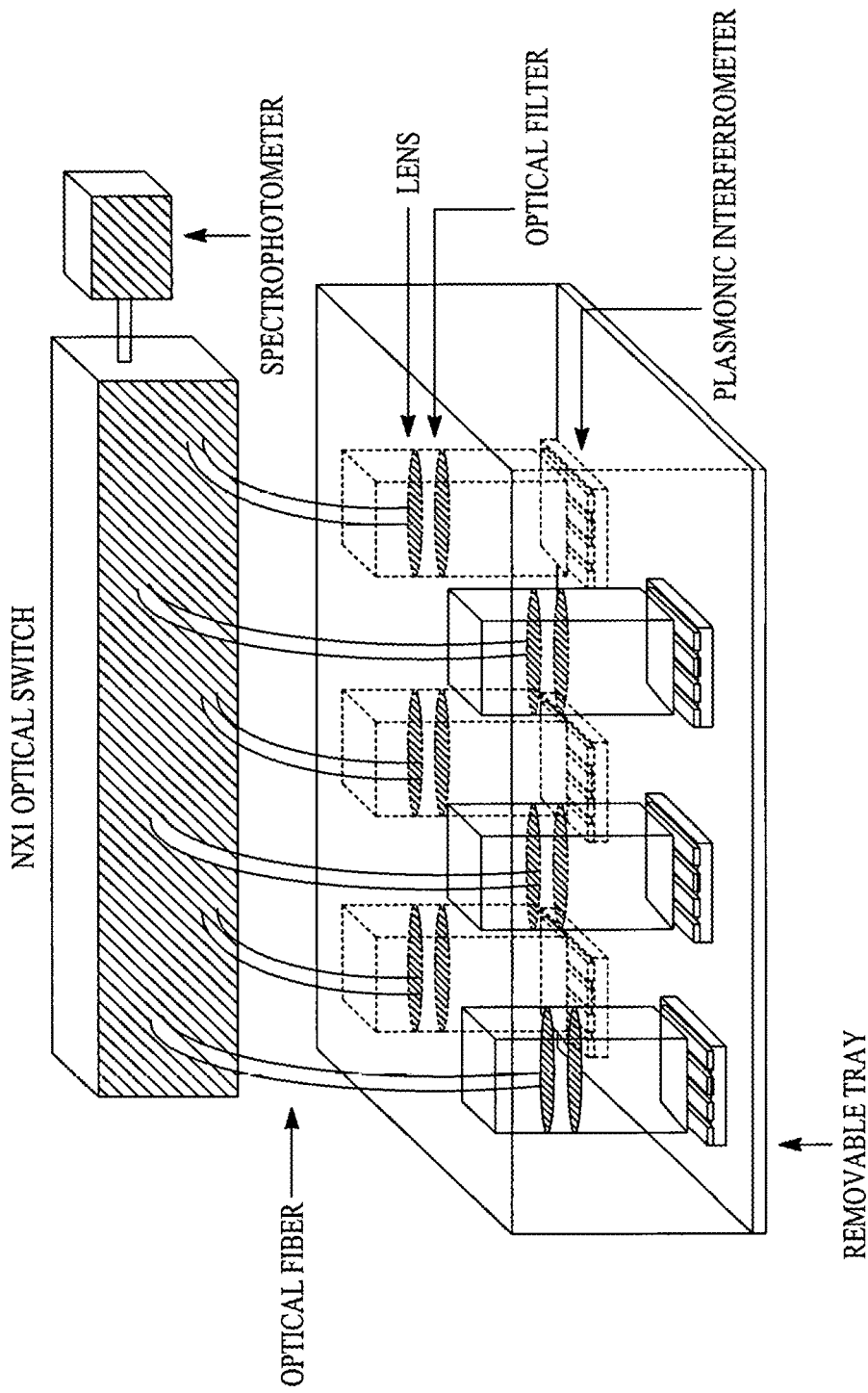
FIG. 19R illustrates an optical assembly of plasmonic interferometer-optical fiber-optical switch-spectrophotometer to measure the interference patterns generated by an array of plasmonic interferometers.

FIG. 19R illustrates an optical assembly of plasmonic interferometer-optical fiber-optical switch-spectrophotometer to measure the interference patterns generated by an array of plasmonic interferometers.

The interference patterns generated by the grooves and center slit is propagated through an optical thin-film filter (to reduce cross-talk from other plasmonic interferometers) and focused by a focusing lens onto an optical fiber. The array of optical fibers is connected with a N×1 optical switch, which is optically connected with a spectrophotometer for spectrum analysis.

Figure 20:
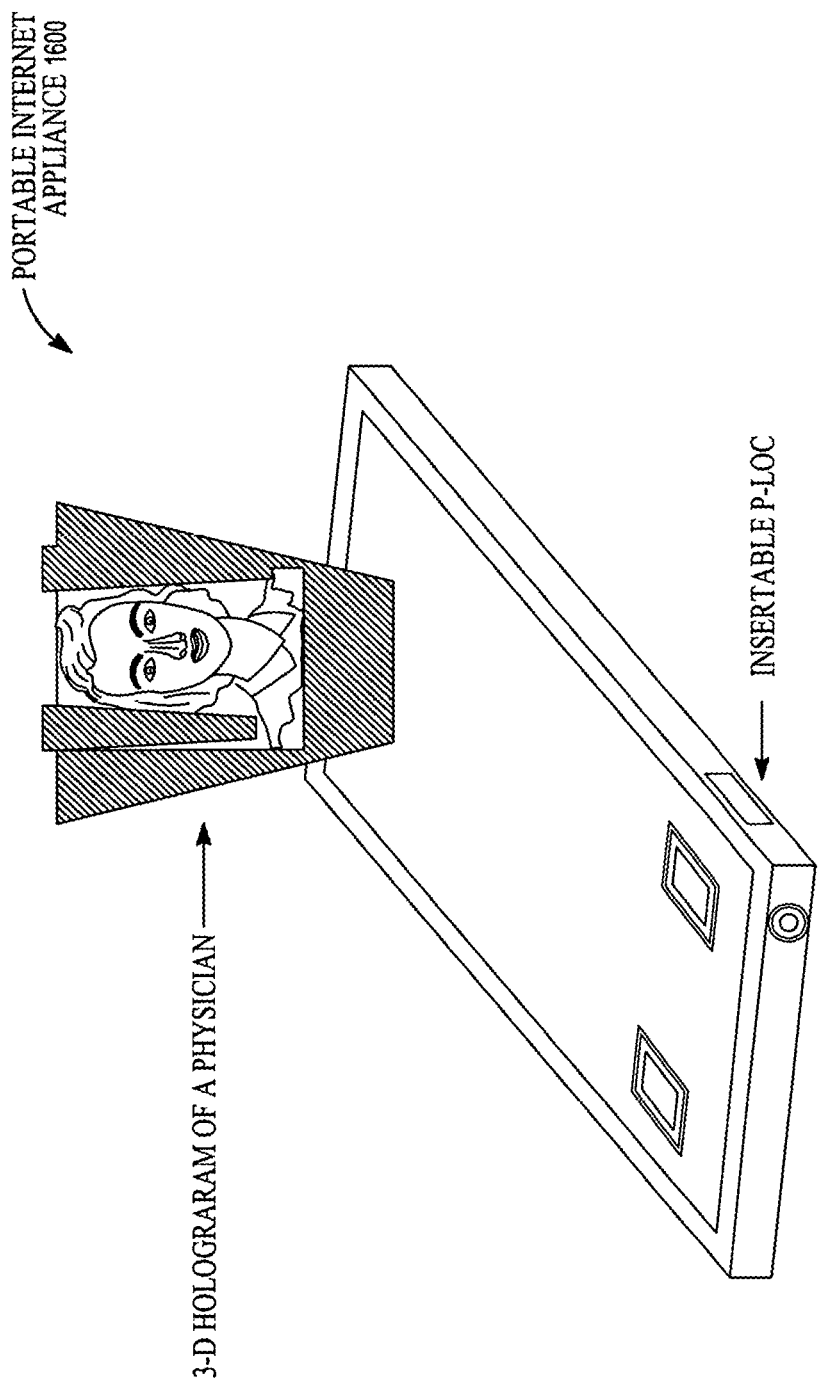
FIG. 20 illustrates an insertable photonics-lab-on-chip into the portable internet appliance.

FIG. 20 illustrates the photonics-lab-on chip, which can be inserted into the portable internet appliance 1600.

FIG. 20 also illustrates interactions of the portable internet appliance 1600 with a hologram. A hologram is an optical illusion enabling a two-dimensional image to appear in a three-dimensional form, out of the portable internet appliance 1600 and it can add a new dimension in video calls and/or multimedia texts.

Furthermore, haptic feedback can be added to the hologram. A user can touch and interact with the hologram and receive tactile responses, as if the hologram were real. Furthermore, various embodiments of holograms have been described/disclosed described in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 and the entire contents of this US Non-Provisional Patent Application are incorporated herein.

Example Applications of Portable Internet Appliance in Daily Life

The portable internet appliance 1600 can book the user on the next flight, when the portable internet appliance 1600 finds out from the internet and other resources that the previous flight is canceled. The portable internet appliance 1600 can communicate with the user's family about the delay in arrival, newly booked flight and then notify/reorder the airport shuttle/taxicab accordingly to pick up the user from the airport. Besides the internet, the other resources may include various search engines (e.g., Bing, Google, Yahoo and Yelp), expert databases, data from existing Question & Answer forums (e.g., ChaCha) and answers drawn from real-time applications that would ask relevant people if they know they answer. What makes the Question & Answer forums powerful is that it keeps track of each and every question and answer pairing ever asked and every answered ever given.

The portable internet appliance 1600 can order and pay (with near-field communication) for a coffee and downloadable movie (from a movie kiosk, utilizing Wi-Fi/millimeter wave (including 60 GHz)/terahertz band transceiver) of the user's preference at the airport terminal without the user input, where the digital signature of the movie can expire after a few days, making the movie unusable, after expiration of the digital signature.

An indoor positioning system can track/map how and where the user spends time both online and offline and if these times are happy or sad.

Example of Other Applications of Portable Internet Appliance in Daily Life

The portable internet appliance 1600 can be integrated with a suitable software application program ("app") to convert/merge both a cell phone number and an e-mail identification into one integrated user identification.

FIG. 21 illustrates the merger of a cell phone number (213) 555-1212 and an e-mail identification mo@yahoo.com into one integrated user identification: 213555.mo@lifepicasso.com. Thus, one integrated user identification can be utilized as the focal point for (a) voice-over-IP, (b) texting with an attachment, (c) microtexting, (d) e-mail with an attachment and (e) convergence of various internet related services. As an example, focal point of near real-time/real-time convergence of various internet related services are: online files, VOIP phone calls, e-mails with attachments/text messages/voice messages/video messages/social media messages, indoor positioning system/global positioning system locations, secure payments/purchases (offline/online) and digital banking data. The above convergence can be configured with encryption, time-shifted and follow-up capabilities.

Furthermore, the one integrated user identification can be utilized as a platform for sending and receiving messages with another user.

Figure 22A:
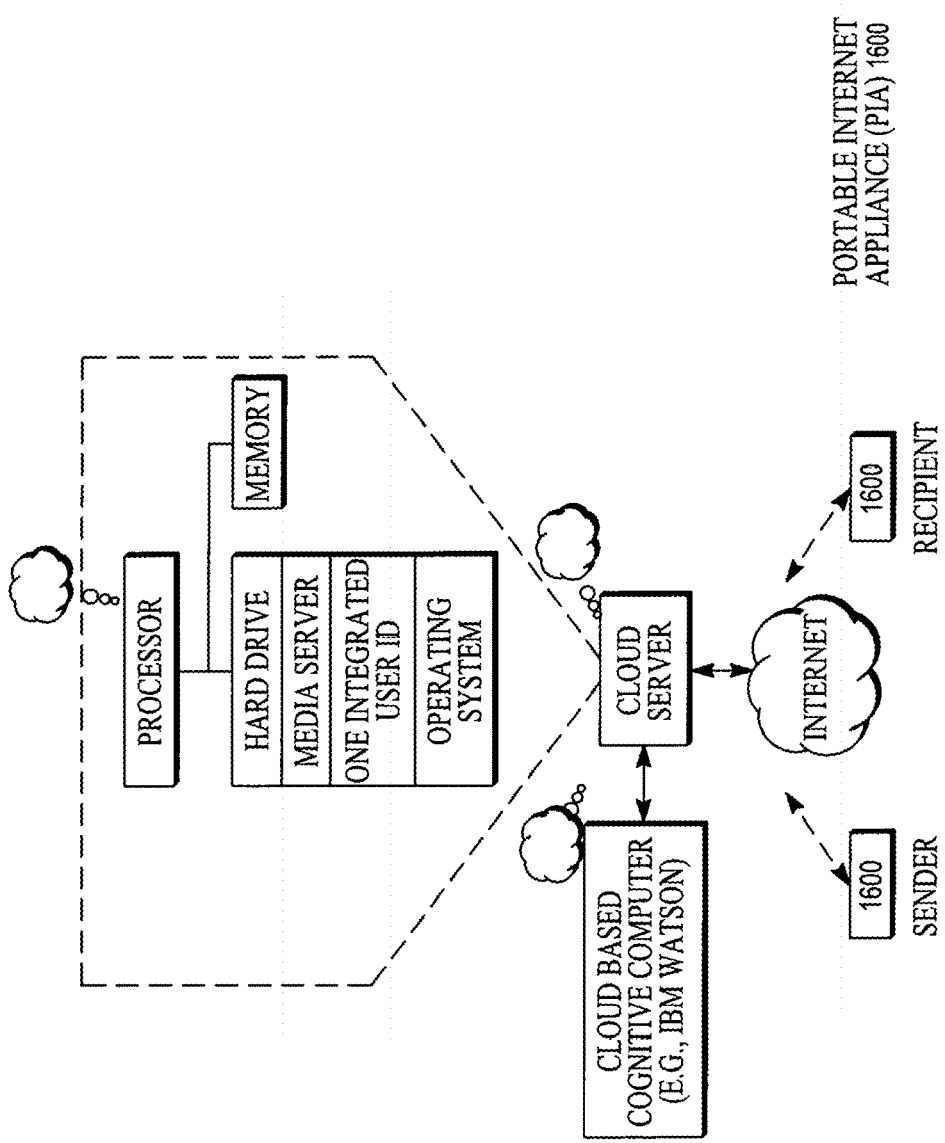
FIG. 22A illustrates a sender's portable internet appliance with a recipient's portable internet appliance via a cloud based server.

FIG. 22A illustrates a hardware configuration of the one integrated user identification with a processor, memory, a hard drive (storage device), a media server and an operating system, stored in a cloud baser server. The cloud based server also connects with a cloud based cognitive computer and the portable internet appliance 1600. The one integrated user identification as a platform is shared between the sender's portable internet appliance 1600 and the recipient's portable internet appliance 1600 over the internet.

Interactions of the users can be stored in a cloud based data storage unit and analyzed by a cloud based expert cognitive/learning computer in near real-time/real-time.

Figure 22B:
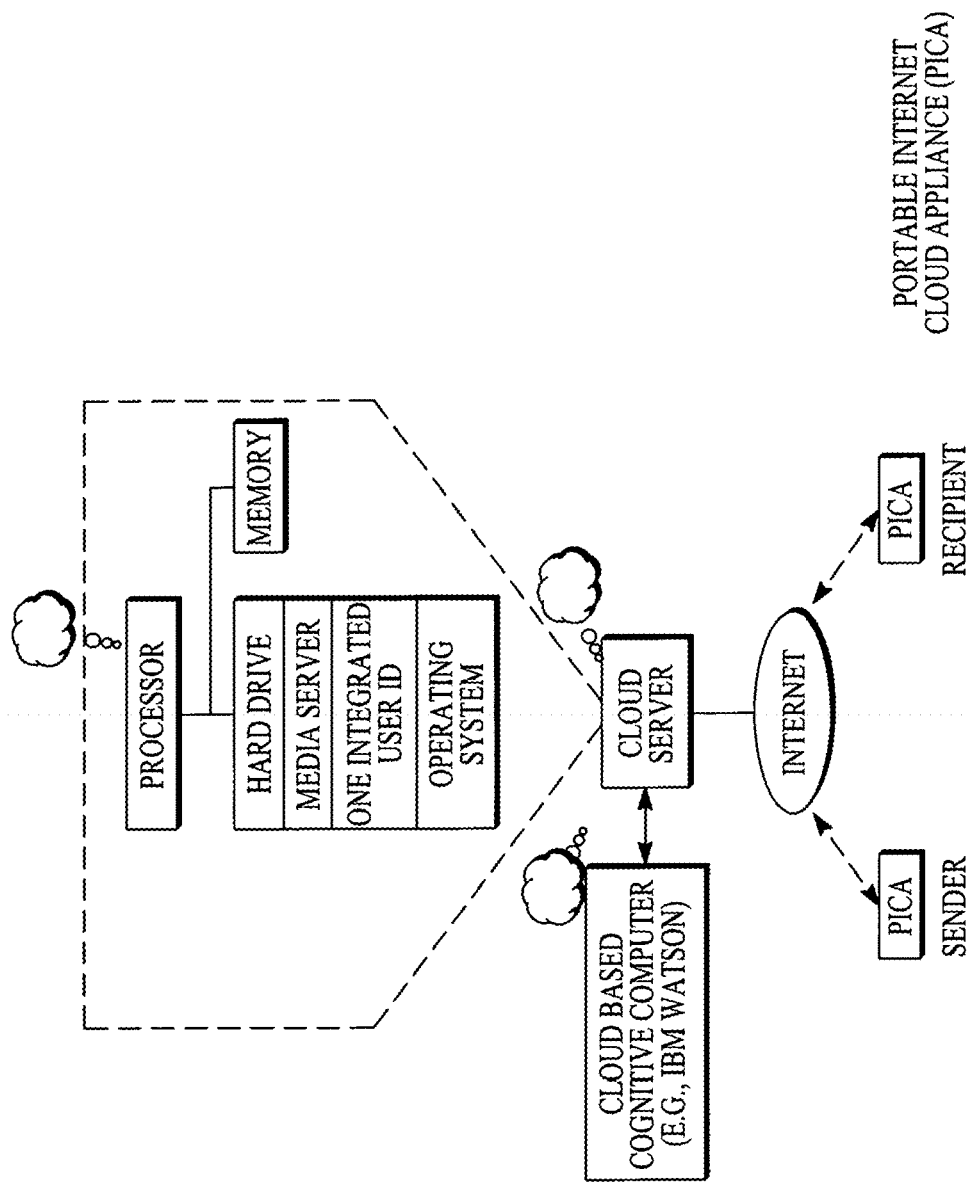
FIG. 22B illustrates a sender's portable internet cloud appliance with a recipient's portable internet cloud appliance via a cloud based server.

FIG. 22B illustrates a sender's portable internet cloud appliance (PICA) with a recipient's portable internet cloud appliance via a cloud based server, where the portable internet cloud appliance could be an internet connected terminal device. The portable internet cloud appliance can replace the portable internet appliance 1600.

Figure 23:
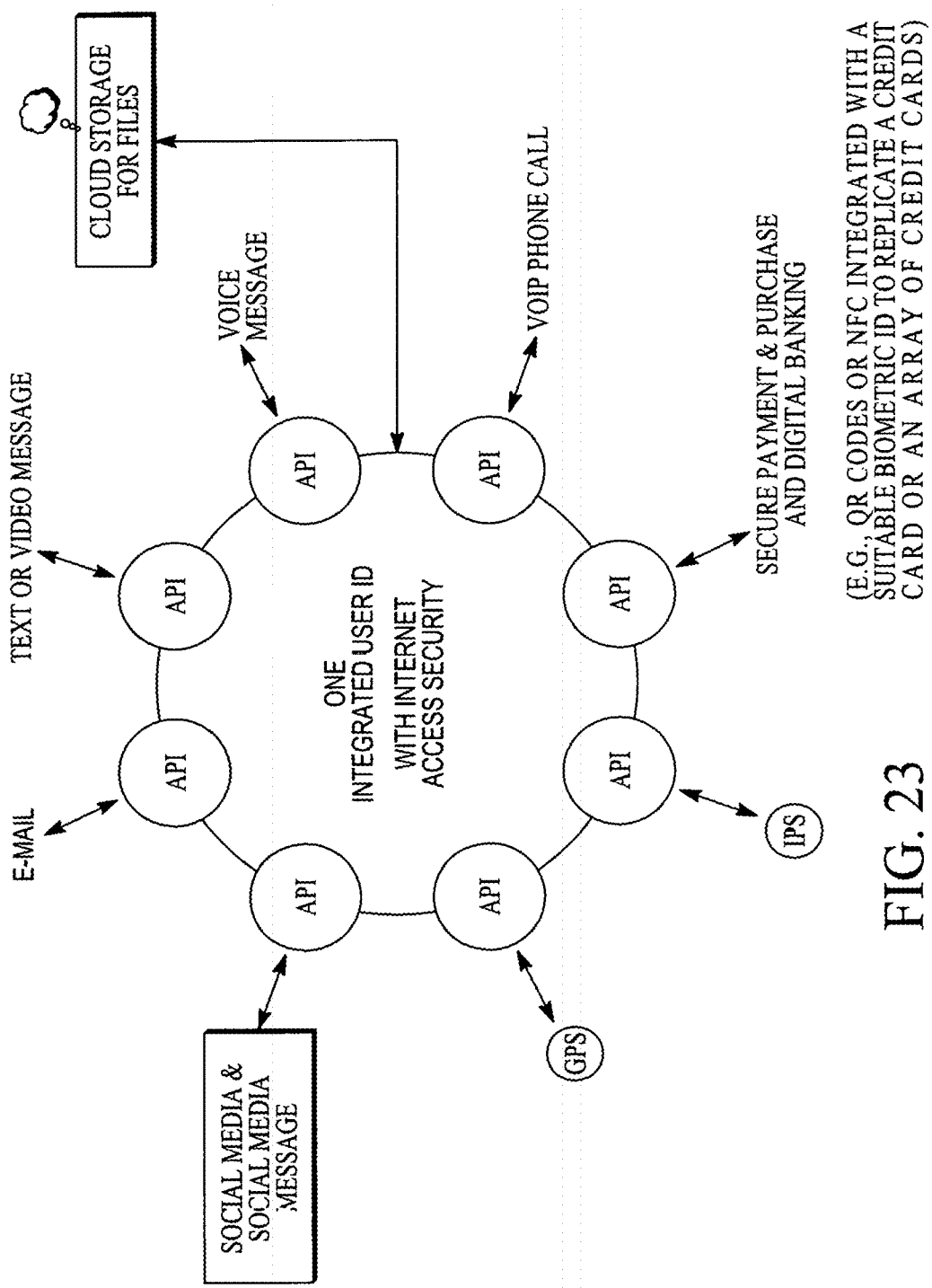
FIG. 23 illustrates a near real-time/real-time focal point convergence of various applications or functions with one integrated user identification.

FIG. 23 illustrates a near real-time/real-time focal point convergence of various applications or functions with one integrated user identification. APIs of many service links can be created by import.io and converged into the one integrated user identification For example, after properly authenticating the user's profile via suitable biometric verification, the user can open a digital bank account entirely online. The digital bank account with a search box can enable the user to type in queries in a question-answer format (e.g., "how much did I spend on travel last week?").

Furthermore, the question-answer format can be enhanced by a fuzzy logic algorithm/neuro-fuzzy logic algorithm. A fuzzy logic algorithm can be implemented as follows: (a) define linguistic variables and terms, (b) construct membership functions, (c) construct rule base, (d) convert crisp inputs into fuzzy values, utilizing membership functions (fuzzification), (e) evaluate rules in the rule base (inference), (f) combine the results of each rules (inference) and (g) convert outputs into non-fuzzy values (de-fuzzification). The key idea of fuzzy logic algorithm is that it uses a simple/easy way to secure the output(s) from the input(s), wherein the outputs can be related to the inputs by using if-statements. Neural networks can approximate a function, but it is impossible to interpret the result in terms of a natural language. The fusion of neural networks and fuzzy logic in a neuro-fuzzy algorithm can provide both learning as well as readability. A neuro-fuzzy algorithm is based on combinations of artificial neural networks and fuzzy logic.

Figure 24:
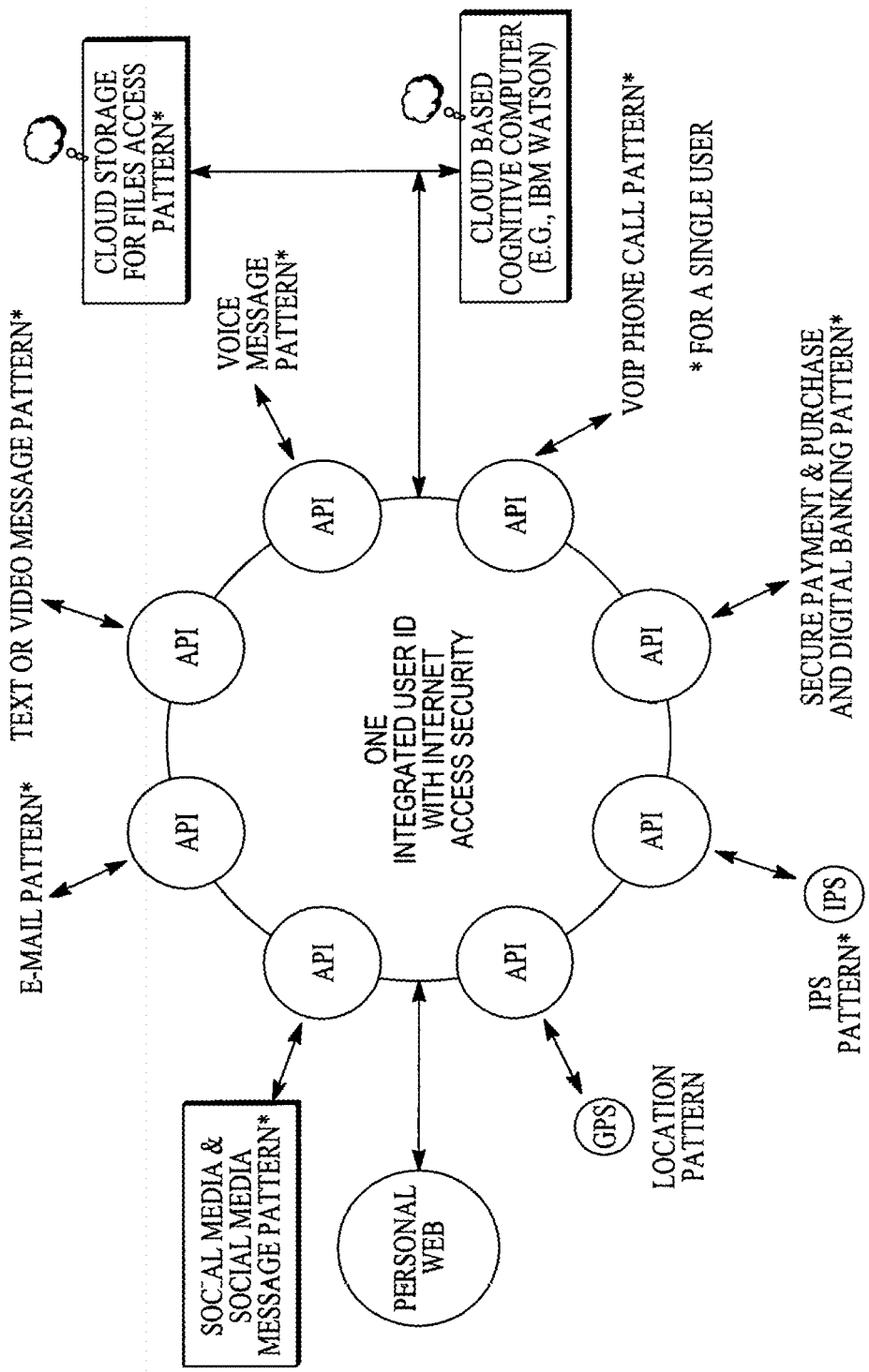
FIG. 24 illustrates patterns of various applications or functions of a single user with a user-centric personal web.

FIG. 24 illustrates patterns of various applications or functions of a single user (as described in FIG. 23) with a user-centric personal web. A user-centric personal web can make life easier in automating routine actions/decisions for the user.

The personal web can relate to (a) social (the people, a user interacts with and the content the user exchanges in social networks), (b) location (the user checks into), (c) product (the things the user buys on Amazon or eBay, the movies the user watches on Snapchat/Netflix/You Tube or the hotels the user books online) and (d) interest (the sort of things the user searches for on Google/You Tube or the things the user like on Facebook)—thus the personal web can reveal a lot about the user.

Building a statistical history, learning and relearning about the user data of social, location, product and interest, the usefulness of a personal web can be enhanced.

Thus, the portable internet appliance 1600 can be configured to know what time the user wants to wake up at, even before the user set an alarm. It knows the user's route to work and monitors traffic along the way, guiding the user through the most efficient route. Before the user's lunch break, the user can get food recommendations based on his/her past eating habits and current health conditions. When the user gets home, a smart thermostat has heated the home to the user's preferred temperature and a smart TV has remembered that the user loves to watch the evening news with CBS Dan Rather after work.

Furthermore, the usefulness of a personal web can be enhanced by connecting it with sensors, wherein the sensors are also connected with the internet and the portable internet appliance 1600.

The user has multiple passwords, identifications, services and devices. But security across them is fragmented. A digital security protector (DSP) will sort through contextual, situational and historical data to verify the user's identity on different devices including the user's identity with biometric data in near real-time/real-time. The digital security protector can learn about the user's social graph (as described in FIG. 25) and make an inference about the user behavior that is out of the norm or may be due to someone stealing that user's identity. Based on the user's social graph, the digital security protector will know the user intimately, for example if a particular user is a vegetarian, but someone is buying a non-vegetarian food with the user's credit card, the digital security protector will automatically close the credit card in question. Thus, the online security is based on intimacy with the user's social graph; rather than a collection of various fragmented passwords.

Furthermore, the one integrated user identification can be embedded with his/her digital security protector.

Figure 25:
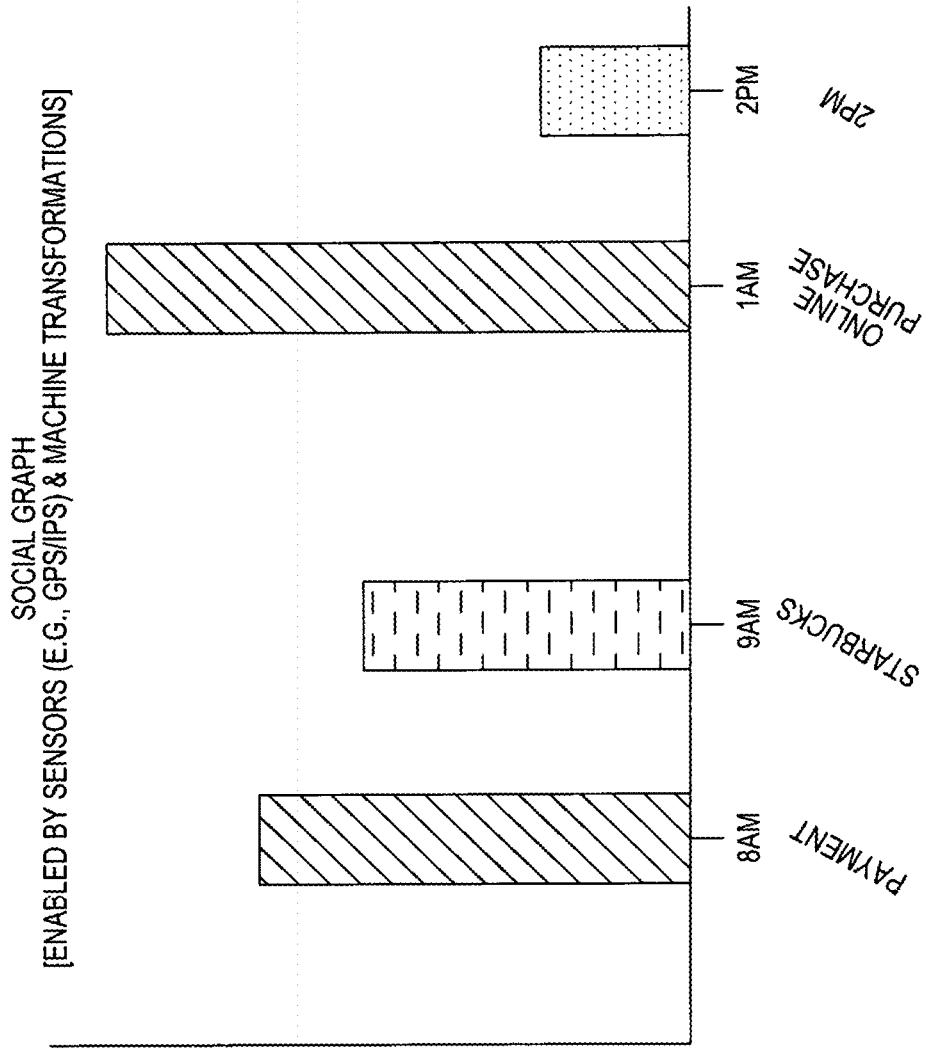
FIG. 25 illustrates a social graph of a user.

FIG. 25 illustrates a social graph of a user, enabled by (a) sensors (e.g., a location determination module-indoor positioning system/global positioning system), (b) individual data patterns of the user, (c) an algorithm for generating the user's social graph with machine transformations, wherein the algorithm for generating the composite social graph with machine transformations can be stored in a local data storage unit of the portable internet appliance 1600 or a cloud based data storage unit and (d) mathematical/statistical algorithm of Big Data stored in a cloud based data storage.

Near real-time/real-time snapshots/holographic snapshots (e.g., images/videos) of the contextual world around the user can be color enhanced/edited/geotagged/personalized (e.g., personalized with emoji/emoticon) by utilizing an algorithm(s). The user's (or the user's one integrated user identification) social graph and/or social geotag can be linked with a virtual avatar.

Near real-time/real-time snapshots/holographic snapshots (e.g., images/videos) by a camera (e.g., camera of the portable internet appliance 1600) can be instantly recognized (with/without much information about the snapshots/holographic snapshots)/color enahanced/edited/geotagaged/personalized by utilizing an algorithm(s). Furthermore, near real-time/real-time snapshots/holographic snapshots can be integrated with the virtual avatar (and the virtual avatar can be linked with a public/consortium/private blockchain) and shared via the internet or a cloud based data storage unit via the portable internet appliance 1600 (the portable internet appliance 1600 and/or near real-time/real-time wearable bioelectronics subsystem 1580, as an augmented reality personal assistant, can be sensor-aware or context-aware) by utilizing an algorithm(s).

The user can store his/her social graph and/or social geotag in his/her personal cloud via a microcomputer (e.g., Raspberry Pi) with properly implemented cryptography. The user can auction/monetize his/her social graph with or without social geotag by utilizing an algorithm(s) or opt out. The price of the user's social graph with or without social geotag can be based on the utility function of his/her social graph and/or social geotag to an advertiser. Furthermore, the user can securely host/store his/her own files and data (which can be used at any place, any time and any device) in his/her personal cloud via a microcomputer. Such a microcomputer can enable secure communication (e.g., Bitmail) and connect with other systems/subsystems/objects/biological objects via a personal network (e.g., Wi-Fi). Instead of talking to a centralized e-mail mail server at Google, Bitmail can distribute messages across networks of peer users, encrypting Bitmail's address and content automatically. Furthermore, peer users can help store and only deliver Bitmail to the intended recipient user. Bitmail can obscure the sender's identity and an alternate Bitmail address can send Bitmail on the user's behalf. Additionally, such a microcomputer can enable online payment, protecting privacy of the user via the user's virtual avatar (which can be linked with a blockchain). Through the user's virtual avatar, the user just would need to supply/apply a fragment of information necessary to receive a service (e.g., purchasing an item). Furthermore, intelligence from the user's social graph and/or social geotag can be realized by an intelligent learning set of instructions, which can include: artificial intelligence (including self-learning artificial intelligence), computer vision (self-learning camera vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

It should be noted that the set of instructions of the self-learning artificial intelligence and/or self-learning neural networks algorithm can include a quantum computer enhanced machine learning algorithm and such realized intelligence can enable targeted advertisement to the user/user's virtual avatar.

Furthermore, the user/user's virtual avatar can interact with targeted advertisement (e.g., images/videos), based on intelligence from the user's social graph and/or social geotag and intelligence from the user in the user interface.

Figure 26:
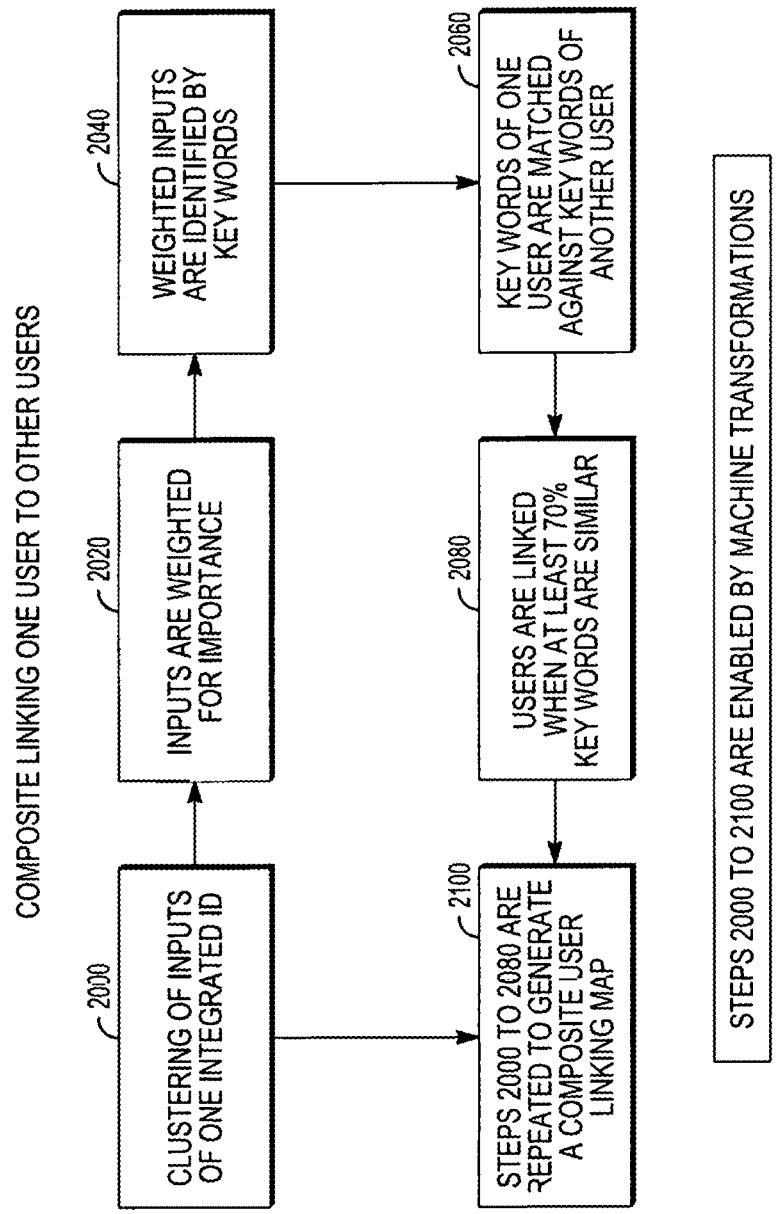
FIG. 26 illustrates a flow chart method of linking of many users, utilizing machine transformations.

FIG. 26 illustrates a flow chart linking one user with many users, utilizing machine transformations. In step 2000, an algorithm performs clustering of inputs from one integrated user identification. In step 2020, the algorithm weighs inputs for importance. In step 2040, weighted inputs are identified for key words. In step 2060, key words of one user are matched with key words of another user. In step 2080, a user is linked with another user, when 70% of key words are matched. In step 2100, all previous steps (from step 2000 to step 2080) are repeated until there is a composite linking map.

Figure 27:
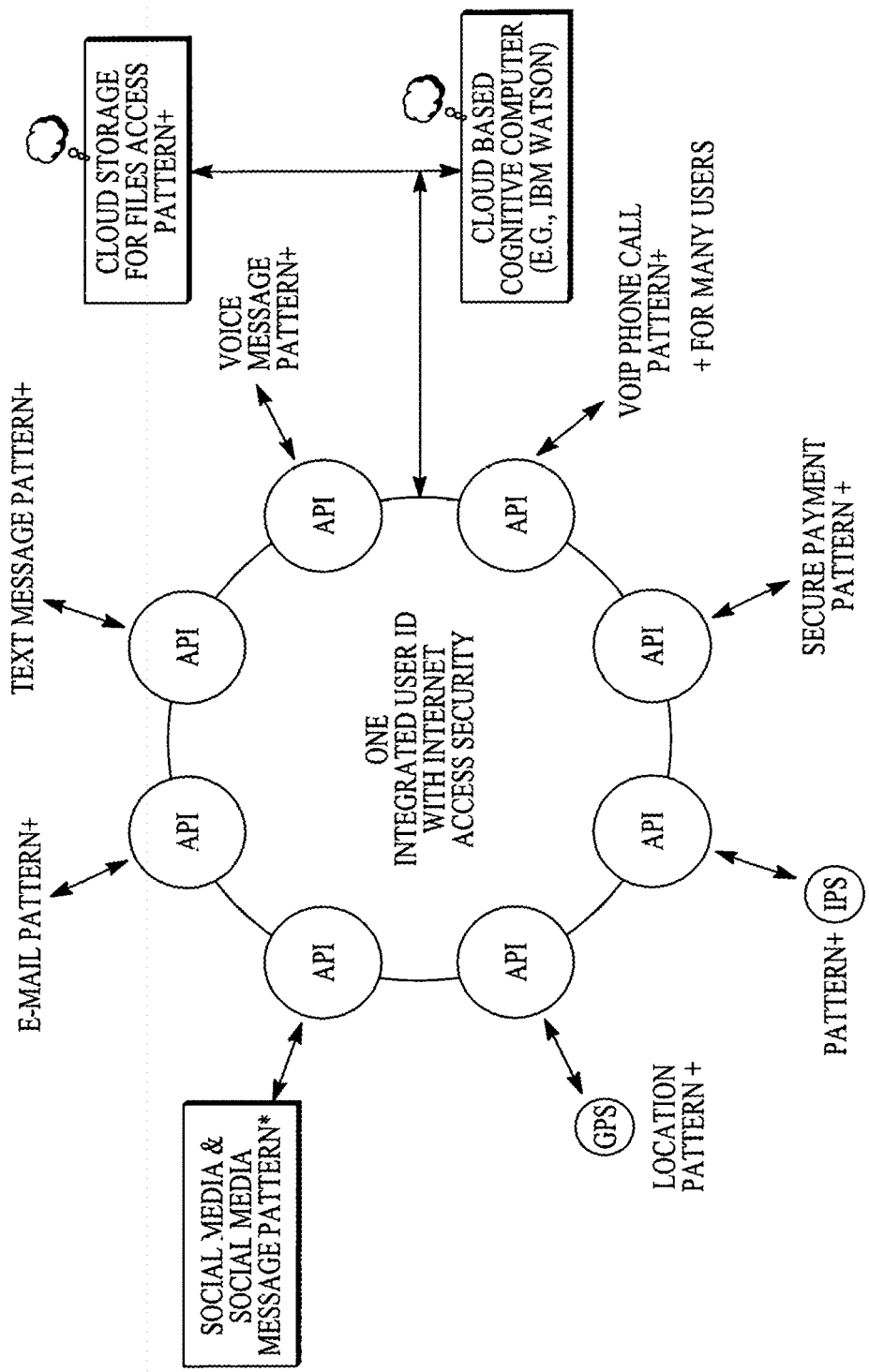
FIG. 27 illustrates patterns of various applications or functions of many users and analysis of such patterns by a cloud based machine learning/deep learning neural networks based learning/relearning interactive expert cognitive computer.

FIG. 27 illustrates patterns of various applications or functions of many users and analyzes such patterns by a cloud based machine learning/deep learning neural networks based learning/relearning expert cognitive computer. Collective complex patterns of many users can be analyzed by topological analysis for data shape/structure and predictive modeling.

Figure 28:
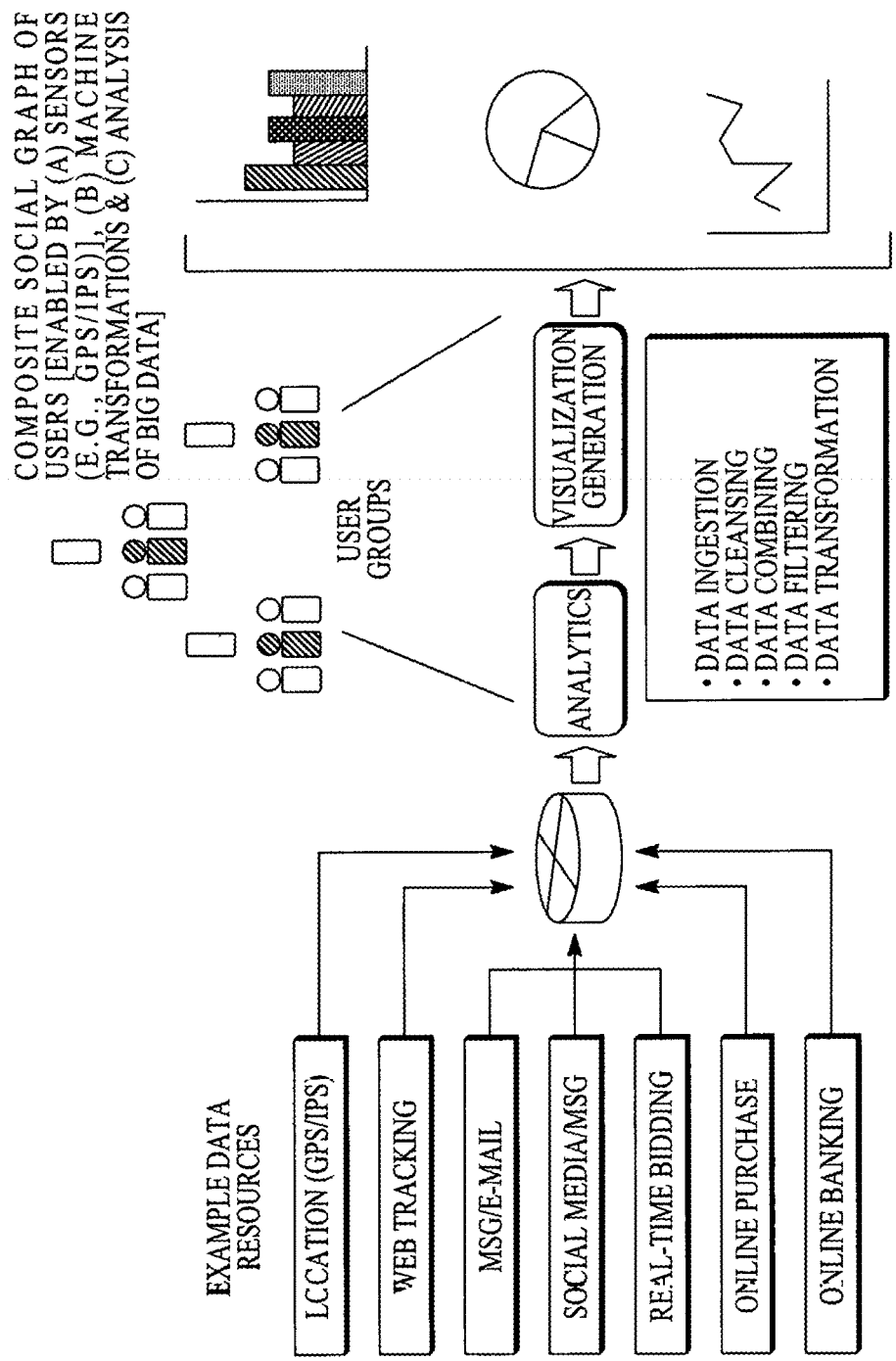
FIG. 28 illustrates a composite social graph of many users.

FIG. 28 illustrates a composite social graph of many users, enabled by (a) sensors (e.g., a location determination module-indoor positioning system/global positioning system), (b) collective data patterns, (c) an algorithm for generating the composite social graph with machine transformations, wherein the algorithm for generating the composite social graph with machine transformations can be stored in a local data storage unit of the portable internet appliance 1600 or a cloud based data storage unit and (d) mathematical/statistical algorithm of Big Data stored in a cloud based data storage unit.

The collective data patterns may include location, web tracking, message/e-mail, social media/message, real-time bidding/auction, online purchase and online/digital banking.

Figure 29:
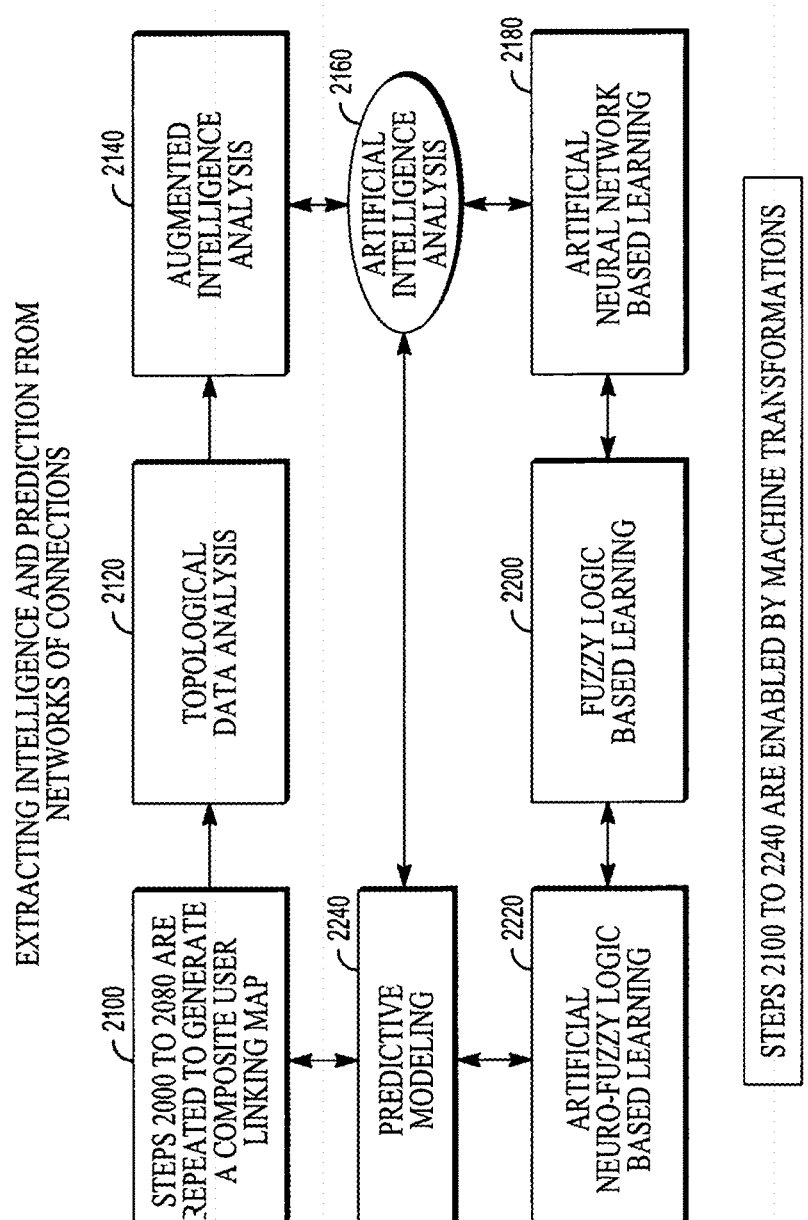
FIG. 29 illustrates a flow chart method of extracting intelligence and prediction from the collective data patterns, utilizing machine transformations.

FIG. 29 illustrates a method of extracting intelligence and prediction from the collective data patterns, utilizing machine transformations. In step 2100, a composite linking map is produced. In step 2120, the structure or shape of data is analyzed by topological data analysis. In step 2140, augmented intelligence analysis is performed. In step 2160, artificial intelligence (including self-learning artificial intelligence) based analysis is performed. In step 2180, artificial neural networks (including self-learning artificial neural networks) based learning is performed. In step 2200, fuzzy logic based learning is performed. In step 2220, artificial neuro-fuzzy logic based learning is performed. In step 2240, predictive modeling is performed. Furthermore, step 2240, of predictive modeling is linked with the step 2160 of artificial intelligence (including self-learning artificial intelligence) based analysis. Steps 2100 to 2240 can be realized by a series of machine transformations in conjunction with the microprocessor/super-processor or system-on-chip/neural networks based system-on-chip. System-on-chip/neural networks based system-on-chip can replace the microprocessor/super-processor and enable cognitive/neural like computing.

Fuzzy logic is a form of approximate reasoning, that can represent variation or imprecision in logic by making use of a natural language in logic. An artificial neural network can approximate a function, but it is impossible to interpret the result in terms of a natural language. Artificial neuro-fuzzy system is based on combinations of artificial neural networks and fuzzy logic.

The one integrated used identification can also enable collaboration, without needing to download any software. A user can click to join for collaboration (with many users) on one integrated used identification platform.

By way of an example of an application and not by way of any limitation, utilizing steps 2120, 2140, 2160, 2180, 2200, 2220 and 2240, a targeted marketing campaign via viral meme can be realized. Furthermore, the marketer can enhance user response to a particular advertisement, by utilizing augmented reality. In another example, a marketer can anticipate what a particular user wants and needs for a car. A marketer can ask if the user would like to see a certain model of a car and then have a salesperson meet the user at a place, where that model of the car is located. Thus, the shopping experience can integrate both online and offline.

Analysis of Big Data Related to Users' Social Graphs/Personal Analytics

Big Data can be converted into a smaller data set, utilizing linear simplification and/or signal clustering, as the underlying data has geometrical structures and patterns (repeated over time). Furthermore, signal clustering can be categorized and weighted for importance. Alternatively, topological data analysis or Bayesian analysis coupled with Markov chain Monte Carlo methods can be utilized for analysis of Big Data. Analysis of Big Data can be coupled with an augmented intelligence modeling algorithm and/or predictive modeling algorithm. Furthermore, analysis of Big Data in an unstructured format/natural language can be realized by a cloud based machine learning/deep learning neural networks based learning/relearning interactive expert cognitive computer. Furthermore, analysis of Big Data can be coupled with an intelligent learning set of instructions. A first intelligent learning set of instructions can include: artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning).

It should be noted that artificial intelligence (including self-learning artificial intelligence), computer vision (including self-learning computer vision), data mining, fuzzy/neuro-fuzzy logic, machine vision (including self-learning machine vision), natural language processing, neural networks (including self-learning neural networks), pattern recognition, reasoning modeling and self-learning (including evidence based self-learning) can be enhanced by quantum computing or quantum computing based machine learning.

A second intelligent learning set of instructions can include: algorithm-as-a-service, behavior modeling, physical search algorithm and software agent.

The behavior modeling can be described as-a user's behavior patterns are stored in a data storage module of the portable internet appliance 1600 or in a cloud based data storage unit. A data mining algorithm and/or a data interpretation algorithm can analyze the user's behavior patterns. Furthermore, a machine learning/deep learning neural networks based learning/relearning software module can learn and relearn the user's behavior patterns to intimately identify the user.

A physical search algorithm can be utilized to search or search about a physical item (e.g., "Google my wallet?"). A software agent can search the internet for a particular topic/physical item with/without a human input. The software agent can further recommend information about the particular topic/physical item to the user.

Additionally, it should be noted that all components/devices and/or application examples and/or embodiments of the near real-time/real-time wearable bioelectronics subsystem 1580, as an augmented reality personal assistant can be utilized with the portable internet appliance 1600.

It should be apparent that one or more features of the portable internet appliance 1600 can be combined with one or more features of the near real-time/real-time wearable bioelectronics subsystem 1580. Additionally, the applications, as illustrated in FIGS. 21, 22A, 22B, 23, 24, 25, 26, 27, 28 and 29 can be realized by the near real-time/real-time wearable bioelectronics subsystem 1580, as an augmented reality personal assistant.

Interactions of Networks of Objects/Biological Objects with the Portable Internet Appliance "Google my wallet?" would give the user the right answer, if the user's wallet is embedded with an object (an object is illustrated in FIGS. 18E, 18F, 18G and 18H).

Furthermore, the object can be fabricated/constructed, as nanostructured mesh (as described in Table-16A and Table-16B), wherein each nanostructured mesh can be integrated with other suitable circuits and sensors.

TABLE 16A

Compositions For A Nanostructured Mesh For An Object

| Compositions | Wt % Material A | Wt % Material B | Wt % Material C | Wt % Material D |
|---|---|---|---|---|
| 1 | 80% Hydrogel | 20% Chitin | | |
| 2 | 80% Hydrogel | 20% Chitosan | | |
| 3 | 80% Hydrogel | 20% Fibroin | | |
| 4 | 80% Hydrogel | 10% Chitin | 10% Chitosan | |
| 5 | 80% Hydrogel | 10% Chitin | 10% Fibroin | |
| 6 | 80% Hydrogel | 10% Chitosan | 10% Fibroin | |
| 7 | 80% Hydrogel | 10% Chitin | 10% PGLA | |
| 8 | 80% Hydrogel | 10% Chitosan | 10% PGLA | |
| 9 | 80% Hydrogel | 10% Fibroin | 10% PGLA | |
| 10 | 70% Hydrogel | 10% Chitin | 10% Fibroin | 10% PGLA |
| 11 | 70% Hydrogel | 10% Chitosan | 10% Fibroin | 10% PGLA |

TABLE 16B

Nanostructured Mesh (For An Object) Integrated With Various Nanowire Field Effect Transistors

| Compositions From Table-16A | Integrated With An Array Of Nanowire Field Effect Transistors |
|---|---|
| 1 | Nanowire$^{P1}$/Nanowire$^{P2}$/Nanowire$^{P3}$/Nanowire$^z$/Nanowire$^c$ |
| 2 | Nanowire$^{P1}$/Nanowire$^{P2}$/Nanowire$^{P3}$/Nanowire$^z$/Nanowire$^c$ |
| 3 | Nanowire$^{P1}$/Nanowire$^{P2}$/Nanowire$^{P3}$/Nanowire$^z$/Nanowire$^c$ |
| 4 | Nanowire$^{P1}$/Nanowire$^{P2}$/Nanowire$^{P3}$/Nanowire$^z$/Nanowire$^c$ |
| 5 | Nanowire$^{P1}$/Nanowire$^{P2}$/Nanowire$^{P3}$/Nanowire$^z$/Nanowire$^c$ |
| 6 | Nanowire$^{P1}$/Nanowire$^{P2}$/Nanowire$^{P3}$/Nanowire$^z$/Nanowire$^c$ |
| 7 | Nanowire$^{P1}$/Nanowire$^{P2}$/Nanowire$^{P3}$/Nanowire$^z$/Nanowire$^c$ |
| 8 | Nanowire$^{P1}$/Nanowire$^{P2}$/Nanowire$^{P3}$/Nanowire$^z$/Nanowire$^c$ |
| 9 | Nanowire$^{P1}$/Nanowire$^{P2}$/Nanowire$^{P3}$/Nanowire$^z$/Nanowire$^c$ |
| 10 | Nanowire$^{P1}$/Nanowire$^{P2}$/Nanowire$^{P3}$/Nanowire$^z$/Nanowire$^c$ |
| 11 | Nanowire$^{P1}$/Nanowire$^{P2}$/Nanowire$^{P3}$/Nanowire$^z$/Nanowire$^c$ |

Nanowire$^{P1}$ field effect transistor is a polymer nanowire field effect transistor (optionally coated with a lipid layer).

Nanowire$^{P2}$ field effect transistor is an engineered protein nanowire field effect transistor (optionally coated with a lipid layer). An engineered protein based field effect transistor can be fabricated/constructed, utilizing a suitable material decorated on engineered protein (e.g., a three-dimensional ball and spike engineered protein-synthesized by a fusion of both Dps and gp5c genes).

Nanowire$^{P3}$ field effect transistor is a proton nanowire field effect transistor (optionally coated with a lipid layer). A natural biopolymer chitosan/melanin based proton field effect transistor, which incorporates a polymer substrate as a gate, a gate oxide insulator film, a source metal thin-film and a drain metal thin-film for proton current.

Nanowire$^z$ field effect transistor is a zinc oxide wire nanowire field effect transistor (optionally coated with a lipid layer).

Nanowire$^C$ field effect transistor is a carbon nanotube nanofiber field effect transistor (optionally coated with a lipid layer).

Similarly, a biological object can be fabricated/constructed, utilizing a nanostructured mesh (as described in Table-16A and Table-16B) integrated with suitable biocompatible circuits and biosensors. A biological object can be fabricated/constructed as biodissolvable, utilizing electronic circuits based on silicon nanowires and/or silk nanowires.

Furthermore, an object/biological object can be decorated/tagged with a nano-scaled label (an array of quantum dots or semiconductor nanocrystals) to absorb and emit light at a specific wavelength for identification. The nano-scaled label can be suitably excited by an invisible ultraviolet (UV) laser from a distance and detected by an infrared camera from a distance.

Furthermore, an object/biological can be integrated with a microelectro-mechanical-system-piezoelectric based actuator for movement or a propeller. Networks of objects/biological objects can be utilized for recording and/or transmitting audio-visual information in a situation (e.g., a battlefield).

Networks of objects/biological objects (wherein each object/biological object is integrated with microelectro-mechanical-system-piezoelectric based actuator) can be utilized as collective assassins (wherein a nano-scaled reservoir within an object/biological object is filled a toxic chemical) in a battlefield.

All the algorithms and/or software programs and/or software application programs ("apps") in the above disclosed specifications reside in a computer system, wherein the computer system generally can include: a premise based computer system and/or a cloud based computer and/or a cloud based machine learning/deep learning neural networks based learning/relearning interactive expert cognitive computer system, wherein the computer system can include: one or more hardware (e.g., microprocessors/super-processors) in communication with a computer readable medium storing one or more algorithms and/or software programs and/or software application programs ("apps") including instructions that are executable by the one or more hardware (e.g., microprocessors/super-processors).

In the above disclosed specifications "/" has been used to indicate an "or" and real-time means near real-time in practice.

The word "unit" is synonymous with the word "media unit" or with the word "media". A cloud based storage unit is synonymous with a cloud based server.

PREFERRED EMBODIMENTS & SCOPE OF THE INVENTION

Any example in the above disclosed specifications is by way of an example only and not by way of any limitation.

The best mode requirement "requires an inventor(s) to disclose the best mode contemplated by him/her, as of the time he/she executes the application, of carrying out the invention." " . . . [T]he existence of a best mode is a purely subjective matter depending upon what the inventor(s) actually believed at the time the application was filed." See Bayer AG v. Schein Pharmaceuticals, Inc. The best mode requirement still exists under the America Invents Act (AIA). At the time of the invention, the inventor(s) described preferred best mode embodiments of the present invention. The sole purpose of the best mode requirement is to restrain the inventor(s) from applying for a patent, while at the same time concealing from the public preferred embodiments of their inventions, which they have in fact conceived. The best mode inquiry focuses on the inventor(s)' state of mind at the time he/she filed the patent application, raising a subjective factual question. The specificity of disclosure required to comply with the best mode requirement must be determined by the knowledge of facts within the possession of the inventor(s) at the time of filing the patent application. See Glaxo, Inc. v. Novopharm LTD., 52 F.3d 1043, 1050 (Fed. Cir. 1995).

The above disclosed specifications are the preferred best mode embodiments of the present invention. However, they are not intended to be limited only to the preferred best mode embodiments of the present invention. Numerous variations and/or modifications are possible within the scope of the present invention. Accordingly, the disclosed preferred best mode embodiments are to be construed as illustrative only.

Those who are skilled in the art can make various variations and/or modifications (e.g., a light emitting diode instead of a laser, or electrically/wirelessly coupled instead of electrically/wirelessly connected, or a cloud based storage unit instead of a cloud based server, whenever it is applicable) without departing from the scope and spirit of this invention. It should be apparent that features of one embodiment can be combined with one or more features of another embodiment to form a plurality of embodiments. The inventor(s) of the present invention is not required to describe each and every conceivable and possible future embodiment in the preferred best mode embodiments of the present invention. See SRI Int'l v. Matsushita Elec. Corp. of America, 775F.2d 1107, 1121, 227 U.S.P.Q. (BNA) 577, 585 (Fed. Cir. 1985) (en-banc).

The scope and spirit of this invention shall be defined by the claims and the equivalents of the claims only. The exclusive use of all variations and/or modifications within the scope of the claims is reserved. The general presumption is that claim terms should be interpreted using their plain and ordinary meaning. See Oxford Immunotec Ltd. v. Qiagen, Inc. et al., Action No. 15-cv-13124-NMG. Unless a claim term is specifically defined in the preferred best mode embodiments, then a claim term has an ordinary meaning, as understood by a person with an ordinary skill in the art, at the time of the present invention. As noted long ago: "Specifications teach. Claims claim". See Rexnord Corp. v. Laitram Corp., 274 F.3d 1336, 1344 (Fed. Cir. 2001). The rights of claims (and rights of the equivalents of the claims) under the Doctrine of Equivalents-meeting the "Triple Identity Test" (a) performing substantially the same function, (b) in substantially the same way and (c) yielding substantially the same result. See Crown Packaging Tech., Inc. v. Rexam Beverage Can Co., 559 F.3d 1308, 1312 (Fed. Cir. 2009)) of the present invention are not narrowed or limited by the selective imports of the specifications (of the preferred embodiments of the present invention) into the claims.

The term "means" was not used nor intended nor implied in the disclosed preferred best mode embodiments of the present invention. Thus, the inventor(s) has not limited the scope of the claims as mean plus function. Additionally, "apparatus claims are not necessarily indefinite for using functional language . . . [f]unctional language may also be employed to limit the claims without using the means-plus-function format." See Microprocessor Enhancement Corp. v. Texas Instruments Inc.

I claim:
1. An optical biomodule comprises:
(a) a fluidic container;
wherein a substrate of the fluidic container comprises: one or more materials,
wherein the fluidic container comprises: a first biomarker binder or a second biomarker binder,
wherein the first biomarker binder is coupled with a first fluorophore or a first photoswitchable fluorophore,
wherein the fluidic container comprises: one or more three-dimensional (3-D) protruded structures,
wherein the first fluorophore or the first photoswitchable fluorophore is positioned horizontally relative to an open space of the one three-dimensional (3-D) protruded structure
or
the second biomarker binder is positioned horizontally relative to the open space of the one three-dimensional (3-D) protruded structure, wherein a dimension or shape of the one three-dimensional (3-D) protruded structure is varied for maximum enhancement of fluorescence emission,
wherein more than the one three-dimensional (3-D) protruded structures are spaced or arranged in a one-dimensional (1-D) array or in a two-dimensional (2-D) array,
wherein a pitch or a gap or a duty cycle of the one-dimensional (1-D) array or the two-dimensional (2-D) array of the three-dimensional (3-D) protruded structures is varied for maximum enhancement of the fluorescence emission;
(b) a light source or light sources directed at the fluidic container for inducing the fluorescence emission due to an interaction of the first biomarker binder or the second biomarker binder with a biomarker; and
(c) a device for detecting the fluorescence emission from the fluidic container.

2. The optical biomodule according to claim 1, wherein the substrate of the fluidic container comprises: a periodic layers of one or more materials.

3. The optical biomodule according to claim 1, wherein the first biomarker binder is selected from the group consisting of: an isolated antibody, a synthetically designed antibody, an aptamer, a wavelength-shifting aptamer and a synthetically designed protein, wherein the synthetically designed protein has a binding site to bind with the biomarker.

4. The optical biomodule according to claim 1, wherein the first biomarker binder is a nano-scaled synthetically designed biomolecular circuit, wherein the nano-scaled synthetically designed biomolecular circuit comprises: (i) a synthetically designed riboswitch or (ii) a DNA sequence of adenine (A), thymine (T), guanine (G) and cytosine (C) or (iii) a DNA sequence of adenine (A), thymine (T), guanine, (G) cytosine (C) and a synthetically designed molecule or (iv) an RNA sequence or (v) a programmable synthetically designed DNA-targeting-cleaving enzyme or (vi) a programmable synthetically designed RNA-targeting-cleaving enzyme.

5. The optical biomodule according to claim 4, wherein the nano-scaled synthetically designed biomolecular circuit further comprises: a synthetically designed biological logic circuit.

6. The optical biomodule according to claim 1, wherein the first biomarker binder comprises: a nanoshell, wherein the nanoshell is decorated with a cleavable biological material, wherein the cleavable biological material is cleaved from a diseased cell or a decorated diseased cell.

7. The optical biomodule according to claim 1, wherein the first biomarker binder comprises: a synthetically designed exosome-specific biomarker binder to couple with a molecule of an exosome.

8. The optical biomodule according to claim 1, wherein the second biomarker binder comprises: an aptamer beacon or a molecular beacon or a noble metal atom nanocluster beacon or a synthetically designed riboswitch beacon.

9. The optical biomodule according to claim 8, wherein the aptamer beacon or the molecular beacon or the noble metal atom nanocluster beacon or the synthetically designed riboswitch beacon comprises: a synthetically designed biological logic circuit.

10. The optical biomodule according to claim 1, wherein the second biomarker binder is coupled with a nanostructural element or the second biomarker binder is coupled with a point defect of the nanostructural element.

11. The optical biomodule according to claim 10, wherein the nanostructural element is electrically conducting, wherein the nanostructural element is electrically activated or electrically coupled with a field effect transistor.

12. The optical biomodule according to claim 1, wherein the second biomarker binder comprises: an aptamer sensor, wherein the aptamer sensor comprises: a first chemical segment to couple with the biomarker and a second chemical segment to couple with a second fluorophore or a second photoswitchable fluorophore.

13. The optical biomodule according to claim 1, wherein the second biomarker binder comprises: a first isolated antibody and a second isolated antibody, wherein the first isolated antibody or the second isolated antibody is coupled with a second fluorophore or a second photoswitchable fluorophore.

14. The optical biomodule according to claim 1, wherein the second biomarker binder comprises: a first synthetically designed antibody and a second synthetically designed antibody, wherein the first synthetically designed antibody or the second synthetically designed antibody is coupled with a second fluorophore or a second photoswitchable fluorophore.

15. The optical biomodule according to claim 14, wherein the first synthetically designed antibody or the second synthetically designed antibody is arranged in three-dimension (3-D).

16. The optical biomodule according to claim 1, wherein the one three-dimensional (3-D) protruded structure is an optical nanoantenna or a three-dimensional (3-D) protruded structure of a two-dimensional (2-D) material or a conducting nanotube or a sharp tip or a hyperbolic metamaterial surface.

17. The optical biomodule according to claim 16, wherein the optical nanoantenna comprises: a room temperature stable topological insulator or a two-dimensional (2-D) material or a nanoparticle.

18. The optical biomodule according to claim 16, wherein the hyperbolic metamaterial surface comprises: nanoholes or gratings.

19. The optical biomodule according to claim 1, wherein the light source of the particular wavelength or the light sources of the distinct wavelengths comprises: a two-dimensional (2-D) material.

20. The optical biomodule according to claim 1, wherein the light sources comprise: a first coherent light source and a second coherent light source, wherein a beam of the first coherent light source is approximately an open toroidal shaped, wherein the first coherent light source and the second coherent light source are activated simultaneously.

21. The optical biomodule according to claim 1, comprises: an abruptly constricted fluid container, wherein a maximum dimension of the abruptly constricted fluid container is less than a maximum dimension of a cell or a stem cell or a T cell.

22. The optical biomodule according to claim 1, comprises: a device to isolate exosomes from a biological fluid and to isolate molecules from the exosomes, wherein the device comprises: a separator module to isolate exosomes-attached magnetic beads or a nano-scaled filter to filter the exosome from the biological fluid.

23. An optical biomodule comprises:
(a) a fluidic container;
wherein a substrate of the fluidic container comprises: one or more materials,
wherein the fluidic container comprises: a first biomarker binder or a second biomarker binder, wherein the first biomarker binder is coupled with a first fluorophore or a first photoswitchable fluorophore,
wherein the fluidic container comprises: one or more three-dimensional (3-D) protruded structures,
   wherein the first fluorophore or the first photoswitchable fluorophore is positioned at about 25 nanometers or less than 25 nanometers horizontally relative to the one three-dimensional (3-D) protruded structure
   or
   the second biomarker binder is positioned at about 25 nanometers or less than 25 nanometers horizontally relative to the one three-dimensional (3-D) protruded structure,
wherein a dimension or shape of the one three-dimensional (3-D) protruded structure is varied for maximum enhancement of fluorescence emission,
   wherein more than the one three-dimensional (3-D) protruded structures are spaced or arranged in a one-dimensional (1-D) array or in a two-dimensional (2-D) array,
   wherein a pitch or a gap or a duty cycle of the one-dimensional (1-D) array or the two-dimensional (2-D) array of the three-dimensional (3-D) protruded structures is varied for maximum enhancement of the fluorescence emission;
(b) a light source or light sources directed at the fluidic container for inducing the fluorescence emission due to an interaction of the first biomarker binder or the second biomarker binder with a biomarker; and
(c) a device for detecting the fluorescence emission from the fluidic container.

24. An optical biomodule to detect fluorescence emission comprises:
(a) a zero-mode waveguide;
   wherein the zero-mode waveguide comprises: one or more side walls,
   wherein the zero-mode waveguide comprises: a bottom base,
   wherein a substrate of the zero-mode waveguide consists of one or more materials,
   wherein the zero-mode waveguide contains or comprises: one or more biomarker binders or immobilized single DNA polymerase molecules,
   wherein the zero-mode waveguide comprises: one three-dimensional (3-D) protruded structure,
(b) a light source or light sources directed at the zero-mode waveguide for inducing the fluorescence emission due to an interaction of the one biomarker binder with a biomarker or the one immobilized single DNA polymerase molecule with a freely moving DNA-interacting protein or a freely moving phospholinked nucleotide; and
(c) a device for detecting the fluorescence emission from the zero-mode waveguide.

25. The optical biomodule according to claim 24, wherein the zero-mode waveguide is functionalized (a) on the one side walls of the zero-mode waveguide with a monolayer of first molecules or (b) at or near the bottom base of the zero-mode waveguide with a monolayer of second molecules or (c) at or near the bottom base of the zero-mode waveguide with a monolayer of third molecules to bind the one biomarker binder or the one immobilized single DNA polymerase molecule.

\* \* \* \* \*

UNITED STATES PATENT AND TRADEMARK OFFICE
CERTIFICATE OF CORRECTION

PATENT NO. : 10,529,003 B2
APPLICATION NO. : 15/731577
DATED : January 7, 2020
INVENTOR(S) : Mohammad A. Mazed It is certified that error appears in the above-identified patent and that said Letters Patent is hereby corrected as shown below:

In the Claims

In Claim 1, Column 211, Line 2:
Please delete "maximum"
And insert --a maximum--

In Claim 1, Column 211, Line 11:
Please delete "maximum"
And insert --a maximum--

In Claim 23, Column 213, Line 17:
Please delete "maximum"
And insert --a maximum--

In Claim 23, Column 213, Line 26:
Please delete "maximum"
And insert --a maximum--

Signed and Sealed this
Fourth Day of July, 2023

Katherine Kelly Vidal
*Director of the United States Patent and Trademark Office*